US011661590B2

(12) United States Patent
Liu et al.

(10) Patent No.: US 11,661,590 B2
(45) Date of Patent: May 30, 2023

(54) PROGRAMMABLE CAS9-RECOMBINASE FUSION PROTEINS AND USES THEREOF

(71) Applicant: President and Fellows of Harvard College, Cambridge, MA (US)

(72) Inventors: David R. Liu, Lexington, MA (US); Brian Chaikind, Oakland, CA (US); Jeffrey L. Bessen, Somerville, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 16/324,476

(22) PCT Filed: Aug. 9, 2017

(86) PCT No.: PCT/US2017/046144

§ 371 (c)(1),
(2) Date: Feb. 8, 2019

(87) PCT Pub. No.: WO2018/031683

PCT Pub. Date: Feb. 15, 2018

(65) Prior Publication Data

US 2019/0367891 A1 Dec. 5, 2019

Related U.S. Application Data

(60) Provisional application No. 62/456,048, filed on Feb. 7, 2017, provisional application No. 62/372,755, filed on Aug. 9, 2016.

(51) Int. Cl.

| | |
|---|---|
| ***C12N 9/12*** | (2006.01) |
| ***C07K 4/00*** | (2006.01) |
| ***C12N 9/22*** | (2006.01) |
| ***C12N 15/113*** | (2010.01) |

(52) U.S. Cl.

CPC .............. *C12N 9/1241* (2013.01); *C07K 4/00* (2013.01); *C12N 9/22* (2013.01); *C12N 15/113* (2013.01); *C07K 2319/09* (2013.01); *C07K 2319/21* (2013.01); *C07K 2319/43* (2013.01); *C12N 2310/20* (2017.05); *C12N 2320/11* (2013.01); *C12Y 207/07* (2013.01)

(58) Field of Classification Search

CPC .......... C12N 9/22; C12N 15/11; C12N 15/90; C12N 15/10; C12N 15/85

See application file for complete search history.

(56) References Cited

U.S. PATENT DOCUMENTS

| | | | |
|---|---|---|---|
| 4,182,449 | A | 1/1980 | Kozlow |
| 4,186,183 | A | 1/1980 | Steck et al. |
| 4,217,344 | A | 8/1980 | Vanlerberghe et al. |
| 4,235,871 | A | 11/1980 | Papahadjopoulos et al. |
| 4,261,975 | A | 4/1981 | Fullerton et al. |
| 4,485,054 | A | 11/1984 | Mezei et al. |
| 4,501,728 | A | 2/1985 | Geho et al. |
| 4,663,290 | A | 5/1987 | Weis et al. |
| 4,737,323 | A | 4/1988 | Martin et al. |
| 4,774,085 | A | 9/1988 | Fidler |
| 4,797,368 | A | 1/1989 | Carter et al. |
| 4,837,028 | A | 6/1989 | Allen |
| 4,873,316 | A | 10/1989 | Meade et al. |
| 4,880,635 | A | 11/1989 | Janoff et al. |
| 4,889,818 | A | 12/1989 | Gelfand et al. |
| 4,897,355 | A | 1/1990 | Eppstein et al. |
| 4,906,477 | A | 3/1990 | Kurono et al. |
| 4,911,928 | A | 3/1990 | Wallach |
| 4,917,951 | A | 4/1990 | Wallach |
| 4,920,016 | A | 4/1990 | Allen et al. |
| 4,921,757 | A | 5/1990 | Wheatley et al. |
| 4,946,787 | A | 8/1990 | Eppstein et al. |
| 4,965,185 | A | 10/1990 | Grischenko et al. |
| 5,017,492 | A | 5/1991 | Kotewicz et al. |
| 5,047,342 | A | 9/1991 | Chatterjee |
| 5,049,386 | A | 9/1991 | Eppstein et al. |
| 5,079,352 | A | 1/1992 | Gelfand et al. |
| 5,139,941 | A | 8/1992 | Muzyczka et al. |
| 5,173,414 | A | 12/1992 | Lebkowski et al. |
| 5,223,409 | A | 6/1993 | Ladner et al. |
| 5,244,797 | A | 9/1993 | Kotewicz et al. |
| 5,270,179 | A | 12/1993 | Chatterjee |
| 5,374,553 | A | 12/1994 | Gelfand et al. |
| 5,405,776 | A | 4/1995 | Kotewicz et al. |
| 5,436,149 | A | 7/1995 | Barnes |
| 5,449,639 | A | 9/1995 | Wei et al. |

(Continued)

FOREIGN PATENT DOCUMENTS

| | | | |
|---|---|---|---|
| AU | 2012244264 | A1 | 11/2012 |
| AU | 2012354062 | A1 | 7/2014 |
| AU | 2015252023 | A1 | 11/2015 |
| AU | 2015101792 | A4 | 1/2016 |
| BR | 112015013786 | A2 | 7/2017 |

(Continued)

OTHER PUBLICATIONS

Bertolotti, Roger, Molecular Therapy, May 2015, vol. 23, Supp. SPPL.1, p. S139, Abstract No. 350.*

(Continued)

*Primary Examiner* — Maryam Monshipouri

(74) *Attorney, Agent, or Firm* — Wolf, Greenfield & Sacks, P.C.

(57) ABSTRACT

Some aspects of this disclosure provide a fusion protein comprising a guide nucleotide sequence-programmable DNA binding protein domain (e.g., a nuclease-inactive variant of Cas9 such as dCas9), an optional linker, and a recombinase catalytic domain (e.g., a tyrosine recombinase catalytic domain or a serine recombinase catalytic domain such as a Gin recombinase catalytic domain). This fusion protein can recombine DNA sites containing a minimal recombinase core site flanked by guide RNA-specified sequences. The instant disclosure represents a step toward programmable, scarless genome editing in unmodified cells that is independent of endogenous cellular machinery or cell state.

13 Claims, 16 Drawing Sheets

Specification includes a Sequence Listing.

(56) References Cited

U.S. PATENT DOCUMENTS 5,496,714 A 3/1996 Comb et al.
5,512,462 A 4/1996 Cheng
5,580,737 A 12/1996 Polisky et al.
5,614,365 A 3/1997 Tabor et al.
5,652,094 A 7/1997 Usman et al.
5,658,727 A 8/1997 Barbas et al.
5,668,005 A 9/1997 Kotewicz et al.
5,677,152 A 10/1997 Birch et al.
5,767,099 A 6/1998 Harris et al.
5,780,053 A 7/1998 Ashley et al.
5,830,430 A 11/1998 Unger et al.
5,834,247 A 11/1998 Comb et al.
5,835,699 A 11/1998 Kimura
5,849,548 A 12/1998 Haseloff et al.
5,851,548 A 12/1998 Dattagupta et al.
5,855,910 A 1/1999 Ashley et al.
5,856,463 A 1/1999 Blankenborg et al.
5,962,313 A 10/1999 Podsakoff et al.
5,981,182 A 11/1999 Jacobs, Jr. et al.
6,015,794 A 1/2000 Haseloff et al.
6,057,153 A 5/2000 George et al.
6,063,608 A 5/2000 Kotewicz et al.
6,077,705 A 6/2000 Duan et al.
6,156,509 A 12/2000 Schellenberger
6,183,998 B1 2/2001 Ivanov et al.
6,355,415 B1 3/2002 Wagner
6,429,298 B1 8/2002 Ellington et al.
6,453,242 B1 9/2002 Eisenberg et al.
6,479,264 B1 11/2002 Louwrier
6,503,717 B2 1/2003 Case et al.
6,534,261 B1 3/2003 Cox, III et al.
6,589,768 B1 7/2003 Kotewicz et al.
6,599,692 B1 7/2003 Case et al.
6,607,882 B1 8/2003 Cox, III et al.
6,610,522 B1 8/2003 Kotewicz et al.
6,689,558 B2 2/2004 Case
6,716,973 B2 4/2004 Baskerville et al.
6,824,978 B1 11/2004 Cox, III et al.
6,933,113 B2 8/2005 Case et al.
6,979,539 B2 12/2005 Cox, III et al.
7,013,219 B2 3/2006 Case et al.
7,045,337 B2 5/2006 Schultz et al.
7,067,650 B1 6/2006 Tanaka
7,070,928 B2 7/2006 Liu et al.
7,078,208 B2 7/2006 Smith et al.
7,083,970 B2 8/2006 Schultz et al.
7,163,824 B2 1/2007 Cox, III et al.
7,192,739 B2 3/2007 Liu et al.
7,223,545 B2 5/2007 Liu et al.
7,354,761 B2 4/2008 Schultz et al.
7,368,275 B2 5/2008 Schultz et al.
7,442,160 B2 10/2008 Liu et al.
7,476,500 B1 1/2009 Liu et al.
7,476,734 B2 1/2009 Liu
7,479,573 B2 1/2009 Chu et al.
7,491,494 B2 2/2009 Liu et al.
7,541,450 B2 6/2009 Liu et al.
7,557,068 B2 7/2009 Liu et al.
7,595,179 B2 9/2009 Chen et al.
7,638,300 B2 12/2009 Schultz et al.
7,670,807 B2 3/2010 Lampson et al.
7,678,554 B2 3/2010 Liu et al.
7,713,721 B2 5/2010 Schultz et al.
7,771,935 B2 8/2010 Liu et al.
7,794,931 B2 9/2010 Breaker et al.
7,807,408 B2 10/2010 Liu et al.
7,851,658 B2 12/2010 Liu et al.
7,915,025 B2 3/2011 Schultz et al.
7,919,277 B2 4/2011 Russell et al.
7,993,672 B2 8/2011 Huang et al.
7,998,904 B2 8/2011 Liu et al.
8,012,739 B2 9/2011 Schultz et al.
8,017,323 B2 9/2011 Liu et al.
8,017,755 B2 9/2011 Liu et al.
8,030,074 B2 10/2011 Schultz et al.
8,067,556 B2 11/2011 Hogrefe et al.
8,114,648 B2 2/2012 Schultz et al.
8,173,364 B2 5/2012 Schultz et al.
8,173,392 B2 5/2012 Schultz et al.
8,183,012 B2 5/2012 Schultz et al.
8,183,178 B2 5/2012 Liu et al.
8,206,914 B2 6/2012 Liu et al.
8,361,725 B2 1/2013 Russell et al.
8,394,604 B2 3/2013 Liu et al.
8,440,431 B2 5/2013 Voytas et al.
8,440,432 B2 5/2013 Voytas et al.
8,450,471 B2 5/2013 Voytas et al.
8,492,082 B2 7/2013 De Franciscis et al.
8,546,553 B2 10/2013 Terns et al.
8,569,256 B2 10/2013 Heyes et al.
8,586,363 B2 11/2013 Voytas et al.
8,680,069 B2 3/2014 de Fougerolles et al.
8,691,729 B2 4/2014 Liu et al.
8,691,750 B2 4/2014 Constien et al.
8,697,359 B1 4/2014 Zhang
8,697,853 B2 4/2014 Voytas et al.
8,709,466 B2 4/2014 Coady et al.
8,728,526 B2 5/2014 Heller
8,748,667 B2 6/2014 Budzik et al.
8,758,810 B2 6/2014 Okada et al.
8,759,103 B2 6/2014 Kim et al.
8,759,104 B2 6/2014 Unciti-Broceta et al.
8,771,728 B2 7/2014 Huang et al.
8,790,664 B2 7/2014 Pitard et al.
8,795,965 B2 8/2014 Zhang
8,822,663 B2 9/2014 Schrum et al.
8,846,578 B2 9/2014 McCray et al.
8,889,418 B2 11/2014 Zhang et al.
8,900,814 B2 12/2014 Yasukawa et al.
8,945,839 B2 2/2015 Zhang
8,975,232 B2 3/2015 Liu et al.
8,993,233 B2 3/2015 Zhang et al.
8,999,641 B2 4/2015 Zhang et al.
9,023,594 B2 5/2015 Liu et al.
9,023,649 B2 5/2015 Mali et al.
9,068,179 B1 6/2015 Liu et al.
9,150,626 B2 10/2015 Liu et al.
9,163,271 B2 10/2015 Schultz et al.
9,163,284 B2 10/2015 Liu et al.
9,181,535 B2 11/2015 Liu et al.
9,200,045 B2 12/2015 Liu et al.
9,221,886 B2 12/2015 Liu et al.
9,228,207 B2 1/2016 Liu et al.
9,234,213 B2 1/2016 Wu
9,243,038 B2 1/2016 Liu et al.
9,267,127 B2 2/2016 Liu et al.
9,322,006 B2 4/2016 Liu et al.
9,322,037 B2 4/2016 Liu et al.
9,340,799 B2 5/2016 Liu et al.
9,340,800 B2 5/2016 Liu et al.
9,359,599 B2 6/2016 Liu et al.
9,388,430 B2 * 7/2016 Liu ...................... C12N 15/907
9,394,537 B2 7/2016 Liu et al.
9,434,774 B2 9/2016 Liu et al.
9,458,484 B2 10/2016 Ma et al.
9,512,446 B1 12/2016 Joung et al.
9,526,724 B2 12/2016 Oshiack et al.
9,526,784 B2 12/2016 Liu et al.
9,534,210 B2 1/2017 Park et al.
9,580,698 B1 2/2017 Xu et al.
9,610,322 B2 4/2017 Liu et al.
9,637,739 B2 5/2017 Siksnys et al.
9,737,604 B2 8/2017 Liu et al.
9,738,693 B2 8/2017 Telford et al.
9,753,340 B2 9/2017 Saitou
9,771,574 B2 9/2017 Liu et al.
9,783,791 B2 10/2017 Hogrefe et al.
9,816,093 B1 11/2017 Donohoue et al.
9,840,538 B2 12/2017 Telford et al.
9,840,690 B2 12/2017 Karli et al.
9,840,699 B2 12/2017 Liu et al.
9,840,702 B2 12/2017 Collingwood et al.
9,850,521 B2 12/2017 Braman et al.
9,873,907 B2 1/2018 Zeiner et al.

(56) References Cited

U.S. PATENT DOCUMENTS 9,879,270 B2 1/2018 Hittinger et al.
9,914,939 B2 3/2018 Church et al.
9,932,567 B1 4/2018 Xu et al.
9,938,288 B1 4/2018 Kishi et al.
9,944,933 B2 4/2018 Storici et al.
9,982,279 B1 5/2018 Gill et al.
9,999,671 B2 6/2018 Liu et al.
10,011,868 B2 7/2018 Liu et al.
10,053,725 B2 8/2018 Liu et al.
10,059,940 B2 8/2018 Zhong
10,077,453 B2 9/2018 Liu et al.
10,113,163 B2 10/2018 Liu et al.
10,150,955 B2 12/2018 Lambowitz et al.
10,167,457 B2 1/2019 Liu et al.
10,179,911 B2 1/2019 Liu et al.
10,189,831 B2 1/2019 Arrington et al.
10,202,593 B2 2/2019 Liu et al.
10,202,658 B2 2/2019 Parkin et al.
10,227,581 B2 3/2019 Liu et al.
10,323,236 B2 6/2019 Liu et al.
10,336,997 B2 7/2019 Liu et al.
10,358,670 B2 7/2019 Janulaitis et al.
10,392,674 B2 8/2019 Liu et al.
10,407,697 B2 9/2019 Doudna et al.
10,465,176 B2 11/2019 Liu et al.
10,508,298 B2 12/2019 Liu et al.
10,597,679 B2 3/2020 Liu et al.
10,612,011 B2 4/2020 Liu et al.
10,682,410 B2 6/2020 Liu et al.
10,704,062 B2 7/2020 Liu et al.
10,745,677 B2 8/2020 Maianti et al.
10,858,639 B2 12/2020 Liu et al.
10,912,833 B2 2/2021 Liu et al.
10,930,367 B2 2/2021 Zhang et al.
10,947,530 B2 3/2021 Liu et al.
10,954,548 B2 3/2021 Liu et al.
11,046,948 B2 6/2021 Liu et al.
11,053,481 B2 7/2021 Liu et al.
11,078,429 B2 8/2021 Liu et al.
11,124,782 B2 9/2021 Liu et al.
11,268,082 B2 3/2022 Liu et al.
11,299,755 B2 4/2022 Liu et al.
11,306,324 B2 4/2022 Liu et al.
11,447,770 B1 9/2022 Liu et al.
2003/0082575 A1 5/2003 Schultz et al.
2003/0087817 A1 5/2003 Cox et al.
2003/0096337 A1 5/2003 Hillman et al.
2003/0108885 A1 6/2003 Schultz et al.
2003/0119764 A1 6/2003 Loeb et al.
2003/0167533 A1 9/2003 Yadav et al.
2003/0203480 A1 10/2003 Kovesdi et al.
2004/0003420 A1 1/2004 Kuhn et al.
2004/0115184 A1 6/2004 Smith et al.
2004/0203109 A1 10/2004 Lal et al.
2005/0136429 A1 6/2005 Guarente et al.
2005/0222030 A1 10/2005 Allison
2005/0260626 A1 11/2005 Lorens et al.
2006/0088864 A1 4/2006 Smolke et al.
2006/0104984 A1 5/2006 Littlefield et al.
2006/0246568 A1 11/2006 Honjo et al.
2007/0015238 A1 1/2007 Snyder et al.
2007/0264692 A1 11/2007 Liu et al.
2007/0269817 A1 11/2007 Shapero
2008/0051317 A1 2/2008 Church et al.
2008/0124725 A1 5/2008 Barrangou et al.
2008/0182254 A1 7/2008 Hall et al.
2008/0220502 A1 9/2008 Schellenberger et al.
2009/0130718 A1 5/2009 Short
2009/0215878 A1 8/2009 Tan et al.
2009/0234109 A1 9/2009 Han et al.
2010/0076057 A1 3/2010 Sontheimer et al.
2010/0093617 A1 4/2010 Barrangou et al.
2010/0104690 A1 4/2010 Barrangou et al.
2010/0273857 A1 10/2010 Thakker et al.
2010/0305197 A1 12/2010 Che
2010/0316643 A1 12/2010 Eckert et al.
2011/0016540 A1 1/2011 Weinstein et al.
2011/0059160 A1 3/2011 Essner et al.
2011/0059502 A1 3/2011 Chalasani
2011/0104787 A1 5/2011 Church et al.
2011/0177495 A1 7/2011 Liu et al.
2011/0189775 A1 8/2011 Ainley et al.
2011/0189776 A1 8/2011 Terns et al.
2011/0217739 A1 9/2011 Terns et al.
2011/0301073 A1 12/2011 Gregory et al.
2012/0129759 A1 5/2012 Liu et al.
2012/0141523 A1 6/2012 Castado et al.
2012/0244601 A1 9/2012 Bertozzi et al.
2012/0270273 A1 10/2012 Zhang et al.
2012/0322861 A1 12/2012 Byrne et al.
2013/0059931 A1 3/2013 Petersen-Mahrt et al.
2013/0117869 A1 5/2013 Duchateau et al.
2013/0130248 A1 5/2013 Haurwitz et al.
2013/0158245 A1 6/2013 Russell et al.
2013/0165389 A1 6/2013 Schellenberger et al.
2013/0309720 A1 11/2013 Schultz et al.
2013/0344117 A1 12/2013 Mirosevich et al.
2013/0345064 A1 12/2013 Liu et al.
2014/0004280 A1 1/2014 Loomis
2014/0005269 A1 1/2014 Ngwuluka et al.
2014/0017214 A1 1/2014 Cost
2014/0018404 A1 1/2014 Chen et al.
2014/0044793 A1 2/2014 Goll et al.
2014/0065711 A1 3/2014 Liu et al.
2014/0068797 A1 3/2014 Doudna et al.
2014/0127752 A1 5/2014 Zhou et al.
2014/0141094 A1 5/2014 Smyth et al.
2014/0141487 A1 5/2014 Feldman et al.
2014/0179770 A1 6/2014 Zhang et al.
2014/0186843 A1 7/2014 Zhang et al.
2014/0186958 A1 7/2014 Zhang et al.
2014/0201858 A1 7/2014 Ostertag et al.
2014/0234289 A1 8/2014 Liu et al.
2014/0248702 A1 9/2014 Zhang et al.
2014/0273037 A1 9/2014 Wu
2014/0273226 A1 9/2014 Wu
2014/0273230 A1 9/2014 Chen et al.
2014/0273234 A1 9/2014 Zhang et al.
2014/0283156 A1 9/2014 Zador et al.
2014/0295556 A1 10/2014 Joung et al.
2014/0295557 A1 10/2014 Joung et al.
2014/0342456 A1 11/2014 Mali et al.
2014/0342457 A1 11/2014 Mali et al.
2014/0342458 A1 11/2014 Mali et al.
2014/0349400 A1 11/2014 Jakimo et al.
2014/0356867 A1 12/2014 Peter et al.
2014/0356956 A1 12/2014 Church et al.
2014/0356958 A1 12/2014 Mali et al.
2014/0356959 A1 12/2014 Church et al.
2014/0357523 A1 12/2014 Zeiner et al.
2014/0377868 A1 12/2014 Joung et al.
2015/0010526 A1 1/2015 Liu et al.
2015/0031089 A1 1/2015 Lindstrom
2015/0031132 A1 1/2015 Church et al.
2015/0031133 A1 1/2015 Church et al.
2015/0044191 A1 2/2015 Liu et al.
2015/0044192 A1 2/2015 Liu et al.
2015/0044772 A1 2/2015 Zhao
2015/0050699 A1 2/2015 Siksnys et al.
2015/0056177 A1 2/2015 Liu et al.
2015/0056629 A1 2/2015 Guthrie-Honea
2015/0064138 A1 3/2015 Lu et al.
2015/0064789 A1 3/2015 Paschon et al.
2015/0071898 A1 3/2015 Liu et al.
2015/0071899 A1 3/2015 Liu et al.
2015/0071900 A1 3/2015 Liu et al.
2015/0071901 A1 3/2015 Liu et al.
2015/0071902 A1 3/2015 Liu et al.
2015/0071903 A1 3/2015 Liu et al.
2015/0071906 A1* 3/2015 Liu .......................... C12N 9/14
435/375
2015/0079680 A1 3/2015 Bradley et al.
2015/0079681 A1 3/2015 Zhang
2015/0098954 A1 4/2015 Hyde et al.

(56) References Cited

U.S. PATENT DOCUMENTS

2015/0118216 A1 4/2015 Liu et al.
2015/0132269 A1 5/2015 Orkin et al.
2015/0140664 A1 5/2015 Byrne et al.
2015/0159172 A1 6/2015 Miller et al.
2015/0165054 A1 6/2015 Liu et al.
2015/0166980 A1 6/2015 Liu et al.
2015/0166981 A1 6/2015 Liu et al.
2015/0166982 A1 6/2015 Liu et al.
2015/0166983 A1 6/2015 Liu et al.
2015/0166984 A1 6/2015 Liu et al.
2015/0166985 A1 6/2015 Liu et al.
2015/0191744 A1 7/2015 Wolfe et al.
2015/0197759 A1 7/2015 Xu et al.
2015/0211058 A1 7/2015 Carstens
2015/0218573 A1 8/2015 Loque et al.
2015/0225773 A1 8/2015 Farmer et al.
2015/0252358 A1 9/2015 Maeder et al.
2015/0275202 A1 10/2015 Liu et al.
2015/0291965 A1 10/2015 Zhang et al.
2015/0307889 A1 10/2015 Petolino et al.
2015/0315252 A1 11/2015 Haugwitz et al.
2015/0344549 A1 12/2015 Muir et al.
2016/0015682 A2 1/2016 Cawthorne et al.
2016/0017393 A1 1/2016 Jacobson et al.
2016/0017396 A1 1/2016 Cann et al.
2016/0032292 A1 2/2016 Storici et al.
2016/0032353 A1 2/2016 Braman et al.
2016/0040155 A1 2/2016 Maizels et al.
2016/0046952 A1 2/2016 Hittinger et al.
2016/0046961 A1 2/2016 Jinek et al.
2016/0046962 A1 2/2016 May et al.
2016/0053272 A1 2/2016 Wurtzel et al.
2016/0053304 A1 2/2016 Wurtzel et al.
2016/0074535 A1 3/2016 Ranganathan et al.
2016/0076093 A1 3/2016 Shendure et al.
2016/0090603 A1 3/2016 Carnes et al.
2016/0090622 A1 3/2016 Liu et al.
2016/0115488 A1 4/2016 Zhang et al.
2016/0138046 A1 5/2016 Wu
2016/0153003 A1 6/2016 Joung et al.
2016/0186214 A1 6/2016 Brouns et al.
2016/0200779 A1 7/2016 Liu et al.
2016/0201040 A1 7/2016 Liu et al.
2016/0201089 A1 7/2016 Gersbach et al.
2016/0206566 A1 7/2016 Lu et al.
2016/0208243 A1 7/2016 Zhang et al.
2016/0208288 A1 7/2016 Liu et al.
2016/0215275 A1 7/2016 Zhong
2016/0215276 A1 7/2016 Liu et al.
2016/0215300 A1 7/2016 May et al.
2016/0244784 A1 8/2016 Jacobson et al.
2016/0244829 A1 8/2016 Bang et al.
2016/0264934 A1 9/2016 Giallourakis et al.
2016/0272593 A1 9/2016 Ritter et al.
2016/0272965 A1 9/2016 Zhang et al.
2016/0281072 A1 9/2016 Zhang
2016/0298136 A1 10/2016 Chen et al.
2016/0304846 A1 10/2016 Liu et al.
2016/0304855 A1 10/2016 Stark et al.
2016/0312304 A1 10/2016 Sorrentino et al.
2016/0319262 A1 11/2016 Doudna et al.
2016/0333389 A1 11/2016 Liu et al.
2016/0340622 A1 11/2016 Abdou
2016/0340662 A1 11/2016 Zhang et al.
2016/0345578 A1 12/2016 Barrangou et al.
2016/0346360 A1 12/2016 Quake et al.
2016/0346361 A1 12/2016 Quake et al.
2016/0346362 A1 12/2016 Quake et al.
2016/0348074 A1 12/2016 Quake et al.
2016/0348096 A1 12/2016 Liu et al.
2016/0350476 A1 12/2016 Quake et al.
2016/0355796 A1 12/2016 Davidson et al.
2016/0369262 A1 12/2016 Reik et al.
2017/0009224 A1 1/2017 Liu et al.
2017/0009242 A1 1/2017 McKinley et al.
2017/0014449 A1 1/2017 Bangera et al.
2017/0020922 A1 1/2017 Wagner et al.
2017/0037432 A1 2/2017 Donohoue et al.
2017/0044520 A1 2/2017 Liu et al.
2017/0044592 A1 2/2017 Peter et al.
2017/0053729 A1 2/2017 Kotani et al.
2017/0058271 A1 3/2017 Joung et al.
2017/0058272 A1 3/2017 Carter et al.
2017/0058298 A1 3/2017 Kennedy et al.
2017/0073663 A1 3/2017 Wang et al.
2017/0073670 A1 3/2017 Nishida et al.
2017/0087224 A1 3/2017 Quake
2017/0087225 A1 3/2017 Quake
2017/0088587 A1 3/2017 Quake
2017/0088828 A1 3/2017 Quake
2017/0107536 A1 4/2017 Zhang et al.
2017/0107560 A1 4/2017 Peter et al.
2017/0114367 A1 4/2017 Hu et al.
2017/0121693 A1 5/2017 Liu et al.
2017/0145394 A1 5/2017 Yeo et al.
2017/0145405 A1 5/2017 Tang et al.
2017/0145438 A1 5/2017 Kantor
2017/0152528 A1 6/2017 Zhang
2017/0152787 A1 6/2017 Kubo et al.
2017/0159033 A1 6/2017 Kamtekar et al.
2017/0166928 A1 6/2017 Vyas et al.
2017/0175104 A1 6/2017 Doudna et al.
2017/0175142 A1 6/2017 Zhang et al.
2017/0191047 A1 7/2017 Terns et al.
2017/0191078 A1 7/2017 Zhang et al.
2017/0198269 A1 7/2017 Zhang et al.
2017/0198277 A1 7/2017 Kmiec et al.
2017/0198302 A1 7/2017 Feng et al.
2017/0226522 A1 8/2017 Hu et al.
2017/0233703 A1 8/2017 Xie et al.
2017/0233708 A1 8/2017 Liu et al.
2017/0233756 A1 8/2017 Begemann et al.
2017/0247671 A1 8/2017 Yung et al.
2017/0247703 A1 8/2017 Sloan et al.
2017/0268022 A1 9/2017 Liu et al.
2017/0275648 A1 9/2017 Barrangou et al.
2017/0275665 A1 9/2017 Silas et al.
2017/0283797 A1 10/2017 Robb et al.
2017/0283831 A1 10/2017 Zhang et al.
2017/0306306 A1 10/2017 Potter et al.
2017/0314016 A1 11/2017 Kim et al.
2017/0362635 A1 12/2017 Chamberlain et al.
2018/0023062 A1 * 1/2018 Lamb .................. C12N 15/902
435/468
2018/0064077 A1 3/2018 Dunham et al.
2018/0066258 A1 3/2018 Powell
2018/0068062 A1 3/2018 Zhang et al.
2018/0073012 A1 3/2018 Liu et al.
2018/0080051 A1 3/2018 Sheikh et al.
2018/0087046 A1 3/2018 Badran et al.
2018/0100147 A1 4/2018 Yates et al.
2018/0105867 A1 4/2018 Xiao et al.
2018/0119118 A1 5/2018 Lu et al.
2018/0127759 A1 5/2018 Lu et al.
2018/0127780 A1 5/2018 Liu et al.
2018/0155708 A1 6/2018 Church et al.
2018/0155720 A1 6/2018 Donohoue et al.
2018/0163213 A1 6/2018 Aneja et al.
2018/0170984 A1 6/2018 Harris et al.
2018/0179503 A1 6/2018 Maianti et al.
2018/0179547 A1 6/2018 Zhang et al.
2018/0201921 A1 7/2018 Malcolm
2018/0230464 A1 8/2018 Zhong
2018/0230471 A1 8/2018 Storici et al.
2018/0236081 A1 8/2018 Liu et al.
2018/0237758 A1 8/2018 Liu et al.
2018/0237787 A1 8/2018 Maianti et al.
2018/0245066 A1 8/2018 Yao et al.
2018/0245075 A1 8/2018 Khalil et al.
2018/0258418 A1 9/2018 Kim
2018/0265864 A1 9/2018 Li et al.
2018/0273939 A1 9/2018 Yu et al.
2018/0282722 A1 10/2018 Jakimo et al.
2018/0298391 A1 10/2018 Jakimo et al.

(56) References Cited

U.S. PATENT DOCUMENTS

| | | | |
|---|---|---|---|
| 2018/0305688 | A1 | 10/2018 | Zhong |
| 2018/0305704 | A1 | 10/2018 | Zhang |
| 2018/0312822 | A1 | 11/2018 | Lee et al. |
| 2018/0312825 | A1 | 11/2018 | Liu et al. |
| 2018/0312828 | A1 | 11/2018 | Liu et al. |
| 2018/0312835 | A1 | 11/2018 | Yao et al. |
| 2018/0327756 | A1 | 11/2018 | Zhang et al. |
| 2018/0346927 | A1 | 12/2018 | Doudna et al. |
| 2018/0371497 | A1 | 12/2018 | Gill et al. |
| 2019/0010481 | A1 | 1/2019 | Joung et al. |
| 2019/0055543 | A1 | 2/2019 | Tran et al. |
| 2019/0062734 | A1 | 2/2019 | Cotta-Ramusino et al. |
| 2019/0093099 | A1 | 3/2019 | Liu et al. |
| 2019/0185883 | A1 | 6/2019 | Liu et al. |
| 2019/0218547 | A1 | 7/2019 | Lee et al. |
| 2019/0225955 | A1 | 7/2019 | Liu et al. |
| 2019/0233847 | A1 | 8/2019 | Savage et al. |
| 2019/0241633 | A1 | 8/2019 | Fotin-Mleczek et al. |
| 2019/0256842 | A1 | 8/2019 | Liu et al. |
| 2019/0264202 | A1 | 8/2019 | Church et al. |
| 2019/0276816 | A1 | 9/2019 | Liu et al. |
| 2019/0322992 | A1 | 10/2019 | Liu et al. |
| 2019/0352632 | A1 | 11/2019 | Liu et al. |
| 2019/0367891 | A1 | 12/2019 | Liu et al. |
| 2020/0010818 | A1 | 1/2020 | Liu et al. |
| 2020/0010835 | A1 | 1/2020 | Maianti et al. |
| 2020/0063127 | A1 | 2/2020 | Lu et al. |
| 2020/0071722 | A1 | 3/2020 | Liu et al. |
| 2020/0109398 | A1 | 4/2020 | Rubens et al. |
| 2020/0172931 | A1 | 6/2020 | Liu et al. |
| 2020/0181619 | A1 | 6/2020 | Tang et al. |
| 2020/0190493 | A1 | 6/2020 | Liu et al. |
| 2020/0216833 | A1 | 7/2020 | Liu et al. |
| 2020/0255868 | A1 | 8/2020 | Liu et al. |
| 2020/0277587 | A1 | 9/2020 | Liu et al. |
| 2020/0323984 | A1 | 10/2020 | Liu et al. |
| 2020/0399619 | A1 | 12/2020 | Maianti et al. |
| 2020/0399626 | A1 | 12/2020 | Liu et al. |
| 2021/0054416 | A1 | 2/2021 | Liu et al. |
| 2021/0115428 | A1 | 4/2021 | Maianti et al. |
| 2021/0196809 | A1 | 7/2021 | Maianti et al. |
| 2021/0198330 | A1 | 7/2021 | Liu et al. |
| 2021/0214698 | A1 | 7/2021 | Liu et al. |
| 2021/0230577 | A1 | 7/2021 | Liu et al. |
| 2021/0254127 | A1 | 8/2021 | Liu et al. |
| 2021/0315994 | A1 | 10/2021 | Liu et al. |
| 2021/0317440 | A1 | 10/2021 | Liu et al. |
| 2022/0033785 | A1 | 2/2022 | Liu et al. |
| 2022/0119785 | A1 | 4/2022 | Liu et al. |
| 2022/0170013 | A1 | 6/2022 | Liu et al. |
| 2022/0177877 | A1 | 6/2022 | Church et al. |
| 2022/0204975 | A1 | 6/2022 | Liu et al. |
| 2022/0213507 | A1 | 7/2022 | Liu et al. |
| 2022/0220462 | A1 | 7/2022 | Liu et al. |
| 2022/0238182 | A1 | 7/2022 | Shen et al. |
| 2022/0249697 | A1 | 8/2022 | Liu et al. |
| 2022/0282275 | A1 | 9/2022 | Liu et al. |
| 2022/0290115 | A1 | 9/2022 | Liu et al. |
| 2022/0307001 | A1 | 9/2022 | Liu et al. |
| 2022/0307003 | A1 | 9/2022 | Liu et al. |
| 2022/0315906 | A1 | 10/2022 | Liu et al. |
| 2022/0356469 | A1 | 11/2022 | Liu et al. |

FOREIGN PATENT DOCUMENTS

| | | | |
|---|---|---|---|
| CA | 2894668 | A1 | 6/2014 |
| CA | 2894681 | A1 | 6/2014 |
| CA | 2894684 | A1 | 6/2014 |
| CA | 2 852 593 | A1 | 11/2015 |
| CN | 1069962 | A | 3/1993 |
| CN | 101460619 | A | 6/2009 |
| CN | 103224947 | A | 7/2013 |
| CN | 103233028 | A | 8/2013 |
| CN | 103388006 | A | 11/2013 |
| CN | 103614415 | A | 3/2014 |
| CN | 103642836 | A | 3/2014 |
| CN | 103668472 | A | 3/2014 |
| CN | 103820441 | A | 5/2014 |
| CN | 103820454 | A | 5/2014 |
| CN | 103911376 | A | 7/2014 |
| CN | 103923911 | A | 7/2014 |
| CN | 103981211 | A | 8/2014 |
| CN | 103981212 | A | 8/2014 |
| CN | 104004778 | A | 8/2014 |
| CN | 104004782 | A | 8/2014 |
| CN | 104017821 | A | 9/2014 |
| CN | 104109687 | A | 10/2014 |
| CN | 104178461 | A | 12/2014 |
| CN | 104342457 | A | 2/2015 |
| CN | 104404036 | A | 3/2015 |
| CN | 104450774 | A | 3/2015 |
| CN | 104480144 | A | 4/2015 |
| CN | 104498493 | A | 4/2015 |
| CN | 104504304 | A | 4/2015 |
| CN | 104531704 | A | 4/2015 |
| CN | 104531705 | A | 4/2015 |
| CN | 104560864 | A | 4/2015 |
| CN | 104561095 | A | 4/2015 |
| CN | 104593418 | A | 5/2015 |
| CN | 104593422 | A | 5/2015 |
| CN | 104611370 | A | 5/2015 |
| CN | 104651392 | A | 5/2015 |
| CN | 104651398 | A | 5/2015 |
| CN | 104651399 | A | 5/2015 |
| CN | 104651401 | A | 5/2015 |
| CN | 104673816 | A | 6/2015 |
| CN | 104725626 | A | 6/2015 |
| CN | 104726449 | A | 6/2015 |
| CN | 104726494 | A | 6/2015 |
| CN | 104745626 | A | 7/2015 |
| CN | 104762321 | A | 7/2015 |
| CN | 104805078 | A | 7/2015 |
| CN | 104805099 | A | 7/2015 |
| CN | 104805118 | A | 7/2015 |
| CN | 104846010 | A | 8/2015 |
| CN | 104894068 | A | 9/2015 |
| CN | 104894075 | A | 9/2015 |
| CN | 104928321 | A | 9/2015 |
| CN | 105039339 | A | 11/2015 |
| CN | 105039399 | A | 11/2015 |
| CN | 105063061 | A | 11/2015 |
| CN | 105087620 | A | 11/2015 |
| CN | 105112422 | A | 12/2015 |
| CN | 105112445 | A | 12/2015 |
| CN | 105112519 | A | 12/2015 |
| CN | 105121648 | A | 12/2015 |
| CN | 105132427 | A | 12/2015 |
| CN | 105132451 | A | 12/2015 |
| CN | 105177038 | A | 12/2015 |
| CN | 105177126 | A | 12/2015 |
| CN | 105210981 | A | 1/2016 |
| CN | 105219799 | A | 1/2016 |
| CN | 105238806 | A | 1/2016 |
| CN | 105255937 | A | 1/2016 |
| CN | 105274144 | A | 1/2016 |
| CN | 105296518 | A | 2/2016 |
| CN | 105296537 | A | 2/2016 |
| CN | 105316324 | A | 2/2016 |
| CN | 105316327 | A | 2/2016 |
| CN | 105316337 | A | 2/2016 |
| CN | 105331607 | A | 2/2016 |
| CN | 105331608 | A | 2/2016 |
| CN | 105331609 | A | 2/2016 |
| CN | 105331627 | A | 2/2016 |
| CN | 105400773 | A | 3/2016 |
| CN | 105400779 | A | 3/2016 |
| CN | 105400810 | A | 3/2016 |
| CN | 105441451 | A | 3/2016 |
| CN | 105462968 | A | 4/2016 |
| CN | 105463003 | A | 4/2016 |
| CN | 105463027 | A | 4/2016 |
| CN | 105492608 | A | 4/2016 |
| CN | 105492609 | A | 4/2016 |
| CN | 105505976 | A | 4/2016 |

(56) References Cited

FOREIGN PATENT DOCUMENTS

| | | | |
|---|---|---|---|
| CN | 105505979 | A | 4/2016 |
| CN | 105518134 | A | 4/2016 |
| CN | 105518135 | A | 4/2016 |
| CN | 105518137 | A | 4/2016 |
| CN | 105518138 | A | 4/2016 |
| CN | 105518139 | A | 4/2016 |
| CN | 105518140 | A | 4/2016 |
| CN | 105543228 | A | 5/2016 |
| CN | 105543266 | A | 5/2016 |
| CN | 105543270 | A | 5/2016 |
| CN | 105567688 | A | 5/2016 |
| CN | 105567689 | A | 5/2016 |
| CN | 105567734 | A | 5/2016 |
| CN | 105567735 | A | 5/2016 |
| CN | 105567738 | A | 5/2016 |
| CN | 105593367 | A | 5/2016 |
| CN | 105594664 | A | 5/2016 |
| CN | 105602987 | A | 5/2016 |
| CN | 105624146 | A | 6/2016 |
| CN | 105624187 | A | 6/2016 |
| CN | 105646719 | A | 6/2016 |
| CN | 105647922 | A | 6/2016 |
| CN | 105647962 | A | 6/2016 |
| CN | 105647968 | A | 6/2016 |
| CN | 105647969 | A | 6/2016 |
| CN | 105671070 | A | 6/2016 |
| CN | 105671083 | A | 6/2016 |
| CN | 105695485 | A | 6/2016 |
| CN | 105779448 | A | 7/2016 |
| CN | 105779449 | A | 7/2016 |
| CN | 105802980 | A | 7/2016 |
| CN | 105821039 | A | 8/2016 |
| CN | 105821040 | A | 8/2016 |
| CN | 105821049 | A | 8/2016 |
| CN | 105821072 | A | 8/2016 |
| CN | 105821075 | A | 8/2016 |
| CN | 105821116 | A | 8/2016 |
| CN | 105838733 | A | 8/2016 |
| CN | 105861547 | A | 8/2016 |
| CN | 105861552 | A | 8/2016 |
| CN | 105861554 | A | 8/2016 |
| CN | 105886498 | A | 8/2016 |
| CN | 105886534 | A | 8/2016 |
| CN | 105886616 | A | 8/2016 |
| CN | 105907758 | A | 8/2016 |
| CN | 105907785 | A | 8/2016 |
| CN | 105925608 | A | 9/2016 |
| CN | 105934516 | A | 9/2016 |
| CN | 105950560 | A | 9/2016 |
| CN | 105950626 | A | 9/2016 |
| CN | 105950633 | A | 9/2016 |
| CN | 105950639 | A | 9/2016 |
| CN | 105985985 | A | 10/2016 |
| CN | 106011104 | A | 10/2016 |
| CN | 106011150 | A | 10/2016 |
| CN | 106011167 | A | 10/2016 |
| CN | 106011171 | A | 10/2016 |
| CN | 106032540 | A | 10/2016 |
| CN | 106047803 | A | 10/2016 |
| CN | 106047877 | A | 10/2016 |
| CN | 106047930 | A | 10/2016 |
| CN | 106086008 | A | 11/2016 |
| CN | 106086028 | A | 11/2016 |
| CN | 106086061 | A | 11/2016 |
| CN | 106086062 | A | 11/2016 |
| CN | 106109417 | A | 11/2016 |
| CN | 106119275 | A | 11/2016 |
| CN | 106119283 | A | 11/2016 |
| CN | 106148286 | A | 11/2016 |
| CN | 106148370 | A | 11/2016 |
| CN | 106148416 | A | 11/2016 |
| CN | 106167525 | A | 11/2016 |
| CN | 106167808 | A | 11/2016 |
| CN | 106167810 | A | 11/2016 |
| CN | 106167821 | A | 11/2016 |
| CN | 106172238 | A | 12/2016 |
| CN | 106190903 | A | 12/2016 |
| CN | 106191057 | A | 12/2016 |
| CN | 106191061 | A | 12/2016 |
| CN | 106191062 | A | 12/2016 |
| CN | 106191064 | A | 12/2016 |
| CN | 106191071 | A | 12/2016 |
| CN | 106191099 | A | 12/2016 |
| CN | 106191107 | A | 12/2016 |
| CN | 106191113 | A | 12/2016 |
| CN | 106191114 | A | 12/2016 |
| CN | 106191116 | A | 12/2016 |
| CN | 106191124 | A | 12/2016 |
| CN | 106222177 | A | 12/2016 |
| CN | 106222193 | A | 12/2016 |
| CN | 106222203 | A | 12/2016 |
| CN | 106244555 | A | 12/2016 |
| CN | 106244557 | A | 12/2016 |
| CN | 106244591 | A | 12/2016 |
| CN | 106244609 | A | 12/2016 |
| CN | 106282241 | A | 1/2017 |
| CN | 106318934 | A | 1/2017 |
| CN | 106318973 | A | 1/2017 |
| CN | 106350540 | A | 1/2017 |
| CN | 106367435 | A | 2/2017 |
| CN | 106399306 | A | 2/2017 |
| CN | 106399311 | A | 2/2017 |
| CN | 106399360 | A | 2/2017 |
| CN | 106399367 | A | 2/2017 |
| CN | 106399375 | A | 2/2017 |
| CN | 106399377 | A | 2/2017 |
| CN | 106434651 | A | 2/2017 |
| CN | 106434663 | A | 2/2017 |
| CN | 106434688 | A | 2/2017 |
| CN | 106434737 | A | 2/2017 |
| CN | 106434748 | A | 2/2017 |
| CN | 106434752 | A | 2/2017 |
| CN | 106434782 | A | 2/2017 |
| CN | 106446600 | A | 2/2017 |
| CN | 106479985 | A | 3/2017 |
| CN | 106480027 | A | 3/2017 |
| CN | 106480036 | A | 3/2017 |
| CN | 106480067 | A | 3/2017 |
| CN | 106480080 | A | 3/2017 |
| CN | 106480083 | A | 3/2017 |
| CN | 106480097 | A | 3/2017 |
| CN | 106544351 | A | 3/2017 |
| CN | 106544353 | A | 3/2017 |
| CN | 106544357 | A | 3/2017 |
| CN | 106554969 | A | 4/2017 |
| CN | 106566838 | A | 4/2017 |
| CN | 106701763 | A | 5/2017 |
| CN | 106701808 | A | 5/2017 |
| CN | 106701818 | A | 5/2017 |
| CN | 106701823 | A | 5/2017 |
| CN | 106701830 | A | 5/2017 |
| CN | 106754912 | A | 5/2017 |
| CN | 106755026 | A | 5/2017 |
| CN | 106755077 | A | 5/2017 |
| CN | 106755088 | A | 5/2017 |
| CN | 106755091 | A | 5/2017 |
| CN | 106755097 | A | 5/2017 |
| CN | 106755424 | A | 5/2017 |
| CN | 106801056 | A | 6/2017 |
| CN | 106834323 | A | 6/2017 |
| CN | 106834341 | A | 6/2017 |
| CN | 106834347 | A | 6/2017 |
| CN | 106845151 | A | 6/2017 |
| CN | 106868008 | A | 6/2017 |
| CN | 106868031 | A | 6/2017 |
| CN | 106906240 | A | 6/2017 |
| CN | 106906242 | A | 6/2017 |
| CN | 106916820 | A | 7/2017 |
| CN | 106916852 | A | 7/2017 |
| CN | 106939303 | A | 7/2017 |
| CN | 106947750 | A | 7/2017 |
| CN | 106947780 | A | 7/2017 |
| CN | 106957830 | A | 7/2017 |
| CN | 106957831 | A | 7/2017 |

(56) References Cited

FOREIGN PATENT DOCUMENTS

| | | | |
|---|---|---|---|
| CN | 106957844 | A | 7/2017 |
| CN | 106957855 | A | 7/2017 |
| CN | 106957858 | A | 7/2017 |
| CN | 106967697 | A | 7/2017 |
| CN | 106967726 | A | 7/2017 |
| CN | 106978428 | A | 7/2017 |
| CN | 106987570 | A | 7/2017 |
| CN | 106987757 | A | 7/2017 |
| CN | 107012164 | A | 8/2017 |
| CN | 107012174 | A | 8/2017 |
| CN | 107012213 | A | 8/2017 |
| CN | 107012250 | A | 8/2017 |
| CN | 107022562 | A | 8/2017 |
| CN | 107034188 | A | 8/2017 |
| CN | 107034218 | A | 8/2017 |
| CN | 107034229 | A | 8/2017 |
| CN | 107043775 | A | 8/2017 |
| CN | 107043779 | A | 8/2017 |
| CN | 107043787 | A | 8/2017 |
| CN | 107058320 | A | 8/2017 |
| CN | 107058328 | A | 8/2017 |
| CN | 107058358 | A | 8/2017 |
| CN | 107058372 | A | 8/2017 |
| CN | 107083392 | A | 8/2017 |
| CN | 107099533 | A | 8/2017 |
| CN | 107099850 | A | 8/2017 |
| CN | 107119053 | A | 9/2017 |
| CN | 107119071 | A | 9/2017 |
| CN | 107129999 | A | 9/2017 |
| CN | 107130000 | A | 9/2017 |
| CN | 107142272 | A | 9/2017 |
| CN | 107142282 | A | 9/2017 |
| CN | 107177591 | A | 9/2017 |
| CN | 107177595 | A | 9/2017 |
| CN | 107177625 | A | 9/2017 |
| CN | 107177631 | A | 9/2017 |
| CN | 107190006 | A | 9/2017 |
| CN | 107190008 | A | 9/2017 |
| CN | 107217042 | A | 9/2017 |
| CN | 107217075 | A | 9/2017 |
| CN | 107227307 | A | 10/2017 |
| CN | 107227352 | A | 10/2017 |
| CN | 107236737 | A | 10/2017 |
| CN | 107236739 | A | 10/2017 |
| CN | 107236741 | A | 10/2017 |
| CN | 107245502 | A | 10/2017 |
| CN | 107254485 | A | 10/2017 |
| CN | 107266541 | A | 10/2017 |
| CN | 107267515 | A | 10/2017 |
| CN | 107287245 | A | 10/2017 |
| CN | 107298701 | A | 10/2017 |
| CN | 107299114 | A | 10/2017 |
| CN | 107304435 | A | 10/2017 |
| CN | 107312785 | A | 11/2017 |
| CN | 107312793 | A | 11/2017 |
| CN | 107312795 | A | 11/2017 |
| CN | 107312798 | A | 11/2017 |
| CN | 107326042 | A | 11/2017 |
| CN | 107326046 | A | 11/2017 |
| CN | 107354156 | A | 11/2017 |
| CN | 107354173 | A | 11/2017 |
| CN | 107356793 | A | 11/2017 |
| CN | 107362372 | A | 11/2017 |
| CN | 107365786 | A | 11/2017 |
| CN | 107365804 | A | 11/2017 |
| CN | 107384894 | A | 11/2017 |
| CN | 107384922 | A | 11/2017 |
| CN | 107384926 | A | 11/2017 |
| CN | 107400677 | A | 11/2017 |
| CN | 107418974 | A | 12/2017 |
| CN | 107435051 | A | 12/2017 |
| CN | 107435069 | A | 12/2017 |
| CN | 107446922 | A | 12/2017 |
| CN | 107446923 | A | 12/2017 |
| CN | 107446924 | A | 12/2017 |
| CN | 107446932 | A | 12/2017 |
| CN | 107446951 | A | 12/2017 |
| CN | 107446954 | A | 12/2017 |
| CN | 107460196 | A | 12/2017 |
| CN | 107474129 | A | 12/2017 |
| CN | 107475300 | A | 12/2017 |
| CN | 107488649 | A | 12/2017 |
| CN | 107502608 | A | 12/2017 |
| CN | 107502618 | A | 12/2017 |
| CN | 107513531 | A | 12/2017 |
| CN | 107519492 | A | 12/2017 |
| CN | 107523567 | A | 12/2017 |
| CN | 107523583 | A | 12/2017 |
| CN | 107541525 | A | 1/2018 |
| CN | 107557373 | A | 1/2018 |
| CN | 107557378 | A | 1/2018 |
| CN | 107557381 | A | 1/2018 |
| CN | 107557390 | A | 1/2018 |
| CN | 107557393 | A | 1/2018 |
| CN | 107557394 | A | 1/2018 |
| CN | 107557455 | A | 1/2018 |
| CN | 107574179 | A | 1/2018 |
| CN | 107586777 | A | 1/2018 |
| CN | 107586779 | A | 1/2018 |
| CN | 107604003 | A | 1/2018 |
| CN | 107619829 | A | 1/2018 |
| CN | 107619837 | A | 1/2018 |
| CN | 107630006 | A | 1/2018 |
| CN | 107630041 | A | 1/2018 |
| CN | 107630042 | A | 1/2018 |
| CN | 107630043 | A | 1/2018 |
| CN | 107641631 | A | 1/2018 |
| CN | 107653256 | A | 2/2018 |
| CN | 107686848 | A | 2/2018 |
| CN | 206970581 | U | 2/2018 |
| CN | 107760652 | A | 3/2018 |
| CN | 107760663 | A | 3/2018 |
| CN | 107760684 | A | 3/2018 |
| CN | 107760715 | A | 3/2018 |
| CN | 107784200 | A | 3/2018 |
| CN | 107794272 | A | 3/2018 |
| CN | 107794276 | A | 3/2018 |
| CN | 107815463 | A | 3/2018 |
| CN | 107828738 | A | 3/2018 |
| CN | 107828794 | A | 3/2018 |
| CN | 107828826 | A | 3/2018 |
| CN | 107828874 | A | 3/2018 |
| CN | 107858346 | A | 3/2018 |
| CN | 107858373 | A | 3/2018 |
| CN | 107880132 | A | 4/2018 |
| CN | 107881184 | A | 4/2018 |
| CN | 107893074 | A | 4/2018 |
| CN | 107893075 | A | 4/2018 |
| CN | 107893076 | A | 4/2018 |
| CN | 107893080 | A | 4/2018 |
| CN | 107893086 | A | 4/2018 |
| CN | 107904261 | A | 4/2018 |
| CN | 107937427 | A | 4/2018 |
| CN | 107937432 | A | 4/2018 |
| CN | 107937501 | A | 4/2018 |
| CN | 107974466 | A | 5/2018 |
| CN | 107988229 | A | 5/2018 |
| CN | 107988246 | A | 5/2018 |
| CN | 107988256 | A | 5/2018 |
| CN | 107988268 | A | 5/2018 |
| CN | 108018316 | A | 5/2018 |
| CN | 108034656 | A | 5/2018 |
| CN | 108048466 | A | 5/2018 |
| CN | 108102940 | A | 6/2018 |
| CN | 108103090 | A | 6/2018 |
| CN | 108103092 | A | 6/2018 |
| CN | 108103098 | A | 6/2018 |
| CN | 108103586 | A | 6/2018 |
| CN | 108148835 | A | 6/2018 |
| CN | 108148837 | A | 6/2018 |
| CN | 108148873 | A | 6/2018 |
| CN | 108192956 | A | 6/2018 |
| CN | 108251423 | A | 7/2018 |
| CN | 108251451 | A | 7/2018 |

(56) References Cited

FOREIGN PATENT DOCUMENTS

| | | | |
|---|---|---|---|
| CN | 108251452 | A | 7/2018 |
| CN | 108342480 | A | 7/2018 |
| CN | 108359691 | A | 8/2018 |
| CN | 108359712 | A | 8/2018 |
| CN | 108384784 | A | 8/2018 |
| CN | 108396027 | A | 8/2018 |
| CN | 108410877 | A | 8/2018 |
| CN | 108410906 | A | 8/2018 |
| CN | 108410907 | A | 8/2018 |
| CN | 108410911 | A | 8/2018 |
| CN | 108424931 | A | 8/2018 |
| CN | 108441519 | A | 8/2018 |
| CN | 108441520 | A | 8/2018 |
| CN | 108486108 | A | 9/2018 |
| CN | 108486111 | A | 9/2018 |
| CN | 108486145 | A | 9/2018 |
| CN | 108486146 | A | 9/2018 |
| CN | 108486154 | A | 9/2018 |
| CN | 108486159 | A | 9/2018 |
| CN | 108486234 | A | 9/2018 |
| CN | 108504657 | A | 9/2018 |
| CN | 108504685 | A | 9/2018 |
| CN | 108504693 | A | 9/2018 |
| CN | 108546712 | A | 9/2018 |
| CN | 108546717 | A | 9/2018 |
| CN | 108546718 | A | 9/2018 |
| CN | 108559730 | A | 9/2018 |
| CN | 108559732 | A | 9/2018 |
| CN | 108559745 | A | 9/2018 |
| CN | 108559760 | A | 9/2018 |
| CN | 108570479 | A | 9/2018 |
| CN | 108588071 | A | 9/2018 |
| CN | 108588123 | A | 9/2018 |
| CN | 108588128 | A | 9/2018 |
| CN | 108588182 | A | 9/2018 |
| CN | 108610399 | A | 10/2018 |
| CN | 108611364 | A | 10/2018 |
| CN | 108624622 | A | 10/2018 |
| CN | 108642053 | A | 10/2018 |
| CN | 108642055 | A | 10/2018 |
| CN | 108642077 | A | 10/2018 |
| CN | 108642078 | A | 10/2018 |
| CN | 108642090 | A | 10/2018 |
| CN | 108690844 | A | 10/2018 |
| CN | 108707604 | A | 10/2018 |
| CN | 108707620 | A | 10/2018 |
| CN | 108707621 | A | 10/2018 |
| CN | 108707628 | A | 10/2018 |
| CN | 108707629 | A | 10/2018 |
| CN | 108715850 | A | 10/2018 |
| CN | 108728476 | A | 11/2018 |
| CN | 108728486 | A | 11/2018 |
| CN | 108753772 | A | 11/2018 |
| CN | 108753783 | A | 11/2018 |
| CN | 108753813 | A | 11/2018 |
| CN | 108753817 | A | 11/2018 |
| CN | 108753832 | A | 11/2018 |
| CN | 108753835 | A | 11/2018 |
| CN | 108753836 | A | 11/2018 |
| CN | 108795902 | A | 11/2018 |
| CN | 108822217 | A | 11/2018 |
| CN | 108823248 | A | 11/2018 |
| CN | 108823249 | A | 11/2018 |
| CN | 108823291 | A | 11/2018 |
| CN | 108841845 | A | 11/2018 |
| CN | 108853133 | A | 11/2018 |
| CN | 108866093 | A | 11/2018 |
| CN | 108893529 | A | 11/2018 |
| CN | 108913664 | A | 11/2018 |
| CN | 108913691 | A | 11/2018 |
| CN | 108913714 | A | 11/2018 |
| CN | 108913717 | A | 11/2018 |
| CN | 109 517 841 | A | 3/2019 |
| EP | 0264166 | A1 | 4/1988 |
| EP | 0321201 | B2 | 6/1989 |
| EP | 0519463 | A1 | 12/1992 |
| EP | 2604255 | A1 | 6/2013 |
| EP | 2840140 | A1 | 2/2015 |
| EP | 2877490 | A2 | 6/2015 |
| EP | 2966170 | A1 | 1/2016 |
| EP | 3009511 | A2 | 4/2016 |
| EP | 3031921 | A | 6/2016 |
| EP | 3045537 | A1 | 7/2016 |
| EP | 3 115 457 | A | 1/2017 |
| EP | 3144390 | A1 | 3/2017 |
| EP | 3199632 | A1 | 8/2017 |
| EP | 3216867 | A1 | 9/2017 |
| EP | 3252160 | A1 | 12/2017 |
| EP | 3450553 | | 12/2019 |
| ES | 2740248 | T3 | 2/2020 |
| GB | 2528177 | A | 1/2016 |
| GB | 2 531 454 | A1 | 4/2016 |
| GB | 2542653 | A | 3/2017 |
| HK | 1208045 | A1 | 2/2016 |
| JP | 2007-501626 | A | 2/2007 |
| JP | 2008-515405 | A | 5/2008 |
| JP | 2010-033344 | A | 2/2010 |
| JP | 2010-535744 | A | 11/2010 |
| JP | 2010-539929 | A | 12/2010 |
| JP | 2011-081011 | A | 4/2011 |
| JP | 2011-523353 | A | 8/2011 |
| JP | 2012-525146 | A | 10/2012 |
| JP | 2012-210172 | A | 11/2012 |
| JP | 2012-531909 | A | 12/2012 |
| JP | 2015-523856 | A | 8/2015 |
| JP | 2015-532654 | A | 11/2015 |
| JP | 2016-525888 | A | 9/2016 |
| JP | 2016-534132 | A | 11/2016 |
| JP | 2017-500035 | A | 1/2017 |
| KR | 101584933 | B1 | 1/2016 |
| KR | 2016-0050069 | A | 5/2016 |
| KR | 20160133380 | A | 11/2016 |
| KR | 20170037025 | A | 4/2017 |
| KR | 20170037028 | A | 4/2017 |
| KR | 101748575 | B1 | 6/2017 |
| KR | 20170128137 | A | 11/2017 |
| KR | 2018-0022465 | A | 3/2018 |
| RU | 2016104674 | A | 8/2017 |
| RU | 2634395 | C1 | 10/2017 |
| RU | 2652899 | C1 | 5/2018 |
| RU | 2015128057 | A | 3/2019 |
| RU | 2015128098 | A | 3/2019 |
| RU | 2687451 | C1 | 5/2019 |
| RU | 2019112514 | A | 6/2019 |
| RU | 2019127300 | A | 9/2019 |
| RU | 2701850 | C2 | 10/2019 |
| SG | 10201707569 | Y | 10/2017 |
| SG | 10201710486X | | 1/2018 |
| SG | 10201710487V | | 1/2018 |
| SG | 10201710488 | T | 1/2018 |
| TW | 1608100 | B | 12/2017 |
| TW | 2018-29773 | A | 8/2018 |
| WO | WO 90/02809 | A1 | 3/1990 |
| WO | WO 1991/003162 | A1 | 3/1991 |
| WO | WO 91/16024 | A1 | 10/1991 |
| WO | WO 91/17271 | A1 | 11/1991 |
| WO | WO 91/17424 | A1 | 11/1991 |
| WO | WO 92/06188 | A2 | 4/1992 |
| WO | WO 92/06200 | A1 | 4/1992 |
| WO | WO 1992/007065 | A1 | 4/1992 |
| WO | WO 1993/015187 | A1 | 8/1993 |
| WO | WO 93/24641 | A2 | 12/1993 |
| WO | WO 94/18316 | A2 | 8/1994 |
| WO | WO 94/026877 | A1 | 11/1994 |
| WO | WO 96/04403 | A1 | 2/1996 |
| WO | WO 96/10640 | A1 | 4/1996 |
| WO | WO 98/32845 | A1 | 7/1998 |
| WO | WO 2001/036452 | A2 | 5/2001 |
| WO | WO 2001/038547 | A2 | 5/2001 |
| WO | WO 2002/059296 | A2 | 8/2002 |
| WO | WO 2002/068676 | A2 | 9/2002 |
| WO | WO 2002/103028 | A2 | 12/2002 |
| WO | WO 2004/007684 | A2 | 1/2004 |
| WO | WO 2005/014791 | A2 | 2/2005 |

(56) References Cited

FOREIGN PATENT DOCUMENTS

| | | | |
|---|---|---|---|
| WO | WO 2005/019415 | A2 | 3/2005 |
| WO | WO 2006/002547 | A1 | 1/2006 |
| WO | WO 2006/042112 | A2 | 4/2006 |
| WO | WO 2007/025097 | A2 | 3/2007 |
| WO | WO 07/066923 | A1 | 6/2007 |
| WO | WO 2007/136815 | A2 | 11/2007 |
| WO | WO 2007/143574 | A1 | 12/2007 |
| WO | WO 08/005529 | A2 | 1/2008 |
| WO | WO 2008/108989 | A2 | 9/2008 |
| WO | WO 2009/098290 | A1 | 8/2009 |
| WO | WO 2009/134808 | A2 | 11/2009 |
| WO | WO 2010/011961 | A2 | 1/2010 |
| WO | WO 2010/028347 | A2 | 3/2010 |
| WO | WO 2010/054108 | A2 | 5/2010 |
| WO | WO 2010/054154 | A2 | 5/2010 |
| WO | WO 2010/068289 | A2 | 6/2010 |
| WO | WO 2010/075424 | A2 | 7/2010 |
| WO | WO 2010/102257 | A2 | 9/2010 |
| WO | WO 2010/129019 | A2 | 11/2010 |
| WO | WO 2010/129023 | A2 | 11/2010 |
| WO | WO 2010/132092 | A2 | 11/2010 |
| WO | WO 2010/144150 | A2 | 12/2010 |
| WO | WO 2011/002503 | A1 | 1/2011 |
| WO | WO 2011/017293 | A2 | 2/2011 |
| WO | WO 2011/053868 | A1 | 5/2011 |
| WO | WO 2011/053982 | A2 | 5/2011 |
| WO | WO 2011/068810 | A1 | 6/2011 |
| WO | WO 2011/075627 | A1 | 6/2011 |
| WO | WO 2011/091311 | A2 | 7/2011 |
| WO | WO 2011/091396 | A1 | 7/2011 |
| WO | WO 2011/109031 | A1 | 9/2011 |
| WO | WO 2011/143124 | A2 | 11/2011 |
| WO | WO 2011/147590 | A2 | 12/2011 |
| WO | WO 2011/159369 | A1 | 12/2011 |
| WO | WO 2012/054726 | A1 | 4/2012 |
| WO | WO 2012/065043 | A2 | 5/2012 |
| WO | WO 2012/088381 | A2 | 6/2012 |
| WO | WO 2012/125445 | A2 | 9/2012 |
| WO | WO 2012/138927 | A2 | 10/2012 |
| WO | WO 2012/149470 | A1 | 11/2012 |
| WO | WO 2012/158985 | A2 | 11/2012 |
| WO | WO 2012/158986 | A2 | 11/2012 |
| WO | WO 2012/164565 | A1 | 12/2012 |
| WO | WO 2012/170930 | A1 | 12/2012 |
| WO | WO 2013/012674 | A1 | 1/2013 |
| WO | WO 2013/013105 | A1 | 1/2013 |
| WO | WO 2013/039857 | A1 | 3/2013 |
| WO | WO 2013/039861 | A2 | 3/2013 |
| WO | WO 2013/045632 | A1 | 4/2013 |
| WO | WO 2013/047844 | A1 | 4/2013 |
| WO | WO 2013/066438 | A2 | 5/2013 |
| WO | WO 2013/086441 | A2 | 6/2013 |
| WO | WO 2013/086444 | A2 | 6/2013 |
| WO | WO 2013/098244 | A1 | 7/2013 |
| WO | WO 2013/119602 | A1 | 8/2013 |
| WO | WO 2013/126794 | A1 | 8/2013 |
| WO | WO 2013/130824 | A1 | 9/2013 |
| WO | WO 2013/141680 | A1 | 9/2013 |
| WO | WO 2013/142578 | A2 | 9/2013 |
| WO | WO 2013/152359 | A1 | 10/2013 |
| WO | WO 2013/160230 | A1 | 10/2013 |
| WO | WO 2013/166315 | A1 | 11/2013 |
| WO | WO 2013/169398 | A2 | 11/2013 |
| WO | WO 2013/169802 | A1 | 11/2013 |
| WO | WO 2013/176772 | A2 | 11/2013 |
| WO | WO 2013/176915 | A1 | 11/2013 |
| WO | WO 2013/176916 | A1 | 11/2013 |
| WO | WO 2013/181440 | A1 | 12/2013 |
| WO | WO 2013/186754 | A2 | 12/2013 |
| WO | WO 2013/188037 | A2 | 12/2013 |
| WO | WO 2013/188522 | A2 | 12/2013 |
| WO | WO 2013/188638 | A2 | 12/2013 |
| WO | WO 2013/192278 | A1 | 12/2013 |
| WO | WO 2013/142378 | A9 | 1/2014 |
| WO | WO 2014/004336 | A2 | 1/2014 |
| WO | WO 2014/005042 | A2 | 1/2014 |
| WO | WO 2014/011237 | A1 | 1/2014 |
| WO | WO 2014/011901 | A2 | 1/2014 |
| WO | WO 2014/018423 | A2 | 1/2014 |
| WO | WO 2014/020608 | A1 | 2/2014 |
| WO | WO 2014/022120 | A1 | 2/2014 |
| WO | WO 2014/022702 | A2 | 2/2014 |
| WO | WO 2014/036219 | A2 | 3/2014 |
| WO | WO 2014/039513 | A2 | 3/2014 |
| WO | WO 2014/039523 | A1 | 3/2014 |
| WO | WO 2014/039585 | A2 | 3/2014 |
| WO | WO 2014/039684 | A1 | 3/2014 |
| WO | WO 2014/039692 | A2 | 3/2014 |
| WO | WO 2014/039702 | A2 | 3/2014 |
| WO | WO 2014/039872 | A1 | 3/2014 |
| WO | WO 2014/039970 | A1 | 3/2014 |
| WO | WO 2014/041327 | A1 | 3/2014 |
| WO | WO 2014/043143 | A1 | 3/2014 |
| WO | WO 2014/047103 | A2 | 3/2014 |
| WO | WO 2014/055782 | A1 | 4/2014 |
| WO | WO 2014/059173 | A2 | 4/2014 |
| WO | WO 2014/059255 | A1 | 4/2014 |
| WO | WO 2014/065596 | A1 | 5/2014 |
| WO | WO 2014/066505 | A1 | 5/2014 |
| WO | WO 2014/068346 | A2 | 5/2014 |
| WO | WO 2014/070887 | A1 | 5/2014 |
| WO | WO 2014/071006 | A1 | 5/2014 |
| WO | WO 2014/071219 | A1 | 5/2014 |
| WO | WO 2014/071235 | A1 | 5/2014 |
| WO | WO 2014/072941 | A1 | 5/2014 |
| WO | WO 2014/081729 | A1 | 5/2014 |
| WO | WO 2014/081730 | A1 | 5/2014 |
| WO | WO 2014/081855 | A1 | 5/2014 |
| WO | WO 2014/082644 | A1 | 6/2014 |
| WO | WO 2014/085261 | A1 | 6/2014 |
| WO | WO 2014/085593 | A1 | 6/2014 |
| WO | WO 2014/085830 | A2 | 6/2014 |
| WO | WO 2014/089212 | A1 | 6/2014 |
| WO | WO 2014/089290 | A1 | 6/2014 |
| WO | WO 2014/089348 | A1 | 6/2014 |
| WO | WO 2014/089513 | A1 | 6/2014 |
| WO | WO 2014/089533 | A2 | 6/2014 |
| WO | WO 2014/089541 | A2 | 6/2014 |
| WO | WO 2014/093479 | A1 | 6/2014 |
| WO | WO 2014/093595 | A1 | 6/2014 |
| WO | WO 2014/093622 | A2 | 6/2014 |
| WO | WO 2014/093635 | A1 | 6/2014 |
| WO | WO 2014/093655 | A2 | 6/2014 |
| WO | WO 2014/093661 | A2 | 6/2014 |
| WO | WO 2014/093694 | A1 | 6/2014 |
| WO | WO 2014/093701 | A1 | 6/2014 |
| WO | WO 2014/093709 | A1 | 6/2014 |
| WO | WO 2014/093712 | A1 | 6/2014 |
| WO | WO 2014/093718 | A1 | 6/2014 |
| WO | WO 2014/093736 | A1 | 6/2014 |
| WO | WO 2014/093768 | A1 | 6/2014 |
| WO | WO 2014/093852 | A1 | 6/2014 |
| WO | WO 2014/096972 | A2 | 6/2014 |
| WO | WO 2014/099744 | A1 | 6/2014 |
| WO | WO 2014/099750 | A2 | 6/2014 |
| WO | WO 2014/104878 | A1 | 7/2014 |
| WO | WO 2014/110006 | A1 | 7/2014 |
| WO | WO 2014/110552 | A1 | 7/2014 |
| WO | WO 2014/113493 | A1 | 7/2014 |
| WO | WO 2014/123967 | A2 | 8/2014 |
| WO | WO 2014/124226 | A1 | 8/2014 |
| WO | WO 2014/125668 | A1 | 8/2014 |
| WO | WO 2014/127287 | A1 | 8/2014 |
| WO | WO 2014/128324 | A1 | 8/2014 |
| WO | WO 2014/128659 | A1 | 8/2014 |
| WO | WO 2014/130706 | A1 | 8/2014 |
| WO | WO 2014/130955 | A1 | 8/2014 |
| WO | WO 2014/131833 | A1 | 9/2014 |
| WO | WO 2014/138379 | A1 | 9/2014 |
| WO | WO 2014/143381 | A1 | 9/2014 |
| WO | WO 2014/144094 | A1 | 9/2014 |
| WO | WO 2014/144155 | A1 | 9/2014 |
| WO | WO 2014/144288 | A1 | 9/2014 |
| WO | WO 2014/144592 | A2 | 9/2014 |

(56) References Cited

FOREIGN PATENT DOCUMENTS

WO WO 2014/144761 A2 9/2014
WO WO 2014/144951 A1 9/2014
WO WO 2014/145599 A2 9/2014
WO WO 2014/145736 A2 9/2014
WO WO 2014/150624 A1 9/2014
WO WO 2014/152432 A2 9/2014
WO WO 2014/152940 A1 9/2014
WO WO 2014/153118 A1 9/2014
WO WO 2014/153470 A2 9/2014
WO WO 2014/158593 A1 10/2014
WO WO 2014/161821 A1 10/2014
WO WO 2014/164466 A1 10/2014
WO WO 2014/165177 A1 10/2014
WO WO 2014/165349 A1 10/2014
WO WO 2014/165612 A2 10/2014
WO WO 2014/165707 A2 10/2014
WO WO 2014/165825 A2 10/2014
WO WO 2014/172458 A1 10/2014
WO WO 2014/172470 A2 10/2014
WO WO 2014/172489 A2 10/2014
WO WO 2014/173955 A1 10/2014
WO WO 2014/182700 A1 11/2014
WO WO 2014/183071 A2 11/2014
WO WO 2014/184143 A1 11/2014
WO WO 2014/184741 A1 11/2014
WO WO 2014/184744 A1 11/2014
WO WO 2014/186585 A2 11/2014
WO WO 2014/186686 A2 11/2014
WO WO 2014/190181 A1 11/2014
WO WO 2014/191128 A1 12/2014
WO WO 2014/191518 A1 12/2014
WO WO 2014/191521 A2 12/2014
WO WO 2014/191525 A1 12/2014
WO WO 2014/191527 A1 12/2014
WO WO 2014/193583 A2 12/2014
WO WO 2014/194190 A1 12/2014
WO WO 2014/197568 A2 12/2014
WO WO 2014/197748 A2 12/2014
WO WO 2014/199358 A1 12/2014
WO WO 2014/200659 A1 12/2014
WO WO 2014/201015 A2 12/2014
WO WO 2014/204578 A1 12/2014
WO WO 2014/204723 A1 12/2014
WO WO 2014/204724 A1 12/2014
WO WO 2014/204725 A1 12/2014
WO WO 2014/204726 A1 12/2014
WO WO 2014/204727 A1 12/2014
WO WO 2014/204728 A1 12/2014
WO WO 2014/204729 A1 12/2014
WO WO 2014/205192 A2 12/2014
WO WO 2014/207043 A1 12/2014
WO WO 2015/002780 A1 1/2015
WO WO 2015/004241 A2 1/2015
WO WO 2015/006290 A1 1/2015
WO WO 2015/006294 A2 1/2015
WO WO 2015/006437 A1 1/2015
WO WO 2015/006498 A2 1/2015
WO WO 2015/006747 A2 1/2015
WO WO 2015/007194 A1 1/2015
WO WO 2015/010114 A1 1/2015
WO WO 2015/011483 A1 1/2015
WO WO 2015/013583 A2 1/2015
WO WO 2015/017866 A1 2/2015
WO WO 2015/018503 A1 2/2015
WO WO 2015/021353 A1 2/2015
WO WO 2015/021426 A1 2/2015
WO WO 2015/021990 A1 2/2015
WO WO 2015/024017 A2 2/2015
WO WO 2015/024986 A1 2/2015
WO WO 2015/026883 A1 2/2015
WO WO 2015/026885 A1 2/2015
WO WO 2015/026886 A1 2/2015
WO WO 2015/026887 A1 2/2015
WO WO 2015/027134 A1 2/2015
WO WO 2015/028969 A2 3/2015
WO WO 2015/030881 A1 3/2015
WO WO 2015/031619 A1 3/2015
WO WO 2015/031775 A1 3/2015
WO WO 2015/032494 A2 3/2015
WO WO 2015/033293 A1 3/2015
WO WO 2015/034872 A2 3/2015
WO WO 2015/034885 A1 3/2015
WO WO 2015/035136 A2 3/2015
WO WO 2015/035139 A2 3/2015
WO WO 2015/035162 A2 3/2015
WO WO 2015/040075 A1 3/2015
WO WO 2015/040402 A1 3/2015
WO WO 2015/042585 A1 3/2015
WO WO 2015/048577 A2 4/2015
WO WO 2015/048690 A1 4/2015
WO WO 2015/048707 A2 4/2015
WO WO 2015/048801 A2 4/2015
WO WO 2015/049897 A1 4/2015
WO WO 2015/051191 A1 4/2015
WO WO 2015/052133 A1 4/2015
WO WO 2015/052231 A2 4/2015
WO WO 2015/052335 A1 4/2015
WO WO 2015/053995 A1 4/2015
WO WO 2015/054253 A1 4/2015
WO WO 2015/054315 A1 4/2015
WO WO 2015/057671 A1 4/2015
WO WO 2015/057834 A1 4/2015
WO WO 2015/057852 A1 4/2015
WO WO 2015/057976 A1 4/2015
WO WO 2015/057980 A1 4/2015
WO WO 2015/059265 A1 4/2015
WO WO 2015/065964 A1 5/2015
WO WO 2015/066119 A1 5/2015
WO WO 2015/066634 A2 5/2015
WO WO 2015/066636 A2 5/2015
WO WO 2015/066637 A1 5/2015
WO WO 2015/066638 A2 5/2015
WO WO 2015/066643 A1 5/2015
WO WO 2015/069682 A2 5/2015
WO WO 2015/070083 A1 5/2015
WO WO 2015/070193 A1 5/2015
WO WO 2015/070212 A1 5/2015
WO WO 2015/071474 A2 5/2015
WO WO 2015/073683 A2 5/2015
WO WO 2015/073867 A1 5/2015
WO WO 2015/073990 A1 5/2015
WO WO 2015/075056 A1 5/2015
WO WO 2015/075154 A2 5/2015
WO WO 2015/075175 A1 5/2015
WO WO 2015/075195 A1 5/2015
WO WO 2015/075557 A2 5/2015
WO WO 2015/077058 A2 5/2015
WO WO 2015/077290 A2 5/2015
WO WO 2015/077318 A1 5/2015
WO WO 2015/079056 A1 6/2015
WO WO 2015/079057 A2 6/2015
WO WO 2015/086795 A1 6/2015
WO WO 2015/086798 A2 6/2015
WO WO 2015/088643 A1 6/2015
WO WO 2015/089046 A1 6/2015
WO WO 2015/089077 A2 6/2015
WO WO 2015/089277 A1 6/2015
WO WO 2015/089351 A1 6/2015
WO WO 2015/089354 A1 6/2015
WO WO 2015/089364 A1 6/2015
WO WO 2015/089406 A1 6/2015
WO WO 2015/089419 A2 6/2015
WO WO 2015/089427 A1 6/2015
WO WO 2015/089462 A1 6/2015
WO WO 2015/089465 A1 6/2015
WO WO 2015/089473 A1 6/2015
WO WO 2015/089486 A2 6/2015
WO WO 2015/095804 A1 6/2015
WO WO 2015/099850 A1 7/2015
WO WO 2015/100929 A1 7/2015
WO WO 2015/103057 A1 7/2015
WO WO 2015/103153 A1 7/2015
WO WO 2015/105928 A1 7/2015
WO WO 2015/108993 A1 7/2015

(56) References Cited

FOREIGN PATENT DOCUMENTS

| | | | |
|---|---|---|---|
| WO | WO 2015/109752 | A1 | 7/2015 |
| WO | WO 2015/110474 | A1 | 7/2015 |
| WO | WO 2015/112790 | A2 | 7/2015 |
| WO | WO 2015/112896 | A2 | 7/2015 |
| WO | WO 2015/113063 | A1 | 7/2015 |
| WO | WO 2015/114365 | A1 | 8/2015 |
| WO | WO 2015/115903 | A1 | 8/2015 |
| WO | WO 2015/116686 | A1 | 8/2015 |
| WO | WO 2015/116969 | A2 | 8/2015 |
| WO | WO 2015/117021 | A1 | 8/2015 |
| WO | WO 2015/117041 | A1 | 8/2015 |
| WO | WO 2015/117081 | A2 | 8/2015 |
| WO | WO 2015/118156 | A1 | 8/2015 |
| WO | WO 2015/119941 | A2 | 8/2015 |
| WO | WO 2015/121454 | A1 | 8/2015 |
| WO | WO 2015/122967 | A1 | 8/2015 |
| WO | WO 2015/123339 | A1 | 8/2015 |
| WO | WO 2015/124715 | A1 | 8/2015 |
| WO | WO 2015/124718 | A1 | 8/2015 |
| WO | WO 2015/126927 | A2 | 8/2015 |
| WO | WO 2015/127428 | A1 | 8/2015 |
| WO | WO 2015/127439 | A1 | 8/2015 |
| WO | WO 2015/129686 | A1 | 9/2015 |
| WO | WO 2015/131101 | A1 | 9/2015 |
| WO | WO 2015/133554 | A1 | 9/2015 |
| WO | WO 2015/134121 | A2 | 9/2015 |
| WO | WO 2015/134812 | A1 | 9/2015 |
| WO | WO 2015/136001 | A1 | 9/2015 |
| WO | WO 2015/138510 | A1 | 9/2015 |
| WO | WO 2015/138739 | A2 | 9/2015 |
| WO | WO 2015/138855 | A1 | 9/2015 |
| WO | WO 2015/138870 | A2 | 9/2015 |
| WO | WO 2015/139008 | A1 | 9/2015 |
| WO | WO 2015/139139 | A1 | 9/2015 |
| WO | WO 2015/143046 | A2 | 9/2015 |
| WO | WO 2015/143177 | A1 | 9/2015 |
| WO | WO 2015/145417 | A1 | 10/2015 |
| WO | WO 2015/148431 | A1 | 10/2015 |
| WO | WO 2015/148670 | A1 | 10/2015 |
| WO | WO 2015/148680 | A1 | 10/2015 |
| WO | WO 2015/148761 | A1 | 10/2015 |
| WO | WO 2015/148860 | A1 | 10/2015 |
| WO | WO 2015/148863 | A2 | 10/2015 |
| WO | WO 2015/153760 | A2 | 10/2015 |
| WO | WO 2015/153780 | A1 | 10/2015 |
| WO | WO 2015/153789 | A1 | 10/2015 |
| WO | WO 2015/153791 | A1 | 10/2015 |
| WO | WO 2015/153889 | A2 | 10/2015 |
| WO | WO 2015/153940 | A1 | 10/2015 |
| WO | WO 2015/155341 | A1 | 10/2015 |
| WO | WO 2015/155686 | A2 | 10/2015 |
| WO | WO 2015/157070 | A2 | 10/2015 |
| WO | WO 2015/157534 | A1 | 10/2015 |
| WO | WO 2015/159068 | A1 | 10/2015 |
| WO | WO 2015/159086 | A1 | 10/2015 |
| WO | WO 2015/159087 | A1 | 10/2015 |
| WO | WO 2015/160683 | A1 | 10/2015 |
| WO | WO 2015/161276 | A2 | 10/2015 |
| WO | WO 2015/163733 | A1 | 10/2015 |
| WO | WO 2015/164740 | A1 | 10/2015 |
| WO | WO 2015/164748 | A1 | 10/2015 |
| WO | WO 2015/165274 | A1 | 11/2015 |
| WO | WO 2015/165275 | A1 | 11/2015 |
| WO | WO 2015/165276 | A1 | 11/2015 |
| WO | WO 2015/166272 | A2 | 11/2015 |
| WO | WO 2015/167766 | A1 | 11/2015 |
| WO | WO 2015/167956 | A1 | 11/2015 |
| WO | WO 2015/168125 | A1 | 11/2015 |
| WO | WO 2015/168158 | A1 | 11/2015 |
| WO | WO 2015/168404 | A1 | 11/2015 |
| WO | WO 2015/168547 | A2 | 11/2015 |
| WO | WO 2015/168800 | A1 | 11/2015 |
| WO | WO 2015/171603 | A1 | 11/2015 |
| WO | WO 2015/171894 | A1 | 11/2015 |
| WO | WO 2015/171932 | A1 | 11/2015 |
| WO | WO 2015/172128 | A1 | 11/2015 |
| WO | WO 2015/173436 | A1 | 11/2015 |
| WO | WO 2015/175642 | A2 | 11/2015 |
| WO | WO 2015/179540 | A1 | 11/2015 |
| WO | WO 2015/183025 | A1 | 12/2015 |
| WO | WO 2015/183026 | A1 | 12/2015 |
| WO | WO 2015/183885 | A1 | 12/2015 |
| WO | WO 2015/184259 | A1 | 12/2015 |
| WO | WO 2015/184262 | A1 | 12/2015 |
| WO | WO 2015/184268 | A1 | 12/2015 |
| WO | WO 2015/188056 | A1 | 12/2015 |
| WO | WO 2015/188065 | A1 | 12/2015 |
| WO | WO 2015/188094 | A1 | 12/2015 |
| WO | WO 2015/188109 | A1 | 12/2015 |
| WO | WO 2015/188132 | A1 | 12/2015 |
| WO | WO 2015/188135 | A1 | 12/2015 |
| WO | WO 2015/188191 | A1 | 12/2015 |
| WO | WO 2015/189693 | A1 | 12/2015 |
| WO | WO 2015/191693 | A2 | 12/2015 |
| WO | WO 2015/191899 | A1 | 12/2015 |
| WO | WO 2015/191911 | A2 | 12/2015 |
| WO | WO 2015/193858 | A1 | 12/2015 |
| WO | WO 2015/195547 | A1 | 12/2015 |
| WO | WO 2015/195621 | A1 | 12/2015 |
| WO | WO 2015/195798 | A1 | 12/2015 |
| WO | WO 2015/198020 | A1 | 12/2015 |
| WO | WO 2015/200334 | A1 | 12/2015 |
| WO | WO 2015/200378 | A1 | 12/2015 |
| WO | WO 2015/200555 | A2 | 12/2015 |
| WO | WO 2015/200805 | A2 | 12/2015 |
| WO | WO 2016/001978 | A1 | 1/2016 |
| WO | WO 2016/004010 | A1 | 1/2016 |
| WO | WO 2016/004318 | A1 | 1/2016 |
| WO | WO 2016/007347 | A1 | 1/2016 |
| WO | WO 2016/007604 | A1 | 1/2016 |
| WO | WO 2016/007948 | A1 | 1/2016 |
| WO | WO 2016/011080 | A2 | 1/2016 |
| WO | WO 2016/011210 | A2 | 1/2016 |
| WO | WO 2016/011428 | A1 | 1/2016 |
| WO | WO 2016/012544 | A2 | 1/2016 |
| WO | WO 2016/012552 | A1 | 1/2016 |
| WO | WO 2016/014409 | A1 | 1/2016 |
| WO | WO 2016/014565 | A2 | 1/2016 |
| WO | WO 2016/014794 | A1 | 1/2016 |
| WO | WO 2016/014837 | A1 | 1/2016 |
| WO | WO 2016/016119 | A1 | 2/2016 |
| WO | WO 2016/016358 | A1 | 2/2016 |
| WO | WO 2016/019144 | A2 | 2/2016 |
| WO | WO 2016/020399 | A1 | 2/2016 |
| WO | WO 2016/021972 | A1 | 2/2016 |
| WO | WO 2016/021973 | A1 | 2/2016 |
| WO | WO 2016/022363 | A2 | 2/2016 |
| WO | WO 2016/022866 | A1 | 2/2016 |
| WO | WO 2016/022931 | A1 | 2/2016 |
| WO | WO 2016/025131 | A1 | 2/2016 |
| WO | WO 2016/025469 | A1 | 2/2016 |
| WO | WO 2016/025759 | A1 | 2/2016 |
| WO | WO 2016/026444 | A1 | 2/2016 |
| WO | WO 2016/028682 | A1 | 2/2016 |
| WO | WO 2016/028843 | A2 | 2/2016 |
| WO | WO 2016/028887 | A1 | 2/2016 |
| WO | WO 2016/033088 | A1 | 3/2016 |
| WO | WO 2016/033230 | A1 | 3/2016 |
| WO | WO 2016/033246 | A1 | 3/2016 |
| WO | WO 2016/033298 | A1 | 3/2016 |
| WO | WO 2016/035044 | A1 | 3/2016 |
| WO | WO 2016/036754 | A1 | 3/2016 |
| WO | WO 2016/037157 | A2 | 3/2016 |
| WO | WO 2016/040030 | A1 | 3/2016 |
| WO | WO 2016/040594 | A1 | 3/2016 |
| WO | WO 2016/044182 | A1 | 3/2016 |
| WO | WO 2016/044416 | A1 | 3/2016 |
| WO | WO 2016/046635 | A1 | 3/2016 |
| WO | WO 2016/049024 | A2 | 3/2016 |
| WO | WO 2016/049163 | A2 | 3/2016 |
| WO | WO 2016/049230 | A1 | 3/2016 |
| WO | WO 2016/049251 | A1 | 3/2016 |
| WO | WO 2016/049258 | A2 | 3/2016 |
| WO | WO 2016/053397 | A2 | 4/2016 |

(56) References Cited

FOREIGN PATENT DOCUMENTS

| | | | |
|---|---|---|---|
| WO | WO 2016/054326 | A1 | 4/2016 |
| WO | WO 2016/057061 | A2 | 4/2016 |
| WO | WO 2016/057821 | A2 | 4/2016 |
| WO | WO 2016/057835 | A2 | 4/2016 |
| WO | WO 2016/057850 | A1 | 4/2016 |
| WO | WO 2016/057951 | A2 | 4/2016 |
| WO | WO 2016/057961 | A1 | 4/2016 |
| WO | WO 2016/061073 | A1 | 4/2016 |
| WO | WO 2016/061374 | A1 | 4/2016 |
| WO | WO 2016/061481 | A1 | 4/2016 |
| WO | WO 2016/061523 | A1 | 4/2016 |
| WO | WO 2016/064894 | A2 | 4/2016 |
| WO | WO 2016/065364 | A1 | 4/2016 |
| WO | WO 2016/069282 | A1 | 5/2016 |
| WO | WO 2016/069283 | A1 | 5/2016 |
| WO | WO 2016/069591 | A2 | 5/2016 |
| WO | WO 2016/069774 | A1 | 5/2016 |
| WO | WO 2016/069910 | A1 | 5/2016 |
| WO | WO 2016/069912 | A1 | 5/2016 |
| WO | WO 2016/070037 | A2 | 5/2016 |
| WO | WO 2016/070070 | A1 | 5/2016 |
| WO | WO 2016/070129 | A1 | 5/2016 |
| WO | WO 2016/072399 | A1 | 5/2016 |
| WO | WO 2016/072936 | A1 | 5/2016 |
| WO | WO 2016/073433 | A1 | 5/2016 |
| WO | WO 2016/073559 | A1 | 5/2016 |
| WO | WO 2016/073990 | A2 | 5/2016 |
| WO | WO 2016/075662 | A2 | 5/2016 |
| WO | WO 2016/076672 | A1 | 5/2016 |
| WO | WO 2016/077273 | A1 | 5/2016 |
| WO | WO 2016/077350 | A1 | 5/2016 |
| WO | WO 2016/080097 | A1 | 5/2016 |
| WO | WO 2016/080795 | A1 | 5/2016 |
| WO | WO 2016/081923 | A2 | 5/2016 |
| WO | WO 2016/081924 | A1 | 5/2016 |
| WO | WO 2016/082135 | A1 | 6/2016 |
| WO | WO 2016/083811 | A1 | 6/2016 |
| WO | WO 2016/084084 | A1 | 6/2016 |
| WO | WO 2016/084088 | A1 | 6/2016 |
| WO | WO 2016/086177 | A2 | 6/2016 |
| WO | WO 2016/089433 | A1 | 6/2016 |
| WO | WO 2016/089866 | A1 | 6/2016 |
| WO | WO 2016/089883 | A1 | 6/2016 |
| WO | WO 2016/090385 | A1 | 6/2016 |
| WO | WO 2016/094679 | A1 | 6/2016 |
| WO | WO 2016/094845 | A2 | 6/2016 |
| WO | WO 2016/094867 | A1 | 6/2016 |
| WO | WO 2016/094872 | A1 | 6/2016 |
| WO | WO 2016/094874 | A1 | 6/2016 |
| WO | WO 2016/094880 | A1 | 6/2016 |
| WO | WO 2016/094888 | A1 | 6/2016 |
| WO | WO 2016/097212 | A1 | 6/2016 |
| WO | WO 2016/097231 | A2 | 6/2016 |
| WO | WO 2016/097751 | A1 | 6/2016 |
| WO | WO 2016/099887 | A1 | 6/2016 |
| WO | WO 2016/100272 | A1 | 6/2016 |
| WO | WO 2016/100389 | A1 | 6/2016 |
| WO | WO 2016/100568 | A1 | 6/2016 |
| WO | WO 2016/100571 | A1 | 6/2016 |
| WO | WO 2016/100951 | A2 | 6/2016 |
| WO | WO 2016/100955 | A2 | 6/2016 |
| WO | WO 2016/100974 | A1 | 6/2016 |
| WO | WO 2016/103233 | A2 | 6/2016 |
| WO | WO 2016/104716 | A1 | 6/2016 |
| WO | WO 2016/106236 | A1 | 6/2016 |
| WO | WO 2016/106239 | A1 | 6/2016 |
| WO | WO 2016/106244 | A1 | 6/2016 |
| WO | WO 2016/106338 | A2 | 6/2016 |
| WO | WO 2016/108926 | A1 | 7/2016 |
| WO | WO 2016/109255 | A1 | 7/2016 |
| WO | WO 2016/109840 | A2 | 7/2016 |
| WO | WO 2016/110214 | A1 | 7/2016 |
| WO | WO 2016/110453 | A1 | 7/2016 |
| WO | WO 2016/110511 | A1 | 7/2016 |
| WO | WO 2016/110512 | A1 | 7/2016 |
| WO | WO 2016/111546 | A2 | 7/2016 |
| WO | WO 2016/112242 | A1 | 7/2016 |
| WO | WO 2016/112351 | A1 | 7/2016 |
| WO | WO 2016/112963 | A1 | 7/2016 |
| WO | WO 2016/113357 | A1 | 7/2016 |
| WO | WO 2016/114972 | A1 | 7/2016 |
| WO | WO 2016/115179 | A1 | 7/2016 |
| WO | WO 2016/115326 | A1 | 7/2016 |
| WO | WO 2016/115355 | A1 | 7/2016 |
| WO | WO 2016/116032 | A1 | 7/2016 |
| WO | WO 2016/120480 | A1 | 8/2016 |
| WO | WO 2016/123071 | A1 | 8/2016 |
| WO | WO 2016/123230 | A1 | 8/2016 |
| WO | WO 2016/123243 | A1 | 8/2016 |
| WO | WO 2016/123578 | A1 | 8/2016 |
| WO | WO 2016/126747 | A1 | 8/2016 |
| WO | WO 2016/130600 | A2 | 8/2016 |
| WO | WO 2016/130697 | A1 | 8/2016 |
| WO | WO 2016/131009 | A1 | 8/2016 |
| WO | WO 2016/132122 | A1 | 8/2016 |
| WO | WO 2016/133165 | A1 | 8/2016 |
| WO | WO 2016/135507 | A1 | 9/2016 |
| WO | WO 2016/135557 | A2 | 9/2016 |
| WO | WO 2016/135558 | A2 | 9/2016 |
| WO | WO 2016/135559 | A2 | 9/2016 |
| WO | WO 2016/137774 | A1 | 9/2016 |
| WO | WO 2016/137949 | A1 | 9/2016 |
| WO | WO 2016/141224 | A1 | 9/2016 |
| WO | WO 2016/141893 | A1 | 9/2016 |
| WO | WO 2016/142719 | A1 | 9/2016 |
| WO | WO 2016/145150 | A2 | 9/2016 |
| WO | WO 2016/148994 | A1 | 9/2016 |
| WO | WO 2016/149484 | A2 | 9/2016 |
| WO | WO 2016/149547 | A1 | 9/2016 |
| WO | WO 2016/150336 | A1 | 9/2016 |
| WO | WO 2016/150855 | A1 | 9/2016 |
| WO | WO 2016/154016 | A2 | 9/2016 |
| WO | WO 2016/154579 | A2 | 9/2016 |
| WO | WO 2016/154596 | A1 | 9/2016 |
| WO | WO 2016/155482 | A1 | 10/2016 |
| WO | WO 2016/161004 | A1 | 10/2016 |
| WO | WO 2016/161207 | A1 | 10/2016 |
| WO | WO 2016/161260 | A1 | 10/2016 |
| WO | WO 2016/161380 | A1 | 10/2016 |
| WO | WO 2016/161446 | A1 | 10/2016 |
| WO | WO 2016/164356 | A1 | 10/2016 |
| WO | WO 2016/164797 | A1 | 10/2016 |
| WO | WO 2016/166340 | A1 | 10/2016 |
| WO | WO 2016/167300 | A1 | 10/2016 |
| WO | WO 2016/168631 | A1 | 10/2016 |
| WO | WO 2016/170484 | A1 | 10/2016 |
| WO | WO 2016/172359 | A2 | 10/2016 |
| WO | WO 2016/172727 | A1 | 10/2016 |
| WO | WO 2016/174056 | A1 | 11/2016 |
| WO | WO 2016/174151 | A1 | 11/2016 |
| WO | WO 2016/174250 | A1 | 11/2016 |
| WO | WO 2016/176191 | A1 | 11/2016 |
| WO | WO 2016/176404 | A1 | 11/2016 |
| WO | WO 2016/176690 | A2 | 11/2016 |
| WO | WO 2016/177682 | A1 | 11/2016 |
| WO | WO 2016/178207 | A1 | 11/2016 |
| WO | WO 2016/179038 | A1 | 11/2016 |
| WO | WO 2016/179112 | A1 | 11/2016 |
| WO | WO 2016/181357 | A1 | 11/2016 |
| WO | WO 2016/182893 | A1 | 11/2016 |
| WO | WO 2016/182917 | A1 | 11/2016 |
| WO | WO 2016/182959 | A1 | 11/2016 |
| WO | WO 2016/183236 | A1 | 11/2016 |
| WO | WO 2016/183298 | A2 | 11/2016 |
| WO | WO 2016/183345 | A1 | 11/2016 |
| WO | WO 2016/183402 | A2 | 11/2016 |
| WO | WO 2016/183438 | A1 | 11/2016 |
| WO | WO 2016/183448 | A1 | 11/2016 |
| WO | WO 2016/184955 | A2 | 11/2016 |
| WO | WO 2016/184989 | A1 | 11/2016 |
| WO | WO 2016/185411 | A1 | 11/2016 |
| WO | WO 2016/186745 | A1 | 11/2016 |
| WO | WO 2016/186772 | A2 | 11/2016 |
| WO | WO 2016/186946 | A1 | 11/2016 |

(56) References Cited

FOREIGN PATENT DOCUMENTS

| | | | |
|---|---|---|---|
| WO | WO 2016/186953 | A1 | 11/2016 |
| WO | WO 2016/187717 | A1 | 12/2016 |
| WO | WO 2016/187904 | A1 | 12/2016 |
| WO | WO 2016/191684 | A1 | 12/2016 |
| WO | WO 2016/191869 | A1 | 12/2016 |
| WO | WO 2016/196273 | A1 | 12/2016 |
| WO | WO 2016/196282 | A1 | 12/2016 |
| WO | WO 2016/196308 | A1 | 12/2016 |
| WO | WO 2016/196361 | A1 | 12/2016 |
| WO | WO 2016/196499 | A1 | 12/2016 |
| WO | WO 2016/196539 | A2 | 12/2016 |
| WO | WO 2016/196655 | A1 | 12/2016 |
| WO | WO 2016/196805 | A1 | 12/2016 |
| WO | WO 2016/196887 | A1 | 12/2016 |
| WO | WO 2016/197132 | A1 | 12/2016 |
| WO | WO 2016/197133 | A1 | 12/2016 |
| WO | WO 2016/197354 | A1 | 12/2016 |
| WO | WO 2016/197355 | A1 | 12/2016 |
| WO | WO 2016/197356 | A1 | 12/2016 |
| WO | WO 2016/197357 | A1 | 12/2016 |
| WO | WO 2016/197358 | A1 | 12/2016 |
| WO | WO 2016/197359 | A1 | 12/2016 |
| WO | WO 2016/197360 | A1 | 12/2016 |
| WO | WO 2016/197361 | A1 | 12/2016 |
| WO | WO 2016/197362 | A1 | 12/2016 |
| WO | WO 2016/198361 | A1 | 12/2016 |
| WO | WO 2016/198500 | A1 | 12/2016 |
| WO | WO 2016/200263 | A1 | 12/2016 |
| WO | WO 2016/201047 | A1 | 12/2016 |
| WO | WO 2016/201138 | A1 | 12/2016 |
| WO | WO 2016/201152 | A1 | 12/2016 |
| WO | WO 2016/201153 | A1 | 12/2016 |
| WO | WO 2016/201155 | A1 | 12/2016 |
| WO | WO 2016/205276 | A1 | 12/2016 |
| WO | WO 2016/205613 | A1 | 12/2016 |
| WO | WO 2016/205623 | A1 | 12/2016 |
| WO | WO 2016/205680 | A1 | 12/2016 |
| WO | WO 2016/205688 | A2 | 12/2016 |
| WO | WO 2016/205703 | A1 | 12/2016 |
| WO | WO 2016/205711 | A1 | 12/2016 |
| WO | WO 2016/205728 | A1 | 12/2016 |
| WO | WO 2016/205745 | A2 | 12/2016 |
| WO | WO 2016/205749 | A1 | 12/2016 |
| WO | WO 2016/205759 | A1 | 12/2016 |
| WO | WO 2016/205764 | A1 | 12/2016 |
| WO | WO 2017/001572 | A1 | 1/2017 |
| WO | WO 2017/001988 | A1 | 1/2017 |
| WO | WO 2017/004261 | A1 | 1/2017 |
| WO | WO 2017/004279 | A2 | 1/2017 |
| WO | WO 2017/004616 | A1 | 1/2017 |
| WO | WO 2017/005807 | A1 | 1/2017 |
| WO | WO 2017/009399 | A1 | 1/2017 |
| WO | WO 2017/010556 | A1 | 1/2017 |
| WO | WO 2017/011519 | A1 | 1/2017 |
| WO | WO 2017/011721 | A1 | 1/2017 |
| WO | WO 2017/011804 | A1 | 1/2017 |
| WO | WO 2017/015015 | A1 | 1/2017 |
| WO | WO 2017/015101 | A1 | 1/2017 |
| WO | WO 2017/015545 | A1 | 1/2017 |
| WO | WO 2017/015567 | A1 | 1/2017 |
| WO | WO 2017/015637 | A1 | 1/2017 |
| WO | WO 2017/017016 | A1 | 2/2017 |
| WO | WO 2017/019867 | A1 | 2/2017 |
| WO | WO 2017/019895 | A1 | 2/2017 |
| WO | WO 2017/023803 | A1 | 2/2017 |
| WO | WO 2017/023974 | A1 | 2/2017 |
| WO | WO 2017/024047 | A1 | 2/2017 |
| WO | WO 2017/024319 | A1 | 2/2017 |
| WO | WO 2017/024343 | A1 | 2/2017 |
| WO | WO 2017/024602 | A1 | 2/2017 |
| WO | WO 2017/025323 | A1 | 2/2017 |
| WO | WO 2017/027423 | A1 | 2/2017 |
| WO | WO 2017/028768 | A1 | 2/2017 |
| WO | WO 2017/029664 | A1 | 2/2017 |
| WO | WO 2017/031360 | A1 | 2/2017 |
| WO | WO 2017/031483 | A1 | 2/2017 |
| WO | WO 2017/035416 | A2 | 3/2017 |
| WO | WO 2017/040348 | A1 | 3/2017 |
| WO | WO 2017/040511 | A1 | 3/2017 |
| WO | WO 2017/040709 | A1 | 3/2017 |
| WO | WO 2017/040786 | A1 | 3/2017 |
| WO | WO 2017/040793 | A1 | 3/2017 |
| WO | WO 2017/040813 | A2 | 3/2017 |
| WO | WO 2017/043573 | A1 | 3/2017 |
| WO | WO 2017/043656 | A1 | 3/2017 |
| WO | WO 2017/044419 | A1 | 3/2017 |
| WO | WO 2017/044776 | A1 | 3/2017 |
| WO | WO 2017/044857 | A2 | 3/2017 |
| WO | WO 2017/048390 | A1 | 3/2017 |
| WO | WO 2017/049129 | A2 | 3/2017 |
| WO | WO 2017/050963 | A1 | 3/2017 |
| WO | WO 2017/053312 | A1 | 3/2017 |
| WO | WO 2017/053431 | A2 | 3/2017 |
| WO | WO 2017/053713 | A1 | 3/2017 |
| WO | WO 2017/053729 | A1 | 3/2017 |
| WO | WO 2017/053753 | A1 | 3/2017 |
| WO | WO 2017/053762 | A1 | 3/2017 |
| WO | WO 2017/053879 | A1 | 3/2017 |
| WO | WO 2017/054721 | A1 | 4/2017 |
| WO | WO 2017/058658 | A2 | 4/2017 |
| WO | WO 2017/059241 | A1 | 4/2017 |
| WO | WO 2017/062605 | A1 | 4/2017 |
| WO | WO 2017/062723 | A1 | 4/2017 |
| WO | WO 2017/062754 | A1 | 4/2017 |
| WO | WO 2017/062855 | A1 | 4/2017 |
| WO | WO 2017/062886 | A1 | 4/2017 |
| WO | WO 2017/062983 | A1 | 4/2017 |
| WO | WO 2017/064439 | A1 | 4/2017 |
| WO | WO 2017/064546 | A1 | 4/2017 |
| WO | WO 2017/064566 | A2 | 4/2017 |
| WO | WO 2017/066175 | A1 | 4/2017 |
| WO | WO 2017/066497 | A2 | 4/2017 |
| WO | WO 2017/066588 | A2 | 4/2017 |
| WO | WO 2017/066707 | A1 | 4/2017 |
| WO | WO 2017/066781 | A1 | 4/2017 |
| WO | WO 2017/068077 | A1 | 4/2017 |
| WO | WO 2017/068377 | A1 | 4/2017 |
| WO | WO 2017/069829 | A2 | 4/2017 |
| WO | WO 2017/070029 | A1 | 4/2017 |
| WO | WO 2017/070032 | A1 | 4/2017 |
| WO | WO 2017/070169 | A1 | 4/2017 |
| WO | WO 2017/070284 | A1 | 4/2017 |
| WO | WO 2017/070598 | A1 | 4/2017 |
| WO | WO 2017/070605 | A1 | 4/2017 |
| WO | WO 2017/070632 | A2 | 4/2017 |
| WO | WO 2017/070633 | A2 | 4/2017 |
| WO | WO 2017/072590 | A1 | 5/2017 |
| WO | WO 2017/074526 | A1 | 5/2017 |
| WO | WO 2017/074962 | A1 | 5/2017 |
| WO | WO 2017/075261 | A1 | 5/2017 |
| WO | WO 2017/075335 | A1 | 5/2017 |
| WO | WO 2017/075475 | A1 | 5/2017 |
| WO | WO 2017/077135 | A1 | 5/2017 |
| WO | WO 2017/077329 | A2 | 5/2017 |
| WO | WO 2017/078751 | A1 | 5/2017 |
| WO | WO 2017/079400 | A1 | 5/2017 |
| WO | WO 2017/079428 | A1 | 5/2017 |
| WO | WO 2017/079673 | A1 | 5/2017 |
| WO | WO 2017/079724 | A1 | 5/2017 |
| WO | WO 2017/081097 | A1 | 5/2017 |
| WO | WO 2017/081288 | A1 | 5/2017 |
| WO | WO 2017/083368 | A1 | 5/2017 |
| WO | WO 2017/083722 | A1 | 5/2017 |
| WO | WO 2017/083766 | A1 | 5/2017 |
| WO | WO 2017/087395 | A1 | 5/2017 |
| WO | WO 2017/090724 | A1 | 6/2017 |
| WO | WO 2017/091510 | A1 | 6/2017 |
| WO | WO 2017/091630 | A1 | 6/2017 |
| WO | WO 2017/092201 | A1 | 6/2017 |
| WO | WO 2017/093370 | A1 | 6/2017 |
| WO | WO 2017/093969 | A1 | 6/2017 |
| WO | WO 2017/095111 | A1 | 6/2017 |
| WO | WO 2017/096041 | A1 | 6/2017 |
| WO | WO 2017/096237 | A1 | 6/2017 |

(56) References Cited

FOREIGN PATENT DOCUMENTS

WO WO 2017/100158 A1 6/2017
WO WO 2017/100431 A2 6/2017
WO WO 2017/104404 A1 6/2017
WO WO 2017/105251 A1 6/2017
WO WO 2017/105350 A1 6/2017
WO WO 2017/105991 A1 6/2017
WO WO 2017/106414 A1 6/2017
WO WO 2017/106528 A2 6/2017
WO WO 2017/106537 A2 6/2017
WO WO 2017/106569 A1 6/2017
WO WO 2017/106616 A1 6/2017
WO WO 2017/106657 A1 6/2017
WO WO 2017/106767 A1 6/2017
WO WO 2017/109134 A1 6/2017
WO WO 2017/109757 A1 6/2017
WO WO 2017/112620 A1 6/2017
WO WO 2017/115268 A1 7/2017
WO WO 2017/117395 A1 7/2017
WO WO 2017/118598 A1 7/2017
WO WO 2017/118720 A1 7/2017
WO WO 2017/123609 A1 7/2017
WO WO 2017/123910 A1 7/2017
WO WO 2017/124086 A1 7/2017
WO WO 2017/124100 A1 7/2017
WO WO 2017/124652 A1 7/2017
WO WO 2017/126987 A1 7/2017
WO WO 2017/127807 A1 7/2017
WO WO 2017/131237 A1 8/2017
WO WO 2017/132112 A1 8/2017
WO WO 2017/132580 A2 8/2017
WO WO 2017/136520 A1 8/2017
WO WO 2017/136629 A1 8/2017
WO WO 2017/136794 A1 8/2017
WO WO 2017/139264 A1 8/2017
WO WO 2017/139505 A2 8/2017
WO WO 2017/141173 A2 8/2017
WO WO 2017/142835 A1 8/2017
WO WO 2017/142999 A2 8/2017
WO WO 2017/143042 A2 8/2017
WO WO 2017/147056 A1 8/2017
WO WO 2017/147278 A1 8/2017
WO WO 2017/147432 A1 8/2017
WO WO 2017/147446 A1 8/2017
WO WO 2017/147555 A1 8/2017
WO WO 2017/151444 A1 9/2017
WO WO 2017/151719 A1 9/2017
WO WO 2017/152015 A1 9/2017
WO WO 2017/155717 A1 9/2017
WO WO 2017/157422 A1 9/2017
WO WO 2017/158153 A1 9/2017
WO WO 2017/160689 A1 9/2017
WO WO 2017/160752 A1 9/2017
WO WO 2017/160890 A1 9/2017
WO WO 2017/161068 A1 9/2017
WO WO 2017/165826 A1 9/2017
WO WO 2017/165862 A1 9/2017
WO WO 2017/172644 A2 10/2017
WO WO 2017/172645 A2 10/2017
WO WO 2017/172860 A1 10/2017
WO WO 2017/173004 A1 10/2017
WO WO 2017/173054 A1 10/2017
WO WO 2017/173092 A1 10/2017
WO WO 2017/174329 A1 10/2017
WO WO 2017/176529 A1 10/2017
WO WO 2017/176806 A1 10/2017
WO WO 2017/178590 A1 10/2017
WO WO 2017/180694 A1 10/2017
WO WO 2017/180711 A1 10/2017
WO WO 2017/180915 A2 10/2017
WO WO 2017/180926 A1 10/2017
WO WO 2017/181107 A2 10/2017
WO WO 2017/181735 A2 10/2017
WO WO 2017/182468 A1 10/2017
WO WO 2017/184334 A1 10/2017
WO WO 2017/184768 A1 10/2017
WO WO 2017/184786 A1 10/2017
WO WO 2017/186550 A1 11/2017
WO WO 2017/189308 A1 11/2017
WO WO 2017/189336 A1 11/2017
WO WO 2017/190041 A1 11/2017
WO WO 2017/190257 A1 11/2017
WO WO 2017/190664 A1 11/2017
WO WO 2017/191210 A1 11/2017
WO WO 2017/191274 A2 11/2017
WO WO 2017/192172 A1 11/2017
WO WO 2017/192512 A2 11/2017
WO WO 2017/192544 A1 11/2017
WO WO 2017/192573 A1 11/2017
WO WO 2017/193029 A2 11/2017
WO WO 2017/193053 A1 11/2017
WO WO 2017/196768 A1 11/2017
WO WO 2017/197038 A1 11/2017
WO WO 2017/197238 A1 11/2017
WO WO 2017/197301 A1 11/2017
WO WO 2017/201476 A1 11/2017
WO WO 2017/205290 A1 11/2017
WO WO 2017/205423 A1 11/2017
WO WO 2017/207589 A1 12/2017
WO WO 2017/208247 A1 12/2017
WO WO 2017/209809 A1 12/2017
WO WO 2017/213896 A1 12/2017
WO WO 2017/213898 A2 12/2017
WO WO 2017/214460 A1 12/2017
WO WO 2017/216392 A1 12/2017
WO WO 2017/216771 A2 12/2017
WO WO 2017/218185 A1 12/2017
WO WO 2017/219027 A1 12/2017
WO WO 2017/219033 A1 12/2017
WO WO 2017/220751 A1 12/2017
WO WO 2017/222370 A1 12/2017
WO WO 2017/222773 A1 12/2017
WO WO 2017/222834 A1 12/2017
WO WO 2017/223107 A1 12/2017
WO WO 2017/223330 A1 12/2017
WO WO 2018/000657 A1 1/2018
WO WO 2018/002719 A1 1/2018
WO WO 2018/005117 A1 1/2018
WO WO 2018/005289 A2 1/2018
WO WO 2018/005691 A1 1/2018
WO WO 2018/005782 A1 1/2018
WO WO 2018/005873 A1 1/2018
WO WO 2018/06693 A1 1/2018
WO WO 2018/009520 A1 1/2018
WO WO 2018/009562 A1 1/2018
WO WO 2018/009822 A1 1/2018
WO WO 2018/013821 A1 1/2018
WO WO 2018/013932 A1 1/2018
WO WO 2018/013990 A1 1/2018
WO WO 2018/014384 A1 1/2018
WO WO 2018/015444 A1 1/2018
WO WO 2018/015936 A2 1/2018
WO WO 2018/017754 A1 1/2018
WO WO 2018/018979 A1 2/2018
WO WO 2018/020248 A1 2/2018
WO WO 2018/021878 A1 2/2018
WO WO 2018/022480 A1 2/2018
WO WO 2018/022634 A1 2/2018
WO WO 2018/025206 A1 2/2018
WO WO 2018/026723 A1 2/2018
WO WO 2018/026976 A1 2/2018
WO WO 2018/027078 A1 2/2018
WO WO 2018/030608 A1 2/2018
WO WO 2018/031683 A1 2/2018
WO WO 2018/035250 A1 2/2018
WO WO 2018/035300 A1 2/2018
WO WO 2018/035423 A1 2/2018
WO WO 2018/035503 A1 2/2018
WO WO 2018/039145 A1 3/2018
WO WO 2018/039438 A1 3/2018
WO WO 2018/039440 A1 3/2018
WO WO 2018/039448 A1 3/2018
WO WO 2018/045630 A1 3/2018
WO WO 2018/048827 A1 3/2018
WO WO 2018/049073 A1 3/2018

(56) References Cited

FOREIGN PATENT DOCUMENTS

| | | | |
|---|---|---|---|
| WO | WO 2018/049168 | A1 | 3/2018 |
| WO | WO 2018/051347 | A1 | 3/2018 |
| WO | WO 2018/058064 | A1 | 3/2018 |
| WO | WO 2018/062866 | A2 | 4/2018 |
| WO | WO 2018/064352 | A1 | 4/2018 |
| WO | WO 2018/064371 | A1 | 4/2018 |
| WO | WO 2018/064516 | A1 | 4/2018 |
| WO | WO 2018/067546 | A1 | 4/2018 |
| WO | WO 2018/067846 | A1 | 4/2018 |
| WO | WO 2018/068053 | A2 | 4/2018 |
| WO | WO 2018/069474 | A1 | 4/2018 |
| WO | WO 2018/071623 | A2 | 4/2018 |
| WO | WO 2018/071663 | A1 | 4/2018 |
| WO | WO 2018/071868 | A1 | 4/2018 |
| WO | WO 2018/071892 | A1 | 4/2018 |
| WO | WO 2018/074979 | A1 | 4/2018 |
| WO | WO 2018/079134 | A1 | 5/2018 |
| WO | WO 2018/080573 | A1 | 5/2018 |
| WO | WO 2018/081504 | A1 | 5/2018 |
| WO | WO 2018/081535 | A2 | 5/2018 |
| WO | WO 2018/081728 | A1 | 5/2018 |
| WO | WO 2018/083128 | A2 | 5/2018 |
| WO | WO 2018/083606 | A1 | 5/2018 |
| WO | WO 2018/085288 | A1 | 5/2018 |
| WO | WO 2018/085414 | A1 | 5/2018 |
| WO | WO 2018/086623 | A1 | 5/2018 |
| WO | WO 2018/089664 | A1 | 5/2018 |
| WO | WO 2018/093990 | A1 | 5/2018 |
| WO | WO 2018/098383 | A1 | 5/2018 |
| WO | WO 2018/098480 | A1 | 5/2018 |
| WO | WO 2018/098587 | A1 | 6/2018 |
| WO | WO 2018/099256 | A1 | 6/2018 |
| WO | WO 2018/103686 | A1 | 6/2018 |
| WO | WO 2018/106268 | A1 | 6/2018 |
| WO | WO 2018/107028 | A1 | 6/2018 |
| WO | WO 2018/107103 | A1 | 6/2018 |
| WO | WO 2018/107129 | A1 | 6/2018 |
| WO | WO 2018/108272 | A1 | 6/2018 |
| WO | WO 2018/109101 | A1 | 6/2018 |
| WO | WO 2018/111946 | A1 | 6/2018 |
| WO | WO 2018/111947 | A1 | 6/2018 |
| WO | WO 2018/112336 | A1 | 6/2018 |
| WO | WO 2018/112446 | A2 | 6/2018 |
| WO | WO 2018/119354 | A1 | 6/2018 |
| WO | WO 2018/119359 | A1 | 6/2018 |
| WO | WO 2018/120283 | A1 | 7/2018 |
| WO | WO 2018/130830 | A1 | 7/2018 |
| WO | WO 2018/135838 | A1 | 7/2018 |
| WO | WO 2018/136396 | A2 | 7/2018 |
| WO | WO 2018/138385 | A1 | 8/2018 |
| WO | WO 2018/142364 | A1 | 8/2018 |
| WO | WO 2018/148246 | A1 | 8/2018 |
| WO | WO 2018/148256 | A1 | 8/2018 |
| WO | WO 2018/148647 | A1 | 8/2018 |
| WO | WO 2018/149418 | A1 | 8/2018 |
| WO | WO 2018/149888 | A1 | 8/2018 |
| WO | WO 2018/149915 | A1 | 8/2018 |
| WO | WO 2018/152197 | A1 | 8/2018 |
| WO | WO 2018/152418 | A1 | 8/2018 |
| WO | WO 2018/154380 | A1 | 8/2018 |
| WO | WO 2018/154387 | A1 | 8/2018 |
| WO | WO 2018/154412 | A1 | 8/2018 |
| WO | WO 2018/154413 | A1 | 8/2018 |
| WO | WO 2018/154418 | A1 | 8/2018 |
| WO | WO 2018/154439 | A1 | 8/2018 |
| WO | WO 2018/154459 | A1 | 8/2018 |
| WO | WO 2018/154462 | A1 | 8/2018 |
| WO | WO 2018/156372 | A1 | 8/2018 |
| WO | WO 2018/156824 | A1 | 8/2018 |
| WO | WO 2018/161009 | A1 | 9/2018 |
| WO | WO 2018/165504 | A1 | 9/2018 |
| WO | WO 2018/165629 | A1 | 9/2018 |
| WO | WO 2018/170015 | A1 | 9/2018 |
| WO | WO 2018/170340 | A1 | 9/2018 |
| WO | WO 2018/175502 | A2 | 9/2018 |
| WO | WO 2018/176009 | A1 | 9/2018 |
| WO | WO 2018/177351 | A1 | 10/2018 |
| WO | WO 2018/179578 | A1 | 10/2018 |
| WO | WO 2018/183403 | A1 | 10/2018 |
| WO | WO 2018/189184 | A1 | 10/2018 |
| WO | WO 2018/191388 | A1 | 10/2018 |
| WO | WO 2018/195402 | A1 | 10/2018 |
| WO | WO 2018/195545 | A2 | 10/2018 |
| WO | WO 2018/195555 | A1 | 10/2018 |
| WO | WO 2018/197020 | A1 | 11/2018 |
| WO | WO 2018/197495 | A1 | 11/2018 |
| WO | WO 2018/202800 | A1 | 11/2018 |
| WO | WO 2018/204493 | A1 | 11/2018 |
| WO | WO 2018/208755 | A1 | 11/2018 |
| WO | WO 2018/208998 | A1 | 11/2018 |
| WO | WO 2018/209158 | A2 | 11/2018 |
| WO | WO 2018/209320 | A1 | 11/2018 |
| WO | WO 2018/213351 | A1 | 11/2018 |
| WO | WO 2018/213708 | A1 | 11/2018 |
| WO | WO 2018/213726 | A1 | 11/2018 |
| WO | WO 2018/213771 | A1 | 11/2018 |
| WO | WO 2018/213791 | A1 | 11/2018 |
| WO | WO 2018/217852 | A1 | 11/2018 |
| WO | WO 2018/217981 | A1 | 11/2018 |
| WO | WO 2018/218166 | A1 | 11/2018 |
| WO | WO 2018/218188 | A2 | 11/2018 |
| WO | WO 2018/218206 | A1 | 11/2018 |
| WO | WO 2019/005884 | A1 | 1/2019 |
| WO | WO 2019/005886 | A1 | 1/2019 |
| WO | WO 2019/010384 | A1 | 1/2019 |
| WO | WO 2019/023680 | A1 | 1/2019 |
| WO | WO 2019/051097 | A1 | 3/2019 |
| WO | WO 2019/079347 | A1 | 4/2019 |
| WO | WO 2019/084062 | A1 | 5/2019 |
| WO | WO 2019/090367 | A1 | 5/2019 |
| WO | WO 2019/092042 | A1 | 5/2019 |
| WO | WO 2019/118935 | A1 | 6/2019 |
| WO | WO 2019/118949 | A1 | 6/2019 |
| WO | WO 2019/123430 | A1 | 6/2019 |
| WO | WO 2019/139645 | A2 | 7/2019 |
| WO | WO 2019/139951 | A1 | 7/2019 |
| WO | WO 2019/147014 | A1 | 8/2019 |
| WO | WO 2019/161251 | A1 | 8/2019 |
| WO | WO 2019/168953 | A1 | 9/2019 |
| WO | WO 2019/226953 | A1 | 11/2019 |
| WO | WO 2019/236566 | A1 | 12/2019 |
| WO | WO 2020/014261 | A1 | 1/2020 |
| WO | WO 2020/028555 | A2 | 2/2020 |
| WO | WO 2020/041751 | A1 | 2/2020 |
| WO | WO 2020/047124 | A1 | 3/2020 |
| WO | WO 2020/051360 | A1 | 3/2020 |
| WO | WO 2020/086908 | A1 | 4/2020 |
| WO | WO 2020/092453 | A1 | 5/2020 |
| WO | WO 2020/102659 | A1 | 5/2020 |
| WO | WO 2020/154500 | A1 | 7/2020 |
| WO | WO 2020/157008 | A1 | 8/2020 |
| WO | WO 2020/180975 | A1 | 9/2020 |
| WO | WO 2020/181178 | A1 | 9/2020 |
| WO | WO 2020/181180 | A1 | 9/2020 |
| WO | WO 2020/181193 | A1 | 9/2020 |
| WO | WO 2020/181195 | A1 | 9/2020 |
| WO | WO 2020/181202 | A1 | 9/2020 |
| WO | WO 2020/191153 | A1 | 9/2020 |
| WO | WO 2020/191171 | A1 | 9/2020 |
| WO | WO 2020/191233 | A1 | 9/2020 |
| WO | WO 2020/191234 | A1 | 9/2020 |
| WO | WO 2020/191239 | A1 | 9/2020 |
| WO | WO 2020/191241 | A1 | 9/2020 |
| WO | WO 2020/191242 | A1 | 9/2020 |
| WO | WO 2020/191243 | A1 | 9/2020 |
| WO | WO 2020/191245 | A1 | 9/2020 |
| WO | WO 2020/191246 | A1 | 9/2020 |
| WO | WO 2020/191248 | A1 | 9/2020 |
| WO | WO 2020/191249 | A1 | 9/2020 |
| WO | WO 2020/210751 | A1 | 10/2020 |
| WO | WO 2020/214842 | A1 | 10/2020 |
| WO | WO 2020/236982 | A1 | 11/2020 |
| WO | WO 2021/025750 | A1 | 2/2021 |
| WO | WO 2021/030666 | A1 | 2/2021 |

(56) References Cited

FOREIGN PATENT DOCUMENTS

| | | |
|---|---|---|
| WO | WO 2021/072328 A1 | 4/2021 |
| WO | WO 2021/108717 A2 | 6/2021 |
| WO | WO 2021/155065 A1 | 8/2021 |
| WO | WO 2021/158921 A2 | 8/2021 |
| WO | WO 2021/158995 A1 | 8/2021 |
| WO | WO 2021/158999 A1 | 8/2021 |
| WO | WO 2021/222318 A1 | 11/2021 |
| WO | WO 2021/226558 A1 | 11/2021 |

OTHER PUBLICATIONS

U.S. Appl. No. 61/716,256, filed Oct. 19, 2012, Jinek et al.
U.S. Appl. No. 61/717,324, filed Oct. 23, 2012, Cho et al.
U.S. Appl. No. 61/734,256, filed Dec. 6, 2012, Chen et al.
U.S. Appl. No. 61/758,624, filed Jan. 30, 2013, Chen et al.
U.S. Appl. No. 61/761,046, filed Feb. 5, 2013, Knight et al.
U.S. Appl. No. 61/794,422, filed Mar. 15, 2013, Knight et al.
U.S. Appl. No. 61/803,599, filed Mar. 20, 2013, Kim et al.
U.S. Appl. No. 61/837,481, filed Jun. 20, 2013, Cho et al.
U.S. Appl. No. 61/838,178, filed Jun. 21, 2013, Joung et al.
U.S. Appl. No. 61/874,682, filed Sep. 6, 2013, Liu et al.
U.S. Appl. No. 61/874,746, filed Sep. 6, 2013, Liu et al.
U.S. Appl. No. 62/288,661, filed Jan. 29, 2016, Muir et al.
U.S. Appl. No. 62/357,332, filed Jun. 30, 2016, Liu et al.
[No Author Listed] Score result for SEQ 355 to W02017032580. Muir et al. 2016.
[No Author Listed], EMBL Accession No. Q99ZW2. Nov. 2012. 2 pages.
[No Author Listed], Invitrogen Lipofectamine™ 2000 product sheets, 2002. 2 pages.
[No Author Listed], Invitrogen Lipofectamine™ 2000 product sheets, 2005. 3 pages.
[No Author Listed], Invitrogen Lipofectamine™ LTX product sheets, 2011. 4 pages.
[No Author Listed], Thermo Fisher Scientific—How Cationic Lipid Mediated Transfection Works, retrieved from the internet Aug. 27, 2015. 2 pages.
Abudayyeh et al., C2c2 is a single-component programmable RNA-guided RNA-targeting CRISPR effector. Science Aug. 2016;353(6299):aaf5573. DOI: 10.1126/science.aaf5573.
Addgene Plasmid # 44246. pdCas9-humanized, 2017, Stanley Qi.
Addgene Plasmid # 73021. PCMV-BE3, 2017, David Liu.
Addgene Plasmid # 79620. pcDNA3.1_pCMV-nCas-PmCDA21-ugi pH1-gRNA(HPRT), 2017, Akihiko Kondo.
Aihara et al., A conformational switch controls the DNA cleavage activity of lambda integrase. Mol Cell. Jul. 2003;12(1):187-98.
Alexandrov et al., Signatures of mutational processes in human cancer. Nature. Aug. 22, 2013;500(7463):415-21. doi: 10.1038/naturel2477. Epub Aug. 14, 2013.
Ames et al., A eubacterial riboswitch class that senses the coenzyme tetrahydrofolate. Chem Biol. Jul. 30, 2010;17(7):681-5. doi: 10.1016/j.chembiol.2010.05.020.
Anders et al., Structural basis of PAM-dependent target DNA recognition by the Cas9 endonuclease. Nature. Sep. 25, 2014;513(7519):569-73. doi: 10.1038/nature13579. Epub Jul. 27, 2014.
Arnold et al., Mutants of Tn3 resolvase which do not require accessory binding sites for recombination activity. EMBO J. Mar. 1, 1999;18(5):1407-14.
Banerjee et al., Cadmium inhibits mismatch repair by blocking the A'lPase activity of the MSH2-MSH6 complex [published correction appears in Nucleic Acids Res. 2005;33(5):1738]. Nucleic Acids Res. 2005;33(4):1410-1419. Published Mar. 3, 2005. doi:10.1093/nar/gki291.
Barnes et al., Repair and genetic consequences of endogenous DNA base damage in mammalian cells. Annu Rev Genet. 2004;38:445-76.
Barrangou et al., CRISPR provides acquired resistance against viruses in prokaryotes. Science. Mar. 23, 2007;315(5819):1709-12.
Barrangou, RNA-mediated programmable DNA cleavage. Nat Biotechnol. Sep. 2012;30(9):836-8. doi: 10.1038/nbt.2357.
Basha et al., Influence of cationic lipid composition on gene silencing properties of lipid nanoparticle formulations of siRNA in antigen-presenting cells. Mol Ther. Dec. 2011;19(12):2186-200. doi: 10.1038/mt.2011.190. Epub Oct. 4, 2011.
Batey et al., Structure of a natural guanine-responsive riboswitch complexed with the metabolite hypoxanthine. Nature. Nov. 18, 2004;432(7015):411-5.
Beale et al., Comparison of the differential context-dependence of DNA deamination by APOBEC enzymes: correlation with mutation spectra in vivo. J Mol Biol. Mar. 26, 2004;337(3):585-96.
Bedell et al., In vivo genome editing using a high-efficiency TALEN system. Nature. Nov. 1, 2012;491(7422):114-8. Doi: 10.1038/naturel 1537. Epub Sep. 23, 2012.
Begley, Scientists unveil the 'most clever CRISPR gadget' so far. STAT, Apr. 20, 2016. https://www.statnews.com/2016/04/20/clever-crispr-advance-unveiled/.
Bershtein et al., Advances in laboratory evolution of enzymes. Curr Opin; Chem Biol. Apr. 2008;12(2):151-8. doi: 10.1016/j.cbpa.2008.01.027. Epub Mar. 7, 2008. Review.
Beumer et al., Efficient gene targeting in *Drosophila* with zinc-finger nucleases. Genetics. Apr. 2006;172(4):2391-403. Epub Feb. 1, 2006.
Billon et al., CRISPR-Mediated Base Editing Enables Efficient Disruption of Eukaryotic Genes through Induction of STOP Codons. Mol Cell. Sep. 21, 2017;67(6):1068-1079.e4. doi: 10.1016/j.molcel.2017.08.008. Epub Sep. 7, 2017.
Birling et al., Site-specific recombinases for manipulation of the mouse genome. Methods Mol Biol. 2009;561:245-63. doi: 10.1007/978-1-60327-019-9_16.
Biswas et al., A structural basis for allosteric control of DNA recombination by lambda integrase. Nature. Jun. 23, 2005;435(7045):1059-66. doi: 10.1038/nature03657.
Bitinaite et al., FokI dimerization is required for DNA cleavage. Proc Natl Acad Sci U S A. Sep. 1, 1998;95(18):10570-5.
Boch, TALEs of genome targeting. Nat Biotechnol. Feb. 2011;29(2):135-6. Doi: 10.1038/nbt.1767.
Böck et al., Selenocysteine: the 21st amino acid. Mol Microbiol. Mar. 1991;5(3):515-20.
Boeckle et al., Melittin analogs with high lytic activity at endosomal pH enhance transfection with purified targeted PEI polyplexes. J Control Release. May 15, 2006; 112(2):240-8. Epub Mar. 20, 2006.
Bogdanove et al., TAL effectors: customizable proteins for DNA targeting. Science. Sep. 30, 2011;333(6051):1843-6. doi: 10.1126/science. 1204094.
Bohlke et al., Sense codon emancipation for proteome-wide incorporation of noncanonical amino acids: rare isoleucine codon AUA as a target for genetic code expansion. FEMS Microbiol Lett. Feb. 2014;351(2):133-44. doi: 10.1111/1574-6968.12371. Epub Jan. 27, 2014.
Bolotin et al., Clustered regularly interspaced short palindrome repeats (CRISPRs) have spacers of extrachromosomal origin. Microbiology. Aug. 2005;151(Pt 8):2551-61.
Borman, Improved route to single-base genome editing. Chemical & Engineering News, Apr. 25, 2016;94(17)p5. http://cen.acs.org/articles/94/i17/Improved-route-single-base-genome.html.
Branden and Tooze, Introduction to Protein Structure. 1999; 2nd edition. Garland Science Publisher: 3-12.
Briner et al., Guide RNA functional modules direct Cas9 activity and orthogonality. Mol Cell. Oct. 23, 2014;56(2):333-339. doi: 10.1016/j.molcel.2014.09.019.
Britt et al., Re-engineering plant gene targeting. Trends Plant Sci. Feb. 2003;8(2):90-5.
Brouns et al., Small CRISPR RNAs guide antiviral defense in prokaryotes. Science. Aug. 15, 2008;321(5891):960-4. doi: 10.1126/science.1159689.
Brown et al., Serine recombinases as tools for genome engineering. Methods. Apr. 2011;53(4):372-9. doi: 10.1016/j.ymeth.2010.12.031. Epub Dec. 30, 2010.
Brusse et al., Spinocerebellar ataxia associated with a mutation in the fibroblast growth factor 14 gene (SCA27): A new phenotype. Mov Disord. Mar. 2006;21(3):396-401.

(56) References Cited

OTHER PUBLICATIONS

Buchholz et al., Alteration of Cre recombinase site specificity by substrate-linked protein evolution. Nat Biotechnol. Nov. 2001;19(11):1047-52.
Buchwald et al., Long-term, continuous intravenous heparin administration by an implantable infusion pump in ambulatory patients with recurrent venous thrombosis. Surgery. Oct. 1980;88(4):507-16.
Budisa et al., Residue-specific bioincorporation of non-natural, biologically active amino acids into proteins as possible drug carriers: structure and stability of the per-thiaproline mutant of annexin V. Proc Natl Acad Sci U S A. Jan. 20, 1998;95(2):455-9.
Budker et al., Protein/amphipathic polyamine complexes enable highly efficient transfection with minimal toxicity. Biotechniques. Jul. 1997;23(1):139, 142-7. doi: 10.2144/97231rr02.
Bulow et al., Multienzyme systems obtained by gene fusion. Trends Biotechnol. Jul. 1991;9(7):226-31.
Burke et al., RNA Aptamers to the Adenosine Moiety of S-adenosyl Methionine: Structural Inferences From Variations on a Theme and the Reproducibility of SELEX. Nucleic Acids Res. May 15, 1997;25(10):2020-4. doi: 10.1093/nar/25.10.2020.
Burstein et al., New CRISPR-Cas systems from uncultivated microbes. Nature Feb. 2017;542(7640):237-240.
Buskirk et al., Directed evolution of ligand dependence: small-molecule-activated protein splicing. Proc Natl Acad Sci U S A. Jul. 20, 2004;101(29):10505-10. Epub Jul. 9, 2004.
Cade et al., Highly efficient generation of heritable zebrafish gene mutations using homo- and heterodimeric TALENs. Nucleic Acids Res. Sep. 2012;40(16):8001-10. Doi: 10.1093/nar/gks518. Epub Jun. 7, 2012.
Caldecott et al., Single-strand break repair and genetic disease. Nat Rev Genet. Aug. 2008;9(8):619-31. doi: 10.1038/nrg2380.
Cameron, Recent advances in transgenic technology. Mol Biotechnol. Jun. 1997;7(3):253-65.
Cargill et al. Characterization of single-nucleotide polymorphisms in coding regions of human genes. Nat Genet. Jul. 1999;22(3):231-8.
Caron et al., Intracellular delivery of a Tat-eGFP fusion protein into muscle cells. Mol Ther. Mar. 2001;3(3):310-8.
Carroll et al., Gene targeting in *Drosophila* and Caenorhabditis elegans with zinc-finger nucleases. Methods Mol Biol. 2008;435:63-77. doi: 10.1007/978-1-59745-232-8_5.
Carroll et al., Progress and prospects: zinc-finger nucleases as gene therapy agents. Gene Ther. Nov. 2008;15(22):1463-8. doi: 10.1038/gt.2008.145. Epub Sep. 11, 2008.
Carroll, A Crispr approach to gene targeting. Mol Ther. Sep. 2012;20(9):1658-60. doi: 10.1038/mt.2012.171.
Carroll, Genome engineering with zinc-finger nucleases. Genetics. Aug. 2011;188(4):773-82. doi: 10.1534/genetics.111.131433. Review.
Cermak et al., Efficient design and assembly of custom TALEN and other TAL effecto-rbased constructs for DNA targeting. Nucleic Acids Res. Jul. 2011;39(12):e82. Doi: 10.1093/nar/gkr218. Epub Apr. 14, 2011.
Chadwick et al., In Vivo Base Editing of PCSK9 (Proprotein Convertase Subtilisin/Kexin Type 9) as a Therapeutic Alternative to Genome Editing. Arterioscler Thromb Vasc Biol. Sep. 2017;37(9):1741-1747. doi: 10.1161/ATVBAHA.117.309881. Epub Jul. 27, 2017.
Chaikind et al., A programmable Cas9-serine recombinase fusion protein that operates on DNA sequences in mammalian cells. Nucleic Acids Res. Nov. 16, 2016;44(20):9758-9770. Epub Aug. 11, 2016.
Charpentier et al., Biotechnology: Rewriting a genome. Nature. Mar. 7, 2013;495(7439):50-1. doi: 10.1038/495050a.
Chavez et al., Highly efficient Cas9-mediated transcriptional programming. Nat Methods. Apr. 2015;12(4):326-8. doi: 10.1038/nmeth.3312. Epub Mar. 2, 2015.
Chavez et al., Precise Cas9 targeting enables genomic mutation prevention. Proc Natl Acad Sci U S A. Apr. 3, 2018;115(14):3669-3673. doi: 10.1073/pnas.l718148115. Epub Mar. 1, 20189. bioRxiv preprint first posted online Jun. 14, 2016.
Chelico et al., Biochemical basis of immunological and retroviral responses to DNA-targeted cytosine deamination by activation-induced cytidine deaminase and APOBEC3G. J Biol Chem. Oct. 9, 2009;284(41):27761-5. doi: 10.1074/jbc.R109.052449. Epub Aug. 13, 2009.
Chelico et al., Stochastic properties of processive cytidine DNA deaminases AID and APOBEC3G. Philos Trans R Soc Lond B Biol Sci. Mar. 12, 2009;364(1517):583-93. doi: 10.1098/rstb.2008.0195.
Chen et al., Fusion protein linkers: property, design and functionality. Adv Drug Deliv Rev. Oct. 2013;65(10):1357-69. doi: 10.1016/j.addr.2012.09.039. Epub Sep. 29, 2012.
Chen et al., Structure of the DNA deaminase domain of the HIV-1 restriction factor APOBEC3G. Nature. Mar. 6, 2008;452(7183):116-9. doi: 10.1038/nature06638. Epub Feb. 20, 2008.
Chesnoy et al., Structure and function of lipid-DNA complexes for gene delivery. Annu Rev Biophys Biomol Struct. 2000;29:27-47.
Chew et al., A multifunctional AAV-CRISPR-Cas9 and its host response. Nat Methods. Oct. 2016;13(10):868-74. doi: 10.1038/nmeth.3993. Epub Sep. 5, 2016.
Chichili et al., Linkers in the structural biology of protein-protein interactions. Protein Science. 2013;22:153-67.
Chipev et al., A leucine—proline mutation in the H1 subdomain of keratin 1 causes epidermolytic hyperkeratosis. Cell. Sep. 4, 1992;70(5):821-8.
Cho et al., Analysis of off-target effects of CRISPR/Cas-derived RNA-guided endonucleases and nickases. Genome Res. Jan. 2014;24(1):132-41. doi: 10.1101/gr. 162339.113. Epub Nov. 19, 2013.
Cho et al., Targeted genome engineering in human cells with the Cas9 RNA-guided endonuclease. Nat Biotechnol. Mar. 2013;31(3):230-2. doi: 10.1038/nbt.2507. Epub Jan. 29, 2013.
Christian et al., Targeting G with TAL effectors: a comparison of activities of TALENs constructed with NN and NK repeat variable di-residues. PLoS One. 2012;7(9):e45383. doi: 10.1371/journal.pone.0045383. Epub Sep. 24, 2012.
Christian et al., Targeting DNA double-strand breaks with TAL effector nucleases. Genetics. Oct. 2010;186(2):757-61. Doi: 10.1534/genetics.110.120717. Epub Jul. 26, 2010.
Chu et al., Increasing the efficiency of homology-directed repair for CRISPR-Cas9-induced precise gene editing in mammalian cells. Nat Biotech. Feb. 13, 2015;33:543-8.
Chung-Il et al., Artificial control of gene expression in mammalian cells by modulating RNA interference through aptamer-small molecule interaction. RNA. May 2006;12(5):710-6. Epub Apr. 10, 2006.
Chylinski et al., The tracrRNA and Cas9 families of type II CRISPR-Cas immunity systems. RNA Biol. May 2013;10(5):726-37. doi: 10.4161/rna.24321. Epub Apr. 5, 2013.
Cobb et al., Directed evolution as a powerful synthetic biology tool. Methods. Mar. 15, 2013;60(1):81-90. doi: 10.1016/j.ymeth.2012.03.009. Epub Mar. 23, 2012.
Cole-Strauss et al., Correction of the mutation responsible for sickle cell anemia by an RNA-DNA oligonucleotide. Science. Sep. 6, 1996;273(5280):1386-9.
Cong et al., Multiplex genome engineering using CRISPR/Cas systems. Science. Feb. 15, 2013;339(6121):819-23. doi: 10.1126/science. 1231143. Epub Jan. 3, 2013.
Conticello, The AID/APOBEC family of nucleic acid mutators. Genome Biol. 2008;9(6):229. doi: 10.1186/GB-2008-9-6-229. Epub Jun. 17, 2008.
Covino et al., The CCL2/CCR2 Axis in the Pathogenesis of HIV-1 Infection: A New Cellular Target for Therapy? Current Drug Targets Dec. 2016;17(1):76-110. DOI: 10.2174/138945011701151217110917.
Cox et al., Conditional gene expression in the mouse inner ear using Cre-loxP. J Assoc Res Otolaryngol. Jun. 2012;13(3):295-322. doi: 10.1007/sl0162-012-0324-5. Epub Apr. 24, 2012.
Cox et al., Therapeutic genome editing: prospects and challenges. Nat Med. Feb. 2015;21(2):121-31. doi: 10.1038/nm.3793.
Cradick et al., CRISPR/Cas9 systems targeting β-globin and CCR5 genes have substantial off-target activity. Nucleic Acids Res. Nov. 1. 2013;41(20):9584-92. doi: 10.1093/nar/gkt714. Epub Aug. 11, 2013.

(56) References Cited

OTHER PUBLICATIONS

Cradick et al., ZFN-site searches genomes for zinc finger nuclease target sites and off-target sites. BMC Bioinformatics. May 13, 2011;12:152. doi: 10.1186/1471-2105-12-152.
Cradick et al., Zinc-finger nucleases as a novel therapeutic strategy for targeting hepatitis B virus DNAs. Mol Ther. May 2010;18(5):947-54. Doi: 10.1038/mt.2010.20. Epub Feb. 16, 2010.
Cui et al., Targeted integration in rat and mouse embryos with zinc-finger nucleases. Nat Biotechnol. Jan. 2011;29(1):64-7. Doi: 10.1038/nbt.1731. Epub Dec. 12, 2010.
Cunningham et al., Ensembl 2015. Nucleic Acids Res. Jan. 2015;43(Database issue):D662-9. doi: 10.1093/nar/gku1010. Epub Oct. 28, 2014.
D'Adda di Fagagna et al., The Gam protein of bacteriophage Mu is an orthologue of eukaryotic Ku. EMBO Rep. Jan. 2003;4(1):47-52.
Dahlem et al., Simple methods for generating and detecting locus-specific mutations induced with TALENs in the zebrafish genome. PLoS Genet. 2012;8(8):e1002861. doi: 10.1371/journal.pgen.1002861. Epub Aug. 16, 2012.
Davis et al., DNA double strand break repair via non-homologous end-joining. Transl Cancer Res. Jun. 2013;2(3):130-143.
Davis et al., Small molecule-triggered Cas9 protein with improved genome-editing specificity. Nat Chem Biol. May 2015;11(5):316-8. doi: 10.1038/nchembio.1793. Epub Apr. 6, 2015.
De Souza, Primer: genome editing with engineered nucleases. Nat Methods. Jan. 2012;9(1):27.
Deltcheva et al., CRISPR RNA maturation by trans-encoded small RNA and host factor RNase III. Nature. Mar. 31, 2011;471(7340):602-7. doi: 10.1038/nature09886.
Dicarlo et al., Genome engineering in *Saccharomyces cerevisiae* using CRISPR-Cas systems. Nucleic Acids Research Apr. 2013;41(7):4336-43.
Ding et al., A Talen genome-editing system for generating human stem cell-based disease models. Cell Stem Cell. Feb. 7, 2013;12(2):238-51. Doi: 10.1016/j.stem.2012.11.011. Epub Dec. 13, 2012.
Ding et al., Permanent alteration of PCSK9 with in vivo CRISPR-Cas9 genome editing. Circ Res. Aug. 15, 2014;115(5):488-92. doi: 10.1161/CIRCRESAHA.115.304351. Epub Jun. 10, 2014.
Dixon et al., Reengineering orthogonally selective riboswitches. Proc Natl Acad Sci U S A. Feb. 16, 2010;107(7):2830-5. doi: 10.1073/pnas.0911209107. Epub Jan. 26, 2010.
Doench et al., Optimized sgRNA design to maximize activity and minimize off-target effects of CRISPR-Cas9. Nat Biotechnol. Feb. 2016;34(2):184-191. doi: 10.1038/nbt.3437.
Doudna et al., Genome editing. The new frontier of genome engineering with CRISPR-Cas9. Science. Nov. 28, 2014;346(6213):1258096. doi: 10.1126/science. 1258096.
Doyon et al., Heritable targeted gene disruption in zebrafish using designed zinc-finger nucleases. Nat Biotechnol. Jun. 2008;26(6):702-8. Doi: 10.1038/nbtl409. Epub May 25, 2008.
Dunaime, Breakthrough method means CRISPR just got a lot more relevant to human health. The Verge. Apr. 20, 2016. http://www.theverge.eom/2016/4/20/l 1450262/crispr-base-editing-single-nucleotides-dna-gene-liu-harvard.
During et al., Controlled release of dopamine from a polymeric brain implant: in vivo characterization. Ann Neurol. Apr. 1989;25(4):351-6.
East-Seletsky et al., Two distinct RNase activities of CRISPR-C2c2 enable guide-RNA processing and RNA detection. Nature Oct. 2016;538(7624):270-3.
Edwards et al., An *Escherichia coli* tyrosine transfer RNA is a leucine-specific transfer RNA in the yeast *Saccharomyces cerevisiae*. Proc Natl Acad Sci U S A. Feb. 15, 1991;88(4):1153-6.
Edwards et al., Crystal structures of the thi-box riboswitch bound to thiamine pyrophosphate analogs reveal adaptive RNA-small molecule recognition. Structure. Sep. 2006; 14(9):1459-68.
Eiler et al., Structural Basis for the Fast Self-Cleavage Reaction Catalyzed by the Twister Ribozyme. Proc Natl Acad Sci U S A. Sep. 9, 2014; 111(36):13028-33. doi: 10.1073/pnas. 1414571111. Epub Aug. 25, 2014.
Eltoukhy et al., Nucleic acid-mediated intracellular protein delivery by lipid-like nanoparticles. Biomaterials. Aug. 2014;35(24):6454-61. doi: 10.1016/j.biomaterials.2014.04.014. Epub May 13, 2014.
Endo et al., Toward establishing an efficient and versatile gene targeting system in higher plants. Biocatalysis and Agricultural Biotechnology 2014;3,(1):2-6.
Esvelt et al., A system for the continuous directed evolution of biomolecules. Nature. Apr. 28, 2011;472(7344):499-503. doi: 10.1038/nature09929. Epub Apr. 10, 2011.
Esvelt et al., Genome-scale engineering for systems and synthetic biology. Mol Syst Biol. 2013;9:641. doi: 10.1038/msb.2012.66.
Esvelt et al., Orthogonal Cas9 proteins for RNA-guided gene regulation and editing. Nat Methods. Nov. 2013;10(11):1116-21. doi: 10.1038/nmeth.2681. Epub Sep. 29, 2013.
Fagerlund et al., The Cpf1 CRISPR-Cas protein expands genome-editing tools. Genome Biology Nov. 17, 2015;16:251. https://doi.org/10.1186/s13059-015-0824-9.
Fang et al., Synthetic Studies Towards Halichondrins: Synthesis of the Left Halves of Norhalichondrins and Homohalichondrins. Tetrahedron Letters 1992;33(12):1557-1560.
Farhood et al., Codelivery to mammalian cells of a transcriptional factor with cis-acting element using cationic liposomes. Anal Biochem. Feb. 10, 1995;225(1):89-93.
Felletti et al., Twister Ribozymes as Highly Versatile Expression Platforms for Artificial Riboswitches. Nat Commun. Sep. 27, 2016;7:12834. doi: 10.1038/ncomms12834.
Ferretti et al., Complete genome sequence of an MI strain of *Streptococcus pyogenes*. Proc Natl Acad Sci U S A. Apr. 10, 2001;98(8):4658-63.
Ferry et al., Rational design of inducible CRISPR guide RNAs for de novo assembly of transcriptional programs. Nat Commun. Mar. 3, 2017;8:14633. doi: 10.1038/ncomms14633.
Fine et al., Trans-spliced Cas9 allows cleavage of HBB and CCR5 genes in human cells using compact expression cassettes. Scientific Reports 2015;5(1):Article No. 10777. doi:10.1038/srep10777. With Supplementary Information.
Fischer et al., Cryptic epitopes induce high-titer humoral immune response in patients with cancer. J Immunol. Sep. 1, 2010;185(5):3095-102. doi: 10.4049/jimmunol.0902166. Epub Jul. 26, 2010.
Fogg et al., New applications for phage integrases. J Mol Biol. Jul. 29, 2014;426(15):2703-16. doi: 10.1016/j.jmb.2014.05.014. Epub May 22, 2014.
Fonfara et al., Phylogeny of Cas9 determines functional exchangeability of dual-RNA and Cas9 among orthologous type II CRISPR-Cas systems. Nucleic Acids Res. Feb. 2014;42(4):2577-90. doi: 10.1093/nar/gkt1074. Epub Nov. 22, 2013.
Freshney, Culture of Animal Cells. A Manual of Basic Technique. Alan R. Liss, Inc. New York. 1983;4.
Fu et al., Improving CRISPR-Cas nuclease specificity using truncated guide RNAs. Nat Biotechnol. Mar. 2014;32(3):279-84. doi: 10.1038/nbt.2808. Epub Jan. 26, 2014.
Fu et al., High-frequency off-target mutagenesis induced by CRISPR-Cas nucleases in human cells. Nat Biotechnol. Sep. 2013;31(9):822-6. doi: 10.1038/nbt.2623. Epub Jun. 23, 2013.
Fuchs et al., Polyarginine as a multifunctional fusion tag. Protein Sci. Jun. 2005; 14(6):1538-44.
Fujisawa et al., Disease-associated mutations in CIAS1 induce cathepsin B-dependent rapid cell death of human THP-1 monocytic cells. Blood. Apr. 1, 2007;109(7):2903-11.
Fukui et al., DNA Mismatch Repair in Eukaryotes and Bacteria. J Nucleic Acids. Jul. 27, 2010;2010. pii: 260512. doi: 10.4061/2010/260512.
Fung et al., Repair at single targeted DNA double-strand breaks in pluripotent and differentiated human cells. PLoS One. 2011;6(5):e20514. doi: 10.1371/journal.pone.0020514. Epub May 25, 2011.
Gaj et al., A comprehensive approach to zinc-finger recombinase customization enables genomic targeting in human cells. Nucleic Acids Res. Feb. 6, 2013;41(6):3937-46.
Gaj et al., Enhancing the specificity of recombinase-mediated genome engineering through dimer interface redesign. J Am Chem Soc. Apr. 2, 2014;136(13):5047-56. doi: 10.1021/ja4130059. Epub Mar. 20, 2014.

(56) References Cited

OTHER PUBLICATIONS

Gaj et al., Expanding the scope of site-specific recombinases for genetic and metabolic engineering. Biotechnol Bioeng. Jan. 2014;111(1):1-15. doi: 10.1002/bit.25096. Epub Sep. 13, 2013.
Gaj et al., ZFN, TALEN, and CRISPR/Cas-based methods for genome engineering. Trends Biotechnol. Jul. 2013;31(7):397-405. doi: 10.1016/j.tibtech.2013.04.004. Epub May 9, 2013.
Gallo et al., A novel pathogenic PSEN1 mutation in a family with Alzheimer's disease: phenotypical and neuropathological features. J Alzheimers Dis. 2011;25(3):425-31. doi: 10.3233/JAD-2011-110185.
Gao et al., DNA-guided genome editing using the Natronobacterium gregoryi Argonaute. Nat Biotechnol. Jul. 2016;34(7):768-73. doi: 10.1038/nbt.3547. Epub May 2, 2016.
Gardlik et al., Vectors and delivery systems in gene therapy. Med Sci Monit. Apr. 2005;11(4):RA1 10-21. Epub Mar. 24, 2005.
Garneau et al., The CRISPR/Cas bacterial immune system cleaves bacteriophage and plasmid DNA. Nature. Nov. 4, 2010;468(7320):67-71. doi: 10.1038/nature09523.
Gasiunas et al., Cas9-crRNA ribonucleoprotein complex mediates specific DNA cleavage for adaptive immunity in bacteria. Proc Natl Acad Sci U S A. Sep. 25, 2012;109(39):E2579-86. Epub Sep. 4, 2012. Supplementary materials included.
Gasiunas et al., RNA-dependent DNA endonuclease Cas9 of the CRISPR system: Holy Grail of genome editing? Trends Microbiol. Nov. 2013;21(11):562-7. doi: 10.1016/j.tim.2013.09.001. Epub Oct. 1, 2013.
GENBANK Submission; NIH/NCBI, Accession No. J04623. Kita et al., Apr. 26, 1993. 2 pages.
GENBANK Submission; NIH/NCBI, Accession No. NC_002737.1. Ferretti et al., Jun. 27, 2013. 1 page.
GENBANK Submission; NIH/NCBI, Accession No. NC_015683.1. Trost et al., Jul. 6, 2013. 1 page.
GENBANK Submission; NIH/NCBI, Accession No. NC_016782.1. Trost et al., Jun. 11, 2013. 1 page.
GENBANK Submission; NIH/NCBI, Accession No. NC_016786.1. Trost et al., Aug. 28, 2013. 1 page.
GENBANK Submission; NIH/NCBI, Accession No. NC_017053.1. Fittipaldi et al., Jul. 6, 2013. 1 page.
GENBANK Submission; NIH/NCBI, Accession No. NC_017317.1. Trost et al., Jun. 11, 2013. 1 page.
GENBANK Submission; NIH/NCBI, Accession No. NC_017861.1. Heidelberg et al., Jun. 11, 2013. 1 page.
GENBANK Submission; NIH/NCBI, Accession No. NC_018010.1. Lucas et al., Jun. 11, 2013. 2 pages.
GENBANK Submission; NIH/NCBI, Accession No. NC_018721.1. Feng et al., Jun. 11, 2013. 1 pages.
GENBANK Submission; NIH/NCBI, Accession No. NC_021284.1. Ku et al., Jul. 12, 2013. 1 page.
GENBANK Submission; NIH/NCBI, Accession No. NC_021314.1. Zhang et al., Jul. 15, 2013. 1 page.
GENBANK Submission; NIH/NCBI, Accession No. NC_021846.1. Lo et al., Jul. 22, 2013. 1 page.
GENBANK Submission; NIH/NCBI, Accession No. NM_174936. Guo et al., Oct. 28, 2015. 6 pages.
GENBANK Submission; NIH/NCBI, Accession No. NP_472073.1. Glaser et al., Jun. 27, 2013. 2 pages.
GENBANK Submission; NIH/NCBI, Accession No. P42212. Prasher et al., Mar. 19, 2014. 7 pages.
GENBANK Submission; NIH/NCBI, Accession No. YP_002342100.1. Bernardini et al., Jun. 10, 2013. 2 pages.
GENBANK Submission; NIH/NCBI, Accession No. YP_002344900.1. Gundogdu et al., Mar. 19, 2014. 2 pages.
GENBANK Submission; NIH/NCBI, Accession No. YP_820832.1. Makarova et al., Aug. 27, 2013. 2 pages.
Gerber et al., RNA editing by base deamination: more enzymes, more targets, new mysteries. Trends Biochem Sci. Jun. 2001;26(6):376-84.
Gersbach et al., Directed evolution of recombinase specificity by split gene reassembly. Nucleic Acids Res. Jul. 2010;38(12):4198-206. doi: 10.1093/nar/gkql25. Epub Mar. 1, 2010.
Gersbach et al., Targeted plasmid integration into the human genome by an engineered zinc-finger recombinase. Nucleic Acids Res. Sep. 1, 2011;39(17):7868-78. doi: 10.1093/nar/pkr421. Epub Jun. 7, 2011.
Gilbert et al., CRISPR-mediated modular RNA-guided regulation of transcription in eukaryotes. Cell. 2013 154(2):442-51.
Gilleron et al., Image-based analysis of lipid nanoparticle-mediated siRNA delivery, intracellular trafficking and endosomal escape. Nat Biotechnol. Jul. 2013;31(7):638-46. doi: 10.1038/nbt.2612. Epub Jun. 23, 2013.
Gonzalez et al., An iCRISPR platform for rapid, multiplexable, and inducible genome editing in human pluripotent stem cells. Cell Stem Cell. Aug. 7, 2014;15(2):215-26. doi: 10.1016/j.stem.2014.05.018. Epub Jun. 12, 2014.
Grainge et al., The integrase family of recombinase: organization and function of the active site. Mol Microbiol. Aug. 1999;33(3):449-56.
Guilinger et al., Broad specificity profiling of TALENs results in engineered nucleases with improved DNA-cleavage specificity. Nat Methods. Apr. 2014;11(4):429-35. doi: 10.1038/nmeth.2845. Epub Feb. 16, 2014.
Guilinger et al., Fusion of catalytically inactive Cas9 to FokI nuclease improves the specificity of genome modification. Nat Biotechnol. Jun. 2014;32(6):577-82. doi: 10.1038/nbt.2909. Epub Apr. 25, 2014.
Guo et al., Protein tolerance to random amino acid change. Proc Natl Acad Sci U S A. Jun. 22, 2004;101(25):9205-10. Epub Jun. 14, 2004.
Haeussler et al., Evaluation of off-target and on-target scoring algorithms and integration into the guide RNA selection tool CRISPOR. Genome Biol. Jul. 5, 2016;17(1):148. doi: 10.1186/s13059-016-1012-2.
Hale et al., RNA-guided RNA cleavage by a CRISPR RNA-Cas protein complex. Cell. Nov. 25, 2009;139(5):945-56. doi: 10.1016/j.cell.2009.07.040.
Hamano-Takaku et al., A mutant *Escherichia coli* tyrosyl-tRNA synthetase utilizes the unnatural amino acid azatyrosine more efficiently than tyrosine. J Biol Chem. Dec. 22, 2000;275(51):40324-8.
Han, New CRISPR/Cas9-based Tech Edits Single Nucleotides Without Breaking DNA. Genome Web, Apr. 20, 2016. https://www.genomeweb.com/gene-silencinggene-editing/new-crisprcas9-based-tech-edits-single-nucleotides-without-breaking-dna.
Harrington et al., Recent developments and current status of gene therapy using viral vectors in the United Kingdom. BMJ. 2004;329(7470):839?842. doi:10.1136/bmj.329.7470.839.
Harris et al., RNA Editing Enzyme APOBEC1 and Some of Its Homologs Can Act as DNA Mutators. Mol Cell. Nov. 2002;10(5):1247-53.
Hartung et al., Correction of metabolic, craniofacial, and neurologic abnormalities in MPS I mice treated at birth with adeno-associated virus vector transducing the human alpha-L-iduronidase gene. Mol Ther. Jun. 2004;9(6):866-75.
Hasadsri et al., Functional protein delivery into neurons using polymeric nanoparticles. J Biol Chem. Mar. 13, 2009;284(11):6972-81. doi: 10.1074/jbc.M805956200. Epub Jan. 7, 2009.
Hayes et al., Stop codons preceded by rare arginine codons are efficient determinants of SsrA tagging in *Escherichia coli*. Proc Natl Acad Sci U S A. Mar. 19, 2002;99(6):3440-5. Epub Mar. 12, 2002.
Heller et al., Replisome assembly and the direct restart of stalled replication forks. Nat Rev Mol Cell Biol. Dec. 2006;7(12):932-43. Epub Nov. 8, 2006.
Hess et al., Directed evolution using dCas9-targeted somatic hypermutation in mammalian cells. Nat Methods. Dec. 2016;13(12):1036-1042. doi: 10.1038/nmeth.4038. Epub Oct. 31, 2016.
Hickford et al., Antitumour polyether macrolides: four new halichondrins from the New Zealand deep-water marine sponge *Lissodendoryx* sp. Bioorg Med Chem. Mar. 15, 2009;17(6):2199-203. doi: 10.1016/j.bmc.2008.10.093. Epub Nov. 19, 2008.

(56) References Cited

OTHER PUBLICATIONS

Hida et al., Directed evolution for drug and nucleic acid; delivery. Adv Drug Deliv Rev. Dec. 22, 2007;59(15):1562-78. Epub Aug. 28, 2007.; Review.

Hill et al., Functional analysis of conserved histidines in ADP-glucose pyrophosphorylase from *Escherichia coli*.Biochem Biophys Res Commun. Mar. 17, 1998;244(2):573-7.

Hilton et al., Enabling functional genomics with genome engineering. Genome Res. Oct. 2015;25(10):1442-55. doi: 10.1101/gr.190124.115.

Hirano et al., Structural Basis for the Altered PAM Specificities of Engineered CRISPR-Cas9. Mol Cell. Mar. 17, 2016;61(6):886-94. doi: 10.1016/j.molcel.2016.02.018.

Hockemeyer et al., Efficient targeting of expressed and silent genes in human ESCs and iPSCs using zinc-finger nucleases. Nat Biotechnol. Sep. 2009;27(9):851-7. doi: 10.1038/nbt.1562. Epub Aug. 13, 2009.

Hockemeyer et al., Genetic engineering of human pluripotent cells using TALE nucleases. Nat Biotechnol. Jul. 7, 2011;29(8):731-4. doi: 10.1038/nbt.1927.

Holden et al., Crystal structure of the anti-viral APOBEC3G catalytic domain and functional implications. Nature. Nov. 6, 2008;456(7218):121-4. doi: 10.1038/nature07357. Epub Oct. 12, 2008.

Hondares et al., Peroxisome Proliferator-activated Receptor ? (PPAR?) Induces PPAR? Coactivator 1? (PGC-1?) Gene Expression and Contributes to Thermogenic Activation of Brown Fat. J Biol. Chem Oct. 2011;286(50):43112-22. doi: 10.1074/jbc.M111.252775.

Horvath et al., CRISPR/Cas, the immune system of bacteria and archaea. Science. Jan. 8, 2010;327(5962): 167-70. doi: 10.1126/science.1179555.

Horvath et al., Diversity, Activity, and Evolution of CRISPR Loci in *Streptococcus thermophilus*. J Bacteriol. Feb. 2008;190(4):1401-12. doi: 10.1128/JB.01415-07. Epub Dec. 7, 2007.

Hou et al., Efficient genome engineering in human pluripotent stem cells using Cas9 from Neisseria meningitidis. Proc Natl Acad Sci U S A. Sep. 24, 2013;110(39): 15644-9. doi: 10.1073/pnas.1313587110. Epub Aug. 12, 2013.

Houdebine, The methods to generate transgenic animals and to control transgene expression. J Biotechnol. Sep. 25, 2002;98(2-3):145-60.

Howard et al., Intracerebral drug delivery in rats with lesion-induced memory deficits. J Neurosurg. Jul. 1989;71(1):105-12.

Hower et al., Shape-based peak identification for ChIP-Seq. BMC Bioinformatics. Jan. 12, 2011;12:15. doi: 10.1186/1471-2105-12-15.

Hsu et al., DNA targeting specificity of RNA-guided Cas9 nucleases. Nat Biotechnol. Sep. 2013;31(9):827-32. doi: 10.1038/nbt.2647. Epub Jul. 21, 2013.

Hu et al., Chemical Biology Approaches to Genome Editing: Understanding, Controlling, and Delivering Programmable Nucleases. Cell Chem Biol. Jan. 21, 2016;23(1):57-73. doi: 10.1016/j.chembiol.2015.12.009.

Hu et al., Evolved Cas9 variants with broad PAM compatibility and high DNA specificity. Nature. Apr. 5, 2018;556(7699):57-63. doi: 10.1038/nature26155. Epub Feb. 28, 2018.

Huang et al., Heritable gene targeting in zebrafish using customized TALENs. Nat Biotechnol. Aug. 5, 2011;29(8):699-700. doi: 10.1038/nbt.1939.

Humbert et al., Targeted gene therapies: tools, applications, optimization. Crit Rev Biochem Mol Biol. May-Jun. 2012;47(3):264-81. doi: 10.3109/10409238.2012.658112.

Hurt et al., Highly specific zinc finger proteins obtained by directed domain shuffling and cell-based selection. Proc Natl Acad Sci U S A. Oct. 14, 2003; 100(21):12271-6. Epub Oct. 3, 2003.

Husimi, Selection and evolution of bacteriophages in cellstat. Adv Biophys. ; 1989;25:1-43. Review.

Hwang et al., Efficient genome editing in zebrafish using a CRISPR-Cas system. Nat Biotechnol. Mar. 2013;31(3):227-9. doi: 10.1038/nbt.2501. Epub Jan. 29, 2013.

Hwang et al., Efficient In Vivo Genome Editing Using RNA-Guided Nucleases. Nat Biotechnol. Mar. 2013; 31(3): 227-229. doi: 10.1038/nbt.2501. Epub Jan. 29, 2013.

Ikediobi et al., Mutation analysis of 24 known cancer genes in the NCI-60 cell line set. Mol Cancer Ther. Nov. 2006;5(11):2606-12. Epub Nov. 6, 2006.

International Preliminary Report on Patentability for PCT/US2017/046144, dated Feb. 21, 2019.

International Search Report and Written Opinion for PCT/US2017/046144, dated Oct. 10, 2017.

Irrthum et al., Congenital hereditary lymphedema caused by a mutation that inactivates VEGFR3 tyrosine kinase. Am J Hum Genet. Aug. 2000;67(2):295-301. Epub Jun. 9, 2000.

Ishino et al., Nucleotide sequence of the iap gene, responsible for alkaline phosphatase isozyme conversion in *Escherichia coli*, and identification of the gene product. J Bacteriol. Dec. 1987;169(12):5429-33.

Jamieson et al., Drug discovery with engineered zinc-finger proteins. Nat Rev Drug Discov. May 2003;2(5):361-8.

Jansen et al., Backbone and nucleobase contacts to glucosamine-6-phosphate in the glmS ribozyme. Nat Struct Mol Biol. Jun. 2006;13(6):517-23. Epub May 14, 2006.

Jansen et al., Identification of genes that are associated with DNA repeats in prokaryotes. Mol Microbiol. Mar. 2002;43(6):1565-75.

Jenkins et al., Comparison of a preQ1 riboswitch aptamer in metabolite-bound and free states with implications for gene regulation. J Biol Chem. Jul. 15, 2011;286(28):24626-37. doi: 10.1074/jbc.M111.230375. Epub May 18, 2011.

Jiang et al., RNA-guided editing of bacterial genomes using CRISPR-Cas systems. Nat Biotechnol. Mar. 2013;31(3):233-9. doi: 10.1038/nbt.2508. Epub Jan. 29, 2013.

Jiang et al., Structural Biology. A Cas9-guide RNA Complex Preorganized for Target DNA Recognition. Science. Jun. 26, 2015;348(6242):1477-81. doi: 10.1126/science.aab1452.

Jiang et al., Structures of a CRISPR-Cas9 R-loop complex primed for DNA cleavage. Science. Feb. 19, 2016;351(6275):867-71. doi: 10.1126/science.aad8282. Epub Jan. 14, 2016.

Jinek et al., A programmable dual-RNA-guided DNA endonuclease in adaptive bacterial immunity. Science. Aug. 17, 2012;337(6096):816-21. doi: 10.1126/science 1225829. Epub Jun. 28, 2012.

Jinek et al., RNA-programmed genome editing in human cells. Elife. Jan. 29, 2013;2:e00471. doi: 10.7554/eLife.00471.

Jinek et al., Structures of Cas9 endonucleases reveal RNA-mediated conformational activation. Science. Mar. 14, 2014;343(6176):1247997. doi: 10.1126/science.1247997. Epub Feb. 6, 2014.

Jore et al., Structural basis for CRISPR RNA-guided DNA recognition by Cascade. Nat Struct Mol Biol. May 2011;18(5):529-36. doi: 10.1038/nsmb.2019. Epub Apr. 3, 2011.

Joung et al.,TALENs: a widely applicable technology for targeted genome editing. Nat Rev Mol Cell Biol. Jan. 2013;14(1):49-55. doi: 10.1038/nrm3486. Epub Nov. 21, 2012.

Kaiser et al., Gene therapy. Putting the fingers on gene repair. Science. Dec. 23, 2005;310(5756):1894-6.

Kakiyama et al., A peptide release system using a photo-cleavable linker in a cell array format for cell-toxicity analysis. Polymer J. Feb. 27, 2013;45:535-9.

Kandavelou et al., Targeted manipulation of mammalian genomes using designed zinc finger nucleases. Biochem Biophys Res Commun. Oct. 9, 2009;388(1):56-61. doi: 10.1016/j.bbrc.2009.07.112. Epub Jul. 25, 2009.

Kang et al., Structural Insights into riboswitch control of the biosynthesis of queuosine, a modified nucleotide found in the anticodon of tRNA. Mol Cell. Mar. 27, 2009;33(6):784-90. doi: 10.1016/j.molcel.2009.02.019. Epub Mar. 12, 2009.

Kappel et al., Regulating gene expression in transgenic animals. Curr Opin Biotechnol. Oct. 1992;3(5):548-53.

Karpenshih et al., From yeast to mammals: recent advances in genetic control of homologous recombination. DNA Repair (Amst). Oct. 1, 2012;11(10):781-8. doi: 10.1016/j.dnarep.2012.07.001. Epub Aug. 11, 2012. Review.

(56) References Cited

OTHER PUBLICATIONS

Karpinsky et al., Directed evolution of a recombinase that excises the provirus of most HIV-1 primary isolates with high specificity. Nat Biotechnol. Apr. 2016;34(4):401-9. doi: 10.1038/nbt.3467. Epub Feb. 22, 2016.
Kaya et al., A bacterial Argonaute with noncanonical guide RNA specificity. Proc. Natl. Acad. Sci. USA Apr. 2016;113(15):4057-62.
Kellendonk et al., Regulation of Cre recombinase activity by the synthetic steroid RU 486. Nucleic Acids Res. Apr. 15, 1996;24(8):1404-11.
Kiga et al., An engineered *Escherichia coli* tyrosyl-tRNA synthetase for site-specific incorporation of an unnatural amino acid into proteins in eukaryotic translation and its application in a wheat germ cell-free system. Proc Natl Acad Sci U S A. Jul. 23, 2002;99(15):9715-20. Epub Jul. 3, 2002.
Kim et al., A library of TAL effector nucleases spanning the human genome. Nat Biotechnol. Mar. 2013;31(3):251-8. Doi: 10.1038/nbt.2517. Epub Feb. 17, 2013.
Kim et al., Genome-wide target specificities of CRISPR RNA-guided programmable deaminases. Nat Biotechnol. May 2017;35(5):475-480. doi: 10.1038/nbt.3852. Epub Apr. 10, 2017.
Kim et al., Highly efficient RNA-guided base editing in mouse embryos. Nat Biotechnol. May 2017;35(5):435-437. doi: 10.1038/nbt.3816. Epub Feb. 27, 2017.
Kim et al., Highly efficient RNA-guided genome editing in human cells via delivery of purified Cas9 ribonucleoproteins. Genome Res. Jun. 2014;24(6):012-9. doi: 10.1101/gr.171322.113. Epub Apr. 2, 2014.
Kim et al., Increasing the genome-targeting scope and precision of base editing with engineered Cas9-cytidine deaminase fusions. Nat Biotechnol. Apr. 2017;35(4):371-376. doi: 10.1038/nbt.3803. Epub Feb. 13, 2017.
Kim et al., TALENs and ZFNs are associated with different mutationsignatures. Nat Methods. Mar. 2013;10(3):185. doi: 10.1038/nmeth.2364. Epub Feb. 10, 2013.
Kim et al., Targeted genome editing in human cells with zinc finger nucleases constructed via modular assembly. Genome Res. Jul. 2009;19(7):1279-88. doi: 10.1101/gr.089417.108. Epub May 21, 2009.
Kim et al., The role of apolipoprotein E in Alzheimer's disease. Neuron. Aug. 13, 2009;63(3):287-303. doi: 10.1016/j.neuron.2009.06.026.
Kim et al., Transcriptional repression by zinc finger peptides. Exploring the potential for applications in gene therapy. J Biol Chem. Nov. 21, 1997;272(47):29795-800.
Kitamura et al., Uracil DNA glycosylase counteracts APOBEC3G-induced hypermutation of hepatitis B viral genomes: excision repair of covalently closed circular DNA. PLoS Pathog. 2013;9(5):e1003361. doi: 10.1371/journal.ppat.1003361. Epub May 16, 2013.
Klauser et al., An engineered small RNA-mediated genetic switch based on a ribozyme expression platform. Nucleic Acids Res. May 1, 2013;41(10):5542-52. doi: 10.1093/nar/gkt253. Epub Apr. 12, 2013.
Klein et al., Cocrystal structure of a class I preQ1 riboswitch reveals a pseudoknot recognizing an essential hypermodified nucleobase. Nat Struct Mol Biol. Mar. 2009;16(3):343-4. doi: 10.1038/nsmb.1563.Epub Feb. 22, 2009.
Kleinstiver et al., Broadening the targeting range of *Staphylococcus aureus* CRISPR-Cas9 by modifying PAM recognition. Nat Biotechnol. Dec. 2015;33(12):1293-1298. doi: 10.1038/nbt.3404. Epub Nov. 2, 2015.
Kleinstiver et al., Engineered CRISPR-Cas9 nucleases with altered PAM specificities. Nature. Jul. 23, 2015;523(7561):481-5. doi: 10.1038/nature14592. Epub Jun. 22, 2015.
Kleinstiver et al., High-fidelity CRISPR-Cas9 nucleases with No. detectable genome-wide off-target effects. Nature. Jan. 28, 2016;529(7587):490-5. doi: 10.1038/nature16526. Epub Jan. 6, 2016.
Kleinstiver et al., Monomeric site-specific nucleases for genome editing. Proc Natl Acad Sci U S A. May 22, 2012;109(21):8061-6. doi: 10.1073/pnas.1117984109. Epub May 7, 2012.
Klippel et al., Isolation and characterization of unusual gin mutants. EMBO J. Dec. 1, 1988;7(12):3983-9.
Klippel et al., The DNA invertase Gin of phage Mu: formation of a covalent complex with DNA via a phosphoserine at amino acid position 9. EMBO J. Apr. 1988;7(4):1229-37.
Kobori et al., Deep Sequencing Analysis of Aptazyme Variants Based on a Pistol Ribozyme. ACS Synth Biol. Jul. 21, 2017;6(7):1283-1288. doi: 10.1021/acssynbio.7b00057. Epub Apr. 14, 2017.
Kohli et al., Local sequence targeting in the AID/APOBEC family differentially impacts retroviral restriction and antibody diversification. J Biol Chem. Dec. 24, 2010;285(52):40956-64. doi: 10.1074/jbc.M1110.177402. Epub Oct. 6, 2010.
Köhrer et al., A possible approach to site-specific insertion of two different unnatural amino acids into proteins in mammalian cells via nonsense suppression. Chem Biol. Nov. 2003;10(11):1095-102.
Köhrer et al., Complete set of orthogonal 21st aminoacyl-tRNA synthetase-amber, ochre and opal suppressor tRNA pairs: concomitant suppression of three different termination codons in an mRNA in mammalian cells. Nucleic Acids Res. Dec. 1, 2004;32(21):6200-11. Print 2004.
Komor et al., CRISPR-Based Technologies for the Manipulation of Eukaryotic Genomes. Cell. Jan. 12, 2017;168(1-2):20-36. doi: 10.1016/j.cell.2016.10.044.
Komor et al., Improved base excision repair inhibition and bacteriophage Mu Gam protein yields C:G-to-T:A base editors with higher efficiency and product purity. Sci Adv. Aug. 30, 2017;3(8):eaao4774. doi: 10.1126/sciadv.aao4774. eCollection Aug. 2017.
Komor et al., Programmable editing of a target base in genomic DNA without double-stranded DNA cleavage. Nature. Apr. 20, 2016;533(7603):420-4. doi: 10.1038/nature17946.
Koonin et al., Diversity, classification and evolution of CRISPR-Cas systems. Curr Opin Microbiol. 2017;37:67?78. doi:10.1016/j.mib.2017.05.008.
Kouzminova et al., Patterns of chromosomal fragmentation due to uracil-DNA incorporation reveal a novel mechanism of replication-dependent double-stranded breaks. Mol Microbiol. Apr. 2008;68(1):202-15. doi: 10.1111/j.1365-2958.2008.06149.x.
Kowal et al., Exploiting unassigned codons in Micrococcus luteus for tRNA-based amino acid mutagenesis. Nucleic Acids Res. Nov. 15, 1997;25(22):4685-9.
Kumar et al., Structural and functional consequences of the mutation of a conserved arginine residue in alphaA and alphaB crystallins. J Biol Chem. Aug. 20, 1999;274(34):24137-41.
Kundu et al., Leucine to proline substitution by SNP at position 197 in Caspase-9 gene expression leads to neuroblastoma: a bioinformatics analysis. 3 Biotech. 2013; 3:225-34.
Kunz et al., DNA Repair in mammalian cells: Mismatched repair: variations on a theme. Cell Mol Life Sci. Mar. 2009;66(6):1021-38. doi: 10.1007/s00018-009-8739-9.
Kury et al., De Novo Disruption of the Proteasome Regulatory Subunit PSMD12 Causes a Syndromic Neurodevelopmental Disorder. Am J Hum Genet. Feb. 2, 2017;100(2):352-363. doi: 10.1016/j.ajhg.2017.01.003. Epub Jan. 26, 2017.
Kuscu et al., CRISPR-STOP: gene silencing through base-editing-induced nonsense mutations. Nat Methods. Jul. 2017;14(7):710-712. doi: 10.1038/nmeth.4327. Epub Jun. 5, 2017.
Kuscu et al., Genome-wide analysis reveals characteristics of off-target sites bound by the Cas9 endonuclease. Nat Biotechnol. Jul. 2014;32(7):677-83. doi: 10.1038/nbt.2916. Epub May 18, 2014.
Kwon et al., Chemical basis of glycine riboswitch cooperativity. RNA. Jan. 2008;14(1):25-34. Epub Nov. 27, 2007.
Landrum et al., ClinVar: public archive of interpretations of clinically relevant variants. Nucleic Acids Res. Jan. 4, 2016;44(D1):D862-8. doi: 10.1093/nar/gkv1222. Epub Nov. 17, 2015.
Langer et al., Chemical and Physical Structure of Polymers as Carriers for Controlled Release of Bioactive Agents: A Review. Journal of Macromolecular Science, 2006;23(1):61-126. DOI: 10.1080/07366578308079439.

(56) References Cited

OTHER PUBLICATIONS

Langer et al., New methods of drug delivery. Science. Sep. 28, 1990;249(4976):1527-33.
Larson et al., CRISPR interference (CRISPRi) for sequence-specific control of gene expression. Nat Protoc. Nov. 2013;8(11):2180-96. doi: 10.1038/nprot.2013.132. Epub Oct. 17, 2013.
Lau et al., Molecular basis for discriminating between normal and damaged bases by the human alkyladenine glycosylase, AAG. Proc Natl Acad Sci U S A. Dec. 5, 2000;97(25):13573-8.
Lavergne et al., Defects in type IIA von Willebrand disease: a cysteine 509 to arginine substitution in the mature von Willebrand factor disrupts a disulphide loop involved in the interaction with platelet glycoprotein Ib-IX. Br J Haematol. Sep. 1992;82(1):66-72.
Lawrence et al., Supercharging proteins can impart unusual resilience. J Am Chem Soc. Aug. 22, 2007; 129(33):10110-2. Epub Aug. 1, 2007.
Lazar et al., Transforming growth factor alpha: mutation of aspartic acid 47 and leucine 48 results in different biological activities. Mol Cell Biol. Mar. 1988;8(3):1247-52.
Ledford, Gene-editing hack yields pinpoint precision. Nature, Apr. 20, 2016. http://www.nature.com/news/gene-editing-hack-yields-pinpoint-precision-1.19773.
Lee et al., A chimeric thyroid hormone receptor constitutively bound to DNA requires retinoid X receptor for hormone-dependent transcriptional activation in yeast. Mol Endocrinol. Sep. 1994;8(9):1245-52.
Lee et al., An allosteric self-splicing ribozyme triggered by a bacterial second messenger. Science. Aug. 13, 2010;329(5993):845-8. doi: 10.1126/science.1190713.
Lee et al., Failure to detect DNA-guided genome editing using Natronobacterium gregoryi Argonaute. Nat Biotechnol. Nov. 28, 2016;35(1):17-18. doi: 10.1038/nbt.3753.
Lee et al., PIK3CA gene is frequently mutated in breast carcinomas and hepatocellular carcinomas. Oncogene. Feb. 17, 2005;24(8):1477-80.
Lee et al., Recognition of liposomes by cells: in vitro binding and endocytosis mediated by specific lipid headgroups and surface charge density. Biochim Biophys Acta. Jan. 31, 1992;1103(2):185-97.
Lee et al., Ribozyme Mediated gRNA Generation for In Vitro and In Vivo CRISPR/Cas9 Mutagenesis. PLoS One. Nov. 10, 2016;11(11):e0166020. doi: 10.1371/journal.pone.0166020. eCollection 2016.
Lei et al., Efficient targeted gene disruption in Xenopus embryos using engineered transcription activator-like effector nucleases (TALENs). Proc Natl Acad Sci U S A. Oct. 23, 2012; 109(43):17484-9. Doi: 10.1073/pnas.1215421109. Epub Oct. 8, 2012.
Lenk et al., Pathogenic mechanism of the FIG4 mutation responsible for Charcot-Marie-Tooth disease CMT4J. PLoS Genet. Jun. 2011;7(6):e1002104. doi: 10.1371/journal.pgen.1002104. Epub Jun. 2, 2011.
Levy et al., Inhibition of calcification of bioprosthetic heart valves by local controlled-release diphosphonate. Science. Apr. 12, 1985;228(4696):190-2.
Lewis et al., A serum-resistant cytofectin for cellular delivery of antisense oligodeoxynucleotides and plasmid DNA. Proc Natl Acad Sci U S A. Apr. 16, 1996;93(8):3176-81.
Lewis et al., Building the Class 2 CRISPR-Cas Arsenal. Mol Cell 2017;65(3);377-379.
Lewis et al., Codon 129 polymorphism of the human prion protein influences the kinetics of amyloid formation. J Gen Virol. Aug. 2006;87(Pt 8):2443-9.
Li et al., Base editing with a Cpf1-cytidine deaminase fusion. Nat Biotechnol. Apr. 2018;36(4):324-327. doi: 10.1038/nbt.4102. Epub Mar. 19, 2018.
Li et al., Current approaches for engineering proteins with diverse biological properties. Adv Exp Med Biol. 2007;620:18-33.
Li et al., Generation of Targeted Point Mutations in Rice by a Modified CRISPR/Cas9 System. Mol Plant. Mar. 6, 2017;10(3):526-529. doi: 10.1016/j.molp.2016.12.001. Epub Dec. 8, 2016.
Li et al., Highly efficient and precise base editing in discarded human tripronuclear embryos. Protein Cell. Aug. 19, 2017. doi: 10.1007/s13238-017-0458-7. [Epub ahead of print].
Li et al., Modularly assembled designer TAL effector nucleases for targeted gene knockout and gene replacement in eukaryotes. Nucleic Acids Res. Aug. 2011;39(14):6315-25. doi: 10.1093/nar/gkr188. Epub Mar. 31, 2011.
Li et al., Multiplex and homologous recombination-mediated genome editing in *Arabidopsis* and Nicotiana benthamiana using guide RNA and Cas9. Nat Biotechnol. Aug. 2013;31(8):688-91. doi: 10.1038/nbt.2654.
Li et al., TAL nucleases (TALNs): hybrid proteins composed of TAL effectors and FokI DNA-cleavage domain. Nucleic Acids Res. Jan. 2011;39(1):359-72. doi: 10.1093/nar/gkq704. Epub Aug. 10, 2010.
Liang et al., Rapid and highly efficient mammalian cell engineering via Cas9 protein transfection. Send to; J Biotechnol. Aug. 20, 2015;208:44-53. doi: 10.1016/j.jbiotec.2015.04.024.
Lieber et al., Mechanism and regulation of human non-homologous DNA end-joining. Nat Rev Mol Cell Biol. Sep. 2003;4(9):712-20.
Lilley, D.M. The Varkud Satellite Ribozyme. RNA. Feb. 2004;10(2):151-8.doi: 10.1261/rna.5217104.
Lin et al., Enhanced homology-directed human genome engineering by controlled timing of CRISPR/Cas9 delivery. Elife. Dec. 15, 2014;3:e04766. doi: 10.7554/eLife.04766.
Link et al., Engineering ligand-responsive gene-control elements: lessons learned from natural riboswitches. Gene Ther. Oct. 2009;16(10):1189-201. doi: 10.1038/gt.2009.81. Epub Jul. 9, 2009. Review.
Liu et al., C2c1-sgRNA Complex Structure Reveals RNA-Guided DNA Cleavage Mechanism. Molecular Cell Jan. 2017;65(2):310-22.
Liu et al., Apolipoprotein E and Alzheimer disease: risk, mechanisms and therapy. Nat Rev Neurol. Feb. 2013;9(2):106-18. doi: 10.1038/nrneurol.2012.263. Epub Jan. 8, 2013.
Liu et al., Balancing AID and DNA repair during somatic hypermutation. Trends Immunol. Apr. 2009;30(4):173-81. doi: 10.1016/j.it.2009.01.007.
Liu et al., Cell-penetrating peptide-mediated delivery of TALEN proteins via bioconjugation for genome engineering. PLoS One. Jan. 20, 2014;9(1):e85755. doi: 10.1371/journal.pone.0085755. eCollection 2014.
Liu et al., Design of polydactyl zinc-finger proteins for unique addressing within complex genomes. Proc Natl Acad Sci U S A. May 27, 1997;94(11):5525-30.
Liu et al., Distance determination by GIY-YIG intron endonucleases: discrimination between repression and cleavage functions. Nucleic Acids Res. Mar. 31, 2006;34(6):1755-64. Print 2006.
Liu et al., Engineering a tRNA and aminoacyl-tRNA synthetase for the site-specific incorporation of unnatural amino acids into proteins in vivo. Proc Natl Acad Sci U S A. Sep. 16, 1997;94(19):10092-7.
Liu et al., Fast Colorimetric Sensing of Adenosine and Cocaine Based on a General Sensor Design Involving Aptamers and Nanoparticles. Angew Chem. Dec. 16, 2006;45(1):90-4. DOI: 10.1002/anie.200502589.
Liu et al., Fast Colorimetric Sensing of Adenosine and Cocaine Based on a General Sensor Design Involving Aptamers and Nanoparticles. Angew Chem. 2006;118(1):96-100.
Liu et al., Functional Nucleic Acid Sensors. Chem Rev. May 2009;109(5): 1948-98. doi: 10.1021/cr030183i.
Lombardo et al., Gene editing in human stem cells using zinc finger nucleases and integrase-defective lentiviral vector delivery. Nat Biotechnol. Nov. 2007;25(11):1298-306. Epub Oct. 28, 2007.
Losey et al., Crystal structure of Staphylococcus sureus tRNA adenosine deaminase tadA in complex with RNA. Nature Struct. Mol. Biol. Feb. 2006;13(2):153-9.
Lu et al., Precise Editing of a Target Base in the Rice Genome Using a Modified CRISPR/Cas9 System. Mol Plant. Mar. 6, 2017;10(3):523-525. doi: 10.1016/j.molp.2016.11.013. Epub Dec. 6, 2016.
Lundberg et al., Delivery of short interfering RNA using endosomolytic cell-penetrating peptides. FASEB J. Sep. 2007;21(11):2664-71. Epub Apr. 26, 2007.

(56) References Cited

OTHER PUBLICATIONS

Lundquist et al., Site-directed mutagenesis and characterization of uracil-DNA glycosylase inhibitor protein. Role of specific carboxylic amino acids in complex formation with *Escherichia coli* uracil-DNA glycosylase. J Biol Chem. Aug. 22, 1997;272(34):21408-19.
Lyons et al., Efficient Recognition of an Unpaired Lesion by a DNA Repair Glycosylase. J. Am. Chem. Soc., 2009;131(49):17742-3. DOI: 10.1021/ja908378y.
Ma et al., Single-Stranded DNA Cleavage by Divergent CRISPR-Cas9 Enzymes. Mol Cell. Nov. 5, 2015;60(3):398-407. doi: 10.1016/j.molcel.2015.10.030.
Ma et al., Targeted AID-mediated mutagenesis (TAM) enables efficient genomic diversification in mammalian cells. Nature Methods. Oct. 2016; 13:1029-35. doi:10.1038/nmeth.4027 .
Maeder et al., CRISPR RNA-guided activation of endogenous human genes. Nat Methods. Oct. 2013;10(10):977-9. doi: 10.1038/nmeth.2598. Epub Jul. 25, 2013.
Maeder et al., Rapid "open-source" engineering of customized zinc-finger nucleases for highly efficient gene modification. Mol Cell. Jul. 25, 2008;31(2):294-301. doi:10.1016/j.molcel.2008.06.016.
Maeder et al., Robust, synergistic regulation of human gene expression using TALE activators. Nat Methods. Mar. 2013;10(3):243-5. doi: 10.1038/nmeth.2366. Epub Feb. 10, 2013.
Mahfouz et al., De novo-engineered transcription activator-like effector (TALE) hybrid nuclease with novel DNA binding specificity creates double-strand breaks. Proc Natl Acad Sci U S A. Feb. 8, 2011;108(6):2623-8. doi: 10.1073/pnas.1019533108. Epub Jan. 24, 2011.
Makarova et al., Prokaryotic homologs of Argonaute proteins are predicted to function as key components of a novel system of defense against mobile genetic elements. Biology Direct 2009;4:29.
Makarova et al., An updated evolutionary classification of CRISPR-Cas systems. Nat Rev Microbiol. Nov. 2015;13(11):722-36. doi: 10.1038/nrmicro3569. Epub Sep. 28, 2015.
Makarova et al., Evolution and classification of the CRISPR-Cas systems. Nat Rev Microbiol. Jun. 2011;9(6):467-77. doi: 10.1038/nrmicro2577. Epub May 9, 2011.
Mali et al., Cas9 as a versatile tool for engineeringbiology. Nat Methods. Oct. 2013;10(10):957-63. doi: 10.1038/nmeth.2649.
Mali et al., CAS9 transcriptional activators for target specificity screening and paired nickases for cooperative genome engineering. Nat Biotechnol. Sep. 2013;31(9):833-8. doi: 10.1038/nbt.2675. Epub Aug. 1, 2013.
Mali et al., RNA-guided human genome engineering via Cas9. Science. Feb. 15, 2013;339(6121):823-6. doi: 10.1126/science.1232033. Epub Jan. 3, 2013.
Mandal et al., Riboswitches Control Fundamental Biochemical Pathways in Bacillus Subtilis and Other Bacteria. Cell. May 30, 2003;113(5):577-86. doi: 10.1016/s0092-8674(03)00391-x.
Mani et al., Design, engineering, and characterization of zinc finger nucleases. Biochem Biophys Res Commun. Sep. 23, 2005;335(2):447-57.
Marioni et al., DNA methylation age of blood predicts all-cause mortality in later life. Genome Biol. Jan. 30, 2015;16:25. doi: 10.1186/s13059-015-0584-6.
Marrafhini et al., CRISPR interference limits horizontal gene transfer in staphylococci by targeting DNA. Science. Dec. 19, 2008;322(5909):1843-5. doi: 10.1126/science.1165771.
Maruyama et al., Increasing the efficiency of precise genome editing with CRISPR-Cas9 by inhibition of nonhomologous end joining. Nat Biotechnol. May 2015;33(5):538-42. doi: 10.1038/nbt.3190. Epub Mar. 23, 2015.
Mei et al., Recent Progress in CRISPR/Cas9 Technology. J Genet Genomics. Feb. 20, 2016;43(2):63-75. doi: 10.1016/j.jgg.2016.01.001. Epub Jan. 18, 2016.
Meng et al., Targeted gene inactivation in zebrafish using engineered zinc-finger nucleases. Nat Biotechnol. Jun. 2008;26(6):695-701. doi: 10.1038/nbt1398. Epub May 25, 2008.
Mercer et al., Chimeric TALE recombinases with programmable DNA sequence specificity. Nucleic Acids Res. Nov. 2012;40(21):11163-72. doi: 10.1093/nar/gks875. Epub Sep. 26, 2012.
Mertens et al., Site-specific recombination in bacteriophage Mu: characterization of binding sites for the DNA invertase Gin. EMBO J. Apr. 1988;7(4):1219-27.
Meyer et al., Breathing life into polycations: functionalization with pH-responsive endosomolytic peptides and polyethylene glycol enables siRNA delivery. J Am Chem Soc. Mar. 19, 2008;130(11):3272-3. doi: 10.1021/ja710344v. Epub Feb. 21, 2008.
Meyer et al., Confirmation of a second natural preQ1 aptamer class in Streptococcaceae bacteria. RNA. Apr. 2008;14(4):685-95. doi: 10.1261/rna.937308. Epub Feb. 27, 2008.
Midoux et al., Chemical vectors for gene delivery: a current review on polymers, peptides and lipids containing histidine or imidazole as nucleic acids carriers. Br J Pharmacol. May 2009;157(2):166-78. doi: 10.1111/j.l476-5381.2009.00288.x.
Miller et al., A TALE nuclease architecture for efficient genome editing. Nat Biotechnol. Feb. 2011;29(2):143-8. doi:10.1038/nbt.1755. Epub Dec. 22, 2010.
Miller et al., An improved zinc-finger nuclease architecture for highly specific genome editing. Nat Biotechnol. Jul. 2007;25(7):778-85. Epub Jul. 1, 2007.
Minoche et al., Evaluation of genomic high-throughput sequencing data generated on Illumina HiSeq and genome analyzer systems. Genome Biol. Nov. 8, 2011;12(11):R112. doi: 10.1186/gb-2011-12-11-r112.
Minoretti et al., A W148R mutation in the human FOXD4 gene segregating with dilated cardiomyopathy, obsessive-compulsive disorder, and suicidality. Int J Mol Med. Mar. 2007;19(3):369-72.
Mir et al., Two Active Site Divalent Ions in the Crystal Structure of the Hammerhead Ribozyme Bound to a Transition State Analogue. Biochemistry. . Feb. 2, 2016;55(4):633-6. doi: 10.1021/acs.biochem.5b01139. Epub Jan. 19, 2016.
Mishina et al., Conditional gene targeting on the pure C57BL/6 genetic background. Neurosci Res. Jun. 2007;58(2):105-12. doi: 10.1016/j.neures.2007.01.004. Epub Jan. 18, 2007.
Mojica et al., Intervening sequences of regularly spaced prokaryotic repeats derive from foreign genetic elements. J Mol Evol. Feb. 2005;60(2):174-82.
Mol et al., Crystal structure of human uracil-DNA glycosylase in complex with a protein inhibitor: protein mimicry of DNA. Cell. Sep. 8, 1995;82(5):701-8.
Monahan et al., Site-specific incorporation of unnatural amino acids into receptors expressed in Mammalian cells. Chem Biol. Jun. 2003;10(6):573-80.
Montange et al., Structure of the S-adenosylmethionine riboswitch regulatory mRNA element. Nature. Jun. 29, 2006;441(7097):1172-5.
Moore et al., Improved somatic mutagenesis in zebrafish using transcription activator-like effector nucleases (TALENs). PloS One. 2012;7(5):e37877. Doi: 10.1371/journal.pone.0037877. Epub May 24, 2012.
Mootz et al., Conditional protein splicing: a new tool to control protein structure and function in vitro and in vivo. J Am Chem Soc. Sep. 3, 2003; 125(35):10561-9.
Mootz et al., Protein splicing triggered by a small molecule. J Am Chem Soc. Aug. 7, 2002;124(31):9044-5.
Morbitzer et al., Assembly of custom TALE-type DNA binding domains by modular cloning. Nucleic Acids Res. Jul. 2011;39(13):5790-9. doi: 10.1093/nar/gkr151. Epub Mar. 18, 2011.
Morris et al., A peptide carrier for the delivery of biologically active proteins into mammalian cells. Nat Biotechnol. Dec. 2001;19(12):1173-6.
Moscou et al., A simple cipher governs DNA recognition by TAL effectors. Science. Dec. 11, 2009;326(5959):1501. doi: 10.1126/science.1178817.
Mullins et al., Transgenesis in nonmurine species. Hypertension. Oct. 1993;22(4):630-3.
Mussolino et al., A novel TALE nuclease scaffold enables high genome editing activity in combination with low toxicity. Nucleic Acids Res. Nov. 2011;39(21):9283-93. Doi: 10.1093/nar/gkr597. Epub Aug. 3, 2011.

(56) References Cited

OTHER PUBLICATIONS

Mussolino et al., TALE nucleases: tailored genome engineering made easy. Curr Opin Biotechnol. Oct. 2012;23(5):644-50. doi: 10.1016/j.copbio.2012.01.013. Epub Feb. 17, 2012.
Nahvi et al., Coenzyme B12 riboswitches are widespread genetic control elements in prokaryotes. Nucleic Acids Res. Jan. 2, 2004;32(1):143-50.
Narayanan et al., Clamping down on weak terminal base pairs: oligonucleotides with molecular caps as fidelity-enhancing elements at the 5'- and 3'-terminal residues. Nucleic Acids Res. May 20, 2004;32(9):2901-11. Print 2004.
Navaratnam et al., An overview of cytidine deaminases. Int J Hematol. Apr. 2006;83(3):195-200.
NCBI Reference Sequence: NM_002427.3. Wu et al., May 3, 2014. 5 pages.
Neel et al., Riboswitches: Classification, function and in silico approach, International Journal of Pharma Sciences and Research. 2010;1(9):409-420.
Nelson et al., Filamentous phage DNA cloning vectors: a noninfective mutant with a nonpolar deletion in gene III. Virology. 1981; 108(2): 338-50.
Ni et al., A PCSK9-binding antibody that structurally mimics the EGF(A) domain of LDL-receptor reduces LDL cholesterol in vivo. J Lipid Res. 2011;52:76-86.
Ni et al., Nucleic acid aptamers: clinical applications and promising new horizons. Curr Med Chem. 2011;18(27):4206-14. Review.
Nishida et al., Targeted nucleotide editing using hybrid prokaryotic and vertebrate adaptive immune systems. Science. Sep. 16, 2016;353(6305):1248. pii: aaf8729. doi: 10.1126/science.aaf8729. Epub Aug. 4, 2016.
Nishikura, Functions and regulation of RNA editing by ADAR deaminases. Annu Rev Biochem. 2010;79:321-349. doi:10.1146/annurev-biochem-060208-105251.
Nishimasu et al., Crystal structure of Cas9 in complex with guide RNA and target DNA. Cell. Feb. 27, 2014;156(5):935-49. doi: 10.1016/j.cell.2014.02.001. Epub Feb. 13, 2014.
Nishimasu et al., Crystal Structure of *Staphylococcus aureus* Cas9. Cell. Aug. 27, 2015;162(5):1113-26. doi: 10.1016/j.cell.2015.08.007.
Nomura et al., Controlling Mammalian Gene Expression by Allosteric Hepatitis Delta Virus Ribozymes. ACS Synth Biol. Dec. 20, 2013;2(12):684-9. doi: 10.1021/sb400037a. Epub May 22, 2013.
Nomura et al., Synthetic mammalian riboswitches based on guanine aptazyme. Chem Commun (Camb). Jul. 21, 2012;48(57):7215-7. doi: 10.1039/c2cc33140c. Epub Jun. 13, 2012.
Noris et al., A phenylalanine-55 to serine amino-acid substitution in the human glycoprotein IX leucine-rich repeat is associated with Bernard-Soulier syndrome. Br J Haematol. May 1997;97(2):312-20.
Nowak et al., Guide RNA Engineering for Versatile Cas9 Functionality. Nucleic Acids Res. Nov. 16, 2016;44(20):9555-9564. doi: 10.1093/nar/gkw908. Epub Oct. 12, 2016.
Numrych et al., A comparison of the effects of single-base and triple-base changes in the integrase arm-type binding sites on the site-specific recombination of bacteriophage lambda. Nucleic Acids Res. Jul. 11, 1990;18(13):3953-9. doi: 10.1093/nar/18.13.3953.
Oakes et al., Protein engineering of Cas9 for enhanced function. Methods Enzymol. 2014;546:491-511.
O'Connell et al., Programmable RNA recognition and cleavage by CRISPR/Cas9. Nature. Dec. 11, 2014;516(7530):263-6. doi: 10.1038/nature13769. Epub Sep. 28, 2014.
Offord, Advances in Genome Editing. The Scientist, Apr. 20, 2016. http://www.the-scientist.com/?articles.view/articleNo/45903/title/Advances-in-Genome-Editing/.
Osborn et al., TALEN-based gene correction for epidermolysis bullosa. Mol Ther. Jun. 2013;21(6):1151-9. doi: 10.1038/mt.2013.56. Epub Apr. 2, 2013.
Pan et al., Biological and biomedical applications of engineered nucleases. Mol Biotechnol. Sep. 2013;55(1):54-62. doi: 10.1007/s12033-012-9613-9.
Parker et al., Admixture mapping identifies a quantitative trait locus associated with FEV1/FVC in the COPDGene Study. Genet Epidemiol. Nov. 2014;38(7):652-9. doi: 10.1002/gepi.21847. Epub Aug. 11, 2014.
Pattanayak et al., Determining the specificities of TALENs, Cas9, and other genome-editing enzymes. Methods Enzymol. 2014;546:47-78. doi: 10.1016/978-0-12-801185-0.00003-9.
Pattanayak et al., High-throughput profiling of off-target DNA cleavage reveals RNA-programmed Cas9 nuclease specificity. Nat Biotechnol. Sep. 2013;31(9):839-43. doi: 10.1038/nbt.2673. Epub Aug. 11, 2013.
Pattanayak et al., Revealing off-target cleavage specificities of zinc-finger nucleases by in vitro selection. Nat Methods. Aug. 7, 2011;8(9):765-70. doi: 10.1038/nmeth.1670.
Pavletich et al., Zinc finger-DNA recognition: crystal structure of a Zif268-DNA complex at 2.1 A. Science. May 10, 1991;252(5007):809-17.
Pearl, Structure and function in the uracil-DNA glycosylase superfamily. Mutat Res. Aug. 30, 2000;460(3-4):165-81.
Peck et al., Directed evolution of a small-molecule-triggered intein with improved splicing properties in mammalian cells. Chem Biol. May 27, 2011;18(5):619-30. doi: 10.1016/j.chembiol.2011.02.014.
Pelletier, CRISPR-Cas systems for the study of the immune function. Nov. 15, 2016. https://doi.org/10.1002/9780470015902.a0026896.
Pennisi et al., The CRISPR craze. Science. Aug. 23, 2013;341(6148):833-6. doi: 10.1126/science.341.6148.833.
Pennisi et al., The tale of the TALEs. Science. Dec. 14, 2012;338(6113):1408-11. doi: 10.1126/science.338.6113.1408.
Perez et al., Establishment of HIV-1 resistance in CD4+ T cells by genome editing using zinc-finger nucleases. Nat Biotechnol. Jul. 2008;26(7):808-16. Doi: 10.1038/nbtl410. Epub Jun. 29, 2008.
Perez-Pinera et al., Advances in targeted genome editing. Curr Opin Chem Biol. Aug. 2012;16(3-4):268-77. doi: 10.1016/j.cbpa.2012.06.007. Epub Jul. 20, 2012.
Perez-Pinera et al., RNA-guided gene activation by CRISPR-Cas9-based transcription factors. Nat Methods. Oct. 2013;10(10):973-6. doi: 10.1038/nmeth.2600. Epub Jul. 25, 2013.
Petek et al., Frequent endonuclease cleavage at off-target locations in vivo. Mol Ther. May 2010;18(5):983-6. Doi: 10.1038/mt.2010.35. Epub Mar. 9, 2010.
Petolino et al., Editing Plant Genomes: a new era of crop improvement. Plant Biotechnol J. Feb. 2016;14(2):435-6. doi: 10.1111/pbi.12542.
Phillips, The challenge of gene therapy and DNA delivery. J Pharm Pharmacol. Sep. 2001;53(9):1169-74.
Plasterk et al., DNA inversions in the chromosome of *Escherichia coli* and in bacteriophage Mu: relationship to other site-specific recombination systems. Proc Natl Acad Sci U S A. Sep. 1983;80(17):5355-8.
Plosky et al., CRISPR-Mediated Base Editing without DNA Double-Strand Breaks. Mol Cell. May 19, 2016;62(4):477-8. doi: 10.1016/j.molcel.2016.05.006.
Pluciennik et al., PCNA function in the activation and strand direction of MutL? endonuclease in mismatch repair. Proc Natl Acad Sci U S A. Sep. 14, 2010;107(37):16066-71. doi: 10.1073/pnas.1010662107. Epub Aug. 16, 2010.
Poller et al., A leucine-to-proline substitution causes a defective alpha 1-antichymotrypsin allele associated with familial obstructive lung disease. Genomics. Sep. 1993;17(3):740-3.
Porteus, Design and testing of zinc finger nucleases for use in mammalian cells. Methods Mol Biol. 2008;435:47-61. doi: 10.1007/978-1-59745-232-8_4.
Pospísilová et al., Hydrolytic cleavage of N6-substituted adenine derivatives by eukaryotic adenine and adenosine deaminases. Biosci Rep. 2008;28(6):335-347. doi:10.1042/BSR20080081.
Pourcel et al., CRISPR elements in Yersinia pestis acquire new repeats by preferential uptake of bacteriophage DNA, and provide additional tools for evolutionary studies. Microbiology. Mar. 2005;151(Pt 3):653-63.
Prashant et al., CAS9 transcriptional activators for target specificity screening and paired nickases for cooperative genome engineering. Nature Biotechnology 2013;31(9):833-8.

(56) References Cited

OTHER PUBLICATIONS

Prorocic et al., Zinc-finger recombinase activities in vitro. Nucleic Acids Res. Nov. 2011;39(21):9316-28. doi: 10.1093/nar/gkr652. Epub Aug. 17, 2011.
Proudfoot et al., Zinc finger recombinases with adaptable DNA sequence specificity. PLoS One. Apr. 29, 2011;6(4):e19537. doi: 10.1371/journal.pone.0019537.
Prykhozhij et al., CRISPR multitargeter: a web tool to find common and unique CRISPR single guide RNA targets in a set of similar sequences. PLoS One. Mar. 5, 2015;10(3):e0119372. doi: 10.1371/journal.pone.0119372. eCollection 2015.
Putnam et al., Protein mimicry of DNA from crystal structures of the uracil-DNA glycosylase inhibitor protein and its complex with *Escherichia coli* uracil-DNA glycosylase. J Mol Biol. Mar. 26, 1999;287(2):331-46.
Qi et al., Engineering naturally occurring trans-acting non-coding RNAs to sense molecular signals. Nucleic Acids Res. Jul. 2012;40(12):5775-86. doi: 10.1093/nar/gks168. Epub Mar. 1, 2012.
Qi et al., Repurposing CRISPR as an RNA-guided platform for sequence-specific control of gene expression. Cell. Feb. 28, 2013;152(5):1173-83. doi: 10.1016/j.cell.2013.02.022.
Rakonjac et al., Roles of PIII in filamentous phage assembly. J Mol Biol. 1998; 282(1)25-41.
Ramakrishna et al., Gene disruption by cell-penetrating peptide-mediated delivery of Cas9 protein and guide RNA. Genome Res. Jun. 2014;24(6):1020-7. doi: 10.1101/gr. 171264.113. Epub Apr. 2, 2014.
Ramirez et al., Engineered zinc finger nickases induce homology-directed repair with reduced mutagenic effects. Nucleic Acids Res. Jul. 2012;40(12):5560-8. doi: 10.1093/nar/gks179. Epub Feb. 28, 2012.
Ramirez et al., Unexpected failure rates for modular assembly of engineered zinc fingers. Nat Methods. May 2008;5(5):374-5. Doi: 10.1038/nmeth0508-374.
Ran et al., Double Nicking by RNA-guided CRISPR Cas9 for Enhanced Genome Editing Specificity. Cell. Sep. 12, 2013;154(6):1380-9. doi: 10.1016/j.cell.2013.08.021. Epub Aug. 29, 2013.
Ran et al., Genome engineering using the CRISPR-Cas9 system. Nat Protoc. Nov. 2013;8(11):2281-308. doi: 10.1038/nprot.2013.143. Epub Oct. 24, 2013.
Ran et al., In vivo genome editing using *Staphylococcus aureus* Cas9. Nature. Apr. 9, 2015;520(7546):186-91. doi: 10.1038/nature14299. Epub Apr. 1, 2015.
Rath et al., Fidelity of end joining in mammalian episomes and the impact of Metnase on joint processing. BMC Mol Biol. Mar. 22, 2014;15:6. doi: 10.1186/1471-2199-15-6.
Ravishankar et al., X-ray analysis of a complex of *Escherichia coli* uracil DNA glycosylase (EcUDG) with a proteinaceous inhibitor. The structure elucidation of a prokaryotic UDG. Nuclei Acids Res. 26 (21): 4880-4887 (1998).
Ray et al., Homologous recombination: ends as the means. Trends Plant Sci. Oct. 2002;7(10):435-40.
Rebuzzini et al., New mammalian cellular systems to study mutations introduced at the break site by non-homologous end-joining. DNA Repair (Amst). May 2, 2005;4(5):546-55.
Rees et al., Improving the DNA specificity and applicability of base editing through protein engineering and protein delivery. Nat Commun. Jun. 6, 2017;8:15790. doi: 10.1038/ncomms15790.
Ren et al., In-line Alignment and $Mg^{2}$? Coordination at the Cleavage Site of the env22 Twister Ribozyme. Nat Commun. Nov. 20, 2014;5:5534. doi: 10.1038/ncomms6534.
Ren et al., Pistol Ribozyme Adopts a Pseudoknot Fold Facilitating Site-Specific In-Line Cleavage. Nat Chem Biol. Sep. 2016;12(9):702-8. doi: 10.1038/nchembio.2125. Epub Jul. 11, 2016.
Reyon et al., FLASH assembly of TALENs for high-throughput genome editing. Nat Biotechnol. May 2012;30(5):460-5. doi: 10.1038/nbt.2170.
Richardson et al., Enhancing homology-directed genome editing by catalytically active and inactive CRISPR-Cas9 using asymmetric donor DNA. Nat Biotechnol. Mar. 2016;34(3):339-44. doi: 10.1038/nbt.3481. Epub Jan. 20, 2016.
Richter et al., Function and regulation of clustered regularly interspaced short palindromic repeats (CRISPR) / CRISPR associated (Cas) systems. Viruses. Oct. 19, 2012;4(10):2291-311. doi: 10.3390/v4102291.
Riechmann et al.,. The C-terminal domain of To1A is the coreceptor for filamentous phage infection of *E. coli*. Cell. 1997; 90(2):351-60. PMID:9244308.
Rong et al., Homologous recombination in human embryonic stem cells using CRISPR/Cas9 nickase and a long DNA donor template. Protein Cell. Apr. 2014;5(4):258-60. doi: 10.1007/S13238-014-0032-5.
Rowland et al., Regulatory mutations in Sin recombinase support a structure-based model of the synaptosome. Mol Microbiol. Oct. 2009;74(2):282-98. doi: 10.1111/j.1365-2958.2009.06756.x. Epub Jun. 8, 2009.
Rudolph et al., Synthetic riboswitches for the conditional control of gene expression in Streptomyces coelicolor. Microbiology. Jul. 2013;159(Pt 7):1416-22. doi: 10.1099/mic.0.067322-0. Epub May 15, 2013.
Sadelain et al., Safe harbours for the integration of new DNA in the human genome. Nat Rev Cancer. Dec. 1, 2011;12(1):51-8. doi: 10.1038/nrc3179.
Sage et al., Proliferation of functional hair cells in vivo in the absence of the retinoblastoma protein. Science. Feb. 18, 2005;307(5712):1114-8. Epub Jan. 13, 2005.
Saleh-Gohari et al., Conservative homologous recombination preferentially repairs DNA double-strand breaks in the S phase of the cell cycle in human cells. Nucleic Acids Res. Jul. 13, 2004;32(12):3683-8. Print 2004.
Samal et al., Cationic polymers and their therapeutic potential. Chem Soc Rev. Nov. 7, 2012;41(21):7147-94. doi: 10.1039/c2cs35094g. Epub Aug. 10, 2012.
Sander et al., CRISPR-Cas systems for editing, regulating and targeting genomes. Nat Biotechnol. Apr. 2014;32(4):347-55. doi: 10.1038/nbt.2842. Epub Mar. 2, 2014.
Sander et al., In silico abstraction of zinc finger nuclease cleavage profiles reveals an expanded landscape of off-target sites. Nucleic Acids Res. Oct. 2013;41(19):el81. doi: 10.1093/nar/gkt716. Epub Aug. 14, 2013.
Sander et al., Targeted gene disruption in somatic zebrafish cells using engineered TALENs. Nat Biotechnol. Aug. 5, 2011;29(8):697-8. doi: 10.1038/nbt.1934.
Sang, Prospects for transgenesis in the chick. Meeh Dev. Sep. 2004;121(9):1179-86.
Sanjana et al., A transcription activator-like effector toolbox for genome engineering. Nat Protoc. Jan. 5, 2012;7(1):171-92. doi: 10.1038/nprot.2011.431.
Santiago et al., Targeted gene knockout in mammalian cells by using engineered zinc-finger nucleases. Proc Natl Acad Sci U S A. Apr. 15, 2008;105(15):5809-14. doi: 10.1073/pnas.0800940105. Epub Mar. 21, 2008.
Sapranauskas et al., The *Streptococcus thermophilus* CRISPR/Cas system provides immunity in *Escherichia coli*. Nucleic Acids Res. Nov. 2011;39(21):9275-82. doi: 10.1093/nar/gkr606. Epub Aug. 3, 2011.
Saraconi et al., The RNA editing enzyme APOBEC 1 induces somatic mutations and a compatible mutational signature is present in esophageal adenocarcinomas. Genome Biol. Jul. 31, 2014;15(7):417. doi: 10.1186/s13059-014-0417-z.
Sashital et al., Mechanism of foreign DNA selection in a bacterial adaptive immune system. Mol Cell. Jun. 8, 2012;46(5):606-15. doi: 10.1016/j.molcel.2012.03.020. Epub Apr. 19, 2012.
Sasidharan et al., The selection of acceptable protein mutations. PNAS; Jun. 12, 2007;104(24):10080-5. www.pnas.org/cgi/doi/10.1073.pnas.0703737104.
Saudek et al., A preliminary trial of the programmable implantable medication system for insulin delivery. N Engl J Med. Aug. 31, 1989;321(9):574-9.

(56) References Cited

OTHER PUBLICATIONS

Schriefer et al., Low pressure DNA shearing: a method for random DNA sequence analysis. Nucleic Acids Res. Dec. 25, 1990;18(24):7455-6.
Schwank et al., Functional repair of CFTR by CRISPR/Cas9 in intestinal stem cell organoids of cystic fibrosis patients. Cell Stem Cell. Dec. 5, 2013;13(6):653-8. doi:10.1016/j.stem.2013.11.002.
Schwartz et al., Post-translational enzyme activation in an animal via optimized conditional protein splicing. Nat Chem Biol. Jan. 2007;3(1):50-4. Epub Nov. 26, 2006.
Schwarze et al., In vivo protein transduction: delivery of a biologically active protein into the mouse. Science. Sep. 3, 1999;285(5433):1569-72.
Sclimenti et al., Directed evolution of a recombinase for improved genomic integration at a native human sequence. Nucleic Acids Res. Dec. 15, 2001;29(24):5044-51.
Sefton et al., Implantable pumps. Crit Rev Biomed Eng. 1987;14(3):201-40.
Segal et al., Toward controlling gene expression at will: selection and design of zinc finger domains recognizing each of the 5'-GNN-3' DNA target sequences. Proc Natl Acad Sci U S A. Mar. 16, 1999;96(6):2758-63.
Sells et al., Delivery of protein into cells using polycationic liposomes. Biotechniques. Jul. 1995;19(1):72-6, 78.
Semenova et al., Interference by clustered regularly interspaced short palindromic repeat (CRISPR) RNA is governed by a seed sequence. Proc Natl Acad Sci U S A. Jun. 21, 2011;108(25):10098-103. doi: 10.1073/pnas.1104144108. Epub Jun. 6, 2011.
Semple et al., Rational design of cationic lipids for siRNA delivery. Nat Biotechnol. Feb. 2010;28(2):172-6. doi: 10.1038/nbt.1602. Epub Jan. 17, 2010.
Serganov et al., Coenzyme recognition and gene regulation by a flavin mononucleotide riboswitch. Nature. Mar. 12, 2009;458(7235):233-7. doi: 10.1038/nature07642. Epub Jan. 25, 2009.
Serganov et al., Structural basis for discriminative regulation of gene expression by adenine-and guanine-sensing mRNAs. Chem Biol. Dec. 2004;11(12):1729-41.
Serganov et al., Structural basis for gene regulation by a thiamine pyrophosphate-sensing riboswitch. Nature. Jun. 29, 2006;441(7097): 1167-71. Epub May 21, 2006.
Seripa et al., The missing ApoE allele. Ann Hum Genet. Jul. 2007;71(Pt 4):496-500. Epub Jan. 22, 2007.
Shah et al., Inteins: nature's gift to protein chemists. Chem Sci. 2014;5(1):446-461.
Shah et al., Kinetic control of one-pot trans-splicing reactions by using a wild-type and designed split intein. Angew Chem Int Ed Engl. Jul. 11, 2011;50(29):6511-5. doi: 10.1002/anie.201102909. Epub Jun. 8, 2011.
Shah et al., Target-specific variants of Flp recombinase mediate genome engineering reactions in mammalian cells. FEBS J. Sep. 2015;282(17):3323-33. doi: 10.1111/febs.13345. Epub Jul. 1, 2015.
Shalem et al., Genome-scale CRISPR-Cas9 knockout screening in human cells. Science. Jan. 3, 2014;343(6166):84-7. doi: 10.1126/science.1247005. Epub Dec. 12, 2013.
Sharbeen et al., Ectopic restriction of DNA repair reveals that UNG2 excises AID-induced uracils predominantly or exclusively during G1 phase. J Exp Med. May 7, 2012;209(5):965-74. doi: 10.1084/jem.20112379. Epub Apr. 23, 2012.
Sharma et al., Efficient introduction of aryl bromide functionality into proteins in vivo. FEBS Lett. Feb. 4, 2000;467(1):37-40.
Shcherbakova et al., Near-infrared fluorescent proteins for multicolor in vivo imaging. Nat Methods. Aug. 2013;10(8):751-4. doi: 10.1038/nmeth.2521. Epub Jun. 16, 2013.
Shee et al., Engineered proteins detect spontaneous DNA breakage in human and bacterial cells. Elife. Oct. 29, 2013;2:e01222. doi: 10.7554/eLife.01222.
Sheridan, First CRISPR-Cas patent opens race to stake out intellectual property. Nat Biotechnol. 2014;32(7):599-601.
Sheridan, Gene therapy finds its niche. Nat Biotechnol. Feb. 2011;29(2):121-8. doi: 10.1038/nbt.1769.
Shimantani et al., Targeted base editing in rice and tomato using a CRISPR-Cas9 cytidine deaminase fusion. Nat Biotechnol. May 2017;35(5):441-443. doi: 10.1038/nbt.3833. Epub Mar. 27, 2017.
Shimojima et al., Spinocerebellar ataxias type 27 derived from a disruption of the fibroblast growth factor 14 gene with mimicking phenotype of paroxysmal non-kinesigenic dyskinesia. Brain Dev. Mar. 2012;34(3):230-3. doi: 10.1016/j.braindev.2011.04.014. Epub May 19, 2011.
Shmakov et al., Discovery and Functional Characterization of Diverse Class 2 CRISPR Cas Systems. Molecular Cell Nov. 2015;60(3):385-97.
Siebert et al., An improved PCR method for walking in uncloned genomic DNA. Nucleic Acids Res. Mar. 25, 1995;23(6):1087-8.
Simonelli et al., Base excision repair intermediates are mutagenic in mammalian cells. Nucleic Acids Res. Aug. 2, 2005;33(14):4404-11. Print 2005.
Sirk et al., Expanding the zinc-finger recombinase repertoire: directed evolution and mutational analysis of serine recombinase specificity determinants. Nucleic Acids Res. Apr. 2014;42(7):4755-66. doi: 10.1093/nar/gkt1389. Epub Jan. 21, 2014.
Sjoblom et al., The consensus coding sequences of human breast and colorectal cancers. Science. Oct. 13, 2006;314(5797):268-74. Epub Sep. 7, 2006.
Skretas et al., Regulation of protein activity with small-molecule-controlled inteins. Protein Sci. Feb. 2005;14(2):523-32. Epub Jan. 4, 2005.
Slaymaker et al., Rationally engineered Cas9 nucleases with improved specificity. Science. Jan. 1, 2016 ;351(6268):84-8. doi: 10.1126/science.aad5227. Epub Dec. 1, 2015.
Smith et al., Expression of a dominant negative retinoic acid receptor γ in Xenopus embryos leads to partial resistance to retinoic acid. Roux Arch Dev Biol. Mar. 1994;203(5):254-265. doi: 10.1007/BF00360521.
Smith, Filamentous fusion phage: novel expression vectors that display cloned antigens on the virion surface. Science. Jun. 14, 1985;228(4705):1315-7.
Stenglein et al., APOBEC3 proteins mediate the clearance of foreign DNA from human cells. Nat Struct Mol Biol. Feb. 2010;17(2):222-9. doi: 10.1038/nsmb.1744. Epub Jan. 10, 2010.
Stephens et al., The landscape of cancer genes and mutational processes in breast cancer. Nature Jun. 2012;486:400-404. doi: 10.1038/nature11017.
Sternberg et al., DNA interrogation by the CRISPR RNA-guided endonuclease Cas9. Nature.Mar. 6, 2014;507(7490):62-7. doi: 10.1038/nature13011. Epub Jan. 29, 2014.
Stevens et al., Design of a Split Intein with Exceptional Protein-Splicing Activity. J Am Chem Soc. Feb. 24, 2016;138(7):2162-5. doi: 10.1021/jacs.5b13528. Epub Feb. 8, 2016.
Sudarsan et al., An mRNA structure in bacteria that controls gene expression by binding lysine. Genes Dev. Nov. 1, 2003;17(21):2688-97.
Suess et al., A theophylline responsive riboswitch based on helix slipping controls gene expression in vivo. Nucleic Acids Res. Mar. 5, 2004;32(4):1610-4.
Sun et al., Optimized TAL effector nucleases (TALENs) for use in treatment of sickle cell disease. Mol Biosyst. Apr. 2012;8(4):1255-63. doi: 10.1039/c2mb05461b. Epub Feb. 3, 2012.
Sun et al., The CRISPR/Cas9 system for gene editing and its potential application in pain research. Transl Periop & Pain Med. Aug. 3, 2016;1(3):22-33.
Swarts et al., Argonaute of the archaeon Pyrococcus furiosus is a DNA-guided nuclease that targets cognate DNA. Nucleic Acids Res. May 26, 2015;43(10):5120-9. doi: 10.1093/nar/gkv415. Epub Apr. 29, 2015.
Swarts et al., DNA-guided DNA interference by a prokaryotic Argonaute. Nature. Mar. 13, 2014;507(7491):258-61. doi: 10.1038/nature12971. Epub Feb. 16, 2014.
Swarts et al., The evolutionary journey of Argonaute proteins. Nat Struct Mol Biol. Sep. 2014;21(9):743-53. doi: 10.1038/nsmb.2879.
Szczepek et al., Structure-based redesign of the dimerization interface reduces the toxicity of zinc-finger nucleases. Nat Biotechnol. Jul. 2007;25(7):786-93. Epub Jul. 1, 2007.

(56) References Cited

OTHER PUBLICATIONS

Tagalakis et al., Lack of RNA-DNA oligonucleotide (chimeraplast) mutagenic activity in mouse embryos. Mol Reprod Dev. Jun. 2005;71(2):140-4.
Tang et al., Aptazyme-embedded guide RNAs enable ligand-responsive genome editing and transcriptional activation. Nat Commun. Jun. 28, 2017;8:15939. doi: 10.1038/ncomms15939.
Tebas et al., Gene editing of CCR5 in autologous CD4 T cells of persons infected with Hiv. N Engl J Med. Mar. 6, 2014;370(10):901-10. doi: 10.1056/NEJMoa1300662.
Tessarollo et al., Targeted mutation in the neurotrophin-3 gene results in loss of muscle sensory neurons. Proc Natl Acad Sci U S A. Dec. 6, 1994;91(25):11844-8.
Tesson et al., Knockout rats generated by embryo microinjection of TALENs. Nat Biotechnol. Aug. 5, 2011;29(8):695-6. doi: 10.1038/nbt.1940.
Thompson et al., Cellular uptake mechanisms and endosomal trafficking of supercharged proteins. Chem Biol. Jul. 27, 2012;19(7):831-43. doi: 10.1016/j.chembiol.2012.06.014.
Thompson et al., Engineering and identifying supercharged proteins for macromolecule delivery into mammalian cells. Methods Enzymol. 2012;503:293-319. doi: 10.1016/B978-0-12396962-0.00012-4.
Thorpe et al., Functional correction of episomal mutations with short DNA fragments and RNA-DNA oligonucleotides. J Gene Med. Mar.-Apr. 2002;4(2):195-204.
Thyagarajan et al., Mammalian genomes contain active recombinase recognition sites. Gene. Feb. 22, 2000;244(1-2):47-54.
Thyagarajan et al., Site-specific genomic integration in mammalian cells mediated by phage phiC31 integrase. Mol Cell Biol. Jun. 2001;21(12):3926-34.
Tirumalai et al., Recognition of core-type DNA sites by lambda integrase. J Mol Biol. Jun. 12, 1998;279(3):513-27.
Tourdot et al., A general strategy to enhance immunogenicity of low-affinity HLA-A2. 1-associated peptides: implication in the identification of cryptic tumor epitopes. Eur J Immunol. Dec. 2000;30(12):3411-21.
Trausch et al., The structure of a tetrahydrofolate-sensing riboswitch reveals two ligand binding sites in a single aptamer. Structure. Oct. 12, 2011;19(10):1413-23. doi: 10.1016/j.str.2011.06.019. Epub Sep. 8, 2011.
Truong et al., Development of an intein-mediated split-Cas9 system for gene therapy. Nucleic Acids Res. Jul. 27, 2015;43(13):6450-8. doi: 10.1093/nar/gkv601. Epub Jun. 16, 2015. With Supplementary Data.
Tsai et al., Dimeric CRISPR RNA-guided FokI nucleases for highly specific genome editing. Nat Biotechnol. Jun. 2014;32(6):569-76. doi: 10.1038/nbt.2908. Epub Apr. 25, 2014.
Tsai et al., GUIDE-seq enables genome-wide profiling of off-target cleavage by CRISPR-Cas nucleases. Nat Biotechnol. Feb. 2015;33(2):187-97. doi: 10.1038/nbt.3117. Epub Dec. 16, 2014.
Turan et al., Recombinase-mediated cassette exchange (RMCE)—a rapidly-expanding toolbox for targeted genomic modifications. Gene. Feb. 15, 2013;515(1):1-27. doi: 10.1016/j.gene.2012.1 1.016. Epub Nov. 29, 2012.
Turan et al., Recombinase-mediated cassette exchange (RMCE): traditional concepts and current challenges. J Mol Biol. Mar. 25, 2011;407(2):193-221. doi: 10.1016/j.jmb.2011.01.004. Epub Jan. 15, 2011.
Turan et al., Site-specific recombinases: from tag-and-target-to tag-and-exchange-based genomic modifications. FASEB J. Dec. 2011;25(12):4088-107. doi: 10.1096/fj.11-186940. Epub Sep. 2, 2011. Review.
UNIPROT Submission; UniProt, Accession No. P01011. Last modified Jun. 11, 2014, version 2. 15 pages.
UNIPROT Submission; UniProt, Accession No. P01011. Last modified Sep. 18, 2013, version 2. 15 pages.
UNIPROT Submission; UniProt, Accession No. P04264. Last modified Jun. 11, 2014, version 6. 15 pages.
UNIPROT Submission; UniProt, Accession No. P04275. Last modified Jul. 9, 2014, version 107. 29 pages.
Urnov et al., Genome editing with engineered zinc finger nucleases. Nat Rev Genet. Sep. 2010;11(9):636-46. doi: 10.1038/nrg2842.
Urnov et al., Highly efficient endogenous human gene correction using designed zinc-finger nucleases. Nature. Jun. 2, 2005;435(7042):646-51. Epub Apr. 3, 2005.
Vagner et al., Efficiency of homologous DNA recombination varies along the Bacillus subtilis chromosome. J Bacteriol. Sep. 1988;170(9):3978-82.
Van Duyne et al., Teaching Cre to follow directions. Proc Natl Acad Sci U S A. Jan. 6, 2009;106(1):4-5. doi: 10.1073/pnas.0811624106. Epub Dec. 31, 2008.
Van Swieten et al., A mutation in the fibroblast growth factor 14 gene is associated with autosomal dominant cerebellar ataxia [corrected]. Am J Hum Genet. Jan. 2003;72(l):191-9. Epub Dec. 13, 2002.
Vanamee et al., FokI requires two specific DNA sites for cleavage. J Mol Biol. May 25, 2001;309(1):69-78.
Vitreschak et al., Regulation of the vitamin B12 metabolism and transport in bacteria by a conserved RNA structural element. RNA. Sep. 2003;9(9):1084-97.
Wacey et al., Disentangling the perturbational effects of amino acid substitutions in the DNA-binding domain of p53. Hum Genet. Jan. 1999;104(1):15-22.
Wadia et al., Modulation of cellular function by TAT mediated transduction of full length proteins. Curr Protein Pept Sci. Apr. 2003;4(2):97-104.
Wadia et al., Transducible TAT-HA fusogenic peptide enhances escape of TAT-fusion proteins after lipid raft macropinocytosis. Nat Med. Mar. 2004;10(3):310-5. Epub Feb. 8, 2004.
Wah et al., Structure of FokI has implications for DNA cleavage. Proc Natl Acad Sci U S A. Sep. 1, 1998;95(18):10564-9.
Wals et al., Unnatural amino acid incorporation in *E. coli*: current and future applications in the design of therapeutic proteins. Front Chem. Apr. 1, 2014;2:15. doi: 10.3389/fchem.2014.00015. eCollection 2014.
Wang et al. CRISPR-Cas9 and CRISPR-Assisted Cytidine Deaminase Enable Precise and Efficient Genome Editing in Klebsiella pneumoniae. Appl Environ Microbiol. 2018;84(23):e01834-18. Published Nov. 15, 2018. doi:10.1128/AEM.01834-18.
Wang et al., CRISPR-Cas9 Targeting of PCSK9 in Human Hepatocytes In Vivo-Brief Report. Arterioscler Thromb Vase Biol. May 2016;36(5):783-6. doi: 10.1161/ATVBAHA.116.307227. Epub Mar. 3, 2016.
Wang et al., Efficient delivery of genome-editing proteins using bioreducible lipid nanoparticles. Proc Natl Acad Sci U S A. Feb. 29, 2016. pii: 201520244. [Epub ahead of print].
Wang et al., Enhanced base editing by co-expression of free uracil DNA glycosylase inhibitor. Cell Res. Oct. 2017;27(1):1289-92. doi: 10.1038/cr.2017.111. Epub Aug. 29, 2017.
Wang et al., Genetic screens in human cells using the CRISPR-Cas9 system. Science. Jan. 3, 2014;343(6166):80-4. doi: 10.1126/science.1246981. Epub Dec. 12, 2013.
Wang et al., Nucleation, propagation and cleavage of target RNAs in Ago silencing complexes. Nature. Oct. 8, 2009;461(7265):754-61. doi: 10.1038/nature08434.
Wang et al., One-step generation of mice carrying mutations in multiple genes by CRISPR/Cas-mediated genome engineering. Cell. May 9, 2013;153(4):910-8. doi: 10.1016/j.cell.2013.04.025. Epub May 2, 2013.
Wang et al., Recombinase technology: applications and possibilities. Plant Cell Rep. Mar. 2011;30(3):267-85. doi: 10.1007/s00299-010-0938-1. Epub Oct. 24, 2010.
Wang et al., Riboswitches that sense S-adenosylhomocysteine and activate genes involved in coenzyme recycling. Mol Cell. Mar. 28, 2008;29(6):691-702. doi: 10.1016/j.molcel.2008.01.012.
Wang et al., Targeted gene addition to a predetermined site in the human genome using a ZHN-based nicking enzyme. Genome Res. Jul. 2012;22(7):1316-26. doi: 10.1101/gr.122879.111. Epub Mar. 20, 2012.
Wang et al., Uracil-DNA glycosylase inhibitor gene of bacteriophage PBS2 encodes a binding protein specific for uracil-DNA glycosylase. J Biol Chem. Jan. 15, 1989;264(2):1163-71.

(56) References Cited

OTHER PUBLICATIONS

Warren et al., A chimeric Cre recombinase with regulated directionality. Proc Natl Acad Sci U S A. Nov. 25, 2008;105(47):18278-83. doi: 10.1073/pnas.0809949105. Epub Nov. 14, 2008.
Warren et al., Mutations in the amino-terminal domain of lambda-integrase have differential effects on integrative and excisive recombination. Mol Microbiol. Feb. 2005;55(4):1104-12.
Weber et al., Assembly of designer TAL effectors by Golden Gate cloning. PLoS One. 2011;6(5):e19722. doi:10.1371/journal.pone.0019722. Epub May 19, 2011.
Weinberg et al., New Classes of Self-Cleaving Ribozymes Revealed by Comparative Genomics Analysis. Nat Chem Biol. Aug. 2015;11(8):606-10. doi: 10.1038/nchembio.1846. Epub Jul. 13, 2015.
Weinberg et al., The aptamer core of SAM-IV riboswitches mimics the ligand-binding site of SAM-I riboswitches. RNA. May 2008;14(5):822-8. doi: 10.1261/rna.988608. Epub Mar. 27, 2008.
Weinberger et al., Disease-causing mutations C277R and C277Y modify gating of human C1C-1 chloride channels in myotonia congenita. J Physiol. Aug. 1, 2012;590(Pt 15):3449-64. doi: 0.1113/jphysiol.2012.232785. Epub May 28, 2012.
Wiedenheft et al., RNA-guided genetic silencing systems in bacteria and archaea. Nature. Feb. 15, 2012;482(7385):331-8. doi: 10.1038/naturel0886. Review.
Wijesinghe et al., Efficient deamination of 5-methylcytosines in DNA by human APOBEC3A, but not by AID or APOBEC3G. Nucleic Acids Res. Oct. 2012;40(18):9206-17. doi: 10.1093/nar/gks685. Epub Jul. 13, 2012.
Wijnker et al., Managing meiotic recombination in plant breeding. Trends Plant Sci. Dec. 2008;13(12):640-6. doi: 10.1016/j.tplants.2008.09.004. Epub Oct. 22, 2008.
Wilson et al., Assessing annotation transfer for genomics: quantifying the relations between protein sequence, structure and function through traditional and probabilistic scores. J Mol Biol 2000;297:233-49.
Wilson et al., In Vitro Selection of Functional Nucleic Acids. Annu Rev Biochem. 1999;68:611-47. doi: 10.1146/annurev.biochem.68.1.611.
Winkler et al., An mRNA structure that controls gene expression by binding FMN. Proc Natl Acad Sci U S A. Dec. 10, 2002;99(25):15908-13. Epub Nov. 27, 2002.
Winkler et al., Control of gene expression by a natural metabolite-responsive ribozyme. Nature. Mar. 18, 2004;428(6980):281-6.
Winkler et al., Thiamine derivatives bind messenger RNAs directly to regulate bacterial gene expression. Nature. Oct. 31, 2002;419(6910):952-6. Epub Oct. 16, 2002.
Wolf et al., tadA, an essential tRNA-specific adenosine deaminase from *Escherichia coli*. Embo J. Jul. 15, 2002;21(14):3841-51.
Wolfe et al., Analysis of zinc fingers optimized via phage display: evaluating the utility of a recognition code. J Mol Biol. Feb. 5, 1999;285(5):1917-34.
Wood et al., Targeted genome editing across species using ZFNs and TALENs. Science. Jul. 15, 2011;333(6040):307. doi: 10.1126/science. 1207773. Epub Jun. 23, 2011.
Wu et al., Correction of a genetic disease in mouse via use of CRISPR-Cas9. Cell Stem Cell. Dec. 5, 2013;13(6):659-62. doi: 10.1016/j.stem.2013.10.016.
Wu et al., Genome-wide binding of the CRISPR endonuclease Cas9 in mammalian cells. Nat Biotechnol. Jul. 2014;32(7):670-6. doi: 10.1038/nbt.2889. Epub Apr. 20, 2014.
Xu et al., Sequence determinants of improved CRISPR sgRNA design. Genome Res. Aug. 2015;25(8):1147-57. doi: 10.1101/gr.191452.115. Epub Jun. 10, 2015.
Yahata et al., Unified, Efficient, and Scalable Synthesis of Halichondrins: Zirconium/Nickel-Mediated One-Pot Ketone Synthesis as the Final Coupling Reaction. Angew Chem Int Ed Engl. Aug. 28, 2017;56(36):10796-10800. doi: 10.1002/anie.201705523. Epub Jul. 28, 2017.
Yamamoto et al., Virological and immunological bases for HIV-1 vaccine design. Uirusu 2007;57(2): 133-139. https://doi.org/10.2222/jsv.57.133.
Yamano et al., Crystal Structure of Cpf1 in Complex with Guide RNA and Target DNA. Cell May 2016;165(4)949-62.
Yang et al., APOBEC: From mutator to editor. J Genet Genomics. Sep. 20, 2017;44(9):423-437. doi: 10.1016/j.jgg.2017.04.009. Epub Aug. 7, 2017.
Yang et al., Engineering and optimising deaminase fusions for genome editing. Nat Commun. Nov. 2, 2016;7:13330. doi: 10.1038/ncomms13330.
Yang et al., Genome editing with targeted deaminases. BioRxiv. Preprint. First posted online Jul. 28, 2016.
Yang et al., New CRISPR-Cas systems discovered. Cell Res. Mar. 2017;27(3):313-314. doi: 10.1038/cr.2017.21. Epub Feb. 21, 2017.
Yang et al., PAM-dependent Target DNA Recognition and Cleavage by C2C1 CRISPR-Cas endonuclease. Cell Dec. 2016;167(7):1814-28.
Yanover et al., Extensive protein and DNA backbone sampling improves structure-based specificity prediction for C2H2 zinc fingers. Nucleic Acids Res. Jun. 2011;39(11):4564-76. doi: 10.1093/nar/gkr048. Epub Feb. 22, 2011.
Yazaki et al., Hereditary systemic amyloidosis associated with a new apolipoprotein AII stop codon mutation Stop78Arg. Kidney Int. Jul. 2003;64(1):-6.
Yin et al., Genome editing with Cas9 in adult mice corrects a disease mutation and phenotype. Nat Biotechnol. Jun. 2014;32(6):551-3. doi: 10.1038/nbt.2884. Epub Mar. 30, 2014.
Young et al., Beyond the canonical 20 amino acids: expanding the genetic lexicon. J Biol Chem. Apr. 9, 2010;285(15):11039-44. doi: 10.1074/jbc.R109.091306. Epub Feb. 10, 2010.
Yu et al., Liposome-mediated in vivo E1 A gene transfer suppressed dissemination of ovarian cancer cells that overexpress HER-2/neu. Oncogene. Oct. 5, 1995;11(7):1383-8.
Yuan et al., Laboratory-directed protein evolution. Microbiol Mol Biol Rev. 2005; 69(3):373-92. PMID: 16148303.
Yuan et al., Tetrameric structure of a serine integrase catalytic domain. Structure. Aug. 6, 2008;16(8):1275-86. doi: 10.1016/j.str.2008.04.018.
Yuen et al., Control of transcription factor activity and osteoblast differentiation in mammalian cells using an evolved small-molecule-dependent intein. J Am Chem Soc. Jul. 12, 2006;128(27):8939-46.
Zelphati et al., Intracellular delivery of proteins with a new lipid-mediated delivery system. J Biol Chem. Sep. 14, 2001;276(37):35103-10. Epub Jul. 10, 2001.
Zetsche et al., A split-Cas9 architecture for inducible genome editing and transcription modulation. Nat Biotechnol. Feb. 2015;33(2):139-42. doi: 10.1038/nbt.3149.
Zetsche et al., Cpf1 is a single RNA-guided endonuclease of a class 2 CRISPR-Cas system. Cell. Oct. 22, 2015;163(3):759-71. doi: 10.1016/j.cell.2015.09.038. Epub Sep. 25, 2015.
Zhang et al., Comparison of non-canonical PAMs for CRISPR/Cas9-mediated DNA cleavage in human cells. Sci Rep. Jun. 2014;4:5405.
Zhang et al., Conditional gene manipulation: Cre-ating a new biological era. J Zhejiang Univ Sci B. Jul. 2012;13(7):511-24. doi: 10.1631/jzus.B1200042. Review.
Zhang et al., CRISPR/Cas9 for genome editing: progress, implications and challenges. Hum Mol Genet. Sep. 15, 2014;23(R1):R40-6. doi: 10.1093/hmg/ddu125. Epub Mar. 20, 2014.
Zhang et al., Efficient construction of sequence-specific TAL effectors for modulating mammalian transcription. Nat Biotechnol. Feb. 2011;29(2):149-53. doi: 10.1038/nbt.1775. Epub Jan. 19, 2011.
Zhang et al., Programmable base editing of zebrafish genome using a modified CRISPR-Cas9 system. Nat Commun. Jul. 25, 2017;8(1):118. doi: 10.1038/s41467-017-00175-6.
Zhang et al., Ribozymes and Riboswitches: Modulation of RNA Function by Small Molecules. Biochemistry. Nov. 2, 2010;49(43):9123-31. doi: 10.1021/bi1012645.
Zhang et al., Stabilized plasmid-lipid particles for regional gene therapy: formulation and transfection properties. Gene Ther. Aug. 1999;6(8):1438-47.

(56) References Cited

OTHER PUBLICATIONS

Zheng et al., DNA editing in DNA/RNA hybrids by adenosine deaminases that act on RNA. Nucleic Acids Res. Apr. 7, 2017;45(6):3369-3377. doi: 10.1093/nar/gkx050.
Zhong et al., Rational Design of Aptazyme Riboswitches for Efficient Control of Gene Expression in Mammalian Cells. Elife. Nov. 2, 2016;5:e18858. doi: 10.7554/eLife.18858.
Zimmermann et al., Molecular interactions and metal binding in the theophylline-binding core of an RNA aptamer. RNA. May 2000;6(5):659-67.
Zong et al., Precise base editing in rice, wheat and maize with a Cas9-cytidine deaminase fusion. Nat Biotechnol. May 2017;35(5):438-440. doi: 10.1038/nbt.3811. Epub Feb. 27, 2017.
Zorko et al., Cell-penetrating peptides: mechanism and kinetics of cargo delivery. Adv Drug Deliv Rev. Feb. 28, 2005;57(4):529-45. Epub Jan. 22, 2005.
Zou et al., Gene targeting of a disease-related gene in human induced pluripotent stem and embryonic stem cells. Cell Stem Cell. Jul. 2, 2009;5(1):97-110. doi: 10.1016/j.stem.2009.05.023. Epub Jun. 18, 2009.
Zuris et al., Cationic lipid-mediated delivery of proteins enables efficient protein-based genome editing in vitro and in vivo. Nat Biotechnol. 2015;33:73-80.
GENBANK Submission; NIH/NCBI, Accession No. NM 174936.3. Bernardini et al., Oct. 28, 2015. 2 pages.
GENBANK Submission; NIH/NCBI, Accession No. YP_009283008.1. Bernardini et al., Sep. 23, 2016. 2 pages.
Anders et al., Structural basis of PAM-dependent target DNA recognition by the Cas9 endonuclease. Nature. Sep. 25, 2014;513(7519):569-73. doi: 10.1038/nature13579. Epub Jul. 27, 2014. Europe PMC Funders Group. Author manuscript. Available OMC Mar. 25, 2015.
Bertolotti et al., Toward genosafe endonuclease-boosted gene targeting using breakthrough CRISP/Cas9 for next generation stem cell gene therapy culminating in efficient ex VIVO in VIVO gene repair/genomic editing. Molecular Therapy. May 2015;23(Suppl1):S139. Abstract 350. 18th Ann Meeting of the American Society of Gene and Cell Therapy. ASGCT 2015. New Orleans, LA. May 13, 2015-May 16, 2015.
Li et al., Protein trans-splicing as a means for viral vector-mediated in vivo gene therapy. Hum GeneTher. Sep. 2008;19(9):958-64. doi: 10.1089/hum.2008.009.
Lienert et al., Two- and three-input TALE-based and logic computation in embryonic stem cells. Nucleic Acids Res. Nov. 2013;41(21):9967-75. doi: 10.1093/nar/gkt758. Epub Aug. 27, 2013.
Rogozin et al., Evolution and diversification of lamprey antigen receptors: evidence for involvement of an AID-APOBEC family cytosine deaminase. Nat Immunol. Jun. 2007;8(6):647-56. doi: 10.1038/ni1463. Epub Apr. 29, 2007.
Wright et al., Rational design of a split-Cas9 enzyme complex. Proc Natl Acad Sci U S A. Mar. 10, 2015;112(10):2984-9. doi: 10.1073/pnas.1501698112. Epub Feb. 23, 2015.
U.S. Appl. No. 17/160,329, filed Jan. 27, 2021, Liu et al.
U.S. Appl. No. 17/130,812, filed Dec. 22, 2020, Liu et al.
U.S. Appl. No. 17/148,059, filed Jan. 13, 2021, Liu et al.
U.S. Appl. No. 16/976,047, filed Aug. 26, 2020, Liu et al.
U.S. Appl. No. 17/289,665, filed Apr. 28, 2021, Liu et al.
U.S. Appl. No. 16/772,747, filed Jun. 12, 2020, Shen et al.
U.S. Appl. No. 17/425,261, filed Jul. 22, 2021, Kim et al.
U.S. Appl. No. 17/270,396, filed Feb. 22, 2021, Liu et al.
U.S. Appl. No. 17/273,688, filed Mar. 4, 2021, Liu et al.
U.S. Appl. No. 17/288,504, filed Apr. 23, 2021, Liu et al.
U.S. Appl. No. 17/219,590, filed Mar. 31, 2021, Liu et al.
U.S. Appl. No. 17/219,635, filed Mar. 31, 2021, Liu et al.
U.S. Appl. No. 17/219,672, filed Mar. 31, 2021, Liu et al.
U.S. Appl. No. 17/294,287, filed May 14, 2021, Liu et al.
U.S. Appl. No. 17/408,306, filed Aug. 20, 2021, Liu et al.
U.S. Appl. No. 17/436,048, filed Sep. 2, 2021, Liu et al.
[No Author Listed] "Human genome." Encyclopedia Britannica. Encyclopedia Brittanica, Inc. Published Feb. 15, 2019. Last accessed online via https://www.britannica.com/science/human-genome on Mar. 19, 2021. 2 pages.
[No Author Listed] HyPhy—Hypothesis testing using Phylogenies. Last modified Apr. 21, 2017. Accessed online via http://hyphy.org/w/index.php/Main_Page on Apr. 28, 2021.
[No Author Listed] NCBI Accession No. XP_015843220.1. C->U editing enzyme APOBEC-1 [Peromyscus maniculatus bairdii], XP002793540. Mar. 21, 2016.
[No Author Listed] NCBI Accession No. XP_021505673.1. C->U editing enzyme APOBEC-1 [Meriones unguiculatus], XP002793541. Jun. 27, 2017.
Abremski et al., Bacteriophage P1 site-specific recombination. Purification and properties of the Cre recombinase protein. J Biol Chem. Feb. 10, 1984;259(3):1509-14.
Abudayyeh et al., A cytosine deaminase for programmable single-base RNA editing. Science. Jul. 26, 2019;365(6451):382-386. doi: 10.1126/science.aax7063. Epub Jul. 11, 2019.
Abudayyeh et al., RNA targeting with CRISPR-Casl3. Nature. Oct. 12, 2017;550(7675):280-284. doi: 10.1038/nature24049. Epub Oct. 4, 2017.
Ada et al., Carbohydrate-protein conjugate vaccines. Clin Microbiol Infect. Feb. 2003;9(2):79-85. doi: 10.1046/j.1469-0691.2003.00530.x.
Adamala et al., Programmable RNA-binding protein composed of repeats of a single modular unit. Proc Natl Acad Sci U S A. May 10, 2016;113(19):E2579-88. doi: 10.1073/pnas.1519368113. Epub Apr. 26, 2016.
Adams et al., New biarsenical ligands and tetracysteine motifs for protein labeling in vitro and in vivo: synthesis and biological applications. J Am Chem Soc. May 29, 2002;124(21):6063-76. doi: 10.1021/ja017687n.
Adli, The CRISPR tool kit for genome editing and beyond. Nat Commun. May 15, 2018;9(1):1911. doi: 10.1038/s41467-018-04252-2.
Aguilo et al., Coordination of m(6)A mRNA Methylation and Gene Transcription by ZFP217 Regulates Pluripotency and Reprogramming. Cell Stem Cell. Dec. 3, 2015;17(6):689-704. doi: 10.1016/j.stem.2015.09.005. Epub Oct. 29, 2015.
Ahmad et al., Antibody-mediated specific binding and cytotoxicity of liposome-entrapped doxorubicin to lung cancer cells in vitro. Cancer Res. Sep. 1, 1992;52(17):4817-20.
Aik et al., Structure of human RNA N?-methyladenine demethylase ALKBH5 provides insights into its mechanisms of nucleic acid recognition and demethylation. Nucleic Acids Res. Apr. 2014;42(7):4741-54. doi: 10.1093/nar/gku085. Epub Jan. 30, 2014.
Aird et al., Increasing Cas9-mediated homology-directed repair efficiency through covalent tethering of DNA repair template. Commun Biol. May 31, 2018; 1:54. doi: 10.1038/s42003-018-0054-2.
Akcakaya et al., In vivo CRISPR editing with no detectable genome-wide off-target mutations. Nature. Sep. 2018;561(7723):416-419. doi: 10.1038/s41586-018-0500-9. Epub Sep. 12, 2018. PMID: 30209390; PMCID: PMC6194229.
Akins et al., Mitochondrial plasmids of Neurospora: integration into mitochondrial DNA and evidence for reverse transcription in mitochondria. Cell. Nov. 21, 1986;47(4):505-16. doi: 10.1016/0092-8674(86)90615-x.
Akinsheye et al., Fetal hemoglobin in sickle cell anemia. Blood. Jul. 7, 2011; 118(1):19-27. doi: 10.1182/blood-2011-03-325258. Epub Apr. 13, 2011.
Alarcón et al., HNRNPA2B1 is a Mediator of m(6)A-Dependent Nuclear RNA Processing Events. Cell. Sep. 10, 2015;162(6):1299-308. doi: 10.1016/j.cell.2015.08.011. Epub Aug. 27, 2015.
Alarcón et al., N6-methyladenosine marks primary microRNAs for processing. Nature. Mar. 26, 2015;519(7544):482-5. doi: 10.1038/nature14281. Epub Mar. 18, 2015.
Alexander, HFE-associated hereditary hemochromatosis. Genet Med. May 2009;11(5):307-13. doi: 10.1097/GIM.0b013e31819d30f2.
Altschul et al., Basic local alignment search tool. J Mol Biol. Oct. 5, 1990;215(3):403-10. doi: 10.1016/S0022-2836(05)80360-2.

(56) References Cited

OTHER PUBLICATIONS

Amrann et al., Tightly regulated tac promoter vectors useful for the expression of unfused and fused proteins in *Escherichia coli*. Gene. Sep. 30, 1988;69(2):301-15.
Anders et al., Chapter One: In Vitro Enzymology of Cas9. in Methods in Enzymology, eds Doudna et al. 2014:546:1-20.
Anderson, Human gene therapy. Science. May 8, 1992;256(5058):808-13. doi: 10.1126/science.1589762.
Anzalone et al., Reprogramming eukaryotic translation with ligand-responsive synthetic RNA switches. Nat Methods. May 2016;13(5):453-8. doi: 10.1038/nmeth.3807. Epub Mar. 21, 2016.
Aplan, Causes of oncogenic chromosomal translocation. Trends Genet. Jan. 2006;22(1):46-55. doi: 10.1016/j.tig.2005.10.002. Epub Oct. 28, 2005.
Arakawa et al., A method to convert mRNA into a gRNA library for CRISPR/Cas9 editing of any organism. Sci Adv. Aug. 24, 2016;2(8):e1600699. doi: 10.1126/sciadv.1600699.
Araki et al., Comparative analysis of right element mutant lox sites on recombination efficiency in embryonic stem cells. BMC Biotechnol. Mar. 31, 2010;10:29. doi: 10.1186/1472-6750-10-29.
Araki et al., Site-specific recombinase, R, encoded by yeast plasmid pSR1. J Mol Biol. May 5, 1992;225(1):25-37. doi: 10.1016/0022-2836(92)91023-i.
Araki et al., Targeted integration of DNA using mutant lox sites in embryonic stem cells. Nucleic Acids Res. Feb. 15, 1997;25(4):868-72. doi: 10.1093/nar/25.4.868.
Arambula et al., Surface display of a massively variable lipoprotein by a Legionella diversity-generating retroelement. Proc Natl Acad Sci U S A. May 14, 2013;110(20):8212-7. doi: 10.1073/pnas.1301366110. Epub Apr. 30, 2013.
Arazoe et al., Targeted Nucleotide Editing Technologies for Microbial Metabolic Engineering. Biotechnol J. Sep. 2018;13(9):e1700596. doi: 10.1002/biot.201700596. Epub Jun. 19, 2018.
Arb Ab et al., Cloning-free CRISPR. Stem Cell Reports. Nov. 10, 2015;5(5):908-917. doi: 10.1016/j.stemcr.2015.09.022. Epub Oct. 29, 2015.
Arezi et al., Novel mutations in Moloney Murine Leukemia Virus reverse transcriptase increase thermostability through tighter binding to template-primer. Nucleic Acids Res. Feb. 2009;37(2):473-81. doi: 10.1093/nar/gkn952. Epub Dec. 4, 2008.
Asante et al., A naturally occurring variant of the human prion protein completely prevents prion disease. Nature. Jun. 25, 2015;522(7557):478-81. doi: 10.1038/nature14510. Epub Jun. 10, 2015.
Auer et al., Highly efficient CRISPR/Cas9-mediated knock-in in zebrafish by homology-independent DNA repair. Genome Res. Jan. 2014;24(1):142-53. doi: 10.1101/gr.161638.113. Epub Oct. 31, 2013.
Autieri et al., IRT-1, a novel interferon-gamma-responsive transcript encoding a growth-suppressing basic leucine zipper protein. J Biol Chem. Jun. 12, 1998;273(24):14731-7. doi: 10.1074/jbc.273.24.14731.
Avidan et al., The processivity and fidelity of DNA synthesis exhibited by the reverse transcriptase of bovine leukemia virus. Eur J Biochem. Feb. 2002;269(3):859-67. doi: 10.1046/j.0014-2956.2001.02719.x.
Babacic et al., CRISPR-cas gene-editing as plausible treatment of neuromuscular and nucleotide-repeat-expansion diseases: A systematic review. PLoS One. Feb. 22, 2019;14(2):e0212198. doi: 10.1371/journal.pone.0212198.
Bacman et al., Specific elimination of mutant mitochondrial genomes in patient-derived cells by mitoTALENs. Nat Med. Sep. 2013;19(9):1111-3. doi: 10.1038/nm.3261. Epub Aug. 4, 2013.
Badran et al., Continuous evolution of Bacillus thuringiensis toxins overcomes insect resistance. Nature. May 5, 2016;533(7601):58-63. doi: 10.1038/nature17938. Epub Apr. 27, 2016.
Badran et al., Development of potent in vivo mutagenesis plasmids with broad mutational spectra. Nat Commun. Oct. 7, 2015;6:8425. doi: 10.1038/ncomms9425.
Bae et al., Microhomology-based choice of Cas9 nuclease target sites. Nat Methods. Jul. 2014;11(7):705-6. doi: 10.1038/nmeth.3015.
Bagyinszky et al., Characterization of mutations in PRNP (prion) gene and their possible roles in neurodegenerative diseases. Neuropsychiatr Dis Treat. Aug. 14, 2018;14:2067-2085. doi: 10.2147/NDT.S165445.
Balakrishnan et al., Flap endonuclease 1. Annu Rev Biochem. 2013;82:119-38. doi: 10.1146/annurev-biochem-072511-122603. Epub Feb. 28, 2013.
Baldari et al., A novel leader peptide which allows efficient secretion of a fragment of human interleukin 1 beta in *Saccharomyces cerevisiae*. EMBO J. Jan. 1987;6(1):229-34.
Banerji et al., A lymphocyte-specific cellular enhancer is located downstream of the joining region in immunoglobulin heavy chain genes. Cell. Jul. 1983;33(3):729-40. doi: 10.1016/0092-8674(83)90015-6.
Bannert et al., Retroelements and the human genome: new perspectives on an old relation. Proc Natl Acad Sci U S A. Oct. 5, 2004;101 Suppl 2(Suppl 2):14572-9. doi: 10.1073/pnas.0404838101. Epub Aug. 13, 2004.
Baranauskas et al., Generation and characterization of new highly thermostable and processive M-MuLV reverse transcriptase variants. Protein Eng Des Sei. Oct. 2012;25(10):657-68. doi: 10.1093/protein/gzs034. Epub Jun. 12, 2012.
Barnes et al., The fidelity of Taq polymerase catalyzing PCR is improved by an N-terminal deletion. Gene. Mar. 1, 1992;112(1):29-35. doi: 10.1016/0378-1119(92)90299-5.
Bartlett et al., Efficient expression of protein coding genes from the murine U1 small nuclear RNA promoters. Proc Natl Acad Sci U S A. Aug. 20, 1996;93(17):8852-7. doi: 10.1073/pnas.93.17.8852.
Bartosovic et al., N6-methyladenosine demethylase FTO targets pre-mRNAs and regulates alternative splicing and 3'-end processing. Nucleic Acids Res. Nov. 2, 2017;45(19):11356-11370. doi: 10.1093/nar/gkx778.
Basturea et al., Substrate specificity and properties of the *Escherichia coli* 16S rRNA methyltransferase, RsmE. RNA. Nov. 2007;13(11):1969-76. doi: 10.1261/rna.700507. Epub Sep. 13, 2007.
Bebenek et al., Error-prone polymerization by HIV-1 reverse transcriptase. Contribution of template-primer misalignment, miscoding, and termination probability to mutational hot spots. J Biol Chem. May 15, 1993;268(14):10324-34.
Behr, Gene transfer with synthetic cationic amphiphiles: prospects for gene therapy. Bioconjug Chem. Sep.-Oct. 1994;5(5):382-9. doi: 10.1021/bc00029a002.
Belshaw et al., Controlling programmed cell death with a cyclophilin-cyclosporin-based chemical inducer of dimerization. Chem Biol. Sep. 1996;3(9):731-8. doi: 10.1016/s1074-5521(96)90249-5.
Belshaw et al., Controlling protein association and subcellular localization with a synthetic ligand that induces heterodimerization of proteins. Proc Natl Acad Sci U S A. May 14, 1996;93(10):4604-7. doi: 10.1073/pnas.93.10.4604.
Bennett et al., Painful and painless channelopathies. Lancet Neurol. Jun. 2014;13(6):587-99. doi: 10.1016/S1474-4422(14)70024-9. Epub May 6, 2014.
Berger et al., Reverse transcriptase and its associated ribonuclease H: interplay of two enzyme activities controls the yield of single-stranded complementary deoxyribonucleic acid. Biochemistry. May 10, 1983;22(10):2365-72. doi: 10.1021/bi00279a010.
Berkhout et al., Identification of an active reverse transcriptase enzyme encoded by a human endogenous HERV-K retrovirus. J Virol. Mar. 1999;73(3):2365-75. doi: 10.1128/JVI.73.3.2365-2375.1999.
Bernhart et al., Local RNA base pairing probabilities in large sequences. Bioinformatics. Mar. 1, 2006;22(5):614-5. doi: 10.1093/bioinformatics/btk014. Epub Dec. 20, 2005.
Bernstein et al., Role for a bidentate ribonuclease in the initiation step of RNA interference. Nature. Jan. 18, 2001;409(6818):363-6. doi: 10.1038/35053110.
Bertrand et al., Localization of ASH1 mRNA particles in living yeast. Mol Cell. Oct. 1998;2(4):437-45. doi: 10.1016/sl097-2765(00)80143-4.

(56) References Cited

OTHER PUBLICATIONS

Bessen et al., High-resolution specificity profiling and off-target prediction for site-specific DNA recombinases. Nat Commun. Apr. 26, 2019;10(1):1937. doi: 10.1038/s41467-019-09987-0.
Bi et al., Pseudo attP sites in favor of transgene integration and expression in cultured porcine cells identified by Streptomyces phage phiC31 integrase. BMC Mol Biol. Sep. 8, 2013;14:20. doi: 10.1186/1471-2199-14-20.
Bibb et al., Integration and excision by the large serine recombinase phiRv1 integrase. Mol Microbiol. Mar. 2005;55(6):1896-910. doi: 10.1111/j.1365-2958.2005.04517.X.
Biehs et al., DNA Double-Strand Break Resection Occurs during Non-homologous End Joining in G1 but is Distinct from Resection during Homologous Recombination. Mol Cell. Feb. 16, 2017;65(4):671-684.e5. doi: 10.1016/j.molcel.2016.12.016. Epub Jan. 26, 2017.
Blaese et al., Vectors in cancer therapy: how will they deliver? Cancer Gene Ther. Dec. 1995;2(4):291-7.
Blain et al., Nuclease activities of Moloney murine leukemia virus reverse transcriptase. Mutants with altered substrate specificities. J Biol Chem. Nov. 5, 1993;268(31):23585-92.
Blaisonneau et al., A circular plasmid from the yeast Torulaspora delbrueckii. Plasmid. 1997;38(3):202-9. doi: 10.1006/plas.1997.1315.
Blau et al., A proliferation switch for genetically?modified?cells. PNAS Apr. 1, 1997 94 (7) 3076-3081; https://doi.org/10.1073/pnas.94.7.3076.
Bloom et al., Evolving strategies for enzyme engineering. Curr Opin Struct Biol. Aug. 2005;15(4):447-52.
Bodi et al., Yeast m6A Methylated mRNAs are Enriched on Translating Ribosomes during Meiosis, and under Rapamycin Treatment. PLoS One. Jul. 17, 2015;10(7):e0132090. doi: 10.1371/journal.pone.0132090.
Boersma et al., Selection strategies for improved biocatalysts. FEBS J. May 2007;274(9):2181-95.
Bogdanove et al., Engineering altered protein-DNA recognition specificity. Nucleic Acids Res. Jun. 1, 2018;46(10):4845-4871. doi: 10.1093/nar/gky289.
Bolusani et al., Evolution of variants of yeast site-specific recombinase Flp that utilize native genomic sequences as recombination target sites. Nucleic Acids Res. 2006;34(18):5259-69. Epub Sep. 26, 2006.
Bondeson et al., Inversion of the IDS gene resulting from recombination with IDS-related sequences is a common cause of the Hunter syndrome. Hum Mol Genet. Apr. 1995;4(4):615-21. doi: 10.1093/hmg/4.4.615.
Borchardt et al., Controlling mRNA stability and translation with the CRISPR endoribonuclease Csy4. RNA. Nov. 2015;21(11):1921-30. doi: 10.1261/rna.051227.115. Epub Sep. 9, 2015.
Boutabout et al., DNA synthesis fidelity by the reverse transcriptase of the yeast retrotransposon Ty1. Nucleic Acids Res. Jun. 1, 2001;29(11):2217-22. doi: 10.1093/nar/29.11.2217.
Box et al., A multi-domain protein system based on the HC fragment of tetanus toxin for targeting DNA to neuronal cells. J Drug Target. Jul. 2003;11(6):333-43. doi: 10.1080/1061186310001634667.
Braun et al., Immunogenic duplex nucleic acids are nuclease resistant. J Immunol. Sep. 15, 1988;141(6):2084-9.
Brown et al., A mammalian protein targeted by G1-arresting rapamycin-receptor complex. Nature. Jun. 30, 1994;369(6483):756-8. doi: 10.1038/369756a0.
Brown et al., Characterization of the genetic elements required for site-specific integration of plasmid pSE211 in Saccharopolyspora erythraea. J Bacteriol. Apr. 1990;172(4):1877-88. doi: 10.1128/jb.172.4.1877-1888.1990.
Brown et al., Structural insights into the stabilization of MALAT1 noncoding RNA by a bipartite triple helix. Nat Struct Mol Biol. Jul. 2014;21(7):633-40. doi: 10.1038/nsmb.2844. Epub Jun. 22, 2014.
Brzezicha et al., Identification of human tRNA:m5C methyltransferase catalysing intron-dependent m5C formation in the first position of the anticodon of the pre-tRNA Leu (CAA). Nucleic Acids Res. 2006;34(20):6034-43. doi: 10.1093/nar/gkl765. Epub Oct. 27, 2006.
Buchschacher et al., Human immunodeficiency virus vectors for inducible expression of foreign genes. J Virol. May 1992;66(5):2731-9. doi: 10.1128/JVI.66.5.2731-2739.1992.
Buckley et al., Targeting the von Hippel-Lindau E3 ubiquitin ligase using small molecules to disrupt the VHL/HIF-1? interaction. J Am Chem Soc. Mar. 14, 2012;134(10):4465-8. doi: 10.1021/ja209924v. Epub Feb. 27, 2012.
Budworth et al., A brief history of triplet repeat diseases. Methods Mol Biol. 2013; 1010:3-17. doi: 10.1007/978-1-62703-411-1_1.
Buskirk et al., In vivo evolution of an RNA-based transcriptional activator. Chem Biol. Jun. 2003;10(6):533-40. doi: 10.1016/s1074-5521(03)00109-1.
Byrne et al., Multiplex gene regulation: a two-tiered approach to transgene regulation in transgenic mice. Proc Natl Acad Sci U S A. Jul. 1989;86(14):5473-7. doi: 10.1073/pnas.86.14.5473.
Cadwell et al., Randomization of genes by PCR mutagenesis. PCR Methods Appl. Aug. 1992;2(1):28-33. doi: 10.1101/gr.2.1.28.
Calame et al., Transcriptional controlling elements in the immunoglobulin and T cell receptor loci. Adv Immunol. 1988;43:235-75. doi: 10.1016/s0065-2776(08)60367-3.
Camarero et al., Biosynthesis of a Head-to-Tail Cyclized Protein with Improved Biological Activity. J. Am. Chem. Soc. May 29, 1999; 121(23):5597-5598. https://doi.org/10.1021/ja990929n.
Camper et al., Postnatal repression of the alpha-fetoprotein gene is enhancer independent. Genes Dev. Apr. 1989;3(4):537-46. doi: 10.1101/gad.3.4.537.
Camps et al., Targeted gene evolution in *Escherichia coli* using a highly error-prone DNA polymerase I. Proc Natl Acad Sci U S A. Aug. 19, 2003;100(17):9727-32. Epub Aug. 8, 2003.
Canchaya et al., Genome analysis of an inducible prophage and prophage remnants integrated in the *Streptococcus pyogenes* strain SF370. Virology. Oct. 25, 2002;302(2):245-58. doi: 10.1006/viro.2002.1570.
Carlier et al., Burkholderia cenocepacia H111 Rhy-family protein. Apr. 16, 2015. Retrieved from the Internet via https://www.ebi.ac.uk/ena/browser/api/embl/CDN65395.1?lineLimit=1000. Last retrieved Apr. 26, 2021.
Carlson et al., Negative selection and stringency modulation in phage-assisted continuous evolution. Nat Chem Biol. Mar. 2014;10(3):216-22. doi: 10.1038/nchembio.l453. Epub Feb. 2, 2014. With Supplementary Results.
Carr et al., Genome engineering. Nat Biotechnol. Dec. 2009;27(12):1151-62. doi: 10.1038/nbt.1590.
Carvalho et al., Evolution in health and medicine Sackler colloquium: Genomic disorders: a window into human gene and genome evolution. Proc Natl Acad Sci USA. Jan. 2, 20106;107 Suppl 1(Suppl 1):1765-71. doi: 10.1073/pnas.0906222107. Epub Jan. 13, 2010.
Cattaneo et al., SEL1L affects human pancreatic cancer cell cycle and invasiveness through modulation of PTEN and genes related to cell-matrix interactions. Neoplasia. 2005;7(11):1030-1038.
Ceccaldi et al., Repair Pathway Choices and Consequences at the Double-Strand Break. Trends Cell Biol. Jan. 2016;26(1):52-64. doi: 10.1016/j.tcb.2015.07.009. Epub Oct. 1, 2015.
Chadalavada et al., Wild-type is the optimal sequence of the HDV ribozyme under cotranscriptional conditions. RNA. Dec. 2007;13(12):2189-201. doi: 10.1261/rna.778107. Epub Oct. 23, 2007.
Chalberg et al., Integration specificity of phage phiC31 integrase in the human genome. J Mol Biol. Mar. 17, 2006;357(1):28-48. doi: 10.1016/j.jmb.2005.11.098. Epub Dec. 22, 2005.
Chalberg et al., phiC31 integrase confers genomic integration and long-term transgene expression in rat retina. Invest Ophthalmol Vis Sci. Jun. 2005;46(6):2140-6. doi: 10.1167/iovs.04-1252.
Chan et al., Novel selection methods for DNA-encoded chemical libraries. Curr Opin Chem Biol. 2015;26:55-61. doi:10.1016/j.cbpa.2015.02.010.
Chan et al., The choice of nucleotide inserted opposite abasic sites formed within chromosomal DNA reveals the polymerase activities participating in translesion DNA synthesis. DNA Repair (Amst). Nov. 2013;12(11):878-89. doi: 10.1016/j.dnarep.2013.07.008. Epub Aug. 26, 2013.

(56) References Cited

OTHER PUBLICATIONS

Chapman et al., Playing the end game: DNA double-strand break repair pathway choice. Mol Cell. Aug. 24, 2012;47(4):497-510. doi: 10.1016/j.molcel.2012.07.029.
Chaturvedi et al., Stabilization of triple-stranded oligonucleotide complexes: use of probes containing alternating phosphodiester and stereo-uniform cationic phosphoramidate linkages. Nucleic Acids Res. Jun. 15, 1996;24(12):2318-23.
Chen et al., Enhanced proofreading governs CRISPR-Cas9 targeting accuracy. Nature. Oct. 19, 2017;550(7676):407-410. doi: 10.1038/nature24268. Epub Sep. 20, 2017.
Chen et al., A general strategy for the evolution of bond-forming enzymes using yeast display. Proc Natl Acad Sci U S A. Jul. 12, 2011;108(28):11399-404. doi: 10.1073/pnas. 1101046108. Epub Jun. 22, 2011.
Chen et al., Highly Efficient Mouse Genome Editing by CRISPR Ribonucleoprotein Electroporation of Zygotes. J Biol Chem. Jul. 8, 2016;291(28):14457-67. doi: 10.1074/jbc.M116.733154. Epub May 5, 2016.
Chen et al., m(6)A RNA methylation is regulated by microRNAs and promotes reprogramming to pluripotency. Cell Stem Cell. Mar. 5, 2015;16(3):289-301. doi: 10.1016/j.stem.2015.01.016. Epub Feb. 12, 2015.
Chew et al., A multifunctional AAV-CRISPR-Cas9 and its host response. Nat Methods. Oct. 2016;13(10):868-74. doi: 10.1038/nmeth.3993. Epub Sep. 5, 2016. Supplementary Information.
Chin, Expanding and reprogramming the genetic code of cells and animals. Annu Rev Biochem. 2014;83:379-408. doi: 10.1146/annurev-biochem-060713-035737. Epub Feb. 10, 2014.
Cho et al., Site-specific recombination of bacteriophage P22 does not require integration host factor. J Bacteriol. Jul. 1999;181(14):4245-9. doi: 10.1128/JB.181.14.4245-4249.1999.
Choe et al., Forging Ahead through Darkness: PCNA, Still the Principal Conductor at the Replication Fork. Mol Cell. Feb. 2, 2017;65(3):380-392. doi: 10.1016/j.molcel.2016.12.020.
Choi et al., N(6)-methyladenosine in mRNA disrupts tRNA selection and translation-elongation dynamics. Nat Struct Mol Biol. Feb. 2016;23(2): 110-5. doi: 10.1038/nsmb.3148. Epub Jan. 11, 2016.
Choi et al., Protein trans-splicing and characterization of a split family B-type DNA polymerase from the hyperthermophilic archaeal parasite Nanoarchaeum equitans. J Mol Biol. Mar. 1, 2006;356(5):1093-106. doi: 10.1016/j.jmb.2005.12.036. Epub Dec. 27, 2005.
Choi et at al., Translesion synthesis across abasic lesions by human B-family and Y-family DNA polymerases ?, ?, ?, ?, ?, and Revl J Mol Biol. Nov. 19, 2010;404(1):34-44. doi: 10.1016/j.jmb.2010.09.015. Epub Oct. 1, 2010.
Chong et al., Modulation of protein splicing of the *Saccharomyces cerevisiae* vacuolar membrane ATPase intein. J Biol Chem. Apr. 24, 1998;273(17): 10567-77. doi: 10.1074/jbc.273.17.10567.
Chong et al., Utilizing the C-terminal cleavage activity of a protein splicing element to purify recombinant proteins in a single chromatographic step. Nucleic Acids Res. Nov. 15, 1998;26(22):5109-15. doi: 10.1093/nar/26.22.5109.
Chong et al., Protein splicing involving the *Saccharomyces cerevisiae* VMA intein. The steps in the splicing pathway, side reactions leading to protein cleavage, and establishment of an in vitro splicing system. J Biol Chem. Sep. 6, 1996;271(36):22159-68. doi: 10.1074/jbc.271.36.22159.
Chong et al., Single-column purification of free recombinant proteins using a self-cleavable affinity tag derived from a protein splicing element. Gene. Jun. 19, 1997;192(2):271-81. doi: 10.1016/s0378 -1119(97)00105-4.
Choudhury et al., Engineering RNA endonucleases with customized sequence specificities. Nat Commun. 2012;3:1147. doi: 10.1038/ncomms2154.
Choulika et al., Induction of homologous recombination in mammalian chromosomes by using the I-SceI system of *Saccharomyces cerevisiae*. Mol Cell Biol. Apr. 1995;15(4):1968-73. doi: 10.1128/MCB.15.4.1968.
Christiansen et al., Characterization of the lactococcal temperate phage TP901-1 and its site-specific integration. J Bacteriol. Feb. 1994;176(4):1069-76. doi: 10.1128/jb.176.4.1069-1076.1994.
Chu et al., Increasing the efficiency of homology-directed repair for CRISPR-Cas9-induced precise gene editing in mammalian cells. Nat Biotech. Feb. 13, 2015;33:543-8. doi: 10.1038/nbt.3198. Epub Mar. 24, 2015.
Chuai et al., DeepCRISPR: optimized CRISPR guide RNA design by deep learning. Genome Biol. Jun. 26, 2018;19(1):80. doi: 10.1186/s13059-018-1459-4.
Chuai et al., In Silico Meets In Vivo: Towards Computational CRISPR-Based sgRNA Design. Trends Biotechnol. Jan. 2017;35(1):12-21. doi: 10.1016/j.tibtech.2016.06.008. Epub Jul. 11, 2016.
Chuang et al., Novel Heterotypic Rox Sites for Combinatorial Dre Recombination Strategies. G3 (Bethesda). Dec. 29, 2015;6(3):559-71. doi: 10.1534/g3.115.025841.
Chujo et al, Trmt61B is a methyltransferase responsible for 1-methyladenosine at position 58 of human mitochondrial tRNAs. RNA. Dec. 2012;18(12):2269-76. doi: 10.1261/rna.035600.112. Epub Oct. 24, 2012.
Clackson et al., Redesigning an FKBP-ligand interface to generate chemical dimerizers with novel specificity. Proc Natl Acad Sci U S A. Sep. 1, 1998;95(18):10437-42. doi: 10.1073/pnas.95.18.10437.
Clement et al., CRISPResso2 provides accurate and rapid genome editing sequence analysis. Nat Biotechnol. Mar. 2019;37(3):224-226. doi: 10.1038/s41587-019-0032-3.
Cokol et al., Finding nuclear localization signals. EMBO Rep. Nov. 2000;1(5):411-5. doi: 10.1093/embo-reports/kvd092.
Cole et al., Reconstructing evolutionary adaptive paths for protein engineering. Methods Mol Biol. 2013;978:115-25. doi: 10.1007/978-l-62703-293-3_8.
Collinge, Prion diseases of humans and animals: their causes and molecular basis. Annu Rev Neurosci. 2001;24:519-50. doi: 10.1146/annurev.neuro.24.1.519.
Conrad et al., A Kaposi's sarcoma virus RNA element that increases the nuclear abundance of intronless transcripts. EMBO J. May 18, 2005;24(10):1831-41. doi: 10.1038/sj.emboj.7600662. Epub Apr. 28, 2005.
Cornu et al., Refining strategies to translate genome editing to the clinic. Nat Med. Apr. 3, 2017;23(4):415-423. doi: 10.1038/nm.4313.
Cotton et al., Insertion of a Synthetic Peptide into a Recombinant Protein Framework:? A Protein Biosensor. J. Am. Chem. Soc. Jan. 22, 1999; 121(5):1100-1. https://doi.org/10.1021/ja983804b.
Cox et al., RNA editing with CRISPR-Cas13. Science. Nov. 24, 2017;358(6366):1019-1027. doi: 10.1126/science.aaq0180. Epub Oct. 25, 2017.
Cox, Proteins pinpoint double strand breaks. Elife. Oct. 29, 2013;2:e01561. doi: 10.7554/eLife.01561.
Crabtree et al., Three-part inventions: intracellular signaling and induced proximity. Trends Biochem Sci. Nov. 1996;21(11):418-22. doi: 10.1016/s0968-0004(96)20027-1.
Crick, On protein synthesis. Symp Soc Exp Biol. 1958;12:138-63.
Crystal, Transfer of genes to humans: early lessons and obstacles to success. Science. Oct. 20, 1995;270(5235):404-10. doi: 10.1126/science.270.5235.404.
Cui et al., Consequences of Cas9 cleavage in the chromosome of *Escherichia coli*. Nucleic Acids Res. May 19, 2016;44(9):4243-51. doi: 10.1093/nar/gkw223. Epub Apr. 8, 2016.
Cui et al., m6A RNA Methylation Regulates the Self-Renewal and Tumorigenesis of Glioblastoma Stem Cells. Cell Rep. Mar. 14, 2017; 18(11):2622-2634. doi: 10.1016/j.cehep.2017.02.059.
Cui et al., Review of CRISPR/Cas9 sgRNA Design Tools. Interdiscip Sci. Jun. 2018;10(2):455-465. doi: 10.1007/s12539-018-0298-z. Epub Apr. 11, 2018.
Cupples et al., A set of lacZ mutations in *Escherichia coli* that allow rapid detection of each of the six base substitutions. Proc Natl Acad Sci U S A. Jul. 1989;86(14):5345-9.
Dahlgren et al., A novel mutation in ribosomal protein S4 that affects the function of a mutated RF1. Biochimie. Aug. 2000;82(8):683-91.

(56) References Cited

OTHER PUBLICATIONS

Dahlman et al., Orthogonal gene knockout and activation with a catalytically active Cas9 nuclease. Nat Biotechnol. Nov. 2015;33(11):1159-61. doi: 10.1038/nbt.3390.
Dandage et al., beditor: A Computational Workflow for Designing Libraries of Guide RNAs for CRISPR-Mediated Base Editing. Genetics. Jun. 2019;212(2):377-385. doi: 10.1534/genetics. 119. 302089. Epub Apr. 1, 2019.
Dang et al., Optimizing sgRNA structure to improve CRISPR-Cas9 knockout efficiency. Genome Biol. Dec. 15, 2015;16:280. doi: 10.1186/s13059-015-0846-3.
Das et al.,The crystal structure of the monomeric reverse transcriptase from Moloney murine leukemia virus. Structure. May 2004;12(5):819-29. doi: 10.1016/j.str.2004.02.032.
Dassa et al., Fractured genes: a novel genomic arrangement involving new split inteins and a new homing endonuclease family. Nucleic Acids Res. May 2009;37(8):2560-73. doi: 10.1093/nar/gkp095. Epub Mar. 5, 2009.
Dassa et al., Trans protein splicing of cyanobacterial split inteins in endogenous and exogenous combinations. Biochemistry. Jan. 9, 2007;46(1):322-30. doi: 10.1021/bi0611762.
Datsenko et al., One-step inactivation of chromosomal genes in *Escherichia coli* K-12 using PCR products. Proc Natl Acad Sci U S A. Jun. 6, 2000;97(12):6640-5.
De Felipe et al., Co-translational, intraribosomal cleavage of polypeptides by the foot-and-mouth disease virus 2A peptide. J Biol Chem. Mar. 28, 2003;278(13): 11441-8. doi: 10.1074/jbc. M211644200. Epub Jan. 8, 2003.
De Wit et al., The Human CD4+ T Cell Response against Mumps Virus Targets a Broadly Recognized Nucleoprotein Epitope. J Virol. Mar. 5, 2019;93(6):e01883-18. doi: 10.1128/JVI.01883-18.
Dean et al., Genetic restriction of HIV-1 infection and progression to AIDS by a deletion allele of the CKR5 structural gene. Hemophilia Growth and Development Study, Multicenter AIDS Cohort Study, Multicenter Hemophilia Cohort Study, San Francisco City Cohort, ALIVE Study. Science. Sep. 27, 1996;273(5283): 1856-62. doi: 10.1126/science.273.5283.1856.
Dekosky et al., Large-scale sequence and structural comparisons of human naive and antigen-experienced antibody repertoires. Proc Natl Acad Sci U S A. May 10, 2016;113(19):E2636-45. doi: 10.1073/pnas.1525510113. Epub Apr. 25, 2016.
Delebecque et al., Organization of intracellular reactions with rationally designed RNA assemblies. Science. Jul. 22, 2011;333(6041):470-4. doi: 10.1126/science. 1206938. Epub Jun. 23, 2011.
Deng et al., Widespread occurrence of N6-methyladenosine in bacterial mRNA. Nucleic Acids Res. Jul. 27, 2015;43(13):6557-67. doi: 10.1093/nar/gkv596. Epub Jun. 11, 2015.
Deriano et al., Modernizing the nonhomologous end-joining repertoire: alternative and classical NHEJ share the stage. Annu Rev Genet. 2013;47:433-55. doi: 10.1146/annurev-genet-110711-155540. Epub Sep. 11, 2013.
Deussing, Targeted mutagenesis tools for modelling psychiatric disorders. Cell Tissue Res. Oct. 2013;354(1):9-25. doi: 10.1007/s00441-013-1708-5. Epub Sep. 10, 2013.
Dever et al., CRISPR/Cas9 ?-globin gene targeting in human haematopoietic stem cells. Nature. Nov. 17, 2016;539(7629):384-389. doi: 10.1038/nature20134. Epub Nov. 7, 2016.
Dianov et al., Mammalian base excision repair: the forgotten archangel. Nucleic Acids Res. Apr. 1, 2013;41(6):3483-90. doi: 10.1093/nar/gkt076. Epub Feb. 13, 2013.
Dicarlo et al., Genome engineering in *Saccharomyces cerevisiae* using CRISPR-Cas systems. Nucleic Acids Res. Apr. 2013;41(7):4336-43. doi: 10.1093/nar/gkt135. Epub Mar. 4, 2013.
Dicarlo et al., Safeguarding CRISPR-Cas9 gene drives in yeast. Nat Biotechnol. Dec. 2015;33(12):1250-1255. doi: 10.1038/nbt.3412. Epub Nov. 16, 2015.
Dickey et al., Single-stranded DNA-binding proteins: multiple domains for multiple functions. Structure. Jul. 2, 2013;21(7):1074-84. doi: 10.1016/j.str.2013.05.013.
Dickinson et al., Experimental interrogation of the path dependence and stochasticity of protein evolution using phage-assisted continuous evolution. Proc Natl Acad Sci U S A. May 2013;110(22):9007-12.
Dillon, Regulating gene expression in gene therapy. Trends Biotechnol. May 1993;11(5):167-73. doi: 10.1016/0167-7799(93)90109-M.
Dingwall et al., Nuclear targeting sequences—a consensus? Trends Biochem Sci. Dec. 1991;16(12):478-81. doi: 10.1016/0968-0004(91)90184-w.
Diver et al., Single-Step Synthesis of Cell-Permeable Protein Dimerizers That Activate Signal Transduction and Gene Expression. J. Am. Chem. Soc. Jun. 4, 1997;119(22):5106-5109. https://doi.org/10.1021/ja963891c.
Dominissini et al., Topology of the human and mouse m6A RNA methylomes revealed by m6A-seq. Nature. Apr. 29, 2012;485(7397):201-6. doi: 10.1038/nature11112.
Dorgan et al., An enzyme-coupled continuous spectrophotometric assay for S-adenosylmethionine-dependent methyltransferases. Anal Biochem. Mar. 15, 2006;350(2):249-55. doi: 10.1016/j.ab.2006.01.004. Epub Feb. 7, 2006.
Dorr et al., Reprogramming the specificity of sortase enzymes. Proc Natl Acad Sci U S A. Sep. 16, 2014;111(37):13343-8. doi: 10.1073/pnas.1411179111. Epub Sep. 3, 2014.
Dove et al., Conversion of the omega subunit of *Escherichia coli* RNA polymerase into a transcriptional activator or an activation target. Genes Dev. Mar. 1, 1998;12(5):745-54.
Doyon et al., Directed evolution and substrate specificity profile of homing endonuclease I-SceI. J Am Chem Soc. Feb. 22, 2006;128(7):2477-84.
Drake, A constant rate of spontaneous mutation in DNA-based microbes. Proc Natl Acad Sci U S A. Aug. 15, 1991;88(16):7160-4.
Dubois et al., Retroviral RNA Dimerization: From Structure to Functions. Front Microbiol. Mar. 22, 2018;9:527. doi: 10.3389/fmicb.2018.00527.
Dunbar et al., Gene therapy comes of age. Science. Jan. 12, 2018;359(6372):eaan4672. doi: 10.1126/science.aan4672.
Dupuy et al., Le syndrome de De La Chapelle [De La Chapelle syndrome]. Presse Med. Mar. 3, 2001;30(8):369-72. French.
Durai et al., A bacterial one-hybrid selection system for interrogating zinc finger-DNA interactions. Comb Chem High Throughput Screen. May 2006;9(4):301-11.
Durai et al., Zinc finger nucleases: custom-designed molecular scissors for genome engineering of plant and mammalian cells. Nucleic Acids Res. Oct. 26, 2005;33(18):5978-90. doi: 10.1093/nar/gki912.
Edlund et al., Cell-specific expression of the rat insulin gene: evidence for role of two distinct 5' flanking elements. Science. Nov. 22, 1985;230(4728):912-6. doi: 10.1126/science.3904002.
Eick et al., Robustness of Reconstructed Ancestral Protein Functions to Statistical Uncertainty. Mol Biol Evol. Feb. 1, 2017;34(2):247-261. doi: 10.1093/molbev/msw223.
Engel et al., The emerging role of mRNA methylation in normal and pathological behavior. Genes Brain Behav. Mar. 2018;17(3):e12428. doi: 10.1111/gbb.12428. Epub Nov. 17, 2017.
Engelward et al., Base excision repair deficient mice lacking the Aag alkyladenine DNA glycosylase. Proc Natl Acad Sci U S A. Nov. 25, 1997;94(24):13087-92.
England, Unnatural amino acid mutagenesis: a precise tool for probing protein structure and function. Biochemistry. Sep. 21, 2004;43(37):11623-9.
Enyeart et al., Biotechnological applications of mobile group II introns and their reverse transcriptases: gene targeting, RNA-seq, and non-coding RNA analysis. Mobile DNA 5, 2 (2014). https://doi.org/10.1186/1759-8753-5-2. https://doi.org/10.1186/1759-8753-5-2.
Eriksson et al., Recurrent de novo point mutations in lamin A cause Hutchinson-Gilford progeria syndrome. Nature. May 15, 2003;423(6937):293-8. doi: 10.1038/nature01629. Epub Apr. 25, 2003. PMID: 12714972.
Evans et al., Semisynthesis of cytotoxic proteins using a modified protein splicing element. Protein Sci. Nov. 1998;7(11):2256-64. doi: 10.1002/pro.5560071103.

(56) References Cited

OTHER PUBLICATIONS

Evans et al., The cyclization and polymerization of bacterially expressed proteins using modified self-splicing inteins. J Biol Chem. Jun. 25, 1999;274(26):18359-63. doi: 10.1074/jbc.274.26.18359.
Evans et al., The in vitro ligation of bacterially expressed proteins using an intein from Methanobacterium thermoautotrophicum. J Biol Chem. Feb. 12, 1999;274(7):3923-6. doi: 10.1074/jbc.274.7.3923.
Evers et al., CRISPR knockout screening outperforms shRNA and CRISPRi in identifying essential genes. Nat Biotechnol. Jun. 2016;34(6):631-3. doi: 10.1038/nbt.3536. Epub Apr. 25, 2016.
Falnes et al., DNA repair by bacterial AlkB proteins. Res Microbiol. Oct. 2003;154(8):531-8. doi: 10.1016/S0923-2508(03)00150-5.
Falnes et al., Repair of methyl lesions in DNA and RNA by oxidative demethylation. Neuroscience. Apr. 14, 2007;145(4):1222-32. doi: 10.1016/j.neuroscience.2006.11.018. Epub Dec. 18, 2006.
Feldstein et al., Two sequences participating in the autolytic processing of satellite tobacco ringspot virus complementary RNA. Gene. Oct. 15, 1989;82(1):53-61. doi: 10.1016/0378-1119(89)90029-2.
Feng et al., Crystal structures of the human RNA demethylase Alkbh5 reveal basis for substrate recognition. J Biol Chem. Apr. 25, 2014;289(17):11571-11583. doi: 10.1074/jbc.M113.546168. Epub Mar. 10, 2014.
Feng et al., Human L1 retrotransposon encodes a conserved endonuclease required for retrotransposition. Cell. Nov. 29, 1996;87(5):905-16. doi: 10.1016/s0092-8674(00)81997-2.
Feuk, Inversion variants in the human genome: role in disease and genome architecture. Genome Med. Feb. 12, 2010;2(2):11. doi: 10.1186/gm132.
Filippov et al., A novel type of RNase III family proteins in eukaryotes. Gene. Mar. 7, 2000;245(1):213-21. doi: 10.1016/s0378-1119(99)00571-5.
Fischbach et al., Directed evolution can rapidly improve the activity of chimeric assembly-line enzymes. Proc Natl Acad Sci U S A. Jul. 17, 2007;104(29):11951-6. doi: 10.1073/pnas.0705348104. Epub Jul. 9, 2007.
Fitzjohn, Diversitree: comparative phylogenetic analyses of diversification in R. Methods in Evology and Evolution. Dec. 2012;3(6):1084-92 .doi: 10.1111/j.2041-210X.2012.00234.x.
Flajolet et al., Woodchuck hepatitis virus enhancer I and enhancer II are both involved in N-myc2 activation in woodchuck liver tumors. J Virol. Jul. 1998;72(7):6175-80. doi: 10.1128/JVI.72.7.6175-6180.1998.
Flynn et al., CRISPR-mediated genotypic and phenotypic correction of a chronic granulomatous disease mutation in human iPS cells. Exp Hematol. Oct. 2015;43(10):838-848.e3. doi: 10.1016/j.exphem.2015.06.002. Epub Jun. 19, 2015. Including supplementary figures and data.
Fogg et al., Genome Integration and Excision by a New Streptomyces Bacteriophage, ?Joe. Appl Environ Microbiol. Feb. 15, 2017;83(5):e02767-16. doi: 10.1128/AEM.02767-16.
Forster et al., Self-cleavage of virusoid RNA is performed by the proposed 55-nucleotide active site. Cell. Jul. 3, 1987;50(1):9-16. doi: 10.1016/0092-8674(87)90657-x.
Foruni et al., Different DNA polymerases are involved in the short- and long-patch base excision repair in mammalian cells. Biochemistry. Mar. 17, 1998;37(11):3575-80. doi: 10.1021/bi972999h.
Fouts et al., Sequencing Bacillus anthracis typing phages gamma and cherry reveals a common ancestry. J Bacteriol. May 2006;188(9):3402-8. doi: 10.1128/JB.188.9.3402-3408.2006.
Freitas et al., Mechanisms and signals for the nuclear import of proteins. Curr Genomics. Dec. 2009;10(8):550-7. doi: 10.2174/138920209789503941.
Fu et al., Promises and Pitfalls of Intracellular Delivery of Proteins. Bioconjugate Chemistry. Aug. 2014;25:1602-8.
Furukawa et al., In vitro selection of allosteric ribozymes that sense the bacterial second messenger c-di-GMP. Methods Mol Biol. 2014;1111:209-20. doi: 10.1007/978-1-62703-755-6_15.
Gaj et al., 3rd. Genome engineering with custom recombinases. Methods Enzymol. 2014;546:79-91. doi: 10.1016/B978-0-12-801185-0.00004-0.
Gajula, Designing an Elusive CoG?GoC CRISPR Base Editor. Trends Biochem Sci. Feb. 2019;44(2):91-94. doi: 10.1016/j.tibs.2018.10.004. Epub Nov. 13, 2018.
Gao et al., Cationic liposome-mediated gene transfer. Gene Ther. Dec. 1995;2(10):710-22.
Gao et al., Treatment of autosomal dominant hearing loss by in vivo delivery of genome editing agents. Nature. Jan. 11, 2018;553(7687):217-221. doi: 10.1038/nature25164. Epub Dec. 20, 2017.
Gapinske et al., CRISPR-SKIP: programmable gene splicing with single base editors. Genome Biol. Aug. 15, 2018;19(1):107. doi: 10.1186/s13059-018-1482-5.
Garibyan et al., Use of the rpoB gene to determine the specificity of base substitution mutations on the *Escherichia coli* chromosome. DNA Repair (Amst). May 13, 2003;2(5):593-608.
Gaudelli et al., Programmable base editing of AoT to GoC in genomic DNA without DNA cleavage. Nature. Nov. 23, 2017;551(7681):464-471. doi: 10.1038/nature24644. Epub Oct. 25, 2017. Erratum in: Nature. May 2, 2018.
Geary, Addgene blog. CRISPR 101: Cas9 nickase design and homology directed repair. 2018. pp. 1-12. https://blog.addgene.org/crispr-101-cas9-nickase-design-and-homlogy-directed-repair. Last retrieved online Jun. 25, 2021.
Gehrke et al., An APOBEC3A-Cas9 base editor with minimized bystander and off-target activities. Nat Biotechnol. Nov. 2018;36(10):977-982. doi: 10.1038/nbt.4199. Epub Jul. 30, 2018.
GenBank Accession No. J01600.1. Brooks et al., *E.coli* dam gene coding for DNA adenine methylase. Apr. 26, 1993.
GenBank Accession No. U07651.1. Lu, *Escherichia coli* K12 negative regulator of replication initiation (seqA) gene, complete cds. Jul. 19, 1994.
GENBANK Submission; NIH/NCBI, Accession No. AAA66622.1. Martinelli et al., May 18, 1995. 2 pages.
GENBANK Submission; NIH/NCBI, Accession No. AGT42196. Farzadfar et al., Nov. 2, 2013. 2 pages.
GENBANK Submission; NIH/NCBI, Accession No. APG80656.1. Burstein et al., Dec. 10, 2016. 1 pages.
GENBANK Submission; NIH/NCBI, Accession No. AYD60528.1. Ram et al., Oct. 2, 2018. 1 page.
GENBANK Submission; NIH/NCBI, Accession No. NP 955579.1. Chen et al., Aug. 13, 2018. 5 pages.
GENBANK Submission; NIH/NCBI, Accession No. RFF81513.1. Zhou et al., Aug. 21, 2018. 2 pages.
GENBANK Submission; NIH/NCBI, Accession No. SNX31424.1. Weckx, S., Feb. 16, 2018. 2 pages.
GENBANK Submission; NIH/NCBI, Accession No. TGH57013. Xu et al., Apr. 9, 2019. 2 pages.
George et al., Adenosine deaminases acting on RNA, RNA editing, and interferon action. J Interferon Cytokine Res. Jan. 2011;31(1):99-117. doi: 10.1089/jir.2010.0097. Epub Dec. 23, 2010. PMID: 21182352; PMCID: PMC3034097.
Gerard et al., Influence on stability in *Escherichia coli* of the carboxy-terminal structure of cloned Moloney murine leukemia virus reverse transcriptase. DNA. Aug. 1986;5(4):271-9. doi: 10.1089/dna.1986.5.271.
Gerard et al., Purification and characterization of the DNA polymerase and RNase H activities in Moloney murine sarcoma-leukemia virus. J Virol. Apr. 1975;15(4):785-97. doi: 10.1128/JVI.15.4.785-797.1975.
Gerard et al., The role of template-primer in protection of reverse transcriptase from thermal inactivation. Nucleic Acids Res. Jul. 15, 2002;30(14):3118-29. doi: 10.1093/nar/gkf417.
Gerber et al., An adenosine deaminase that generates inosine at the wobble position of tRNAs. Science. Nov. 5, 1999;286(5442):1146-9. doi: 10.1126/science.286.5442.1146.
Ghahfarokhi et al., Blastocyst Formation Rate and Transgene Expression are Associated with Gene Insertion into Safe and Non-Safe Harbors in the Cattle Genome. Sci Rep. Nov. 13, 2017;7(1):15432. doi: 10.1038/s41598-017-15648-3.

(56) References Cited

OTHER PUBLICATIONS

Gil, Position-dependent sequence elements downstream of AAUAAA are required for efficient rabbit beta-globin mRNA 3' end formation. Cell. May 8, 1987;49(3):399-406. doi: 10.1016/0092-8674(87)90292-3.
Glasgow et al.,DNA-binding properties of the Hin recombinase. J Biol Chem. Jun. 15, 1989;264(17):10072-82.
Glassner et al., Generation of a strong mutator phenotype in yeast by imbalanced base excision repair. Proc Natl Acad Sci U S A. Aug. 15, 1998;95(17):9997-10002.
Goldberg et al., Epigenetics: a landscape takes shape. Cell. Feb. 23, 2007;128(4):635-8. doi: 10.1016/j.cell.2007.02.006.
Gong et al., Active DNA demethylation by oxidation and repair. Cell Res. Dec. 2011;21(12):1649-51. doi: 10.1038/cr.2011.140. Epub Aug. 23, 2011.
Goodnough et al., Development of a delivery vehicle for intracellular transport of botulinum neurotoxin antagonists. FEBS Lett. Feb. 27, 2002;513(2-3):163-8.
Gou et al., Designing single guide RNA for CIRSPR-Cas9 base editor by deep learning. Peer reviewed Thesis/Dissertation. UCLA Electronic Theses and Dissertations. Jan. 1, 2019. Retrieved from the Internet via https://escholarship.org/uc/item/7vf9z54t. Last accessed on Apr. 29, 2021.
Gregory et al., Integration site for Streptomyces phage phiBT1 and development of site-specific integrating vectors. J Bacteriol. Sep. 2003;185(17):5320-3. doi: 10.1128/jb. 185.17.5320-5323.2003.
Griffiths, Endogenous retroviruses in the human genome sequence. Genome Biol. 2001 ;2(6):Reviews 1017. doi: 10.1186/GB-2001-2-6-reviews1017. Epub Jun. 5, 2001.
Grishok et al., Genes and Mechanisms Related to RNA Interference Regulate Expression of the Small Temporal RNAs that Control C. elegans Developmental Timing. Jul. 13, 2001:106(1):P23-4.
Groher et al., Synthetic riboswitches—A tool comes of age. Biochim Biophys Acta. Oct. 2014;1839(10):964-973. doi: 10.1016/j.bbagrm.2014.05.005. Epub May 17, 2014.
Groth et al., Construction of transgenic *Drosophila* by using the site-specific integrase from phage phiC31. Genetics. Apr. 2004; 166(4):1775-82. doi: 10.1534/genetics. 166.4.1775.
Gruber et al., Strategies for measuring evolutionary conservation of RNA secondary structures. BMC Bioinformatics. Feb. 26, 2008;9:122. doi: 10.1186/1471-2105-9-122.
Grunebaum et al., Recent advances in understanding and managing adenosine deaminase and purine nucleoside phosphorylase deficiencies. Curr Opin Allergy Clin Immunol. Dec. 2013;13(6):630-8. doi: 10.1097/ACI.0000000000000006.
Grünewald et al., Transcriptome-wide off-target RNA editing induced by CRISPR-guided DNA base editors. Nature. May 2019;569(7756):433-437. doi: 10.1038/s41586-019-1161-z. Epub Apr. 17, 2019.
Guo et al., Facile functionalization of FK506 for biological studies by the thiol-ene 'click' reaction. RSC Advances. 2014;22:11400-3.
Gupta et al., Cross-talk between cognate and noncognate RpoE sigma factors and Zn(2+)-binding anti-sigma factors regulates photooxidative stress response in Azospirillum brasilense. Antioxid Redox Signal. Jan. 1, 2014;20(1):42-59. doi: 10.1089/ars.2013.5314. Epub Jul. 19, 2013.
Gupta et al., Sequences in attB that affect the ability of phiC31 integrase to synapse and to activate DNA cleavage. Nucleic Acids Res. 2007;35(10):3407-19. doi: 10.1093/nar/gkm206. Epub May 3, 2007.
Guzman et al., Tight regulation, modulation, and high-level expression by vectors containing the arabinose PBAD promoter. J Bacteriol. 1995;177(14):4121-4130.
Haapaniemi et al., CRISPR-Cas9 genome editing induces a p53-mediated DNA damage response. Nat Med. Jul. 2018;24(7):927-930. doi: 10.1038/s41591-018-0049-z. Epub Jun. 11, 2018.
Haddada et al., Gene therapy using adenovirus vectors. Curr Top Microbiol Immunol. 1995; 199 ( Pt 3):297-306. doi: 10.1007/978-3-642-79586-2_14.
Halmai et al., Targeted CRIPSR/dCas9-mediated reactivation of epigenetically silenced genes suggests limited escape from the inactive X chromosome. 2nd Inti Conf on Epigenetics and Bioengineering. Oct. 4, 2018; Retrieved from the Internet: https://aiche.confex.com/aiche/epibio18/webprogram/paper544785.html. Retrieved Jun. 29, 2020.
Halvas et al., Role of murine leukemia virus reverse transcriptase deoxyribonucleoside triphosphate-binding site in retroviral replication and in vivo fidelity. J Virol. Nov. 2000;74(22):10349-58. doi: 10.1128/jvi.74.22.10349-10358.2000.
Handa et al., Template-assisted synthesis of adenine-mutagenized cDNA by a retroelement protein complex. Nucleic Acids Res. Oct. 12, 2018;46(18):9711-9725. doi: 10.1093/nar/gky620.
Hanson et al., Codon optimality, bias and usage in translation and mRNA decay. Nat Rev Mol Cell Biol. Jan. 2018;19(1):20-30. doi: 10.1038/nrm.2017.91. Epub Oct. 11, 2017.
Harms et al., Evolutionary biochemistry: revealing the historical and physical causes of protein properties. Nat Rev Genet. Aug. 2013;14(8):559-71. doi: 10.1038/nrg3540.
Harrington et al., A thermostable Cas9 with increased lifetime in human plasma. Nat Commun. Nov. 10, 2017;8(1):1424. doi: 10.1038/s41467-017-01408-4.
Hasegawa et al., Spontaneous mutagenesis associated with nucleotide excision repair in *Escherichia coli*. Genes Cells. May 2008;13(5):459-69. doi: 10.1111/j.1365-2443.2008.01185.x.
Hector et al., CDKL5 variants: Improving our understanding of a rare neurologic disorder. Neurol Genet. Dec. 15, 2017;3(6):e200. doi: 10.1212/NXG.0000000000000200.
Heidenreich et al., Non-homologous end joining as an important mutagenic process in cell cycle-arrested cells. EMBO J. May 1, 2003;22(9):2274-83. doi: 10.1093/emboj/cdg203.
Held et al., In vivo correction of murine hereditary tyrosinemia type I by phiC31 integrase-mediated gene delivery. Mol Ther. Mar. 2005;11(3):399-408. doi: 10.1016/j.ymthe.2004.11.001.
Hendricks et al., The S. cerevisiae Mag1 3-methyladenine DNA glycosylase modulates susceptibility to homologous recombination. DNA Repair (Amst). 2002;1(8):645-659.
Hermonat et al., Use of adeno-associated virus as a mammalian DNA cloning vector: transduction of neomycin resistance into mammalian tissue culture cells. Proc Natl Acad Sci U S A. Oct. 1984;81(20):6466-70. doi: 10.1073/pnas.81.20.6466.
Herschhorn et al., Retroviral reverse transcriptases. Cell Mol Life Sci. Aug. 2010;67(16):2717-47. doi: 10.1007/s00018-010-0346-2. Epub Apr. 1, 2010.
Herzig et al., A Novel Leu92 Mutant of HIV-1 Reverse Transcriptase with a Selective Deficiency in Strand Transfer Causes a Loss of Viral Replication. J Virol. Aug. 2015;89(16):8119-29. doi: 10.1128/JVI.00809-15. Epub May 20, 2015.
Higgs et al., Genetic complexity in sickle cell disease. Proc Natl Acad Sci U S A. Aug. 19, 2008;105(33):11595-6. doi: 10.1073/pnas.0806633105. Epub Aug. 11, 2008.
Hille et al., The Biology of CRISPR-Cas: Backward and Forward. Cell. Mar. 8, 2018;172(6):1239-1259. doi: 10.1016/j.cell.2017.11.032.
Hoang et al., UFBoot2: Improving the Ultrafast Bootstrap Approximation. Mol Biol Evol. Feb. 1, 2018;35(2):518-522. doi: 10.1093/molbev/msx281.
Hoernes et al., Translating the epitranscriptome. Wiley Interdiscip Rev RNA. Jan. 2017;8(1):e1375. doi: 10.1002/wrna.1375. Epub Jun. 27, 2016.
Hollis et al., Phage integrases for the construction and manipulation of transgenic mammals. Reprod Biol Endocrinol. Nov. 7, 2003;1:79. doi: 10.1186/1477-7827-1-79.
Holsinger et al., Signal transduction in T lymphocytes using a conditional allele of Sos. Proc Natl Acad Sci U S A. Oct. 10, 1995;92(21):9810-4. doi: 10.1073/pnas.92.21.9810.
Hsu et al., DNA targeting specificity of RNA-guided Cas9 nucleases. Nat Biotechnol. Sep. 2013;31(9):827-32. doi: 10.1038/nbt.2647. Epub Jul. 21, 2013. Supplementary Information. 27 pages.
Huang et al., Circularly permuted and PAM-modified Cas9 variants broaden the targeting scope of base editors. Nat Biotechnol. Jun. 2019;37(6):626-631. doi: 10.1038/s41587-019-0134-y. Epub May 20, 2019. Including Supplementary Information.

(56) References Cited

OTHER PUBLICATIONS

Huggins et al., Flap endonuclease 1 efficiently cleaves base excision repair and DNA replication intermediates assembled into nucleosomes. Mol Cell. Nov. 2002;10(5):1201-11. doi: 10.1016/s1097-2765(02)00736-0.
Hung et al., Protein localization in disease and therapy. J Cell Sci. Oct. 15, 2011;124(Pt 20):3381-92. doi: 10.1242/jcs.089110.
Hwang et al., Web-based design and analysis tools for CRISPR base editing. BMC Bioinformatics. Dec. 27, 2018;19(1):542. doi: 10.1186/s12859-018-2585-4.
Ibba et al., Substrate specificity is determined by amino acid binding pocket size in *Escherichia coli* phenylalanyl-tRNA synthetase. Biochemistry. Jun. 14, 1994;33(23):7107-12.
Ihry et al., p53 inhibits CRISPR-Cas9 engineering in human pluripotent stem cells. Nat Med. Jul. 2018;24(7):939-946. doi: 10.1038/s41591-018-0050-6. Epub Jun. 11, 2018.
Iida et al., A site-specific, conservative recombination system carried by bacteriophage P1. Mapping the recombinase gene cin and the cross-over sites cix for the inversion of the C segment. EMBO J. 1982;1(11):1445-53.
Iida et al., The Min DNA inversion enzyme of plasmid p15B of *Escherichia coli* 15T-: a new member of the Din family of site-specific recombinases. Mol Microbiol. Jun. 1990;4(6):991-7. doi: 10.1111/j.1365-2958.1990.tb00671.x.
Imanishi et al., Detection of N6-methyladenosine based on the methyl-sensitivity of MazF RNA endonuclease. Chem Commun (Camb). Nov. 30, 2017;53(96): 2930-12933. doi: 10.1039/c7cc07699a.
Imburgio et al., Studies of promoter recognition and start site selection by T7 RNA polymerase using a comprehensive collection of promoter variants. Biochemistry. Aug. 29, 2000;39(34):10419-30.
Ingram, A specific chemical difference between the globins of normal human and sickle-cell anaemia haemoglobin. Nature. Oct. 13, 1956;178(4537):792-4. doi: 10.1038/178792a0.
Iwai et al., Circular beta-lactamase: stability enhancement by cyclizing the backbone. FEBS Lett. Oct. 8, 1999;459(2):166-72. doi: 10.1016/s0014-5793(99)01220-x.
Iwai et al., Highly efficient protein trans-splicing by a naturally split DnaE intein from Nostoc punctiforme. FEBS Lett. Mar. 20, 2006;580(7):1853-8. doi: 10.1016/j.febslet.2006.02.045. Epub Feb. 24, 2006.
Jaffrey et al., Emerging links between m6A and misregulated mRNA methylation in cancer. Genome Med. Jan. 12, 2017;9(1):2. doi: 10.1186/s13073-016-0395-8.
Jardine et al., HIV-1 Vaccines. Priming a broadly neutralizing antibody response to HIV-1 using a germline-targeting immunogen. Science. Jul. 10, 2015;349(6244):156-61. doi: 10.1126/science.aac5894. Epub Jun. 18, 2015.
Jasin et al., Repair of strand breaks by homologous recombination. Cold Spring Harb Perspect Biol. Nov. 10, 2013;5(11):a012740. doi: 10.1101/cshperspect.a012740.
Jeggo, DNA breakage and repair. Adv Genet. 1998;38:185-218. doi: 10.1016/s0065-2660(08)60144-3.
Jeong et al., Measurement of deoxyinosine adduct: Can it be a reliable tool to assess oxidative or nitrosative DNA damage? Toxicol Lett. Oct. 17, 2012;214(2):226-33. doi: 10.1016/j.toxlet.2012.08.013. Epub Aug. 23, 2012.
Jiang et al., CRISPR-Cas9 Structures and Mechanisms. Annu Rev Biophys. May 22, 2017;46:505-529. doi: 10.1146/annurev-biophys-062215-010822. Epub Mar. 30, 2017.
Jin et al., Cytosine, but not adenine, base editors induce genome-wide off-target mutations in rice. Science. Apr. 19, 2019;364(6437):292-295. doi: 10.1126/science.aaw7166. Epub Feb. 28, 2019.
Jiricny, The multifaceted mismatch-repair system. Nat Rev Mol Cell Biol. May 2006;7(5):335-46. doi: 10.1038/nrm1907.
Johann et al., GLVR1, a receptor for gibbon ape leukemia virus, is homologous to a phosphate permease of Neurospora crassa and is expressed at high levels in the brain and thymus. J Virol. Mar. 1992;66(3):1635-40. doi: 10.1128/JVI.66.3.1635-1640.1992.
Johansson et al., RNA Recognition by the MS2 Phage Coat Protein. Seminars in Virology. 1997;8(3):176-85. https://doi.org/10.1006/smvy.1997.0120.
Johansson et al., Selenocysteine in proteins-properties and biotechnological use. Biochim Biophys Acta. Oct. 30, 2005;1726(1):1-13. Epub Jun. 1, 2005.
Johns et al., The promise and peril of continuous in vitro evolution. J Mol Evol. Aug. 2005;61(2):253-63. Epub Jun. 27, 2005.
Joho et al., Identification of a region of the bacteriophage T3 and T7 Rna polymerases that determines promoter specificity. J Mol Biol. Sep. 5, 1990;215(1):31-9.
Joyce et al., Amplification, mutation and selection of catalytic RNA. Gene. Oct. 15, 1989;82(1):83-7. doi: 10.1016/0378-1119(89)90033-4.
Jusiak et al., Comparison of Integrases Identifies Bxb1-GA Mutant as the Most Efficient Site-Specific Integrase System in Mammalian Cells. ACS Synth Biol. Jan. 18, 2019;8(1):16-24. doi: 10.1021/acssynbio.8b00089. Epub Jan. 9, 2019.
Jyothy et al., Translocation Down syndrome. Indian J Med Sci. Mar. 2002;56(3):122-6.
Kacian et al., Purification of the DNA polymerase of avian myeloblastosis virus. Biochim Biophys Acta. Sep. 24, 1971;246(3):365-83. doi: 10.1016/0005-2787(71)90773-8.
Kaczmarczyk et al., Manipulating the Prion Protein Gene Sequence and Expression Levels with CRISPR/Cas9. PLoS One. Apr. 29, 2016;11(4):e0154604. doi: 10.1371/journal.pone.0154604.
Kadoch et al., Reversible disruption of mSWI/SNF (BAF) complexes by the SS18-SSX oncogenic fusion in synovial sarcoma. Cell. Mar. 28, 2013;153(1):71-85. doi: 10.1016/j.cell.2013.02.036.
Kahmann et al., G inversion in bacteriophage Mu DNA is stimulated by a site within the invertase gene and a host factor. Cell. Jul. 1985;41(3):771-80. doi: 10.1016/s0092-8674(85)80058-1.
Kalyaanamoorthy et al., ModelFinder: fast model selection for accurate phylogenetic estimates. Nat Methods. Jun. 2017;14(6):587-589. doi: 10.1038/nmeth.4285. Epub May 8, 2017.
Kao et al., Cleavage specificity of *Saccharomyces cerevisiae* flap endonuclease 1 suggests a double-flap structure as the cellular substrate. J Biol Chem. Apr. 26, 2002;277(17):14379-89. doi: 10.1074/jbc.M110662200. Epub Feb. 1, 2002.
Karimova et al., Discovery of Nigri/nox and Panto/pox site-specific recombinase systems facilitates advanced genome engineering. Sci Rep. Jul. 22, 2016;6:30130. doi: 10.1038/srep30130.
Karimova et al., Vika/vox, a novel efficient and specific Cre/loxP-like site-specific recombination system. Nucleic Acids Res. Jan. 2013;41(2):e37. doi: 10.1093/nar/gks1037. Epub Nov. 9, 2012.
Katafuchi et al., DNA polymerases involved in the incorporation of oxidized nucleotides into DNA: their efficiency and template base preference. Mutat Res. Nov. 28, 2010;703(1):24-31. doi: 10.1016/j.mrgentox.2010.06.004. Epub Jun. 11, 2010.
Kato et al., Improved purification and enzymatic properties of three forms of reverse transcriptase from avian myeloblastosis virus. J Virol Methods. Dec. 1984;9(4):325-39. doi: 10.1016/0166-0934(84)90058-2.
Katoh et al., MAFFT multiple sequence alignment software version 7: improvements in performance and usability. Mol Biol Evol. Apr. 2013;30(4):772-80. doi: 10.1093/molbev/mst010. Epub Jan. 16, 2013.
Kaufman et al., Translational efficiency of polycistronic mRNAs and their utilization to express heterologous genes in mammalian cells. EMBO J. Jan. 1987;6(1):187-93.
Kavli et al., Excision of cytosine and thymine from DNA by mutants of human uracil-DNA glycosylase. EMBO J. Jul. 1, 1996;15(13):3442-7.
Kawarasaki et al., Enhanced crossover SCRATCHY: construction and high-throughput screening of a combinatorial library containing multiple non-homologous crossovers. Nucleic Acids Res. Nov. 1, 2003;31(21):e126.
Keijzers et al., Human exonuclease 1 (EXO1) activity characterization and its function on flap structures. Biosci Rep. Apr. 25. 2015;35(3):e00206. doi: 10.1042/BSR20150058.
Kelman, PCNA: structure, functions and interactions. Oncogene. Feb. 13, 1997;14(6):629-40. doi: 10.1038/sj.onc.1200886.

(56) References Cited

OTHER PUBLICATIONS

Kessel et al., Murine developmental control genes. Science. Jul. 27, 1990;249(4967):374-9. doi: 10.1126/science. 1974085.
Kessler et al., Gene delivery to skeletal muscle results in sustained expression and systemic delivery of a therapeutic protein. Proc Natl Acad Sci U S A. Nov. 26, 1996;93(24):14082-7. doi: 10.1073/pnas. 93.24.14082.
Ketha et al., Application of bioinformatics-coupled experimental analysis reveals a new transport-competent nuclear localization signal in the nucleoprotein of Influenza A virus strain. BMC Cell Biol. Apr. 28, 2008; 9:22. https://doi.org/10.1186/1471-2121-9-22.
Kilcher et al., Brochothrix thermosphacta bacteriophages feature heterogeneous and highly mosaic genomes and utilize unique prophage insertion sites. J Bacteriol. Oct. 2010;192(20):5441-53. doi: 10.1128/JB.00709-10. Epub Aug. 13, 2010.
Kim et al., DJ-1, a novel regulator of the tumor suppressor PTEN. Cancer Cell. 2005;7(3):263-273.
Kim et al., Genome-wide target specificity of CRISPR RNA-guided adenine base editors. Nat Biotechnol. Apr. 2019;37(4):430-435. doi: 10.1038/s41587-019-0050-1. Epub Mar. 4, 2019.
Kim et al., An anionic human protein mediates cationic liposome delivery of genome editing proteins into mammalian cells. Nat Commun. Jul. 2, 2019;10(1):2905. doi: 10.1038/s41467-019-10828-3.
Kim et al., Evaluating and Enhancing Target Specificity of Gene-Editing Nucleases and Deaminases. Annu Rev Biochem. Jun. 20, 2019;88:191-220. doi: 10.1146/annurev-biochem-013118-111730. Epub Mar. 18, 2019.
Kim et al., High cleavage efficiency of a 2A peptide derived from porcine teschovirus-1 in human cell lines, zebrafish and mice. PLoS One. 2011;6(4):e18556. doi: 10.1371/journal.pone.0018556. Epub Apr. 29, 2011.
Kim et al., In vivo high-throughput profiling of CRISPR-Cpf1 activity. Nat Methods. Feb. 2017;14(2): 153-159. doi: 10.1038/nmeth.4104. Epub Dec. 19, 2016.
Kim et al., Mycobacteriophage Bxb1 integrates into the *Mycobacterium smegmatis* groEL1 gene. Mol Microbiol. Oct. 2003;50(2):463-73. doi: 10.1046/j.1365-2958.2003.03723.X.
Kim et al., Structural and kinetic characterization of *Escherichia coli* TadA, the wobble-specific tRNA deaminase. Biochemistry. May 23, 2006;45(20):6407-16. doi: 10.1021/bi0522394. PMID: 16700551.
Klapacz et al., Frameshift mutagenesis and micro satellite instability induced by human alkyladenine DNA glycosylase. Mol Cell. Mar. 26, 2010;37(6):843-53. doi: 10.1016/j.molcel.2010.01.038.
Kleiner et al., In vitro selection of a DNA-templated small-molecule library reveals a class of macrocyclic kinase inhibitors. J Am Chem Soc. Aug. 25, 2010;132(33):11779-91. doi: 10.1021/ja104903x.
Klement et al., Discrimination between bacteriophage T3 and T7 promoters by the T3 and T7 RNA polymerases depends primarily upon a three base-pair region located 10 to 12 base-pairs upstream from the start site. J Mol Biol. Sep. 5, 1990;215(1):21-9.
Klompe et al., Transposon-encoded CRISPR-Cas systems direct RNA-guided DNA integration. Nature. Jul. 2019;571(7764):219-225. doi: 10.1038/s41586-019-1323-z. Epub Jun. 12, 2019.
Knott et al., Guide-bound structures of an RNA-targeting A-cleaving CRISPR-Cas13a enzyme. Nat Struct Mol Biol. Oct. 2017;24(10):825-833. doi: 10.1038/nsmb.3466. Epub Sep. 11, 2017.
Koblan et al., Improving cytidine and adenine base editors by expression optimization and ancestral reconstruction. Nat Biotechnol. Oct. 2018;36(9):843-846. doi: 10.1038/nbt.4172. Epub May 29, 2018.
Kohli et al., A portable hot spot recognition loop transfers sequence preferences from APOBEC family members to activation-induced cytidine deaminase. J Biol Chem. Aug. 21, 2009;284(34):22898-904. doi: 10.1074/jbc.M109.025536. Epub Jun. 26, 2009.
Koike-Yusa et al., Genome-wide recessive genetic screening in mammalian cells with a lentiviral CRISPR-guide RNA library. Nat Biotechnol. Mar. 2014;32(3):267-73. doi: 10.1038/nbt.2800. Epub Dec. 23, 2013.
Kolot et al., Kolot M, Malchin N, Elias A, Gritsenko N, Yagil E. Site promiscuity of coliphage HK022 integrase as a tool for gene therapy. Gene Ther. Jul. 2015;22(7):521-7. doi: 10.1038/gt.2015.9. Epub Mar. 12, 2015.
Kolot et al., Site-specific recombination in mammalian cells expressing the Int recombinase of bacteriophage HK022. Mol Biol Rep. Aug. 1999;26(3):207-13. doi: 10.1023/a:1007096701720.
Komor, Editing the Genome Without Double-Stranded DNA Breaks. ACS Chem Biol. Feb. 16, 2018;13(2):383-388. doi: 10.1021/acschembio.7b00710. Epub Oct. 9, 2017.
Konermann et al., Genome-scale transcriptional activation by an engineered CRISPR-Cas9 complex. Nature. Jan. 29, 2015;517(7536):583-8. doi: 10.1038/nature14136. Epub Dec. 10, 2014.
Kosicki et al., Repair of double-strand breaks induced by CRISPR-Cas9 leads to large deletions and complex rearrangements. Nat Biotechnol. Sep. 2018;36(8):765-771. doi: 10.1038/nbt.4192. Epub Jul. 16, 2018.
Kotewicz et al., Cloning and overexpression of Moloney murine leukemia virus reverse transcriptase in *Escherichia coli*. Gene. 1985;35(3):249-58. doi: 10.1016/0378-1119(85)90003-4.
Kotewicz et al., Isolation of cloned Moloney murine leukemia virus reverse transcriptase lacking ribonuclease H activity. Nucleic Acids Res. Jan. 11, 1988;16(1):265-77. doi: 10.1093/nar/16.1.265.
Kotin, Prospects for the use of adeno-associated virus as a vector for human gene therapy. Hum Gene Ther. Jul. 1994;5(7):793-801. doi: 10.1089/hum.1994.5.7-793.
Kowalski et al., Delivering the Messenger: Advances in Technologies for Therapeutic mRNA Delivery. Mol Ther. Apr. 10, 2019;27(4):710-728. doi: 10.1016/j.ymthe.2019.02.012. Epub Feb. 19, 2019.
Kozak, An analysis of 5'-noncoding sequences from 699 vertebrate messenger RNAs. Nucleic Acids Res. Oct. 26, 1987;15(20):8125-48. doi: 10.1093/nar/15.20.8125.
Kraft et al., Deletions, Inversions, Duplications: Engineering of Structural Variants using CRISPR/Cas in Mice. Cell Rep. Feb. 10, 2015;10(5):833-839. doi: 10.1016/j.celrep.2015.01.016. Epub Feb. 7, 2015.
Kremer et al., Adenovirus and adeno-associated virus mediated gene transfer. Br Med Bull. Jan. 1995;51(1):31-44. doi: 10.1093/oxfordjournals.bmb.a072951.
Krokan et al., Uracil in DNA—occurrence, consequences and repair. Oncogene. Dec. 16, 2002;21(58):8935-48. doi: 10.1038/sj.onc.1205996.
Krokan et al., Base excision repair. Cold Spring Harb Perspect Biol. Apr. 1, 2013;5(4):a012583. doi: 10.1101/cshperspect.a012583.
Krzywkowski et al., Limited reverse transcriptase activity of phi29 DNA polymerase. Nucleic Acids Res. Apr.20, 2018;46(7):3625-3632. doi: 10.1093/nar/gky190.
Kügler et al., Human synapsin 1 gene promoter confers highly neuron-specific long-term transgene expression from an adenoviral vector in the adult rat brain depending on the transduced area. Gene Ther. Feb. 2003;10(4):337-47. doi: 10.1038/sj.gt.3301905.
Kunkel et al., Eukaryotic Mismatch Repair in Relation to DNA Replication. Annu Rev Genet. 2015;49:291-313. doi: 10.1146/annurev-genet-112414-054722.
Kurjan et al., Structure of a yeast pheromone gene (MF alpha): a putative alpha-factor precursor contains four tandem copies of mature alpha-factor. Cell. Oct. 1982;30(3):933-43. doi: 10.1016/0092-8674(82)90298-7.
Kuscu et al., CRISPR-Cas9-AID base editor is a powerful gain-of-function screening tool. Nat Methods. Nov. 29, 2016;13(12):983-984. doi: 10.1038/nmeth.4076.
Kwart et al., Precise and efficient scarless genome editing in stem cells using CORRECT. Nat Protoc. Feb. 2017;12(2):329-354. doi: 10.1038/nprot.2016.171. Epub Jan. 19, 2017.
Kweon et al., Fusion guide RNAs for orthogonal gene manipulation with Cas9 and Cpf1. Nat Commun. Nov. 23, 2017;8(1):1723. doi: 10.1038/s41467-017-01650-w. Erratum in: Nat Commun. Jan. 16, 2018;9(1):303.
Lada et al., Mutator effects and mutation signatures of editing deaminases produced in bacteria and yeast. Biochemistry (Mosc). Jan. 2011;76(1):131-46.

(56) References Cited

OTHER PUBLICATIONS

Lakich et al., Inversions disrupting the factor VIII gene are a common cause of severe haemophilia A. Nat Genet. Nov. 1993;5(3):236-41. doi: 10.1038/ng1193-236.
Landrum et al., ClinVar: public archive of relationships among sequence variation and human phenotype. Nucleic Acids Res. Jan. 2014;42(Database issue):D980-5. doi: 10.1093/nar/gkt1113. Epub Nov. 14, 2013.
Lauer et al., Construction, characterization, and use of two Listeria monocytogenes sitespecific phage integration vectors. J Bacteriol. Aug. 2002;184(15):4177-86. doi: 10.1128/jb.184.15.4177-4186. 2002.
Lawyer et al., High-level expression, purification, and enzymatic characterization of full-length Thermus aquaticus DNA polymerase and a truncated form deficient in 5' to 3' exonuclease activity. PCR Methods Appl. May 1993;2(4):275-87. doi: 10.1101/gr.2.4.275.
Le Grice et al., Purification and characterization of recombinant equine infectious anemia virus reverse transcriptase. J Virol. Dec. 1991;65(12):7004-7. doi: 10.1128/JVI.65.12.7004-7007.1991.
Leaver-Fay et al., ROSETTA3: an object-oriented software suite for the simulation and design of macromolecules. Methods Enzymol. 2011;487:545-74. doi: 10.1016/B978-0-12-381270-4.00019-6.
Leconte et al., A population-based experimental model for protein evolution: effects of mutation rate and selection stringency on evolutionary outcomes. Biochemistry. Feb. 26, 2013;52(8):1490-9. doi: 10.1021/bi3016185. Epub Feb. 14, 2013.
Lee et al., Group I Intron-Based Therapeutics Through Trans-Splicing Reaction. Prog Mol Biol Transl Sci. 2018;159:79-100. doi: 10.1016/bs.pmbts.2018.07.001. Epub Aug. 9, 2018.
Lee et al., Simultaneous targeting of linked loci in mouse embryos using base editing. Sci Rep. Feb. 7, 2019;9(1):1662. doi: 10.1038/s41598-018-33533-5.
Lee et al., Site-specific integration of mycobacteriophage L5: integration-proficient vectors for *Mycobacterium smegmatis, Mycobacterium tuberculosis*, and bacille Calmette-Guerin. Proc Natl Acad Sci U S A. Apr. 15, 1991;88(8):3111-5. doi: 10.1073/pnas.88.8.3111.
Lee et al., Synthetically modified guide RNA and donor DNA are a versatile platform for CRISPR-Cas9 engineering. Elife. May 2, 2017;6:e25312. doi: 10.7554/eLife.25312.
Lee et al., Targeted chromosomal deletions in human cells using zinc finger nucleases. Genome Res. Jan. 2010 20: 81-89; Published in Advance Dec. 1, 2009, doi:10.1101/gr.099747.109.
Lee et al., Targeting fidelity of adenine and cytosine base editors in mouse embryos. Nat Commun. Nov. 15, 2018;9(1):4804. doi: 10.1038/s41467-018-07322-7.
Lee et al., Transcriptional regulation and its misregulation in disease. Cell. Mar. 14, 2013;152(6):1237-51. doi: 10.1016/j.cell.2013.02.014.
Lei et al., Site-specificity of serine integrase demonstrated by the attB sequence preference of ?BT1 integrase. FEBS Lett. Apr. 2018;592(8):1389-1399. doi: 10.1002/1873-3468.13023. Epub Mar. 25, 2018.
Lemos et al., CRISPR/Cas9 cleavages in budding yeast reveal templated insertions and strand-specific insertion/deletion profiles. Proc Natl Acad Sci U SA . Feb. 27, 2018;115(9):E2040-E2047. doi: 10.1073/pnas.1716855115. Epub Feb. 13, 2018.
Levy et al., Membrane-associated guanylate kinase dynamics reveal regional and developmental specificity of synapse stability. J Physiol. Mar. 1, 2017;595(5):1699-1709. doi: 10.1113/JP273147. Epub Jan. 18, 2017.
Lew et al., Protein splicing in vitro with a semisynthetic two-component minimal intein. J Biol Chem. Jun. 26, 1998;273(26):15887-90. doi: 10.1074/jbc.273.26.15887.
Lewis et al., Cytosine deamination and the precipitous decline of spontaneous mutation during Earth's history. Proc Natl Acad Sci U S A. Jul. 19, 2016;113(29):8194-9. doi: 10.1073/pnas.1607580113. Epub Jul. 5, 2016.
Lewis et al., RNA modifications and structures cooperate to guide RNA-protein interactions. Nat Rev Mol Cell Biol. Mar. 2017;18(3):202-210. doi: 10.1038/nrm.2016.163. Epub Feb. 1, 2017.
Li et al., A Radioactivity-Based Assay for Screening Human m6A-RNA Methyltransferase, METTL3-METTL14 Complex, and Demethylase ALKBH5. J Biomol Screen. Mar. 2016;21(3):290-7. doi: 10.1177/1087057115623264. Epub Dec. 23, 2015.
Li et al., Fast and accurate short read alignment with Burrows-Wheeler transform. Bioinformatics. Jul. 15, 2009;25(14):1754-60. doi: 10.1093/bioinformatics/btp324. Epub May 18, 2009.
Li et al., Lagging strand DNA synthesis at the eukaryotic replication fork involves binding and stimulation of FEN-1 by proliferating cell nuclear antigen. J Biol Chem. Sep. 22, 1995;270(38):22109-12. doi: 10.1074/jbc.270.38.22109.
Li et al., Loss of post-translational modification sites in disease. Pac Symp Biocomput. 2010:337-47. doi: 10.1142/9789814295291_0036.
Li et al., RSEM: accurate transcript quantification from RNA-Seq data with or without a reference genome. BMC Bioinformatics. Aug. 4, 2011;12:323. doi: 10.1186/1471-2105-12-323.
Li, Mechanisms and functions of DNA mismatch repair. Cell Res. Jan. 2008;18(1):85-98. doi: 10.1038/cr.2007.115.
Liang et al., Correction of ?-thalassemia mutant by base editor in human embryos. Protein Cell. Nov. 2017;8(11):811-822. doi: 10.1007/sl3238-017-0475-6. Epub Sep. 23, 2017.
Liang et al., Homology-directed repair is a major double-strand break repair pathway in mammalian cells. Proc Natl Acad Sci U S A. Apr. 28, 1998;95(9):5172-7. doi: 10.1073/pnas.95.9.5172.
Lim et al., Crystal structure of the moloney murine leukemia virus RNase H domain. J Virol. Sep. 2006;80(17):8379-89. doi: 10.1128/JVI.00750-06.
Lin et al., The human REV1 gene codes for a DNA template-dependent dCMP transferase. Nucleic Acids Res. Nov. 15, 1999;27(22):4468-75. doi: 10.1093/nar/27.22.4468.
Liu et al., Split dnaE genes encoding multiple novel inteins in Trichodesmium erythraeum. J Biol Chem. Jul. 18, 2003;278(29):26315-8. doi: 10.1074/jbc.C300202200. Epub May 24, 2003.
Liu et al., A METTL3-METTL14 complex mediates mammalian nuclear RNA N6-adenosine methylation. Nat Chem Biol. Feb. 2014;10(2):93-5. doi: 10.1038/nchembio.1432. Epub Dec. 6, 2013.
Liu et al., Adding new chemistries to the genetic code. Annu Rev Biochem. 2010;79:413-44. doi: 10.1146/annurev.biochem.052308.105824.
Liu et al., Calcineurin is a common target of cyclophilin-cyclosporin A and FKBP-FK506 complexes. Cell. Aug. 23, 1991;66(4):807-15. doi: 10.1016/0092-8674(91)90124-h.
Liu et al., CasX enzymes comprise a distinct family of RNA-guided genome editors. Nature. Feb. 2019;566(7743):218-223. doi: 10.1038/s41586-019-0908-x. Epub Feb. 4, 2019. Author manuscript entitled CRISPR-CasX is an RNA-dominated enzyme active for human genome editing.
Liu et al., Editing DNA Methylation in the Mammalian Genome. Cell. Sep. 22, 2016;167(1):233-247.e17. doi: 10.1016/j.cell.2016.08.056.
Liu et al., Flap endonuclease 1: a central component of DNA metabolism. Annu Rev Biochem. 2004;73:589-615. doi: 10.1146/annurev.biochem.73.012803.092453.
Liu et al., Genetic incorporation of unnatural amino acids into proteins in mammalian cells. Nat Methods. Mar. 2007;4(3):239-44. Epub Feb. 25, 2007.
Liu et al., Highly efficient RNA-guided base editing in rabbit. Nat Commun. Jul. 13, 2018;9(1):2717. doi: 10.1038/s41467-018-05232-2.
Liu et al., N(6)-methyladenosine-dependent RNA structural switches regulate RNA-protein interactions. Nature. Feb. 26, 2015;518(7540):560-4. doi: 10.1038/nature14234.
Liu et al., Probing N6-methyladenosine RNA modification status at single nucleotide resolution in mRNA and long noncoding RNA. RNA. Dec. 2013;19(12): 1848-56. doi: 10.1261/rna.041178.113. Epub Oct. 18, 2013.
Liu et al., Reverse transcriptase of foamy virus. Purification of the enzymes and immunological identification. Arch Virol. 1977;55(3):187-200. doi: 10.1007/BF01319905.
Liu et al., Reverse transcriptase-mediated tropism switching in Bordetella bacteriophage. Science. Mar. 15, 2002;295(5562):2091-4. doi: 10.1126/science. 1067467.

(56) References Cited

OTHER PUBLICATIONS

Liu et al., *Saccharomyces cerevisiae* flap endonuclease 1 uses flap equilibration to maintain triplet repeat stability. Mol Cell Biol. May 2004;24(9):4049-64. doi: 10.1128/MCB.24.9.4049-4064.2004.
Liu et al., The Molecular Architecture for RNA-Guided RNA Cleavage by Cas13a. Cell. Aug. 10, 2017;170(4):714-726.el0. doi: 10.1016/j.cell.2017.06.050. Epub Jul. 27, 2017.
Loessner et al., Complete nucleotide sequence, molecular analysis and genome structure of bacteriophage A118 of Listeria monocytogenes: implications for phage evolution. Mol Microbiol. Jan. 2000;35(2):324-40. doi: 10.1046/j.1365-2958.2000.01720.X.
Long et al., Postnatal genome editing partially restores dystrophin expression in a mouse model of muscular dystrophy. Science. Jan. 22, 2016;351(6271):400-3. doi: 10.1126/science.aad5725. Epub Dec. 31, 2015.
Lopez-Girona et al., Cereblon is a direct protein target for immunomodulatory and antiproliferative activities of lenalidomide and pomalidomide. Leukemia. Nov. 2012;26(11):2326-35. doi: 10.1038/leu.2012.119. Epub May 3, 2012.
Lorenz et al., ViennaRNA Package 2.0. Algorithms Mol Biol. Nov. 24, 2011;6:26. doi: 10.1186/1748-7188-6-26.
Luan et al., Reverse transcription of R2Bm RNA is primed by a nick at the chromosomal target site: a mechanism for non-L'IR retrotransposition. Cell. Feb. 26, 1993;72(4):595-605. doi: 10.1016/0092-8674(93)90078-5.
Luckow et al., High level expression of nonfused foreign genes with Autographa califomica nuclear polyhedrosis virus expression vectors. Virology. May 1989;170(1):31-9. doi: 10.1016/0042-6822(89)90348-6.
Lukacsovich et al., Repair of a specific double-strand break generated within a mammalian chromosome by yeast endonuclease I-SceI. Nucleic Acids Res. Dec. 25, 1994;22(25):5649-57. doi: 10.1093/nar/22.25.5649.
Lüke et al., Partial purification and characterization of the reverse transcriptase of the simian immunodeficiency virus TYO-7 isolated from an African green monkey. Biochemistry. Feb. 20, 1990;29(7):1764-9. doi: 10.1021/bi00459a015.
Ma et al., Identification of pseudo attP sites for phage phiC31 integrase in bovine genome. Biochem Biophys Res Commun. Jul. 7, 2006;345(3):984-8. doi: 10.1016/j.bbrc.2006.04.145. Epub May 3, 2006.
Ma et al., In vitro protein engineering using synthetic tRNA(Ala) with different anticodons. Biochemistry. Aug. 10, 1993;32(31):7939-45.
Ma et al., PhiC31 integrase induces efficient site-specific recombination in the Capra hircus genome. DNA Cell Biol. Aug. 2014;33(8):484-91. doi: 10.1089/dna.2013.2124. Epub Apr. 22, 2014.
Maas et al., Identification and characterization of a human tRNA-specific adenosine deaminase related to the ADAR family of pre-mRNA editing enzymes. Proc Natl Acad Sci USA. Aug. 3, 1999;96(16):8895-900. doi: 10.1073/pnas.96.16.8895.
MacBeth et al., Inositol hexakisphosphate is bound in the ADAR2 core and required for RNA editing. Science. Sep. 2, 2005;309(5740): 1534-9. doi: 10.1126/science. 1113150.
Macrae et al., Ribonuclease revisited: structural insights into ribonuclease III family enzymes. Curr Opin Struct Biol. Feb. 2007;17(1):138-45. doi: 10.1016/j.sbi.2006.12.002. Epub Dec. 27, 2006.
Magin et al., Corf, the Rev/Rex homologue of HTDV/HERV-K, encodes an arginine-rich nuclear localization signal that exerts a trans-dominant phenotype when mutated. Virology. Aug. 15, 2000;274(1):11-6. doi: 10.1006/viro.2000.0438.
Maji et al., A High-Throughput Platform to Identify Small-Molecule Inhibitors of CRISPR-Cas9. Cell. May 2, 2019;177(4):1067-1079. el9. doi: 10.1016/j.cell.2019.04.009.
Makarova et al., Classification and Nomenclature of CRISPR-Cas Systems: Where from Here? Crispr J. Oct. 2018;1(5):325-336. doi: 10.1089/crispr.2018.0033.
Makeyev et al., Evolutionary potential of an RNA virus. J Virol. Feb. 2004;78(4):2114-20.
Malashkevich et al., Crystal structure of tRNA adenosine deaminase TadA from *Escherichia coli*. Deposited: Mar. 10, 2005 Released: Feb. 21, 2006 doi:10.2210/pdb1z3a/pdb (2006).
Malito et al., Structural basis for lack of toxicity of the diphtheria toxin mutant CRM197. Proc Natl Acad Sci U S A. Apr. 3, 2012;109(14):5229-34. doi: 10.1073/pnas.1201964109. Epub Mar. 19, 2012.
Mandal et al., Efficient ablation of genes in human hematopoietic stem and effector cells using CRISPR/Cas9. Cell Stem Cell. Nov. 6, 2014;15(5):643-52. doi: 10.1016/j.stem.2014.10.004. Epub Nov. 6, 2014.
Marceau, Functions of single-strand DNA-binding proteins in DNA replication, recombination, and repair. Methods Mol Biol. 2012;922:1-21. doi: 10.1007/978-1-62703-032-8_1.
Maresca et al., Obligate ligation-gated recombination (ObLiGaRe): custom-designed nuclease-mediated targeted integration through nonhomologous end joining. Genome Res. Mar. 2013;23(3):539-46. Doi: 10.1101/gr.145441.112. Epub Nov. 14, 2012.
Martinez et al., Hypermutagenesis of RNA using human immunodeficiency virus type 1 reverse transcriptase and biased dNTP concentrations. Proc Natl Acad Sci U S A. Dec. 6, 1994;91(25):11787-91. doi: 10.1073/pnas.91.25.11787.
Martsolf et al., Complete trisomy 17p a relatively new syndrome. Ann Genet. 1988;31(3):172-4.
Mascola et al., HIV-1 neutralizing antibodies: understanding nature's pathways. Immunol Rev. Jul. 2013;254(1):225-44. doi: 10.1111/imr.12075.
Mathys et al., Characterization of a self-splicing mini-intein and its conversion into autocatalytic N- and C-terminal cleavage elements: facile production of protein building blocks for protein ligation. Gene. Apr. 29, 1999;231(1-2):1-13. doi: 10.1016/s0378-1119(99)00103-1.
Matsuura et al., A gene essential for the site-specific excision of actinophage r4 prophage genome from the chromosome of a lysogen. J Gen Appl Microbiol. 1995;41(1):53-61.
Matthews, Structures of human ADAR2 bound to dsRNA reveal base-flipping mechanism and basis for site selectivity. Nat Struct Mol Biol. May 2016;23(5):426-33. doi: 10.1038/nsmb.3203. Epub Apr. 11, 2016.
May et al., Emergent lineages of mumps virus suggest the need for a polyvalent vaccine. Int J Infect Dis. Jan. 2018;66:1-4. doi: 10.1016/j.ijid.2017.09.024. Epub Oct. 4, 2017.
McCarroll et al., Copy-number variation and association studies of human disease. Nat Genet. Jul. 2007;39(7 Suppl):S37-42. doi: 10.1038/ng2080.
McDonald et al., Characterization of mutations at the mouse phenylalanine hydroxylase locus. Genomics. Feb. 1, 1997;39(3):402-5. doi: 10.1006/geno.1996.4508.
McKenna et al., Recording development with single cell dynamic lineage tracing. Development. Jun. 27, 2019;146(12):dev169730. doi: 10.1242/dev.169730.
McKenna et al., Whole-organism lineage tracing by combinatorial and cumulative genome editing. Science. Jul. 29, 2016;353(6298):aaf7907. doi: 10.1126/science.aaf7907. Epub May 26, 2016.
McNaughton et al., Mammalian cell penetration, siRNA transfection, and DNA transfection by supercharged proteins. Proc Natl Acad Sci U S A. Apr. 14, 2009;106(15):6111-6. doi: 10.1073/pnas.0807883106. Epub Mar. 23, 2009.
McVey et al., MMEJ repair of double-strand breaks (director's cut): deleted sequences and alternative endings. Trends Genet. Nov. 2008;24(11):529-38. doi: 10.1016/j.tig.2008.08.007. Epub Sep. 21, 2008.
Mead et al., A novel protective prion protein variant that colocalizes with kuru exposure. N Engl J Med. Nov. 19, 2009;361(21):2056-65. doi: 10.1056/NEJMoa0809716.
Meinke et al., Cre Recombinase and Other Tyrosine Recombinases. Chem Rev. Oct. 26, 2016;116(20):12785-12820. doi: 10.1021/acs.chemrev.6b00077. Epub May 10, 2016.
Meyer et al., Comprehensive analysis of mRNA methylation reveals enrichment in 3' U TRs and near stop codons. Cell. Jun. 22, 2012;149(7):1635-46. doi: 10.1016/j.cell.2012.05.003. Epub May 17, 2012.

(56) References Cited

OTHER PUBLICATIONS

Meyer et al., Library generation by gene shuffling. Curr Protoc Mol Biol. Jan. 6, 2014;105:Unit 15.12.. doi: 10.1002/0471142727. mb1512s105.

Meyer et al., The dynamic epitranscriptome: N6-methyladenosine and gene expression control. Nat Rev Mol Cell Biol. May 2014;15(5):313-26. doi: 10.1038/nrm3785. Epub Apr. 9, 2014.

Michel et al., Mitochondrial class II introns encode proteins related to the reverse transcriptases of retroviruses. Nature. Aug. 15-21, 1985;316(6029):641-3. doi: 10.1038/316641a0.

Mihai et al., PTEN inhibition improves wound healing in lung epithelia through changes in cellular mechanics that enhance migration. Am J Physiol Lung Cell Mol Physiol. 2012;302(3):L287-L299.

Mijakovic et al., Bacterial single-stranded DNA-binding proteins are phosphorylated on tyrosine. Nucleic Acids Res. Mar. 20, 2006;34(5):1588-96. doi: 10.1093/nar/gkj514.

Miller et al., Construction and properties of retrovirus packaging cells based on gibbon ape leukemia virus. J Virol. May 1991;65(5):2220-4. doi: 10.1128/JVI.65.5.2220-2224.1991.

Miller, Human gene therapy comes of age. Nature. Jun. 11, 1992;357(6378):455-60. doi: 10.1038/357455a0.

Mills et al., Protein splicing in trans by purified N- and C-terminal fragments of the *Mycobacterium tuberculosis* RecA intein. Proc Natl Acad Sci U S A. Mar. 31, 1998;95(7):3543-8. doi: 10.1073/pnas.95.7.3543.

Mitani et al., Delivering therapeutic genes—matching approach and application. Trends Biotechnol. May 1993;11(5):162-6. doi: 10.1016/0167-7799(93)90108-L.

Mitton-Fry et al., Poly(A) tail recognition by a viral RNA element through assembly of a triple helix. Science. Nov. 26, 2010;330(6008):1244-7. doi: 10.1126/science. 1195858.

Miyaoka et al., Systematic quantification of HDR and NHEJ reveals effects of locus, nuclease, and cell type on genome-editing. Sci Rep. Mar. 31, 2016;6:23549. doi: 10.1038/srep23549.

Mohr et al., A Reverse Transcriptase-Cas1 Fusion Protein Contains a Cas6 Domain Required for Both CRISPR RNA Biogenesis and RNA Spacer Acquisition. Mol Cell. Nov. 15, 2018;72(4):700-714. e8. doi: 10.1016/j.molcel.2018.09.013. Epub Oct. 18, 2018. Including Supplemental Information.

Mohr et al., Thermostable group II intron reverse transcriptase fusion proteins and their use in cDNA synthesis and next-generation RNA sequencing. RNA. Jul. 2013;19(7):958-70. doi: 10.1261/ma.039743.113. Epub May 22, 2013.

Mol et al., Crystal structure and mutational analysis of human uracil-DNA glycosylase: structural basis for specificity and catalysis. Cell. Mar. 24, 1995;80(6):869-78. doi: 10.1016/0092-8674(95)90290-2.

Molla et al., CRISPR/Cas-Mediated Base Editing: Technical Considerations and Practical Applications. Trends Biotechnol. Oct. 2019;37(10):1121-1142. doi: 10.1016/j.tibtech.2019.03.008. Epub Apr. 14, 2019.

Monot et al., The specificity and flexibility of l1 reverse transcription priming at imperfect T-tracts. PLoS Genet. May 2013;9(5):e1003499. doi: 10.1371/journal.pgen.1003499. Epub May 9, 2013.

Morita et al., The site-specific recombination system of actinophage TG1. FEMS Microbiol Lett. Aug. 2009;297(2):234-40. doi: 10.1111/j.1574-6968.2009.01683.x.

Muir et al., Expressed protein ligation: a general method for protein engineering. Proc Natl Acad Sci U S A. Jun. 9, 1998;95(12):6705-10. doi: 10.1073/pnas.95.12.6705.

Muller et al., Nucleotide exchange and excision technology (NExT) DNA shuffling: a robust method for DNA fragmentation and directed evolution. Nucleic Acids Res. Aug. 1, 2005;33(13):e117. doi: 10.1093/nar/gni116. PMID: 16061932; PMCID: PMC1182171.

Mumtsidu et al., Structural features of the single-stranded DNA-binding protein of Epstein-Barr virus. J Struct Biol. Feb. 2008;161(2):172-87. doi: 10.1016/j.jsb.2007.10.014. Epub Nov. 1, 2007.

Muzyczka et al., Adeno-associated virus (AAV) vectors: will they work? J Clin Invest. Oct. 1994;94(4):1351. doi: 10.1172/JCI117468.

Myerowitz et al., The major defect in Ashkenazi Jews with Tay-Sachs disease is an insertion in the gene for the alpha-chain of beta-hexosaminidase. J Biol Chem. Dec. 15, 1988;263(35):18587-9.

Myers et al., Insulin signal transduction and the IRS proteins. Annu Rev Pharmacol Toxicol. 1996;36:615-58. doi: 10.1146/annurev.pa.36.040196.003151.

Nabel et al., Direct gene transfer for immunotherapy and immunization. Trends Biotechnol. May 1993;11(5):211-5. doi: 10.1016/0167-7799(93)90117-R.

Nahar et al., A G-quadruplex motif at the 3' end of sgRNAs improves CRISPR-Cas9 based genome 40editing efficiency. Chem Commun (Camb). Mar. 7, 2018;54(19):2377-2380. doi: 10.1039/c7cc08893k. Epub Feb. 16, 2018.

Nakade et al., Microhomology-mediated end-joining-dependent integration of donor DNA in cells and animals using TALENs and CRISPR/Cas9. Nat Commun. Nov. 20, 2014;5:5560. doi: 10.1038/ncomms6560.

Nakamura et al., Codon usage tabulated from international DNA sequence databases: status for the year 2000. Nucleic Acids Res. Jan. 1, 2000;28(1):292. doi: 10.1093/nar/28.1.292.

Naorem et al., DGR mutagenic transposition occurs via hypermutagenic reverse transcription primed by nicked template RNA. Proc Natl Acad Sci U S A. Nov. 21, 2017;114(47):E10187-E10195. doi: 10.1073/pnas.1715952114. Epub Nov. 6, 2017.

Nern et al., Multiple new site-specific recombinases for use in manipulating animal genomes. Proc Natl Acad Sci U SA . Aug. 23, 2011;108(34):14198-203. doi: 10.1073/pnas.1111704108. Epub Aug. 9, 2011.

Nguyen et al., Evolutionary drivers of thermoadaptation in enzyme catalysis. Science. Jan. 20, 2017;355(6322):289-294. doi: 10.1126/science.aah3717. Epub Dec. 22, 2016.

Nguyen et al., IQ-TREE: a fast and effective stochastic algorithm for estimating maximumlikelihood phylogenies. Mol Biol Evol. Jan. 2015;32(1):268-74. doi: 10.1093/molbev/msu300. Epub Nov. 3, 2014.

Nishimasu et al., Engineered CRISPR-Cas9 nuclease with expanded targeting space. Science. Sep. 21, 2018;361(6408):1259-1262. doi: 10.1126/science.aas9129. Epub Aug. 30, 2018.

Nottingham et al., RNA-seq of human reference RNA samples using a thermostable group II intron reverse transcriptase. RNA. Apr. 2016;22(4):597-613. doi: 10.1261/ma.055558.115. Epub Jan. 29, 2016.

Nowak et al., Characterization of single-stranded DNA-binding proteins from the psychrophilic bacteria Desulfotalea psychrophila, Flavobacterium psychrophilum, Psychrobacter arcticus, Psychrobacter cryohalolentis, Psychromonas ingrahamii, Psychroflexus torquis, and Photobacterium profundum. BMC Microbiol. Apr. 14, 2014;14:91. doi: 10.1186/1471-2180-14-91.

Nowak et al., Structural analysis of monomeric retroviral reverse transcriptase in complex with an RNA/DNA hybrid. Nucleic Acids Res. Apr. 1, 2013 ;41(6):3874-87. doi: 10.1093/nar/gkt053. Epub Feb. 4, 2013.

Nyerges et al., A highly precise and portable genome engineering method allows comparison of mutational effects across bacterial species. Proc Natl Acad Sci U S A. Mar. 1, 2016;113(9):2502-7. doi: 10.1073/pnas.1520040113. Epub Feb. 16, 2016.

Oakes et al., CRISPR-Cas9 Circular Permutants as Programmable Scaffolds for Genome Modification. Cell. Jan. 10, 2019;176(1-2):254-267.e116. doi: 10.1016/j.cell.2018.11.052.

Oakes et al., Profiling of engineering hotspots identifies an allosteric CRISPR-Cas9 switch. Nat Biotechnol. Jun. 2016;34(6):646-51. doi: 10.1038/nbt.3528. Epub May 2, 2016.

Odsbu et al., Specific N-terminal interactions of the *Escherichia coli* SeqA protein are required to form multimers that restrain negative supercoils and form foci. Genes Cells. Nov. 2005;10(11):1039-49.

Oeemig et al., Solution structure of DnaE intein from Nostoc punctiforme: structural basis for the design of a new split intein suitable for site-specific chemical modification. FEBS Lett. May 6, 2009;583(9):1451-6.

(56) References Cited

OTHER PUBLICATIONS

Oh et al., Positional cloning of a gene for Hermansky-Pudlak syndrome, a disorder of cytoplasmic organelles. Nat Genet. Nov. 1996;14(3):300-6. doi: 10.1038/ng1196-300.
Ohe et al., Purification and properties of xanthine dehydrogenase from *Streptomyces cyanogenus*. J Biochem. Jul. 1979;86(1):45-53.
Olorunniji et al., Purification and In Vitro Characterization of Zinc Finger Recombinases. Methods Mol Biol. 2017;1642:229-245. doi: 10.1007/978-1-4939-7169-5_15.
Olorunniji et al., Site-specific recombinases: molecular machines for the Genetic Revolution. Biochem J. Mar. 15, 2016;473(6):673-84. doi: 10.1042/BJ20151112.
O'Maille et al., Structure-based combinatorial protein engineering (Scope). J Mol Biol. Aug. 23, 2002;321(4):677-91.
Orlando et al., Zinc-finger nuclease-driven targeted integration into mammalian genomes using donors with limited chromosomal homology. Nucleic Acids Res. Aug. 2010;38(15):e152. doi: 10.1093/nar/gkq512. Epub Jun. 8, 2010.
Orthwein et al., A mechanism for the suppression of homologous recombination in G1 cells. Nature. Dec. 17, 2015;528(7582):422-6. doi: 10.1038/nature16142. Epub Dec. 9, 2015.
Ortiz-Urda et al., Stable nonviral genetic correction of inherited human skin disease. Nat Med. Oct. 2002;8(10):1166-70. doi: 10.1038/nm766. Epub Sep. 16, 2002. Erratum in: Nat Med. Feb. 2003;9(2):237.
Osborn et al., Base Editor Correction of COL7A1 in Recessive Dystrophic Epidermolysis Bullosa Patient-Derived Fibroblasts and iPSCs. J Invest Dermatol. Feb. 2020;140(2):338-347.e5. doi: 10.1016/j.jid.2019.07.701. Epub Aug. 19, 2019.
Ostermeier et al., A combinatorial approach to hybrid enzymes independent of DNA homology. Nat Biotechnol. Dec. 1999;17(12):1205-9.
Ostertag et al., Biology of mammalian L1 retrotransposons. Annu Rev Genet. 2001;35:501-38. doi: 10.1146/annurev.genet.35.102401.091032.
Otomo et al., Improved segmental isotope labeling of proteins and application to a larger protein. J Biomol NMR. Jun. 1999;14(2):105-14. doi: 10.1023/a:1008308128050.
Otomo et al., NMR observation of selected segments in a larger protein: central-segment isotope labeling through intein-mediated ligation. Biochemistry. Dec. 7, 1999;38(49):16040-4. doi: 10.1021/bi991902j.
Otto et al., The probability of fixation in populations of changing size. Genetics. Jun. 1997;146(2):723-33.
Packer et al., Methods for the directed evolution of proteins. Nat Rev Genet. Jul. 2015;16(7):379-94. doi: 10.1038/nrg3927. Epub Jun. 9, 2015.
Packer et al., Phage-assisted continuous evolution of proteases with altered substrate specificity. Nat Commun. Oct. 16, 2017;8(1):956. doi: 10.1038/s41467-017-01055-9.
Paige et al., RNA mimics of green fluorescent protein. Science. Jul. 29, 2011;333(6042):642-6. doi: 10.1126/science.1207339.
Paiva et al., Targeted protein degradation: elements of PROTAC design. Curr Opin Chem Biol. Jun. 2019;50:111-119. doi: 10.1016/j.cbpa.2019.02.022. Epub Apr. 17, 2019.
Paquet et al., Efficient introduction of specific homozygous and heterozygous mutations using CRISPR/Cas9. Nature. May 5, 2016;533(7601):125-9. doi: 10.1038/nature17664. Epub Apr. 27, 2016.
Park et al., Digenome-seq web tool for profiling CRISPR specificity. Nat Methods. May 30, 2017;14(6):548-549. doi: 10.1038/nmeth.4262.
Park et al., Sendai virus, an RNA virus with No. risk of genomic integration, delivers CRISPR/Cas9 for efficient gene editing. Mol Ther Methods Clin Dev. Aug. 24, 2016;3:16057. doi: 10.1038/mtm.2016.57.
Patel et al., Flap endonucleases pass 5'-flaps through a flexible arch using a disorder-thread-order mechanism to confer specificity for free 5'-ends. Nucleic Acids Res. May 2012;40(10):4507-19. doi: 10.1093/nar/gks051. Epub Feb. 8, 2012.
Pawson et al., Protein phosphorylation in signaling—50 years and counting. Trends Biochem Sci. Jun. 2005;30(6):286-90. doi: 10.1016/j.tibs.2005.04.013.
Pellenz et al., New human chromosomal safe harbor sites for genome engineering with CRISPR/Cas9, TAL effector and homing endonucleases. Aug. 20, 2018. bioRxiv doi: https://doi.org/10.1101/396390.
Perach et al., Catalytic features of the recombinant reverse transcriptase of bovine leukemia virus expressed in bacteria. Virology. Jun. 20, 1999;259(1):176-89. doi: 10.1006/viro.1999.9761.
Perler et al., Protein splicing and autoproteolysis mechanisms. Curr Opin Chem Biol. Oct. 1997;1(3):292-9. doi: 10.1016/s1367-5931(97)80065-8.
Perler et al., Protein splicing elements: inteins and exteins—a definition of terms and recommended nomenclature. Nucleic Acids Res. Apr. 11, 1994;22(7):1125-7. doi: 10.1093/nar/22.7.1125.
Perler, InBase, the New England Biolabs Intein Database. Nucleic Acids Res. Jan. 1, 1999;27(1):346-7. doi: 10.1093/nar/27.1.346.
Perler, Protein splicing of inteins and hedgehog autoproteolysis: structure, function, and evolution. Cell. Jan. 9, 1998;92(1):1-4. doi: 10.1016/s0092-8674(00)80892-2.
Petersen-Mahrt et al., AID mutates *E. coli* suggesting a DNA deamination mechanism for antibody diversification. Nature. Jul. 4, 2002;418(6893):99-103.
Peyrottes et al., Oligodeoxynucleoside phosphoramidates (P-NH2): synthesis and thermal stability of duplexes with DNA and RNA targets. Nucleic Acids Res. May 15, 1996;24(10):1841-8.
Pfeiffer et al., Mechanisms of DNA double-strand break repair and their potential to induce chromosomal aberrations. Mutagenesis. Jul. 2000;15(4):289-302. doi: 10.1093/mutage/15.4.289.
Pickart et al., Ubiquitin: structures, functions, mechanisms. Biochim Biophys Acta. Nov. 29, 2004;1695(1-3):55-72. doi: 10.1016/j.bbamcr.2004.09.019.
Pinkert et al., An albumin enhancer located 10 kb upstream functions along with its promoter to direct efficient, liver-specific expression in transgenic mice. Genes Dev. May 1987;1(3):268-76. doi: 10.1101/gad.1.3.268.
Pirakitikulr et al., PCRless library mutagenesis via oligonucleotide recombination in yeast. Protein Sci. Dec. 2010;19(12):2336-46. doi: 10.1002/pro.513.
Popp et al., Sortagging: a versatile method for protein labeling. Nat Chem Biol. Nov. 2007;3(11):707-8. doi: 10.1038/nchembio.2007.31. Epub Sep. 23, 2007.
Posnick et al., Imbalanced base excision repair increases spontaneous mutation and alkylation sensitivity in *Escherichia coli*. J Bacteriol. Nov. 1999;181(21):6763-71.
Prasad et al., Rev1 is a base excision repair enzyme with 5'-deoxyribose phosphate lyase activity. Nucleic Acids Res. Dec. 15, 2016;44(22):10824-10833. doi: 10.1093/nar/gkw869. Epub Sep. 28, 2016.
Pruschy et al., Mechanistic studies of a signaling pathway activated by the organic dimerizer FK1012. Chem Biol. Nov. 1994;1(3):163-72. doi: 10.1016/1074-5521(94)90006-x.
Pu et al., Evolution of a split RNA polymerase as a versatile biosensor platform. Nat Chem Biol. Apr. 2017;13(4):432-438. doi: 10.1038/nchembio.2299. Epub Feb. 13, 2017.
Qu et al., Global mapping of binding sites for phic31 integrase in transgenic maden-darby bovine kidney cells using ChIP-seq. Hereditas. Jan. 14, 2019;156:3. doi: 10.1186/s41065-018-0079-z.
Queen et al., Immunoglobulin gene transcription is activated by downstream sequence elements. Cell. Jul. 1983;33(3):741-8. doi: 10.1016/0092-8674(83)90016-8.
Radany et al., Increased spontaneous mutation frequency in human cells expressing the phage PBS2-encoded inhibitor of uracil-DNA glycosylase. Mutat Res. Sep. 15, 2000;461(1):41-5 8. doi: 10.1016/s0921-8777(00)00040-9.
Raina et al., PROTAC-induced BET protein degradation as a therapy for castration-resistant prostate cancer. Proc Natl Acad Sci U S A. Jun. 28, 2016;113(26):7124-9. doi: 10.1073/pnas.1521738113. Epub Jun. 6, 2016.

(56) References Cited

OTHER PUBLICATIONS

Ramamurthy et al., Identification of immunogenic B-cell epitope peptides of rubella virus E1 glycoprotein towards development of highly specific immunoassays and/or vaccine. Conference Abstract. 2019.

Ranzau et al., Genome, Epigenome, and Transcriptome Editing via Chemical Modification of Nucleobases in Living Cells. Biochemistry. Feb. 5, 2019;58(5):330-335. doi: 10.1021/acs.biochem.8b00958. Epub Dec. 12, 2018.

Rashel et al., A novel site-specific recombination system derived from bacteriophage phiMR11. Biochem Biophys Res Commun. Apr. 4, 2008;368(2):192-8. doi: 10.1016/j.bbrc.2008.01.045. Epub Jan. 22, 2008.

Rasila et al., Critical evaluation of random mutagenesis by error-prone polymerase chain reaction protocols, *Escherichia coli* mutator strain, and hydroxylamine treatment. Anal Biochem. May 1, 2009;388(1):71-80. doi: 10.1016/j.ab.2009.02.008. Epub Feb. 10, 2009.

Raskin et al., Substitution of a single bacteriophage T3 residue in bacteriophage T7 RNA polymerase at position 748 results in a switch in promoter specificity. J Mol Biol. Nov. 20, 1992;228(2):506-15.

Raskin et al., T7 RNA polymerase mutants with altered promoter specificities. Proc Natl Acad Sci U S A. Apr. 15, 1993;90(8):3147-51.

Rauch et al., Programmable RNA Binding Proteins for Imaging and Therapeutics. Biochemistry. Jan. 30, 2018;57(4):363-364. doi: 10.1021/acs.biochem.7b01101. Epub Nov. 17, 2017.

Ray et al., A compendium of RNA-binding motifs for decoding gene regulation. Nature. Jul. 11, 2013;499(7457):172-7. doi: 10.1038/nature12311.

Rebar et al., Phage display methods for selecting zinc finger proteins with novel DNA-binding specificities. Methods Enzymol. 1996;267:129-49.

Rees et al., Analysis and minimization of cellular RNA editing by DNA adenine base editors. Sci Adv. May 8, 2019;5(5):eaax5717. doi: 10.1126/sciadv.aax5717.

Rees et al., Base editing: precision chemistry on the genome and transcriptome of living cells. Nat Rev Genet. Dec. 2018;19(12):770-788. doi: 10.1038/s41576-018-0059-1.

Rees et al., Development of hRad51-Cas9 nickase fusions that mediate HDR without double-stranded breaks. Nat Commun. May 17, 2019;10(1):2212. doi: 10.1038/s41467-019-09983-4.

Remy et al., Gene transfer with a series of lipophilic DNA-binding molecules. Bioconjug Chem. Nov.-Dec. 1994;5(6):647-54. doi: 10.1021/bc00030a021.

Ribeiro et al., Protein Engineering Strategies to Expand CRISPR-Cas9 Applications. Int J Genomics. Aug. 2, 2018;2018:1652567. doi: 10.1155/2018/1652567.

Ringrose et al., The Kw recombinase, an integrase from Kluyveromyces waltii. Eur J Biochem. Sep. 15, 1997;248(3):903-12. doi: 10.1111/j.1432-1033.1997.00903.x.

Risso et al., Hyperstability and substrate promiscuity in laboratory resurrections of Precambrian ?-lactamases. J Am Chem Soc. Feb. 27, 2013;135(8):2899-902. doi: 10.1021/ja311630a. Epub Feb. 14, 2013.

Ritchie et al., limma powers differential expression analyses for RNA-sequencing and microarray studies. Nucleic Acids Res. Apr. 20, 2015;43(7):e47. doi: 10.1093/nar/gkv007. Epub Jan. 20, 2015.

Robertson et al.,DNA repair in mammalian cells: Base excision repair: the long and short of it. Cell Mol Life Sci. Mar. 2009;66(6):981-93. doi: 10.1007/s00018-009-8736-z.

Robinson et al., The protein tyrosine kinase family of the human genome. Oncogene. Nov. 20, 2000;19(49):5548-57. doi: 10.1038/sj.onc.1203957.

Roth et al., A widespread self-cleaving ribozyme class is revealed by bioinformatics. Nat Chem Biol. Jan. 2014;10(1):56-60. doi: 10.1038/nchembio.l386. Epub Nov. 17, 2013.

Roth et al., Purification and characterization of murine retroviral reverse transcriptase expressed in *Escherichia coli*. J Biol Chem. Aug. 5, 1985;260(16):9326-35.

Rouet et al., Expression of a site-specific endonuclease stimulates homologous recombination in mammalian cells. Proc Natl Acad Sci U S A. Jun. 21, 1994;91(13):6064-8. doi: 10.1073/pnas.91.13.6064.

Rouet et al., Introduction of double-strand breaks into the genome of mouse cells by expression of a rare-cutting endonuclease. Mol Cell Biol. Dec. 1994;14(12):8096-106. doi: 10.1128/mcb. 14.12.8096.

Rouet et al., Receptor-Mediated Delivery of CRISPR-Cas9 Endonuclease for Cell-Type-Specific Gene Editing. J Am Chem Soc. May 30, 2018;140(21):6596-6603. doi: 10.1021/jacs.8b01551. Epub May 18, 2018.

Roundtree et al.,YTHDC1 mediates nuclear export of N6-methyladenosine methylated mRNAs. Elife. Oct. 6, 2017;6:e31311. doi: 10.7554/eLife.31311.

Rowland et al., Sin recombinase from *Staphylococcus aureus*: synaptic complex architecture and transposon targeting. Mol Microbiol. May 2002;44(3):607-19. doi: 10.1046/j.1365-2958.2002.02897.x.

Rowley, Chromosome translocations: dangerous liaisons revisited. Nat Rev Cancer. Dec. 2001;1(3):245-50. doi: 10.1038/35106108.

Rubio et al., An adenosine-to-inosine tRNA-editing enzyme that can perform C-to-U deamination of DNA. Proc Natl Acad Sci U S A. May 8, 2007;104(19):7821-6. doi: 10.1073/pnas.0702394104. Epub May 1, 2007. PMID: 17483465; PMCID: PMC1876531.

Rubio et al., Transfer RNA travels from the cytoplasm to organelles. Wiley Interdiscip Rev RNA. Nov.-Dec. 2011;2(6):802-17. doi: 10.1002/wrna.93. Epub Jul. 11, 2011.

Rüfer et al., Non-contact positions impose site selectivity on Cre recombinase. Nucleic Acids Res. Jul. 1, 2002;30(13):2764-71. doi: 10.1093/nar/gkf399.

Rutherford et al., Attachment site recognition and regulation of directionality by the serine integrases. Nucleic Acids Res. Sep. 2013;41(17):8341-56. doi: 10.1093/nar/gkt580. Epub Jul. 2, 2013.

Ryu et al., Adenine base editing in mouse embryos and an adult mouse model of Duchenne muscular dystrophy. Nat Biotechnol. Jul. 2018;36(6):536-539. doi: 10.1038/nbt.4148. Epub Apr. 27, 2018.

Sadowski, The Flp recombinase of the 2-microns plasmid of *Saccharomyces cerevisiae*. Prog Nucleic Acid Res Mol Biol. 1995;51:53-91.

Sakuma et al., MMEJ-assisted gene knock-in using TALENs and CRISPR-Cas9 with the PITCh systems. Nat Protoc. Jan. 2016;11(1):118-33. doi: 10.1038/nprot.2015.140. Epub Dec. 17, 2015.

Sale et al., Y-family DNA polymerases and their role in tolerance of cellular DNA damage. Nat Rev Mol Cell Biol. Feb. 23, 2012;13(3):141-52. doi: 10.1038/nrm3289.

Samulski et al., Helper-free stocks of recombinant adeno-associated viruses: normal integration does not require viral gene expression. J Virol. Sep. 1989;63(9):3822-8. doi: 10.1128/JVI.63.9.3822-3828.1989.

Sang et al., A unique uracil-DNA binding protein of the uracil DNA glycosylase superfamily. Nucleic Acids Res. Sep. 30, 2015;43(17):8452-63. doi: 10.1093/nar/gkv854. Epub Aug. 24, 2015.

Santoro et al., Directed evolution of the site specificity of Cre recombinase. Proc Natl Acad Sci U S A. Apr. 2, 2002;99(7):4185-90. Epub Mar. 19, 2002.

Saparbaev et al., Excision of hypoxanthine from DNA containing dIMP residues by the *Escherichia coli*, yeast, rat, and human alkylpurine DNA glycosylases. Proc Natl Acad Sci U S A. Jun. 21, 1994;91(13):5873-7. doi: 10.1073/pnas.91.13.5873.

Sarkar et al., HIV-1 pro viral DNA excision using an evolved recombinase. Science. Jun. 29, 2007;316(5833):1912-5. doi: 10.1126/science. 1141453.

Satomura et al., Precise genome-wide base editing by the CRISPR Nickase system in yeast. Sci Rep. May 18, 2017;7(1):2095. doi: 10.1038/s41598-017-02013-7.

Sauer et al., DNA recombination with a heterospecific Cre homolog identified from comparison of the pac-c1 regions of P1-related phages. Nucleic Acids Res. Nov. 18, 2004;32(20):6086-95. doi: 10.1093/nar/gkh941.

(56) References Cited

OTHER PUBLICATIONS

Savic et al., Covalent linkage of the DNA repair template to the CRISPR-Cas9 nuclease enhances homology-directed repair. Elife. May 29, 2018;7:e33761. doi: 10.7554/eLife.33761.
Saville et al., A site-specific self-cleavage reaction performed by a novel RNA in Neurospora mitochondria. Cell. May 18, 1990;61(4):685-96. doi: 10.1016/0092-8674(90)90480-3.
Savva et al., The structural basis of specific base-excision repair by uracil-DNA glycosylase. Nature. Feb. 9, 1995;373(6514):487-93. doi: 10.1038/373487a0.
Schaaper et al., Base selection, proofreading, and mismatch repair during DNA replication in *Escherichia coli*. J Biol Chem. Nov. 15, 1993;268(32):23762-5.
Schaaper et al., Spectra of spontaneous mutations in *Escherichia coli* strains defective in mismatch correction: the nature of in vivo DNA replication errors. Proc Natl Acad Sci U S A. Sep. 1987;84(17):6220-4.
Schaefer et al., Understanding RNA modifications: the promises and technological bottlenecks of the 'epitranscriptome'. Open Biol. May 2017;7(5):170077. doi: 10.1098/rsob. 170077.
Schechner et al., Multiplexable, locus-specific targeting of long RNAs with CRISPR-Display. Nat Methods. Jul. 2015;12(7):664-70. doi: 10.1038/nmeth.3433. Epub Jun. 1, 2015. Author manuscript entitled CRISPR Display: A modular method for locus-specific targeting of long noncoding RNAs and synthetic RNA devices in vivo.
Schek et al., Definition of the upstream efficiency element of the simian virus 40 late polyadenylation signal by using in vitro analyses. Mol Cell Biol. Dec. 1992;12(12):5386-93. doi: 10.1128/mcb.12.12.5386.
Schenk et al., MPDU1 mutations underlie a novel human congenital disorder of glycosylation, designated type If. J Clin Invest. Dec. 2001;108(11):1687-95. doi: 10.1172/JCI13419.
Schmitz et al., Behavioral abnormalities in prion protein knockout mice and the potential relevance of PrP(C) for the cytoskeleton. Prion. 2014;8(6):381-6. doi: 10.4161/19336896.2014.983746.
Schöller et al., Interactions, localization, and phosphorylation of the m6A generating METTL3-METTL14-WTAP complex. RNA. Apr. 2018;24(4):499-512. doi: 10.1261/rna.064063.117. Epub Jan. 18, 2018.
Schultz et al., Expression and secretion in yeast of a 400-kDa envelope glycoprotein derived from Epstein-Barr virus. Gene. 1987;54(1):113-23. doi: 10.1016/0378-1119(87)90353-2.
Schultz et al., Oligoo-2'-fluoro-2'-deoxynucleotide N3'—>P5' phosphoramidates: synthesis and properties. Nucleic Acids Res. Aug. 1, 1996;24(15):2966-73.
Scott et al., Production of cyclic peptides and proteins in vivo. Proc Natl Acad Sci U S A. Nov. 23, 1999;96(24):13638-43. doi: 10.1073/pnas.96.24.13638.
Sebastín-Martín et al., Transcriptional inaccuracy threshold attenuates differences in RNA-dependent DNA synthesis fidelity between retroviral reverse transcriptases. Sci Rep. Jan. 12, 2018;8(1):627. doi: 10.1038/s41598-017-18974-8.
Seed, An LFA-3 cDNA encodes a phospholipid-linked membrane protein homologous to its receptor CD2. Nature. Oct. 29-Nov 4, 1987;329(6142):840-2. doi: 10.1038/329840a0.
Serrano-Heras et al., Protein p56 from the Bacillus subtilis phage phi29 inhibits DNA-binding ability of uracil-DNA glycosylase. Nucleic Acids Res. 2007;35(16):5393-401. Epub Aug. 13, 2007.
Setten et al., The current state and future directions of RNAi-based therapeutics. Nat Rev Drug Discov. Jun. 2019;18(6):421-446. doi: 10.1038/s41573-019-0017-4.
Severinov et al., Expressed protein ligation, a novel method for studying protein-protein interactions in transcription. J Biol Chem. Jun. 26, 1998;273(26):16205-9. doi: 10.1074/jbc.273.26.16205.
Sha et al., Monobodies and other synthetic binding proteins for expanding protein science. Protein Sci. May 2017;26(5):910-924. doi: 10.1002/pro.3148. Epub Mar. 24, 2017.
Shah et al., Protospacer recognition motifs: mixed identities and functional diversity. RNA Biol. May 2013;10(5):891-9. doi: 10.4161/rna.23764. Epub Feb. 12, 2013.
Shalem et al., High-throughput functional genomics using CRISPR-Cas9. Nat Rev Genet. May 2015;16(5):299-311. doi: 10.1038/nrg3899. Epub Apr. 9, 2015.
Sharer et al., The ARF-like 2 (ARL2)-binding protein, BART. Purification, cloning, and initial characterization. J Biol Chem. Sep. 24, 1999;274(39):27553-61. doi: 10.1074/jbc.274.39.27553.
Sharon et al., Functional Genetic Variants Revealed by Massively Parallel Precise Genome Editing. Cell. Oct. 4, 2018;175(2):544-557.el6. doi: 10.1016/j.cell.2018.08.057. Epub Sep. 20, 2018.
Shaw et al., Implications of human genome architecture for rearrangement-based disorders: the genomic basis of disease. Hum Mol Genet. Apr. 1, 2004 ;13 Spec No. 1:R57-64. doi: 10.1093/hmg/ddh073. Epub Feb. 5, 2004.
Shen et al., Predictable and precise template-free CRISPR editing of pathogenic variants. Nature. Nov. 2018;563(7733):646-651. doi: 10.1038/s41586-018-0686-x. Epub Nov. 7, 2018.
Shen, Data processing, Modeling and Analysis scripts for CRISPR-inDelphi. GitHub—maxwshen/indelphi-dataprocessinganalysis at 6b68e3cec73c9358fef6e5f178a935f3c2a4118f. Apr. 10, 2018. Retrieved online via https://github.com/maxwshen/indelphi-sataprocessinganalysis/tree/6b68e3cec73c9358fef6e5f178a935f3c2a4118f Last retrieved on Jul. 26, 2021. 2 pages.
Sherwood et al., Discovery of directional and nondirectional pioneer transcription factors by modeling DNase profile magnitude and shape. Nat Biotechnol. Feb. 2014;32(2):171-178. doi: 10.1038/nbt.2798. Epub Jan. 19, 2014.
Shi et al., Structural basis for targeted DNA cytosine deamination and mutagenesis by APOBEC3A and APOBEC3B. Nat Struct Mol Biol. Feb. 2017;24(2):131-139. doi: 10.1038/nsmb.3344. Epub Dec. 19, 2016.
Shi et al., YTHDF3 facilitates translation and decay of N6-methyladenosine-modified RNA. Cell Res. Mar. 2017;27(3):315-328. doi: 10.1038/cr.2017.15. Epub Jan. 20, 2017.
Shin et al., CRISPR/Cas9 targeting events cause complex deletions and insertions at 17 sites in the mouse genome. Nat Commun. May 31, 2017;8:15464. doi: 10.1038/ncomms15464.
Shindo et al., A Comparison of Two Single-Stranded DNA Binding Models by Mutational Analysis of APOBEC3G. Biology (Basel). Aug. 2, 2012;1(2):260-76. doi: 10.3390/biology1020260.
Shingledecker et al., Molecular dissection of the *Mycobacterium tuberculosis* RecA intein: design of a minimal intein and of a trans-splicing system involving two intein fragments. Gene. Jan. 30, 1998;207(2):187-95. doi: 10.1016/s0378-1119(97)00624-0.
Shmakov et al., Diversity and evolution of class 2 CRISPR-Cas systems. Nat Rev Microbiol. Mar. 2017;15(3):169-182. doi: 10.1038/nrmicro.2016.184. Epub Jan. 23, 2017.
Shultz et al., A genome-wide analysis of FRT-like sequences in the human genome. PLoS One. Mar. 23, 2011;6(3):e18077. doi: 10.1371/journal.pone.0018077.
Silas et al., Direct CRISPR spacer acquisition from RNA by a natural reverse transcriptase-Cas1 fusion protein. Science. Feb. 26, 2016;351(6276):aad4234. doi: 10.1126/science.aad4234.
Silva et al., Selective disruption of the DNA polymerase III α-β complex by the umuD gene products. Nucleic Acids Res. Jul. 2012;40(12):5511-22. doi: 10.1093/nar/gks229. Epub Mar. 9, 2012.
Singh et al., Cross-talk between diverse serine integrases. J Mol Biol. Jan. 23, 2014;426(2):318-31. doi: 10.1016/j.jmb.2013.10.013. Epub Oct. 22, 2013.
Singh et al., Real-time observation of DNA recognition and rejection by the RNA-guided endonuclease Cas9. Nat Commun. Sep. 14, 2016;7:12778. doi: 10.1038/ncomms12778.
Sivalingam et al., Biosafety assessment of site-directed transgene integration in human umbilical cord-lining cells. Mol Ther. Jul. 2010;18(7):1346-56. doi: 10.1038/mt.2010.61. Epub Apr. 27, 2010.
Sledz et al., Structural insights into the molecular mechanism of the m(6)A writer complex. Elife. Sep. 14, 2016;5:e18434. doi: 10.7554/eLife.18434.
Slupphaug et al., A nucleotide-flipping mechanism from the structure of human uracil-DNA glycosylase bound to DNA. Nature. Nov. 7, 1996;384(6604):87-92. doi: 10.1038/384087a0.

(56) References Cited

OTHER PUBLICATIONS

Smargon et al., Cas 13b is a Type VLB CRISPR-Associated RNA-Guided RNase Differentially Regulated by Accessory Proteins Csx27 and Csx28. Mol Cell. Feb. 16, 2017;65(4):618-630.e7. doi: 10.1016/j.molcel.2016.12.023. Epub Jan. 5, 2017.
Smith et al., Production of human beta interferon in insect cells infected with a baculovirus expression vector. Mol Cell Biol. Dec. 1983;3(12):2156-65. doi: 10.1128/mcb.3.12.2156.
Smith et al., Single-step purification of polypeptides expressed in *Escherichia coli* as fusions with glutathione S-transferase. Gene. Jul. 15, 1988;67(1):31-40. doi: 10.1016/0378-1119(88)90005-4.
Smith, Phage-encoded Serine Integrases and Other Large Serine Recombinases. Microbiol Spectr. Aug. 2015;3(4). doi: 10.1128/microbiolspec.MDNA3-0059-2014.
Sommerfelt et al., Receptor interference groups of 20 retroviruses plating on human cells. Virology. May 1990;176(1):58-69. doi: 10.1016/0042-6822(90)90230-o.
Song et al., Adenine base editing in an adult mouse model of tyrosinaemia. Nat Biomed Eng. Jan. 2020;4(1):125-130. doi: 10.1038/s41551-019-0357-8. Epub Feb. 25, 2019.
Southworth et al., Control of protein splicing by intein fragment reassembly. EMBO J. Feb. 16, 1998;17(4):918-26. doi: 10.1093/emboj/17.4.918.
Southworth et al., Purification of proteins fused to either the amino or carboxy terminus of the *Mycobacterium xenopi* gyrase A intein. Biotechniques. Jul. 1999;27(1):110-4, 116, 118-20. doi: 10.2144/99271st04.
Spencer et al., A general strategy for producing conditional alleles of Src-like tyrosine kinases. Proc Natl Acad Sci U S A. Oct. 10, 1995;92(21):9805-9. doi: 10.1073/pnas.92.21.9805.
Spencer et al., Controlling signal transduction with synthetic ligands. Science. Nov. 12, 1993;262(5136):1019-24. doi: 10.1126/science.7694365.
Spencer et al., Functional analysis of Fas signaling in vivo using synthetic inducers of dimerization. Curr Biol. Jul. 1, 1996;6(7):839-47. doi: 10.1016/s0960-9822(02)00607-3.
Srivastava et al., An inhibitor of nonhomologous end-joining abrogates double-strand break repair and impedes cancer progression. Cell. Dec. 21, 2012;151(7):1474-87. doi: 10.1016/j.cell.2012.1 1.054.
Stadtman, Selenocysteine. Annu Rev Biochem. 1996;65:83-100.
Stamos et al., Structure of a Thermostable Group II Intron Reverse Transcriptase with Template-Primer and Its Functional and Evolutionary Implications. Mol Cell. Dec. 7, 2017;68(5):926-939.e4. doi: 10.1016/j.molcel.2017.10.024. Epub Nov. 16, 2017.
Steele et al., The prion protein knockout mouse: a phenotype under challenge. Prion. Apr.-Jun. 2007;1(2):83-93. doi: 10.4161/pri.1.2.4346. Epub Apr. 25, 2007.
Stella et al., Structure of the Cpf1 endonuclease R-loop complex after target DNA cleavage. Nature. Jun. 22, 2017;546(7659):559-563. doi: 10.1038/nature22398. Epub May 31, 2017.
Stenson et al., The Human Gene Mutation Database: towards a comprehensive repository of inherited mutation data for medical research, genetic diagnosis and next-generation sequencing studies. Hum Genet. Jun. 2017;136(6):665-677. doi: 10.1007/s00439-017-1779-6. Epub Mar. 27, 2017.
Sternberg et al., Conformational control of DNA target cleavage by CRISPR-Cas9. Nature. Nov. 5, 2015;527(7576):110-3. doi: 10.1038/nature15544. Epub Oct. 28, 2015.
Sterne-Weiler et al., Exon identity crisis: disease-causing mutations that disrupt the splicing code. Genome Biol. Jan. 23, 2014;15(1):201. doi: 10.1186/gb4150.
Stevens et al., A promiscuous split intein with expanded protein engineering applications. Proc Natl Acad Sci U S A. Aug. 8, 2017;114(32):8538-8543. doi: 10.1073/pnas.1701083114. Epub Jul. 24, 2017.
Stockwell et al., Probing the role of homomeric and heteromeric receptor interactions in TGF-beta signaling using small molecule dimerizers. Curr Biol. Jun. 18, 1998;8(13):761-70. doi: 10.1016/s0960-9822(98)70299-4.
Strecker et al., RNA-guided DNA insertion with CRISPR-associated transposases. Science. 2019 Jul5;365(6448):48-53. doi: 10.1126/science.aax9181. Epub Jun. 6, 2019.
Strutt et al., RNA-dependent RNA targeting by CRISPR-Cas9. Elife. Jan. 5, 2018;7:e32724. doi: 10.7554/eLife.32724.
Su et al., Human DNA polymerase ? has reverse transcriptase activity in cellular environments. J Biol Chem. Apr. 12, 2019;294(15):6073-6081. doi: 10.1074/jbc.RAl 19.007925. Epub Mar. 6, 2019.
Sudarsan et al., Riboswitches in eubacteria sense the second messenger cyclic di-GMP. Science. Jul. 18, 2008;321(5887):411-3. doi: 10.1126/science.1159519.
Surun et al., High Efficiency Gene Correction in Hematopoietic Cells by Donor-Template-Free CRISPR/Cas9 Genome Editing. Mol Ther Nucleic Acids. Mar. 2, 2018;10:1-8. doi: 10.1016/j.omtn.2017.11.001. Epub Nov. 10, 2017.
Suzuki et al., In vivo genome editing via CRISPR/Cas9 mediated homology-independent targeted integration. Nature. Dec. 1, 2016;540(7631):144-149. doi: 10.1038/nature20565. Epub Nov. 16, 2016.
Suzuki et al., VCre/VloxP and SCre/SloxP: new site-specific recombination systems for genome engineering. Nucleic Acids Res. Apr. 2011;39(8):e49. doi: 10.1093/nar/gkq1280. Epub Feb. 1, 2011.
Tabebordbar et al., In vivo gene editing in dystrophic mouse muscle and muscle stem cells. Science. Jan. 22, 2016;351(6271):407-411. doi: 10.1126/science.aad5177. Epub Dec. 31, 2015.
Tahara et al., Potent and Selective Inhibitors of 8-Oxoguanine DNA Glycosylase. J Am Chem Soc. Feb. 14, 2018;140(6):2105-2114. doi: 10.1021/jacs.7b09316. Epub Feb. 5, 2018.
Tajiri et al., Functional cooperation of MutT, MutM and MutY proteins in preventing mutations caused by spontaneous oxidation of guanine nucleotide in *Escherichia coli*. Mutat Res. May 1995;336(3):257-67. doi: 10.1016/0921-8777(94)00062-b.
Takimoto et al., Stereochemical basis for engineered pyrrolysyl-tRNA synthetase and the efficient in vivo incorporation of structurally divergent non-native amino acids. ACS Chem Biol. Jul. 15, 2011;6(7):733-43. doi: 10.1021/cb200057a. Epub May 5, 2011.
Tanenbaum et al., A protein-tagging system for signal amplification in gene expression and fluorescence imaging. Cell. Oct. 23, 2014;159(3):635-46. doi: 10.1016/j.cell.2014.09.039. Epub Oct. 9, 2014.
Tanese et al., Expression of enzymatically active reverse transcriptase in *Escherichia coli*. Proc Natl Acad Sci U S A. Aug. 1985;82(15):4944-8. doi: 10.1073/pnas.82.15.4944.
Tang et al., Evaluation of Bioinformatic Programmes for the Analysis of Variants within Splice Site Consensus Regions. Adv Bioinformatics. 2016;2016:5614058. doi: 10.1155/2016/5614058. Epub May 24, 2016.
Tang et al., Rewritable multi-event analog recording in bacterial and mammalian cells. Science. Apr. 13, 2018;360(6385):eaap8992. doi: 10.1126/science.aap8992. Epub Feb. 15, 2018.
Tassabehji, Williams-Beuren syndrome: a challenge for genotype-phenotype correlations. Hum Mol Genet. Oct. 15, 2003;12 Spec No. 2:R229-37. doi: 10.1093/hmg/ddg299. Epub Sep. 2, 2003.
Taube et al., Reverse transcriptase of mouse mammary tumour virus: expression in bacteria, purification and biochemical characterization. Biochem J. Feb. 1, 1998;329 ( Pt 3)(Pt 3):579-87. doi: 10.1042/bj3290579. Erratum in: Biochem J Jun. 15, 1998;332(Pt 3):808.
Tee et al., Polishing the craft of genetic diversity creation in directed evolution. Biotechnol Adv. Dec. 2013;31(8):1707-21. doi: 10.1016/j.biotechadv.2013.08.021. Epub Sep. 6, 2013.
Telenti et al., The *Mycobacterium xenopi* GyrA protein splicing element: characterization of a minimal intein. J Bacteriol. Oct. 1997;179(20):6378-82. doi: 10.1128/jb.179.20.6378-6382.1997.
Telesnitsky et al., RNase H domain mutations affect the interaction between Moloney murine leukemia virus reverse transcriptase and its primer-template. Proc Natl Acad Sci U S A. Feb. 15, 1993;90(4):1276-80. doi: 10.1073/pnas.90.4.1276.
Thomson et al., Mutational analysis of loxP sites for efficient Cre-mediated insertion into genomic DNA. Genesis. Jul. 2003;36(3):162-7. doi: 10.1002/gene.10211.

(56) References Cited

OTHER PUBLICATIONS

Thuronyi et al., Continuous evolution of base editors with expanded target compatibility and improved activity. Nat Biotechnol. Sep. 2019;37(9):1070-1079. doi: 10.1038/s41587-019-0193-0. Epub Jul. 22, 2019.
Thyagarajan et al., Creation of engineered human embryonic stem cell lines using phiC31 integrase. Stem Cells. Jan. 2008;26(1):119-26. doi: 10.1634/stemcells.2007-0283. Epub Oct. 25, 2007.
Tinland et al., The T-DNA-linked VirD2 protein contains two distinct functional nuclear localization signals. Proc Natl Acad Sci U S A. Aug. 15, 1992;89(16):7442-6. doi: 10.1073/pnas.89.16.7442.
Tom et al., Mechanism whereby proliferating cell nuclear antigen stimulates flap endonuclease 1. J Biol Chem. Apr. 7, 2000;275(14):10498-505. doi: 10.1074/jbc.275.14.10498.
Toor et al., Crystal structure of a self-spliced group II intron. Science. Apr. 4, 2008;320(5872):77-82. doi: 10.1126/science.1153803.
Toro et al., On the Origin and Evolutionary Relationships of the Reverse Transcriptases Associated With Type III CRISPR-Cas Systems. Front Microbiol. Jun. 15, 2018;9:1317. doi: 10.3389/fmicb.2018.01317.
Toro et al., The Reverse Transcriptases Associated with CRISPR-Cas Systems. Sci Rep. Aug. 2, 2017;7(1):7089. doi: 10.1038/s41598-017-07828-y.
Torres et al., Non-integrative lentivirus drives high-frequency cre-mediated cassette exchange in human cells. PLoS One. 2011;6(5):el9794. doi: 10.1371/journal.pone.0019794. Epub May 23, 2011.
Townsend et al., Role of HFE in iron metabolism, hereditary haemochromatosis, anaemia of chronic disease, and secondary iron overload. Lancet. Mar. 2, 2002;359(9308):786-90. doi: 10.1016/S0140-6736(02)07885-6.
Tracewell et al., Directed enzyme evolution: climbing fitness peaks one amino acid at a time. Curr Opin Chem Biol. Feb. 2009;13(1):3-9. doi: 10.1016/j.cbpa.2009.01.017. Epub Feb. 25, 2009.
Tratschin et al., A human parvovirus, adeno-associated virus, as a eucaryotic vector: transient expression and encapsidation of the procaryotic gene for chloramphenicol acetyltransferase. Mol Cell Biol. Oct. 1984;4(10):2072-81. doi: 10.1128/mcb.4.10.2072.
Tratschin et al., Adeno-associated virus vector for high-frequency integration, expression, and rescue of genes in mammalian cells. Mol Cell Biol. Nov. 1985;5(11):3251-60. doi: 10.1128/mcb.5.11.3251.
Traxler et al., A genome-editing strategy to treat ?-hemoglobinopathies that recapitulates a mutation associated with a benign genetic condition. Nat Med. Sep. 2016;22(9):987-90. doi: 10.1038/nm.4170. Epub Aug. 15, 2016.
Trudeau et al., On the Potential Origins of the High Stability of Reconstructed Ancestral Proteins. Mol Biol Evol. Oct. 2016;33(10):2633-41. doi: 10.1093/molbev/msw138. Epub Jul. 12, 2016.
Tsai et al., CIRCLE-seq: a highly sensitive in vitro screen for genome-wide CRISPR-Cas9 nuclease off-targets. Nat Methods. Jun. 2017;14(6):607-614. doi: 10.1038/nmeth.4278. Epub May 1, 2017.
Tsang et al., Specialization of the DNA-cleaving activity of a group I ribozyme through in vitro evolution. J Mol Biol. Sep. 13, 1996;262(1):31-42. doi: 10.1006/jmbi.1996.0496.
Tsutakawa et al., Human flap endonuclease structures, DNA double-base flipping, and a unified understanding of the FEN1 superfamily. Cell. Apr. 15, 2011;145(2):198-211. doi: 10.1016/j.cell.2011 .03.004.
Tycko et al., Pairwise library screen systematically interrogates *Staphylococcus aureus* Cas9 specificity in human cells. bioRxiv. doi: https://doi.org/10.1101/269399 Posted Feb. 22, 2018.
Uniprot Consortium, UniProt: the universal protein knowledgebase. Nucleic Acids Res. Mar. 16, 2018;46(5):2699. doi: 10.1093/nar/gky092.
UNIPROTKB Submission; Accession No. F0NH53. May 3, 2011. 4 pages.
UNIPROTKB Submission; Accession No. P0DOC6. No Author Listed., Oct. 5, 2016. 5 pages.
UNIPROTKB Submission; Accession No. T0D7A2. Oct. 16, 2013. 10 pages.
Urasaki et al., Functional dissection of the To12 transposable element identified the minimal cis-sequence and a highly repetitive sequence in the subterminal region essential for transposition. Genetics. Oct. 2006;174(2):639-49. doi: 10.1534/genetics.106.060244. Epub Sep. 7, 2006.
Van Brunt et al., Genetically Encoded Azide Containing Amino Acid in Mammalian Cells Enables Site-Specific Antibody-Drug Conjugates Using Click Cycloaddition Chemistry. Bioconjug Chem. Nov. 18, 2015;26(11):2249-60. doi: 10.1021/acs.bioconjchem.5b00359. Epub Sep. 11, 2015.
Van Brunt et al., Molecular Farming: Transgenic Animals as Bioreactors. Biotechnology (N Y). 1988;6(10):1149-1154. doi: 10.1038/nbt1088-1149.
Van Overbeek et al., DNA Repair Profiling Reveals Nonrandom Outcomes at Cas9-Mediated Breaks. Mol Cell. Aug. 18, 2016;63(4):633-646. doi: 10.1016/j.molcel.2016.06.037. Epub Aug. 4, 2016.
Van Wijk et al., Identification of 51 novel exons of the Usher syndrome type 2A (USH2A) gene that encode multiple conserved functional domains and that are mutated in patients with Usher syndrome type II. Am J Hum Genet. Apr. 2004;74(4):738-44. doi: 10.1086/383096. Epub Mar. 10, 2004.
Varga et al., Progressive vascular smooth muscle cell defects in a mouse model of Hutchinson-Gilford progeria syndrome. Proc Natl Acad Sci U S A. Feb. 28, 2006;103(9):3250-5. doi: 10.1073/pnas.0600012103. Epub Feb. 21, 2006.
Vellore et al., A group II intron-type open reading frame from the thermophile Bacillus (Geobacillus) stearothermophilus encodes a heat-stable reverse transcriptase. Appl Environ Microbiol. Dec. 2004;70(12):7140-7. doi: 10.1128/AEM.70.12.7140-7147.2004.
Verma, The reverse transcriptase. Biochim Biophys Acta. Mar. 21, 1977;473(1):1-38. doi: 10.1016/0304-419x(77)90005-1.
Vigne et al., Third-generation adenovectors for gene therapy. Restor Neurol Neurosci. Jan. 1, 1995;8(1):35-6. doi: 10.3233/RNN-1995-81208.
Vik et al., Endonuclease V cleaves at inosines in RNA. Nat Commun. 2013;4:2271. doi: 10.1038/ncomms3271.
Vilenchik et al., Endogenous DNA double-strand breaks: production, fidelity of repair, and induction of cancer. Proc Natl Acad Sci U S A. Oct. 28, 2003;100(22):12871-6. doi: 10.1073/pnas.2135498100. Epub Oct. 17, 2003.
Voigt et al., Rational evolutionary design: the theory of in vitro protein evolution. Adv Protein Chem. 2000;55:79-160.
Vriend et al., Nick-initiated homologous recombination: Protecting the genome, one strand at a time. DNA Repair (Amst). Feb. 2017;50:1-13. doi: 10.1016/j.dnarep.2016.12.005. Epub Dec. 29, 2016.
Wang et al., AID upmutants isolated using a high-throughput screen highlight the immunity/cancer balance limiting DNA deaminase activity. Nat Struct Mol Biol. Jul. 2009;16(7):769-76. doi: 10.1038/nsmb.1623. Epub Jun. 21, 2009.
Wang et al., Continuous directed evolutions of proteins with improved soluble expression. Nature Chemical Biology. Nat Publishing Group. Aug. 20, 2018; 14(10):972-980.
Wang et al., Evolution of new nonantibody proteins via iterative somatic hypermutation. Proc Natl Acad Sci U S A. Nov. 30, 2004;101(48):16745-9. Epub Nov. 19, 2004.
Wang et al., Expanding the genetic code. Annu Rev Biophys Biomol Struct. 2006;35:225-49. Review.
Wang et al., Highly efficient CRISPR/HDR-mediated knock-in for mouse embryonic stem cells and zygotes. Biotechniques. 2015:59,201-2;204;206-8.
Wang et al., N(6)-methyladenosine Modulates Messenger RNA Translation Efficiency. Cell. Jun. 4, 2015;161(6):1388-99. doi: 10.1016/j.cell.2015.05.014.
Wang et al., N6-methyladenosine-dependent regulation of messenger RNA stability. Nature. Jan. 2, 2014;505(7481):117-20. doi: 10.1038/nature12730. Epub Nov. 27, 2013.

(56) References Cited

OTHER PUBLICATIONS

Wang et al., Programming cells by multiplex genome engineering and accelerated evolution. Nature. Aug. 13, 2009;460(7257):894-8. Epub Jul. 26, 2009.
Wang et al., Reading RNA methylation codes through methyl-specific binding proteins. RNA Biol. 2014;ll(6):669-72. doi: 10.4161/rna.28829. Epub Apr. 24, 2014.
Wang et al., *Staphylococcus aureus* protein SAUGI acts as a uracil-DNA glycosylase inhibitor. Nucleic Acids Res. Jan. 2014;42(2):1354-64. doi: 10.1093/nar/gkt964. Epub Oct. 22, 2013.
Wang et al., Structural basis of N(6)-adenosine methylation by the METTL3-METTL14 complex. Nature. Jun. 23, 2016;534(7608):575-8. doi: 10.1038/nature18298. Epub May 25, 2016.
Watowich, The erythropoietin receptor: molecular structure and hematopoietic signaling pathways. J Investig Med. Oct. 2011;59(7):1067-72. doi: 10.2310/JIM.0b013e31820fb28c.
Waxman et al., Regulating excitability of peripheral afferents: emerging ion channel targets. Nat Neurosci. Feb. 2014;17(2):153-63. doi: 10.1038/nn.3602. Epub Jan. 28, 2014.
Weill et al., DNA polymerases in adaptive immunity. Nat Rev Immunol. Apr. 2008;8(4):302-12. doi: 10.1038/nri2281. Epub Mar. 14, 2008.
Weinert et al., Unbiased detection of CRISPR off-targets in vivo using DISCOVER-Seq. Science. Apr. 19, 2019;364(6437):286-289. doi: 10.1126/science.aav9023. Epub Apr. 18, 2019.
Wen et al., Inclusion of a universal tetanus toxoid CD4(+) T cell epitope P2 significantly enhanced the immunogenicity of recombinant rotavirus ?VP8* subunit parenteral vaccines. Vaccine. Jul. 31, 2014;32(35):4420-4427. doi: 10.1016/j.vaccine.2014.06.060. Epub Jun. 21, 2014.
West et al., Gene expression in adeno-associated virus vectors: the effects of chimeric mRNA structure, helper virus, and adenovirus VA1 RNA. Virology. Sep. 1987;160(1):38-47. doi: 10.1016/0042-6822(87)90041-9.
Wharton et al., A new-specificity mutant of 434 repressor that defines an amino acid-base pair contact. Nature. Apr. 30-May 6, 1987;326(6116):888-91.
Wharton et al., Changing the binding specificity of a repressor by redesigning an alpha-helix. Nature. Aug. 15-21, 1985;316(6029):601-5.
Wheeler et al., The thermostability and specificity of ancient proteins. Curr Opin Struct Biol. Jun. 2016;38:37-43. doi: 10.1016/j.sbi.2016.05.015. Epub Jun. 9, 2016.
Wienert et al., KLF1 drives the expression of fetal hemoglobin in British HPFH. Blood. Aug. 10, 2017;130(6):803-807. doi: 10.1182/blood-2017-02-767400. Epub Jun. 28, 2017.
Williams et al., Assessing the accuracy of ancestral protein reconstruction methods. PLoS Comput Biol. Jun. 23, 2006;2(6):e69. doi: 10.1371/journal.pcbi.0020069. Epub Jun. 23, 2006.
Wilson et al., Formation of infectious hybrid virions with gibbon ape leukemia virus and human T-cell leukemia virus retroviral envelope glycoproteins and the gag and pol proteins of Moloney murine leukemia vims. J Virol. May 1989;63(5):2374-8. doi: 10.1128/JVI.63.5.2374-2378.1989.
Wilson et al., Kinase dynamics. Using ancient protein kinases to unravel a modern cancer drug's mechanism. Science. Feb. 20, 2015;347(6224):882-6. doi: 10.1126/science.aaa1823.
Winoto et al., A novel, inducible and T cell-specific enhancer located at the 3' end of the T cell receptor alpha locus. EMBO J. Mar. 1989;8(3):729-33.
Winter et al., Drug Development. Phthalimide conjugation as a strategy for in vivo target protein degradation. Science. Jun. 19, 2015;348(6241):1376-81. doi:; 10.1126/science.aab1433. Epub May 21, 2015.
Winter et al., Targeted exon skipping with AAV-mediated split adenine base editors. Cell Discov. Aug. 20, 2019;5:41. doi: 10.1038/s41421-019-0109-7.
Wold, Replication protein A: a heterotrimeric, single-stranded DNA-binding protein required for eukaryotic DNA metabolism. Annu Rev Biochem. 1997;66:61-92. doi: 10.1146/annurev.biochem.66.1.61.
Wong et al., A statistical analysis of random mutagenesis methods used for directed protein evolution. J Mol Biol. Jan. 27, 2006;355(4):858-71. Epub Nov. 17, 2005.
Wong et al., The Diversity Challenge in Directed Protein Evolution. Comb Chem High Throughput Screen. May 2006;9(4):271-88.
Wood et al., A genetic system yields self-cleaving inteins for bioseparations. Nat Biotechnol. Sep. 1999;17(9):889-92. doi: 10.1038/12879.
Wright et al., Continuous in vitro evolution of catalytic function. Science. Apr. 25, 1997;276(5312):614-7.
Wu et al., Human single-stranded DNA binding proteins: guardians of genome stability. Acta Biochim Biophys Sin (Shanghai). Jul. 2016;48(7):671-7. doi: 10.1093/abbs/gmw044. Epub May 23, 2016.
Wu et al., Protein trans-splicing and functional mini-inteins of a cyanobacterial dnaB intein. Biochim Biophys Acta. Sep. 8, 1998;1387(1-2):422-32. doi: 10.1016/s0167-4838(98)00157-5.
Wu et al., Protein trans-splicing by a split intein encoded in a split DnaE gene of *Synechocystis* sp. PCC6803. Proc Natl Acad Sci U S A. Aug. 4, 1998;95(16):9226-31. doi: 10.1073/pnas.95.16.9226.
Wu et al., Readers, writers and erasers of N6-methylated adenosine modification. Curr Opin Struct Biol. Dec. 2017;47:67-76. doi: 10.1016/j.sbi.2017.05.011. Epub Jun. 16, 2017.
Xiang et al., RNA m6A methylation regulates the ultraviolet-induced DNA damage response. Nature. Mar. 23, 2017;543(7646):573-576. doi: 10.1038/nature21671. Epub Mar. 15, 2017.
Xiao et al., Genetic incorporation of multiple unnatural amino acids into proteins in mammalian cells. Angew Chem Int Ed Engl. Dec. 23, 2013;52(52):14080-3. doi: 10.1002/anie.201308137. Epub Nov. 8, 2013.
Xiao et al., Nuclear m(6)A Reader YTHDC1 Regulates mRNA Splicing. Mol Cell. Feb. 18, 2016;61(4):507-519. doi: 10.1016/j.molcel.2016.01.012. Epub Feb. 11, 2016.
Xie et al., Adjusting the attB site in donor plasmid improves the efficiency of ?C31 integrase system. DNA Cell Biol. Jul. 2012;31(7):1335-40. doi: 10.1089/dna.2011.1590. Epub Apr. 10, 2012.
Xiong et al., Origin and evolution of retroelements based upon their reverse transcriptase sequences. EMBO J. Oct. 1990;9(10):3353-62.
Xu et al., Chemical ligation of folded recombinant proteins: segmental isotopic labeling of domains for NMR studies. Proc Natl Acad Sci U S A. Jan. 19, 1999;96(2):388-93. doi: 10.1073/pnas.96.2.388.
Xu et al., Accuracy and efficiency define Bxb1 integrase as the best of fifteen candidate serine recombinases for the integration of DNA into the human genome. BMC Biotechnol. Oct. 20, 2013;13:87. doi: 10.1186/1472-6750-13-87.
Xu et al., Protein splicing: an analysis of the branched intermediate and its resolution by succinimide formation. EMBO J. Dec. 1, 1994;13(23):5517-22.
Xu et al., PTMD: A Database of Human Disease-associated Post-translational Modifications. Genomics Proteomics Bioinformatics. Aug. 2018;16(4):244-251. doi: 10.1016/j.gpb.2018.06.004. Epub Sep. 21, 2018.
Xu et al., Structures of human ALKBH5 demethylase reveal a unique binding mode for specific single-stranded N6-methyladenosine RNA demethylation. J Biol Chem. Jun. 20, 2014;289(25):17299-311. doi: 10.1074/jbc.M114.550350. Epub Apr. 28, 2014.
Xu et al., The mechanism of protein splicing and its modulation by mutation. EMBO J. Oct. 1, 1996;15(19):5146-53.
Yamamoto et al., The ons and offs of inducible transgenic technology: a review. Neurobiol Dis. Dec. 2001;8(6):923-32.
Yamazaki et al., Segmental Isotope Labeling for Protein NMR Using Peptide Splicing. J. Am. Chem. Soc. May 22, 1998; 120(22):5591-2. https://doi.org/10.1021/ja980776o.
Yan et al., Cas13d is a Compact RNA-Targeting Type VI CRISPR Effector Positively Modulated by a WYL-Domain-Containing Accessory Protein. Mol Cell. Apr. 19, 2018;70(2):327-339.e5. doi: 10.1016/j.molcel.2018.02.028. Epub Mar. 15, 2018.

(56) References Cited

OTHER PUBLICATIONS

Yang et al., Construction of an integration-proficient vector based on the site-specific recombination mechanism of enterococcal temperate phage phiFC1. J Bacteriol. Apr. 2002;184(7):1859-64. doi: 10.1128/jb.184.7.1859-1864.2002.
Yang et al., Increasing targeting scope of adenosine base editors in mouse and rat embryos through fusion of TadA deaminase with Cas9 variants. Protein Cell. Sep. 2018;9(9):814-819. doi: 10.1007/s13238-018-0568-x.
Yang et al., One-step generation of mice carrying reporter and conditional alleles by CRISPR/Cas-mediated genome engineering. Cell. Sep. 12, 2013;154(6):1370-9. doi: 10.1016/j.cell.2013.08.022. Epub Aug. 29, 2013.
Yang et al., Permanent genetic memory with >1-byte capacity. Nat Methods. Dec. 2014;11(12):1261-6. doi: 10.1038/nmeth.3147. Epub Oct. 26, 2014.
Yang et al., Preparation of RNA-directed DNA polymerase from spleens of Balb-c mice infected with Rauscher leukemia virus. Biochem Biophys Res Commun. Apr. 28, 1972;47(2):505-11. doi: 10.1016/0006-291x(72)90743-7.
Yang et al., Small-molecule control of insulin and PDGF receptor signaling and the role of membrane attachment. Curr Biol. Jan. 1, 1998;8(1):11-8. doi: 10.1016/s0960-9822(98)70015-6.
Yang, Nucleases: diversity of structure, function and mechanism. Q Rev Biophys. Feb. 2011;44(1):1-93. doi: 10.1017/S0033583510000181. Epub Sep. 21, 2010.
Yang, PAML 4: phylogenetic analysis by maximum likelihood. Mol Biol Evol. Aug. 2007;24(8):1586-91. doi: 10.1093/molbev/msm088. Epub May 4, 2007.
Yasui et al., Miscoding Properties of 2'-Deoxyinosine, a Nitric Oxide-Derived DNA Adduct, during Translesion Synthesis Catalyzed by Human DNA Polymerases. J Molec Biol. Apr. 4, 2008;377(4):1015-23.
Yasui, Alternative excision repair pathways. Cold Spring Harb Perspect Biol. Jun. 1, 2013;5(6):a012617. doi: 10.1101/cshperspect.a012617.
Yasukawa et al., Characterization of Moloney murine leukaemia virus/avian myeloblastosis virus chimeric reverse transcriptases. J Biochem. Mar. 2009;145(3):315-24. doi: 10.1093/jb/mvn166. Epub Dec. 6, 2008.
Yeh et al., In vivo base editing of post-mitotic sensory cells. Nat Commun. Jun. 5, 2018;9(1):2184. doi: 10.1038/s41467-018-04580-3.
Yu et al., Circular permutation: a different way to engineer enzyme structure and function. Trends Biotechnol. Jan. 2011;29(1):18-25. doi: 10.1016/j.tibtech.2010.10.004. Epub Nov. 17, 2010.
Yu et al., Progress towards gene therapy for HIV infection. Gene Ther. Jan. 1994;1(1):13-26.
Yu et al., Small molecules enhance CRISPR genome editing in pluripotent stem cells. Cell Stem Cell. Feb. 5, 2015;16(2):142-7. doi: 10.1016/j.stem.2015.01.003.
Yu et al., Synthesis-dependent microhomology-mediated end joining accounts for multiple types of repair junctions. Nucleic Acids Res. Sep. 2010;38(17):5706-17. doi: 10.1093/nar/gkq379. Epub May 11, 2010.
Zakas et al., Enhancing the pharmaceutical properties of protein drugs by ancestral sequence reconstruction. Nat Biotechnol. Jan. 2017;35(1):35-37. doi: 10.1038/nbt.3677. Epub Sep. 26, 2016.
Zalatan et al., Engineering complex synthetic transcriptional programs with CRISPR RNA scaffolds. Cell. Jan. 15, 2015;160(1-2):339-50. doi: 10.1016/j.cell.2014.11.052. Epub Dec. 18, 2014.
Zettler et al., The naturally split Npu DnaE intein exhibits an extraordinarily high rate in the protein trans-splicing reaction. FEBS Lett. Mar. 4, 2009;583(5):909-14. doi: 10.1016/j.febslet.2009.02.003. Epub Feb. 10, 2009.
Zhang et al., II-Clamp-mediated cysteine conjugation. Nat Chem. Feb. 2016;8(2):120-8. doi: 10.1038/nchem.2413. Epub Dec. 21, 2015.
Zhang et al., A new strategy for the site-specific modification of proteins in vivo. Biochemistry. Jun. 10, 2003;42(22):6735-46.
Zhang et al., Circular intronic long noncoding RNAs. Mol Cell. Sep. 26, 2013;51(6):792-806. doi: 10.1016/j.molcel.2013.08.017. Epub Sep. 12, 2013.
Zhang et al., Copy number variation in human health, disease, and evolution. Annu Rev Genomics Hum Genet. 2009;10:451-81. doi: 10.1146/annurev.genom.9.081307.164217.
Zhang et al., Myoediting: Toward Prevention of Muscular Dystrophy by Therapeutic Genome Editing. Physiol Rev. Jul. 1, 2018;98(3):1205-1240. doi: 10.1152/physrev.00046.2017.
Zhao et al., An ultraprocessive, accurate reverse transcriptase encoded by a metazoan group II intron. RNA. Feb. 2018;24(2):183-195. doi: 10.1261/rna.063479.117. Epub Nov. 6, 2017.
Zhao et al., Post-transcriptional gene regulation by mRNA modifications. Nat Rev Mol Cell Biol. Jan. 2017;18(1):31-42. doi: 10.1038/nrm.2016.132. Epub Nov. 3, 2016.
Zheng et al., ALKBH5 is a mammalian RNA demethylase that impacts RNA metabolism and mouse fertility. Mol Cell. Jan. 10, 2013;49(1):18-29. doi: 10.1016/j.molcel.2012.10.015. Epub Nov. 21, 2012.
Zheng et al., Highly efficient base editing in bacteria using a Cas9-cytidine deaminase fusion. Commun Biol. Apr. 19, 2018;1:32. doi: 10.1038/s42003-018-0035-5.
Zheng et al., Structural basis for the complete resistance of the human prion protein mutant G127V to prion disease. Sci Rep. Sep. 4, 2018;8(1):13211. doi: 10.1038/s41598-018-31394-6.
Zhou et al., Dynamic m(6)A mRNA methylation directs translational control of heat shock response. Nature. Oct. 22, 2015;526(7574):591-4. doi: 10.1038/nature15377. Epub Oct. 12, 2015.
Zhou et al., Off-target RNA mutation induced by DNA base editing and its elimination by mutagenesis. Nature. Jul. 2019;571(7764):275-278. doi: 10.1038/s41586-019-1314-0. Epub Jun. 10, 2019.
Zhou et al., Seamless Genetic Conversion of SMN2 to SMN1 via CRISPR/Cpf1 and Single-Stranded Oligodeoxynucleotides in Spinal Muscular Atrophy Patient-Specific Induced Pluripotent Stem Cells. Hum Gene Ther. Nov. 2018;29(11):1252-1263. doi: 10.1089/hum.2017.255. Epub May 9, 2018.
Zielenski, Genotype and phenotype in cystic fibrosis. Respiration. 2000;67(2):117-33. doi: 10.1159/000029497.
Zimmerly et al., An Unexplored Diversity of Reverse Transcriptases in Bacteria. Microbiol Spectr. Apr. 2015;3(2):MDNA3-0058-2014. doi: 10.1128/microbiolspec.MDNA3-0058-2014.
Zimmerly et al., Group II intron mobility occurs by target DNA-primed reverse transcription. Cell. Aug. 25, 1995;82(4):545-54. doi: 10.1016/0092-8674(95)90027-6.
Zufferey et al., Woodchuck hepatitis virus posttranscriptional regulatory element enhances expression of transgenes delivered by retroviral vectors. J Virol. Apr. 1999;73(4):2886-92. doi: 10.1128/JVI.73.4.2886-2892.1999.
Zuker et al., Optimal computer folding of large RNA sequences using thermodynamics and auxiliary information. Nucleic Acids Res. Jan. 10, 1981;9(1):133-48. doi: 10.1093/nar/9.1.133.
Zuo et al., Cytosine base editor generates substantial off-target single-nucleotide variants in mouse embryos. Science. Apr. 19, 2019;364(6437):289-292. doi: 10.1126/science.aav9973. Epub Feb. 28, 2019.
[No Author Listed] "Human genome." Encyclopedia Britannica. Encyclopedia Britannica, Inc. Published Feb. 15, 2019. Last accessed online via https://www.britannica.com/science/human-genome on Mar. 19, 2021. 2 pages.
Akopian et al., Chimeric recombinases with designed DNA sequence recognition. Proc Natl Acad Sci U S A. Jul. 22, 2003;100(15):8688-91. Epub Jul. 1, 2003.
Amato et al., Interpreting elevated fetal hemoglobin in pathology and health at the basic laboratory level: new and known γ-gene mutations associated with hereditary persistence of fetal hemoglobin. Int J Lab Hematol. Feb. 2014;36(1):13-9. doi: 10.1111/ijlh.12094. Epub Apr. 29, 2013.
André et al., Axotomy-induced expression of calcium-activated chloride current in subpopulations of mouse dorsal root ganglion neurons. J Neurophysiol. Dec. 2003;90(6):3764-73. doi: 10.1152/jn.00449.2003. Epub Aug. 27, 2003.

(56) References Cited

OTHER PUBLICATIONS

Atkins et al., Ribosomal frameshifting and transcriptional slippage: From genetic steganography and cryptography to adventitious use. Nucleic Acids Res. Sep. 6, 2016;44(15):7007-78. doi: 10.1093/nar/gkw530. Epub Jul. 19, 2016.
Benarroch, HCN channels: function and clinical implications. Neurology. Jan. 15, 2013;80(3):304-10. doi: 10.1212/WNL.0b013e31827dec42.
Berges et al., Transduction of brain by herpes simplex virus vectors. Mol Ther. Jan. 2007;15(1):20-9. doi: 10.1038/sj.mt.6300018.
Bhagwat, DNA-cytosine deaminases: from antibody maturation to antiviral defense. DNA Repair (Amst). Jan. 5, 2004;3(1):85-9.
Bourinet et al., Silencing of the Cav3.2 T-type calcium channel gene in sensory neurons demonstrates its major role in nociception. EMBO J. Jan. 26, 2005;24(2):315-24. doi: 10.1038/sj.emboj.7600515. Epub Dec. 16, 2004.
Burke et al., Activating mutations of Tn3 resolvase marking interfaces important in recombination catalysis and its regulation. Mol Microbiol. Feb. 2004;51(4):937-48.
Cai et al., Reconstruction of ancestral protein sequences and its applications. BMC Evol Biol. Sep. 17, 2004;4:33. doi: 10.1186/1471-2148-4-33.
Canver et al., Customizing the genome as therapy for the β-hemoglobinopathies. Blood. May 26, 2016;127(21):2536-45. doi: 10.1182/blood-2016-01-678128. Epub Apr. 6, 2016.
Caspi et al., Distribution of split DnaE inteins in cyanobacteria. Mol Microbiol. Dec. 2003;50(5):1569-77. doi: 10.1046/j.1365-2958.2003.03825.x.
Chan et al., Molecular recording of mammalian embryogenesis. Nature. Jun. 2019;570(7759):77-82. doi: 10.1038/s41586-019-1184-5. Epub May 13, 2019.
Chari et al., Unraveling CRISPR-Cas9 genome engineering parameters via a library-on-library approach. Nat Methods. Sep. 2015;12(9):823-6. doi: 10.1038/nmeth.3473. Epub Jul. 13, 2015.
Chavez et al., Therapeutic applications of the ?C31 integrase system. Curr Gene Ther. Oct. 2011;11(5):375-81. Review.
Chen et al., Genome-wide CRISPR screen in a mouse model of tumor growth and metastasis. Cell. Mar. 12, 2015;160(6): 1246-60. doi: 10.1016/j.cell.2015.02.038. Epub Mar. 5, 2015.
Cheng et al., Multiplexed activation of endogenous genes by CRISPR-on, an RNA-guided transcriptional activator system. Cell Res. Oct. 2013;23(10):1163-71. doi: 10.1038/cr.2013.122. Epub Aug. 27, 2013.
Chester et al., The apolipoprotein B mRNA editing complex performs a multifunctional cycle and suppresses nonsense-mediated decay. EMBO J. Aug. 1, 2003;22(15):3971-82. doi: 10.1093/emboj/cdg369.
Cho et al., The calcium-activated chloride channel anoctamin 1 acts as a heat sensor in nociceptive neurons. Nat Neurosci. May 27, 2012;15(7):1015-21. doi: 10.1038/nn.3111.
Chong et al., Protein splicing of the *Saccharomyces cerevisiae* VMA intein without the endonuclease motifs. J Biol Chem. Jun. 20, 1997;272(25):15587-90. doi: 10.1074/jbc.272.25.15587.
Costa et al., Frequent use of the same tertiary motif by self-folding RNAs. EMBO J. Mar. 15, 1995;14(6):1276-85.
Cox et al., An SCN9A channelopathy causes congenital inability to experience pain. Nature. Dec. 14, 2006;444(7121):894-8. doi: 10.1038/nature05413.
Cox et al., Congenital insensitivity to pain: novel SCN9A missense and in-frame deletion mutations. Hum Mutat. Sep. 2010;31(9):E1670-86. doi: 10.1002/humu.21325.
Cronican et al., A class of human proteins that deliver functional proteins into mammalian cells in vitro and in vivo. Chem Biol. Jul. 29, 2011;18(7):833-8. doi: 10.1016/j.chembiol.2011.07.003.
Cronican et al., Potent delivery of functional proteins into Mammalian cells in vitro and in vivo using a supercharged protein. ACS Chem Biol. Aug. 20, 2010;5(8):747-52. doi:10.1021/cb1001153.
Database EBI Accession No. ADE34233 Jan. 29, 2004.
Database EBI Accession No. BFF09785. May 31, 2018. 2 pages.
Database EBI Accession No. BGE38086. Jul. 25, 2019. 2 pages.
Database UniProt Accession No. G8I3E0. Jan. 14, 2012.
Davidson et al., Viral vectors for gene delivery to the nervous system. Nat Rev Neurosci. May 2003;4(5):353-64. doi: 10.1038/nrn1104.
Deverman et al., Cre-dependent selection yields AAV variants for widespread gene transfer to the adult brain. Nat Biotechnol. Feb. 2016;34(2):204-9. doi: 10.1038/nbt.3440. Epub Feb. 1, 2016.
Devigili et al., Paroxysmal itch caused by gain-of-function Nav1.7 mutation. Pain. Sep. 2014;155(9):1702-1707. doi: 10.1016/j.pain.2014.05.006. Epub May 10, 2014.
Doench et al., Rational design of highly active sgRNAs for CRISPR-Cas9-mediated gene inactivation. Nat Biotechnol. Dec. 2014;32(12):1262-7. doi: 10.1038/nbt.3026. Epub Sep. 3, 2014.
Emery et al., HCN2 ion channels play a central role in inflammatory and neuropathic pain. Science. Sep. 9, 2011;333(6048):1462-6. doi: 10.1126/science.1206243.
Epstein, HSV-1-based amplicon vectors: design and applications. Gene Ther. Oct. 2005;12 Suppl 1:S154-8. doi: 10.1038/sj.gt.3302617.
Estacion et al., A sodium channel gene SCN9A polymorphism that increases nociceptor excitability. Ann Neurol. Dec. 2009;66(6):862-6. doi: 10.1002/ana.21895.
Evans et al., Protein trans-splicing and cyclization by a naturally split intein from the dnaE gene of *Synechocystis* species PCC6803. J Biol Chem. Mar. 31, 2000;275(13):9091-4. doi: 10.1074/jbc.275.13.9091.
Farboud et al., Dramatic enhancement of genome editing by CRISPR/Cas9 through improved guide RNA design. Genetics. Apr. 2015;199(4):959-71. doi: 10.1534/genetics.115.175166. Epub Feb. 18, 2015.
Fawcett et al., Transposable elements controlling I-R hybrid dysgenesis in D. melanogaster are similar to mammalian LINEs. Cell. Dec. 2, 1986;47(6):1007-15. doi: 10.1016/0092-8674(86)90815-9.6
Fire et al., Potent and specific genetic interference by double-stranded RNA in Caenorhabditis elegans. Nature. Feb. 19, 1998;391(6669):806-11. doi: 10.1038/35888.
Flaman et al., A rapid PCR fidelity assay. Nucleic Acids Res. Aug. 11, 1994;22(15):3259-60. doi: 10.1093/nar/22.15.3259.
Fusi et al., In Silico Predictive Modeling of CRISPR/Cas9 guide efficiency. Jun. 26, 2015; bioRxiv. http://dx.doi.org/10.1101/021568.
Gaj et al., Structure-guided reprogramming of serine recombinase DNA sequence specificity. Proc Natl Acad Sci U S A. Jan. 11, 2011;108(2):498-503. doi: 10.1073/pnas.1014214108. Epub Dec. 27, 2010.
Gao et al., Self-processing of ribozyme-flanked RNAs into guide RNAs in vitro and in vivo for CRISPR-mediated genome editing. J Integr Plant Biol. Apr. 2014;56(4):343-9. doi: 10.1111/jipb.12152. Epub Mar. 6, 2014.
Garcia et al., Transglycosylation: a mechanism for RNA modification (and editing?). Bioorg Chem. Jun. 2005;33(3):229-51. doi: 10.1016/j.bioorg.2005.01.001. Epub Feb. 23, 2005.
Gearing, Addgene blog. CRISPR 101: Cas9 nickase design and homology directed repair. 2018. pp. 1-12. https://blog.addgene.org/crispr-101-cas9-nickase-design-and-homlogy-directed-repair. Last retrieved online Jun. 25, 2021.
GENBANK Submission; NIH/NCBI, Accession No. BDB43378. Zhang et al., Aug. 11, 2016. 2 pages.
GENBANK Submission; NIH/NCBI, Accession No. KR710351.1. Sahni et al., Jun. 1, 2015. 2 pages.
GENBANK Submission; NIH/NCBI, Accession No. NM_002945.3. Weiser et al., Sep. 3, 2017. 5 pages.
GENBANK Submission; NIH/NCBI, Accession No. NM 002947.4. Xiao et al., May 1, 2019. 4 pages.
GENBANK Submission; NIH/NCBI, Accession No. NP_358988.1. Hoskins et al., Jan. 11, 2017. 2 pages.
GENBANK Submission; NIH/NCBI, Accession No. NP_628093.1. Hsiao et al., Aug. 3, 2016. 2 pages.
GENBANK Submission; NIH/NCBI, Accession No. YP_009137104.1. Davison, Aug. 13, 2018. 2 pages.
Gibson et al., Enzymatic assembly of DNA molecules up to several hundred kilobases. Nat Methods. May 2009;6(5):343-5. doi: 10.1038/nmeth.l318. Epub Apr. 12, 2009.

(56) References Cited

OTHER PUBLICATIONS

Goldberg et al., Loss-of-function mutations in the Nav1.7 gene underlie congenital indifference to pain in multiple human populations. Clin Genet. Apr. 2007;71(4):311-9. doi: 10.1111/j.1399-0004.2007.00790.X.
Gordley et al., Evolution of programmable zinc finger-recombinases with activity in human cells. J Mol Biol. Mar. 30, 2007;367(3):802-13. Epub Jan. 12, 2007.
Gordley et al., Synthesis of programmable integrases. Proc Natl Acad Sci U S A. Mar. 31, 2009;106(13):5053-8. doi: 10.1073/pnas.0812502106. Epub Mar. 12, 2009.
Groth et al., Phage integrases: biology and applications. J Mol Biol. Jan. 16, 2004;335(3):667-78.
Gruber et al., The Vienna RNA websuite. Nucleic Acids Res. Jul. 1, 2008;36(Web Server issue):W70-4. doi: 10.1093/nar/gkn188. Epub Apr. 19, 2008.
Gumulya et al., Exploring the past and the future of protein evolution with ancestral sequence reconstruction: the 'retro' approach to protein engineering. Biochem J. Jan. 1, 2017;474(1):1-19. doi: 10.1042/BCJ20160507.
Guo et al., Structure of Cre recombinase complexed with DNA in a site-specific recombination synapse. Nature. Sep. 4, 1997;389(6646):40-6.
Halperin et al., CRISPR-guided DNA polymerases enable diversification of all nucleotides in a tunable window. Nature. Aug. 2018;560(7717):248-252. doi: 10.1038/s41586-018-0384-8. Epub Aug. 1, 2018.
Hartung et al., Cre mutants with altered DNA binding properties. J Biol Chem. Sep. 4, 1998;273(36):22884-91.
Hirano et al., Site-specific recombinases as tools for heterologous gene integration. Appl Microbiol Biotechnol. Oct. 2011;92(2):227-39. doi: 10.1007/s00253-011-3519-5. Epub Aug. 7, 2011. Review.
Holt et al., Human hematopoietic stem/progenitor cells modified by zinc-finger nucleases targeted to CCR5 control HIV-1 in vivo. Nat Biotechnol. Aug. 2010;28(8):839-47. doi: 10.1038/nbt.1663. Epub Jul. 2, 2010.
Hoogenboom et al., Natural and designer binding sites made by phage display technology. Immunol Today. Aug. 2000;21(8):371-8.
Hotta et al., [Neurotropic viruses—classification, structure and characteristics]. Nihon Rinsho. Apr. 1997;55(4):777-82. Japanese.
Housden et al., Identification of potential drug targets for tuberous sclerosis complex by synthetic screens combining CRISPR-based knockouts with RNAi. Sci Signal. Sep. 8, 2015;8(393):rs9. doi: 10.1126/scisignal.aab3729.
Hu et al., Evolved Cas9 variants with broad PAM compatibility and high DNA specificity. Nature. Apr. 5, 2018;556(7699):57-63 and Extended/Supplementary Data, doi: 10.1038/nature26155. Epub Feb. 28, 2018. 21 pages.
Ibba et al., Relaxing the substrate specificity of an aminoacyl-tRNA synthetase allows in vitro and in vivo synthesis of proteins containing unnatural amino acids. FEBS Lett. May 15, 1995;364(3):272-5.
Irion et al., Identification and targeting of the ROSA26 locus in human embryonic stem cells. Nat Biotechnol. Dec. 2007;25(12):1477-82. doi: 10.1038/nbt1362. Epub Nov. 25, 2007.
Jemiflity et al., Novel "anti-reverse" cap analogs with superior translational properties. RNA. Sep. 2003;9(9):1108-22. doi: 10.1261/rna.5430403.
Kay et al., Viral vectors for gene therapy: the art of turning infectious agents into vehicles of therapeutics. Nat Med. Jan. 2001;7(1):33-40.
Keravala et al., A diversity of serine phage integrases mediate site-specific recombination in mammalian cells. Mol Genet Genomics. Aug. 2006;276(2): 135-46. doi: 10.1007/s00438-006-0129-5. Epub May 13, 2006.
Kilbride et al., Determinants of product topology in a hybrid Cre-Tn3 resolvase site-specific recombination system. J Mol Biol. Jan. 13, 2006;355(2):185-95. Epub Nov. 9, 2005.
Kim et al., In vivo genome editing with a small Cas9 orthologue derived from Campylobacter jejuni. Nat Commun. Feb. 21, 2017;8:14500. doi: 10.1038/ncomms 14500. PMID: 28220790; PMCID: PMC5473640.
Kim et al., Rescue of high-specificity Cas9 variants using sgRNAs with matched 5' nucleotides. Genome Biol. Nov. 15, 2017;18(1):218. doi: 10.1186/s13059-017-1355-3.
Kleinstiver et al., Engineered CRISPR-Cas9 nucleases with altered PAM specificities. Nature. Jul. 23, 2015;523(7561):481-5 and Supplementary Materials, doi: 10.1038/nature14592. Epub Jun. 22, 2015. 27 pages.
Kolot et al., Site promiscuity of coliphage HK022 integrase as a tool for gene therapy. Gene Ther. Jul. 2015;22(7):521-7. doi: 10.1038/gt.2015.9. Epub Mar. 12, 2015.
Lancaster et al., Limited trafficking of a neurotropic virus through inefficient retrograde axonal transport and the type I interferon response. PLoS Pathog. Mar. 5, 2010;6(3):e1000791. doi: 10.1371/journal.ppat.1000791.
Lazarevic et al., Nucleotide sequence of the Bacillus subtilis temperate bacteriophage SPbetac2. Microbiology (Reading). May 1999;145 ( Pt 5):1055-1067. doi: 10.1099/13500872-145-5-1055.
Leipold et al., A de novo gain-of-function mutation in SCN11A causes loss of pain perception. Nat Genet. Nov. 2013;45(11):1399-404. doi: 10.1038/ng.2767. Epub Sep. 15, 2013.
Lim et al., Viral vectors for neurotrophic factor delivery: a gene therapy approach for neurodegenerative diseases of the CNS. Pharmacol Res. Jan. 2010;61(1):14-26. doi: 10.1016/j.phrs.2009.10.002. Epub Oct. 17, 2009.
Liu et al., Direct Promoter Repression by BCL11A Controls the Fetal to Adult Hemoglobin Switch. Cell. Apr. 5, 2018;173(2):430-442.e17. doi: 10.1016/j.cell.2018.03.016. Epub Mar. 29, 2018.
Lynch, Evolution of the mutation rate. Trends Genet. Aug. 2010;26(8):345-52. doi: 10.1016/j.tig.2010.05.003. Epub Jun. 30, 2010.
Maizels et al., Initiation of homologous recombination at DNA nicks. Nucleic Acids Res. Aug. 21, 2018;46(14):6962-6973. doi: 10.1093/nar/gky588.
McInerney et al., Error Rate Comparison during Polymerase Chain Reaction by DNA Polymerase. Mol Biol Int. 2014;2014:287430. doi: 10.1155/2014/287430. Epub Aug. 17, 2014.
Menéndez-Arias, Mutation rates and intrinsic fidelity of retroviral reverse transcriptases. Viruses. Dec. 1, 2009;(3):1137-65. doi: 10.3390/vl031137. Epub Dec. 4, 2009.
Mir et al., Type II-C CRISPR-Cas9 Biology, Mechanism, and Application. ACS Chem Biol. Feb. 16, 2018;13(2):357-365. doi: 10.1021/acschembio.7b00855. Epub Dec. 20, 2017.
Moede et al., Identification of a nuclear localization signal, RRMKWKK, in the homeodomain transcription factor PDX-1. FEBS Lett. Nov. 19, 1999;461(3):229-34. doi: 10.1016/s0014-5793(99)01446-5.
Moreno-Mateos et al., CRISPRscan: designing highly efficient sgRNAs for CRISPR-Cas9 targeting in vivo. Nat Methods. Oct. 2015;12(10):982-8. doi: 10.1038/nmeth.3543. Epub Aug. 31, 2015.
Mougiakos et al., Characterizing a thermostable Cas9 for bacterial genome editing and silencing. Nat Commun. Nov. 21, 2017;8(1):1647. doi: 10.1038/s41467-017-01591-4.
Murphy, Phage recombinases and their applications. Adv Virus Res. 2012;83:367-414. doi: 10.1016/B978-0-12-394438-2.00008-6. Review.
Olivares et al., Site-specific genomic integration produces therapeutic Factor IX levels in mice. Nat Biotechnol. Nov. 2002;20(11):1124-8. doi: 10.1038/nbt753. Epub Oct. 15, 2002.
Olorunniji et al., Synapsis and catalysis by activated Tn3 resolvase mutants. Nucleic Acids Res. Dec. 2008;36(22):7181-91. doi: 10.1093/nar/gkn885. Epub Nov. 10, 2008.
Raghavan et al., Abstract 27: Therapeutic Targeting of Human Lipid Genes with in vivo CRISPR-Cas9 Genome Editing. Oral Abstract Presentations: Lipoprotein Metabolism and Therapeutic Targets. Arterioscler THromb Vase Biol. 2015;35(Suppl. 1):Abstract 27. 5 pages.
Relph et al., Recent developments and current status of gene therapy using viral vectors in the United Kingdom. BMJ. 2004;329(7470):839-842. doi:10.1136/bmj.329.7470.839.
Reynaud et al., What role for AID: mutator, or assembler of the immunoglobulin mutasome? Nat Immunol. Jul. 2003;4(7):631-8.

(56) References Cited

OTHER PUBLICATIONS

Rongrong et al., Effect of deletion mutation on the recombination activity of Cre recombinase. Acta Biochim Pol. 2005;52(2):541-4. Epub May 15, 2005.
Sapunar et al., Dorsal root ganglion—a potential new therapeutic target for neuropathic pain. J Pain Res. 2012;5:31-8. doi: 10.2147/JPR.S26603. Epub Feb. 16, 2012.
Score Results for Luetticken et al., Complete genome sequence of a *Streptococcus dysgalactiae* subsp. RT equisimilis strain possessing Lancefield's group A antigen. RL Submitted to the EMBL/GenBank/DDBJ databases. May 2012. 3 pages.
Score Results for Okumura et al., Evolutionary paths of streptococcal and staphylococcal superantigens. RL BMC Genomics. 2012;13:404-404. 3 pages.
Score Results for Shimomura et al., Complete Genome Sequencing and Analysis of a Lancefield Group G RT *Streptococcus dysagalactiae* Subsp. Equisimilis Strain Causing Streptococcal RT Toxic Shock Syndrome (STSS). RL BMC Genomics. 2011;12:17-17. 3 pages.
Shaikh et al., Chimeras of the Flp and Cre recombinases: tests of the mode of cleavage by Flp and Cre. J Mol Biol. Sep. 8, 2000;302(1):27-48.
Shen et al., Herpes simplex virus 1 (HSV-1) for cancer treatment. Cancer Gene Ther. Nov. 2006;13(11):975-92. doi: 10.1038/sj.cgt.7700946. Epub Apr. 7, 2006.
Singh et al., Real-time observation of DNA target interrogation and product release by the RNA-guided endonuclease CRISPR Cpf1 (Cas12a). Proc Natl Acad Sci U S A. May 22, 2018;115(21):5444-5449. doi: 10.1073/pnas.1718686115. Epub May 7, 2018.
Siu et al., Riboregulated toehold-gated gRNA for programmable CRISPR-Cas9 function. Nat Chem Biol. Mar. 2019;15(3):217-220. doi: 10.1038/s41589-018-01861. Epub Dec. 10, 2018.
Smith et al., Diversity in the serine recombinases. Mol Microbiol. Apr. 2002;44(2):299-307. Review.
Smith et al., Herpesvirus transport to the nervous system and back again. Annu Rev Microbiol. 2012;66:153-76. doi: 10.1146/annurev-micro-092611-150051. Epub Jun. 15, 2012.
Somanathan et al., AAV vectors expressing LDLR gain-of-function variants demonstrate increased efficacy in mouse models of familial hypercholesterolemia. Circ Res. Aug. 29, 2014;115(6):591-9. doi: 10.1161/CIRCRESAHA.115.304008. Epub Jul. 14, 2014.
Steiner et al., The neurotropic herpes viruses: herpes simplex and varicella-zoster. Lancet Neurol. Nov. 2007;6(11):1015-28. doi: 10.1016/S1474-4422(07)70267-3.
Strecker et al., Engineering of CRISPR-Cas12b for human genome editing. Nat Commun. Jan. 22, 2019;10(1):212. doi: 10.1038/s41467-018-08224-4.
Su et al., Human DNA polymerase η has reverse transcriptase activity in cellular environments. J Biol Chem. Apr. 12, 2019;294(15):6073-6081. doi: 10.1074/jbc.RA119.007925. Epub Mar. 6, 2019.
Tambunan et al., Vaccine Design for H5N1 Based on B- and T-cell Epitope Predictions. Bioinform Biol Insights. Apr. 28, 2016;10:27-35. doi: 10.4137/BBI.S38378.
Teng et al., Mutational analysis of apolipoprotein B mRNA editing enzyme (APOBEC1). structure-function relationships of RNA editing and dimerization. J Lipid Res. Apr. 1999;40(4):623-35.
Tone et al., Single-stranded DNA binding protein Gp5 of Bacillus subtilis phage ?29 is required for viral DNA replication in growth-temperature dependent fashion. Biosci Biotechnol Biochem. 2012;76(12):2351-3. doi: 10.1271/bbb.120587. Epub Dec. 7, 2012.
UNIPROTKB Submission; Accession No. F0NN87. May 3, 2011. 4 pages.
Venken et al., Genome-wide manipulations of *Drosophila melanogaster* with transposons, Flp recombinase, and ΦC31 integrase. Methods Mol Biol. 2012;859:203-28. doi: 10.1007/978-1-61779-603-6_12.
Wang et al., Optimized paired-sgRNA/Cas9 cloning and expression cassette triggers high-efficiency multiplex genome editing in kiwifruit. Plant Biotechnol J. Aug. 2018;16(8):1424-1433. doi: 10.1111/pbi.12884. Epub Feb. 6, 2018.
Weiss et al., Loss-of-function mutations in sodium channel Nav1.7 cause anosmia. Nature. Apr. 14, 2011;472(7342):186-90. doi: 10.1038/nature09975. Epub Mar. 23, 2011.
Woods et al., The phenotype of congenital insensitivity to pain due to the NaV1.9 variant p.L811P. Eur J Hum Genet. May 2015;23(5):561-3. doi: 10.1038/ejhg.2014.166. Epub Aug. 13, 2014.
Yamada et al., Crystal Structure of the Minimal Cas9 from Campylobacter jejuni Reveals the Molecular Diversity in the CRISPR-Cas9 Systems. Mol Cell. Mar. 16, 2017;65(6):P1109-1121./doi.org/10.1016/j .molcel.2017.02.007.
Yan et al., Functionally diverse type V CRISPR-Cas systems. Science. Jan. 4, 2019;363(6422):88-91. doi: 10.1126/science.aav7271. Epub Dec. 6, 2018.
Yang et al., Mutations in SCN9A, encoding a sodium channel alpha subunit, in patients with primary erythermalgia. J Med Genet. Mar. 2004;41(3):171-4. doi: 10.1136/jmg.2003.012153.
Yang, Development of Human Genome Editing Tools for the Study of Genetic Variations and Gene Therapies. Doctoral Dissertation. Harvard University. 2013. Accessible via nrs.harvard.edu/urn-3:HUL.InstRepos:11181072. 277 pages.
Yokoe et al., Spatial dynamics of GFP-tagged proteins investigated by local fluorescence enhancement. Nat Biotechnol. Oct. 1996;14(10):1252-6. doi: 10.1038/nbt1096-1252.
Zhao et al., Crystal structures of a group II intron maturase reveal a missing link in spliceosome evolution. Nat Struct Mol Biol. Jun. 2016;23(6):558-65. doi: 10.1038/nsmb.3224. Epub May 2, 2016.
Zhou et al., Protective V127 prion variant prevents prion disease by interrupting the formation of dimer and fibril from molecular dynamics simulations. Sci Rep. Feb. 24, 2016;6:21804. doi: 10.1038/srep21804.
[No Author Listed], "Lambda DNA" from Catalog & Technical Reference. New England Biolabs Inc. 2002/2003. pp. 133 and 270-273.
[No Author Listed], Mus musculus (Mouse). UniProtKB Accession No. P51908 (ABEC1_MOUSE). Oct. 1, 1996. 10pages.
Asokan et al., The AAV vector toolkit: poised at the clinical crossroads. Mol Ther. Apr. 2012;20(4):699-708. doi: 10.1038/mt.2011.287. Epub Jan. 24, 2012.
Auricchio et al., Exchange of surface proteins impacts on viral vector cellular specificity and transduction characteristics: the retina as a model. Hum Mol Genet. Dec. 15, 2001;10(26):3075-81. doi: 10.1093/hmg/10.26.3075.
Baba et al., Construction of *Escherichia coli* K-12 in-frame, single-gene knockout mutants: the Keio collection. Mol Syst Biol. 2006;2:2006.0008. doi: 10.1038/msb4100050. Epub Feb. 21, 2006.
Badran et al., In vivo continuous directed evolution. Curr Opin Chem Biol. Feb. 2015;24:1-10. doi: 10.1016/j.cbpa.2014.09.040. Epub Nov. 7, 2014.
Bae et al., Cas-OFFinder: a fast and versatile algorithm that searches for potential off-target sites of Cas9 RNA-guided endonucleases. Bioinformatics. May 15, 2014;30(10):1473-5. doi: 10.1093/bioinformatics/btu048. Epub Jan. 24, 2014.
Bagal et al., Recent progress in sodium channel modulators for pain. Bioorg Med Chem Lett. Aug. 15, 2014;24(16):3690-9. doi: 10.1016/j.bmcl.2014.06.038. Epub Jun. 21, 2014.
Banno et al., Deaminase-mediated multiplex genome editing in *Escherichia coli*. Nat Microbiol. Apr. 2018;3(4):423-429. doi: 10.1038/s41564-017-0102-6. Epub Feb. 5, 2018.
Barmania et al., C-C chemokine receptor type five (CCR5): An emerging target for the control of HIV infection. Appl Transl Genom. May 26, 2013;2:3-16. doi: 10.1016/j.atg.2013.05.004.
Bass, B.L., RNA editing by adenosine deaminases that act on RNA. Annu Rev Biochem. 2002;71:817-46. doi: 10.1146/annurev.biochem.71.110601.135501. Epub Nov. 9, 2001.
Beaudry et al., Directed evolution of an RNA enzyme. Science. Jul. 31, 1992;257(5070):635-41. doi: 10.1126/science.1496376.
Bell et al., Ribozyme-catalyzed excision of targeted sequences from within RNAs. Biochemistry. Dec. 24, 2002;41(51):15327-33. doi: 10.1021/bi0267386.
Bentin, T., A ribozyme transcribed by a ribozyme. Artif DNA PNA XNA. Apr. 2011;2(2):40-42. doi: 10.4161/adna.2.2.16852.

(56) References Cited

OTHER PUBLICATIONS

Blauw et al., SMN1 gene duplications are associated with sporadic ALS. Neurology. Mar. 13, 2012;78(11):776-80. doi: 10.1212/WNL.0b013e318249f697. Epub Feb. 8, 2012.
Bothmer et al., Characterization of the interplay between DNA repair and CRISPR/Cas9-induced DNA lesions at an endogenous locus. Nat Commun. Jan. 9, 2017;8:13905. doi: 10.1038/ncomms13905.
Brierley et al., Viral RNA pseudoknots: versatile motifs in gene expression and replication. Nat Rev Microbiol. Aug. 2007;5(8):598-610. doi: 10.1038/nrmicro1704.
Butt et al., Efficient CRISPR/Cas9-Mediated Genome Editing Using a Chimeric Single-Guide RNA Molecule. Front Plant Sci. Aug. 24, 2017;8:1441(1-8). doi: 10.3389/fpls.2017.01441.
Canny et al., Inhibition of 53BP1 Favors Homology-Dependent DNA Repair and Increases CRISPR-Cas9 Genome-Editing Efficiency. Nat Biotechnol. Jan. 2018;36(1):95-102. doi: 10.1038/nbt.4021. Epub Nov. 27, 2017.
Cao et al., Rapamycin reverses cellular phenotypes and enhances mutant protein clearance in Hutchinson-Gilford progeria syndrome cells. Sci Transl Med. Jun. 29, 2011;3(89):89ra58. doi: 10.1126/scitranslmed.3002346.
Cartegni et al., Determinants of exon 7 splicing in the spinal muscular atrophy genes, SMN1 and SMN2. Am J Hum Genet. Jan. 2006;78(1):63-77. doi: 10.1086/498853. Epub Nov. 16, 2005.
Chang et al., Degradation of survival motor neuron (SMN) protein is mediated via the ubiquitin/proteasome pathway. Neurochem Int. Dec. 2004;45(7):1107-12. doi: 10.1016/j.neuint.2004.04.005.
Chatterjee et al., Robust Genome Editing of Single-Base PAM Targets; with Engineered ScCas9 Variants. bioRxiv. doi: 10.1101/620351. Posted Apr. 26, 2019.
Chawla et al., An atlas of RNA base pairs involving modified nucleobases with optimal geometries and accurate energies. Nucleic Acids Res. Aug. 18, 2015;43(14):6714-29. doi: 10.1093/nar/gkv606. Epub Jun. 27, 2015.
Chen et al., Alterations in PMS2, MSH2 and MLH1 expression in human prostate cancer. Int J Oncol. May 2003;22(5):1033-43.
Chen et al., Targeting genomic rearrangements in tumor cells through Cas9-mediated insertion of a suicide gene. Nat Biotechnol. Jun. 2017;35(6):543-550. doi: 10.1038/nbt.3843. Epub May 1, 2017.
Cho et al., A degron created by SMN2 exon 7 skipping is a principal contributor to spinal muscular atrophy severity. Genes Dev. Mar. 1, 2010;24(5):438-42. doi: 10.1101/gad.1884910.
Choudhury et al., CRISPR-dCas9 mediated TET1 targeting for selective DNA demethylation at BRCA1 promoter. Oncotarget. Jul. 19, 2016;7(29):46545-46556. doi: 10.18632/oncotarget.10234.
Corcia et al., The importance of the SMN genes in the genetics of sporadic ALS. Amyotroph Lateral Scler. Oct.-Dec. 2009;10(5-6):436-40. doi: 10.3109/17482960902759162.
Corti et al., Genetic correction of human induced pluripotent stem cells from patients with spinal muscular atrophy. Sci Transl Med. Dec. 19, 2012;4(165):165ra162. doi: 10.1126/scitranslmed.3004108.
Cucchiarini et al., Enhanced expression of the central survival of motor neuron (SMN) protein during the pathogenesis of osteoarthritis. J Cell Mol Med. Jan. 2014;18(1):115-24. doi: 10.1111/jcmm. 12170. Epub Nov. 17, 2013.
D'Ydewalle et al., The Antisense Transcript SMN-AS1 Regulates SMN Expression and is a Novel Therapeutic Target for Spinal Muscular Atrophy. Neuron. Jan. 4, 2017;93(1):66-79 and Supplemental Information, doi: 10.1016/j.neuron.2016.11.033. Epub Dec. 22, 2016.
Davis et al., Assaying Repair at DNA Nicks. Methods Enzymol. 2018;601:71-89. doi: 10.1016/bs.mie.2017.12.001. Epub Feb. 1, 2018.
Davis et al., Homology-directed repair of DNA nicks via pathways distinct from canonical double-strand break repair. Proc Natl Acad Sci U S A. Mar. 11, 2014;111(10):E924-32. doi: 10.1073/pnas.1400236111. Epub Feb. 20, 2014.
Davis et al., Two Distinct Pathways Support Gene Correction by Single-Stranded Donors at DNA Nicks. Cell Rep. Nov. 8, 2016;17(7):1872-1881. doi: 10.1016/j.celrep.2016.10.049.
De La Peña et al., The Hammerhead Ribozyme: A Long History for a Short RNA. Molecules. Jan. 4, 2017;22(1):78. doi: 10.3390/molecules22010078.
De Sandre-Giovannoli et al., Lamin a truncation in Hutchinson-Gilford progeria. Science. Jun. 27, 2003;300(5628):2055. doi: 10.1126/science.1084125. Epub Apr. 17, 2003.
Denizio et al., Harnessing natural DNA modifying activities for editing of the genome and epigenome. Curr Opin Chem Biol. Aug. 2018;45:10-17. doi: 10.1016/j.cbpa.2018.01.016. Epub Feb. 13, 2018.
Dolan et al., Trans-splicing with the group I intron ribozyme from Azoarcus. RNA. Feb. 2014;20(2):202-13. doi: 10.1261/rna.041012.113. Epub Dec. 16, 2013.
Drost et al., Inactivation of DNA mismatch repair by variants of uncertain significance in the PMS2 gene. Hum Mutat. Nov. 2013;34(11):1477-80. doi: 10.1002/humu.22426. Epub Sep. 11, 2013.
Duan et al., Enhancement of muscle gene delivery with pseudotyped adeno-associated virus type 5 correlates with myoblast differentiation. J Virol. Aug. 2001;75(16):7662-71. doi: 10.1128/JVI.75.16.7662-7671.2001.
Dugar et al., CRISPR RNA-Dependent Binding and Cleavage of Endogenous RNAs by the Campylobacter jejuni Cas9. Mol Cell. Mar. 1, 2018;69(5):893-905.e7. doi: 10.1016/j.molcel.2018.01.032.
Eisenberg et al., A-to-I RNA editing—immune protector and transcriptome diversifier. Nat Rev Genet. Aug. 2018;19(8):473-490. doi: 10.1038/s41576-018-0006-1.
Friedman, J. H., Greedy function approximation: A gradient boosting machine. Ann. Statist. Oct. 2001;29(5):1189-232. doi: 10.1214/aos/1013203451.
Gangopadhyay et al., Precision Control of CRISPR-Cas9 Using Small Molecules and Light. Biochemistry. Jan. 29, 2019;58(4):234-244. doi: 10.1021/acs.biochem.8b01202. Epub Jan. 22, 2019.
GENBANK Submission; NIH/NCBI Accession No. 4UN5_B. Anders et al., Jul. 23, 2014. 5 pages.
GENBANK Submission; NIH/NCBI, Accession No. AIT42264.1. Hyun et al., Oct. 15, 2014. 2 pages.
GENBANK Submission; NIH/NCBI, Accession No. AKA60242.1. Tong et al., Apr. 5, 2015. 1 page.
GENBANK Submission; NIH/NCBI, Accession No. AKQ21048.1. Gilles et al., Jul. 19, 2015. 1 page.
GENBANK Submission; NIH/NCBI, Accession No. AKS40380.1. Nodvig et al., Aug. 2, 2015. 1 page.
GENBANK Submission; NIH/NCBI, Accession No. NG_008692.2. McClintock et al., Aug. 27, 2018. 33 pages.
GENBANK Submission; NIH/NCBI, Accession No. NP_001075493.1. Schiaffella et al., Jun. 24, 2018. 2 pages.
GENBANK Submission; NIH/NCBI, Accession No. NP_001157741.1. Zeng et al., Sep. 17, 2018. 3 pages.
GENBANK Submission; NIH/NCBI, Accession No. NP_001157742.1. Zeng et al., Oct. 21, 2018. 3 pages.
GENBANK Submission; NIH/NCBI, Accession No. NP_033040.2. Liu et al., Jun. 23, 2018. 2 pages.
GENBANK Submission; NIH/NCBI, Accession No. WP_002989955.1. No Author Listed, May 6, 2013. 1 page.
GENBANK Submission; NIH/NCBI, Accession No. WP_010922251.1. No Author Listed, May 15, 2013. 1 page.
GENBANK Submission; NIH/NCBI, Accession No. WP_011054416.1. No Author Listed, May 15, 2013. 1 page.
GENBANK Submission; NIH/NCBI, Accession No. WP_011284745.1. No Author Listed, May 16, 2013. 1 page.
GENBANK Submission; NIH/NCBI, Accession No. WP_011285506.1. No Author Listed, May 16, 2013. 1 page.
GENBANK Submission; NIH/NCBI, Accession No. WP_011527619.1. No Author Listed, May 16, 2013. 1 page.
GENBANK Submission; NIH/NCBI, Accession No. WP_012560673.1. No Author Listed, May 17, 2013. 1 page.
GENBANK Submission; NIH/NCBI, Accession No. WP_014407541.1. No Author Listed, May 18, 2013. 1 page.

(56) References Cited

OTHER PUBLICATIONS

GENBANK Submission; NIH/NCBI, Accession No. WP_020905136. 1. No Author Listed, Jul. 25, 2013. 1 page.
GENBANK Submission; NIH/NCBI, Accession No. WP_023080005. 1. No Author Listed, Oct. 27, 2013. 1 page.
GENBANK Submission; NIH/NCBI, Accession No. WP_023610282. 1. No Author Listed, Nov. 27, 2013. 1 page.
GENBANK Submission; NIH/NCBI, Accession No. WP_030125963. 1. No Author Listed, Jul. 9, 2014. 1 page.
GENBANK Submission; NIH/NCBI, Accession No. WP_030126706. 1. No Author Listed, Jul. 9, 2014. 1 page.
GENBANK Submission; NIH/NCBI, Accession No. WP_031488318. 1. No Author Listed., Aug. 5, 2014. 1 page.
GENBANK Submission; NIH/NCBI, Accession No. WP_032460140. 1. No Author Listed, Oct. 4, 2014. 1 page.
GENBANK Submission; NIH/NCBI, Accession No. WP_032461047. 1. No Author Listed, Oct. 4, 2014. 1 page.
GENBANK Submission; NIH/NCBI, Accession No. WP_032462016. 1. Haft et al., Oct. 4, 2014. 1 page.
GENBANK Submission; NIH/NCBI, Accession No. WP_032462936. 1. No Author Listed, Oct. 4, 2014. 1 page.
GENBANK Submission; NIH/NCBI, Accession No. WP_032464890. 1. No Author Listed, Oct. 4, 2014. 1 page.
GENBANK Submission; NIH/NCBI, Accession No. WP_038431314. 1. No Author Listed, Dec. 26, 2014. 1 page.
GENBANK Submission; NIH/NCBI, Accession No. WP_038432938. 1. No Author Listed, Dec. 26, 2014. 1 page.
GENBANK Submission; NIH/NCBI, Accession No. WP_038434062. 1. No Author Listed, Dec. 26, 2014. 1 page.
GENBANK Submission; NIH/NCBI, Accession No. WP_048327215. 1. No Author Listed, Jun. 26, 2015. 1 page.
GENBANK Submission; NIH/NCBI, Accession No. WP_049519324. 1. No Author Listed, Jul. 20, 2015. 1 page.
GENBANK Submission; NIH/NCBI, Accession No. XP_003314669. 1. No Author Listed, Mar. 20, 2018. 2 pages.
GENBANK Submission; NIH/NCBI, Accession No. XP_026671085. 1. No Author Listed, Oct. 17, 2018. 1 page.
Guedon et al., Current gene therapy using viral vectors for chronic pain. Mol Pain. May 13, 2015;11:27. doi: 10.1186/s12990-015-0018-1.
Guo et al., Evolution of Tetrahymenaribozyme mutants with increased structural stability. Nat Struct Biol. Nov. 2002;9(11):855-61. doi: 10.1038/nsb850.
Gutschner et al., Post-translational Regulation of Cas9 during G1 Enhances Homology-Directed Repair. Cell Rep. Feb. 16, 2016;14(6):1555-1566. doi: 10.1016/j.celrep.2016.01.019. Epub Feb. 4, 2016.
Halbert et al., Repeat transduction in the mouse lung by using adeno-associated virus vectors with different serotypes. J Virol. Feb. 2000;74(3):1524-32. doi: 10.1128/jvi.74.3.1524-1532.2000.
Hardt et al.,Missense variants in hMLH1 identified in patients from the German HNPCC consortium and functional studies. Fam Cancer. Jun. 2011;10(2):273-84. doi: 10.1007/s10689-011-9431-4.
Harmsen et al., DNA mismatch repair and oligonucleotide end-protection promote base-pair substitution distal from a CRISPR/Cas9-induced DNA break. Nucleic Acids Res. Apr. 6, 2018;46(6):2945-2955. doi: 10.1093/nar/gky076.
Harrington et al., Programmed DNA destruction by miniature CRISPR-Cas14 enzymes. Science. Nov. 16, 2018;362(6416):839-842. doi: 10.1126/science.aav4294. Epub Oct. 18, 2018.
Hart et al., High-Resolution CRISPR Screens Reveal Fitness Genes and Genotype-Specific Cancer Liabilities. Cell. Dec. 3, 2015;163(6):1515-26. doi: 10.1016/j.cell.2015.11.015. Epub Nov. 25, 2015.
Hilbers et al., New developments in structure determination of pseudoknots. Biopolymers. 1998;48(2-3):137-53. doi: 10.1002/(SICI)1097-0282(1998)48:2<137::AID-BIP4>3.0.CO;2-H.
Hua et al., Expanding the base editing scope in rice by using Cas9 variants. Plant Biotechnol J. Feb. 2019;17(2):499-504. doi: 10.1111/pbi.12993. Epub Oct. 5, 2018.
Hua et al., Precise A•T to G•C Base Editing in the Rice Genome. Mol Plant. Apr. 2, 2018;11(4):627-630. doi: 10.1016/j.molp.2018.02.007. Epub Feb. 21, 2018.
Isaacs et al., Engineered riboregulators enable post-transcriptional control of gene expression. Nat Biotechnol. Jul. 2004;22(7):841-7. doi: 10.1038/nbt986. Epub Jun. 20, 2004.
Ishizuka et al., Loss of ADAR1 in tumours overcomes resistance to immune checkpoint blockade. Nature. Jan. 2019;565(7737):43-48. doi: 10.1038/s41586-018-0768-9. Epub Dec. 17, 2018.
Iyama et al., DNA repair mechanisms in dividing and non-dividing cells. DNA Repair (Amst). Aug. 2013;12(8):620-36. doi: 10.1016/j.dnarep.2013.04.015. Epub May 16, 2013.
Jia et al., The MLH1 A'lPase domain is needed for suppressing aberrant formation of interstitial telomeric sequences. DNA Repair (Amst). May 2018;65:20-25. doi: 10.1016/j.dnarep.2018.03.002. Epub Mar. 7, 2018.
Johnson et al., Trans insertion-splicing: ribozyme-catalyzed insertion of targeted sequences into RNAs. Biochemistry. Aug. 9, 2005;44(31):10702-10. doi: 10.1021/bi0504815.
Kan et al., Mechanisms of precise genome editing using oligonucleotide donors. Genome Res. Jul. 2017;27(7):1099-1111. doi: 10.1101/gr.214775.116. Epub Mar. 29, 2017.
Kang et al., Precision genome engineering through adenine base editing in plants. Nat Plants. Jul. 2018;4(7):427-431. doi: 10.1038/s41477-018-0178-x. Epub Jun. 4, 2018. Erratum in: Nat Plants. Sep. 2018;4(9):730.
Kim et al., RAD51 mutants cause replication defects and chromosomal instability. Mol Cell Biol. Sep. 2012;32(18):3663-80. doi: 10.1128/MCB.00406-12. Epub Jul. 9, 2012.
King et al., No gain, no pain: NaV1.7 as an analgesic target. ACS Chem Neurosci. Sep. 17, 2014;5(9):749-51. doi: 10.1021/cn500171p. Epub Aug. 1, 2014.
Knott et al., CRISPR-Cas guides the future of genetic engineering. Science. Aug. 31, 2018;361(6405):866-869. doi: 10.1126/science.aat5011.
Kumar et al., Gene therapy for chronic neuropathic pain: how does it work and where do we stand today? Pain Med. May 2011;12(5):808-22. doi: 10.1111/j.1526-4637.2011.01120.x.
Le et al., SMNDelta7, the major product of the centromeric survival motor neuron (SMN2) gene, extends survival in mice with spinal muscular atrophy and associates with full-length SMN. Hum Mol Genet. Mar. 15, 2005;14(6):845-57. doi: 10.1093/hmg/ddi078. Epub Feb. 9, 2005.
Lee et al., A monoclonal antibody that targets a NaV1.7 channel voltage sensor for pain and itch relief. Cell. Jun. 5, 2014;157(6):1393-1404. doi: 10.1016/j.cell.2014.03.064. Epub May 22, 2014. Retraction in: Cell. Jun. 25, 2020;181(7):1695.
Lefebvre et al., Identification and characterization of a spinal muscular atrophy-determining gene. Cell. Jan. 13, 1995;80(1):155-65. doi: 10.1016/0092-8674(95)90460-3.
Li et al., Programmable Single and Multiplex Base-Editing in Bombyx mori Using RNA-Guided Cytidine Deaminases. G3 (Bethesda). May 4, 2018;8(5):1701-1709. doi: 10.1534/g3.118.200134.
Liao et al., One-step assembly of large CRISPR arrays enables multi-functional targeting and reveals constraints on array design. bioRxiv. May 2, 2018. doi: 10.1101/312421. 45 pages.
Liefke et al., The oxidative demethylase ALKBH3 marks hyperactive gene promoters in human cancer cells. Genome Med. Jun. 30, 2015;7(1):66. doi: 10.1186/s13073-015-0180-0.
Lin et al., [Construction and evaluation of DnaB split intein high expression vector and a six amino acids cyclic peptide library]. Sheng Wu Gong Cheng Xue Bao. Nov. 2008;24(11):1924-30. Chinese.
Lindahl, T., Instability and decay of the primary structure of DNA. Nature. Apr. 22, 1993;362(6422):709-15. doi: 10.1038/362709a0.
Liu et al., Human BRCA2 protein promotes RAD51 filament formation on RPA-covered single-stranded DNA. Nat Struct Mol Biol. Oct. 2010;17(10):1260-2. doi: 10.1038/nsmb.1904. Epub Aug. 22, 2010.
Liu et al., Intrinsic Nucleotide Preference of Diversifying Base Editors Guides Antibody Ex Vivo Affinity Maturation. Cell Rep. Oct. 23, 2018;25(4):884-892.e3. doi: 10.1016/j.celrep.2018.09.090.

(56) References Cited

OTHER PUBLICATIONS

Lorson et al., A single nucleotide in the SMN gene regulates splicing and is responsible for spinal muscular atrophy. Proc Natl Acad Sci U S A. May 25, 1999;96(11):6307-11. doi: 10.1073/pnas.96.11.6307.

Lutz et al., Postsymptomatic restoration of SMN rescues the disease phenotype in a mouse model of severe spinal muscular atrophy. J Clin Invest. Aug. 2011;121(8):3029-41. doi: 10.1172/JCI57291. Epub Jul. 25, 2011.

Ma et al., Human RAD52 interactions with replication protein A and the RAD51 presynaptic complex. J Biol Chem. Jul. 14, 2017;292(28):11702-11713. doi: 10.1074/jbc.M117.794545. Epub May 27, 2017.

Madura et al., Structural basis for ineffective T-cell responses to MHC anchor residue-improved "heteroclitic" peptides. Eur J Immunol. Feb. 2015;45(2):584-91. doi: 10.1002/eji.201445114. Epub Dec. 28, 2014.

Marsden et al., The Tumor-Associated Variant RAD51 G151D Induces a HyperRecombination Phenotype. PLoS Genet. Aug. 11, 2016;12(8):e1006208. doi: 10.1371/journal.pgen.1006208.

Martz, L., Nav-i-gating antibodies for pain. Science-Business exchange. Jun. 12, 2014;7(662):1-2. doi: 10.1038/scibx.2014.662.

Mason et al., Non-enzymatic roles of human RAD51 at stalled replication forks. bioRxiv. Jul. 31, 2019; doi.org/10.1101/359380. 36 pages. bioRxiv preprint first posted online Jul. 31, 2019.

Mendell et al., Single-Dose Gene-Replacement Therapy for Spinal Muscular Atrophy. N Engl J Med. Nov. 2, 2017;377(18):1713-1722. doi: 10.1056/NEJMoa1706198.

Meyer et al., Ribosome biogenesis factor Tsr3 is the aminocarboxypropyl transferase responsible for 18S rRNA hypermodification in yeast and humans. Nucleic Acids Res. May 19, 2016;44(9):4304-16. doi: 10.1093/nar/gkw244. Epub Apr. 15, 2016.

Monani et al., A single nucleotide difference that alters splicing patterns distinguishes the SMA gene SMN1 from the copy gene SMN2. Hum Mol Genet. Jul. 1999;8(7): 1177-83. doi: 10.1093/hmg/8.7.1177.

Mootz et al., Protein splicing triggered by a small molecule. J Am Chem Soc. Aug. 7, 2002;124(31):9044-5 and Supporting Information, doi: 10.1021/ja026769o. 4 pages.

Muller, U.F., Design and Experimental Evolution of trans-Splicing Group I Intron Ribozymes. Molecules. Jan. 2, 2017;22(1):75. doi: 10.3390/molecules22010075.

Murray et al., Selective vulnerability of motor neurons and dissociation of pre- and post-synaptic pathology at the neuromuscular junction in mouse models of spinal muscular atrophy. Hum Mol Genet. Apr. 1, 2008;17(7):949-62. doi: 10.1093/hmg/ddm367. Epub Dec. 8, 2007.

Murugan et al., The Revolution Continues: Newly Discovered Systems Expand the CRISPR-Cas Toolkit. Mol Cell. Oct. 5, 2017;68(1):15-25. doi: 10.1016/j.molcel.2017.09.007.

Nelson et al., In vivo genome editing improves muscle function in a mouse model of Duchenne muscular dystrophy. Science. Jan. 22, 2016;351(6271):403-7. doi: 10.1126/science.aad5143. Epub Dec. 31, 2015.

Nelson et al., The unstable repeats—three evolving faces of neurological disease. Neuron. Mar. 6, 2013;77(5):825-43. doi: 10.1016/j.neuron.2013.02.022.

Noack et al., Epitranscriptomics: A New Regulatory Mechanism of Brain Development and Function. Front Neurosci. Feb. 20, 2018;12:85. doi: 10.3389/fnins.2018.00085. 9 pages.

Ottesen, ISS-N1 makes the First FDA-approved Drug for Spinal Muscular Atrophy. Transl Neurosci. Jan. 26, 2017;8:1-6. doi: 10.1515/tnsci-2017-0001.

Parente et al., Advances in spinal muscular atrophy therapeutics. Ther Adv Neurol Disord. Feb. 5, 2018;11:1756285618754501. doi: 10.1177/1756285618754501. 13 pages.

Passini et al., Antisense oligonucleotides delivered to the mouse CNS ameliorate symptoms of severe spinal muscular atrophy. Sci Transl Med. Mar. 2, 2011;3(72):72ra18. doi: 10.1126/scitranslmed.3001777.

Pellegrini et al., Insights into DNA recombination from the structure of a RAD51-BRCA2 complex. Nature. Nov. 21, 2002;420(6913):287-93. doi: 10.1038/nature01230. Epub Nov. 10, 2002.

Perez-Palma et al., Simple ClinVar: an interactive web server to explore and retrieve gene and disease variants aggregated in ClinVar database. Nucleic Acids Res. Jul. 2, 2019;47(W1):W99-W105. doi: 10.1093/nar/gkz411.

Perreault et al., Mixed deoxyribo- and ribo-oligonucleotides with catalytic activity. Nature. Apr. 5, 1990;344(6266):565-7. doi: 10.1038/344565a0.

Pieken et al., Kinetic characterization of ribonuclease-resistant 2'-modified hammerhead ribozymes. Science. Jul. 19, 1991;253(5017):314-7. doi: 10.1126/science.1857967.

Porensky et al., A single administration of morpholino antisense oligomer rescues spinal muscular atrophy in mouse. Hum Mol Genet. Apr. 1, 2012;21(7):1625-38. doi: 10.1093/hmg/ddr600. Epub Dec. 2, 2011.

Prasad et al., Visualizing the assembly of human Rad51 filaments on double-stranded DNA. J Mol Biol. Oct. 27, 2006;363(3):713-28. doi: 10.1016/j.jmb.2006.08.046. Epub Aug. 22, 2006.

Raillard et al., Targeting sites within HIV-1 cDNA with a DNA-cleaving ribozyme. Biochemistry. Sep. 10, 1996;35(36):11693-701. doi: 10.1021/bi960845g.

Rajagopal et al., High-throughput mapping of regulatory DNA. Nat Biotechnol. Feb. 2016;34(2):167-74. doi: 10.1038/nbt.3468. Epub Jan. 25, 2016.

Richardson et al., CRISPR-Cas9 genome editing in human cells occurs via the Fanconi anemia pathway. Nat Genet. Aug. 2018;50(8):1132-1139. doi: 10.1038/s41588-018-0174-0. Epub Jul. 27, 2018.

Richardson et al., Frequent chromosomal translocations induced by DNA double-strand breaks. Nature. Jun. 8, 2000;405(6787):697-700. doi: 10.1038/35015097.

Robertson et al., Selection in vitro of an RNA enzyme that specifically cleaves single-stranded DNA. Nature. Mar. 29, 1990;344(6265):467-8. doi: 10.1038/344467a0.

Rodriguez-Muela et al., Single-Cell Analysis of SMN Reveals Its Broader Role in Neuromuscular Disease. Cell Rep. Feb. 7, 2017;18(6):1484-1498 and Supplemental Information. doi: 10.1016/j.celrep.2017.01.035.

Safari et al., CRISPR Cpf1 proteins: structure, function and implications for genome editing. Cell Biosci. May 9, 2019;9:36. doi: 10.1186/s13578-019-0298-7.

Samanta et al., A reverse transcriptase ribozyme. Elife. Sep. 26, 2017;6:e31153. doi: 10.7554/eLife.31153.

San Filippo et al., Mechanism of eukaryotic homologous recombination. Annu Rev Biochem. 2008;77:229-57. doi: 10.1146/annurev.biochem.77.061306.125255.

Schlacher et al., Double-strand break repair-independent role for BRCA2 in blocking stalled replication fork degradation by MRE11. Cell. May 13, 2011;145(4):529-42. doi: 10.1016/j.cell.2011.03.041. Erratum in: Cell. Jun. 10, 2011;145(6):993.

Schrank et al., Inactivation of the survival motor neuron gene, a candidate gene for human spinal muscular atrophy, leads to massive cell death in early mouse embryos. Proc Natl Acad Sci U S A. Sep. 2, 1997;94(18):9920-5. doi: 10.1073/pnas.94.18.9920.

Sharma et al., Identification of novel methyltransferases, Bmt5 and Bmt6, responsible for the m3U methylations of 25S rRNA in *Saccharomyces cerevisiae*. Nucleic Acids Res. Mar. 2014;42(5):3246-60. doi: 10.1093/nar/gkt1281. Epub Dec. 11, 2013.

Shechner et al., Multiplexable, locus-specific targeting of long RNAs with CRISPR-Display. Nat Methods. Jul. 2015;12(7):664-70. doi: 10.1038/nmeth.3433. Epub Jun. 1, 2015.

Shen et al., Efficient genome modification by CRISPR-Cas9 nickase with minimal off-target effects. Nat Methods. Apr. 2014;11(4):399-402. doi: 10.1038/nmeth.2857. Epub Mar. 2, 2014.

Singh et al., Splicing of a critical exon of human Survival Motor Neuron is regulated by a unique silencer element located in the last intron. Mol Cell Biol. Feb. 2006;26(4):1333-46. doi: 10.1128/MCB.26.4.1333-1346.2006.

Song et al., RS-1 enhances CRISPR/Cas9- and TALEN-mediated knock-in efficiency. Nat Commun. Jan. 28, 2016;7:10548. doi: 10.1038/ncomms10548.

(56) References Cited

OTHER PUBLICATIONS

Stark et al., ATP hydrolysis by mammalian RAD51 has a key role during homology-directed DNA repair. J Biol Chem. Jun. 7, 2002;277(23):20185-94. doi: 10.1074/jbc.M112132200. Epub Mar. 28, 2002.

Sullenger et al., Ribozyme-mediated repair of defective mRNA by targeted, trans-splicing. Nature. Oct. 13, 1994;371(6498):619-22. doi: 10.1038/371619a0.

Sumner et al., Two breakthrough gene-targeted treatments for spinal muscular atrophy: challenges remain. J Clin Invest. Aug. 1, 2018;128(8):3219-3227. doi: 10.1172/JCI121658. Epub Jul. 9, 2018.

Suzuki et al., Crystal structures reveal an elusive functional domain of pyrrolysyl-tRNA synthetase. Nat Chem Biol. Dec. 2017;13(12):1261-1266. doi: 10.1038/nchembio.2497. Epub Oct. 16, 2017.

Talbot et al., Spinal muscular atrophy. Semin Neurol. Jun. 2001;21(2):189-97. doi: 10.1055/s-2001-15264.

Tan et al., Engineering of high-precision base editors for site-specific single nucleotide replacement. Nat Commun. Jan. 25, 2019;10(1):439. doi: 10.1038/s41467-018-08034-8. Erratum in: Nat Commun. May 1, 2019;10(1):2019.

Thompson et al., The Future of Multiplexed Eukaryotic Genome Engineering. ACS Chem Biol. Feb. 16, 2018;13(2):313-325. doi: 10.1021/acschembio.7b00842. Epub Dec. 28, 2017.

Trojan et al., Functional analysis of hMLH1 variants and HNPCC-related mutations using a human expression system. Gastroenterology. Jan. 2002;122(1):211-9. doi: 10.1053/gast.2002.30296.

Usman et al., Exploiting the chemical synthesis of RNA. Trends Biochem Sci. Sep. 1992;17(9):334-9. doi: 10.1016/0968-0004(92)90306-t.

Vakulskas et al., A high-fidelity Cas9 mutant delivered as a ribonucleoprotein complex enables efficient gene editing in human hematopoietic stem and progenitor cells. Nat Med. Aug. 2018;24(8):1216-1224. doi: 10.1038/s41591-018-0137-0. Epub Aug. 6, 2018.

Van Den Oord et al., Pixel Recurrent Neural Networks. Proceedings of the 33rd International Conference on Machine Learning. Journal of Machine Learning Research. Aug. 19, 2016. vol. 48. 11 pages.

Villiger et al., Treatment of a metabolic liver disease by in vivo genome base editing in adult mice. Nat Med. Oct. 2018;24(10):1519-1525. doi: 10.1038/s41591-018-02091. Epub Oct. 8, 2018.

Wan et al., Material solutions for delivery of CRISPR/Cas-based genome editing tools: Current status and future outlook. Materials Today. Jun. 2019;26:40-66. doi: 10.1016/j.mattod.2018.12.003.

Wills et al., Pseudoknot-dependent read-through of retroviral gag termination codons: importance of sequences in the spacer and loop 2. EMBO J. Sep. 1, 1994;13(17):4137-44. doi: 10.1002/j.1460-2075.1994.tb06731.x.

Wirth et al., Mildly affected patients with spinal muscular atrophy are partially protected by an increased SMN2 copy number. Hum Genet. May 2006;119(4):422-8. doi: 10.1007/s00439-006-0156-7. Epub Mar. 1, 2006.

Woo et al., Gene activation of SMN by selective disruption of lncRNA-mediated recruitment of PRC2 for the treatment of spinal muscular atrophy. Proc Natl Acad Sci U S A. Feb. 21, 2017;114(8):E1509-E1518 .doi:10.1073/pnas.1616521114. Epub Feb. 13, 2017.

Yamane et al., Deep-sequencing identification of the genomic targets of the cytidine deaminase AID and its cofactor RPA in B lymphocytes. Nat Immunol. Jan. 2011;12(1):62-9. doi: 10.1038/ni.1964. Epub Nov. 28, 2010.

Yan et al., Highly Efficient A•T to G•C Base Editing by Cas9n-Guided tRNA Adenosine Deaminase in Rice. Mol Plant. Apr. 2, 2018;11(4):631-634. doi: 10.1016/j.molp.2018.02.008. Epub Feb. 22, 2018.

Yang et al., BRCA2 function in DNA binding and recombination from a BRCA2-DSS1-ssDNA structure. Science. Sep. 13, 2002;297(5588):1837-48. doi: 10.1126/science.297.5588.1837.

Yang et al., Genome-wide inactivation of porcine endogenous retroviruses (PERVs). Science. Nov. 27, 2015;350(6264):1101-4. doi: 10.1126/science.aad1191. Epub Oct. 11, 2015.

Yang et al., The BRCA2 homologue Brh2 nucleates RAD51 filament formation at a dsDNA-ssDNA junction. Nature. Feb. 10, 2005;433(7026):653-7. doi: 10.1038/nature03234.

Yu et al., Dynamic control of Rad51 recombinase by self-association and interaction with BRCA2. Mol Cell. Oct. 2003;12(4):1029-41. doi: 10.1016/s1097-2765(03)00394-0.

Zeng et al., Correction of the Marfan Syndrome Pathogenic FBN1 Mutation by Base Editing in Human Cells and Heterozygous Embryos. Mol Ther. Nov. 7, 2018;26(11):2631-2637. doi: 10.1016/j.ymthe.2018.08.007. Epub Aug. 14, 2018.

Zhang et al., Efficient precise knockin with a double cut HDR donor after CRISPR/Cas9-mediated double-stranded DNA cleavage. Genome Biol. Feb. 20, 2017;18(1):35. doi: 10.1186/s13059-017-1164-8.

Zhang et al., Global analysis of small RNA and mRNA targets of Hfq. Mol Microbiol. Nov. 2003;50(4):1111-24. doi: 10.1046/j.1365-2958.2003.03734.x.

Zhang et al., Large genomic fragment deletions and insertions in mouse using CRISPR/Cas9. PLoS One. Mar. 24, 2015;10(3):e0120396. doi: 10.1371/journal.pone.0120396. 14 pages.

Zhang et al., Reversible RNA Modification N1-methyladenosine (m1A) in mRNA and tRNA. Genomics Proteomics Bioinformatics. Jun. 2018;16(3):155-161. doi: 10.1016/j.gpb.2018.03.003. Epub Jun. 14, 2018.

Zhou et al., GISSD: Group I Intron Sequence and Structure Database. Nucleic Acids Res. Jan. 2008;36(Database issue):D31-7. doi: 10.1093/nar/gkm766. Epub Oct. 16, 2007.

Zolotukhin et al., Production and purification of serotype 1, 2, and 5 recombinant adeno-associated viral vectors. Methods. Oct. 2002;28(2):158-67. doi: 10.1016/s1046-2023(02)00220-7.

* cited by examiner

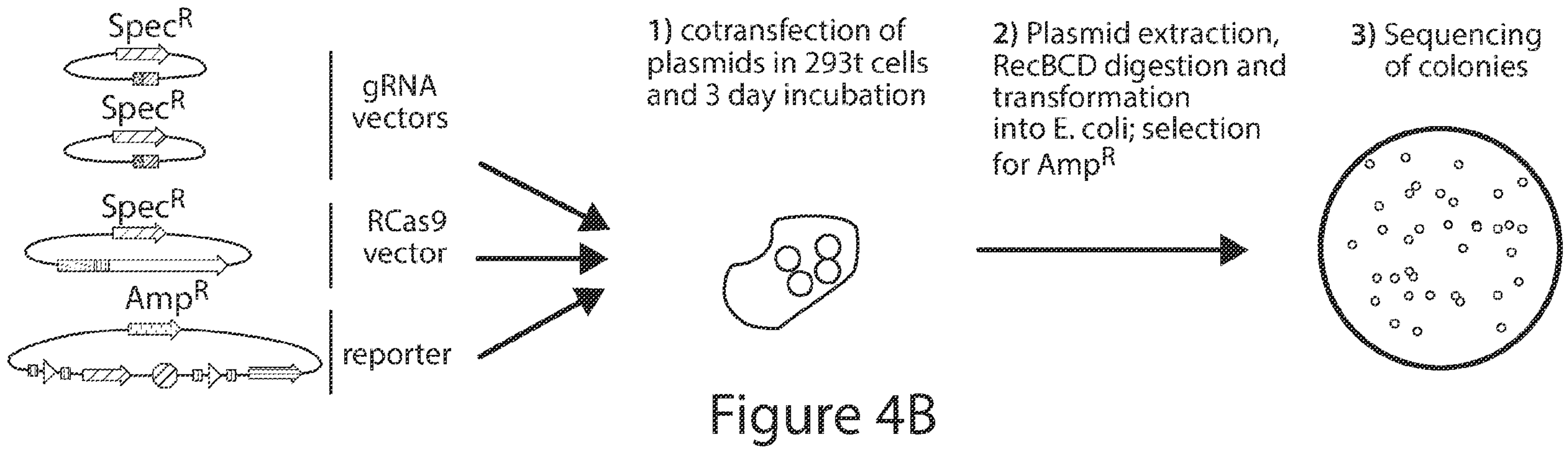
Figure 4B
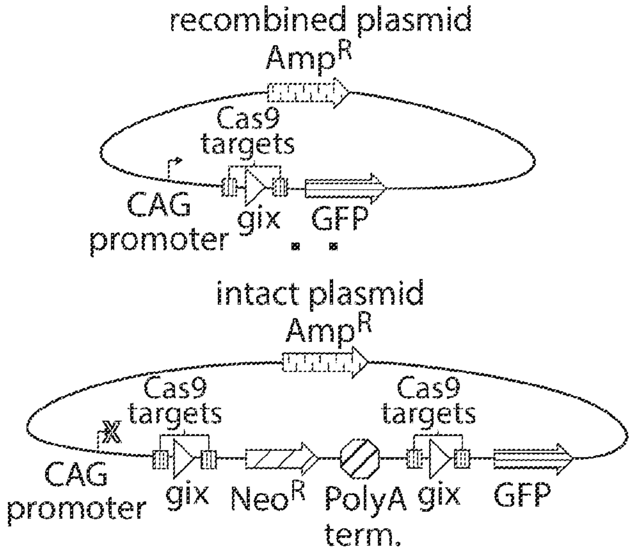
Figure 4C
gRNA/RCas9 Combinations
| Reporter | gRNAs Chr. 5-site 1 | gRNAs Chr. 12 | gRNAs Chr. 13-FGF14 | pUC control |
|---|---|---|---|---|
| | GinB-8GGS- -dCas9 | GinB-8GGS- -dCas9 | GinB-8GGS- -dCas9 | pUC control |
| Reporter: Chr. 5 Site 1 | 11.96±0.54% | 0.00% | 0.00% | 0.00% |
| Reporter: Chr. 12 | 0.00% | 23.49±0.41% | 0.00% | 0.00% |
| Reporter: Chr. 13 FGF14 | 0.00% | 0.00% | 31.73±4.27% | 0.00% |
Figure 4D

*Nested PCR template*

| | Sample 1 | Sample 2 | Sample 3 | Untransfected control |
|---|---|---|---|---|
| **Minimum Deletion** | 0.036±0.0233% | 0.011±0.0072% | 0.021±0.0091% | <0.0072% |

PROGRAMMABLE CAS9-RECOMBINASE FUSION PROTEINS AND USES THEREOF

RELATED APPLICATIONS

This application is a national stage filing under 35 U.S.C. § 371 of international PCT application, PCT/US2017/046144, filed Aug. 9, 2017, which claims priority under 35 U.S.C. § 119(e) to U.S. provisional patent application Ser. No. 62/372,755, filed Aug. 9, 2016, and U.S. provisional patent application Ser. No. 62/456,048, filed Feb. 7, 2017, each of which is incorporated herein by reference.

GOVERNMENT FUNDING

This invention was made with government support under EB022376 and GM118062 awarded by National Institutes of Health (NIH). The government has certain rights in this invention.

BACKGROUND OF THE INVENTION

Efficient, programmable, and site-specific homologous recombination remains a longstanding goal of genetics and genome editing. Early attempts at directing recombination to loci of interest relied on the transfection of donor DNA with long flanking sequences that are homologous to a target locus. This strategy was hampered by very low efficiency and thus the need for a stringent selection to identify integrants. More recent efforts have exploited the ability of double-stranded DNA breaks (DSBs) to induce homology-directed repair (HDR). Homing endonucleases and later programmable endonucleases such as zinc finger nucleases, TALE nucleases, Cas9, and fCas9 have been used to introduce targeted DSBs and induce HDR in the presence of donor DNA. In most post-mitotic cells, however, DSB-induced HDR is strongly down regulated and generally inefficient. Moreover, repair of DSBs by error-prone repair pathways such as non-homologous end-joining (NHEJ) or single-strand annealing (SSA) causes random insertions or deletions (indels) of nucleotides at the DSB site at a higher frequency than HDR. The efficiency of HDR can be increased if cells are subjected to conditions forcing cell-cycle synchronization or if the enzymes involved in NHEJ are inhibited. However, such conditions can cause many random and unpredictable events, limiting potential applications. The instant disclosure provides a fusion protein that can recombine DNA sites containing a minimal recombinase core site flanked by guide RNA-specified sequences and represents a step toward programmable, scarless genome editing in unmodified cells that is independent of endogenous cellular machinery or cell state.

SUMMARY OF THE INVENTION

The instant disclosure describes the development of a fusion protein comprising a guide nucleotide sequence-programmable DNA binding protein domain, an optional linker, and a recombinase catalytic domain (e.g., a serine recombinase catalytic domain such as a Gin recombinase catalytic domain, a tyrosine recombinase catalytic domain, or any evolved recombinase catalytic domain). This fusion protein operates on a minimal gix core recombinase site (NNNNAAASSWWSSTTTNNNN, SEQ ID NO: 19) flanked by two guide RNA-specified DNA sequences. Recombination mediated by the described fusion protein is dependent on both guide RNAs, resulting in orthogonality among different guide nucleotide:fusion protein complexes, and functions efficiently in cultured human cells on DNA sequences matching those found in the human genome. The fusion protein of the disclosure can also operate directly on the genome of human cells (e.g., cultured human cells), catalyzing a deletion, insertion, inversion, translocation, or recombination between two recCas9 psuedosites located approximately 14 kilobases apart. This work provides engineered enzymes that can catalyze gene insertion, deletion, inversion, or chromosomal translocation with user-defined, single base-pair resolution in unmodified genomes.

In one aspect, the instant disclosure provides a fusion protein comprising: (i) a guide nucleotide sequence-programmable DNA binding protein domain; (ii) an optional linker; and (iii) a recombinase catalytic domain such as any serine recombinase catalytic domain (including but not limited to a Gin, Sin, Tn3, Hin, β, γδ, or PhiC31 recombinase catalytic domain), any tyrosine recombinase domain (including, but not limited to a Cre or FLP recombinase catalytic domain), or any evolved recombinase catalytic domain.

The guide nucleotide sequence-programmable DNA binding protein domain may be selected from the group consisting of nuclease inactive Cas9 (dCas9) domains, nuclease inactive Cpf1 domains, nuclease inactive Argonaute domains, and variants thereof. In certain embodiments, the guide nucleotide sequence-programmable DNA-binding protein domain is a nuclease inactive Cas9 (dCas9) domain. In certain embodiments, the amino acid sequence of the dCas9 domain comprises mutations corresponding to a D10A and/or H840A mutation in SEQ ID NO: 1. In another embodiment, the amino acid sequence of the dCas9 domain comprises a mutation corresponding to a D10A mutation in SEQ ID NO: 1 and a mutation corresponding to an H840A mutation in SEQ ID NO: 1. In another embodiment, the amino acid sequence of the dCas9 domain further does not include the N-terminal methionine shown in SEQ ID NO: 1. In a certain embodiment, the amino acid sequence of the dCas9 domain comprises SEQ ID NO: 712. In one embodiment, the amino acid sequence of the dCas9 domain has a greater than 95% sequence identity with SEQ ID NO: 712. In one embodiment, the amino acid sequence of the dCas9 domain has a greater than 96, 97, 98, 99% or greater sequence identity with SEQ ID NO: 712. In some embodiments, the recombinase catalytic domain is a serine recombinase catalytic domain or a tyrosine recombinase catalytic domain.

In one embodiment, the amino acid sequence of the recombinase catalytic domain is a Gin recombinase catalytic domain. In some embodiments, the Gin recombinase catalytic domain comprises a mutation corresponding to one or more of the mutations selected from: a H106Y, I127L, I136R and/or G137F mutation in SEQ ID NO: 713. In an embodiment, the amino acid sequence of the Gin recombinase catalytic domain comprises mutations corresponding to two or more of the mutations selected from: a I127L, I136R and/or G137F mutation in SEQ ID NO: 713. In an embodiment, the amino acid sequence of the Gin recombinase catalytic domain comprises mutations corresponding to a I127L, I136R and G137F mutation in SEQ ID NO: 713. In another embodiment, the amino acid sequence of the Gin recombinase has been further mutated. In a specific embodiment, the amino acid sequence of the Gin recombinase catalytic domain comprises SEQ ID NO: 713.

In another embodiment, the amino acid sequence of the recombinase catalytic domain is a Hin recombinase, β recombinase, Sin recombinase, Tn3 recombinase, γδ recombinase, Cre recombinase; FLP recombinase; or a phiC31 recombinase catalytic domain.

In one embodiment, the amino acid sequence of the Cre recombinase is truncated. In another embodiment, the tyrosine recombinase catalytic domain is the 25 kDa carboxy-terminal domain of the Cre recombinase. In another embodiment, the Cre recombinase begins with amino acid R118, A127, E138, or R154 (preceded in each case by methionine). In one embodiment, the amino acid sequence of the recombinase has been further mutated. In certain embodiments, the recombinase catalytic domain is an evolved recombinase catalytic domain. In some embodiments, the amino acid sequence of the recombinase has been further mutated.

In some embodiments, the linker (e.g., the first, second, or third linker) may have a length of about 0 angstroms to about 81 angstroms. The linker typically has a length of about 33 angstroms to about 81 angstroms. The linker may be peptidic, non-peptidic, or a combination of both types of linkers. In certain embodiments, the linker is a peptide linker. In certain embodiments, the peptide linker comprises an XTEN linker SGSETPGTSESATPES (SEQ ID NO: 7), SGSETPGTSESA (SEQ ID NO: 8), or SGSETPGTSESATPEGGSGGS (SEQ ID NO: 9), an amino acid sequence comprising one or more repeats of the tri-peptide GGS, or any of the following amino acid sequences: VPFLLEPDNINGKTC (SEQ ID NO: 10), GSAGSAAGSGEF (SEQ ID NO: 11), SIVAQLSRPDPA (SEQ ID NO: 12), MKIIEQLPSA (SEQ ID NO: 13), VRHKLKRVGS (SEQ ID NO: 14), GHGTGSTGSGSS (SEQ ID NO: 15), MSRPDPA (SEQ ID NO: 16), or GGSM (SEQ ID NO: 17). In another embodiment, the peptide linker comprises one or more repeats of the tri-peptide GGS. In one embodiment, the peptide linker comprises from one to five repeats of the tri-peptide GGS. In another embodiment, the peptide linker comprises from six to ten repeats of the tri-peptide GGS. In a specific embodiment, the peptide linker comprises eight repeats of the tri-peptide GGS. In another embodiment, the peptide linker is from 18 to 27 amino acids long. In certain embodiments, the peptide linker is 24 amino acids long. In certain embodiments, the peptide linker has the amino acid sequence GGSGGSGGSGGSGGSGGSGGSGGS (SEQ ID NO: 183).

In certain embodiments, the linker is a non-peptide linker. In certain embodiments, the non-peptide linker comprises polyethylene glycol (PEG), polypropylene glycol (PPG), co-poly(ethylene/propylene) glycol, polyoxyethylene (POE), polyurethane, polyphosphazene, polysaccharides, dextran, polyvinyl alcohol, polyvinylpyrrolidones, polyvinyl ethyl ether, polyacryl amide, polyacrylate, polycyanoacrylates, lipid polymers, chitins, hyaluronic acid, heparin, or an alkyl linker. In certain embodiments, the alkyl linker has the formula: $—NH—(CH_2)_s—C(O)—$, wherein s is any integer between 1 and 100, inclusive. In certain embodiments, s is any integer from 1-20, inclusive.

In another embodiment, the fusion protein further comprises a nuclear localization signal (NLS) domain. In certain embodiments, the NLS domain is bound to the guide nucleotide sequence-programmable DNA binding protein domain or the recombinase catalytic domain via one or more second linkers.

In one embodiment, the fusion protein comprises the structure $NH_2$-[recombinase catalytic domain]-[optional linker sequence]-[guide nucleotide sequence-programmable DNA binding protein domainHoptional, second linker sequence]-[NLS domain]-COOH. In certain embodiments, the fusion protein has greater than 85%, 90%, 95%, 98%, or 99% sequence identity with the amino acid sequence shown in SEQ ID NO: 719. In a specific embodiment, the fusion protein comprises the amino acid sequence shown in SEQ ID NO: 719. In one embodiment, the fusion protein consists of the amino acid sequence shown in SEQ ID NO: 719.

In another embodiment, the fusion protein further comprises one or more affinity tags. In one embodiment, the affinity tag is selected from the group consisting of a FLAG tag, a polyhistidine (poly-His) tag, a polyarginine (poly-Arg) tag, a Myc tag, and an HA tag. In an embodiment, the affinity tag is a FLAG tag. In a specific embodiment, the FLAG tag has the sequence PKKKRKV (SEQ ID NO: 702). In another embodiment, the one or more affinity tags are bound to the guide nucleotide sequence-programmable DNA binding protein domain, the recombinase catalytic domain, or the NLS domain via one or more third linkers. In certain embodiments, the third linker is a peptide linker.

The elements of the fusion protein described herein may be in any order, without limitation. In some embodiments, the fusion protein has the structure $NH_2$-[recombinase catalytic domain]-[linker sequence]-[guide nucleotide sequence-programmable DNA binding protein domain]-[optional linker sequence]-[NLS domain]-[optional linker sequence]-[optional affinity tag]-COOH, $NH_2$-[guide nucleotide sequence-programmable DNA binding protein domain]-[linker sequence]-[recombinase catalytic domain]-[optional linker sequence]-[NLS domain]-[optional linker sequence]-[optional affinity tag]-COOH, or $NH_2$—[N-terminal portion of a bifurcated or circularly permuted guide nucleotide sequence-programmable DNA binding protein domain]-[optional linker sequence]-[recombinase catalytic domain]-[optional linker sequence]-[C-terminal portion of a bifurcated or circularly permuted guide nucleotide sequence-programmable DNA binding protein domain]-[optional linker sequence]-[NLS domain]-[optional linker sequence]-[optional affinity tag]-COOH.

In some embodiments, the fusion protein has the structure $NH_2$-[optional affinity tag]-[optional linker sequence]-[recombinase catalytic domain]-[linker sequence]-[guide nucleotide sequence-programmable DNA binding protein domain]-[optional linker sequence]-[NLS domain]-COOH, $NH_2$-[optional affinity tag]-[optional linker sequence]-[guide nucleotide sequence-programmable DNA binding protein domain]-[linker sequence]-[recombinase catalytic domain]-[optional linker sequence]-[NLS domain]-COOH, or $NH_2$-[optional affinity tag]-[optional linker sequence]-[N-terminal portion of a bifurcated or circularly permuted guide nucleotide sequence-programmable DNA binding protein domain]-[optional linker sequence]-[recombinase catalytic domain]-[optional linker sequence]-[C-terminal portion of a bifurcated or circularly permuted guide nucleotide sequence-programmable DNA binding protein domain]-[optional linker sequence]-[NLS domain]-COOH.

In a certain embodiment, the fusion protein has greater than 85%, 90%, 95%, 98%, or 99% sequence identity with the amino acid sequence shown in SEQ ID NO: 185. In a specific embodiment, the fusion protein has the amino acid sequence shown in SEQ ID NO: 185. In certain embodiments, the recombinase catalytic domain of the fusion protein has greater than 85%, 90%, 95%, 98%, or 99% sequence identity with the amino acid sequence shown in amino acids 1-142 of SEQ ID NO: 185, which is identical to the sequence shown in SEQ ID NO: 713. In certain embodiments, the dCas9 domain has greater than 90%, 95%, or 99% sequence identity with the amino acid sequence shown in amino acids 167-1533 of SEQ ID NO: 185, which is identical to the sequence shown in SEQ ID NO: 712. In certain embodiments, the fusion protein of the instant disclosure has greater than 90%, 95%, or 99% sequence identity with the amino acid sequence shown in amino acids 1-1544 of SEQ ID NO: 185, which is identical to the sequence shown in SEQ ID NO: 719. In one embodiment, the fusion protein is bound to a guide RNA (gRNA).

In one aspect, the instant disclosure provides a dimer of the fusion protein described herein. In certain embodiments, the dimer is bound to a target DNA molecule. In certain embodiments, each fusion protein of the dimer is bound to the same strand of the target DNA molecule. In certain embodiments, each fusion protein of the dimer is bound to an opposite strand of the target DNA molecule. In certain embodiments, the gRNAs of the dimer hybridize to gRNA binding sites flanking a recombinase site of the target DNA molecule. In certain embodiments, the recombinase site comprises a res, gix, hix, six, resH, LoxP, FTR, or att core, or related core sequence. In certain embodiments, the recombinase site comprises a gix core or gix-related core sequence. In further embodiments, the distance between the gix core or gix-related core sequence and at least one gRNA binding site is from 3 to 7 base pairs. In certain embodiments, the distance between the gix core or gix-related core sequence and at least one gRNA binding site is from 5 to 6 base pairs.

In certain embodiments, a first dimer binds to a second dimer thereby forming a tetramer of the fusion protein. In one aspect, the instant disclosure provides a tetramer of the fusion protein described herein. In certain embodiments, the tetramer is bound to a target DNA molecule. In certain embodiments, each dimer is bound to an opposite strand of DNA. In other embodiments, each dimer is bound to the same strand of DNA.

In another aspect, the instant disclosure provides methods for site-specific recombination between two DNA molecules, comprising: (a) contacting a first DNA with a first fusion protein, wherein the guide nucleotide sequence-programmable DNA binding protein domain binds a first gRNA that hybridizes to a first region of the first DNA; (b) contacting the first DNA with a second fusion protein, wherein the guide nucleotide sequence-programmable DNA binding protein domain of the second fusion protein binds a second gRNA that hybridizes to a second region of the first DNA; (c) contacting a second DNA with a third fusion protein, wherein the guide nucleotide sequence-programmable DNA binding protein domain of the third fusion protein binds a third gRNA that hybridizes to a first region of the second DNA; and (d) contacting the second DNA with a fourth fusion protein, wherein the guide nucleotide sequence-programmable DNA binding protein domain of the fourth fusion protein binds a fourth gRNA that hybridizes to a second region of the second DNA; wherein the binding of the fusion proteins in steps (a)-(d) results in the tetramerization of the recombinase catalytic domains of the fusion proteins, under conditions such that the DNAs are recombined, and wherein the first, second, third, and/or fourth fusion protein is any of the fusion proteins described herein.

In one embodiment, the first and second DNA molecules have different sequences. In another embodiment, the gRNAs of steps (a) and (b) hybridize to opposing strands of the first DNA, and the gRNAs of steps (c) and (d) hybridize to opposing strands of the second DNA. In another embodiment, wherein the gRNAs of steps (a) and (b); and/or the gRNAs of steps (c) and (d) hybridize to regions of their respective DNAs that are no more than 10, no more than 15, no more than 20, no more than 25, no more than 30, no more than 40, no more than 50, no more than 60, no more than 70, no more than 80, no more than 90, or no more than 100 base pairs apart. In certain embodiments, the gRNAs of steps (a) and (b), and/or the gRNAs of steps (c) and (d) hybridize to regions of their respective DNAs at gRNA binding sites that flank a recombinase site (see, for example, FIG. 1D). In certain embodiments, the recombinase site comprises a res, gix, hix, six, resH, LoxP, FTR, or att core, or related core sequence. In certain embodiments, the recombinase site comprises a gix core or gix-related core sequence. In certain embodiments, the distance between the gix core or gix-related core sequence and at least one gRNA binding site is from 3 to 7 base pairs. In certain embodiments, the distance between the gix core or gix-related core sequence and at least one gRNA binding site is from 5 to 6 base pairs.

The method for site-specific recombination provided herein may also be used with a single DNA molecule. In one aspect, the instant disclosure provides a method for site-specific recombination between two regions of a single DNA molecule, comprising: (a) contacting the DNA with a first fusion protein, wherein the guide nucleotide sequence-programmable DNA binding protein domain binds a first gRNA that hybridizes to a first region of the DNA; (b) contacting the DNA with a second fusion protein, wherein the guide nucleotide sequence-programmable DNA binding protein domain of the second fusion protein binds a second gRNA that hybridizes to a second region of the DNA; (c) contacting the DNA with a third fusion protein, wherein the guide nucleotide sequence-programmable DNA binding protein domain of the third fusion protein binds a third gRNA that hybridizes to a third region of the DNA; and (d) contacting the DNA with a fourth fusion protein, wherein the guide nucleotide sequence-programmable DNA binding protein domain of the fourth fusion protein binds a fourth gRNA that hybridizes to a fourth region of the DNA; wherein the binding of the fusion proteins in steps (a)-(d) results in the tetramerization of the recombinase catalytic domains of the fusion proteins, under conditions such that the DNA is recombined, and wherein the first, second, third, and/or fourth fusion protein is any of the fusion proteins described.

In certain embodiments, the two regions of the single DNA molecule that are recombined have different sequences. In another embodiment, the recombination results in the deletion of a region of the DNA molecule. In a specific embodiment, the region of the DNA molecule that is deleted is prone to cross-over events in meiosis. In one embodiment, the first and second gRNAs of steps (a)-(d) hybridize to the same strand of the DNA, and the third and fourth gRNAs of steps (a)-(d) hybridize to the opposing strand of the DNA. In another embodiment, the gRNAs of steps (a) and (b) hybridize to regions of the DNA that are no more than 50, no more than 60, no more than 70, no more than 80, no more than 90, or no more than 100 base pairs apart, and the gRNAs of steps (c) and (d) hybridize to regions of the DNA that are no more than 10, no more than 15, no more than 20, no more than 25, no more than 30, no more than 40, no more than 50, no more than 60, no more than 70, no more than 80, no more than 90, or no more than 100 base pairs apart. In certain embodiments, the gRNAs of steps (a) and (b); and/or the gRNAs of steps (c) and (d) hybridize to gRNA binding sites flanking a recombinase site. In certain embodiments, the recombinase site comprises a res, gix, hix, six, resH, LoxP, FTR, or att core or related core sequence. In one embodiment, the recombinase site comprises a gix core or gix-related core sequence. In certain embodiments, the distance between the gix core or gix-related core sequence and at least one gRNA binding site is from 3 to 7 base pairs. In certain embodiments, the distance between the gix core or gix-related core sequence and at least one gRNA binding site is from 5 to 6 base pairs.

The DNA described herein may be in a cell. In certain embodiments, the cell is a eukaryotic cell. In certain embodiments, the cell is a plant cell. In certain embodiments, the cell is a prokaryotic cell. In some embodiments, the cell may be a mammalian cell. In some embodiments, the cell may be a human cell. In certain embodiments, the cell is in a subject. In some embodiments, the subject may be a mammal. In certain embodiments, the subject is a human. In certain embodiments, the cell may be a plant cell.

In one aspect, the instant disclosure provides a polynucleotide encoding any of the fusion proteins disclosed herein. In certain embodiments, the instant disclosure provides a vector comprising the polynucleotide encoding any of the fusion proteins disclosed herein.

In another aspect, the instant disclosure provides a cell comprising a genetic construct for expressing any fusion protein disclosed herein.

In one aspect, the instant disclosure provides a kit comprising any fusion protein disclosed herein. In another aspect, the instant disclosure provides a kit comprising a polynucleotide encoding any fusion protein disclosed herein. In another aspect, the instant disclosure provides a kit comprising a vector for recombinant protein expression, wherein the vector comprises a polynucleotide encoding any fusion protein disclosed herein. In another aspect, the instant disclosure provides a kit comprising a cell that comprises a genetic construct for expressing any fusion protein disclosed herein. In one embodiment, the kit further comprises one or more gRNAs and/or vectors for expressing one or more gRNAs.

The details of certain embodiments of the invention are set forth in the Detailed Description of Certain Embodiments, as described below. Other features, objects, and advantages of the invention will be apparent from the Definitions, Examples, Figures, and Claims.

BRIEF DESCRIPTION OF THE DRAWINGS

(FIG. 2A) A portion of the target site is shown with guide RNA target sites in black with dashed underline and a gix core sequence site in black. The 5' and 3' sequences on either side of the pseudo-gix sites are identical, but inverted, and are recognized by pHU6-NT1. The number of base pairs spacers separating the gix pseudo-site from the 5' and 3' binding sites is represented by an X and Y, respectively. This figure depicts SEQ ID NOs: 700 and 703, respectively. (FIG. 2B) Z represents the number of GGS repeats connecting Ginβ to dCas9. recCas9 activity is assessed when X=Y for (FIG. 2C) $(GGS)_2$ (SEQ ID NO: 182), (FIG. 2D) $(GGS)_5$ (SEQ ID NO: 701), and (FIG. 2E) $(GGS)_8$ (SEQ ID NO: 183) linkers connecting the Gin catalytic domain to the dCas9 domain. (FIG. 2F) The activity of recCas9 on target sites composed of uneven base pair spacers (X≠Y) was determined; X=Y=6 is included for comparison. All experiments are performed in triplicate and background fluorescence is subtracted from these experiments. The percentage of eGFP-positive cells is of only those transfected (i.e., expressing a constitutively expressed iRFP gene) and at least 6,000 live events are recorded for each experiment. Guide RNA expression vectors and guide RNA sequences are abbreviated as "gRNA". Values and error bars represent the mean and standard deviation, respectively, of three independent biological replicates.

(FIG. 3A) A sequence found within PCDH15 replaces the target site tested in FIGS. 1A-1D. Two offset sequences can be targeted by guide RNAs on both the 5' and 3' sides of a pseudo-gix core site. This figure depicts SEQ ID NOs: 704-705, respectively. (FIG. 3B) recCas9 activity was measured by co-transfecting a recCas9 expression vector and reporter plasmid with all four guide RNA expression vector pairs and individual guide RNA vectors with off target (O.T.) guide RNA vectors. The off-target forward and reverse contained guide RNA sequences targeting CLTA and VEGF, respectively. Control experiments transfected with the reporter plasmid but without a target guide RNA are also shown. The results of reporter plasmid cotransfected with different guide RNA expression vectors, but without recCas9 expression vectors, are also shown. All experiments were performed in quadruplicate, and background fluorescence is not subtracted from these experiments. The percentage of eGFP-positive cells is of only those transfected (i.e., expressing a constitutively expressed iRFP gene), and at least 6,000 live events are recorded for each experiment. Guide RNA expression vectors and guide RNA sequences are abbreviated as gRNA. Values and error bars represent the mean and standard deviation, respectively, of four independent biological replicates.

FIGS. 4A-4D. recCas9 can target multiple sequences identical to those in the human genome. (FIG. 4A) The target sites shown in FIGS. 1A-1D are replaced by sequences found within the human genome. See Table 6 for sequences. A recCas9 expression vector was cotransformed with all combinations of guide RNA vectors pairs and reporter plasmids. Off-target guide RNA vectors were also cotransformed with the recCas9 expression vector and reporter plasmids and contain guide RNA sequences targeting CLTA and VEGF (see, e.g., Guilinger et al., Fusion of catalytically inactive Cas9 to FokI nuclease improves the specificity of genome modification. Nature biotechnology, (2014), the entire contents of which is hereby incorporated by reference). The percentage of eGFP-positive cells reflects that of transfected (iRFP-positive) cells. At least 6,000 live events are recorded for each experiment. Values and error bars represent the mean and standard deviation, respectively, of at least three independent biological replicates. (FIG. 4B) Transfection experiments were performed again, replacing the resistance marker in the recCas9 expression vector and pUC with SpecR. After cotransfection and incubation, episomal DNA was extracted, transformed into *E. coli* and selected for carbenicillin resistance. Colonies were then sequenced to determine (FIG. 4C) the ratio of recombined to fully intact plasmids. (FIG. 4D) Sequencing data from episomal extractions isolated from transfected cells. Columns and rows represent the transfection conditions. Each cell shows the percent of recombined plasmid and the ratio.

The values shown reflect the mean and standard deviation of two independent biological replicates. The average difference between the mean and each replicate is shown as the error. Guide RNA expression vectors and guide RNA sequences are abbreviated as gRNA.

FIGS. 5A-5D. recCas9 mediates guide RNA- and recCas9-dependent deletion of genomic DNA in cultured human cells. (FIG. 5A) Schematic showing predicted recCas9 target sites located within an intronic region of the FAM19A2 locus of chromosome 12 and the positions of primers used for nested PCR. This figure depicts SEQ ID NOs: 706-709 from top to bottom and left to right, respectively. (FIG. 5B) Representative results of nested genomic PCR of template from cells transfected with the indicated expression vectors (n=3 biological replicates; NTC=no template control). The asterisk indicates the position of the 1.3-kb predicted primary PCR product. Arrow indicates the predicted deletion product after the secondary PCR. Both panes are from the same gel but were cut to remove blank lanes. (FIG. 5C) Sanger sequencing of PCR products resulting from nested genomic PCR of cells transfected with all four gRNA expression vectors, and the recCas9 expression vector matches the predicted post-recombination product. This figure depicts SEQ ID NOs: 710 and 711 from top to bottom, respectively. (FIG. 5D) Estimated minimum deletion efficiency of FAM19A2 locus determined by limiting-dilution nested PCR. The values shown reflect the mean and standard deviation of three replicates.

Figure 6:
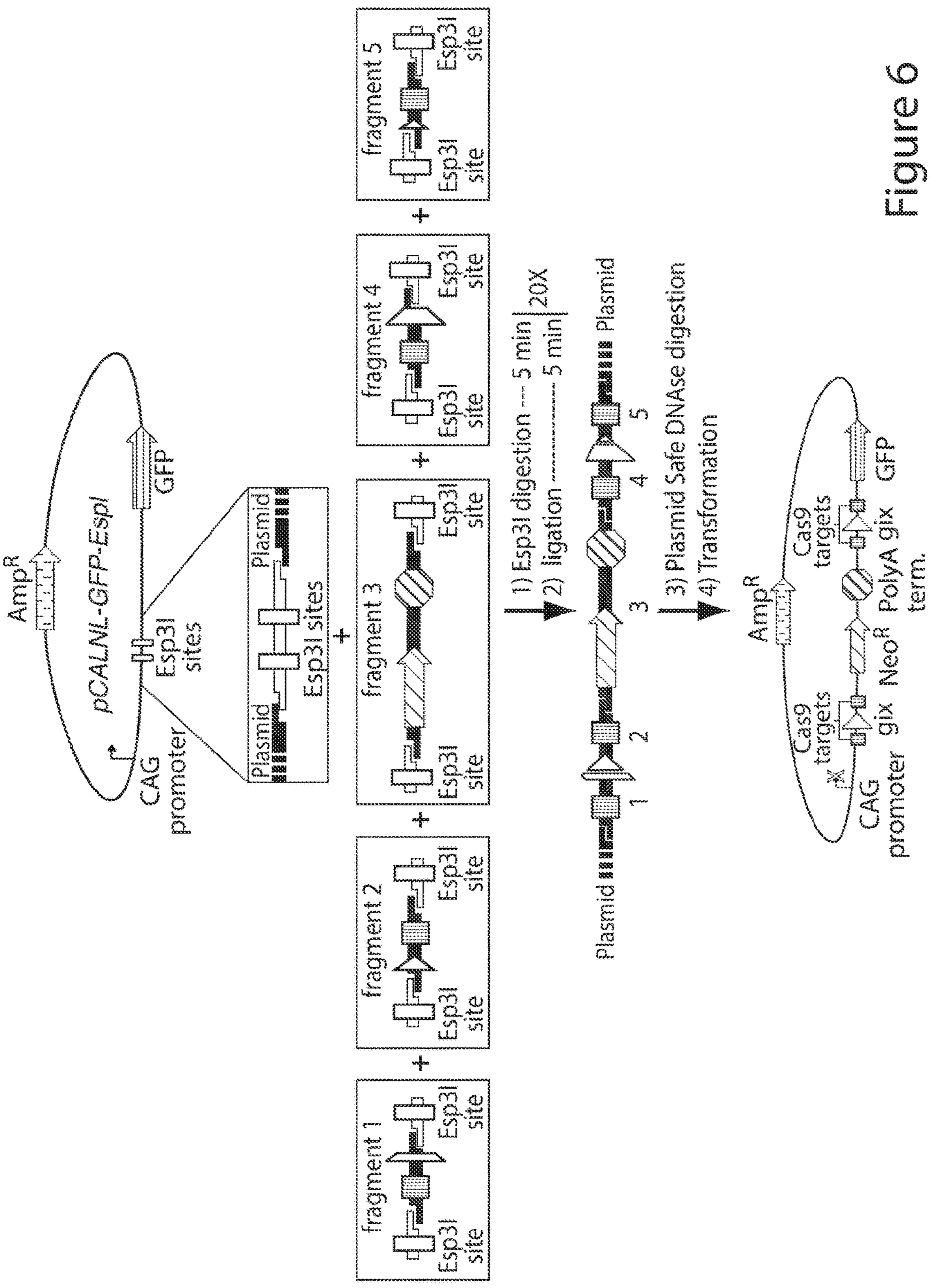

FIG. 6. Reporter plasmid construction. Golden Gate assembly was used to construct the reporter plasmids described in this work. All assemblies started with a common plasmid, pCALNL-EGFP-Esp3I, that was derived from pCALNL-EGFP and contained to Esp3I restriction sites. The fragments shown are flanked by Esp3I sites. Esp3I digestion creates a series of compatible, unique 4-base pair 5' overhangs so that assembly occurs in the order shown. To assemble the target sites, Esp3I (ThermoFisher Scientific, Waltham, Mass.) and five fragments were added to a single reaction tube to allow for iterative cycles of Esp3I digestion and T7 ligation. Reactions were then digested with Plasmid-Safe-ATP-dependent DNAse (Epicentre, Madison, Wis.) to reduce background. Colonies were analyzed by colony PCR to identify PCR products that matched the expected full length 5 part assembly product; plasmid from these colonies was then sent for sanger sequencing. For the genomic reporters shown in FIG. 4, fragments 1 and 2 as well as fragments 4 and 5 were combined into two gBlocks (IDT, Coralville, Iowa) fragments encoding the entire target site (not shown in the figure). Assembly was then completed as described above. Details for construction can be found in the methods for the supporting material. Oligonucleotides and gBLOCKS for creation of fragments can be found in Table 2.

Figure 7A:
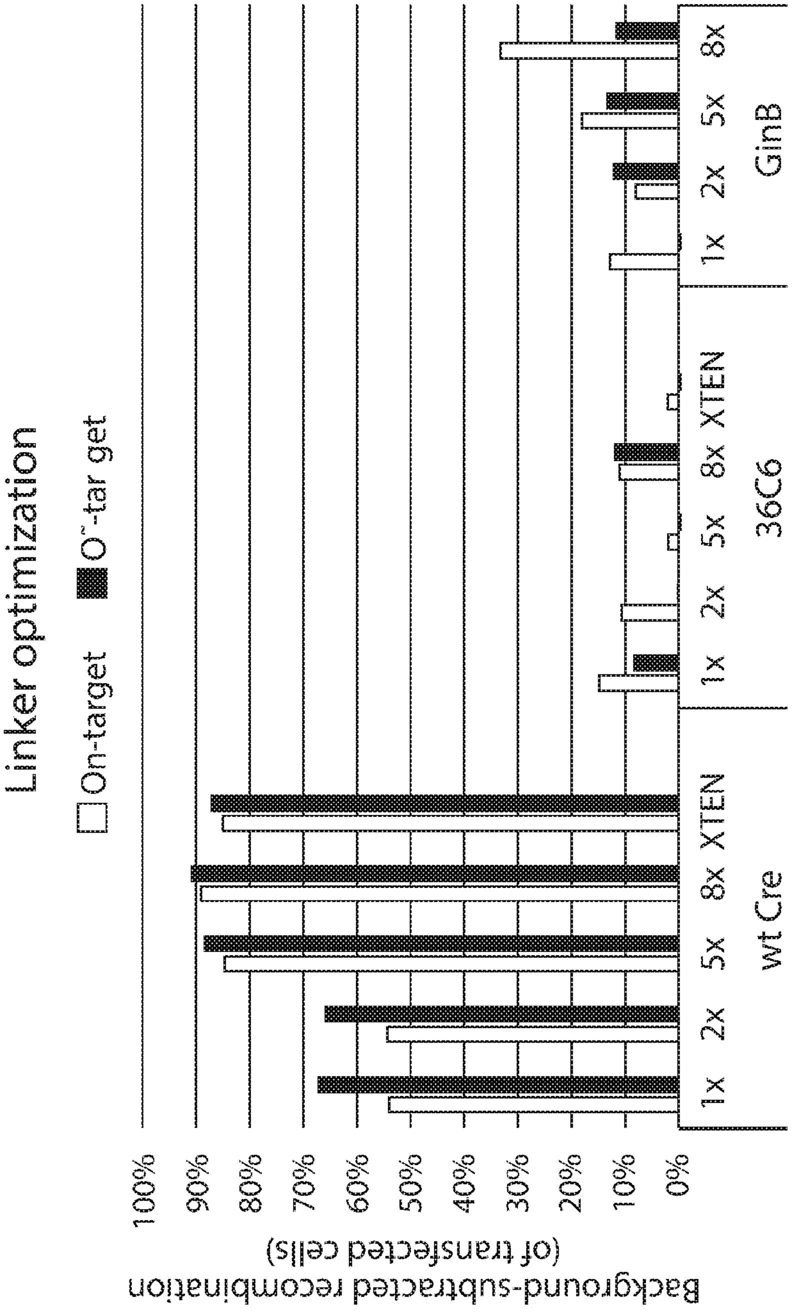
Figure 7B:
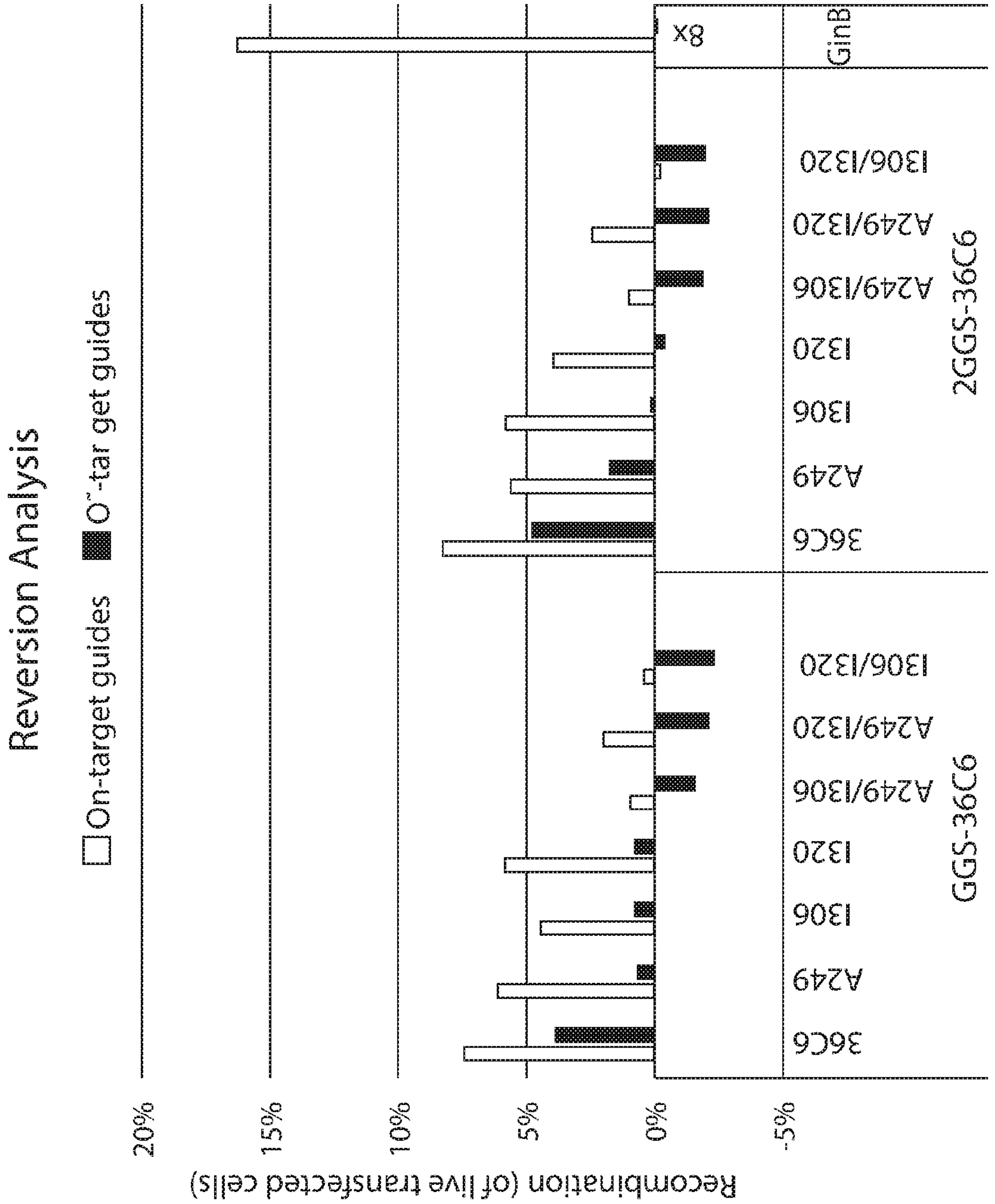

FIGS. 7A and 7B. A Cre recombinase evolved to target a site in the Rosa locus of the human genome called “36C6” was fused to dCas9. This fusion was then used to recombine a plasmid-based reporter containing the Rosa target site in a guide-RNA dependent fashion. FIG. 7A demonstrates the results of linker optimization using wild-type Cre and 36C6. A GinB construct, targeting its cognate reporter, is shown for reference. The 1×2×, 5×, and 8× linkers shown are the number of GGS repeats in the linker. FIG. 7B shows the results of a reversion analysis which demonstrated that making mutations to 36C6 fused to dCas9 could impact the relative guide dependence of the chimeric fusion. A GinB construct, targeting its cognate reporter, is shown for reference. GGS-36C6: 1×GGS linker; 2GGS-36C6 (using linker SEQ ID NO: 181): 2×GGS linker (using linker SEQ ID NO: 181).

Figure 8:
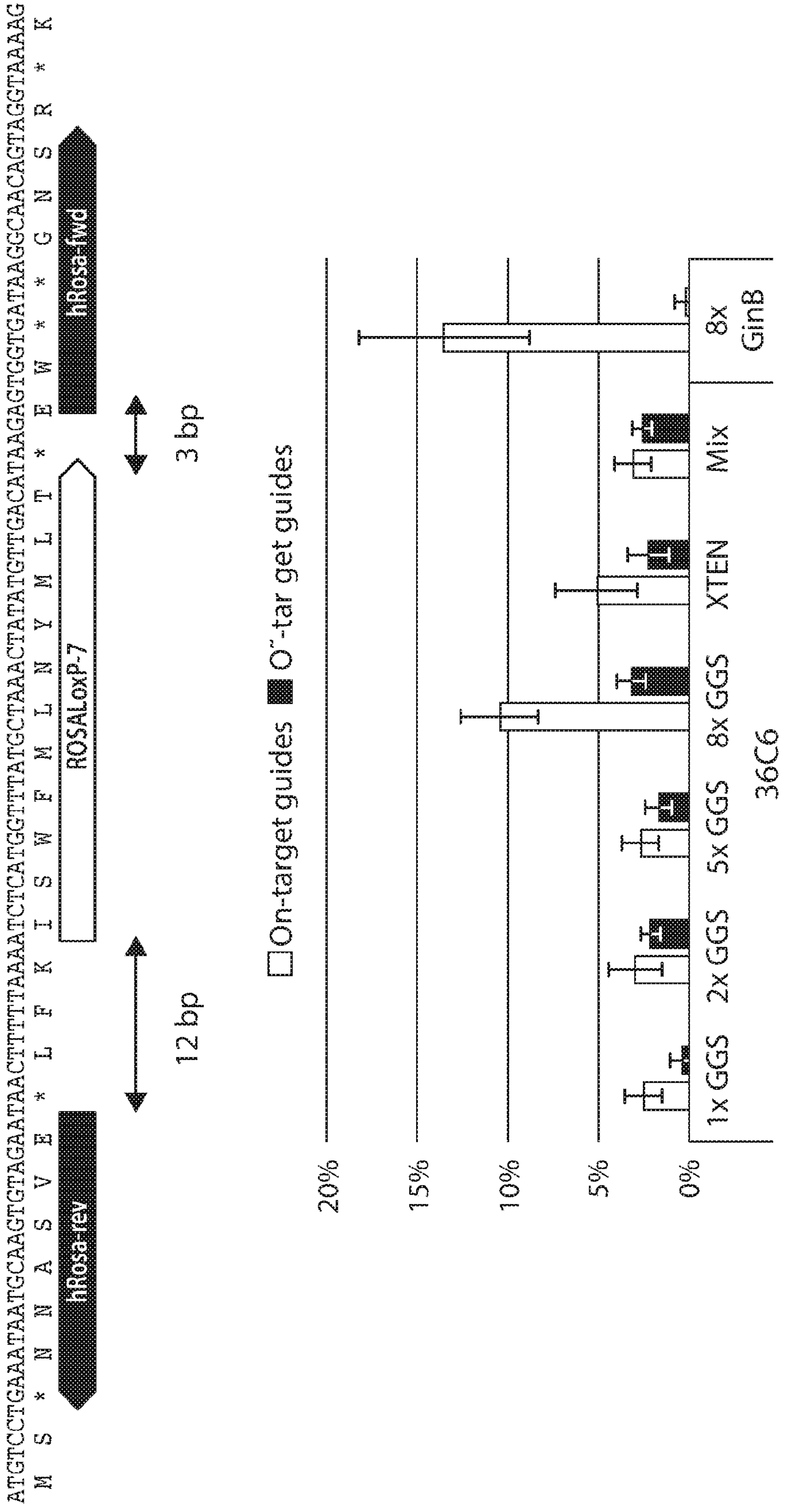

FIG. 8. PAMs were identified flanking the Rosa26 site in the human genome that could support dCas9 binding (see at top). Guide RNAs and a plasmid reporter were designed to test whether the endogenous protospacers could support dCas9-36C6 activity. A GinB construct, targeting the gix reporter, is shown for reference. Mix: equal parts mixture of all 5 linker variants between Cas9 and 36C6. The sequences correspond to SEQ ID NO: 769 (the nucleotide sequence) and 770, 776, and 777 (the amino acid sequences from left to right).

Figure 9A:
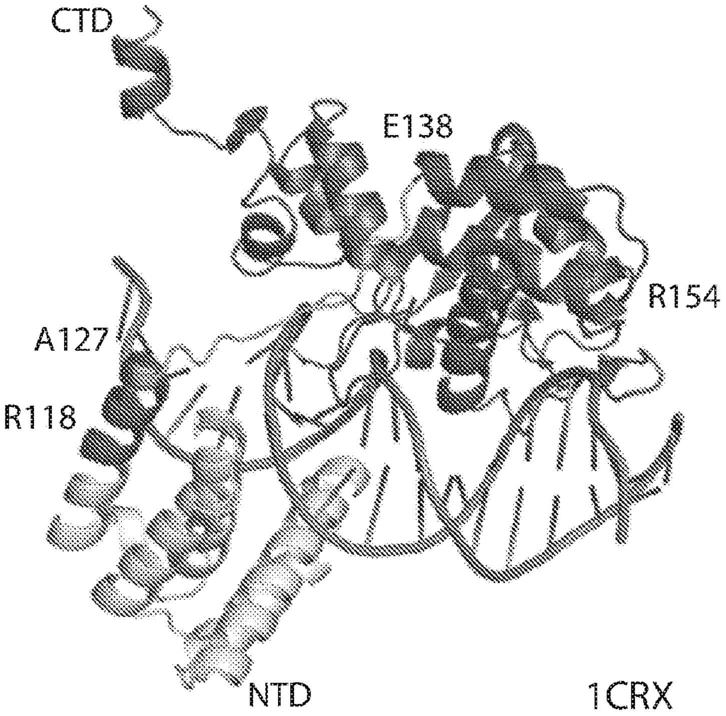
Figure 9B:
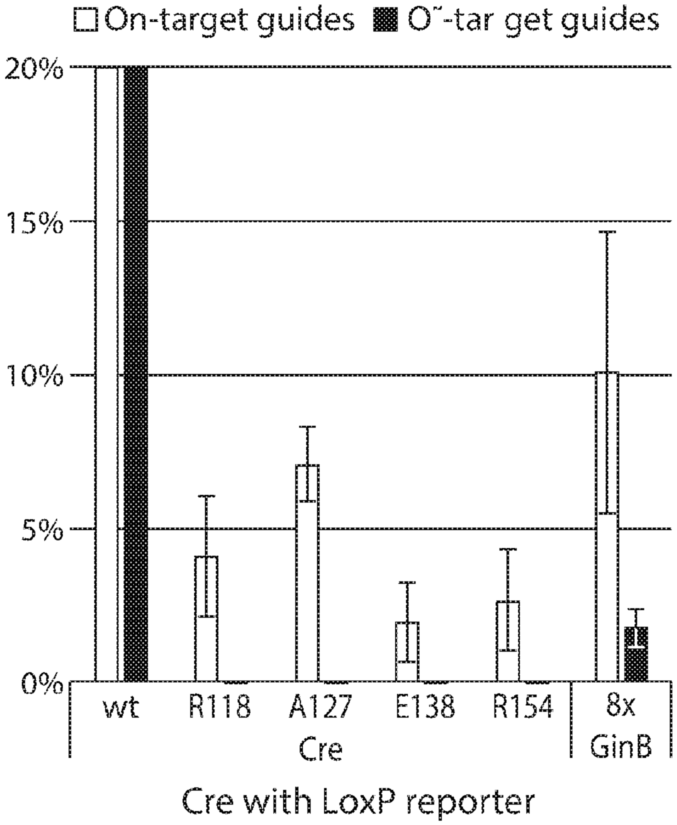

FIGS. 9A-9B. Locations of various tested truncations of Cre recombinase are shown in FIG. 9A. Truncated variants of Cre recombinase fused to dCas9 show both appreciable recombinase activity as well as a strict reliance on the presence of guide RNA in a Lox plasmid reporter system (FIG. 9B). Wild type Cre fused to dCas9 is shown as a positive control.

DEFINITIONS

As used herein, the singular forms “a,” “an,” and “the” include the singular and the plural reference unless the context clearly indicates otherwise. Thus, for example, a reference to “an agent” includes a single agent and a plurality of such agents.

Non-limiting, exemplary RNA-programmable DNA-binding proteins include Cas9 nucleases, Cas9 nickases, nuclease inactive Cas9 (dCas9), CasX, CasY, Cpf1, C2c1, C2c2, C2C3, and Argonaute. The term “Cas9” or “Cas9 nuclease” refers to an RNA-guided nuclease comprising a Cas9 protein, or a fragment thereof (e.g., a protein comprising an active or inactive DNA cleavage domain of Cas9, and/or the gRNA binding domain of Cas9). Cas9 has two cleavage domains, which cut specific DNA strands (e.g., sense and antisense strands). Cas9 nickases can be generated that cut either strand (including, but not limited to D10A and H840A of spCas9). A Cas9 domain (e.g., nuclease active Cas9, nuclease inactive Cas9, or Cas9 nickases) may be used without limitation in the fusion proteins and methods described herein. Further, any of the guide nucleotide sequence-programmable DNA binding proteins described herein may be useful as nickases.

A Cas9 nuclease is also referred to sometimes as a casn1 nuclease or a CRISPR (clustered regularly interspaced short palindromic repeat)-associated nuclease. CRISPR is an adaptive immune system that provides protection against mobile genetic elements (viruses, transposable elements, and conjugative plasmids). CRISPR clusters contain spacers, sequences complementary to antecedent mobile elements, and target invading nucleic acids. CRISPR clusters are transcribed and processed into CRISPR RNA (crRNA). In type II CRISPR systems correct processing of pre-crRNA requires a trans-encoded small RNA (tracrRNA), endogenous ribonuclease 3 (rnc), and a Cas9 protein. The tracrRNA serves as a guide for ribonuclease 3-aided processing of pre-crRNA. Subsequently, Cas9/crRNA/tracrRNA endonucleolytically cleaves a linear or circular dsDNA target complementary to the spacer. The target strand not complementary to crRNA is first cut endonucleolytically, then trimmed 3'-5' exonucleolytically. In nature, DNA-binding and cleavage typically requires protein and both RNA sequences. However, single guide RNAs (“sgRNA”, or simply “gRNA”) can be engineered so as to incorporate aspects of both the crRNA and tracrRNA into a single RNA species. See, e.g., Jinek M., Chylinski K., Fonfara I., Hauer M., Doudna J. A., Charpentier E. *Science* 337:816-821(2012), the entire contents of which is hereby incorporated by reference. Cas9 recognizes a short motif in the CRISPR repeat sequences (the PAM or protospacer adjacent motif) to help distinguish self versus non-self. Cas9 nuclease sequences and structures are well known to those of skill in the art (see, e.g., "Complete genome sequence of an M1 strain of *Streptococcus pyogenes*." Ferretti et al., J. J., McShan W. M., Ajdic D. J., Savic D. J., Savic G., Lyon K., Primeaux C., Sezate S., Suvorov A. N., Kenton S., Lai H. S., Lin S. P., Qian Y., Jia H. G., Najar F. Z., Ren Q., Zhu H., Song L., White J., Yuan X., Clifton S. W., Roe B. A., McLaughlin R. E., Proc. Natl. Acad. Sci. U.S.A. 98:4658-4663(2001); "CRISPR RNA maturation by trans-encoded small RNA and host factor RNase III." Deltcheva E., Chylinski K., Sharma C. M., Gonzales K., Chao Y., Pirzada Z. A., Eckert M. R., Vogel J., Charpentier E., Nature 471:602-607(2011); and "A programmable dual-RNA-guided DNA endonuclease in adaptive bacterial immunity." Jinek M., Chylinski K., Fonfara I., Hauer M., Doudna J. A., Charpentier E. *Science* 337:816-821(2012), the entire contents of each of which are incorporated herein by reference). Cas9 orthologs have been described in various species, including, but not limited to, *S. pyogenes* and *S. thermophilus*. Additional suitable Cas9 nucleases and sequences will be apparent to those of skill in the art based on this disclosure, and such Cas9 nucleases and sequences include Cas9 sequences from the organisms and loci disclosed in Chylinski, Rhun, and Charpentier, "The tracrRNA and Cas9 families of type II CRISPR-Cas immunity systems" (2013) RNA Biology 10:5, 726-737; the entire contents of which are incorporated herein by reference. In some embodiments, a Cas9 nuclease has an inactive (e.g., an inactivated) DNA cleavage domain, that is, the Cas9 is a nickase. As one example, the Cas9 nuclease (e.g., Cas9 nickase) may cleave the DNA strand that is bound to the gRNA. As another example, the Cas9 nuclease (e.g., Cas9 nickase) may cleave the DNA strand that is not bound to the gRNA. In another embodiment, any of the guide nucleotide sequence-programmable DNA binding proteins may have an inactive (e.g., an inactivated) DNA cleavage domain, that is, the guide nucleotide sequence-programmable DNA binding protein is a nickase. As one example, the guide nucleotide sequence-programmable DNA binding protein may cleave the DNA strand that is bound to the gRNA. As another example, the guide nucleotide sequence-programmable DNA binding protein may cleave the DNA strand that is not bound to the gRNA.

Additional exemplary Cas9 sequences may be found in International Publication No.: WO/2017/070633, published Apr. 27, 2017, and entitled "Evolved Cas9 Proteins for Gene Editing."

A nuclease-inactivated Cas9 protein may interchangeably be referred to as a "dCas9" protein (for nuclease "dead" Cas9). In some embodiments, dCas9 corresponds to, or comprises in part or in whole, the amino acid set forth as SEQ ID NO: 1, below. In some embodiments, variants of dCas9 (e.g., variants of SEQ ID NO: 1) are provided. For example, in some embodiments, variants having mutations other than D10A and H840A are provided, which e.g., result in nuclease inactivated Cas9 (dCas9). Such mutations, by way of example, include other amino acid substitutions at D10 and H840, or other substitutions within the nuclease domains of Cas9 (e.g., substitutions in the HNH nuclease subdomain and/or the RuvC1 subdomain). In some embodiments, variants or homologues of dCas9 (e.g., variants of SEQ ID NO: 1) are provided which are at least about 70% identical, at least about 80% identical, at least about 90% identical, at least about 95% identical, at least about 98% identical, at least about 99% identical, at least about 99.5% identical, or at least about 99.9% to SEQ ID NO: 1. In some embodiments, variants of dCas9 (e.g., variants of SEQ ID NO: 1) are provided having amino acid sequences which are shorter, or longer than SEQ ID NO: 1, by about 5 amino acids, by about 10 amino acids, by about 15 amino acids, by about 20 amino acids, by about 25 amino acids, by about 30 amino acids, by about 40 amino acids, by about 50 amino acids, by about 75 amino acids, by about 100 amino acids, or more.

```
dCas9 (D10A and H840A):
                                             (SEQ ID NO: 1)
MDKKYSIGLAIGTNSVGWAVITDEYKVPSKKFKVLGNTDRHSIKKNLIGA

LLFDSGETAEATRLKRTARRRYTRRKNRICYLQEIFSNEMAKVDDSFFHR

LEESFLVEEDKKHERHPIFGNIVDEVAYHEKYPTIYHLRKKLVDSTDKAD

LRLIYLALAHMIKFRGHFLIEGDLNPDNSDVDKLFIQLVQTYNQLFEENP

INASGVDAKAILSARLSKSRRLENLIAQLPGEKKNGLFGNLIALSLGLTP

NFKSNFDLAEDAKLQLSKDTYDDDLDNLLAQIGDQYADLFLAAKNLSDAI

LLSDILRVNTEITKAPLSASMIKRYDEHHQDLTLLKALVRQQLPEKYKEI

FFDQSKNGYAGYIDGGASQEEFYKFIKPILEKMDGTEELLVKLNREDLLR

KQRTFDNGSIPHQIHLGELHAILRRQEDFYPFLKDNREKIEKILTFRIPY

YVGPLARGNSRFAWMTRKSEETITPWNFEEVVDKGASAQSFIERMTNFDK

NLPNEKVLPKHSLLYEYFTVYNELTKVKYVTEGMRKPAFLSGEQKKAIVD

LLFKTNRKVTVKQLKEDYFKKIECFDSVEISGVEDRFNASLGTYHDLLKI

IKDKDFLDNEENEDILEDIVLTLTLFEDREMIEERLKTYAHLFDDKVMKQ

LKRRRYTGWGRLSRKLINGIRDKQSGKTILDFLKSDGFANRNFMQLIHDD

SLTFKEDIQKAQVSGQGDSLHEHIANLAGSPAIKKGILQTVKVVDELVKV

MGRHKPENIVIEMARENQTTQKGQKNSRERMKRIEEGIKELGSQILKEHP

VENTQLQNEKLYLYYLQNGRDMYVDQELDINRLSDYDVDAIVPQSFLKDD

SIDNKVLTRSDKNRGKSDNVPSEEVVKKMKNYWRQLLNAKLITQRKFDNL

TKAERGGLSELDKAGFIKRQLVETRQITKHVAQILDSRMNTKYDENDKLI

REVKVITLKSKLVSDFRKDFQFYKVREINNYHHAHDAYLNAVVGTALIKK

YPKLESEFVYGDYKVYDVRKMIAKSEQEIGKATAKYFFYSNIMNFFKTEI

TLANGEIRKRPLIETNGETGEIVWDKGRDFATVRKVLSMPQVNIVKKTEV

QTGGFSKESILPKRNSDKLIARKKDWDPKKYGGFDSPTVAYSVLVVAKVE

KGKSKKLKSVKELLGITIMERSSFEKNPIDFLEAKGYKEVKKDLIIKLPK

YSLFELENGRKRMLASAGELQKGNELALPSKYVNFLYLASHYEKLKGSPE

DNEQKQLFVEQHKHYLDEIIEQISEFSKRVILADANLDKVLSAYNKHRDK

PIREQAENIIHLFTLTNLGAPAAFKYFDTTIDRKRYTSTKEVLDATLIHQ

SITGLYETRIDLSQLGGD
```

Methods for generating a Cas9 protein (or a fragment thereof) having an inactive DNA cleavage domain are known (See, e.g., Jinek et al., *Science.* 337:816-821(2012); Qi et al., "Repurposing CRISPR as an RNA-Guided Platform for Sequence-Specific Control of Gene Expression" (2013) *Cell.* 28; 152(5):1173-83, the entire contents of each of which are incorporated herein by reference). For example, the DNA cleavage domain of Cas9 is known to include two subdomains, the HNH nuclease subdomain and the RuvC1 subdomain. The HNH subdomain cleaves the strand complementary to the gRNA, whereas the RuvC1 subdomain cleaves the non-complementary strand. Mutations within these subdomains can silence the nuclease activity of Cas9. For example, the mutations D10A and H840A completely inactivate the nuclease activity of *S. pyogenes* Cas9 (See e.g., Jinek et al., *Science.* 337:816-821(2012); Qi et al., *Cell.* 28; 152(5):1173-83 (2013)). In some embodiments, proteins comprising fragments of Cas9 are provided. For example, in some embodiments, a protein comprises one of two Cas9 domains: (1) the gRNA binding domain of Cas9; or (2) the DNA cleavage domain of Cas9. In some embodiments, proteins comprising Cas9, or fragments thereof, are referred to as "Cas9 variants." A Cas9 variant shares homology to Cas9, or a fragment thereof. For example, a Cas9 variant is at least about 70% identical, at least about 80% identical, at least about 85% identical, at least about 90% identical, at least about 95% identical, at least about 98% identical, at least about 99% identical, at least about 99.5% identical, or at least about 99.9% to wild type Cas9. In some embodiments, the Cas9 variant comprises a fragment of Cas9 (e.g., a gRNA binding domain or a DNA-cleavage domain), such that the fragment is at least about 70% identical, at least about 80% identical, at least about 85% identical, at least about 90% identical, at least about 95% identical, at least about 98% identical, at least about 99% identical, at least about 99.5% identical, or at least about 99.9% to the corresponding fragment of wild type Cas9. In some embodiments, wild type Cas9 corresponds to Cas9 from *Streptococcus pyogenes* (NCBI Reference Sequence: NC_017053.1, SEQ ID NO: 2 (nucleotide); SEQ ID NO: 3 (amino acid)). In some embodiments the Cas9 domain comprises an amino acid sequence that is at least 60%, at least 65%, at least 70%, at least 75%, at least 80%, at least 85%, at least 90%, at least 95%, at least 96%, at least 97%, at least 98%, at least 99%, or at least 99.5% identical to wild type Cas9. In some embodiments, the Cas9 domain comprises an amino acid sequence that has 1, 2, 3, 4, 5, 6, 7, 8, 9, 10, 11, 12, 13, 14, 15, 16, 17, 18, 19, 20, 21, 22, 21, 24, 25, 26, 27, 28, 29, 30, 31, 32, 33, 34, 35, 36, 37, 38, 39, 40, 41, 42, 43, 44, 45, 46, 47, 48, 49, 50 or more or more mutations compared to wild type Cas9. In some embodiments, the Cas9 domain comprises an amino acid sequence that has at least 10, at least 15, at least 20, at least 30, at least 40, at least 50, at least 60, at least 70, at least 80, at least 90, at least 100, at least 150, at least 200, at least 250, at least 300, at least 350, at least 400, at least 500, at least 600, at least 700, at least 800, at least 900, at least 1000, at least 1100, or at least 1200 identical contiguous amino acid residues as compared to wild type Cas9. In some embodiments, the Cas9 variant comprises a fragment of Cas9 (e.g., a gRNA binding domain or a DNA-cleavage domain), such that the fragment is at least about 70% identical, at least about 80% identical, at least about 90% identical, at least about 95% identical, at least about 96% identical, at least about 97% identical, at least about 98% identical, at least about 99% identical, at least about 99.5% identical, or at least about 99.9% identical to the corresponding fragment of wild type Cas9. In some embodiments, the fragment is at least 30%, at least 35%, at least 40%, at least 45%, at least 50%, at least 55%, at least 60%, at least 65%, at least 70%, at least 75%, at least 80%, at least 85%, at least 90%, at least 95% identical, at least 96%, at least 97%, at least 98%, at least 99%, or at least 99.5% of the amino acid length of a corresponding wild type Cas9.

In some embodiments, the fragment is at least 100 amino acids in length. In some embodiments, the fragment is at least 100, 150, 200, 250, 300, 350, 400, 450, 500, 550, 600, 650, 700, 750, 800, 850, 900, 950, 1000, 1050, 1100, 1150, 1200, 1250, or 1300 amino acids in length.

```
                                                (SEQ ID NO: 2)
ATGGATAAGAAATACTCAATAGGCTTAGATATCGGCACAAATAGCGTCGG

ATGGGCGGTGATCACTGATGATTATAAGGTTCCGTCTAAAAAGTTCAAGG

TTCTGGGAAATACAGACCGCCACAGTATCAAAAAAAATCTTATAGGGGCT

CTTTTATTTGGCAGTGGAGAGACAGCGGAAGCGACTCGTCTCAAACGGAC

AGCTCGTAGAAGGTATACACGTCGGAAGAATCGTATTTGTTATCTACAGG

AGATTTTTTCAAATGAGATGGCGAAAGTAGATGATAGTTTCTTTCATCGA

CTTGAAGAGTCTTTTTTGGTGGAAGAAGACAAGAAGCATGAACGTCATCC

TATTTTTGGAAATATAGTAGATGAAGTTGCTTATCATGAGAAATATCCAA

CTATCTATCATCTGCGAAAAAAATTGGCAGATTCTACTGATAAAGCGGAT

TTGCGCTTAATCTATTTGGCCTTAGCGCATATGATTAAGTTTCGTGGTCA

TTTTTTGATTGAGGGAGATTTAAATCCTGATAATAGTGATGTGGACAAAC

TATTTATCCAGTTGGTACAAATCTACAATCAATTATTTGAAGAAAACCCT

ATTAACGCAAGTAGAGTAGATGCTAAAGCGATTCTTTCTGCACGATTGAG

TAAATCAAGACGATTAGAAAATCTCATTGCTCAGCTCCCCGGTGAGAAGA

GAAATGGCTTGTTTGGGAATCTCATTGCTTTGTCATTGGGATTGACCCCT

AATTTTAAATCAAATTTTGATTTGGCAGAAGATGCTAAATTACAGCTTTC

AAAAGATACTTACGATGATGATTTAGATAATTTATTGGCGCAAATTGGAG

ATCAATATGCTGATTTGTTTTTGGCAGCTAAGAATTTATCAGATGCTATT

TTACTTTCAGATATCCTAAGAGTAAATAGTGAAATAACTAAGGCTCCCCT

ATCAGCTTCAATGATTAAGCGCTACGATGAACATCATCAAGACTTGACTC

TTTTAAAAGCTTTAGTTCGACAACAACTTCCAGAAAAGTATAAAGAAATC

TTTTTTGATCAATCAAAAAACGGATATGCAGGTTATATTGATGGGGGAGC

TAGCCAAGAAGAATTTTATAAATTTATCAAACCAATTTTAGAAAAAATGG

ATGGTACTGAGGAATTATTGGTGAAACTAAATCGTGAAGATTTGCTGCGC

AAGCAACGGACCTTTGACAACGGCTCTATTCCCCATCAAATTCACTTGGG

TGAGCTGCATGCTATTTTGAGAAGACAAGAAGACTTTTATCCATTTTTAA

AAGACAATCGTGAGAAGATTGAAAAAATCTTGACTTTTCGAATTCCTTAT

TATGTTGGTCCATTGGCGCGTGGCAATAGTCGTTTTGCATGGATGACTCG

GAAGTCTGAAGAAACAATTACCCCATGGAATTTTGAAGAAGTTGTCGATA

AAGGTGCTTCAGCTCAATCATTTATTGAACGCATGACAAACTTTGATAAA

AATCTTCCAAATGAAAAAGTACTACCAAAACATAGTTTGCTTTATGAGTA

TTTTACGGTTTATAACGAATTGACAAAGGTCAAATATGTTACTGAGGGAA

TGCGAAAACCAGCATTTCTTTCAGGTGAACAGAAGAAAGCCATTGTTGAT

TTACTCTTCAAAACAAATCGAAAAGTAACCGTTAAGCAATTAAAAGAAGA

TTATTTCAAAAAAATAGAATGTTTTGATAGTGTTGAAATTTCAGGAGTTG
```

-continued

AAGATAGATTTAATGCTTCATTAGGCGCCTACCATGATTTGCTAAAAATT

ATTAAAGATAAAGATTTTTTGGATAATGAAGAAAATGAAGATATCTTAGA

GGATATTGTTTTAACATTGACCTTATTTGAAGATAGGGGGATGATTGAGG

AAAGACTTAAAACATATGCTCACCTCTTTGATGATAAGGTGATGAAACAG

CTTAAACGTCGCCGTTATACTGGTTGGGGACGTTTGTCTCGAAAATTGAT

TAATGGTATTAGGGATAAGCAATCTGGCAAAACAATATTAGATTTTTTGA

AATCAGATGGTTTTGCCAATCGCAATTTTATGCAGCTGATCCATGATGAT

AGTTTGACATTTAAAGAAGATATTCAAAAAGCACAGGTGTCTGGACAAGG

CCATAGTTTACATGAACAGATTGCTAACTTAGCTGGCAGTCCTGCTATTA

AAAAAGGTATTTTACAGACTGTAAAAATTGTTGATGAACTGGTCAAAGTA

ATGGGGCATAAGCCAGAAAATATCGTTATTGAAATGGCACGTGAAAATCA

GACAACTCAAAAGGGCCAGAAAAATTCGCGAGAGCGTATGAAACGAATCG

AAGAAGGTATCAAAGAATTAGGAAGTCAGATTCTTAAAGAGCATCCTGTT

GAAAATACTCAATTGCAAAATGAAAAGCTCTATCTCTATTATCTACAAAA

TGGAAGAGACATGTATGTGGACCAAGAATTAGATATTAATCGTTTAAGTG

ATTATGATGTCGATCACATTGTTCCACAAAGTTTCATTAAAGACGATTCA

ATAGACAATAAGGTACTAACGCGTTCTGATAAAAATCGTGGTAAATCGGA

TAACGTTCCAAGTGAAGAAGTAGTCAAAAAGATGAAAAACTATTGGAGAC

AACTTCTAAACGCCAAGTTAATCACTCAACGTAAGTTTGATAATTTAACG

AAAGCTGAACGTGGAGGTTTGAGTGAACTTGATAAAGCTGGTTTTATCAA

ACGCCAATTGGTTGAAACTCGCCAAATCACTAAGCATGTGGCACAAATTT

TGGATAGTCGCATGAATACTAAATACGATGAAAATGATAAACTTATTCGA

GAGGTTAAAGTGATTACCTTAAAATCTAAATTAGTTTCTGACTTCCGAAA

AGATTTCCAATTCTATAAAGTACGTGAGATTAACAATTACCATCATGCCC

ATGATGCGTATCTAAATGCCGTCGTTGGAACTGCTTTGATTAAGAAATAT

CCAAAACTTGAATCGGAGTTTGTCTATGGTGATTATAAAGTTTATGATGT

TCGTAAAATGATTGCTAAGTCTGAGCAAGAAATAGGCAAAGCAACCGCAA

AATATTTCTTTTACTCTAATATCATGAACTTCTTCAAAACAGAAATTACA

CTTGCAAATGGAGAGATTCGCAAACGCCCTCTAATCGAAACTAATGGGGA

AACTGGAGAAATTGTCTGGGATAAAGGGCGAGATTTTGCCACAGTGCGCA

AAGTATTGTCCATGCCCCAAGTCAATATTGTCAAGAAAACAGAAGTACAG

ACAGGCGGATTCTCCAAGGAGTCAATTTTACCAAAAAGAAATTCGGACAA

GCTTATTGCTCGTAAAAAAGACTGGGATCCAAAAAAATATGGTGGTTTTG

ATAGTCCAACGGTAGCTTATTCAGTCCTAGTGGTTGCTAAGGTGGAAAAA

GGGAAATCGAAGAAGTTAAAATCCGTTAAAGAGTTACTAGGGATCACAAT

TATGGAAAGAAGTTCCTTTGAAAAAAATCCGATTGACTTTTTAGAAGCTA

AAGGATATAAGGAAGTTAAAAAAGACTTAATCATTAAACTACCTAAATAT

AGTCTTTTTGAGTTAGAAAACGGTCGTAAACGGATGCTGGCTAGTGCCGG

AGAATTACAAAAAGGAAATGAGCTGGCTCTGCCAAGCAAATATGTGAATT

TTTTATATTTAGCTAGTCATTATGAAAAGTTGAAGGGTAGTCCAGAAGAT

AACGAACAAAAACAATTGTTTGTGGAGCAGCATAAGCATTATTTAGATGA

GATTATTGAGCAAATCAGTGAATTTTCTAAGCGTGTTATTTTAGCAGATG

CCAATTTAGATAAAGTTCTTAGTGCATATAACAAACATAGAGACAAACCA

ATACGTGAACAAGCAGAAAATATTATTCATTTATTTACGTTGACGAATCT

TGGAGCTCCCGCTGCTTTTAAATATTTTGATACAACAATTGATCGTAAAC

GATATACGTCTACAAAAGAAGTTTTAGATGCCACTCTTATCCATCAATCC

ATCACTGGTCTTTATGAAACACGCATTGATTTGAGTCAGCTAGGAGGTGA

CTGA (SEQ ID NO: 3)

MDKKYSIGLDIGTNSVGWAVITDDYKVPSKKFKVLGNTDRHSIKKNLIGA

LLFGSGETAEATRLKRTARRRYTRRKNRICYLQEIFSNEMAKVDDSFFHR

LEESFLVEEDKKHERHPIFGNIVDEVAYHEKYPTIYHLRKKLADSTDKAD

LRLIYLALAHMIKFRGHFLIEGDLNPDNSDVDKLFIQLVQIYNQLFEENP

INASRVDAKAILSARLSKSRRLENLIAQLPGEKRNGLFGNLIALSLGLTP

NFKSNFDLAEDAKLQLSKDTYDDDLDNLLAQIGDQYADLFLAAKNLSDAI

LLSDILRVNSEITKAPLSASMIKRYDEHHQDLTLLKALVRQQLPEKYKEI

FFDQSKNGYAGYIDGGASQEEFYKFIKPILEKMDGTEELLVKLNREDLLR

KQRTFDNGSIPHQIHLGELHAILRRQEDFYPFLKDNREKIEKILTFRIPY

YVGPLARGNSRFAWMTRKSEETITPWNFEEVVDKGASAQSFIERMTNFDK

NLPNEKVLPKHSLLYEYFTVYNELTKVKYVTEGMRKPAFLSGEQKKAIVD

LLFKTNRKVTVKQLKEDYFKKIECFDSVEISGVEDRFNASLGAYHDLLKI

IKDKDFLDNEENEDILEDIVLTLTLFEDRGMIEERLKTYAHLFDDKVMKQ

LKRRRYTGWGRLSRKLINGIRDKQSGKTILDFLKSDGFANRNFMQLIHDD

SLTFKEDIQKAQVSGQGHSLHEQIANLAGSPAIKKGILQTVKIVDELVKV

MGHKPENIVIEMARENQTTQKGQKNSRERMKRIEEGIKELGSQILKEHPV

ENTQLQNEKLYLYYLQNGRDMYVDQELDINRLSDYDVDHIVPQSFIKDDS

IDNKVLTRSDKNRGKSDNVPSEEVVKKMKNYWRQLLNAKLITQRKFDNLT

KAERGGLSELDKAGFIKRQLVETRQITKHVAQILDSRMNTKYDENDKLIR

EVKVITLKSKLVSDFRKDFQFYKVREINNYHHAHDAYLNAVVGTALIKKY

PKLESEFVYGDYKVYDVRKMIAKSEQEIGKATAKYFFYSNIMNFFKTEIT

LANGEIRKRPLIETNGETGEIVWDKGRDFATVRKVLSMPQVNIVKKTEVQ

TGGFSKESILPKRNSDKLIARKKDWDPKKYGGFDSPTVAYSVLVVAKVEK

GKSKKLKSVKELLGITIMERSSFEKNPIDFLEAKGYKEVKKDLIIKLPKY

SLFELENGRKRMLASAGELQKGNELALPSKYVNFLYLASHYEKLKGSPED

NEQKQLFVEQHKHYLDEIIEQISEFSKRVILADANLDKVLSAYNKHRDKP

IREQAENIIHLFTLTNLGAPAAFKYFDTTIDRKRYTSTKEVLDATLIHQS

ITGLYETRIDLSQLGGD

In some embodiments, wild type Cas9 corresponds to or comprises, SEQ ID NO: 4 (nucleotide) and/or SEQ ID NO: 5 (amino acid).

(SEQ ID NO: 4)

ATGGATAAAAAGTATTCTATTGGTTTAGACATCGGCAC

TAATTCCGTTGGATGGGCTGTCATAACCGATGAATAC

-continued

AAAGTACCTTCAAAGAAATTTAAGGTGTTGGGGAACAC

AGACCGTCATTCGATTAAAAAGAATCTTATCGGTGCC

CTCCTATTCGATAGTGGCGAAACGGCAGAGGCGACTCG

CCTGAAACGAACCGCTCGGAGAAGGTATACACGTCGC

AAGAACCGAATATGTTACTTACAAGAAATTTTTAGCAA

TGAGATGGCCAAAGTTGACGATTCTTTCTTTCACCGT

TTGGAAGAGTCCTTCCTTGTCGAAGAGGACAAGAAACA

TGAACGGCACCCCATCTTTGGAAACATAGTAGATGAG

GTGGCATATCATGAAAAGTACCCAACGATTTATCACCT

CAGAAAAAAGCTAGTTGACTCAACTGATAAAGCGGAC

CTGAGGTTAATCTACTTGGCTCTTGCCCATATGATAAA

GTTCCGTGGGCACTTTCTCATTGAGGGTGATCTAAAT

CCGGACAACTCGGATGTCGACAAACTGTTCATCCAGTT

AGTACAAACCTATAATCAGTTGTTTGAAGAGAACCCT

ATAAATGCAAGTGGCGTGGATGCGAAGGCTATTCTTAG

CGCCCGCCTCTCTAAATCCCGACGGCTAGAAAACCTG

ATCGCACAATTACCCGGAGAGAAGAAAAATGGGTTGTT

CGGTAACCTTATAGCGCTCTCACTAGGCCTGACACCA

AATTTTAAGTCGAACTTCGACTTAGCTGAAGATGCCAA

ATTGCAGCTTAGTAAGGACACGTACGATGACGATCTC

GACAATCTACTGGCACAAATTGGAGATCAGTATGCGGA

CTTATTTTTGGCTGCCAAAAACCTTAGCGATGCAATC

CTCCTATCTGACATACTGAGAGTTAATACTGAGATTAC

CAAGGCGCCGTTATCCGCTTCAATGATCAAAAGGTAC

GATGAACATCACCAAGACTTGACACTTCTCAAGGCCCT

AGTCCGTCAGCAACTGCCTGAGAAATATAAGGAAATA

TTCTTTGATCAGTCGAAAAACGGGTACGCAGGTTATAT

TGACGGCGGAGCGAGTCAAGAGGAATTCTACAAGTTT

ATCAAACCCATATTAGAGAAGATGGATGGGACGGAAGA

GTTGCTTGTAAAACTCAATCGCGAAGATCTACTGCGA

AAGCAGCGGACTTTCGACAACGGTAGCATTCCACATCA

AATCCACTTAGGCGAATTGCATGCTATACTTAGAAGG

CAGGAGGATTTTTATCCGTTCCTCAAAGACAATCGTGA

AAAGATTGAGAAAATCCTAACCTTTCGCATACCTTAC

TATGTGGGACCCCTGGCCCGAGGGAACTCTCGGTTCGC

ATGGATGACAAGAAAGTCCGAAGAAACGATTACTCCA

TGGAATTTTGAGGAAGTTGTCGATAAAGGTGCGTCAGC

TCAATCGTTCATCGAGAGGATGACCAACTTTGACAAG

AATTTACCGAACGAAAAAGTATTGCCTAAGCACAGTTT

ACTTTACGAGTATTTCACAGTGTACAATGAACTCACG

AAAGTTAAGTATGTCACTGAGGGCATGCGTAAACCCGC

-continued

CTTTCTAAGCGGAGAACAGAAGAAAGCAATAGTAGAT

CTGTTATTCAAGACCAACCGCAAAGTGACAGTTAAGCA

ATTGAAAGAGGACTACTTTAAGAAAATTGAATGCTTC

GATTCTGTCGAGATCTCCGGGGTAGAAGATCGATTTAA

TGCGTCACTTGGTACGTATCATGACCTCCTAAAGATA

ATTAAAGATAAGGACTTCCTGGATAACGAAGAGAATGA

AGATATCTTAGAAGATATAGTGTTGACTCTTACCCTC

TTTGAAGATCGGGAAATGATTGAGGAAAGACTAAAAAC

ATACGCTCACCTGTTCGACGATAAGGTTATGAAACAG

TTAAAGAGGCGTCGCTATACGGGCTGGGGACGATTGTC

GCGGAAACTTATCAACGGGATAAGAGACAAGCAAAGT

GGTAAAACTATTCTCGATTTTCTAAAGAGCGACGGCTT

CGCCAATAGGAACTTTATGCAGCTGATCCATGATGAC

TCTTTAACCTTCAAAGAGGATATACAAAAGGCACAGGT

TTCCGGACAAGGGGACTCATTGCACGAACATATTGCG

AATCTTGCTGGTTCGCCAGCCATCAAAAAGGGCATACT

CCAGACAGTCAAAGTAGTGGATGAGCTAGTTAAGGTC

ATGGGACGTCACAAACCGGAAAACATTGTAATCGAGAT

GGCACGCGAAAATCAAACGACTCAGAAGGGGCAAAAA

AACAGTCGAGAGCGGATGAAGAGAATAGAAGAGGGTAT

TAAAGAACTGGGCAGCCAGATCTTAAAGGAGCATCCT

GTGGAAAATACCCAATTGCAGAACGAGAAACTTTACCT

CTATTACCTACAAAATGGAAGGGACATGTATGTTGAT

CAGGAACTGGACATAAACCGTTTATCTGATTACGACGT

CGATCACATTGTACCCCAATCCTTTTTGAAGGACGAT

TCAATCGACAATAAAGTGCTTACACGCTCGGATAAGAA

CCGAGGGAAAAGTGACAATGTTCCAAGCGAGGAAGTC

GTAAAGAAAATGAAGAACTATTGGCGGCAGCTCCTAAA

TGCGAAACTGATAACGCAAAGAAAGTTCGATAACTTA

ACTAAAGCTGAGAGGGGTGGCTTGTCTGAACTTGACAA

GGCCGGATTTATTAAACGTCAGCTCGTGGAAACCCGC

CAAATCACAAAGCATGTTGCACAGATACTAGATTCCCG

AATGAATACGAAATACGACGAGAACGATAAGCTGATT

CGGGAAGTCAAAGTAATCACTTTAAAGTCAAAATTGGT

GTCGGACTTCAGAAAGGATTTTCAATTCTATAAAGTT

AGGGAGATAAATAACTACCACCATGCGCACGACGCTTA

TCTTAATGCCGTCGTAGGGACCGCACTCATTAAGAAA

TACCCGAAGCTAGAAAGTGAGTTTGTGTATGGTGATTA

CAAAGTTTATGACGTCCGTAAGATGATCGCGAAAAGC

GAACAGGAGATAGGCAAGGCTACAGCCAAATACTTCTT

TTATTCTAACATTATGAATTTCTTTAAGACGGAAATC

-continued

ACTCTGGCAAACGGAGAGATACGCAAACGACCTTTAAT

TGAAACCAATGGGGAGACAGGTGAAATCGTATGGGAT

AAGGGCCGGGACTTCGCGACGGTGAGAAAAGTTTTGTC

CATGCCCCAAGTCAACATAGTAAAGAAAACTGAGGTG

CAGACCGGAGGGTTTTCAAAGGAATCGATTCTTCCAAA

AAGGAATAGTGATAAGCTCATCGCTCGTAAAAAGGAC

TGGGACCCGAAAAAGTACGGTGGCTTCGATAGCCCTAC

AGTTGCCTATTCTGTCCTAGTAGTGGCAAAAGTTGAG

AAGGGAAAATCCAAGAAACTGAAGTCAGTCAAAGAATT

ATTGGGGATAACGATTATGGAGCGCTCGTCTTTTGAA

AAGAACCCCATCGACTTCCTTGAGGCGAAAGGTTACAA

GGAAGTAAAAAAGGATCTCATAATTAAACTACCAAAG

TATAGTCTGTTTGAGTTAGAAAATGGCCGAAAACGGAT

GTTGGCTAGCGCCGGAGAGCTTCAAAAGGGGAACGAA

CTCGCACTACCGTCTAAATACGTGAATTTCCTGTATTT

AGCGTCCCATTACGAGAAGTTGAAAGGTTCACCTGAA

GATAACGAACAGAAGCAACTTTTTGTTGAGCAGCACAA

ACATTATCTCGACGAAATCATAGAGCAAATTTCGGAA

TTCAGTAAGAGAGTCATCCTAGCTGATGCCAATCTGGA

CAAAGTATTAAGCGCATACAACAAGCACAGGGATAAA

CCCATACGTGAGCAGGCGGAAAATATTATCCATTTGTT

TACTCTTACCAACCTCGGCGCTCCAGCCGCATTCAAG

TATTTTGACACAACGATAGATCGCAAACGATACACTTC

TACCAAGGAGGTGCTAGACGCGACACTGATTCACCAA

TCCATCACGGGATTATATGAAACTCGGATAGATTTGTC

ACAGCTTGGGGGTGACGGATCCCCCAAGAAGAAGAGG

AAAGTCTCGAGCGACTACAAAGACCATGACGGTGATTA

TAAAGATCATGACATCGATTACAAGGATGACGATGAC

AAGGCTGCAGGA (SEQ ID NO: 5)

MDKKYSIGLAIGTNSVGWAVITDEYKVPSKKFKVLGNT

DRHSIKKNLIGALLFDSGETAEATRLKRTARRRYTRR

KNRICYLQEIFSNEMAKVDDSFFHRLEESFLVEEDKKH

ERHPIFGNIVDEVAYHEKYPTIYHLRKKLVDSTDKAD

LRLIYLALAHMIKFRGHFLIEGDLNPDNSDVDKLFIQL

VQTYNQLFEENPINASGVDAKAILSARLSKSRRLENL

IAQLPGEKKNGLFGNLIALSLGLTPNFKSNFDLAEDAK

LQLSKDTYDDDLDNLLAQIGDQYADLFLAAKNLSDAI

LLSDILRVNTEITKAPLSASMIKRYDEHHQDLTLLKAL

VRQQLPEKYKEIFFDQSKNGYAGYIDGGASQEEFYKF

IKPILEKMDGTEELLVKLNREDLLRKQRTFDNGSIPHQ

-continued

IHLGELHAILRRQEDFYPFLKDNREKIEKILTFRIPY

YVGPLARGNSRFAWMTRKSEETITPWNFEEVVDKGASA

QSFIERMTNFDKNLPNEKVLPKHSLLYEYFTVYNELT

KVKYVTEGMRKPAFLSGEQKKAIVDLLFKTNRKVTVKQ

LKEDYFKKIECFDSVEISGVEDRFNASLGTYHDLLKI

IKDKDFLDNEENEDILEDIVLTLTLFEDREMIEERLKT

YAHLFDDKVMKQLKRRRYTGWGRLSRKLINGIRDKQS

GKTILDFLKSDGFANRNFMQLIHDDSLTFKEDIQKAQV

SGQGDSLHEHIANLAGSPAIKKGILQTVKVVDELVKV

MGRHKPENIVIEMARENQTTQKGQKNSRERMKRIEEGI

KELGSQILKEHPVENTQLQNEKLYLYYLQNGRDMYVD

QELDINRLSDYDVDHIVPQSFLKDDSIDNKVLTRSDKN

RGKSDNVPSEEVVKKMKNYWRQLLNAKLITQRKFDNL

TKAERGGLSELDKAGFIKRQLVETRQITKHVAQILDSR

MNTKYDENDKLIREVKVITLKSKLVSDFRKDFQFYKV

REINNYHHAHDAYLNAVVGTALIKKYPKLESEFVYGDY

KVYDVRKMIAKSEQEIGKATAKYFFYSNIMNFFKTEI

TLANGEIRKRPLIETNGETGEIVWDKGRDFATVRKVLS

MPQVNIVKKTEVQTGGFSKESILPKRNSDKLIARKKD

WDPKKYGGFDSPTVAYSVLVVAKVEKGKSKKLKSVKEL

LGITIMERSSFEKNPIDFLEAKGYKEVKKDLIIKLPK

YSLFELENGRKRMLASAGELQKGNELALPSKYVNFLYL

ASHYEKLKGSPEDNEQKQLFVEQHKHYLDEIIEQISE

FSKRVILADANLDKVLSAYNKHRDKPIREQAENIIHLF

TLTNLGAPAAFKYFDTTIDRKRYTSTKEVLDATLIHQ

SITGLYETRIDLSQLGGD

In some embodiments, Cas9 refers to Cas9 from: *Corynebacterium ulcerans* (NCBI Refs: NC_015683.1, NC_017317.1); *Corynebacterium diphtheria* (NCBI Refs: NC_016782.1, NC_016786.1); *Spiroplasma syrphidicola* (NCBI Ref: NC_021284.1); *Prevotella intermedia* (NCBI Ref: NC_017861.1); *Spiroplasma taiwanense* (NCBI Ref: NC_021846.1); *Streptococcus iniae* (NCBI Ref: NC_021314.1); *Belliella baltica* (NCBI Ref: NC_018010.1); *Psychroflexus torquisl* (NCBI Ref: NC_018721.1); *Streptococcus* thermophiles (NCBI Ref: YP_820832.1), *Listeria innocua* (NCBI Ref: NP_472073.1); *Campylobacter jejuni* (NCBI Ref: YP_002344900.1); or *Neisseria meningitidis* (NCBI Ref: YP_002342100.1) or to a Cas9 from any other organism.

Cas9 recognizes a short motif (PAM motif) in the CRISPR repeat sequences in the target DNA sequence. A "PAM motif," or "protospacer adjacent motif," as used herein, refers a DNA sequence immediately following the DNA sequence targeted by the Cas9 nuclease in the CRISPR bacterial adaptive immune system. PAM is a component of the invading virus or plasmid, but is not a component of the bacterial CRISPR locus. Naturally, Cas9 will not successfully bind to or cleave the target DNA sequence if it is not followed by the PAM sequence. PAM is a targeting component (not found in the bacterial genome) which distinguishes bacterial self from non-self DNA, thereby preventing the CRISPR locus from being targeted and destroyed by the Cas9 nuclease activity.

Wild-type *Streptococcus pyogenes* Cas9 recognizes a canonical PAM sequence (e.g., Cas9 from *Streptococcus thermophiles, Staphylococcus aureus, Neisseria meningitidis*, or *Treponema denticolaor*) and Cas9 variants thereof have been described in the art to have different, or more relaxed PAM requirements. Typically, Cas9 proteins, such as Cas9 from *S. pyogenes* (spCas9), require a canonical NGG PAM sequence to bind a particular nucleic acid region, where the "N" in "NGG" is adenine (A), thymine (T), guanine (G), or cytosine (C), and the G is guanine. This may limit the ability to edit desired bases within a genome. In some embodiments, the base editing fusion proteins provided herein need to be positioned at a precise location, for example, where a target base is within a 4 base region (e.g., a "deamination window"), which is approximately 15 bases upstream of the PAM. See Komor, A. C., et al., "Programmable editing of a target base in genomic DNA without double-stranded DNA cleavage" *Nature* 533, 420-424 (2016), the entire contents of which are hereby incorporated by reference. In some embodiments, the deamination window is within a 2, 3, 4, 5, 6, 7, 8, 9, or 10 base region. In some embodiments, the deamination window is 5, 6, 7, 8, 9, 10, 11, 12, 13, 14, 15, 16, 17, 18, 19, 20, 21, 22, 23, 24, or 25 bases upstream of the PAM. Accordingly, in some embodiments, any of the fusion proteins provided herein may contain a Cas9 domain that is capable of binding a nucleotide sequence that does not contain a canonical (e.g., NGG) PAM sequence. Cas9 domains that bind to non-canonical PAM sequences have been described in the art and would be apparent to the skilled artisan. For example, Cas9 domains that bind non-canonical PAM sequences have been described in Kleinstiver, B. P., et al., "Engineered CRISPR-Cas9 nucleases with altered PAM specificities" *Nature* 523, 481-485 (2015); and Kleinstiver, B. P., et al., "Broadening the targeting range of *Staphylococcus aureus* CRISPR-Cas9 by modifying PAM recognition" *Nature Biotechnology* 33, 1293-1298 (2015); the entire contents of each are hereby incorporated by reference. See also: Klenstiver et al., *Nature* 529, 490-495, 2016; Ran et al., *Nature*, April 9; 520(7546): 186-191, 2015; Hou et al., *Proc Natl Acad Sci USA,* 110 (39):15644-9, 2014; Prykhozhij et al., *PLoS One,* 10(3): e0119372, 2015; Zetsche et al., *Cell* 163, 759-771, 2015; Gao et al., *Nature Biotechnology*, doi:10.1038/nbt.3547, 2016; Want et al., *Nature* 461, 754-761, 2009; Chavez et al., doi: dx dot doi dot org/10.1101/058974; Fagerlund et al., *Genome Biol.* 2015; 16: 25, 2015; Zetsche et al., *Cell,* 163, 759-771, 2015; and Swarts et al., *Nat Struct Mol Biol,* 21(9):743-53, 2014, the entire contents of each of which is incorporated herein by reference.

Thus, the guide nucleotide sequence-programmable DNA-binding protein of the present disclosure may recognize a variety of PAM sequences including, without limitation: NGG, NGAN (SEQ ID NO: 741), NGNG (SEQ ID NO: 742), NGAG (SEQ ID NO: 743), NGCG (SEQ ID NO: 744), NNGRRT (SEQ ID NO: 745), NGRRN (SEQ ID NO: 746), NNNRRT (SEQ ID NO: 747), NNNGATT (SEQ ID NO: 748), NNAGAAW (SEQ ID NO: 749), NAAAC (SEQ ID NO: 750), TTN, TTTN (SEQ ID NO: 751), and YTN, wherein Y is a pyrimidine, and N is any nucleobase.

One example of an RNA-programmable DNA-binding protein that has different PAM specificity is Clustered Regularly Interspaced Short Palindromic Repeats from *Prevotella* and *Francisella* 1 (Cpf1). Similar to Cas9, Cpf1 is also a class 2 CRISPR effector. It has been shown that Cpf1 mediates robust DNA interference with features distinct from Cas9. Cpf1 is a single RNA-guided endonuclease lacking tracrRNA, and it utilizes a T-rich protospacer-adjacent motif (TTN, TTTN (SEQ ID NO: 751), or YTN). Moreover, Cpf1 cleaves DNA via a staggered DNA double-stranded break. Out of 16 Cpf1-family proteins, two enzymes from Acidaminococcus and Lachnospiraceae are shown to have efficient genome-editing activity in human cells.

Also provided herein are nuclease-inactive Cpf1 (dCpf1) variants that may be used as a RNA-programmable DNA-binding protein domain. The Cpf1 protein has a RuvC-like endonuclease domain that is similar to the RuvC domain of Cas9 but does not have a HNH endonuclease domain, and the N-terminal of Cpf1 does not have the alpha-helical recognition lobe of Cas9. It was shown in Zetsche et al., *Cell,* 163, 759-771, 2015 (the entire contents of which is incorporated herein by reference) that the RuvC-like domain of Cpf1 is responsible for cleaving both DNA strands and inactivation of the RuvC-like domain inactivates Cpf1 nuclease activity. For example, mutations corresponding to D917A, E1006A, or D1255A in *Francisella novicida* Cpf1 (SEQ ID NO: 714) inactivates Cpf1 nuclease activity. In some embodiments, the dCpf1 of the present disclosure comprises mutations corresponding to D917A, E1006A, D1255A, D917A/E1006A, D917A/D1255A, E1006A/D1255A, or D917A/E1006A/D1255A in SEQ ID NO: 714. It is to be understood that any mutations, e.g., substitution mutations, deletions, or insertions that inactivates the RuvC domain of Cpf1 may be used in accordance with the present disclosure.

In some embodiments, the guide nucleotide sequence-programmable DNA-binding protein domain of the present disclosure has no requirements for a PAM sequence. One example of such a guide nucleotide sequence-programmable DNA-binding protein may be an Argonaute protein from *Natronobacterium gregoryi* (NgAgo). NgAgo is a ssDNA-guided endonuclease. NgAgo binds 5' phosphorylated ssDNA of ~24 nucleotides (gDNA) to guide it to its target site and will make DNA double-strand breaks at gDNA site. In contrast to Cas9, the NgAgo-gDNA system does not require a protospacer-adjacent motif (PAM). Using a nuclease inactive NgAgo (dNgAgo) can greatly expand the codons that may be targeted. The characterization and use of NgAgo have been described in Gao et al., *Nat Biotechnol. Epub* 2016 May 2. PubMed PMID: 27136078; Swarts et al., *Nature.* 507(7491) (2014):258-61; and Swarts et al., *Nucleic Acids Res.* 43(10) (2015):5120-9, the entire contents of each of which are incorporated herein by reference. The sequence of *Natronobacterium gregoryi* Argonaute is provided in SEQ ID NO: 718.

Also provided herein are Cas9 variants that have relaxed PAM requirements (PAMless Cas9). PAMless Cas9 exhibits an increased activity on a target sequence that does not comprise a canonical PAM (NGG) at its 3'-end as compared to *Streptococcus pyogenes* Cas9 as provided by SEQ ID NO: 1, e.g., increased activity by at least 5-fold, at least 10-fold, at least 50-fold, at least 100-fold, at least 500-fold, at least 1,000-fold, at least 5,000-fold, at least 10,000-fold, at least 50,000-fold, at least 100,000-fold, at least 500,000-fold, or at least 1,000,000-fold. Thus, the dCas9 or Cas9 nickase of the present disclosure may further comprise mutations that relax the PAM requirements, e.g., mutations that correspond to A262T, K294R, S409I, E480K, E543D, M694I, or E1219V in SEQ ID NO: 1.

It should be appreciated that additional Cas9 proteins (e.g., a nuclease dead Cas9 (dCas9), a Cas9 nickase (nCas9), or a nuclease active Cas9), including variants and homologs thereof, are within the scope of this disclosure. Exemplary Cas9 proteins include, without limitation, those provided below. In some embodiments, the Cas9 protein is a nuclease dead Cas9 (dCas9). In some embodiments, the dCas9 comprises the amino acid sequence shown below. In some embodiments, the Cas9 protein is a Cas9 nickase (nCas9). In some embodiments, the nCas9 comprises the amino acid sequence shown below. In some embodiments, the Cas9 protein is a nuclease active Cas9. In some embodiments, the nuclease active Cas9 comprises the amino acid sequence shown below.

```
Exemplary catalytically inactive Cas9 (dCas9):
                                              (SEQ ID NO: 752)
DKKYSIGLAIGTNSVGWAVITDEYKVPSKKFKVLGNTDRHSIKKNLIGALLFDSGETA

EATRLKRTARRRYTRRKNRICYLQEIFSNEMAKVDDSFFHRLEESFLVEEDKKHERH

PIFGNIVDEVAYHEKYPTIYHLRKKLVDSTDKADLRLIYLALAHMIKFRGHFLIEGDL

NPDNSDVDKLFIQLVQTYNQLFEENPINASGVDAKAILSARLSKSRRLENLIAQLPGE

KKNGLFGNLIALSLGLTPNFKSNFDLAEDAKLQLSKDTYDDDLDNLLAQIGDQYADL

FLAAKNLSDAILLSDILRVNTEITKAPLSASMIKRYDEHHQDLTLLKALVRQQLPEKY

KEIFFDQSKNGYAGYIDGGASQEEFYKFIKPILEKMDGTEELLVKLNREDLLRKQRTF

DNGSIPHQIHLGELHAILRRQEDFYPFLKDNREKIEKILTFRIPYYVGPLARGNSRFAW

MTRKSEETITPWNFEEVVDKGASAQSFIERMTNFDKNLPNEKVLPKHSLLYEYFTVY

NELTKVKYVTEGMRKPAFLSGEQKKAIVDLLFKTNRKVTVKQLKEDYFKKIECFDS

VEISGVEDRFNASLGTYHDLLKIIKDKDFLDNEENEDILEDIVLTLTLFEDREMIEERL

KTYAHLFDDKVMKQLKRRRYTGWGRLSRKLINGIRDKQSGKTILDFLKSDGFANRN

FMQLIHDDSLTFKEDIQKAQVSGQGDSLHEHIANLAGSPAIKKGILQTVKVVDELVK

VMGRHKPENIVIEMARENQTTQKGQKNSRERMKRIEEGIKELGSQILKEHPVENTQL

QNEKLYLYYLQNGRDMYVDQELDINRLSDYDVDAIVPQSFLKDDSIDNKVLTRSDK

NRGKSDNVPSEEVVKKMKNYWRQLLNAKLITQRKFDNLTKAERGGLSELDKAGFIK

RQLVETRQITKHVAQILDSRMNTKYDENDKLIREVKVITLKSKLVSDFRKDFQFYKV

REINNYHHAHDAYLNAVVGTALIKKYPKLESEFVYGDYKVYDVRKMIAKSEQEIGK

ATAKYFFYSNIMNFFKTEITLANGEIRKRPLIETNGETGEIVWDKGRDFATVRKVLSM

PQVNIVKKTEVQTGGFSKESILPKRNSDKLIARKKDWDPKKYGGFDSPTVAYSVLVV

AKVEKGKSKKLKSVKELLGITIMERSSFEKNPIDFLEAKGYKEVKKDLIIKLPKYSLFE

LENGRKRMLASAGELQKGNELALPSKYVNFLYLASHYEKLKGSPEDNEQKQLFVEQ

HKHYLDEIIEQISEFSKRVILADANLDKVLSAYNKHRDKPIREQAENIIHLFTLTNLGA

PAAFKYFDTTIDRKRYTSTKEVLDATLIHQSITGLYETRIDLSQLGGD

Exemplary Cas9 nickase (nCas9):
                                              (SEQ ID NO: 753)
DKKYSIGLAIGTNSVGWAVITDEYKVPSKKFKVLGNTDRHSIKKNLIGALLFDSGETA

EATRLKRTARRRYTRRKNRICYLQEIFSNEMAKVDDSFFHRLEESFLVEEDKKHERH

PIFGNIVDEVAYHEKYPTIYHLRKKLVDSTDKADLRLIYLALAHMIKFRGHFLIEGDL

NPDNSDVDKLFIQLVQTYNQLFEENPINASGVDAKAILSARLSKSRRLENLIAQLPGE

KKNGLFGNLIALSLGLTPNFKSNFDLAEDAKLQLSKDTYDDDLDNLLAQIGDQYADL

FLAAKNLSDAILLSDILRVNTEITKAPLSASMIKRYDEHHQDLTLLKALVRQQLPEKY

KEIFFDQSKNGYAGYIDGGASQEEFYKFIKPILEKMDGTEELLVKLNREDLLRKQRTF

DNGSIPHQIHLGELHAILRRQEDFYPFLKDNREKIEKILTFRIPYYVGPLARGNSRFAW

MTRKSEETITPWNFEEVVDKGASAQSFIERMTNFDKNLPNEKVLPKHSLLYEYFTVY

NELTKVKYVTEGMRKPAFLSGEQKKAIVDLLFKTNRKVTVKQLKEDYFKKIECFDS
```

-continued

VEISGVEDRFNASLGTYHDLLKIIKDKDFLDNEENEDILEDIVLTLTLFEDREMIEERL

KTYAHLFDDKVMKQLKRRRYTGWGRLSRKLINGIRDKQSGKTILDFLKSDGFANRN

FMQLIHDDSLTFKEDIQKAQVSGQGDSLHEHIANLAGSPAIKKGILQTVKVVDELVK

VMGRHKPENIVIEMARENQTTQKGQKNSRERMKRIEEGIKELGSQILKEHPVENTQL

QNEKLYLYYLQNGRDMYVDQELDINRLSDYDVDHIVPQSFLKDDSIDNKVLTRSDK

NRGKSDNVPSEEVVKKMKNYWRQLLNAKLITQRKFDNLTKAERGGLSELDKAGFIK

RQLVETRQITKHVAQILDSRMNTKYDENDKLIREVKVITLKSKLVSDFRKDFQFYKV

REINNYHHAHDAYLNAVVGTALIKKYPKLESEFVYGDYKVYDVRKMIAKSEQEIGK

ATAKYFFYSNIMNFFKTEITLANGEIRKRPLIETNGETGEIVWDKGRDFATVRKVLSM

PQVNIVKKTEVQTGGFSKESILPKRNSDKLIARKKDWDPKKYGGFDSPTVAYSVLVV

AKVEKGKSKKLKSVKELLGITIMERSSFEKNPIDFLEAKGYKEVKKDLIIKLPKYSLFE

LENGRKRMLASAGELQKGNELALPSKYVNFLYLASHYEKLKGSPEDNEQKQLFVEQ

HKHYLDEIIEQISEFSKRVILADANLDKVLSAYNKHRDKPIREQAENIIHLFTLTNLGA

PAAFKYFDTTIDRKRYTSTKEVLDATLIHQSITGLYETRIDLSQLGGD

Exemplary catalytically active Cas9:

(SEQ ID NO: 754)

DKKYSIGLDIGTNSVGWAVITDEYKVPSKKFKVLGNTDRHSIKKNLIGALLFDSGETA

EATRLKRTARRRYTRRKNRICYLQEIFSNEMAKVDDSFFHRLEESFLVEEDKKHERH

PIFGNIVDEVAYHEKYPTIYHLRKKLVDSTDKADLRLIYLALAHMIKFRGHFLIEGDL

NPDNSDVDKLFIQLVQTYNQLFEENPINASGVDAKAILSARLSKSRRLENLIAQLPGE

KKNGLFGNLIALSLGLTPNFKSNFDLAEDAKLQLSKDTYDDDLDNLLAQIGDQYADL

FLAAKNLSDAILLSDILRVNTEITKAPLSASMIKRYDEHHQDLTLLKALVRQQLPEKY

KEIFFDQSKNGYAGYIDGGASQEEFYKFIKPILEKMDGTEELLVKLNREDLLRKQRTF

DNGSIPHQIHLGELHAILRRQEDFYPFLKDNREKIEKILTFRIPYYVGPLARGNSRFAW

MTRKSEETITPWNFEEVVDKGASAQSFIERMTNFDKNLPNEKVLPKHSLLYEYFTVY

NELTKVKYVTEGMRKPAFLSGEQKKAIVDLLFKTNRKVTVKQLKEDYFKKIECFDS

VEISGVEDRFNASLGTYHDLLKIIKDKDFLDNEENEDILEDIVLTLTLFEDREMIEERL

KTYAHLFDDKVMKQLKRRRYTGWGRLSRKLINGIRDKQSGKTILDFLKSDGFANRN

FMQLIHDDSLTFKEDIQKAQVSGQGDSLHEHIANLAGSPAIKKGILQTVKVVDELVK

VMGRHKPENIVIEMARENQTTQKGQKNSRERMKRIEEGIKELGSQILKEHPVENTQL

QNEKLYLYYLQNGRDMYVDQELDINRLSDYDVDHIVPQSFLKDDSIDNKVLTRSDK

NRGKSDNVPSEEVVKKMKNYWRQLLNAKLITQRKFDNLTKAERGGLSELDKAGFIK

RQLVETRQITKHVAQILDSRMNTKYDENDKLIREVKVITLKSKLVSDFRKDFQFYKV

REINNYHHAHDAYLNAVVGTALIKKYPKLESEFVYGDYKVYDVRKMIAKSEQEIGK

ATAKYFFYSNIMNFFKTEITLANGEIRKRPLIETNGETGEIVWDKGRDFATVRKVLSM

PQVNIVKKTEVQTGGFSKESILPKRNSDKLIARKKDWDPKKYGGFDSPTVAYSVLVV

AKVEKGKSKKLKSVKELLGITIMERSSFEKNPIDFLEAKGYKEVKKDLIIKLPKYSLFE

LENGRKRMLASAGELQKGNELALPSKYVNFLYLASHYEKLKGSPEDNEQKQLFVEQ

HKHYLDEIIEQISEFSKRVILADANLDKVLSAYNKHRDKPIREQAENIIHLFTLTNLGA

PAAFKYFDTTIDRKRYTSTKEVLDATLIHQSITGLYETRIDLSQLGGD

In some embodiments, Cas9 refers to a Cas9 from arehaea (e.g. nanoarchaea), which constitute a domain and kingdom of single-celled prokaryotic microbes. In some embodiments, Cas9 refers to CasX or CasY, which have been described in, for example, Burstein et al., "New CRISPR-Cas systems from uncultivated microbes." Cell Res. 2017 Feb. 21. doi: 10.1038/cr.2017.21, the entire contents of which is hereby incorporated by reference. Using genome-resolved metagenomics, a number of CRISPR-Cas systems were identified, including the first reported Cas9 in the archaeal domain of life. This divergent Cas9 protein was found in little-studied nanoarchaea as part of an active CRISPR-Cas system. In bacteria, two previously unknown systems were discovered, CRISPR-CasX and CRISPR-CasY, which are among the most compact systems yet discovered. In some embodiments, Cas9 refers to CasX, or a variant of CasX. In some embodiments, Cas9 refers to a CasY, or a variant of CasY. It should be appreciated that other RNA-guided DNA binding proteins may be used as a guide nucleotide sequence-programmable DNA-binding protein, and are within the scope of this disclosure.

In some embodiments, the guide nucleotide sequence-programmable DNA-binding protein domain of any of the fusion proteins provided herein may be a CasX or CasY protein. In some embodiments, guide nucleotide sequence-programmable DNA-binding protein domain is a CasX protein. In some embodiments, the guide nucleotide sequence-programmable DNA-binding protein domain is a CasY protein. In some embodiments, the guide nucleotide sequence-programmable DNA-binding protein domain comprises an amino acid sequence that is at least 85%, at least 90%, at least 91%, at least 92%, at least 93%, at least 94%, at least 95%, at least 96%, at least 97%, at least 98%, at least 99%, or at ease 99.5% identical to a naturally-occurring CasX or CasY protein. In some embodiments, the guide nucleotide sequence-programmable DNA-binding protein domain is a naturally-occurring CasX or CasY protein. In some embodiments, the guide nucleotide sequence-programmable DNA-binding protein domain comprises an amino acid sequence that is at least 85%, at least 90%, at least 91%, at least 92%, at least 93%, at least 94%, at least 95%, at least 96%, at least 97%, at least 98%, at least 99%, or at least 99.5% identical to any one of of the exemplary CasX or CasY proteins described herein. In some embodiments, the guide nucleotide sequence-programmable DNA-binding protein domain comprises an amino acid sequence of any one of of the exemplary CasX or CasY proteins described herein. It should be appreciated that CasX and CasY from other bacterial species may also be used in accordance with the present disclosure.

CasX (uniprot.org/uniprot/F0NN87; uniprot.org/uniprot/F0NH53)
>tr|F0NN87|F0NN87_SULIH CRISPR-associated Casx protein OS = *Sulfolobus islandicus* (strain HVE10/4) GN = SiH_0402 PE = 4 SV = 1

(SEQ ID NO: 755)

MEVPLYNIFGDNYIIQVATEAENSTIYNNKVEIDDEELRNVLNLAYKIAK

NNEDAAAERRGKAKKKKGEEGETTTSNIILPLSGNDKNPWTETLKCYNFP

TTVALSEVFKNFSQVKECEEVSAPSFVKPEFYEFGRSPGMVERTRRVKLE

VEPHYLIIAAAGWVLTRLGKAKVSEGDYVGVNVFTPTRGILYSLIQNVNG

IVPGIKPETAFGLWIARKVVSSVTNPNVSVVRIYTISDAVGQNPTTINGG

-continued

FSIDLTKLLEKRYLLSERLEAIARNALSISSNMRERYIVLANYIYEYLTG

SKRLEDLLYFANRDLIMNLNSDDGKVRDLKLISAYVNGELIRGEG

>tr|F0NH53|F0NH53_SULIR CRISPR associated protein, Casx OS = *Sulfolobus islandicus* (strain REY15A) GN = SiRe_0771 PE = 4 SV = 1

(SEQ ID NO: 756)

MEVPLYNIFGDNYIIQVATEAENSTIYNNKVEIDDEELRNVLNLAYKIAK

NNEDAAAERRGKAKKKKGEEGETTTSNIILPLSGNDKNPWTETLKCYNFP

TTVALSEVFKNFSQVKECEEVSAPSFVKPEFYKFGRSPGMVERTRRVKLE

VEPHYLIMAAAGWVLTRLGKAKVSEGDYVGVNVFTPTRGILYSLIQNVNG

IVPGIKPETAFGLWIARKVVSSVTNPNVSVVSIYTISDAVGQNPTTINGG

FSIDLTKLLEKRDLLSERLEAIARNALSISSNMRERYIVLANYIYEYLTG

SKRLEDLLYFANRDLIMNLNSDDGKVRDLKLISAYVNGELIRGEG

CasY (ncbi.nlm.nih.gov/protein/APG80656.1)

>APG80656.1 CRISPR-associated protein CasY [uncultured *Parcubacteria group bacterium*]

(SEQ ID NO: 757)

MSKRHPRISGVKGYRLHAQRLEYTGKSGAMRTIKYPLYSSPSGGRTVPRE

IVSAINDDYVGLYGLSNFDDLYNAEKRNEEKVYSVLDFWYDCVQYGAVFS

YTAPGLLKNVAEVRGGSYELTKTLKGSHLYDELQIDKVIKFLNKKEISRA

NGSLDKLKKDIIDCFKAEYRERHKDQCNKLADDIKNAKKDAGASLGERQK

KLFRDFFGISEQSENDKPSFTNPLNLTCCLLPFDTVNNNRNRGEVLFNKL

KEYAQKLDKNEGSLEMWEYIGIGNSGTAFSNFLGEGFLGRLRENKITELK

KAMMDITDAWRGQEQEEELEKRLRILAALTIKLREPKFDNHWGGYRSDIN

GKLSSWLQNYINQTVKIKEDLKGHKKDLKKAKEMINRFGESDTKEEAVVS

SLLESIEKIVPDDSADDEKPDIPAIAIYRRFLSDGRLTLNRFVQREDVQE

ALIKERLEAEKKKKPKKRKKKSDAEDEKETIDFKELFPHLAKPLKLVPNF

YGDSKRELYKKYKNAAIYTDALWKAVEKIYKSAFSSSLKNSFFDTDFDKD

FFIKRLQKIFSVYRRFNTDKWKPIVKNSFAPYCDIVSLAENEVLYKPKQS

RSRKSAAIDKNRVRLPSTENIAKAGIALARELSVAGFDWKDLLKKEEHEE

YIDLIELHKTALALLLAVTETQLDISALDFVENGTVKDFMKTRDGNLVLE

GRFLEMFSQSIVFSELRGLAGLMSRKEFITRSAIQTMNGKQAELLYIPHE

FQSAKITTPKEMSRAFLDLAPAEFATSLEPESLSEKSLLKLKQMRYYPHY

FGYELTRTGQGIDGGVAENALRLEKSPVKKREIKCKQYKTLGRGQNKIVL

YVRSSYYQTQFLEWFLHRPKNVQTDVAVSGSFLIDEKKVKTRWNYDALTV

ALEPVSGSERVFVSQPFTIFPEKSAEEEGQRYLGIDIGEYGIAYTALEIT

GDSAKILDQNFISDPQLKTLREEVKGLKLDQRRGTFAMPSTKIARIRESL

VHSLRNRIHHLALKHKAKIVYELEVSRFEEGKQKIKKVYATLKKADVYSE

IDADKNLQTTVWGKLAVASEISASYTSQFCGACKKLWRAEMQVDETITTQ

ELIGTVRVIKGGTLIDAIKDFMRPPIFDENDTPFPKYRDFCDKHHISKKM

RGNSCLFICPFCRANADADIQASQTIALLRYVKEEKKVEDYFERFRKLKN

IKVLGQMKKI

The terms "conjugating," "conjugated," and "conjugation" refer to an association of two entities, for example, of two molecules such as two proteins, two domains (e.g., a binding domain and a cleavage domain), or a protein and an agent, e.g., a protein binding domain and a small molecule. In some aspects, the association is between a protein (e.g., RNA-programmable nuclease) and a nucleic acid (e.g., a guide RNA). The association can be, for example, via a direct or indirect (e.g., via a linker) covalent linkage. In some embodiments, the association is covalent. In some embodiments, two molecules are conjugated via a linker connecting both molecules. For example, in some embodiments where two proteins are conjugated to each other, e.g., a binding domain and a cleavage domain of an engineered nuclease, to form a protein fusion, the two proteins may be conjugated via a polypeptide linker, e.g., an amino acid sequence connecting the C-terminus of one protein to the N-terminus of the other protein.

The term "consensus sequence," as used herein in the context of nucleic acid sequences, refers to a calculated sequence representing the most frequent nucleotide residues found at each position in a plurality of similar sequences. Typically, a consensus sequence is determined by sequence alignment in which similar sequences are compared to each other and similar sequence motifs are calculated. In the context of recombinase target site sequences, a consensus sequence of a recombinase target site may, in some embodiments, be the sequence most frequently bound, or bound with the highest affinity, by a given recombinase.

The term "engineered," as used herein refers to a protein molecule, a nucleic acid, complex, substance, or entity that has been designed, produced, prepared, synthesized, and/or manufactured by a human. Accordingly, an engineered product is a product that does not occur in nature.

The term "effective amount," as used herein, refers to an amount of a biologically active agent that is sufficient to elicit a desired biological response. In some embodiments, an effective amount of a recombinase may refer to the amount of the recombinase that is sufficient to induce recombination at a target site specifically bound and recombined by the recombinase. As will be appreciated by the skilled artisan, the effective amount of an agent, e.g., a nuclease, a recombinase, a hybrid protein, a fusion protein, a protein dimer, a complex of a protein (or protein dimer) and a polynucleotide, or a polynucleotide, may vary depending on various factors as, for example, on the desired biological response, the specific allele, genome, target site, cell, or tissue being targeted, and the agent being used.

A "guide nucleotide sequence-programmable DNA-binding protein," as used herein, refers to a protein, a polypeptide, or a domain that is able to bind DNA, and the binding to its target DNA sequence is mediated by a guide nucleotide sequence. The "guide nucleotide" may be an RNA or DNA molecule (e.g., a single-stranded DNA or ssDNA molecule) that is complementary to the target sequence and can guide the DNA binding protein to the target sequence. As such, a guide nucleotide sequence-programmable DNA-binding protein may be a RNA-programmable DNA-binding protein, or an ssDNA-programmable DNA-binding protein. "Programmable" means the DNA-binding protein may be programmed to bind any DNA sequence that the guide nucleotide targets. The guide nucleotide sequence-programmable DNA-binding protein referred to herein may be any guide nucleotide sequence-programmable DNA-binding protein known in the art without limitation including, but not limited to, a bifurcated or circularly permuted guide nucleotide sequence-programmable DNA-binding protein. The term "circularly permuted" refers to proteins in which the order of the amino acids in a protein has been altered, resulting in a protein structure with altered connectivity but a similar (overall) three-dimensional shape. Circular permutations are formed when the original n and c terminal amino acids are connected via a peptide bond; the peptide sequence is then broken in another location within the peptide sequence, causing a new n and c-terminus. Circular permutations may occur through a number of processes including evolutionary events, post-translational modifications, or artificially engineered mutations. For example, circular permutations may be used to improve the catalytic activity or thermostability of proteins. A circularly permuted guide nucleotide sequence-programmable DNA-binding protein may be used with any of the embodiments described herein. The term "bifurcated" typically refers to a monomeric protein that is split into two parts. Typically both parts are required for the function of the monomeric protein. Bifurcated proteins may or may not dimerize on their own to reconstitute a functional protein. Bifurcations may occur through a number of processes including evolutionary events, post-translational modifications, or artificially engineered mutations. Other protein domains, when fused to bifurcated domains, can be used to force the reassembly of the bifurcated protein. In some cases, protein domains, whose interaction depends on a small molecule, can be fused to each bifurcated domain, resulting in the small-molecule regulated dimerization of the bifurcated protein.

The term "homologous," as used herein, is an art-understood term that refers to nucleic acids or polypeptides that are highly related at the level of nucleotide and/or amino acid sequence. Nucleic acids or polypeptides that are homologous to each other are termed "homologues." Homology between two sequences can be determined by sequence alignment methods known to those of skill in the art. In accordance with the invention, two sequences are considered to be homologous if they are at least about 50-60% identical, e.g., share identical residues (e.g., amino acid residues) in at least about 50-60% of all residues comprised in one or the other sequence, at least about 70% identical, at least about 80% identical, at least about 85% identical, at least about 90% identical, at least about 95% identical, at least about 98% identical, at least about 99% identical, at least about 99.5% identical, or at least about 99.9% identical, for at least one stretch of at least 20, at least 30, at least 40, at least 50, at least 60, at least 70, at least 80, at least 90, at least 100, at least 120, at least 150, or at least 200 amino acids.

The term "sequence identity" or "percent sequence identity" as used herein, may refer to the percentage of nucleic acid or amino acid residues within a given DNA or protein, respectively, that are identical to the reference sequence. See, for example: Christopher M. Holman, Protein Similarity Score: A Simplified Version of the BLAST Score as a Superior Alternative to Percent Identity for Claiming Genuses of Related Protein Sequences, 21 SANTA CLARA COMPUTER & HIGH TECH. L. J. 55, 60 (2004), which is herein incorporated by reference in its entirety.

The term "linker," as used herein, refers to a bond (e.g., covalent bond), chemical group, or a molecule linking two molecules or moieties, e.g., two domains of a fusion protein, such as, for example, a nuclease-inactive Cas9 domain and a nucleic acid-editing domain (e.g., an adenosine deaminase). In some embodiments, a linker joins a gRNA binding domain of an RNA-programmable nuclease, including a Cas9 nuclease domain, and the catalytic domain of a nucleic-acid editing protein. In some embodiments, a linker joins a dCas9 and a nucleic-acid editing protein. Typically, the linker is positioned between, or flanked by, two groups, molecules, or other moieties and connected to each one via a covalent bond, thus connecting the two. In some embodiments, the linker is an amino acid or a plurality of amino acids (e.g., a peptide or protein). In some embodiments, the linker is an organic molecule, group, polymer, or chemical moiety. In some embodiments, the linker is 5-100 amino acids in length, for example, 5, 6, 7, 8, 9, 10, 11, 12, 13, 14, 15, 16, 17, 18, 19, 20, 21, 22, 23, 24, 25, 26, 27, 28, 29, 30, 30-35, 35-40, 40-45, 45-50, 50-60, 60-70, 70-80, 80-90, 90-100, 100-150, or 150-200 amino acids in length. Longer or shorter linkers are also contemplated. In some embodiments, a linker comprises the amino acid sequence SGSETPGTSESATPES (SEQ ID NO: 7), which may also be referred to as the XTEN linker. In some embodiments, a linker comprises the amino acid sequence SGGS (SEQ ID NO: 758). In some embodiments, a linker comprises $(SGGS)_n$ (SEQ ID NO: 758), $(GGGS)_n$ (SEQ ID NO: 759), $(GGGGS)_n$ (SEQ ID NO: 722), $(G)_n$, (EAAAK). (SEQ ID NO: 723), $(GGS)_n$, or $(XP)_n$ motif, or a combination of any of these, wherein n is independently an integer between 1 and 30, and wherein X is any amino acid. In some embodiments, n is 1, 2, 3, 4, 5, 6, 7, 8, 9, 10, 11, 12, 13, 14, or 15.

The term "mutation," as used herein, refers to a substitution of a residue within a sequence, e.g., a nucleic acid or amino acid sequence, with another residue, or a deletion or insertion of one or more residues within a sequence. Mutations are typically described herein by identifying the original residue followed by the position of the residue within the sequence and by the identity of the newly substituted residue. Various methods for making the amino acid substitutions (mutations) provided herein are well known in the art, and are provided by, for example, Green and Sambrook, *Molecular Cloning: A Laboratory Manual* ($4^{th}$ ed., Cold Spring Harbor Laboratory Press, Cold Spring Harbor, N.Y. (2012)).

The term "nuclear localization sequence" or "NLS" refers to an amino acid sequence that promotes import of a protein into the cell nucleus, for example, by nuclear transport. Nuclear localization sequences are known in the art and would be apparent to the skilled artisan. For example, NLS sequences are described in Plank et al., international PCT application, PCT/EP2000/011690, filed Nov. 23, 2000, published as WO/2001/038547 on May 31, 2001, the contents of which are incorporated herein by reference for their disclosure of exemplary nuclear localization sequences. In some embodiments, a NLS comprises the amino acid sequence PKKKRKV (SEQ ID NO: 702) or MDSLLMNRRKFLYQFKNVRWAKGRRETYLC (SEQ ID NO: 761).

The term "nuclease," as used herein, refers to an agent, for example, a protein, capable of cleaving a phosphodiester bond connecting two nucleotide residues in a nucleic acid molecule. In some embodiments, "nuclease" refers to a protein having an inactive DNA cleavage domain, such that the nuclease is incapable of cleaving a phosphodiester bond. In some embodiments, a nuclease is a protein, e.g., an enzyme that can bind a nucleic acid molecule and cleave a phosphodiester bond connecting nucleotide residues within the nucleic acid molecule. A nuclease may be an endonuclease, cleaving a phosphodiester bonds within a polynucleotide chain, or an exonuclease, cleaving a phosphodiester bond at the end of the polynucleotide chain. In some embodiments, a nuclease is a site-specific nuclease, binding and/or cleaving a specific phosphodiester bond within a specific nucleotide sequence, which is also referred to herein as the "recognition sequence," the "nuclease target site," or the "target site." In some embodiments, a nuclease is a RNA-guided (i.e., RNA-programmable) nuclease, which is associated with (e.g., binds to) an RNA (e.g., a guide RNA, "gRNA") having a sequence that complements a target site, thereby providing the sequence specificity of the nuclease. In some embodiments, a nuclease recognizes a single stranded target site, while in other embodiments, a nuclease recognizes a double-stranded target site, for example, a double-stranded DNA target site. The target sites of many naturally occurring nucleases, for example, many naturally occurring DNA restriction nucleases, are well known to those of skill in the art. A nuclease protein typically comprises a "binding domain" that mediates the interaction of the protein with the nucleic acid substrate, and also, in some cases, specifically binds to a target site, and a "cleavage domain" that catalyzes the cleavage of the phosphodiester bond within the nucleic acid backbone. In some embodiments a nuclease protein can bind and cleave a nucleic acid molecule in a monomeric form, while, in other embodiments, a nuclease protein has to dimerize or multimerize in order to cleave a target nucleic acid molecule. Binding domains and cleavage domains of naturally occurring nucleases, as well as modular binding domains and cleavage domains that can be fused to create nucleases binding specific target sites, are well known to those of skill in the art. For example, the binding domain of a guide nucleotide sequence-programmable DNA binding protein such as an RNA-programmable nucleases (e.g., Cas9), or a Cas9 protein having an inactive DNA cleavage domain, can be used as a binding domain (e.g., that binds a gRNA to direct binding to a target site) to specifically bind a desired target site, and fused or conjugated to a cleavage domain.

The terms "nucleic acid" and "nucleic acid molecule," as used herein, refer to a compound comprising a nucleobase and an acidic moiety, e.g., a nucleoside, a nucleotide, or a polymer of nucleotides. Typically, polymeric nucleic acids, e.g., nucleic acid molecules comprising three or more nucleotides are linear molecules, in which adjacent nucleotides are linked to each other via a phosphodiester linkage. In some embodiments, "nucleic acid" refers to individual nucleic acid residues (e.g., nucleotides and/or nucleosides). In some embodiments, "nucleic acid" refers to an oligonucleotide chain comprising three or more individual nucleotide residues. As used herein, the terms "oligonucleotide" and "polynucleotide" can be used interchangeably to refer to a polymer of nucleotides (e.g., a string of at least three nucleotides). In some embodiments, "nucleic acid" encompasses RNA as well as single and/or double-stranded DNA. Nucleic acids may be naturally occurring, for example, in the context of a genome, a transcript, an mRNA, tRNA, rRNA, siRNA, snRNA, gRNA, plasmid, cosmid, chromosome, chromatid, or other naturally occurring nucleic acid molecule. On the other hand, a nucleic acid molecule may be a non-naturally occurring molecule, e.g., a recombinant DNA or RNA, an artificial chromosome, an engineered genome, or fragment thereof, or a synthetic DNA, RNA, DNA/RNA hybrid, or including non-naturally occurring nucleotides or nucleosides. Furthermore, the terms "nucleic acid," "DNA," "RNA," and/or similar terms include nucleic acid analogs, i.e., analogs having other than a phosphodiester backbone. Nucleic acids can be purified from natural sources, produced using recombinant expression systems and optionally purified, chemically synthesized, etc. Where appropriate, e.g., in the case of chemically synthesized molecules, nucleic acids can comprise nucleoside analogs such as analogs having chemically modified bases or sugars, and backbone modifications. A nucleic acid sequence is presented in the 5' to 3' direction unless otherwise indicated. In some embodiments, a nucleic acid is or comprises natural nucleosides (e.g., adenosine, thymidine, guanosine, cytidine, uridine, deoxyadenosine, deoxythymidine, deoxyguanosine, and deoxycytidine); nucleoside analogs (e.g., 2-aminoadenosine, 2-thiothymidine, inosine, pyrrolo-pyrimidine, 3-methyl adenosine, 5-methylcytidine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages).

The term "orthogonal" refers to biological components that interact minimally, if at all. Recombinase target sites containing different gRNA binding sites are orthogonal if the gRNA-directed recCas9 proteins do not interact, or interact minimally, with other potential recombinase sites. The term "orthogonality" refers to the idea that system components can be varied independently without affecting the performance of the other components. The gRNA directed nature of the complex makes the set of gRNA molecules complexed to recCas9 proteins capable of directing recombinase activity at only the gRNA-directed site. Orthogonality of the system is demonstrated by the complete or near complete dependence of the set of gRNA molecules on the enzymatic activity on a targeted recombinase site.

The term "pharmaceutical composition," as used herein, refers to a composition that can be administrated to a subject in the context of treatment and/or prevention of a disease or disorder. In some embodiments, a pharmaceutical composition comprises an active ingredient, e.g., a recombinase fused to a Cas9 protein, or fragment thereof (or a nucleic acid encoding a such a fusion), and optionally a pharmaceutically acceptable excipient. In some embodiments, a pharmaceutical composition comprises inventive Cas9 variant/fusion (e.g., fCas9) protein(s) and gRNA(s) suitable for targeting the Cas9 variant/fusion protein(s) to a target nucleic acid. In some embodiments, the target nucleic acid is a gene. In some embodiments, the target nucleic acid is an allele associated with a disease, wherein the allele is cleaved by the action of the Cas9 variant/fusion protein(s). In some embodiments, the allele is an allele of the CLTA gene, the VEGF gene, the PCDH15, gene or the FAM19A2 gene. See, e.g., the Examples.

The term "proliferative disease," as used herein, refers to any disease in which cell or tissue homeostasis is disturbed in that a cell or cell population exhibits an abnormally elevated proliferation rate. Proliferative diseases include hyperproliferative diseases, such as pre-neoplastic hyperplastic conditions and neoplastic diseases. Neoplastic diseases are characterized by an abnormal proliferation of cells and include both benign and malignant neoplasms. Malignant neoplasia is also referred to as cancer. In some embodiments, the compositions and methods provided herein are useful for treating a proliferative disease. For example, in some embodiments, pharmaceutical compositions comprising Cas9 (e.g., fCas9) protein(s) and gRNA(s) suitable for targeting the Cas9 protein(s) to an VEGF allele, wherein the allele is inactivated by the action of the Cas9 protein(s). See, e.g., the Examples.

The terms "protein," "peptide," and "polypeptide" are used interchangeably herein, and refer to a polymer of amino acid residues linked together by peptide (amide) bonds. The terms refer to a protein, peptide, or polypeptide of any size, structure, or function. Typically, a protein, peptide, or polypeptide will be at least three amino acids long. A protein, peptide, or polypeptide may refer to an individual protein or a collection of proteins. One or more of the amino acids in a protein, peptide, or polypeptide may be modified, for example, by the addition of a chemical entity such as a carbohydrate group, a hydroxyl group, a phosphate group, a farnesyl group, an isofarnesyl group, a fatty acid group, a linker for conjugation, functionalization, or other modification, etc. A protein, peptide, or polypeptide may also be a single molecule or may be a multi-molecular complex. A protein, peptide, or polypeptide may be just a fragment of a naturally occurring protein or peptide. A protein, peptide, or polypeptide may be naturally occurring, recombinant, or synthetic, or any combination thereof. The term "fusion protein" as used herein refers to a hybrid polypeptide that comprises protein domains from at least two different proteins. One protein may be located at the amino-terminal (N-terminal) portion of the fusion protein or at the carboxy-terminal (C-terminal) protein thus forming an "amino-terminal fusion protein" or a "carboxy-terminal fusion protein," respectively. Any of the proteins provided herein may be produced by any method known in the art. For example, the proteins provided herein may be produced via recombinant protein expression and purification, which is especially suited for fusion proteins comprising a peptide linker. Methods for recombinant protein expression and purification are well known, and include those described by Green and Sambrook, *Molecular Cloning: A Laboratory Manual* ($4^{th}$ ed., Cold Spring Harbor Laboratory Press, Cold Spring Harbor, N.Y. (2012)), the entire contents of which are incorporated herein by reference. A specific fusion protein referred to herein is recCas9, an RNA programmed small serine recombinase capable of functioning in mammalian cells created by fusion a catalytically inactive dCas9 to the catalytic domain of recombinase.

A "pseudo-gix" site or a "gix pseudo-site" as discussed herein is a specific pseudo-palindromic core DNA sequence that resembles the Gix recombinases' natural DNA recognition sequence. See, for example, N. D. F. Grindley, K. L. Whiteson, P. A. Rice, Mechanisms of site-specific recombination. *Annu Rev Biochem* 75, 567-605 (2006), which is incorporated by reference herein in its entirety. Similarly, a "pseudo-hix" or "hix-pseudo-site;" a "pseudo-six" or "six-pseudo site;" a "pseudo-resH" or "resH-pseudo-site;" "pseudo-res" or "res-pseudo-site;" "pseudo-LoxP" or "LoxP-pseudo-site;" "pseudo-att" or "att-pseudo-site;" "pseudo-FTR" or "FTR-pseudo-site" is a specific pseudo-palindromic core DNA sequence that resembles the Hin recombinase's, β recombinase's, Sin recombinase's, Tn3 or γδ recombinase's, Cre recombinase's, λ phage integrase's, or FLP recombinase's natural DNA recognition sequence.

The terms "RNA-programmable nuclease" and "RNA-guided nuclease" are used interchangeably herein and refer to a nuclease that forms a complex with (e.g., binds or associates with) one or more RNA that is not a target for cleavage. In some embodiments, an RNA-programmable nuclease, when in a complex with an RNA, may be referred to as a nuclease:RNA complex. Typically, the bound RNA(s) is referred to as a guide RNA (gRNA). gRNAs can exist as a complex of two or more RNAs, or as a single RNA molecule. gRNAs that exist as a single RNA molecule may be referred to as single-guide RNAs (sgRNAs), though "gRNA" is used interchangeabley to refer to guide RNAs that exist as either single molecules or as a complex of two or more molecules. Typically, gRNAs that exist as single RNA species comprise two domains: (1) a domain that shares homology to a target nucleic acid (e.g., and directs binding of a Cas9 complex to the target); and (2) a domain that binds a Cas9 protein. In some embodiments, domain (2) corresponds to a sequence known as a tracrRNA, and comprises a stem-loop structure. For example, in some embodiments, domain (2) is homologous to a tracrRNA as depicted in FIG. 1E of Jinek et al., *Science* 337:816-821 (2012), the entire contents of which is incorporated herein by reference. Other examples of gRNAs (e.g., those including domain 2) can be found in U.S. Provisional Patent Application Ser. No. 61/874,682, filed Sep. 6, 2013, entitled "Switchable Cas9 Nucleases And Uses Thereof;" U.S. Provisional Patent Application Ser. No. 61/874,746, filed Sep. 6, 2013, entitled "Delivery System For Functional Nucleases;" PCT Application WO 2013/176722, filed Mar. 15, 2013, entitled "Methods and Compositions for RNA-Directed Target DNA Modification and for RNA-Directed Modulation of Transcription;" and PCT Application WO 2013/142578, filed Mar. 20, 2013, entitled "RNA-Directed DNA Cleavage by the Cas9-crRNA Complex;" the entire contents of each are hereby incorporated by reference in their entirety. Still other examples of gRNAs are provided herein. See e.g., the Examples. In some embodiments, a gRNA comprises two or more of domains (1) and (2), and may be referred to as an "extended gRNA." For example, an extended gRNA will e.g., bind two or more Cas9 proteins and bind a target nucleic acid at two or more distinct regions, as described herein. The gRNA comprises a nucleotide sequence that complements a target site, which mediates binding of the nuclease/RNA complex to said target site, providing the sequence specificity of the nuclease:RNA complex. In some embodiments, the guide nucleotide sequence-programmable DNA binding protein is an RNA-programmable nuclease such as the (CRISPR-associated system) Cas9 endonuclease, for example, Cas9 (Csn1) from *Streptococcus pyogenes* (see, e.g., "Complete genome sequence of an M1 strain of *Streptococcus pyogenes*." Ferretti J. J., McShan W. M., Ajdic D. J., Savic D. J., Savic G., Lyon K., Primeaux C., Sezate S., Suvorov A. N., Kenton S., Lai H. S., Lin S. P., Qian Y., Jia H. G., Najar F. Z., Ren Q., Zhu H., Song L., White J., Yuan X., Clifton S. W., Roe B. A., McLaughlin R. E., Proc. Natl. Acad. Sci. U.S.A. 98:4658-4663(2001); "CRISPR RNA maturation by trans-encoded small RNA and host factor RNase III." Deltcheva E., Chylinski K., Sharma C. M., Gonzales K., Chao Y., Pirzada Z. A., Eckert M. R., Vogel J., Charpentier E., Nature 471:602-607(2011); and "A programmable dual-RNA-guided DNA endonuclease in adaptive bacterial immunity." Jinek M., Chylinski K., Fonfara I., Hauer M., Doudna J. A., Charpentier E. Science 337:816-821(2012), the entire contents of each of which are incorporated herein by reference.

Because RNA-programmable nucleases (e.g., Cas9) use RNA:DNA hybridization to determine target DNA cleavage sites, these proteins are able to cleave, in principle, any sequence specified by the guide RNA. Methods of using RNA-programmable nucleases, such as Cas9, for site-specific cleavage (e.g., to modify a genome) are known in the art (see e.g., Cong, L. et al. Multiplex genome engineering using CRISPR/Cas systems. *Science* 339, 819-823 (2013); Mali, P. et al. RNA-guided human genome engineering via Cas9. *Science* 339, 823-826 (2013); Hwang, W. Y. et al. Efficient genome editing in zebrafish using a CRISPR-Cas system. *Nature biotechnology* 31, 227-229 (2013); Jinek, M. et al. RNA-programmed genome editing in human cells. *eLife* 2, e00471 (2013); Dicarlo, J. E. et al. Genome engineering in *Saccharomyces cerevisiae* using CRISPR-Cas systems. *Nucleic acids research* (2013); Jiang, W. et al. RNA-guided editing of bacterial genomes using CRISPR-Cas systems. *Nature biotechnology* 31, 233-239 (2013); the entire contents of each of which are incorporated herein by reference).

The term "recombinase," as used herein, refers to a site-specific enzyme that mediates the recombination of DNA between recombinase recognition sequences, which results in the excision, integration, inversion, or exchange (e.g., translocation) of DNA fragments between the recombinase recognition sequences. Recombinases can be classified into two distinct families: serine recombinases (e.g., resolvases and invertases) and tyrosine recombinases (e.g., integrases). Examples of serine recombinases include, without limitation, Hin, Gin, Tn3, β-six, CinH, ParA, γδ, Bxb1, ϕC31, TP901, TG1, ϕBT1, R4, ϕRV1, ϕFC1, MR11, A118, U153, and gp29. Examples of tyrosine recombinases include, without limitation, Cre, FLP, R, Lambda, HK101, HK022, and pSAM2. The Gin recombinase referred to herein may be any Gin recombinase known in the art including, but not limited to, the Gin recombinases presented in T. Gaj et al., A comprehensive approach to zinc-finger recombinase customization enables genomic targeting in human cells. *Nucleic Acids Research* 41, 3937-3946 (2013), incorporated herein by reference in its entirety. In certain embodiments, the Gin recombinase catalytic domain has greater than 85%, 90%, 95%, 98%, or 99% sequence identity with the amino acid sequence shown in SEQ ID NO: 713. In another embodiment, the amino acid sequence of the Gin recombinase catalytic domain comprises a mutation corresponding to H106Y, and/or I127L, and/or I136R and/or G137F. In yet another embodiment, the amino acid sequence of the Gin recombinase catalytic domain comprises a mutation corresponding to H106Y, I127L, I136R, and G137F. In a further embodiment, the amino acid sequence of the Gin recombinase has been further mutated. In a specific embodiment, the amino acid sequence of the Gin recombinase catalytic domain comprises SEQ ID NO: 713. Gin recombinases bind to gix target sites (also referred to herein as "gix core," "minimal gix core," or "gix-related core" sequences). The minimal gix core recombinase site is NNNNAAASSWWSSTTTNNNN (SEQ ID NO: 19), wherein N is defined as any amino acid, W is an A or a T, and S is a G or a C. The gix target site may include any other mutations known in the art. In certain embodiments, the gix target site has greater than 90%, 95%, or 99% sequence identity with the amino acid sequence shown in SEQ ID NO: 19. The distance between the gix core or gix-related core sequence and at least one gRNA binding site may be from 1 to 10 base pairs, from 3 to 7 base pairs, from 5 to 7 base pairs, or from 5 to 6 base pairs. The distance between the gix core or gix-related core sequence and at least one gRNA binding site may be 1, 2, 3, 4, 5, 6, 7, 8, 9, or 10 base pairs.

The serine and tyrosine recombinase names stem from the conserved nucleophilic amino acid residue that the recombinase uses to attack the DNA and which becomes covalently linked to the DNA during strand exchange. Recombinases have numerous applications, including the creation of gene knockouts/knock-ins and gene therapy applications. See, e.g., Brown et al., "Serine recombinases as tools for genome engineering." *Methods.* 2011; 53(4):372-9; Hirano et al., "Site-specific recombinases as tools for heterologous gene integration." *Appl. Microbiol. Biotechnol.* 2011; 92(2): 227-39; Chavez and Calos, "Therapeutic applications of the ΦC31 integrase system." *Curr. Gene Ther.* 2011; 11(5):375-81; Turan and Bode, "Site-specific recombinases: from tag-and-target- to tag-and-exchange-based genomic modifications." *FASEB J.* 2011; 25(12):4088-107; Venken and Bellen, "Genome-wide manipulations of *Drosophila mela-*

*nogaster* with transposons, Flp recombinase, and ΦC31 integrase." *Methods Mol. Biol.* 2012; 859:203-28; Murphy, "Phage recombinases and their applications." *Adv. Virus Res.* 2012; 83:367-414; Zhang et al., "Conditional gene manipulation: Creating a new biological era." *J. Zhejiang Univ. Sci. B.* 2012; 13(7):511-24; Karpenshif and Bernstein, "From yeast to mammals: recent advances in genetic control of homologous recombination." *DNA Repair* (*Amst*). 2012; 1; 11(10):781-8; the entire contents of each are hereby incorporated by reference in their entirety. The recombinases provided herein are not meant to be exclusive examples of recombinases that can be used in embodiments of the invention. The methods and compositions of the invention can be expanded by mining databases for new orthogonal recombinases or designing synthetic recombinases with defined DNA specificities (See, e.g., Groth et al., "Phage integrases: biology and applications." *J. Mol. Biol.* 2004; 335, 667-678; Gordley et al., "Synthesis of programmable integrases." *Proc. Natl. Acad. Sci. USA.* 2009; 106, 5053-5058; the entire contents of each are hereby incorporated by reference in their entirety).

Other examples of recombinases that are useful in the methods and compositions described herein are known to those of skill in the art, and any new recombinase that is discovered or generated is expected to be able to be used in the different embodiments of the invention. In some embodiments, the catalytic domains of a recombinase are fused to a nuclease-inactivated RNA-programmable nuclease (e.g., dCas9, or a fragment thereof), such that the recombinase domain does not comprise a nucleic acid binding domain or is unable to bind to a target nucleic acid that subsequently results in enzymatic catalysis (e.g., the recombinase domain is engineered such that it does not have specific DNA binding activity). Recombinases lacking part of their DNA binding activity and those that act independently of accessory proteins and methods for engineering such are known, and include those described by Klippel et al., "Isolation and characterisation of unusual gin mutants." *EMBO J.* 1988; 7: 3983-3989: Burke et al., "Activating mutations of Tn3 resolvase marking interfaces important in recombination catalysis and its regulation. *Mol Microbiol.* 2004; 51: 937-948; Olorunniji et al., "Synapsis and catalysis by activated Tn3 resolvase mutants." *Nucleic Acids Res.* 2008; 36: 7181-7191; Rowland et al., "Regulatory mutations in Sin recombinase support a structure-based model of the synaptosome." *Mol Microbiol.* 2009; 74: 282-298; Akopian et al., "Chimeric recombinases with designed DNA sequence recognition." *Proc Natl Acad Sci USA.* 2003; 100: 8688-8691; Gordley et al., "Evolution of programmable zinc finger-recombinases with activity in human cells. *J Mol Biol.* 2007; 367: 802-813; Gordley et al., "Synthesis of programmable integrases." *Proc Natl Acad Sci USA.* 2009; 106: 5053-5058; Arnold et al., "Mutants of Tn3 resolvase which do not require accessory binding sites for recombination activity." *EMBO J.* 1999; 18: 1407-1414; Gaj et al., "Structure-guided reprogramming of serine recombinase DNA sequence specificity." *Proc Natl Acad Sci USA.* 2011; 108(2):498-503; and Proudfoot et al., "Zinc finger recombinases with adaptable DNA sequence specificity." *PLoS One.* 2011; 6(4):e19537; the entire contents of each are hereby incorporated by reference. For example, serine recombinases of the resolvase-invertase group, e.g., Tn3 and γδ resolvases and the Hin and Gin invertases, have modular structures with partly autonomous catalytic and DNA-binding domains (See, e.g., Grindley et al., "Mechanism of site-specific recombination." *Ann Rev Biochem.* 2006; 75: 567-605, the entire contents of which are incorporated by reference). The catalytic domains of these recombinases are therefore amenable to being recombined with nuclease-inactivated RNA-programmable nucleases (e.g., dCas9, or a fragment thereof) as described herein, e.g., following the isolation of 'activated' recombinase mutants which do not require any accessory factors (e.g., DNA binding activities) (See, e.g., Klippel et al., "Isolation and characterisation of unusual gin mutants." *EMBO J.* 1988; 7: 3983-3989: Burke et al., "Activating mutations of Tn3 resolvase marking interfaces important in recombination catalysis and its regulation. *Mol Microbiol.* 2004; 51: 937-948; Olorunniji et al., "Synapsis and catalysis by activated Tn3 resolvase mutants." *Nucleic Acids Res.* 2008; 36: 7181-7191; Rowland et al., "Regulatory mutations in Sin recombinase support a structure-based model of the synaptosome." *Mol Microbiol.* 2009; 74: 282-298; Akopian et al., "Chimeric recombinases with designed DNA sequence recognition." *Proc Natl Acad Sci USA.* 2003; 100: 8688-8691).

Additionally, many other natural serine recombinases having an N-terminal catalytic domain and a C-terminal DNA binding domain are known (e.g., phiC31 integrase, TnpX transposase, IS607 transposase), and their catalytic domains can be co-opted to engineer programmable site-specific recombinases as described herein (See, e.g., Smith et al., "Diversity in the serine recombinases." *Mol Microbiol.* 2002; 44: 299-307, the entire contents of which are incorporated by reference). Similarly, the core catalytic domains of tyrosine recombinases (e.g., Cre, λ integrase) are known, and can be similarly co-opted to engineer programmable site-specific recombinases as described herein (See, e.g., Guo et al., "Structure of Cre recombinase complexed with DNA in a site-specific recombination synapse." *Nature.* 1997; 389:40-46; Hartung et al., "Cre mutants with altered DNA binding properties." *J Biol Chem* 1998; 273:22884-22891; Shaikh et al., "Chimeras of the Flp and Cre recombinases: Tests of the mode of cleavage by Flp and Cre. *J Mol Biol.* 2000; 302:27-48; Rongrong et al., "Effect of deletion mutation on the recombination activity of Cre recombinase." *Acta Biochim Pol.* 2005; 52:541-544; Kilbride et al., "Determinants of product topology in a hybrid Cre-Tn3 resolvase site-specific recombination system." *J Mol Biol.* 2006; 355: 185-195; Warren et al., "A chimeric cre recombinase with regulated directionality." *Proc Natl Acad Sci USA.* 2008 105:18278-18283; Van Duyne, "Teaching Cre to follow directions." *Proc Natl Acad Sci USA.* 2009 Jan. 6; 106(1): 4-5; Numrych et al., "A comparison of the effects of single-base and triple-base changes in the integrase arm-type binding sites on the site-specific recombination of bacteriophage λ." *Nucleic Acids Res.* 1990; 18:3953-3959; Tirumalai et al., "The recognition of core-type DNA sites by λ integrase." *J Mol Biol.* 1998; 279:513-527; Aihara et al., "A conformational switch controls the DNA cleavage activity of k integrase." *Mol Cell.* 2003; 12:187-198; Biswas et al., "A structural basis for allosteric control of DNA recombination by k integrase." *Nature.* 2005; 435:1059-1066; and Warren et al., "Mutations in the amino-terminal domain of λ-integrase have differential effects on integrative and excisive recombination." *Mol Microbiol.* 2005; 55:1104-1112; the entire contents of each are incorporated by reference).

The term "recombine" or "recombination," in the context of a nucleic acid modification (e.g., a genomic modification), is used to refer to the process by which two or more nucleic acid molecules, or two or more regions of a single nucleic acid molecule, are modified by the action of a recombinase protein (e.g., an inventive recombinase fusion protein provided herein). Recombination can result in, inter alia, the insertion, inversion, excision, or translocation of nucleic acids, e.g., in or between one or more nucleic acid molecules.

The term "recombinant" as used herein in the context of proteins or nucleic acids refers to proteins or nucleic acids that do not occur in nature, but are the product of human engineering. For example, in some embodiments, a recombinant protein or nucleic acid molecule comprises an amino acid or nucleotide sequence that comprises at least one, at least two, at least three, at least four, at least five, at least six, or at least seven mutations as compared to any naturally occurring sequence.

The term "subject," as used herein, refers to an individual organism, for example, an individual mammal. In some embodiments, the subject is a human. In some embodiments, the subject is a non-human mammal. In some embodiments, the subject is a non-human primate. In some embodiments, the subject is a rodent. In some embodiments, the subject is a sheep, a goat, a cattle, a cat, or a dog. In some embodiments, the subject is a vertebrate, an amphibian, a reptile, a fish, an insect, a fly, or a nematode. In some embodiments, the subject is a research animal. In some embodiments, the subject is genetically engineered, e.g., a genetically engineered non-human subject. The subject may be of either sex and at any stage of development. In some embodiments, the subject is genetically engineered, e.g., a genetically engineered non-human subject. The subject may be of either sex and at any stage of development.

The terms "target nucleic acid," and "target genome," as used herein in the context of nucleases, refer to a nucleic acid molecule or a genome, respectively, that comprises at least one target site of a given nuclease. In the context of fusions comprising a (nuclease-inactivated) RNA-programmable nuclease and a recombinase domain, a "target nucleic acid" and a "target genome" refers to one or more nucleic acid molecule(s), or a genome, respectively, that comprises at least one target site. In some embodiments, the target nucleic acid(s) comprises at least two, at least three, at least four, at least five, at least six, at least seven, or at least eight target sites. In some embodiments, the target nucleic acid(s) comprise four target sites.

The term "target site" refers to a sequence within a nucleic acid molecule that is bound and recombined (e.g., at or nearby the target site) by a recombinase (e.g., a dCas9-recombinase fusion protein provided herein). A target site may be single-stranded or double-stranded. For example, in some embodiments, four recombinase monomers are coordinated to recombine a target nucleic acid(s), each monomer being fused to a (nuclease-inactivated) Cas9 protein guided by a gRNA. In such an example, each Cas9 domain is guided by a distinct gRNA to bind a target nucleic acid(s), thus the target nucleic acid comprises four target sites, each site targeted by a separate dCas9-recombinase fusion (thereby coordinating four recombinase monomers which recombine the target nucleic acid(s)). For the RNA-guided nuclease-inactivated Cas9 (or gRNA-binding domain thereof) and inventive fusions of Cas9, the target site may be, in some embodiments, 17-20 base pairs plus a 3 base pair PAM (e.g., NNN, wherein N independently represents any nucleotide). Typically, the first nucleotide of a PAM can be any nucleotide, while the two downstream nucleotides are specified depending on the specific RNA-guided nuclease. Exemplary target sites (e.g., comprising a PAM) for RNA-guided nucleases, such as Cas9, are known to those of skill in the art and include, without limitation, NNG, NGN, NAG, and NGG, wherein each N is independently any nucleotide. In addition, Cas9 nucleases from different species (e.g., *S. thermophilus* instead of *S. pyogenes*) recognize a PAM that comprises the sequence NGGNG (SEQ ID NO: 763). Additional PAM sequences are known, including, but not limited to, NNAGAAW (SEQ ID NO: 749) and NAAR (SEQ ID NO: 771) (see, e.g., Esvelt and Wang, Molecular Systems Biology, 9:641 (2013), the entire contents of which are incorporated herein by reference). In some aspects, the target site of an RNA-guided nuclease, such as, e.g., Cas9, may comprise the structure $[N_Z]$-[PAM], where each N is independently any nucleotide, and z is an integer between 1 and 50, inclusive. In some embodiments, z is at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 25, at least 30, at least 35, at least 40, at least 45, or at least 50. In some embodiments, z is 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50. In some embodiments, z is 20. In certain embodiments, a "PAMless" RNA-guided nuclease (e.g., a Pamless Cas9) or an RNA-guided nuclease with relaxed PAM requirements as further described herein may be used. In some embodiments, "target site" may also refer to a sequence within a nucleic acid molecule that is bound but not cleaved by a nuclease. For example, certain embodiments described herein provide proteins comprising an inactive (or inactivated) Cas9 DNA cleavage domain. Such proteins (e.g., when also including a Cas9 RNA binding domain) are able to bind the target site specified by the gRNA; however, because the DNA cleavage site is inactivated, the target site is not cleaved by the particular protein. In some embodiments, such proteins are conjugated, fused, or bound to a recombinase (or a catalytic domain of a recombinase), which mediates recombination of the target nucleic acid. In some embodiments, the sequence actually cleaved or recombined will depend on the protein (e.g., recombinase) or molecule that mediates cleavage or recombination of the nucleic acid molecule, and in some cases, for example, will relate to the proximity or distance from which the inactivated Cas9 protein(s) is/are bound.

The term "Transcriptional Activator-Like Effector," (TALE) as used herein, refers to bacterial proteins comprising a DNA binding domain, which contains a highly conserved 33-34 amino acid sequence comprising a highly variable two-amino acid motif (Repeat Variable Diresidue, RVD). The RVD motif determines binding specificity to a nucleic acid sequence and can be engineered according to methods known to those of skill in the art to specifically bind a desired DNA sequence (see, e.g., Miller, Jeffrey; et. al. (February 2011). "A TALE nuclease architecture for efficient genome editing". *Nature Biotechnology* 29 (2): 143-8; Zhang, Feng; et. al. (February 2011). "Efficient construction of sequence-specific TAL effectors for modulating mammalian transcription" *Nature Biotechnology* 29 (2): 149-53; Geiβler, R.; Scholze, H.; Hahn, S.; Streubel, J.; Bonas, U.; Behrens, S. E.; Boch, J. (2011), Shiu, Shin-Han. ed. "Transcriptional Activators of Human Genes with Programmable DNA-Specificity". *PLoS ONE* 6 (5): e19509; Boch, Jens (February 2011). "TALEs of genome targeting". *Nature Biotechnology* 29 (2): 135-6; Boch, Jens; et. al. (December 2009). "Breaking the Code of DNA Binding Specificity of TAL-Type III Effectors". *Science* 326 (5959): 1509-12; and Moscou, Matthew J.; Adam J. Bogdanove (December 2009). "A Simple Cipher Governs DNA Recognition by TAL Effectors" *Science* 326 (5959): 1501; the entire contents of each of which are incorporated herein by reference). The simple relationship between amino acid sequence and DNA recognition has allowed for the engineering of specific DNA binding domains by selecting a combination of repeat segments containing the appropriate RVDs.

The term "Transcriptional Activator-Like Element Nuclease," (TALEN) as used herein, refers to an artificial nuclease comprising a transcriptional activator-like effector DNA binding domain to a DNA cleavage domain, for example, a FokI domain. A number of modular assembly schemes for generating engineered TALE constructs have been reported (see e.g., Zhang, Feng; et. al. (February 2011). "Efficient construction of sequence-specific TAL effectors for modulating mammalian transcription". *Nature Biotechnology* 29 (2): 149-53; Geiβler, R.; Scholze, H.; Hahn, S.; Streubel, J.; Bonas, U.; Behrens, S. E.; Boch, J. (2011), Shiu, Shin-Han. ed. "Transcriptional Activators of Human Genes with Programmable DNA-Specificity". *PLoS ONE* 6 (5): e19509; Cermak, T.; Doyle, E. L.; Christian, M.; Wang, L.; Zhang, Y.; Schmidt, C.; Baller, J. A.; Somia, N. V. et al. (2011). "Efficient design and assembly of custom TALEN and other TAL effector-based constructs for DNA targeting". *Nucleic Acids Research*; Morbitzer, R.; Elsaesser, J.; Hausner, J.; Lahaye, T. (2011). "Assembly of custom TALE-type DNA binding domains by modular cloning". *Nucleic Acids Research*; Li, T.; Huang, S.; Zhao, X.; Wright, D. A.; Carpenter, S.; Spalding, M. H.; Weeks, D. P.; Yang, B. (2011). "Modularly assembled designer TAL effector nucleases for targeted gene knockout and gene replacement in eukaryotes". *Nucleic Acids Research*.; Weber, E.; Gruetzner, R.; Werner, S.; Engler, C.; Marillonnet, S. (2011). Bendahmane, Mohammed. ed. "Assembly of Designer TAL Effectors by Golden Gate Cloning". *PLoS ONE* 6 (5): e19722; the entire contents of each of which are incorporated herein by reference).

The terms "treatment," "treat," and "treating," refer to a clinical intervention aimed to reverse, alleviate, delay the onset of, or inhibit the progress of a disease or disorder, or one or more symptoms thereof, as described herein. As used herein, the terms "treatment," "treat," and "treating" refer to a clinical intervention aimed to reverse, alleviate, delay the onset of, or inhibit the progress of a disease or disorder, or one or more symptoms thereof, as described herein. In some embodiments, treatment may be administered after one or more symptoms have developed and/or after a disease has been diagnosed. In other embodiments, treatment may be administered in the absence of symptoms, e.g., to prevent or delay onset of a symptom or inhibit onset or progression of a disease. For example, treatment may be administered to a susceptible individual prior to the onset of symptoms (e.g., in light of a history of symptoms and/or in light of genetic or other susceptibility factors). Treatment may also be continued after symptoms have resolved, for example, to prevent or delay their recurrence.

The term "vector" refers to a polynucleotide comprising one or more recombinant polynucleotides of the present invention, e.g., those encoding a Cas9 protein (or fusion thereof) and/or gRNA provided herein. Vectors include, but are not limited to, plasmids, viral vectors, cosmids, artificial chromosomes, and phagemids. The vector may be able to replicate in a host cell and may further be characterized by one or more endonuclease restriction sites at which the vector may be cut and into which a desired nucleic acid sequence may be inserted. Vectors may contain one or more marker sequences suitable for use in the identification and/or selection of cells which have or have not been transformed or genomically modified with the vector. Markers include, for example, genes encoding proteins which increase or decrease either resistance or sensitivity to antibiotics (e.g., kanamycin, ampicillin) or other compounds, genes which encode enzymes whose activities are detectable by standard assays known in the art (e.g., β-galactosidase, alkaline phosphatase, or luciferase), and genes which visibly affect the phenotype of transformed or transfected cells, hosts, colonies, or plaques. Any vector suitable for the transformation of a host cell (e.g., *E. coli*, mammalian cells such as CHO cell, insect cells, etc.) as embraced by the present invention, for example, vectors belonging to the pUC series, pGEM series, pET series, pBAD series, pTET series, or pGEX series. In some embodiments, the vector is suitable for transforming a host cell for recombinant protein production. Methods for selecting and engineering vectors and host cells for expressing proteins (e.g., those provided herein), transforming cells, and expressing/purifying recombinant proteins are well known in the art, and are provided by, for example, Green and Sambrook, *Molecular Cloning: A Laboratory Manual* ($4^{th}$ ed., Cold Spring Harbor Laboratory Press, Cold Spring Harbor, N.Y. (2012)).

The term "zinc finger," as used herein, refers to a small nucleic acid-binding protein structural motif characterized by a fold and the coordination of one or more zinc ions that stabilize the fold. Zinc fingers encompass a wide variety of differing protein structures (see, e.g., Klug A, Rhodes D (1987). "Zinc fingers: a novel protein fold for nucleic acid recognition". *Cold Spring Harb. Symp. Quant. Biol.* 52: 473-82, the entire contents of which are incorporated herein by reference). Zinc fingers can be designed to bind a specific sequence of nucleotides, and zinc finger arrays comprising fusions of a series of zinc fingers, can be designed to bind virtually any desired target sequence. Such zinc finger arrays can form a binding domain of a protein, for example, of a nuclease, e.g., if conjugated to a nucleic acid cleavage domain. Different types of zinc finger motifs are known to those of skill in the art, including, but not limited to, $Cys_2His_2$, Gag knuckle, Treble clef, Zinc ribbon, $Zn_2/Cys_6$, and TAZ2 domain-like motifs (see, e.g., Krishna S S, Majumdar I, Grishin N V (January 2003). "Structural classification of zinc fingers: survey and summary". *Nucleic Acids Res.* 31 (2): 532-50). Typically, a single zinc finger motif binds 3 or 4 nucleotides of a nucleic acid molecule. Accordingly, a zinc finger domain comprising 2 zinc finger motifs may bind 6-8 nucleotides, a zinc finger domain comprising 3 zinc finger motifs may bind 9-12 nucleotides, a zinc finger domain comprising 4 zinc finger motifs may bind 12-16 nucleotides, and so forth. Any suitable protein engineering technique can be employed to alter the DNA-binding specificity of zinc fingers and/or design novel zinc finger fusions to bind virtually any desired target sequence from 3-30 nucleotides in length (see, e.g., Pabo C O, Peisach E, Grant R A (2001). "Design and selection of novel cys2His2 Zinc finger proteins". *Annual Review of Biochemistry* 70: 313-340; Jamieson A C, Miller J C, Pabo C O (2003). "Drug discovery with engineered zinc-finger proteins". *Nature Reviews Drug Discovery* 2 (5): 361-368; and Liu Q, Segal D J, Ghiara J B, Barbas C F (May 1997). "Design of polydactyl zinc-finger proteins for unique addressing within complex genomes". *Proc. Natl. Acad. Sci. U.S.A.* 94 (11); the entire contents of each of which are incorporated herein by reference). Fusions between engineered zinc finger arrays and protein domains that cleave a nucleic acid can be used to generate a "zinc finger nuclease." A zinc finger nuclease typically comprises a zinc finger domain that binds a specific target site within a nucleic acid molecule, and a nucleic acid cleavage domain that cuts the nucleic acid molecule within or in proximity to the target site bound by the binding domain. Typical engineered zinc finger nucleases comprise a binding domain having between 3 and 6 individual zinc finger motifs and binding target sites ranging from 9 base pairs to 18 base pairs in length. Longer target sites are particularly attractive in situations where it is desired to bind and cleave a target site that is unique in a given genome.

The term "zinc finger nuclease," as used herein, refers to a nuclease comprising a nucleic acid cleavage domain conjugated to a binding domain that comprises a zinc finger array. In some embodiments, the cleavage domain is the cleavage domain of the type II restriction endonuclease FokI. Zinc finger nucleases can be designed to target virtually any desired sequence in a given nucleic acid molecule for cleavage, and the possibility to design zinc finger binding domains to bind unique sites in the context of complex genomes allows for targeted cleavage of a single genomic site in living cells, for example, to achieve a targeted genomic alteration of therapeutic value. Targeting a double-strand break to a desired genomic locus can be used to introduce frame-shift mutations into the coding sequence of a gene due to the error-prone nature of the non-homologous DNA repair pathway. Zinc finger nucleases can be generated to target a site of interest by methods well known to those of skill in the art. For example, zinc finger binding domains with a desired specificity can be designed by combining individual zinc finger motifs of known specificity. The structure of the zinc finger protein Zif268 bound to DNA has informed much of the work in this field and the concept of obtaining zinc fingers for each of the 64 possible base pair triplets and then mixing and matching these modular zinc fingers to design proteins with any desired sequence specificity has been described (Pavletich N P, Pabo C O (May 1991). "Zinc finger-DNA recognition: crystal structure of a Zif268-DNA complex at 2.1 A". *Science* 252 (5007): 809-17, the entire contents of which are incorporated herein). In some embodiments, separate zinc fingers that each recognizes a 3 base pair DNA sequence are combined to generate 3-, 4-, 5-, or 6-finger arrays that recognize target sites ranging from 9 base pairs to 18 base pairs in length. In some embodiments, longer arrays are contemplated. In other embodiments, 2-finger modules recognizing 6-8 nucleotides are combined to generate 4-, 6-, or 8-zinc finger arrays. In some embodiments, bacterial or phage display is employed to develop a zinc finger domain that recognizes a desired nucleic acid sequence, for example, a desired nuclease target site of 3-30 bp in length. Zinc finger nucleases, in some embodiments, comprise a zinc finger binding domain and a cleavage domain fused or otherwise conjugated to each other via a linker, for example, a polypeptide linker. The length of the linker determines the distance of the cut from the nucleic acid sequence bound by the zinc finger domain. If a shorter linker is used, the cleavage domain will cut the nucleic acid closer to the bound nucleic acid sequence, while a longer linker will result in a greater distance between the cut and the bound nucleic acid sequence. In some embodiments, the cleavage domain of a zinc finger nuclease has to dimerize in order to cut a bound nucleic acid. In some such embodiments, the dimer is a heterodimer of two monomers, each of which comprise a different zinc finger binding domain. For example, in some embodiments, the dimer may comprise one monomer comprising zinc finger domain A conjugated to a FokI cleavage domain, and one monomer comprising zinc finger domain B conjugated to a FokI cleavage domain. In this non-limiting example, zinc finger domain A binds a nucleic acid sequence on one side of the target site, zinc finger domain B binds a nucleic acid sequence on the other side of the target site, and the dimerize FokI domain cuts the nucleic acid in between the zinc finger domain binding sites.

DETAILED DESCRIPTION OF CERTAIN EMBODIMENTS OF THE INVENTION

The function and advantage of these and other embodiments of the present invention will be more fully understood from the Examples below. The following Examples are intended to illustrate the benefits of the present invention and to describe particular embodiments, but are not intended to exemplify the full scope of the invention. Accordingly, it will be understood that the Examples are not meant to limit the scope of the invention.

Guide Nucleotide Sequence-Programmable DNA Binding Protein

The fusion proteins and methods described herein may use any programmable DNA binding domain.

In some embodiments, the programmable DNA binding protein domain comprises the DNA binding domain of a zinc finger nuclease (ZFN) or a transcription activator-like effector domain (TALE). In some embodiments, the programmable DNA binding protein domain may be programmed by a guide nucleotide sequence and is thus referred as a "guide nucleotide sequence-programmable DNA binding-protein domain." In some embodiments, the guide nucleotide sequence-programmable DNA binding protein is a nuclease inactive Cas9, or dCas9. A dCas9, as used herein, encompasses a Cas9 that is completely inactive in its nuclease activity, or partially inactive in its nuclease activity (e.g., a Cas9 nickase). Thus, in some embodiments, the guide nucleotide sequence-programmable DNA binding protein is a Cas9 nickase. In some embodiments, the guide nucleotide sequence-programmable DNA binding protein is a nuclease inactive Cpf1. In some embodiments, the guide nucleotide sequence-programmable DNA binding protein is a nuclease inactive Argonaute.

In some embodiments, the guide nucleotide sequence-programmable DNA binding protein is a dCas9 domain. In some embodiments, the guide nucleotide sequence-programmable DNA binding protein is a Cas9 nickase. In some embodiments, the dCas9 domain comprises an amino acid sequence of SEQ ID NO: 2 or SEQ ID NO: 3. In some embodiments, the dCas9 domain comprises an amino acid sequence that is at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or at least 99.5% identical to any one of the Cas9 domains provided herein, and comprises mutations corresponding to D10X (X is any amino acid except for D) and/or H840X (X is any amino acid except for H) in SEQ ID NO: 1. In some embodiments, the dCas9 domain comprises an amino acid sequence that is at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or at least 99.5% identical to any one of the Cas9 domains provided herein, and comprises mutations corresponding to D10A and/or H840A in SEQ ID NO: 1. In some embodiments, the Cas9 nickase comprises an amino acid sequence that is at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or at least 99.5% identical to any one of the Cas9 domains provided herein, and comprises mutations corresponding to D10X (X is any amino acid except for D) in SEQ ID NO: 1 and a histidine at a position correspond to position 840 in SEQ ID NO: 1. In some embodiments, the Cas9 nickase comprises an amino acid sequence that is at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or at least 99.5% identical to any one of the Cas9 domains provided herein, and comprises mutations corresponding to D10A in SEQ ID NO: 1 and a histidine at a position correspond to position 840 in SEQ ID NO: 1. In some embodiments, variants or homologues of dCas9 or Cas9 nickase (e.g., variants of SEQ ID NO: 2 or SEQ ID NO: 3, respectively) are provided which are at least about 70% identical, at least about 80% identical, at least about 90% identical, at least about 95% identical, at least about 98% identical, at least about 99% identical, at least about 99.5% identical, or at least about 99.9% identical to SEQ ID NO: 2 or SEQ ID NO: 3, respectively, and comprises mutations corresponding to D10A and/or H840A in SEQ ID NO: 1. In some embodiments, variants of Cas9 (e.g., variants of SEQ ID NO: 2) are provided having amino acid sequences which are shorter, or longer than SEQ ID NO: 2, by about 5 amino acids, by about 10 amino acids, by about 15 amino acids, by about 20 amino acids, by about 25 amino acids, by about 30 amino acids, by about 40 amino acids, by about 50 amino acids, by about 75 amino acids, by about 100 amino acids, or more, provided that the dCas9 variants comprise mutations corresponding to D10A and/or H840A in SEQ ID NO: 1. In some embodiments, variants of Cas9 nickase (e.g., variants of SEQ ID NO: 3) are provided having amino acid sequences which are shorter, or longer than SEQ ID NO: 3, by about 5 amino acids, by about 10 amino acids, by about 15 amino acids, by about 20 amino acids, by about 25 amino acids, by about 30 amino acids, by about 40 amino acids, by about 50 amino acids, by about 75 amino acids, by about 100 amino acids, or more, provided that the dCas9 variants comprise mutations corresponding to D10A and comprises a histidine at a position corresponding to position 840 in SEQ ID NO: 1.

Additional suitable nuclease-inactive dCas9 domains will be apparent to those of skill in the art based on this disclosure and knowledge in the field, and are within the scope of this disclosure. Such additional exemplary suitable nuclease-inactive Cas9 domains include, but are not limited to, D10A/H840A, D10A/D839A/H840A, D10A/D839A/H840A/N863A mutant domains in SEQ ID NO: 1 (See, e.g., Prashant et al., Nature Biotechnology. 2013; 31(9): 833-838, which is incorporated herein by reference), or K603R (See, e.g., Chavez et al., Nature Methods 12, 326-328, 2015, which is incorporated herein by reference).

In some embodiments, the nucleobase editors described herein comprise a Cas9 domain with decreased electrostatic interactions between the Cas9 domain and a sugar-phosphate backbone of a DNA, as compared to a wild-type Cas9 domain. In some embodiments, a Cas9 domain comprises one or more mutations that decreases the association between the Cas9 domain and a sugar-phosphate backbone of a DNA. In some embodiments, the nucleobase editors described herein comprises a dCas9 (e.g., with D10A and H840A mutations in SEQ ID NO: 1) or a Cas9 nickase (e.g., with D10A mutation in SEQ ID NO: 1), wherein the dCas9 or the Cas9 nickase further comprises one or more of a N497X, a R661X, a Q695X, and/or a Q926X mutation of the amino acid sequence provided in SEQ ID NO: 10, or a corresponding mutation in any of the amino acid sequences provided in SEQ ID NOs: 11-260, wherein X is any amino acid. In some embodiments, the nucleobase editors described herein comprises a dCas9 (e.g., with D10A and H840A mutations in SEQ ID NO: 1) or a Cas9 nickase (e.g., with D10A mutation in SEQ ID NO: 1), wherein the dCas9 or the Cas9 nickase further comprises one or more of a N497A, a R661A, a Q695A, and/or a Q926A mutation of the amino acid sequence provided in SEQ ID NO: 10, or a corresponding mutation in any of the amino acid sequences provided in SEQ ID NOs: 11-260. In some embodiments, the Cas9 domain (e.g., of any of the nucleobase editors provided herein) comprises the amino acid sequence as set forth in SEQ ID NO: 720. In some embodiments, the nucleobase editor comprises the amino acid sequence as set forth in SEQ ID NO: 721. Cas9 domains with high fidelity are known in the art and would be apparent to the skilled artisan. For example, Cas9 domains with high fidelity have been described in Kleinstiver, B. P., et al. "High-fidelity CRISPR-Cas9 nucleases with no detectable genome-wide off-target effects." *Nature* 529, 490-495 (2016); and Slaymaker, I. M., et al. "Rationally engineered Cas9 nucleases with improved specificity." *Science* 351, 84-88 (2015); the entire contents of each are incorporated herein by reference.

Cas9 variant with decreased electrostatic interactions between the Cas9 and DNA backbone (SEQ ID NO: 720)

```
DKKYSIGLAIGTNSVGWAVITDEYKVPSKKFKVLGNTDRHSIKKNLIGALLFDSGETA

EATRLKRTARRRYTRRKNRICYLQEIFSNEMAKVDDSFFHRLEESFLVEEDKKHERH

PIFGNIVDEVAYHEKYPTIYHLRKKLVDSTDKADLRLIYLALAHMIKFRGHFLIEGDL

NPDNSDVDKLFIQLVQTYNQLFEENPINASGVDAKAILSARLSKSRRLENLIAQLPGE

KKNGLFGNLIALSLGLTPNFKSNFDLAEDAKLQLSKDTYDDDLDNLLAQIGDQYADL

FLAAKNLSDAILLSDILRVNTEITKAPLSASMIKRYDEHHQDLTLLKALVRQQLPEKY

KEIFFDQSKNGYAGYIDGGASQEEFYKFIKPILEKMDGTEELLVKLNREDLLRKQRTF

DNGSIPHQIHLGELHAILRRQEDFYPFLKDNREKIEKILTFRIPYYVGPLARGNSRFAW

MTRKSEETITPWNFEEVVDKGASAQSFIERMTAFDKNLPNEKVLPKHSLLYEYFTVY

NELTKVKYVTEGMRKPAFLSGEQKKAIVDLLFKTNRKVTVKQLKEDYFKKIECFDS

VEISGVEDRFNASLGTYHDLLKIIKDKDFLDNEENEDILEDIVLTLTLFEDREMIEERL
```

-continued

KTYAHLFDDKVMKQLKRRRYTGWGALSRKLINGIRDKQSGKTILDFLKSDGFANRN

FMALIHDDSLTFKEDIQKAQVSGQGDSLHEHIANLAGSPAIKKGILQTVKVVDELVK

VMGRHKPENIVIEMARENQTTQKGQKNSRERMKRIEEGIKELGSQILKEHPVENTQL

QNEKLYLYYLQNGRDMYVDQELDINRLSDYDVDHIVPQSFLKDDSIDNKVLTRSDK

NRGKSDNVPSEEVVKKMKNYWRQLLNAKLITQRKFDNLTKAERGGLSELDKAGFIK

RQLVETRAITKHVAQILDSRMNTKYDENDKLIREVKVITLKSKLVSDFRKDFQFYKV

REINNYHHAHDAYLNAVVGTALIKKYPKLESEFVYGDYKVYDVRKMIAKSEQEIGK

ATAKYFFYSNIMNFFKTEITLANGEIRKRPLIETNGETGEIVWDKGRDFATVRKVLSM

PQVNIVKKTEVQTGGFSKESILPKRNSDKLIARKKDWDPKKYGGFDSPTVAYSVLVV

AKVEKGKSKKLKSVKELLGITIMERSSFEKNPIDFLEAKGYKEVKKDLIIKLPKYSLFE

LENGRKRMLASAGELQKGNELALPSKYVNFLYLASHYEKLKGSPEDNEQKQLFVEQ

HKHYLDEIIEQISEFSKRVILADANLDKVLSAYNKHRDKPIREQAENIIHLFTLTNLGA

PAAFKYFDTTIDRKRYTSTKEVLDATLIHQSITGLYETRIDLSQLGGD

High fidelity nucleobase editor (SEQ ID NO: 721)

MSSETGPVAVDPTLRRRIEPHEFEVFFDPRELRKETCLLYEINWGGRHSIWRHTSQNT

NKHVEVNFIEKFTTERYFCPNTRCSITWFLSWSPCGECSRAITEFLSRYPHVTLFIYIAR

LYHHADPRNRQGLRDLISSGVTIQIMTEQESGYCWRNFVNYSPSNEAHWPRYPHLW

VRLYVLELYCIILGLPPCLNILRRKQPQLTFFTIALQSCHYQRLPPHILWATGLKSGSET

PGTSESATPESDKKYSIGLAIGTNSVGWAVITDEYKVPSKKFKVLGNTDRHSIKKNLI

GALLFDSGETAEATRLKRTARRRYTRRKNRICYLQEIFSNEMAKVDDSFFHRLEESFL

VEEDKKHERHPIFGNIVDEVAYHEKYPTIYHLRKKLVDSTDKADLRLIYLALAHMIK

FRGHFLIEGDLNPDNSDVDKLFIQLVQTYNQLFEENPINASGVDAKAILSARLSKSRR

LENLIAQLPGEKKNGLFGNLIALSLGLTPNFKSNFDLAEDAKLQLSKDTYDDDLDNL

LAQIGDQYADLFLAAKNLSDAILLSDILRVNTEITKAPLSASMIKRYDEHHQDLTLLK

ALVRQQLPEKYKEIFFDQSKNGYAGYIDGGASQEEFYKFIKPILEKMDGTEELLVKLN

REDLLRKQRTFDNGSIPHQIHLGELHAILRRQEDFYPFLKDNREKIEKILTFRIPYYVGP

LARGNSRFAWMTRKSEETITPWNFEEVVDKGASAQSFIERMTAFDKNLPNEKVLPK

HSLLYEYFTVYNELTKVKYVTEGMRKPAFLSGEQKKAIVDLLFKTNRKVTVKQLKE

DYFKKIECFDSVEISGVEDRFNASLGTYHDLLKIIKDKDFLDNEENEDILEDIVLTLTLF

EDREMIEERLKTYAHLFDDKVMKQLKRRRYTGWGALSRKLINGIRDKQSGKTILDFL

KSDGFANRNFMALIHDDSLTFKEDIQKAQVSGQGDSLHEHIANLAGSPAIKKGILQTV

KVVDELVKVMGRHKPENIVIEMARENQTTQKGQKNSRERMKRIEEGIKELGSQILKE

HPVENTQLQNEKLYLYYLQNGRDMYVDQELDINRLSDYDVDHIVPQSFLKDDSIDN

KVLTRSDKNRGKSDNVPSEEVVKKMKNYWRQLLNAKLITQRKFDNLTKAERGGLS

ELDKAGFIKRQLVETRAITKHVAQILDSRMNTKYDENDKLIREVKVITLKSKLVSDFR

KDFQFYKVREINNYHHAHDAYLNAVVGTALIKKYPKLESEFVYGDYKVYDVRKMI

AKSEQEIGKATAKYFFYSNIMNFFKTEITLANGEIRKRPLIETNGETGEIVWDKGRDFA

TVRKVLSMPQVNIVKKTEVQTGGFSKESILPKRNSDKLIARKKDWDPKKYGGFDSPT

VAYSVLVVAKVEKGKSKKLKSVKELLGITIMERSSFEKNPIDFLEAKGYKEVKKDLII

KLPKYSLFELENGRKRMLASAGELQKGNELALPSKYVNFLYLASHYEKLKGSPEDN

-continued

EQKQLFVEQHKHYLDEIIEQISEFSKRVILADANLDKVLSAYNKHRDKPIREQAENIIH

LFTLTNLGAPAAFKYFDTTIDRKRYTSTKEVLDATLIHQSITGLYETRIDLSQLGGD

The Cas9 protein recognizes a short motif (PAM motif) within the target DNA sequence, which is required for the Cas9-DNA interaction but that is not determined by complementarity to the guide RNA nucleotide sequence. A "PAM motif" or "protospacer adjacent motif," as used herein, refers to a DNA sequence adjacent to the 5'- or 3'-immediately following the DNA sequence that is complementary to the guide RNA oligonucleotide sequence. Cas9 will not successfully bind to, cleave, or nick the target DNA sequence if it is not followed by an appropriate PAM sequence. Without wishing to be bound by any particular theory, specific amino acid residues in the Cas9 enzyme are responsible for interacting with the bases of the PAM and determine the PAM specificity. Therefore, changes in these residues or nearby residues leads to a different or relaxed PAM specificity. Changing or relaxing the PAM specificity may shift the places where Cas9 can bind, as will be apparent to those of skill in the art based on the instant disclosure.

Wild-type *Streptococcus pyogenes* Cas9 recognizes a canonical PAM sequence (5'-NGG-3'). Other Cas9 nucleases (e.g., Cas9 from *Streptococcus thermophiles, Staphylococcus aureus, Neisseria meningitidis*, or *Treponema denticolaor*) and Cas9 variants thereof have been described in the art to have different, or more relaxed PAM requirements. For example, in Kleinstiver et al., Nature 523, 481-485, 2015; Klenstiver et al., Nature 529, 490-495, 2016; Ran et al., Nature, April 9; 520(7546): 186-191, 2015; Kleinstiver et al., Nat Biotechnol, 33(12):1293-1298, 2015; Hou et al., Proc Natl Acad Sci USA, 110(39):15644-9, 2014; Prykhozhij et al., PLoS One, 10(3): e0119372, 2015; Zetsche et al., Cell 163, 759-771, 2015; Gao et al., Nature Biotechnology, doi:10.1038/nbt.3547, 2016; Want et al., Nature 461, 754-761, 2009; Chavez et al., doi: dx.doi dot org/10.1101/058974; Fagerlund et al., Genome Biol. 2015; 16: 25, 2015; Zetsche et al., Cell, 163, 759-771, 2015; and Swarts et al., Nat Struct Mol Biol, 21(9):743-53, 2014, each of which is incorporated herein by reference.

Thus, the guide nucleotide sequence-programmable DNA-binding protein of the present disclosure may recognize a variety of PAM sequences including, without limitation PAM sequences that are on the 3' or the 5' end of the DNA sequence determined by the guide RNA. For example, the sequence may be: NGG, NGAN (SEQ ID NO: 741), NGNG (SEQ ID NO: 742), NGAG (SEQ ID NO: 743), NGCG (SEQ ID NO: 744), NNGRRT (SEQ ID NO: 745), NGRRN (SEQ ID NO: 746), NNNRRT (SEQ ID NO: 747), NNNGATT (SEQ ID NO: 748), NNAGAAW (SEQ ID NO: 749), NAAAC (SEQ ID NO: 750), TTN, TTTN (SEQ ID NO: 751), and YTN, wherein Y is a pyrimidine, R is a purine, and N is any nucleobase.

Some aspects of the disclosure provide RNA-programmable DNA binding proteins, which may be used to guide a protein, such as a base editor, to a specific nucleic acid (e.g., DNA or RNA) sequence. Nucleic acid programmable DNA binding proteins include, without limitation, Cas9 (e.g., dCas9 and nCas9), CasX, CasY, Cpf1, C2c1, C2c2, C2C3, and Argonaute. One example of an RNA-programmable DNA-binding protein that has different PAM specificity is Clustered Regularly Interspaced Short Palindromic Repeats from *Prevotella* and *Francisella* 1 (Cpf1). Similar to Cas9, Cpf1 is also a class 2 CRISPR effector. It has been shown that Cpf1 mediates robust DNA interference with features distinct from Cas9. Cpf1 is a single RNA-guided endonuclease lacking tracrRNA, and it may utilize a T-rich protospacer-adjacent motif (e.g., TTN, TTTN (SEQ ID NO: 751), or YTN), which is on the 5'-end of the DNA sequence determined by the guide RNA. Moreover, Cpf1 cleaves DNA via a staggered DNA double-stranded break. Out of 16 Cpf1-family proteins, two enzymes from Acidaminococcus and Lachnospiraceae are shown to have efficient genome-editing activity in human cells. Cpf1 proteins are known in the art and have been described previously, for example Yamano et al., "Crystal structure of Cpf1 in complex with guide RNA and target DNA." *Cell* (165) 2016, p. 949-962; the entire contents of which is hereby incorporated by reference.

Also useful in the present compositions and methods are nuclease-inactive Cpf1 (dCpf1) variants that may be used as a guide nucleotide sequence-programmable DNA-binding protein domain. The Cpf1 protein has a RuvC-like endonuclease domain that is similar to the RuvC domain of Cas9 but does not have a HNH endonuclease domain, and the N-terminal of Cpf1 does not have the alfa-helical recognition lobe of Cas9. It was shown in Zetsche et al., Cell, 163, 759-771, 2015 (which is incorporated herein by reference) that, the RuvC-like domain of Cpf1 is responsible for cleaving both DNA strands and inactivation of the RuvC-like domain inactivates Cpf1 nuclease activity. For example, mutations corresponding to D917A, E1006A, or D1255A in *Francisella novicida* Cpf1 (SEQ ID NO: 714) inactivate Cpf1 nuclease activity. In some embodiments, the dCpf1 of the present disclosure may comprise mutations corresponding to D917A, E1006A, D1255A, D917A/E1006A, D917A/D1255A, E1006A/D1255A, or D917A/E1006A/D1255A in SEQ ID NO: 714. In other embodiments, the Cpf1 nickase of the present disclosure may comprise mutations corresponding to D917A, E1006A, D1255A, D917A/E1006A, D917A/D1255A, E1006A/D1255A, or D917A/E1006A/D1255A in SEQ ID NO: 714. A Cpf1 nickase useful for the embodiments of the instant disclosure may comprise other mutations and/or further mutations known in the field. It is to be understood that any mutations, e.g., substitution mutations, deletions, or insertions that fully or partially inactivates the RuvC domain of Cpf1 may be used in accordance with the present disclosure, and that these mutations of Cpf1 may result in, for example, a dCpf1 or Cpf1 nickase.

Thus, in some embodiments, the guide nucleotide sequence-programmable DNA binding protein is a nuclease inactive Cpf1 (dCpf1). In some embodiments, the dCpf1 comprises an amino acid sequence of any one SEQ ID NOs: 714-717. In some embodiments, the dCpf1 comprises an amino acid sequence that is at least 85%, at least 90%, at least 91%, at least 92%, at least 93%, at least 94%, at least 95%, at least 96%, at least 97%, at least 98%, at least 99%, or at ease 99.5% identical to any one of SEQ ID NOs: 714-717, and comprises mutations corresponding to D917A, E1006A, D1255A, D917A/E1006A, D917A/D1255A, E1006A/D1255A, or D917A/E1006A/D1255A in SEQ ID NO: 714. Cpf1 from other bacterial species may also be used in accordance with the present disclosure, as a dCpf1 or Cpf1 nickase.

Wild type *Francisella novicida* Cpf1 (D917, E1006, and D1255 are bolded and underlined)

(SEQ ID NO: 714)

MSIYQEFVNKYSLSKTLRFELIPQGKTLENIKARGLILDDEKRAKDYKKAKQIIDKYH

QFFIEEILSSVCISEDLLQNYSDVYFKLKKSDDDNLQKDFKSAKDTIKKQISEYIKDSE

KFKNLFNQNLIDAKKGQESDLILWLKQSKDNGIELFKANSDITDIDEALEIIKSFKGWT

TYFKGFHENRKNVYSSNDIPTSIIYRIVDDNLPKFLENKAKYESLKDKAPEAINYEQIK

KDLAEELTFDIDYKTSEVNQRVFSLDEVFEIANFNNYLNQSGITKFNTIIGGKFVNGEN

TKRKGINEYINLYSQQINDKTLKKYKMSVLFKQILSDTESKSFVIDKLEDDSDVVTTM

QSFYEQIAAFKTVEEKSIKETLSLLFDDLKAQKLDLSKIYFKNDKSLTDLSQQVFDDY

SVIGTAVLEYITQQIAPKNLDNPSKKEQELIAKKTEKAKYLSLETIKLALEEFNKHRDI

DKQCRFEEILANFAAIPMIFDEIAQNKDNLAQISIKYQNQGKKDLLQASAEDDVKAIK

DLLDQTNNLLHKLKIFHISQSEDKANILDKDEHFYLVFEECYFELANIVPLYNKIRNYI

TQKPYSDEKFKLNFENSTLANGWDKNKEPDNTAILFIKDDKYYLGVMNKKNNKIFD

DKAIKENKGEGYKKIVYKLLPGANKMLPKVFFSAKSIKFYNPSEDILRIRNHSTHTKN

GSPQKGYEKFEFNIEDCRKFIDFYKQSISKHPEWKDFGFRFSDTQRYNSIDEFYREVE

NQGYKLTFENISESYIDSVVNQGKLYLFQIYNKDFSAYSKGRPNLHTLYWKALFDER

NLQDVVYKLNGEAELFYRKQSIPKKITHPAKEAIANKNKDNPKKESVFEYDLIKDKR

FTEDKFFFHCPITINFKSSGANKFNDEINLLLKEKANDVHILSIDRGERHLAYYTLVDG

KGNIIKQDTFNIIGNDRMKTNYHDKLAAIEKDRDSARKDWKKINNIKEMKEGYLSQV

VHEIAKLVIEYNAIVVFEDLNFGFKRGRFKVEKQVYQKLEKMLIEKLNYLVFKDNEF

DKTGGVLRAYQLTAPFETFKKMGKQTGIIYYVPAGFTSKICPVTGFVNQLYPKYESV

SKSQEFFSKFDKICYNLDKGYFEFSFDYKNFGDKAAKGKWTIASFGSRLINFRNSDKN

HNWDTREVYPTKELEKLLKDYSIEYGHGECIKAAICGESDKKFFAKLTSVLNTILQM

RNSKTGTELDYLISPVADVNGNFFDSRQAPKNMPQDADANGAYHIGLKGLMLLGRI

KNNQEGKKLNLVIKNEEYFEFVQNRNN

*Francisella novicida* Cpf1 D917A (SEQ ID NO: 715)

MSIYQEFVNKYSLSKTLRFELIPQGKTLENIKARGLILDDEKRAKDYKKAKQIIDKYH

QFFIEEILSSVCISEDLLQNYSDVYFKLKKSDDDNLQKDFKSAKDTIKKQISEYIKDSE

KFKNLFNQNLIDAKKGQESDLILWLKQSKDNGIELFKANSDITDIDEALEIIKSFKGWT

TYFKGFHENRKNVYSSNDIPTSIIYRIVDDNLPKFLENKAKYESLKDKAPEAINYEQIK

KDLAEELTFDIDYKTSEVNQRVFSLDEVFEIANFNNYLNQSGITKFNTIIGGKFVNGEN

TKRKGINEYINLYSQQINDKTLKKYKMSVLFKQILSDTESKSFVIDKLEDDSDVVTTM

QSFYEQIAAFKTVEEKSIKETLSLLFDDLKAQKLDLSKIYFKNDKSLTDLSQQVFDDY

SVIGTAVLEYITQQIAPKNLDNPSKKEQELIAKKTEKAKYLSLETIKLALEEFNKHRDI

DKQCRFEEILANFAAIPMIFDEIAQNKDNLAQISIKYQNQGKKDLLQASAEDDVKAIK

DLLDQTNNLLHKLKIFHISQSEDKANILDKDEHFYLVFEECYFELANIVPLYNKIRNYI

TQKPYSDEKFKLNFENSTLANGWDKNKEPDNTAILFIKDDKYYLGVMNKKNNKIFD

DKAIKENKGEGYKKIVYKLLPGANKMLPKVFFSAKSIKFYNPSEDILRIRNHSTHTKN

GSPQKGYEKFEFNIEDCRKFIDFYKQSISKHPEWKDFGFRFSDTQRYNSIDEFYREVE

NQGYKLTFENISESYIDSVVNQGKLYLFQIYNKDFSAYSKGRPNLHTLYWKALFDER

NLQDVVYKLNGEAELFYRKQSIPKKITHPAKEAIANKNKDNPKKESVFEYDLIKDKR

-continued

FTEDKFFFHCPITINFKSSGANKFNDEINLLLKEKANDVHILSIARGERHLAYYTLVDG

KGNIIKQDTFNIIGNDRMKTNYHDKLAAIEKDRDSARKDWKKINNIKEMKEGYLSQV

VHEIAKLVIEYNAIVVFEDLNFGFKRGRFKVEKQVYQKLEKMLIEKLNYLVFKDNEF

DKTGGVLRAYQLTAPFETFKKMGKQTGIIYYVPAGFTSKICPVTGFVNQLYPKYESV

SKSQEFFSKFDKICYNLDKGYFEFSFDYKNFGDKAAKGKWTIASFGSRLINFRNSDKN

HNWDTREVYPTKELEKLLKDYSIEYGHGECIKAAICGESDKKFFAKLTSVLNTILQM

RNSKTGTELDYLISPVADVNGNFFDSRQAPKNMPQDADANGAYHIGLKGLMLLGRI

KNNQEGKKLNLVIKNEEYFEFVQNRNN

*Francisella novicida* Cpf1 E1006A (SEQ ID NO: 716)

MSIYQEFVNKYSLSKTLRFELIPQGKTLENIKARGLILDDEKRAKDYKKAKQIIDKYH

QFFIEEILSSVCISEDLLQNYSDVYFKLKKSDDDNLQKDFKSAKDTIKKQISEYIKDSE

KFKNLFNQNLIDAKKGQESDLILWLKQSKDNGIELFKANSDITDIDEALEIIKSFKGWT

TYFKGFHENRKNVYSSNDIPTSIIYRIVDDNLPKFLENKAKYESLKDKAPEAINYEQIK

KDLAEELTFDIDYKTSEVNQRVFSLDEVFEIANFNNYLNQSGITKFNTIIGGKFVNGEN

TKRKGINEYINLYSQQINDKTLKKYKMSVLFKQILSDTESKSFVIDKLEDDSDVVTTM

QSFYEQIAAFKTVEEKSIKETLSLLFDDLKAQKLDLSKIYFKNDKSLTDLSQQVFDDY

SVIGTAVLEYITQQIAPKNLDNPSKKEQELIAKKTEKAKYLSLETIKLALEEFNKHRDI

DKQCRFEEILANFAAIPMIFDEIAQNKDNLAQISIKYQNQGKKDLLQASAEDDVKAIK

DLLDQTNNLLHKLKIFHISQSEDKANILDKDEHFYLVFEECYFELANIVPLYNKIRNYI

TQKPYSDEKFKLNFENSTLANGWDKNKEPDNTAILFIKDDKYYLGVMNKKNNKIFD

DKAIKENKGEGYKKIVYKLLPGANKMLPKVFFSAKSIKFYNPSEDILRIRNHSTHTKN

GSPQKGYEKFEFNIEDCRKFIDFYKQSISKHPEWKDFGFRFSDTQRYNSIDEFYREVE

NQGYKLTFENISESYIDSVVNQGKLYLFQIYNKDFSAYSKGRPNLHTLYWKALFDER

NLQDVVYKLNGEAELFYRKQSIPKKITHPAKEAIANKNKDNPKKESVFEYDLIKDKR

FTEDKFFFHCPITINFKSSGANKFNDEINLLLKEKANDVHILSIDRGERHLAYYTLVDG

KGNIIKQDTFNIIGNDRMKTNYHDKLAAIEKDRDSARKDWKKINNIKEMKEGYLSQV

VHEIAKLVIEYNAIVVFADLNFGFKRGRFKVEKQVYQKLEKMLIEKLNYLVFKDNEF

DKTGGVLRAYQLTAPFETFKKMGKQTGIIYYVPAGFTSKICPVTGFVNQLYPKYESV

SKSQEFFSKFDKICYNLDKGYFEFSFDYKNFGDKAAKGKWTIASFGSRLINFRNSDKN

HNWDTREVYPTKELEKLLKDYSIEYGHGECIKAAICGESDKKFFAKLTSVLNTILQM

RNSKTGTELDYLISPVADVNGNFFDSRQAPKNMPQDADANGAYHIGLKGLMLLGRI

KNNQEGKKLNLVIKNEEYFEFVQNRNN

*Francisella novicida* Cpf1 D1255A (SEQ ID NO: 717)

MSIYQEFVNKYSLSKTLRFELIPQGKTLENIKARGLILDDEKRAKDYKKAKQIIDKYH

QFFIEEILSSVCISEDLLQNYSDVYFKLKKSDDDNLQKDFKSAKDTIKKQISEYIKDSE

KFKNLFNQNLIDAKKGQESDLILWLKQSKDNGIELFKANSDITDIDEALEIIKSFKGWT

TYFKGFHENRKNVYSSNDIPTSIIYRIVDDNLPKFLENKAKYESLKDKAPEAINYEQIK

KDLAEELTFDIDYKTSEVNQRVFSLDEVFEIANFNNYLNQSGITKFNTIIGGKFVNGEN

TKRKGINEYINLYSQQINDKTLKKYKMSVLFKQILSDTESKSFVIDKLEDDSDVVTTM

QSFYEQIAAFKTVEEKSIKETLSLLFDDLKAQKLDLSKIYFKNDKSLTDLSQQVFDDY

SVIGTAVLEYITQQIAPKNLDNPSKKEQELIAKKTEKAKYLSLETIKLALEEFNKHRDI

-continued

```
DKQCRFEEILANFAAIPMIFDEIAQNKDNLAQISIKYQNQGKKDLLQASAEDDVKAIK

DLLDQTNNLLHKLKIFHISQSEDKANILDKDEHFYLVFEECYFELANIVPLYNKIRNYI

TQKPYSDEKFKLNFENSTLANGWDKNKEPDNTAILFIKDDKYYLGVMNKKNNKIFD

DKAIKENKGEGYKKIVYKLLPGANKMLPKVFFSAKSIKFYNPSEDILRIRNHSTHTKN

GSPQKGYEKFEFNIEDCRKFIDFYKQSISKHPEWKDFGFRFSDTQRYNSIDEFYREVE

NQGYKLTFENISESYIDSVVNQGKLYLFQIYNKDFSAYSKGRPNLHTLYWKALFDER

NLQDVVYKLNGEAELFYRKQSIPKKITHPAKEAIANKNKDNPKKESVFEYDLIKDKR

FTEDKFFFHCPITINFKSSGANKFNDEINLLLKEKANDVHILSIDRGERHLAYYTLVDG

KGNIIKQDTFNIIGNDRMKTNYHDKLAAIEKDRDSARKDWKKINNIKEMKEGYLSQV

VHEIAKLVIEYNAIVVFEDLNFGFKRGRFKVEKQVYQKLEKMLIEKLNYLVFKDNEF

DKTGGVLRAYQLTAPFETFKKMGKQTGIIYYVPAGFTSKICPVTGFVNQLYPKYESV

SKSQEFFSKFDKICYNLDKGYFEFSFDYKNFGDKAAKGKWTIASFGSRLINFRNSDKN

HNWDTREVYPTKELEKLLKDYSIEYGHGECIKAAICGESDKKFFAKLTSVLNTILQM

RNSKTGTELDYLISPVADVNGNFFDSRQAPKNMPQDAAANGAYHIGLKGLMLLGRI

KNNQEGKKLNLVIKNEEYFEFVQNRNN
```

In addition to Cas9 and Cpf1, three distinct Class 2 CRISPR-Cas systems (C2c1, C2c2, and C2c3) have been described by Shmakov et al., "Discovery and Functional Characterization of Diverse Class 2 CRISPR Cas Systems", Mol. Cell, 2015 Nov. 5; 60(3): 385-397, the entire contents of which is hereby incorporated by reference. Effectors of two of the systems, C2c1 and C2c3, contain RuvC-like endonuclease domains related to Cpf1. A third system, C2c2 contains an effector with two predicated HEPN RNase domains. Production of mature CRISPR RNA is tracrRNA-independent, unlike production of CRISPR RNA by C2c1. C2c1 depends on both CRISPR RNA and tracrRNA for DNA cleavage. Bacterial C2c2 has been shown to possess a unique RNase activity for CRISPR RNA maturation distinct from its RNA-activated single-stranded RNA degradation activity. These RNase functions are different from each other and from the CRISPR RNA-processing behavior of Cpf1. See, e.g., East-Seletsky, et al., "Two distinct RNase activities of CRISPR-C2c2 enable guide-RNA processing and RNA detection", Nature, 2016 Oct. 13; 538(7624):270-273, the entire contents of which are hereby incorporated by reference. In vitro biochemical analysis of C2c2 in Leptotrichia shahii has shown that C2c2 is guided by a single CRISPR RNA and can be programmed to cleave ssRNA targets carrying complementary protospacers. Catalytic residues in the two conserved HEPN domains mediate cleavage. Mutations in the catalytic residues generate catalytically inactive RNA-binding proteins. See e.g., Abudayyeh et al., "C2c2 is a single-component programmable RNA-guided RNA-targeting CRISPR effector", *Science,* 2016 Aug. 5; 353(6299), the entire contents of which are hereby incorporated by reference.

The crystal structure of *Alicyclobaccillus acidoterrastris* C2c1 (AacC2c1) has been reported in complex with a chimeric single-molecule guide RNA (sgRNA). See, e.g., Liu et al., "C2c1-sgRNA Complex Structure Reveals RNA-Guided DNA Cleavage Mechanism", *Mol. Cell,* 2017 Jan. 19; 65(2):310-322, the entire contents of which are hereby incorporated by reference. The crystal structure has also been reported in *Alicyclobacillus acidoterrestris* C2c1 bound to target DNAs as ternary complexes. See, e.g., Yang et al., "PAM-dependent Target DNA Recognition and Cleavage by C2C1 CRISPR-Cas endonuclease", *Cell,* 2016 Dec. 15; 167(7):1814-1828, the entire contents of which are hereby incorporated by reference. Catalytically competent conformations of AacC2c1, both with target and non-target DNA strands, have been captured independently positioned within a single RuvC catalytic pocket, with C2c1-mediated cleavage resulting in a staggered seven-nucleotide break of target DNA. Structural comparisons between C2c1 ternary complexes and previously identified Cas9 and Cpf1 counterparts demonstrate the diversity of mechanisms used by CRISPR-Cas9 systems.

In some embodiments, the guide nucleotide sequence-programmable DNA-binding protein of any of the fusion proteins provided herein may be a C2c1, a C2c2, or a C2c3 protein. In some embodiments, the guide nucleotide sequence-programmable DNA-binding protein is a C2c1 protein. In some embodiments, the guide nucleotide sequence-programmable DNA-binding protein is a C2c2 protein. In some embodiments, the guide nucleotide sequence-programmable DNA-binding protein is a C2c3 protein. In some embodiments, the guide nucleotide sequence-programmable DNA-binding protein comprises an amino acid sequence that is at least 85%, at least 90%, at least 91%, at least 92%, at least 93%, at least 94%, at least 95%, at least 96%, at least 97%, at least 98%, at least 99%, or at least 99.5% identical to a naturally-occurring C2c1, C2c2, or C2c3 protein. In some embodiments, the guide nucleotide sequence-programmable DNA-binding protein is a naturally-occurring C2c1, C2c2, or C2c3 protein. In some embodiments, the guide nucleotide sequence-programmable DNA-binding protein comprises an amino acid sequence that is at least 85%, at least 90%, at least 91%, at least 92%, at least 93%, at least 94%, at least 95%, at least 96%, at least 97%, at least 98%, at least 99%, or at least 99.5% identical to any of the C2c1, C2c2, or C2c3 proteins described herein. In some embodiments, the guide nucleotide sequence-programmable DNA-binding protein comprises an amino acid sequence of any one of the C2c1, C2c2, or C2c3 proteins described herein. It should be appreciated that C2c1, C2c2, or C2c3 from other bacterial species may also be used in accordance with the present disclosure.

C2c1 (uniprot.org/uniprot/T0D7A2#)
sp|T0D7A2|C2C1_ALIAG CRISPR-associated endonuclease C2c1 OS = *Alicyclobacillus acidoterrestris* (strain ATCC 49025/DSM 3922/ CIP 6132/NCIMB 13137/GD3B) GN = c2c1 PE = 1 SV = 1

(SEQ ID NO: 762)

MAVKSIKVKLRLDDMPEIRAGLWKLHKEVNAGVRYYTEWLSLLRQENLYR

RSPNGDGEQECDKTAEECKAELLERLRARQVENGHRGPAGSDDELLQLAR

QLYELLVPQAIGAKGDAQQIARKFLSPLADKDAVGGLGIAKAGNKPRWVR

MREAGEPGWEEEKEKAETRKSADRTADVLRALADFGLKPLMRVYTDSEMS

SVEWKPLRKGQAVRTWDRDMFQQAIERMMSWESWNQRVGQEYAKLVEQKN

RFEQKNFVGQEHLVHLVNQLQQDMKEASPGLESKEQTAHYVTGRALRGSD

KVFEKWGKLAPDAPFDLYDAEIKNVQRRNTRRFGSHDLFAKLAEPEYQAL

WREDASFLTRYAVYNSILRKLNHAKMFATFTLPDATAHPIWTRFDKLGGN

LHQYTFLFNEFGERRHAIRFHKLLKVENGVAREVDDVTVPISMSEQLDNL

LPRDPNEPIALYFRDYGAEQHFTGEFGGAKIQCRRDQLAHMHRRRGARDV

YLNVSVRVQSQSEARGERRPPYAAVFRLVGDNHRAFVHFDKLSDYLAEHP

DDGKLGSEGLLSGLRVMSVDLGLRTSASISVFRVARKDELKPNSKGRVPF

FFPIKGNDNLVAVHERSQLLKLPGETESKDLRAIREERQRTLRQLRTQLA

YLRLLVRCGSEDVGRRERSWAKLIEQPVDAANHMTPDWREAFENELQKLK

SLHGICSDKEWMDAVYESVRRVWRHMGKQVRDWRKDVRSGERPKIRGYAK

DVVGGNSIEQIEYLERQYKFLKSWSFFGKVSGQVIRAEKGSRFAITLREH

IDHAKEDRLKKLADRIIMEALGYVYALDERGKGKWVAKYPPCQLILLEEL

SEYQFNNDRPPSENNQLMQWSHRGVFQELINQAQVHDLLVGTMYAAFSSR

FDARTGAPGIRCRRVPARCTQEHNPEPFPWWLNKFVVEHTLDACPLRADD

LIPTGEGEIFVSPFSAEEGDFHQIHADLNAAQNLQQRLWSDFDISQIRLR

CDWGEVDGELVLIPRLTGKRTADSYSNKVFYTNTGVTYYERERGKKRRKV

FAQEKLSEEEAELLVEADEAREKSVVLMRDPSGIINRGNWTRQKEFWSMV

NQRIEGYLVKQIRSRVPLQDSACENTGDI

C2c2 (uniprot.org/uniprot/P0DOC6)

>sp|P0DOC6|C2C2_LEPSD CRISPR-associated endoribonuclease C2c2 OS = *Leptotrichiashahii* (strain DSM 19757/CCUG 47503/ CIP 107916/JCM 16776/LB37) GN = c2c2 PE = 1 SV = 1

(SEQ ID NO: 764)

MGNLFGHKRWYEVRDKKDFKIKRKVKVKRNYDGNKYILNINENNNKEKID

NNKFIRKYINYKKNDNILKEFTRKFHAGNILFKLKGKEGIIRIENNDDFL

ETEEVVLYIEAYGKSEKLKALGITKKKIIDEAIRQGITKDDKKIEIKRQE

NEEEIEIDIRDEYTNKTLNDCSIILRIIENDELETKKSIYEIFKNINMSL

YKIIEKIIENETEKVFENRYYEEHLREKLLKDDKIDVILTNFMEIREKIK

SNLEILGFVKFYLNVGGDKKKSKNKKMLVEKILNINVDLTVEDIADFVIK

ELEFWNITKRIEKVKKVNNEFLEKRRNRTYIKSYVLLDKHEKFKIERENK

KDKIVKFFVENIKNNSIKEKIEKILAEFKIDELIKKLEKELKKGNCDTEI

-continued

FGIFKKHYKVNFDSKKFSKKSDEEKELYKIIYRYLKGRIEKILVNEQKVR

LKKMEKIEIEKILNESILSEKILKRVKQYTLEHIMYLGKLRHNDIDMTTV

NTDDFSRLHAKEELDLELITFFASTNMELNKIFSRENINNDENIDFFGGD

REKNYVLDKKILNSKIKIIRDLDFIDNKNNITNNFIRKFTKIGTNERNRI

LHAISKERDLQGTQDDYNKVINIIQNLKISDEEVSKALNLDVVFKDKKNI

ITKINDIKISEENNNDIKYLPSFSKVLPEILNLYRNNPKNEPFDTIETEK

IVLNALIYVNKELYKKLILEDDLEENESKNIFLQELKKTLGNIDEIDENI

IENYYKNAQISASKGNNKAIKKYQKKVIECYIGYLRKNYEELFDFSDFKM

NIQEIKKQIKDINDNKTYERITVKTSDKTIVINDDFEYIISIFALLNSNA

VINKIRNRFFATSVWLNTSEYQNIIDILDEIMQLNTLRNECITENWNLNL

EEFIQKMKEIEKDFDDFKIQTKKEIFNNYYEDIKNNILTEFKDDINGCDV

LEKKLEKIVIFDDETKFEIDKKSNILQDEQRKLSNINKKDLKKKVDQYIK

DKDQEIKSKILCRIIFNSDFLKKYKKEIDNLIEDMESENENKFQEIYYPK

ERKNELYIYKKNLFLNIGNPNFDKIYGLISNDIKMADAKFLFNIDGKNIR

KNKISEIDAILKNLNDKLNGYSKEYKEKYIKKLKENDDFFAKNIQNKNYK

SFEKDYNRVSEYKKIRDLVEFNYLNKIESYLIDINWKLAIQMARFERDMH

YIVNGLRELGIIKLSGYNTGISRAYPKRNGSDGFYTTTAYYKFFDEESYK

KFEKICYGFGIDLSENSEINKPENESIRNYISHFYIVRNPFADYSIAEQI

DRVSNLLSYSTRYNNSTYASVFEVFKKDVNLDYDELKKKFKLIGNNDILE

RLMKPKKVSVLELESYNSDYIKNLIIELLTKIENTNDTL

In some embodiments, the guide nucleotide sequence-programmable DNA-binding protein domain of the present disclosure has no requirements for a PAM sequence. One example of such a guide nucleotide sequence-programmable DNA-binding protein may be an Argonaute protein from *Natronobacterium gregoryi* (NgAgo). NgAgo is a ssDNA-guided endonuclease. NgAgo binds 5' phosphorylated ssDNA of ~24 nucleotides (gDNA) to guide it to its target site and will make DNA double-strand breaks at the gDNA site. In contrast to Cas9, the NgAgo-gDNA system does not require a protospacer-adjacent motif (PAM). Using a nuclease inactive NgAgo (dNgAgo) can greatly expand the codons that may be targeted. The characterization and use of NgAgo have been described in Gao et al., Nat Biotechnol., 2016 July; 34(7):768-73. PubMed PMID: 27136078; Swarts et al., Nature. 507(7491) (2014):258-61; and Swarts et al., Nucleic Acids Res. 43(10) (2015):5120-9, each of which is incorporated herein by reference. The sequence of *Natronobacterium gregoryi* Argonaute is provided in SEQ ID NO: 718.

Wild type *Natronobacterium gregoryi* Argonaute (SEQ ID NO: 718)

MTVIDLDSTTTADELTSGHTYDISVTLTGVYDNTDEQHPRMSLAFEQDNG

ERRYITLWKNTTPKDVFTYDYATGSTYIFTNIDYEVKDGYENLTATYQTT

VENATAQEVGTTDEDETFAGGEPLDHHLDDALNETPDDAETESDSGHVMT

SFASRDQLPEWTLHTYTLTATDGAKTDTEYARRTLAYTVRQELYTDHDAA

PVATDGLMLLTPEPLGETPLDLDCGVRVEADETRTLDYTTAKDRLLAREL

VEEGLKRSLWDDYLVRGIDEVLSKEPVLTCDEFDLHERYDLSVEVGHSGR

-continued

```
AYLHINFRHRFVPKLTLADIDDDNIYPGLRVKTTYRPRRGHIVWGLRDEC

ATDSLNTLGNQSVVAYHRNNQTPINTDLLDAIEAADRRVVETRRQGHGDD

AVSFPQELLAVEPNTHQIKQFASDGFHQQARSKTRLSASRCSEKAQAFAE

RLDPVRLNGSTVEFSSEFFTGNNEQQLRLLYENGESVLTFRDGARGAHPD

ETFSKGIVNPPESFEVAVVLPEQQADTCKAQWDTMADLLNQAGAPPTRSE

TVQYDAFSSPESISLNVAGAIDPSEVDAAFVVLPPDQEGFADLASPTETY

DELKKALANMGIYSQMAYFDRFRDAKIFYTRNVALGLLAAAGGVAFTTEH

AMPGDADMFIGIDVSRSYPEDGASGQINIAATATAVYKDGTILGHSSTRP

QLGEKLQSTDVRDIMKNAILGYQQVTGESPTHIVIHRDGFMNEDLDPATE

FLNEQGVEYDIVEIRKQPQTRLLAVSDVQYDTPVKSIAAINQNEPRATVA

TFGAPEYLATRDGGGLPRPIQIERVAGETDIETLTRQVYLLSQSHIQVHN

STARLPITTAYADQASTHATKGYLVQTGAFESNVGFL
```

Also provided herein are Cas9 variants that have relaxed PAM requirements (PAMless Cas9). PAMless Cas9 exhibits an increased activity on a target sequence that does not include a canonical PAM (e.g., NGG) sequence at its 3'-end as compared to *Streptococcus pyogenes* Cas9 as provided by SEQ ID NO: 1, e.g., increased activity by at least 5-fold, at least 10-fold, at least 50-fold, at least 100-fold, at least 500-fold, at least 1,000-fold, at least 5,000-fold, at least 10,000-fold, at least 50,000-fold, at least 100,000-fold, at least 500,000-fold, or at least 1,000,000-fold. Such Cas9 variants that have relaxed PAM requirements are described in US Provisional Application Ser. No. 62/245,828, filed Oct. 23, 2015; 62/279,346, filed Jan. 15, 2016; 62/311,763, filed Mar. 22, 2016; 62/322,178, filed Apr. 13, 2016; and 62/357,332, filed Jun. 30, 2016, each of which is incorporated herein by reference. In some embodiments, the dCas9 or Cas9 nickase useful in the present disclosure may further comprise mutations that relax the PAM requirements, e.g., mutations that correspond to A262T, K294R, S409I, E480K, E543D, M694I, or E1219V in SEQ ID NO: 1.

The “-” used in the general architecture discussed herein may indicate the presence of an optional linker. The term “linker,” as used herein, refers to a chemical group or a molecule linking two molecules or moieties, e.g., two domains of a fusion protein, such as, for example, a guide nucleotide sequence-programmable DNA binding protein domain and a recombinase catalytic domain. Typically, the linker is positioned between, or flanked by, two groups, molecules, or other moieties and connected to each one via a covalent bond, thus connecting the two. In some embodiments, the linker is an amino acid or a plurality of amino acids (e.g., a peptide or protein). In some embodiments, the linker is an organic molecule, group, polymer, or chemical moiety. In some embodiments, the linker is 5-100 amino acids in length, for example, 5, 6, 7, 8, 9, 10, 11, 12, 13, 14, 15, 16, 17, 18, 19, 20, 21, 22, 23, 24, 25, 26, 27, 28, 29, 30, 30-35, 35-40, 40-45, 45-50, 50-60, 60-70, 70-80, 80-90, 90-100, 100-150, or 150-200 amino acids in length. Longer or shorter linkers are also contemplated. Linkers may be of any form known in the art. The linkers may also be unstructured, structured, helical, or extended.

In some embodiments, the guide nucleotide sequence-programmable DNA binding protein domain and the recombinase catalytic domain are fused to each other via a linker. Various linker lengths and flexibilities between the guide nucleotide sequence-programmable DNA binding protein domain and the recombinase catalytic domain can be employed (e.g., ranging from flexible linkers of the form (GGGS)n (SEQ ID NO: 759), (GGGGS)n (SEQ ID NO: 722), (GGS)n, and (G)n to more rigid linkers of the form (EAAAK)n (SEQ ID NO: 723), SGSETPGTSESATPES (SEQ ID NO: 724) (see, e.g., Guilinger et al., Nat. Biotechnol. 2014; 32(6): 577-82; the entire contents of which is incorporated herein by reference), (XP)n, or a combination of any of these, wherein X is any amino acid, and n is independently an integer between 1 and 30, in order to achieve the optimal length for activity for the specific application. In some embodiments, n is independently 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30, or, if more than one linker or more than one linker motif is present, any combination thereof. In some embodiments, the linker comprises a (GGS)n motif, wherein n is 1, 2, 3, 4, 5, 6, 7, 8, 9, 10, 11, 12, 13, 14 or 15. In some embodiments, the linker comprises a (GGS)n motif, wherein n is 1, 3, or 7. In some embodiments, the linker comprises an XTEN linker. The XTEN linker may have the sequence SGSETPGTSESATPES (SEQ ID NO: 7), SGSETPGTSESA (SEQ ID NO: 8), or SGSETPGTSESATPEGGSGGS (SEQ ID NO: 9). In some embodiments, the linker comprises an amino acid sequence chosen from the group including, but not limited to, AGVF (SEQ ID NO: 772), GFLG (SEQ ID NO: 773), FK, AL, ALAL (SEQ ID NO: 774), and ALALA (SEQ ID NO: 775). In some embodiments, suitable linker motifs and configurations include those described in Chen et al., Fusion protein linkers: property, design and functionality. Adv Drug Deliv Rev. 2013; 65(10):1357-69, which is incorporated herein by reference. In some embodiments, the linker may comprise any of the following amino acid sequences: VPFLLEPDNINGKTC (SEQ ID NO: 10), GSAGSAAGSGEF (SEQ ID NO: 11), SIVAQLSRPDPA (SEQ ID NO: 12), MKIIEQLPSA (SEQ ID NO: 13), VRHKLKRVGS (SEQ ID NO: 14), GHGTGSTGSGSS (SEQ ID NO: 15), MSRPDPA (SEQ ID NO: 16), GSAGSAAGSGEF (SEQ ID NO: 7), SGSETPGTSESA (SEQ ID NO: 8), SGSETPGTSESATPEGGSGGS (SEQ ID NO: 9), and GGSM (SEQ ID NO: 17).

Additional suitable linker sequences will be apparent to those of skill in the art based on the instant disclosure. In certain embodiments, the linker may have a length of about 33 angstroms to about 81 angstroms. In another embodiment, the linker may have a length of about 54 angstroms to about 81 angstroms. In a further embodiment, the linker may have a length of about 63 to about 81 angstroms. In another embodiment, the linker may have a length of about 65 angstroms to about 75 angstroms. In some embodiments, the linker may have a weight of about 1.20 kDa to about 1.85 kDa. In certain embodiments, the linker may have a weight of about 1.40 kDa to about 1.85 kDa. In certain embodiments, the linker may have a weight of about 1.60 kDa to about 1.7 kDa. In some embodiments, the linker is an amino acid or a plurality of amino acids (e.g., a peptide or protein). In some embodiments, the linker is an organic molecule, group, polymer, or chemical moiety. In some embodiments, the linker is a peptide linker. In some embodiments, the peptide linker is any stretch of amino acids having at least 1, at least 2, at least 3, at least 4, at least 5, at least 6, at least 7, at least 8, at least 9, at least 10, at least 15, at least 20, at least 25, at least 30, at least 40, at least 50, or more amino acids. In certain embodiments, the peptide linker is from 18 to 27 amino acids long. In a specific embodiment, the peptide linker is 24 amino acids long. In some embodiments, the peptide linker comprises repeats of the tri-peptide Gly- Gly-Ser, e.g., comprising the sequence (GGS)$_n$, wherein n represents at least 1, 2, 3, 4, 5, 6, 7, 8, 9, 10, or more repeats. In some embodiments, the linker comprises the sequence $(GGS)_6$ (SEQ ID NO: 6). In some embodiments, the peptide linker is the 16 residue "XTEN" linker, or a variant thereof (See, e.g., the Examples; and Schellenberger et al. A recombinant polypeptide extends the in vivo half-life of peptides and proteins in a tunable manner. Nat. Biotechnol. 27, 1186-1190 (2009)). In some embodiments, the XTEN linker comprises the sequence SGSETPGTSESATPES (SEQ ID NO: 7), SGSETPGTSESA (SEQ ID NO: 8), or SGSETPGTSESATPEGGSGGS (SEQ ID NO: 9). In some embodiments, the peptide linker is selected from VPFLLEPDNINGKTC (SEQ ID NO: 10), GSAGSAAGSGEF (SEQ ID NO: 11), SIVAQLSRPDPA (SEQ ID NO: 12), MKIIEQLPSA (SEQ ID NO: 13), VRHKLKRVGS (SEQ ID NO: 14), GHGTGSTGSGSS (SEQ ID NO: 15), MSRPDPA (SEQ ID NO: 16); or GGSM (SEQ ID NO: 17). In some embodiments, the linker is a non-peptide linker. In certain embodiments, the non-peptide linker comprises one or more of polyethylene glycol (PEG), polypropylene glycol (PPG), co-poly(ethylene/propylene) glycol, polyoxyethylene (POE), polyurethane, polyphosphazene, polysaccharides, dextran, polyvinyl alcohol, polyvinylpyrrolidones, polyvinyl ethyl ether, polyacryl amide, polyacrylate, polycyanoacrylates, lipid polymers, chitins, hyaluronic acid, heparin, or an alkyl linker. In one embodiment, the alkyl linker has the formula $—NH—(CH_2)_s—C(O)—$, wherein s may be any integer. In a further embodiment, s may be any integer from 1-20.

Recombinase Catalytic Domain

The recombinase catalytic domain for use in the compositions and methods of the instant disclosure may be from any recombinase. Suitable recombinases catalytic domains for use in the disclosed methods and compositions may be obtained from, for example, and without limitation, tyrosine recombinases and serine recombinases. Some exemplary suitable recombinases provided herein include, for example, and without limitation, Gin recombinase (acting on gix sites), Hin recombinase (acting on hix sites), β recombinase (acting on six sites), Sin recombinase (acting on resH sites), Tn3 recombinase (acting on res sites), γδ recombinase (acting on res sites), Cre recombinase from bacteriophage P1 (acting on LoxP sites); FLP recombinases of fungal origin (acting on FTR sites); and phiC31 integrase (acting on att sites). Non-limiting sequences of exemplary suitable recombinases may be found below.

Cre recombinase sequence
(SEQ ID NO: 725)

MSNLLTVHQNLPALPVDATSDEVRKNLMDMFRDRQAFSEHTWKMLLSVCR

SWAAWCKLNNRKWFPAEPEDVRDYLLYLQARGLAVKTIQQHLGQLNMLHR

RSGLPRPSDSNAVSLVMRRIRKENVDAGERAKQALAFERTDFDQVRSLME

NSDRCQDIRNLAFLGIAYNTLLRIAEIARIRVKDISRTDGGRMLIHIGRT

KTLVSTAGVEKALSLGVTKLVERWISVSGVADDPNNYLFCRVRKNGVAAP

SATSQLSTRALEGIFEATHRLIYGAKDDSGQRYLAWSGHSARVGAARDMA

RAGVSIPEIMQAGGWTNVNIVMNYIRNLDSETGAMVRLLEDGD

FLP recombinase
(SEQ ID NO: 726)

MPQFGILCKTPPKVLVRQFVERFERPSGEKIALCAAELTYLCWMITHNGT

AIKRATFMSYNTIISNSLSFDIVNKSLQFKYKTQKATILEASLKKLIPAW

-continued

EFTIIPYYGQKHQSDITDIVSSLQLQFESSEEADKGNSHSKKMLKALLSE

GESIWEITEKILNSFEYTSRFTKTKTLYQFLFLATFINCGRFSDIKNVDP

KSFKLVQNKYLGVIIQCLVTETKTSVSRHIYFFSARGRIDPLVYLDEFLR

NSEPVLKRVNRTGNSSSNKQEYQLLKDNLVRSYNKALKKNAPYSIFAIKN

GPKSHIGRHLMTSFLSMKGLTELTNVVGNWSDKRASAVARTTYTHQITAI

PDHYFALVSRYYAYDPISKEMIALKDETNPIEEWQHIEQLKGSAEGSIRY

PAWNGIISQEVLDYLSSYINRRI

γδ recombinase (Gamma Delta resolvase)
(SEQ ID NO: 727)

MRLFGYARVSTSQQSLDIQVRALKDAGVKANRIFTDKASGSSSDRKGLDL

LRMKVEEGDVILVKKLDRLGRDTADMIQLIKEFDAQGVSIRFIDDGISTD

GEMGKMVVTILSAVAQAERQRILERTNEGRQEAMAKGVVFGRKR

γδ recombinase (E124Q mutation)
(SEQ ID NO: 728)

MRLFGYARVSTSQQSLDIQVRALKDAGVKANRIFTDKASGSSSDRKGLDL

LRMKVEEGDVILVKKLDRLGRDTADMIQLIKEFDAQGVSIRFIDDGISTD

GEMGKMVVTILSAVAQAERQRILQRTNEGRQEAMAKGVVFGRKR

γδ recombinase (E102Y/E124Q mutation)
(SEQ ID NO: 729)

MRLFGYARVSTSQQSLDIQVRALKDAGVKANRIFTDKASGSSSDRKGLDL

LRMKVEEGDVILVKKLDRLGRDTADMIQLIKEFDAQGVSIRFIDDGISTD

GYMGKMVVTILSAVAQAERQRILQRTNEGRQEAMAKGVVFGRKR

β recombinase
(SEQ ID NO: 730)

MAKIGYARVSSKEQNLDRQLQALQGVSKVFSDKLSGQSVERPQLQAMLNY

IREGDIVVVTELDRLGRNNKELTELMNAIQQKGATLEVLDLPSMNGIEDE

NLRRLINNLVIELYKYQAESERKRIKERQAQGIEIAKSKGKFKGRQH

β recombinase (N95D mutation)
(SEQ ID NO: 731)

MAKIGYARVSSKEQNLDRQLQALQGVSKVFSDKLSGQSVERPQLQAMLNY

IREGDIVVVTELDRLGRNNKELTELMNAIQQKGATLEVLDLPSMDGIEDE

NLRRLINNLVIELYKYQAESERKRIKERQAQGIEIAKSKGKFKGRQH

Sin recombinase
(SEQ ID NO: 732)

MIIGYARVSSLDQNLERQLENLKTFGAEKIFTEKQSGKSIENRPILQKAL

NFVRMGDRFIVESIDRLGRNYNEVIHTVNYLKDKEVQLMITSLPMMNEVI

GNPLLDKFMKDLIIQILAMVSEQERNESKRRQAQGIQVAKEKGVYKGRPL

Sin recombinase (Q87R/Q115R mutations)
(SEQ ID NO: 733)

MIIGYARVSSLDQNLERQLENLKTFGAEKIFTEKQSGKSIENRPILQKAL

NFVRMGDRFIVESIDRLGRNYNEVIHTVNYLKDKEVRLMITSLPMMNEVI

GNPLLDKFMKDLIIRILAMVSEQERNESKRRQAQGIQVAKEKGVYKGRPL

Tn3 recombinase
(SEQ ID NO: 734)

MRLFGYARVSTSQQSLDLQVRALKDAGVKANRIFTDKASGSST

DREGLDLLRMKVKEGDVILVKKLDRLGRDTADMLQLIKEFDAQGVAV

RFIDDGISTDGDMGQMVVTILSAVAQAERRRILERTNEGRQEAK

LKGIKFGRRR

-continued

Tn3 recombinase (G70S/D102Y, E124Q mutations)

(SEQ ID NO: 735)

MRLFGYARVSTSQQSLDLQVRALKDAGVKANRIFTDKASGSSTDREGLDL

LRMKVKEGDVILVKKLDRLSRDTADMLQLIKEFDAQGVAVRFIDDGISTD

GYMGQMVVTILSAVAQAERRRILQRTNEGRQEAKLKGIKFGRRR

Hin recombinase (SEQ ID NO: 736)

MATIGYIRVSTIDQNIDLQRNALTSANCDRIFED

RISGKIANRPGLKRALKYVNKGDTLVVWKLDRLGRSVKNLVALISELHER

GAHFHSLTDSIDTSSAMGRFFFHVMSALAEMERELIVERTLAGLAAARAQ

GRLGGRPV

Hin recombinase (H107Y mutation)

(SEQ ID NO: 737)

MATIGYIRVSTIDQNIDLQRNALTSANCDRIFEDRISGKIANRPGLKRAL

KYVNKGDTLVVWKLDRLGRSVKNLVALISELHERGAHFHSLTDSIDTSSA

MGRFFFYVMSALAEMERELIVERTLAGLAAARAQGRLGGRPV

PhiC31 recombinase (SEQ ID NO: 738)

MDTYAGAYDRQSRERENSSAASPATQRSANEDKAADLQREVERDGGRFRF

VGHFSEAPGTSAFGTAERPEFERILNECRAGRLNMIIVYDVSRFSRLKVM

DAIPIVSELLALGVTIVSTQEGVFRQGNVMDLIHLIMRLDASHKESSLKS

AKILDTKNLQRELGGYVGGKAPYGFELVSETKEITRNGRMVNVVINKLAH

STTPLTGPFEFEPDVIRWWWREIKTHKHLPFKPGSQAAIHPGSITGLCKR

MDADAVPTRGETIGKKTASSAWDPATVMRILRDPRIAGFAAEVIYKKKPD

GTPTTKIEGYRIQRDPITLRPVELDCGPIIEPAEWYELQAWLDGRGRGKG

LSRGQAILSAMDKLYCECGAVMTSKRGEESIKDSYRCRRRKVVDPSAPGQ

HEGTCNVSMAALDKFVAERIFNKIRHAEGDEETLALLWEAARRFGKLTEA

PEKSGERANLVAERADALNALEELYEDRAAGAYDGPVGRKHFRKQQAALT

LRQQGAEERLAELEAAEAPKLPLDQWFPEDADADPTGPKSWWGRASVDDK

RVFVGLFVDKIVVTKSTTGRGQGTPIEKRASITWAKPPTDDDEDDAQDGT

EDVAATGA

Recombinases for use with the disclosed compositions and methods may also include further mutations. Some aspects of this disclosure provide recombinases comprising an amino acid sequence that is at least 70%, at least 80%, at least 90%, at least 95%, or at least 97% identical to the sequence of the recombinase sequence discussed herein, wherein the amino acid sequence of the recombinase comprises at least one mutation as compared to the sequence of the recombinase sequence discussed herein. In some embodiments, the amino acid sequence of the recombinase comprises at least 2, at least 3, at least 4, at least 5, at least 6, at least 7, at least 8, at least 9, at least 10, at least 11, at least 12, at least 13, at least 14, or at least 15 mutations as compared to the sequence of the recombinase sequence discussed herein.

For example, the γδ recombinase may comprise one or more mutations from the list: R2A, E56K, G1015, E102Y, M1031, or E124Q. In one embodiment, the γδ recombinase may comprise an E102Y mutation, an E124Q mutation, or both an E102Y and E124Q mutation. In another embodiment, the β recombinase may comprise one or more mutations including, but not limited to N95D. See, for example, Sirk et al., "Expanding the zinc-finger recombinase repertoire: directed evolution and mutational analysis of serine recombinase specificity determinants" Nucl Acids Res (2014) 42 (7): 4755-4766. In another embodiment, the Sin recombinase may have one or more mutations including, but not limited to: Q87R, Q115R, or Q87R and Q115R. In another embodiment, the Tn3 recombinase may have one or more mutations including, but not limited to: G705, D102Y, E124Q, and any combination thereof. In another embodiment, the Hin recombinase may have one or more mutations including, but not limited to: H107Y. In another embodiment, the Sin recombinase may have one or more mutations including, but not limited to: H107Y. Any of the recombinase catalytic domains for use with the disclosed compositions and methods may have greater than 85%, 90%, 95%, 98%, or 99% sequence identity with the native (or wild type) amino acid sequence. For example, in certain embodiments, the Gin recombinase catalytic domain has greater than 85%, 90%, 95%, 98%, or 99% sequence identity with the amino acid sequence shown in SEQ ID NO: 713. In another embodiment, the amino acid sequence of the Gin recombinase catalytic domain comprises a mutation corresponding to H106Y, and/or I127L, and/or I136R and/or G137F. In yet another embodiment, the amino acid sequence of the Gin recombinase catalytic domain comprises a mutation corresponding to H106Y, I127L, I136R, and G137F. In a further embodiment, the amino acid sequence of the Gin recombinase has been further mutated. In a specific embodiment, the amino acid sequence of the Gin recombinase catalytic domain comprises SEQ ID NO: 713.

The recombinase catalytic domain for use in the compositions and methods of the instant disclosure may be from an evolved recombinase. As used herein, the term "evolved recombinase" refers to a recombinase that has been altered (e.g., through mutation) to recognize non-native DNA target sequences.

Suitable recombinases that can be evolved include, for example, and without limitation, tyrosine recombinases and serine recombinases (e.g., any of the recombinases discussed herein). Some exemplary suitable recombinases that can be evolved by the methods and strategies provided herein include, for example, and without limitation, Gin recombinase (acting on gix sites), Hin recombinase (acting on hix sites), β recombinase (acting on six sites), Sin recombinase (acting on resH sites), Tn3 recombinase (acting on res sites), γδ recombinase (acting on res sites), Cre recombinase from bacteriophage P1 (acting on LoxP sites); λ phage integrase (acting on att sites); FLP recombinases of fungal origin (acting on FTR sites); phiC31 integrase; Dre recombinase, BxB 1; and prokaryotic β-recombinase.

For example, the evolved recombinase for use with the compositions and methods of the instant disclosure may have been altered to interact with (e.g., bind and recombine) a non-canonical recombinase target sequence. As a non-limiting example, the non-canonical recombinase target sequence may be naturally occurring, such as, for example, sequences within a "safe harbor" genomic locus in a mammalian genome, e.g., a genomic locus that is known to be tolerant to genetic modification without any undesired effects. Recombinases targeting such sequences allow, e.g., for the targeted insertion of nucleic acid constructs at a specific genomic location without the need for conventional time- and labor-intensive gene targeting procedures, e.g., via homologous recombination technology. In addition, the directed evolution strategies provided herein can be used to evolve recombinases with an altered activity profile, e.g., recombinases that favor integration of a nucleic acid sequence over excision of that sequence or vice versa.

Evolved recombinases exhibit altered target sequence preferences as compared to their wild type counterparts, can be used to target virtually any target sequence for recombinase activity. Accordingly, the evolved recombinases can be used to modify, for example, any sequence within the genome of a cell or subject. Because recombinases can effect an insertion of a heterologous nucleic acid molecule into a target nucleic acid molecule, an excision of a nucleic acid sequence from a nucleic acid molecule, an inversion, or a replacement of nucleic acid sequences, the technology provided herein enables the efficient modification of genomic targets in a variety of ways (e.g., integration, deletion, inversion, exchange of nucleic acid sequences).

Catalytic domains from evolved recombinases for use with the methods and compositions of the instant disclosure comprise an amino acid sequence that is at least 70%, at least 80%, at least 90%, at least 95%, or at least 97% identical to the sequence of a wild-type recombinase, wherein the amino acid sequence of the evolved recombinase comprises at least one mutation as compared to the sequence of the wild-type recombinase, and wherein the evolved recombinase recognizes a DNA recombinase target sequence that differs from the canonical recombinase target sequence by at least one nucleotide. In some embodiments, the evolved recombinase recognizes a DNA recombinase target sequence that differs from the canonical recombinase target sequence (e.g., a res, gix, hix, six, resH, LoxP, FTR, or att core or related core sequence) by at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20 at least 25, or at least 30 nucleotides. In some embodiments, the evolved recombinase recognizes a DNA recombinase target sequence that differs from the canonical recombinase target sequence by 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides.

In some embodiments, only a portion of the recombinase is used in the fusion proteins and methods described herein. As a non-limiting embodiment, only the C-terminal portion of the recombinase may be used in the fusion proteins and methods described herein. In a specific embodiment, the 25 kDa carboxy-terminal domain of Cre recombinase may be used in the compositions and methods. See, for example, Hoess et al, "DNA Specificity of the Cre Recombinase Resides in the 25 kDa Carboxyl Domain of the Protein," J. Mol. Bio. 1990 Dec. 20, 216(4):873-82, which is incorporated by reference herein for all purposes. The 25 kDa carboxy-terminal domain of Cre recombinase is the portion stretching from R118 to the carboxy terminus of the protein. In some embodiments, the 25 kDa carboxy-terminal domain of Cre recombinase for use in the instant fusion proteins and methods may differ from the canonical 25 kDa carboxy-terminal domain of Cre recombinase by at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, or at least 20 amino acids. In some embodiments, the 25 kDa carboxy-terminal domain of Cre recombinase for use in the instant fusion proteins and methods may differ from the canonical 25 kDa carboxy-terminal domain of Cre recombinase by 1, 2, 3, 4, 5, 6, 7, 8, 9, 10, 11, 12, 13, 14, 15, 16, 17, 18, 19, or 20 amino acids. In certain embodiments, only a portion of the 25 kDa carboxy-terminal domain of Cre recombinase may be used in the fusion proteins and methods described herein. For example, the portion of Cre recombinase used may be R130 to the carboxy terminus of the protein, T140 to the carboxy terminus of the protein, E150 to the carboxy terminus of the protein, N160 to the carboxy terminus of the protein, T170 to the carboxy terminus of the protein, 1180 to the carboxy terminus of the protein, G190 to the carboxy terminus of the protein, T200 to the carboxy terminus of the protein, E210 to the carboxy terminus of the protein, L220 to the carboxy terminus of the protein, V230 to the carboxy terminus of the protein, C240 to the carboxy terminus of the protein, P250 to the carboxy terminus of the protein, A260 to the carboxy terminus of the protein, R270 to the carboxy terminus of the protein, G280 to the carboxy terminus of the protein, S290 to the carboxy terminus of the protein, A300 to the carboxy terminus of the protein, or M310 to the carboxy terminus of the protein. As another set of non-limiting examples, the portion of Cre recombinase used may be R118-E340, R118-5330, R1184320, R118-M310, R118-A300, R118-S290, R118-G280, R118-R270, R118-A260, R118-P250, R118-C240, R118-V230, R118-L220, or R118-E210. As a further set of non-limiting examples, the portion of Cre recombinase used may be R118-E210, G190-R270, E210-5290, P250-M310, or R270 to the carboxy terminus of the protein.

In some embodiments, the Cre recombinase used in the fusion proteins and methods described herein may be truncated at any position. In a specific embodiment, the Cre recombinase used in the fusion proteins and methods described herein may be truncated such that it begins with amino acid R118, A127, E138, or R154) (preceded in each case by methionine). In another set of non-limiting embodiments, the Cre recombinase used in the fusion proteins and methods described herein may be truncated within 10 amino acids, 9 amino acids, 8 amino acids, 7 amino acids, 6 amino acids, 5 amino acids, 4 amino acids, 3 amino acids, 2 amino acids, or 1 amino acid of R118, A127, E138, or R154.

In some embodiments, the recombinase target sequence is between 10-50 nucleotides long. In some embodiments, the recombinase is a Cre recombinase, a Hin recombinase, or a FLP recombinase. In some embodiments, the canonical recombinase target sequence is a LoxP site (5'-ATAACTTCGTATA GCATACAT TATACGAAGTTAT-3' (SEQ ID NO: 739). In some embodiments, the canonical recombinase target sequence is an FRT site (5'-GAAGTTCCTATTCTCTAGAAA GTATAGGAACTTC-3') (SEQ ID NO: 740). In some embodiments, the amino acid sequence of the evolved recombinase comprises at least 2, at least 3, at least 4, at least 5, at least 6, at least 7, at least 8, at least 9, at least 10, at least 11, at least 12, at least 13, at least 14, or at least 15 mutations as compared to the sequence of the wild-type recombinase. In some embodiments, the evolved recombinase recognizes a DNA recombinase target sequence that comprises a left half-site, a spacer sequence, and a right half-site, and wherein the left half-site is not a palindrome of the right half-site.

In some embodiments, the evolved recombinase recognizes a DNA recombinase target sequence that comprises a naturally occurring sequence. In some embodiments, the evolved recombinase recognizes a DNA recombinase target sequence that is comprised in the genome of a mammal. In some embodiments, the evolved recombinase recognizes a DNA recombinase target sequence comprised in the genome of a human. In some embodiments, the evolved recombinase recognizes a DNA recombinase target sequence that occurs only once in the genome of a mammal. In some embodiments, the evolved recombinase recognizes a DNA recombinase target sequence in the genome of a mammal that differs from any other site in the genome by at least 1, at least 2, at least 3, at least 4, at least 5, at least 6, at least 7, at least 8, at least 9, at least 10, at least 11, at least 12, at least 13, at least 14, or at least 15 nucleotide(s). In some embodiments, the evolved recombinase recognizes a DNA recombinase target sequence located in a safe harbor genomic locus. In some embodiments, the safe harbor genomic locus is a Rosa26 locus. In some embodiments, the evolved recombinase recognizes a DNA recombinase target sequence located in a genomic locus associated with a disease or disorder.

In certain embodiments, the evolved recombinase may target a site in the Rosa locus of the human genome (e.g., 36C6). A non-limiting set of such recombinases may be found, for example, in International PCT Publication, WO 2017/015545A1, published Jan. 26, 2017, entitled "Evolution of Site Specific Recombinases," which is incorporated by reference herein for this purpose. In some embodiments, the amino acid sequence of the evolved recombinase comprises at least 2, at least 3, at least 4, at least 5, at least 6, at least 7, at least 8, at least 9, at least 10, at least 11, at least 12, at least 13, at least 14, or at least 15 mutations as compared to the sequence of the wild-type recombinase. The nucleotide sequence encoding 36C6 is shown below in bold; those encoding GGS linkers are shown in italics; those encoding dCas9 linkers are black; those encoding the FLAG tag and NLS are underlined and in lowercase, respectively.

```
dCas9-36C6 (nucleotide)
                                                                  (SEQ ID NO: 765)
ATGTCCAACCTCCTTACCGTCCACCAGAATCTCCCTGCCCTTCCGGTGGATGCCACCTCTGATGAAGTGCGAAAA

AACCTGATGGATATGTTTCGCGATAGGCAAGCTTTTTCTGAACACACGTGGAAGATGCTCCTGTCAGTGTGTAGA

AGCTGGGCAGCTTGGTGCAAGTTGAACAACCGAAAATGGTTTCCTGCCGAACCCGAAGATGTGAGAGACTACCTC

CTCTACCTGCAGGCTCGAGGGCTCGCCGTGAAAACAATCCAACAACACTTGGGTCAGCTCAACATGCTGCACAGG

AGATCTGGGCTGCCCCGGCCGAGTGACTCTAATGCCGTTAGTCTCGTAATGCGGCGCATTCGCAAAGAGAATGTG

GATGCTGGAGAACGGGCGAAACAGGCACTGGCTTTTGAACGGACCGACTTCGATCAGGTGCGGAGTCTTATGGAG

AATAGTGACAGATGCCAGGACATTCGGAACCTTGCATTCCTGGGTATCGCGTATAATACCCTGCTGAGAATCGCT

GAGATCGCCAGAATCAGGGTAAAGGATATTTCTCGAACGGACGGGGGACGGATGTTGATTCATATCGGTCGCACT

AAAACACTTGTGAGTACCGCCGGGGTAGAGAAAGCCCTGAGCCTTGGAGTTACTAAACTGGTGGAGCGGTGGATT

AGCGTGTCCGGCGTGGCGGATGACCCAAACAATTACTTGTTTTGTAGGGTGCGGAAAAATGGTGTAGCCGCTCCA

TCCGCTACCTCACAGTTGAGTACACGCGCGTTGGAGGGGATTTTCGAAGCCACACATCGCTTGATCTACGGCGCC

AAGGACGATTCAGGCCAGCGATATCTTGCCTGGAGCGGGCATAGTGCCCGGGTGGGTGCCGCCCGAGACATGGCA

AGGGCTGGCGTGTCAATTCCTGAAATCATGCAGGCCGGCGGGTGGACCAACGTGAACATTGTGATGAACTATATC

CGGAACCTGGATAGCGAGACCGGAGCAATGGTCAGACTGCTTGAGGATGGCGAC*GGTGGATCCGGAGGGTCCGGA*

*GGTAGTGGCGGCAGCGGTGGTTCAGGTGGCAGCGGAGGGTCAGGAGGCTCTGA*TAAAAAGTATTCTATTGGTTTA

GCTATCGGCACTAATTCCGTTGGATGGGCTGTCATAACCGATGAATACAAAGTACCTTCAAAGAAATTTAAGGTG

TTGGGGAACACAGACCGTCATTCGATTAAAAAGAATCTTATCGGTGCCCTCCTATTCGATAGTGGCGAAACGGCA

GAGGCGACTCGCCTGAAACGAACCGCTCGGAGAAGGTATACACGTCGCAAGAACCGAATATGTTACTTACAAGAA

ATTTTTAGCAATGAGATGGCCAAAGTTGACGATTCTTTCTTTCACCGTTTGGAAGAGTCCTTCCTTGTCGAAGAG

GACAAGAAACATGAACGGCACCCCATCTTTGGAAACATAGTAGATGAGGTGGCATATCATGAAAAGTACCCAACG

ATTTATCACCTCAGAAAAAAGCTAGTTGACTCAACTGATAAAGCGGACCTGAGGTTAATCTACTTGGCTCTTGCC

CATATGATAAAGTTCCGTGGGCACTTTCTCATTGAGGGTGATCTAAATCCGGACAACTCGGATGTCGACAAACTG

TTCATCCAGTTAGTACAAACCTATAATCAGTTGTTTGAAGAGAACCCTATAAATGCAAGTGGCGTGGATGCGAAG

GCTATTCTTAGCGCCCGCCTCTCTAAATCCCGACGGCTAGAAAACCTGATCGCACAATTACCCGGAGAGAAGAAA

AATGGGTTGTTCGGTAACCTTATAGCGCTCTCACTAGGCCTGACACCAAATTTTAAGTCGAACTTCGACTTAGCT

GAAGATGCCAAATTGCAGCTTAGTAAGGACACGTACGATGACGATCTCGACAATCTACTGGCACAAATTGGAGAT

CAGTATGCGGACTTATTTTTGGCTGCCAAAAACCTTAGCGATGCAATCCTCCTATCTGACATACTGAGAGTTAAT

ACTGAGATTACCAAGGCGCCGTTATCCGCTTCAATGATCAAAAGGTACGATGAACATCACCAAGACTTGACACTT

CTCAAGGCCCTAGTCCGTCAGCAACTGCCTGAGAAATATAAGGAAATATTCTTTGATCAGTCGAAAAACGGGTAC

GCAGGTTATATTGACGGCGGAGCGAGTCAAGAGGAATTCTACAAGTTTATCAAACCCATATTAGAGAAGATGGAT

GGGACGGAAGAGTTGCTTGTAAAACTCAATCGCGAAGATCTACTGCGAAAGCAGCGGACTTTCGACAACGGTAGC
```

-continued

ATTCCACATCAAATCCACTTAGGCGAATTGCATGCTATACTTAGAAGGCAGGAGGATTTTTATCCGTTCCTCAAA

GACAATCGTGAAAAGATTGAGAAAATCCTAACCTTTCGCATACCTTACTATGTGGGACCCCTGGCCCGAGGGAAC

TCTCGGTTCGCATGGATGACAAGAAAGTCCGAAGAAACGATTACTCCATGGAATTTTGAGGAAGTTGTCGATAAA

GGTGCGTCAGCTCAATCGTTCATCGAGAGGATGACCAACTTTGACAAGAATTTACCGAACGAAAAAGTATTGCCT

AAGCACAGTTTACTTTACGAGTATTTCACAGTGTACAATGAACTCACGAAAGTTAAGTATGTCACTGAGGGCATG

CGTAAACCCGCCTTTCTAAGCGGAGAACAGAAGAAAGCAATAGTAGATCTGTTATTCAAGACCAACCGCAAAGTG

ACAGTTAAGCAATTGAAAGAGGACTACTTTAAGAAAATTGAATGCTTCGATTCTGTCGAGATCTCCGGGGTAGAA

GATCGATTTAATGCGTCACTTGGTACGTATCATGACCTCCTAAAGATAATTAAAGATAAGGACTTCCTGGATAAC

GAAGAGAATGAAGATATCTTAGAAGATATAGTGTTGACTCTTACCCTCTTTGAAGATCGGGAAATGATTGAGGAA

AGACTAAAAACATACGCTCACCTGTTCGACGATAAGGTTATGAAACAGTTAAAGAGGCGTCGCTATACGGGCTGG

GGACGATTGTCGCGGAAACTTATCAACGGGATAAGAGACAAGCAAAGTGGTAAAACTATTCTCGATTTTCTAAAG

AGCGACGGCTTCGCCAATAGGAACTTTATGCAGCTGATCCATGATGACTCTTTAACCTTCAAAGAGGATATACAA

AAGGCACAGGTTTCCGGACAAGGGGACTCATTGCACGAACATATTGCGAATCTTGCTGGTTCGCCAGCCATCAAA

AAGGGCATACTCCAGACAGTCAAAGTAGTGGATGAGCTAGTTAAGGTCATGGGACGTCACAAACCGGAAAACATT

GTAATCGAGATGGCACGCGAAAATCAAACGACTCAGAAGGGGCAAAAAAACAGTCGAGAGCGGATGAAGAGAATA

GAAGAGGGTATTAAAGAACTGGGCAGCCAGATCTTAAAGGAGCATCCTGTGGAAAATACCCAATTGCAGAACGAG

AAACTTTACCTCTATTACCTACAAAATGGAAGGGACATGTATGTTGATCAGGAACTGGACATAAACCGTTTATCT

GATTACGACGTCGATGCCATTGTACCCCAATCCTTTTTGAAGGACGATTCAATCGACAATAAAGTGCTTACACGC

TCGGATAAGAACCGAGGGAAAAGTGACAATGTTCCAAGCGAGGAAGTCGTAAAGAAAATGAAGAACTATTGGCGG

CAGCTCCTAAATGCGAAACTGATAACGCAAAGAAAGTTCGATAACTTAACTAAAGCTGAGAGGGGTGGCTTGTCT

GAACTTGACAAGGCCGGATTTATTAAACGTCAGCTCGTGGAAACCCGCCAAATCACAAAGCATGTTGCACAGATA

CTAGATTCCCGAATGAATACGAAATACGACGAGAACGATAAGCTGATTCGGGAAGTCAAAGTAATCACTTTAAAG

TCAAAATTGGTGTCGGACTTCAGAAAGGATTTTCAATTCTATAAAGTTAGGGAGATAAATAACTACCACCATGCG

CACGACGCTTATCTTAATGCCGTCGTAGGGACCGCACTCATTAAGAAATACCCGAAGCTAGAAAGTGAGTTTGTG

TATGGTGATTACAAAGTTTATGACGTCCGTAAGATGATCGCGAAAAGCGAACAGGAGATAGGCAAGGCTACAGCC

AAATACTTCTTTTATTCTAACATTATGAATTTCTTTAAGACGGAAATCACTCTGGCAAACGGAGAGATACGCAAA

CGACCTTTAATTGAAACCAATGGGGAGACAGGTGAAATCGTATGGGATAAGGGCCGGGACTTCGCGACGGTGAGA

AAAGTTTTGTCCATGCCCCAAGTCAACATAGTAAAGAAAACTGAGGTGCAGACCGGAGGGTTTTCAAAGGAATCG

ATTCTTCCAAAAAGGAATAGTGATAAGCTCATCGCTCGTAAAAAGGACTGGGACCCGAAAAAGTACGGTGGCTTC

GATAGCCCTACAGTTGCCTATTCTGTCCTAGTAGTGGCAAAAGTTGAGAAGGGAAAATCCAAGAAACTGAAGTCA

GTCAAAGAATTATTGGGGATAACGATTATGGAGCGCTCGTCTTTTGAAAAGAACCCCATCGACTTCCTTGAGGCG

AAAGGTTACAAGGAAGTAAAAAAGGATCTCATAATTAAACTACCAAAGTATAGTCTGTTTGAGTTAGAAAATGGC

CGAAAACGGATGTTGGCTAGCGCCGGAGAGCTTCAAAAGGGGAACGAACTCGCACTACCGTCTAAATACGTGAAT

TTCCTGTATTTAGCGTCCCATTACGAGAAGTTGAAAGGTTCACCTGAAGATAACGAACAGAAGCAACTTTTTGTT

GAGCAGCACAAACATTATCTCGACGAAATCATAGAGCAAATTTCGGAATTCAGTAAGAGAGTCATCCTAGCTGAT

GCCAATCTGGACAAAGTATTAAGCGCATACAACAAGCACAGGGATAAACCCATACGTGAGCAGGCGGAAAATATT

ATCCATTTGTTTACTCTTACCAACCTCGGCGCTCCAGCCGCATTCAAGTATTTTGACACAACGATAGATCGCAAA

CGATACACTTCTACCAAGGAGGTGCTAGACGCGACACTGATTCACCAATCCATCACGGGATTATATGAAACTCGG

ATAGATTTGTCACAGCTTGGGGGTGAC*GGTGGCTCC*GATTATAAGGATGATGACGACAAG*GGAGGTTCC*ccaaag aagaaaaggaaggtcTGA -continued dCas9-36C6 (amino acid)

(SEQ ID NO: 766)

MSNLLTVHQNLPALPVDATSDEVRKNLMDMFRDRQAFSEHTWKMLLSVCRSWAAWCKLNNRKWFPAEPEDVRDYL

LYLQARGLAVKTIQQHLGQLNMLHRRSGLPRPSDSNAVSLVMRRIRKENVDAGERAKQALAFERTDFDQVRSLME

NSDRCQDIRNLAFLGIAYNTLLRIAEIARIRVKDISRTDGGRMLIHIGRTKTLVSTAGVEKALSLGVTKLVERWI

SVSGVADDPNNYLFCRVRKNGVAAPSATSQLSTRALEGIFEATHRLIYGAKDDSGQRYLAWSGHSARVGAARDMA

RAGVSIPEIMQAGGWTNVNIVMNYIRNLDSETGAMVRLLEDGD*GGSGGSGGSGGSGGSGGSGGSGGS*DKKYSIGL

AIGTNSVGWAVITDEYKVPSKKFKVLGNTDRHSIKKNLIGALLFDSGETAEATRLKRTARRRYTRRKNRICYLQE

IFSNEMAKVDDSFFHRLEESFLVEEDKKHERHPIFGNIVDEVAYHEKYPTIYHLRKKLVDSTDKADLRLIYLALA

HMIKFRGHFLIEGDLNPDNSDVDKLFIQLVQTYNQLFEENPINASGVDAKAILSARLSKSRRLENLIAQLPGEKK

NGLFGNLIALSLGLTPNFKSNFDLAEDAKLQLSKDTYDDDLDNLLAQIGDQYADLFLAAKNLSDAILLSDILRVN

TEITKAPLSASMIKRYDEHHQDLTLLKALVRQQLPEKYKEIFFDQSKNGYAGYIDGGASQEEFYKFIKPILEKMD

GTEELLVKLNREDLLRKQRTFDNGSIPHQIHLGELHAILRRQEDFYPFLKDNREKIEKILTFRIPYYVGPLARGN

SRFAWMTRKSEETITPWNFEEVVDKGASAQSFIERMTNFDKNLPNEKVLPKHSLLYEYFTVYNELTKVKYVTEGM

RKPAFLSGEQKKAIVDLLFKTNRKVTVKQLKEDYFKKIECFDSVEISGVEDRFNASLGTYHDLLKIIKDKDFLDN

EENEDILEDIVLTLTLFEDREMIEERLKTYAHLFDDKVMKQLKRRRYTGWGRLSRKLINGIRDKQSGKTILDFLK

SDGFANRNFMQLIHDDSLTFKEDIQKAQVSGQGDSLHEHIANLAGSPAIKKGILQTVKVVDELVKVMGRHKPENI

VIEMARENQTTQKGQKNSRERMKRIEEGIKELGSQILKEHPVENTQLQNEKLYLYYLQNGRDMYVDQELDINRLS

DYDVDAIVPQSFLKDDSIDNKVLTRSDKNRGKSDNVPSEEVVKKMKNYWRQLLNAKLITQRKFDNLTKAERGGLS

ELDKAGFIKRQLVETRQITKHVAQILDSRMNTKYDENDKLIREVKVITLKSKLVSDFRKDFQFYKVREINNYHHA

HDAYLNAVVGTALIKKYPKLESEFVYGDYKVYDVRKMIAKSEQEIGKATAKYFFYSNIMNFFKTEITLANGEIRK

RPLIETNGETGEIVWDKGRDFATVRKVLSMPQVNIVKKTEVQTGGFSKESILPKRNSDKLIARKKDWDPKKYGGF

DSPTVAYSVLVVAKVEKGKSKKLKSVKELLGITIMERSSFEKNPIDFLEAKGYKEVKKDLIIKLPKYSLFELENG

RKRMLASAGELQKGNELALPSKYVNFLYLASHYEKLKGSPEDNEQKQLFVEQHKHYLDEIIEQISEFSKRVILAD

ANLDKVLSAYNKHRDKPIREQAENIIHLFTLTNLGAPAAFKYFDTTIDRKRYTSTKEVLDATLIHQSITGLYETR

IDLSQLGGD*GGS*DYKDDDDK*GGS*pkkkrkv Stop

Some aspects of this disclosure provide evolved recombinases (e.g., a Cre recombinase) comprising an amino acid sequence that is at least 70%, at least 80%, at least 90%, at least 95%, or at least 97% identical to the sequence of the recombinase sequence (e.g., a Cre recombinase) discussed herein, wherein the amino acid sequence of the recombinase (e.g., a Cre recombinase) comprises at least one mutation as compared to the sequence of the recombinase (e.g., a Cre recombinase) sequence discussed herein, and wherein the recombinase (e.g., a Cre recombinase) recognizes a DNA recombinase target sequence that differs from the canonical LoxP site 5'-ATAACTTCGTATA GCATACAT TATACGAAGTTAT-3' (SEQ ID NO: 739) in at least one nucleotide.

In some embodiments, the amino acid sequence of the evolved recombinase (e.g., a Cre recombinase) comprises at least 2, at least 3, at least 4, at least 5, at least 6, at least 7, at least 8, at least 9, at least 10, at least 11, at least 12, at least 13, at least 14, or at least 15 mutations as compared to the sequence of the recombinase (e.g., a Cre recombinase) sequence discussed herein and recognizes a DNA recombinase target sequence that differs from the canonical target site (e.g., a LoxP site) in at least 1, at least 2, at least 3, at least 4, at least 5, at least 6, at least 7, at least 8, at least 9, at least 10, at least 11, at least 12, at least 13, at least 14, or at least 15 nucleotides.

In some embodiments, the evolved Cre recombinase recognizes a DNA recombinase target sequence that comprises a left half-site, a spacer sequence, and a right half-site, wherein the left half-site is not a palindrome of the right half-site. In some embodiments, the evolved Cre recombinase recognizes a DNA recombinase target sequence that comprises a naturally occurring sequence. In some embodiments, the evolved Cre recombinase recognizes a DNA recombinase target sequence that is comprised in the genome of a mammal.

In some embodiments, the evolved Cre recombinase recognizes a DNA recombinase target sequence that is comprised in the genome of a human. In some embodiments, the evolved Cre recombinase recognizes a DNA recombinase target sequence that is comprised only once in the genome of a mammal. In some embodiments, the evolved Cre recombinase recognizes a DNA recombinase target sequence in the genome of a mammal that differs from any other site in the genome by at least 1, at least 2, at least 3, at least 4, at least 5, at least 6, at least 7, at least 8, at least 9, at least 10, at least 11, at least 12, at least 13, at least 14, or at least 15 nucleotide(s). In some embodiments, the evolved Cre recombinase recognizes a DNA recombinase target sequence located in a safe harbor genomic locus. In some embodiments, the safe harbor genomic locus is a Rosa26 locus. In some embodiments, the evolved Cre recombinase recognizes a DNA recombinase target sequence located in a genomic locus associated with a disease or disorder.

Additional evolved recombinases (and methods for making the same) for use with the instant methods and compositions may be found in, for example, U.S. patent application Ser. No. 15/216,844, which is incorporated herein by reference.

Additional suitable recombinases will be apparent to those of skill in the art for both providing recombinase catalytic domains or evolved recombinase catalytic domains, and such suitable recombinases include, without limitation, those disclosed in Hirano et al., Site-specific recombinases as tools for heterologous gene integration. Appl Microbiol Biotechnol. 2011 October; 92(2):227-39; Fogg et al., New applications for phage integrases. J Mol Biol. 2014 Jul. 29; 426(15):2703; Brown et al., Serine recombinases as tools for genome engineering. Methods. 2011 April; 53(4):372-9; Smith et al., Site-specific recombination by phiC31 integrase and other large serine recombinases. Biochem Soc Trans. 2010 April; 38(2):388-94; Grindley et al., Mechanisms of site-specific recombination. Annu Rev Biochem. 2006; 75:567-605; Smith et al., Diversity in the serine recombinases. Mol Microbiol. 2002 April; 44(2):299-307; Grainge et al., The integrase family of recombinase: organization and function of the active site. Mol Microbiol. 1999 August; 33(3):449-56; Gopaul et al., Structure and mechanism in site-specific recombination. Curr Opin Struct Biol. 1999 February; 9(1):14-20; Cox et al., Conditional gene expression in the mouse inner ear using Cre-loxP. J Assoc Res Otolaryngol. 2012 June; 13(3):295-322; Birling et al., Site-specific recombinases for manipulation of the mouse genome. Methods Mol Biol. 2009; 561:245-63; and Mishina M, Sakimura K. Conditional gene targeting on the pure C57BL/6 genetic background. Neurosci Res. 2007 June; 58(2):105-12; the entire contents of each of which are incorporated herein by reference.

Structure of the Fusion Protein

The fusion protein of the instant instant disclosure may be any combination and order of the elements described herein. Exemplary fusion proteins include, but are not limited to, any of the following structures: $NH_2$-[recombinase catalytic domain]-[linker sequence]-[guide nucleotide sequence-programmable DNA binding protein domain]-[optional linker sequence]-[optional NLS domain]-[optional linker sequence]-[optional affinity tag]-COOH. In another embodiment, the fusion protein has the structure $NH_2$-[recombinase catalytic domain]-[linker sequence]-[guide nucleotide sequence-programmable DNA binding protein domain]-[optional linker sequence]-[NLS domain]-[optional linker sequence]-[optional affinity tag]-COOH. In another embodiment, the fusion protein has the structure $NH_2$-[recombinase catalytic domain]-[linker sequence]-[guide nucleotide sequence-programmable DNA binding protein domain]-[optional linker sequence]-[NLS domain]-[optional linker sequence]-[affinity tag]-COOH. In another embodiment, the fusion protein has the structure $NH_2$-[recombinase catalytic domain]-[linker sequence]-[guide nucleotide sequence-programmable DNA binding protein domain]-[linker sequence]-[NLS domain]-[linker sequence]-[affinity tag]-COOH.

In another embodiment, the fusion protein has the structure $NH_2$-[recombinase catalytic domain]-[optional linker sequence]-[guide nucleotide sequence-programmable DNA binding protein domain]-[optional linker sequence]-[NLS domain]-[optional linker sequence]-[affinity tag]-COOH, $NH_2$-[guide nucleotide sequence-programmable DNA binding protein domain]-[linker sequence]-[recombinase catalytic domain]-[optional linker sequence]-[NLS domain]-[optional linker sequence]-[optional affinity tag]-COOH, $NH_2$—[N-terminal portion of a bifurcated or circularly permuted guide nucleotide sequence-programmable DNA binding protein domain]-[optional linker sequence]-[recombinase catalytic domain]-[optional linker sequence]-[C-terminal portion of a bifurcated or circularly permuted guide nucleotide sequence-programmable DNA binding protein domain]-[optional linker sequence]-[NLS domain]-[optional linker sequence]-[optional affinity tag]-COOH, $NH_2$-[affinity tag]-[optional linker sequence]-[recombinase catalytic domain]-[linker sequence]-[guide nucleotide sequence-programmable DNA binding protein domain]-[optional linker sequence]-[NLS domain]-COOH, $NH_2$-[affinity tag]-[optional linker sequence]-[guide nucleotide sequence-programmable DNA binding protein domain]-[linker sequence]-[recombinase catalytic domain]-[optional linker sequence]-[NLS domain]-COOH, or $NH_2$-[affinity tag]-[optional linker sequence]-[N-terminal portion of a bifurcated or circularly permuted guide nucleotide sequence-programmable DNA binding protein domain]-[optional linker sequence]-[recombinase catalytic domain]-[optional linker sequence]-[C-terminal portion of a bifurcated or circularly permuted guide nucleotide sequence-programmable DNA binding protein domain]-[optional linker sequence]-[NLS domain]-COOH.

In another embodiment, the fusion protein has the structure: $NH_2$-[guide nucleotide sequence-programmable DNA binding protein domain]-[linker sequence]-[recombinase catalytic domain]-[optional linker sequence]-[optional NLS domain]-[optional linker sequence]-[optional affinity tag]-COOH. In one embodiment, the fusion protein comprises the structure $NH_2$-[guide nucleotide sequence-programmable DNA binding protein domain]-[linker sequence]-[recombinase catalytic domain]-[optional linker sequence]-[NLS domain]-[optional linker sequence]-[optional affinity tag]-COOH. In one embodiment, the fusion protein comprises the structure $NH_2$-[guide nucleotide sequence-programmable DNA binding protein domain]-[linker sequence]-[recombinase catalytic domain]-[optional linker sequence]-[NLS domain]-[optional linker sequence]-[affinity tag]-COOH. In one embodiment, the fusion protein comprises the structure $NH_2$-[guide nucleotide sequence-programmable DNA binding protein domain]-[linker sequence]-[recombinase catalytic domain]-[linker sequence]-[NLS domain]-[linker sequence]-[affinity tag]-COOH.

In another embodiment, the fusion protein has the structure $NH_2$—[N-terminal portion of a bifurcated or circularly permuted guide nucleotide sequence-programmable DNA binding protein domain]-[optional linker sequence]-[recombinase catalytic domain]-[optional linker sequence]-[C-terminal portion of a bifurcated or circularly permuted guide nucleotide sequence-programmable DNA binding protein domain]-[optional linker sequence]-[optional NLS domain]-[optional linker sequence]-[optional affinity tag]-COOH. In another embodiment, the fusion protein comprises the structure $NH_2$—[N-terminal portion of a bifurcated or circularly permuted guide nucleotide sequence-programmable DNA binding protein domain]-[optional linker sequence]-[recombinase catalytic domain]-[optional linker sequence]-[C-terminal portion of a bifurcated or circularly permuted guide nucleotide sequence-programmable DNA binding protein domain]-[optional linker sequence]-[NLS domain]-[optional linker sequence]-[optional affinity tag]-COOH. In another embodiment, the fusion protein comprises the structure $NH_2$—[N-terminal portion of a bifurcated or circularly permuted guide nucleotide sequence-programmable DNA binding protein domain]-[optional linker sequence]-[recombinase catalytic domain]-[optional linker sequence]-[C-terminal portion of a bifurcated or circularly permuted guide nucleotide sequence-programmable DNA binding protein domain]-[optional linker sequence]-[NLS domain]-[optional linker sequence]-[affinity tag]-COOH. In another embodiment, the fusion protein comprises the structure $NH_2$—[N-terminal portion of a bifurcated or circularly permuted guide nucleotide sequence-programmable DNA binding protein domain]-[optional linker sequence]-[recombinase catalytic domain]-[optional linker sequence]-[C-terminal portion of a bifurcated or circularly permuted guide nucleotide sequence-programmable DNA binding protein domain]-[linker sequence]-[NLS domain]-[linker sequence]-[affinity tag]-COOH.

In another embodiment, the fusion protein has the structure $NH_2$—[N-terminal portion of a bifurcated or circularly permuted guide nucleotide sequence-programmable DNA binding protein domain]-[linker sequence]-[recombinase catalytic domain]-[optional linker sequence]-[C-terminal portion of a bifurcated or circularly permuted guide nucleotide sequence-programmable DNA binding protein domain]-[optional linker sequence]-[optional NLS domain]-[optional linker sequence]-[optional affinity tag]-COOH. In another embodiment, the fusion protein comprises the structure $NH_2$—[N-terminal portion of a bifurcated or circularly permuted guide nucleotide sequence-programmable DNA binding protein domain]-[linker sequence]-[recombinase catalytic domain]-[optional linker sequence]-[C-terminal portion of a bifurcated or circularly permuted guide nucleotide sequence-programmable DNA binding protein domain]-[optional linker sequence]-[NLS domain]-[optional linker sequence]-[optional affinity tag]-COOH. In another embodiment, the fusion protein comprises the structure $NH_2$—[N-terminal portion of a bifurcated or circularly permuted guide nucleotide sequence-programmable DNA binding protein domain]-[linker sequence]-[recombinase catalytic domain]-[optional linker sequence]-[C-terminal portion of a bifurcated or circularly permuted guide nucleotide sequence-programmable DNA binding protein domain]-[optional linker sequence]-[NLS domain]-[optional linker sequence]-[affinity tag]-COOH. In another embodiment, the fusion protein comprises the structure $NH_2$—[N-terminal portion of a bifurcated or circularly permuted guide nucleotide sequence-programmable DNA binding protein domain]-[linker sequence]-[recombinase catalytic domain]-[optional linker sequence]-[C-terminal portion of a bifurcated or circularly permuted guide nucleotide sequence-programmable DNA binding protein domain]-[linker sequence]-[NLS domain]-[linker sequence]-[affinity tag]-COOH.

In another embodiment, the fusion protein has the structure $NH_2$—[N-terminal portion of a bifurcated or circularly permuted guide nucleotide sequence-programmable DNA binding protein domain]-[optional linker sequence]-[recombinase catalytic domain]-[linker sequence]-[C-terminal portion of a bifurcated or circularly permuted guide nucleotide sequence-programmable DNA binding protein domain]-[optional linker sequence]-[optional NLS domain]-[optional linker sequence]-[optional affinity tag]-COOH. In another embodiment, the fusion protein comprises the structure $NH_2$—[N-terminal portion of a bifurcated or circularly permuted guide nucleotide sequence-programmable DNA binding protein domain]-[optional linker sequence]-[recombinase catalytic domain]-[linker sequence]-[C-terminal portion of a bifurcated or circularly permuted guide nucleotide sequence-programmable DNA binding protein domain]-[optional linker sequence]-[NLS domain]-[optional linker sequence]-[optional affinity tag]-COOH. In another embodiment, the fusion protein comprises the structure $NH_2$—[N-terminal portion of a bifurcated or circularly permuted guide nucleotide sequence-programmable DNA binding protein domain]-[optional linker sequence]-[recombinase catalytic domain]-[linker sequence]-[C-terminal portion of a bifurcated or circularly permuted guide nucleotide sequence-programmable DNA binding protein domain]-[optional linker sequence]-[NLS domain]-[optional linker sequence]-[affinity tag]-COOH. In another embodiment, the fusion protein comprises the structure $NH_2$—[N-terminal portion of a bifurcated or circularly permuted guide nucleotide sequence-programmable DNA binding protein domain]-[optional linker sequence]-[recombinase catalytic domain]-[linker sequence]-[C-terminal portion of a bifurcated or circularly permuted guide nucleotide sequence-programmable DNA binding protein domain]-[linker sequence]-[NLS domain]-[linker sequence]-[affinity tag]-COOH.

In another embodiment, the fusion protein has the structure $NH_2$—[N-terminal portion of a bifurcated or circularly permuted guide nucleotide sequence-programmable DNA binding protein domain]-[linker sequence]-[recombinase catalytic domain]-[linker sequence]-[C-terminal portion of a bifurcated or circularly permuted guide nucleotide sequence-programmable DNA binding protein domain]-[optional linker sequence]-[optional NLS domain]-[optional linker sequence]-[optional affinity tag]-COOH. In another embodiment, the fusion protein comprises the structure $NH_2$—[N-terminal portion of a bifurcated or circularly permuted guide nucleotide sequence-programmable DNA binding protein domain]-[linker sequence]-[recombinase catalytic domain]-[linker sequence]-[C-terminal portion of a bifurcated or circularly permuted guide nucleotide sequence-programmable DNA binding protein domain]-[optional linker sequence]-[NLS domain]-[optional linker sequence]-[optional affinity tag]-COOH. In another embodiment, the fusion protein comprises the structure $NH_2$—[N-terminal portion of a bifurcated or circularly permuted guide nucleotide sequence-programmable DNA binding protein domain]-[linker sequence]-[recombinase catalytic domain]-[linker sequence]-[C-terminal portion of a bifurcated or circularly permuted guide nucleotide sequence-programmable DNA binding protein domain]-[optional linker sequence]-[NLS domain]-[optional linker sequence]-[affinity tag]-COOH. In another embodiment, the fusion protein comprises the structure $NH_2$—[N-terminal portion of a bifurcated or circularly permuted guide nucleotide sequence-programmable DNA binding protein domain]-[linker sequence]-[recombinase catalytic domain]-[linker sequence]-[C-terminal portion of a bifurcated or circularly permuted guide nucleotide sequence-programmable DNA binding protein domain]-[linker sequence]-[NLS domain]-[linker sequence]-[affinity tag]-COOH.

In one embodiment, the fusion protein has the structure $NH_2$-[optional affinity tag]-[optional linker sequence]-[optional NLS domain]-[optional linker sequence]-[recombinase catalytic domain]-[linker sequence]-[guide nucleotide sequence-programmable DNA binding protein domain]-COOH. In one embodiment, the fusion protein comprises the structure $NH_2$-[optional affinity tag]-[optional linker sequence]-[NLS domain]-[optional linker sequence]-[recombinase catalytic domain]-[linker sequence]-[guide nucleotide sequence-programmable DNA binding protein domain]-COOH. In one embodiment, the fusion protein comprises the structure $NH_2$-[affinity tag]-[optional linker sequence]-[NLS domain]-[optional linker sequence]-[recombinase catalytic domain]-[linker sequence]-[guide nucleotide sequence-programmable DNA binding protein domain]-COOH. In one embodiment, the fusion protein comprises the structure $NH_2$-[affinity tag]-[linker sequence]-[NLS domain]-[linker sequence]-[recombinase catalytic domain]-[linker sequence]-[guide nucleotide sequence-programmable DNA binding protein domain]-COOH.

In one embodiment, the fusion protein has the structure $NH_2$-[optional affinity tag]-[optional linker sequence]-[optional NLS domain]-[optional linker sequence]-[guide nucleotide sequence-programmable DNA binding protein domain]-[linker sequence]-[recombinase catalytic domain]-COOH. In one embodiment, the fusion protein comprises the structure $NH_2$-[optional affinity tag]-[optional linker sequence]-[NLS domain]-[optional linker sequence]-[guide nucleotide sequence-programmable DNA binding protein domain]-[linker sequence]-[recombinase catalytic domain]-COOH. In one embodiment, the fusion protein comprises the structure $NH_2$-[affinity tag]-[optional linker sequence]-[NLS domain]-[optional linker sequence]-[guide nucleotide sequence-programmable DNA binding protein domain]-[linker sequence]-[recombinase catalytic domain]-COOH. In one embodiment, the fusion protein comprises the structure $NH_2$-[affinity tag]-[linker sequence]-[NLS domain]-[linker sequence]-[guide nucleotide sequence-programmable DNA binding protein domain]-[linker sequence]-[recombinase catalytic domain]-COOH.

In another embodiment, the fusion protein has the structure $NH_2$-[optional affinity tag]-[optional linker sequence]-[optional NLS domain]-[optional linker sequence]-[N-terminal portion of a bifurcated or circularly permuted guide nucleotide sequence-programmable DNA binding protein domain]-[optional linker sequence]-[recombinase catalytic domain]-[optional linker sequence]-[C-terminal portion of a bifurcated or circularly permuted guide nucleotide sequence-programmable DNA binding protein domain]-COOH. In another embodiment, the fusion protein comprises the structure $NH_2$-[optional affinity tag]-[optional linker sequence]-[NLS domain]-[optional linker sequence]-[N-terminal portion of a bifurcated or circularly permuted guide nucleotide sequence-programmable DNA binding protein domain]-[optional linker sequence]-[recombinase catalytic domain]-[optional linker sequence]-[C-terminal portion of a bifurcated or circularly permuted guide nucleotide sequence-programmable DNA binding protein domain]-COOH. In another embodiment, the fusion protein comprises the structure $NH_2$-[affinity tag]-[optional linker sequence]-[NLS domain]-[optional linker sequence]-[N-terminal portion of a bifurcated or circularly permuted guide nucleotide sequence-programmable DNA binding protein domain]-[optional linker sequence]-[recombinase catalytic domain]-[optional linker sequence]-[C-terminal portion of a bifurcated or circularly permuted guide nucleotide sequence-programmable DNA binding protein domain]-COOH. In another embodiment, the fusion protein comprises the structure $NH_2$-[affinity tag]-[linker sequence]-[NLS domain]-[linker sequence]-[N-terminal portion of a bifurcated or circularly permuted guide nucleotide sequence-programmable DNA binding protein domain]-[optional linker sequence]-[recombinase catalytic domain]-[optional linker sequence]-[C-terminal portion of a bifurcated or circularly permuted guide nucleotide sequence-programmable DNA binding protein domain]-COOH.

In another embodiment, the fusion protein has the structure $NH_2$-[optional affinity tag]-[optional linker sequence]-[optional NLS domain]-[optional linker sequence]-[N-terminal portion of a bifurcated or circularly permuted guide nucleotide sequence-programmable DNA binding protein domain]-[linker sequence]-[recombinase catalytic domain]-[optional linker sequence]-[C-terminal portion of a bifurcated or circularly permuted guide nucleotide sequence-programmable DNA binding protein domain]-COOH. In another embodiment, the fusion protein comprises the structure $NH_2$-[optional affinity tag]-[optional linker sequence]-[NLS domain]-[optional linker sequence]-[N-terminal portion of a bifurcated or circularly permuted guide nucleotide sequence-programmable DNA binding protein domain]-[linker sequence]-[recombinase catalytic domain]-[optional linker sequence]-[C-terminal portion of a bifurcated or circularly permuted guide nucleotide sequence-programmable DNA binding protein domain]-COOH. In another embodiment, the fusion protein comprises the structure $NH_2$-[affinity tag]-[optional linker sequence]-[NLS domain]-[optional linker sequence]-[N-terminal portion of a bifurcated or circularly permuted guide nucleotide sequence-programmable DNA binding protein domain]-[linker sequence]-[recombinase catalytic domain]-[optional linker sequence]-[C-terminal portion of a bifurcated or circularly permuted guide nucleotide sequence-programmable DNA binding protein domain]-COOH. In another embodiment, the fusion protein comprises the structure $NH_2$-[affinity tag]-[linker sequence]-[NLS domain]-[linker sequence]-[N-terminal portion of a bifurcated or circularly permuted guide nucleotide sequence-programmable DNA binding protein domain]-[linker sequence]-[recombinase catalytic domain]-[optional linker sequence]-[C-terminal portion of a bifurcated or circularly permuted guide nucleotide sequence-programmable DNA binding protein domain]-COOH.

In another embodiment, the fusion protein has the structure $NH_2$-[optional affinity tag]-[optional linker sequence]-[optional NLS domain]-[optional linker sequence]-[N-terminal portion of a bifurcated or circularly permuted guide nucleotide sequence-programmable DNA binding protein domain]-[optional linker sequence]-[recombinase catalytic domain]-[linker sequence]-[C-terminal portion of a bifurcated or circularly permuted guide nucleotide sequence-programmable DNA binding protein domain]-COOH. In another embodiment, the fusion protein comprises the structure $NH_2$-[optional affinity tag]-[optional linker sequence]-[NLS domain]-[optional linker sequence]-[N-terminal portion of a bifurcated or circularly permuted guide nucleotide sequence-programmable DNA binding protein domain]-[optional linker sequence]-[recombinase catalytic domain]-[linker sequence]-[C-terminal portion of a bifurcated or circularly permuted guide nucleotide sequence-programmable DNA binding protein domain]-COOH. In another embodiment, the fusion protein comprises the structure $NH_2$-[affinity tag]-[optional linker sequence]-[NLS domain]-[optional linker sequence]-[N-terminal portion of a bifurcated or circularly permuted guide nucleotide sequence-programmable DNA binding protein domain]-[optional linker sequence]-[recombinase catalytic domain]-[linker sequence]-[C-terminal portion of a bifurcated or circularly permuted guide nucleotide sequence-programmable DNA binding protein domain]-COOH. In another embodiment, the fusion protein comprises the structure $NH_2$-[affinity tag]-[linker sequence]-[NLS domain]-[linker sequence]-[N-terminal portion of a bifurcated or circularly permuted guide nucleotide sequence-programmable DNA binding protein domain]-[optional linker sequence]-[recombinase catalytic domain]-[linker sequence]-[C-terminal portion of a bifurcated or circularly permuted guide nucleotide sequence-programmable DNA binding protein domain]-COOH.

In another embodiment, the fusion protein has the structure $NH_2$-[optional affinity tag]-[optional linker sequence]-[optional NLS domain]-[optional linker sequence]-[N-terminal portion of a bifurcated or circularly permuted guide nucleotide sequence-programmable DNA binding protein domain]-[linker sequence]-[recombinase catalytic domain]-[linker sequence]-[C-terminal portion of a bifurcated or circularly permuted guide nucleotide sequence-programmable DNA binding protein domain]-COOH. In another embodiment, the fusion protein comprises the structure $NH_2$-[optional affinity tag]-[optional linker sequence]-[NLS domain]-[optional linker sequence]-[N-terminal portion of a bifurcated or circularly permuted guide nucleotide sequence-programmable DNA binding protein domain]-[linker sequence]-[recombinase catalytic domain]-[linker sequence]-[C-terminal portion of a bifurcated or circularly permuted guide nucleotide sequence-programmable DNA binding protein domain]-COOH. In another embodiment, the fusion protein comprises the structure $NH_2$-[affinity tag]-[optional linker sequence]-[NLS domain]-[optional linker sequence]-[N-terminal portion of a bifurcated or circularly permuted guide nucleotide sequence-programmable DNA binding protein domain]-[linker sequence]-[recombinase catalytic domain]-[linker sequence]-[C-terminal portion of a bifurcated or circularly permuted guide nucleotide sequence-programmable DNA binding protein domain]-COOH. In another embodiment, the fusion protein comprises the structure $NH_2$-[affinity tag]-[linker sequence]-[NLS domain]-[linker sequence]-[N-terminal portion of a bifurcated or circularly permuted guide nucleotide sequence-programmable DNA binding protein domain]-[linker sequence]-[recombinase catalytic domain]-[linker sequence]-[C-terminal portion of a bifurcated or circularly permuted guide nucleotide sequence-programmable DNA binding protein domain]-COOH.

The fusion protein may further comprise one or more affinity tags. Suitable affinity tags provided herein include, but are not limited to, biotin carboxylase carrier protein (BCCP) tags, myc-tags, calmodulin-tags, FLAG-tags, hemagglutinin (HA)-tags, polyhistidine tags, also referred to as histidine tags or His-tags, polyarginine (poly-Arg) tags, maltose binding protein (MBP)-tags, nus-tags, glutathione-S-transferase (GST)-tags, green fluorescent protein (GFP)-tags, thioredoxin-tags, S-tags, Softags (e.g., Softag 1, Softag 3), strep-tags, biotin ligase tags, FlAsH tags, V5 tags, and SBP-tags. Additional suitable sequences will be apparent to those of skill in the art. The FLAG tag may have the sequence PKKKRKV (SEQ ID NO: 702). The one or more affinity tags are bound to the guide nucleotide sequence-programmable DNA binding protein domain, the recombinase catalytic domain, or the NLS domain via one or more third linkers. The third linker may be any peptide linker described herein. For example, the third linker may be a peptide linker.

As a non-limiting set of examples, the third linker may comprise an XTEN linker SGSETPGTSESATPES (SEQ ID NO: 7), SGSETPGTSESA (SEQ ID NO: 8), or SGSETPGTSESATPEGGSGGS (SEQ ID NO: 9), an amino acid sequence comprising one or more repeats of the tri-peptide GGS, or any of the following amino acid sequences: VPFLLEPDNINGKTC (SEQ ID NO: 10), GSAGSAAGSGEF (SEQ ID NO: 11), SIVAQLSRPDPA (SEQ ID NO: 12), MKIIEQLPSA (SEQ ID NO: 13), VRHKLKRVGS (SEQ ID NO: 14), GHGTGSTGSGSS (SEQ ID NO: 15), MSRPDPA (SEQ ID NO; 16), or GGSM (SEQ ID NO: 17). In certain embodiments, the third linker comprises one or more repeats of the tri-peptide GGS. In an embodiment, the third linker comprises from one to five repeats of the tri-peptide GGS. In another embodiment, the third linker comprises one repeat of the tri-peptide GGS. In a specific embodiment, the third linker has the sequence GGS.

The third linker may also be a non-peptide linker. In certain embodiments, the non-peptide linker comprises polyethylene glycol (PEG), polypropylene glycol (PPG), co-poly(ethylene/propylene) glycol, polyoxyethylene (POE), polyurethane, polyphosphazene, polysaccharides, dextran, polyvinyl alcohol, polyvinylpyrrolidones, polyvinyl ethyl ether, polyacryl amide, polyacrylate, polycyanoacrylates, lipid polymers, chitins, hyaluronic acid, heparin, or an alkyl linker. In other embodiments, the alkyl linker has the formula: $—NH—(CH_2)_s—C(O)—$, wherein s may be any integer between 1 and 100, inclusive. In a specific embodiment, s is any integer between 1 and 20, inclusive.

The fusion protein of the instant disclosure has greater than 90%, 95%, or 99% sequence identity with the amino acid sequence shown in amino acids 1-1544 of SEQ ID NO: 185, which is identical to the sequence shown in SEQ ID NO: 719.

(SEQ ID NO: 719)

MLIGYVRVSTNDQNTDLQRNALVCAGCEQIFEDKLSGTRTDRPGLKRALK

RLQKGDTLVVWKLDRLGRSMKHLISLVGELRERGINFRSLTDSIDTSSPM

GRFFFYVMGALAEMERELIIERTMAGLAAARNKGRRFGRPPK_GGSGGSGG_

_SGGSGGSGGSGGSGGS_DKKYSIGLAIGTNSVGWAVITDEYKVPSKKFKVL

GNTDRHSIKKNLIGALLFDSGETAEATRLKRTARRRYTRRKNRICYLQEI

FSNEMAKVDDSFFHRLEESFLVEEDKKHERHPIFGNIVDEVAYHEKYPTI

YHLRKKLVDSTDKADLRLIYLALAHMIKFRGHFLIEGDLNPDNSDVDKLF

IQLVQTYNQLFEENPINASGVDAKAILSARLSKSRRLENLIAQLPGEKKN

GLFGNLIALSLGLTPNFKSNFDLAEDAKLQLSKDTYDDDLDNLLAQIGDQ

YADLFLAAKNLSDAILLSDILRVNTEITKAPLSASMIKRYDEHHQDLTLL

KALVRQQLPEKYKEIFFDQSKNGYAGYIDGGASQEEFYKFIKPILEKMDG

TEELLVKLNREDLLRKQRTFDNGSIPHQIHLGELHAILRRQEDFYPFLKD

NREKIEKILTFRIPYYVGPLARGNSRFAWMTRKSEETITPWNFEEVVDKG

ASAQSFIERMTNFDKNLPNEKVLPKHSLLYEYFTVYNELTKVKYVTEGMR

KPAFLSGEQKKAIVDLLFKTNRKVTVKQLKEDYFKKIECFDSVEISGVED

RFNASLGTYHDLLKIIKDKDFLDNEENEDILEDIVLTLTLFEDREMIEER

LKTYAHLFDDKVMKQLKRRRYTGWGRLSRKLINGIRDKQSGKTILDFLKS

DGFANRNFMQLIHDDSLTFKEDIQKAQVSGQGDSLHEHIANLAGSPAIKK

GILQTVKVVDELVKVMGRHKPENIVIEMARENQTTQKGQKNSRERMKRIE

EGIKELGSQILKEHPVENTQLQNEKLYLYYLQNGRDMYVDQELDINRLSD

YDVDAIVPQSFLKDDSIDNKVLTRSDKNRGKSDNVPSEEVVKKMKNYWRQ

LLNAKLITQRKFDNLTKAERGGLSELDKAGFIKRQLVETRQITKHVAQIL

DSRMNTKYDENDKLIREVKVITLKSKLVSDFRKDFQFYKVREINNYHHAH

DAYLNAVVGTALIKKYPKLESEFVYGDYKVYDVRKMIAKSEQEIGKATAK

-continued

YFFYSNIMNFFKTEITLANGEIRKRPLIETNGETGEIVWDKGRDFATVRK

VLSMPQVNIVKKTEVQTGGFSKESILPKRNSDKLIARKKDWDPKKYGGFD

SPTVAYSVLVVAKVEKGKSKKLKSVKELLGITIMERSSFEKNPIDFLEAK

GYKEVKKDLIIKLPKYSLFELENGRKRMLASAGELQKGNELALPSKYVNF

LYLASHYEKLKGSPEDNEQKQLFVEQHKHYLDEIIEQISEFSKRVILADA

NLDKVLSAYNKHRDKPIREQAENIIHLFTLTNLGAPAAFKYFDTTIDRKR

YTSTKEVLDATLIHQSITGLYETRIDLSQLGGD*GGS*DYKDDDDK Stop

In the context of proteins that dimerize (or multimerize) such as, for example, fusions between a nuclease-inactivated Cas9 (or a Cas9 gRNA binding domain) and a recombinase (or catalytic domain of a recombinase), a target site typically comprises a left-half site (bound by one protein), a right-half site (bound by the second protein), and a spacer sequence between the half sites in which the recombination is made. In some embodiments, either the left-half site or the right half-site (and not the spacer sequence) is recombined. In other embodiments, the spacer sequence is recombined. This structure ([left-half site]-[spacer sequence]-[right-half site]) is referred to herein as an LSR structure. In some embodiments, the left-half site and/or the right-half site correspond to an RNA-guided target site (e.g., a Cas9 target site). In some embodiments, either or both half-sites are shorter or longer than e.g., a typical region targeted by Cas9, for example shorter or longer than 20 nucleotides. In some embodiments, the left and right half sites comprise different nucleic acid sequences. In some embodiments, the spacer sequence is at least 5, at least 6, at least 7, at least 8, at least 9, at least 10, at least 11, at least 12, at least 13, at least 14, at least 15, at least 16, at least 17, at least 18, at least 19, at least 20, at least 25, at least 30, at least 35, at least 40, at least 45, at least 50, at least 60, at least 70, at least 80, at least 90, at least 100, at least 125, at least 150, at least 175, at least 200, or at least 250 bp long. In some embodiments, the spacer sequence is between approximately 15 bp and approximately 25 bp long. In some embodiments, the spacer sequence is approximately 15 bp long. In some embodiments, the spacer sequence is approximately 25 bp long.

EXAMPLES

Example 1: A Programmable Cas9-Serine Recombinase Fusion Protein that Operates on DNA Sequences in Mammalian Cells Materials and Methods Oligonucleotides and PCR All oligonucleotides were purchased from Integrated DNA Technologies (IDT, Coralville, Calif.) and are listed in Tables 1-5. Enzymes, unless otherwise noted, were purchased from New England Biolabs (Ipswich, Mass.). Plasmid Safe ATP-dependent DNAse was purchased from Epicentre (Madison, Wis.). All assembled vectors were transformed into One Shot Mach1-T1 phage-resistant chemically competent cells (Fisher Scientific, Waltham, Mass.). Unless otherwise noted, all PCR reactions were performed with Q5 Hot Start High-Fidelity 2× Master Mix. Phusion polymerse was used for circular polymerase extension cloning (CPEC) assemblies.

TABLE 1

Oligonucleotides for gRNA construction

| Oligonucleotide Name | Sequence | SEQ ID NO: |
|---|---|---|
| R.pHU6.TSS(-1).univ | GGTGTTTCGTCCTTTCCACAAG | 20 |
| F.non-target | GCACACTAGTTAGGGATAACAGTTTTAG AGCTAGAAATAGC | 21 |
| F.Chr10-1 | GCCCATGACCCTTCTCCTCTGTTTTAGAG CTAGAAATAGC | 22 |
| F.Chr10-1-rev | GCTCAGGGCCTGTGATGGGAGGTTTTAG AGCTAGAAATAGC | 23 |
| F.Chr10-2 | GGCCCATGACCCTTCTCCTCGTTTTAGAG CTAGAAATAGC | 24 |
| F.Chr10-2rev | GCCTCAGGGCCTGTGATGGGAGTTTTAG AGCTAGAAATAGC | 25 |
| F.Centromere_Chr_1_5_19-gRNA-for | GACTTGAAACACTCTTTTTCGTTTTAGAG CTAGAAATAGC | 26 |
| F.Centromere_Chr_1_5_19-gRNA-rev | GAGTTGAAGACACACAACACAGTTTTAG AGCTAGAAATAGC | 27 |
| F.Ch5_155183064-gRNA-for | GGAACTCATGTGATTAACTGGTTTTAGA GCTAGAAATAGC | 28 |
| F.Ch5_155183064-gRNA-rev-1 | GTCTACCTCTCATGAGCCGGTGTTTTAGA GCTAGAAATAGC | 29 |
| F.Ch5_169395198-gRNA-for | GTTTCCCGCAGGATGTGGGATGTTTTAG AGCTAGAAATAGC | 30 |
| F.Ch5_169395198-gRNA-rev | GCCTGGGGATTTATGTTCTTAGTTTTAGA GCTAGAAATAGC | 31 |

TABLE 1-continued

| Oligonucleotides for gRNA construction | | |
|---|---|---|
| Oligonucleotide Name | Sequence | SEQ ID NO: |
| F.Ch12_62418577-gRNA-for | GAAATAGCACAATGAATGGAAGTTTTAG AGCTAGAAATAGC | 32 |
| F.Ch12_62418577-gRNA-rev | GACTTTTTGGGGGAGAGGGAGGTTTTAG AGCTAGAAATAGC | 33 |
| F.Ch13_102010574-gRNA-for | GGAGACTTAAGTCCAAAACCGTTTTAGA GCTAGAAATAGC | 34 |
| F.Ch13_102010574-gRNA-rev | GTCAGCTATGATCACTTCCCTGTTTTAGA GCTAGAAATAGC | 35 |

TABLE 2

| Oligonucleotides and gBlocks for reporter construction | | |
|---|---|---|
| Construct Name | Sequence | SEQ ID NO: |
| 1-0bp-for | TCGTCTCGGCGTCCCCAATTTTCCCAAACAGAG GTCTGTAAACCGAGGTGAGACGG | 36 |
| 1-0bp-rev | CCGTCTCACCTCGGTTTACAGACCTCTGTTTGG GAAAATTGGGGACGCCGAGACGA | 37 |
| 1-1bp-for | TCGTCTCGGCGTCCCCAATTTTCCCAAACAGAG GTtCTGTAAACCGAGGTGAGACGG | 38 |
| 1-1bp-rev | CCGTCTCACCTCGGTTTACAGaACCTCTGTTTGG GAAAATTGGGGACGCCGAGACGA | 39 |
| 1-2bp-for | TCGTCTCGGCGTCCCCAATTTTCCCAAACAGAG GTatCTGTAAACCGAGGTGAGACGG | 40 |
| 1-2bp-rev | CCGTCTCACCTCGGTTTACAGatACCTCTGTTTG GGAAAATTGGGGACGCCGAGACGA | 41 |
| 1-3bp-for | TCGTCTCGGCGTCCCCAATTTTCCCAAACAGAG GTaatCTGTAAACCGAGGTGAGACGG | 42 |
| 1-3bp-rev | CCGTCTCACCTCGGTTTACAGattACCTCTGTTTG GGAAAATTGGGGACGCCGAGACGA | 43 |
| 1-4bp-for | TCGTCTCGGCGTCCCCAATTTTCCCAAACAGAG GTaaatCTGTAAACCGAGGTGAGACGG | 44 |
| 1-4bp-rev | CCGTCTCACCTCGGTTTACAGatttACCTCTGTTT GGGAAAATTGGGGACGCCGAGACGA | 45 |
| 1-5bp-for | TCGTCTCGGCGTCCCCAATTTTCCCAAACAGAG GTgaaatCTGTAAACCGAGGTGAGACGG | 46 |
| 1-5bp-rev | CCGTCTCACCTCGGTTTACAGatttcACCTCTGTTT GGGAAAATTGGGGACGCCGAGACGA | 47 |
| 1-6bp-for | TCGTCTCGGCGTCCCCAATTTTCCCAAACAGAG GTcgaaatCTGTAAACCGAGGTGAGACGG | 48 |
| 1-6bp-rev | CCGTCTCACCTCGGTTTACAGatttcgACCTCTGTT TGGGAAAATTGGGGACGCCGAGACGA | 49 |
| 1-7bp-for | TCGTCTCGGCGTCCCCAATTTTCCCAAACAGAG GTtcgaaatCTGTAAACCGAGGTGAGACGG | 50 |
| 1-7bp-rev | CCGTCTCACCTCGGTTTACAGatttcgaACCTCTGT TTGGGAAAATTGGGGACGCCGAGACGA | 51 |
| 2-0bp-for | TCGTCTCGGAGGTTTTGGAACCTCTGTTTGGGA AAATTGGGGAGTCTGAGACGG | 52 |
| 2-0bp-rev | CCGTCTCAGACTCCCCAATTTTCCCAAACAGAG GTTCCAAAACCTCCGAGACGA | 53 |

TABLE 2-continued

| Oligonucleotides and gBlocks for reporter construction | | |
|---|---|---|
| Construct Name | Sequence | SEQ ID NO: |
| 2-1bp-for | TCGTCTCGGAGGTTTTGGACACCTCTGTTTGGG AAAATTGGGGAGTCTGAGACGG | 54 |
| 2-1bp-rev | CCGTCTCAGACTCCCCAATTTTCCCAAACAGAG GTGTCCAAAACCTCCGAGACGA | 55 |
| 2-2bp-for | TCGTCTCGGAGGTTTTGGACTACCTCTGTTTGG GAAAATTGGGGAGTCTGAGACGG | 56 |
| 2-2bp-rev | CCGTCTCAGACTCCCCAATTTTCCCAAACAGAG GTAGTCCAAAACCTCCGAGACGA | 57 |
| 2-3bp-for | TCGTCTCGGAGGTTTTGGACTTACCTCTGTTTG GGAAAATTGGGGAGTCTGAGACGG | 58 |
| 2-3bp-rev | CCGTCTCAGACTCCCCAATTTTCCCAAACAGAG GTAAGTCCAAAACCTCCGAGACGA | 59 |
| 2-4bp-for | TCGTCTCGGAGGTTTTGGACTTAACCTCTGTTT GGGAAAATTGGGGAGTCTGAGACGG | 60 |
| 2-4bp-rev | CCGTCTCAGACTCCCCAATTTTCCCAAACAGAG GTTAAGTCCAAAACCTCCGAGACGA | 61 |
| 2-5bp-for | TCGTCTCGGAGGTTTTGGACTTAGACCTCTGTT TGGGAAAATTGGGGAGTCTGAGACGG | 62 |
| 2-5bp-rev | CCGTCTCAGACTCCCCAATTTTCCCAAACAGAG GTCTAAGTCCAAAACCTCCGAGACGA | 63 |
| 2-6bp-for | TCGTCTCGGAGGTTTTGGACTTAGCACCTCTGT TTGGGAAAATTGGGGAGTCTGAGACGG | 64 |
| 2-6bp-rev | CCGTCTCAGACTCCCCAATTTTCCCAAACAGAG GTGCTAAGTCCAAAACCTCCGAGACGA | 65 |
| 2-7bp-for | TCGTCTCGGAGGTTTTGGACTTAGCTACCTCTG TTTGGGAAAATTGGGGAGTCTGAGACGG | 66 |
| 2-7bp-rev | CCGTCTCAGACTCCCCAATTTTCCCAAACAGAG GTAGCTAAGTCCAAAACCTCCGAGACGA | 67 |
| 4-0bp-for | TCGTCTCTGCACCCCCAATTTTCCCAAACAGAG GTCTGTAAACCGATGAGACGG | 68 |
| 4-0bp-rev | CCGTCTCATCGGTTTACAGACCTCTGTTTGGGA AAATTGGGGGTGCAGAGACGA | 69 |
| 4-1bp-for | TCGTCTCTGCACCCCCAATTTTCCCAAACAGAG GTtCTGTAAACCGATGAGACGG | 70 |
| 4-1bp-rev | CCGTCTCATCGGTTTACAGaACCTCTGTTTGGG AAAATTGGGGGTGCAGAGACGA | 71 |
| 4-2bp-for | TCGTCTCTGCACCCCCAATTTTCCCAAACAGAG GTatCTGTAAACCGATGAGACGG | 72 |
| 4-2bp-rev | CCGTCTCATCGGTTTACAGatACCTCTGTTTGGG AAAATTGGGGGTGCAGAGACGA | 73 |
| 4-3bp-for | TCGTCTCTGCACCCCCAATTTTCCCAAACAGAG GTaatCTGTAAACCGATGAGACGG | 74 |
| 4-3bp-rev | CCGTCTCATCGGTTTACAGattACCTCTGTTTGGG AAAATTGGGGGTGCAGAGACGA | 75 |
| 4-4bp-for | TCGTCTCTGCACCCCCAATTTTCCCAAACAGAG GTaaatCTGTAAACCGATGAGACGG | 76 |
| 4-4bp-rev | CCGTCTCATCGGTTTACAGatttACCTCTGTTTGG GAAAATTGGGGGTGCAGAGACGA | 77 |
| 4-5bp-for | TCGTCTCTGCACCCCCAATTTTCCCAAACAGAG GTgaaatCTGTAAACCGATGAGACGG | 78 |

TABLE 2-continued

Oligonucleotides and gBlocks for reporter construction

| Construct Name | Sequence | SEQ ID NO: |
|---|---|---|
| 4-5bp-rev | CCGTCTCATCGGTTTACAGatttcACCTCTGTTTGG GAAAATTGGGGGTGCAGAGACGA | 79 |
| 4-6bp-for | TCGTCTCTGCACCCCCAATTTTCCCAAACAGAG GTcgaaatCTGTAAACCGATGAGACGG | 80 |
| 4-6bp-rev | CCGTCTCATCGGTTTACAGatttcgACCTCTGTTTG GGAAAATTGGGGGTGCAGAGACGA | 81 |
| 4-7bp-for | TCGTCTCTGCACCCCCAATTTTCCCAAACAGAG GTtcgaaatCTGTAAACCGATGAGACGG | 82 |
| 4-7bp-rev | CCGTCTCATCGGTTTACAGatttcgaACCTCTGTTT GGGAAAATTGGGGGTGCAGAGACGA | 83 |
| 5-0bp-for | TCGTCTCGCCGAGGTTTTGGAACCTCTGTTTGG GAAAATTGGGGCTCGTGAGACGG | 84 |
| 5-0bp-rev | CCGTCTCACGAGCCCCAATTTTCCCAAACAGAG GTTCCAAAACCTCGGCGAGACGA | 85 |
| 5-1bp-for | TCGTCTCGCCGAGGTTTTGGACACCTCTGTTTG GGAAAATTGGGGCTCGTGAGACGG | 86 |
| 5-1bp-rev | CCGTCTCACGAGCCCCAATTTTCCCAAACAGAG GTGTCCAAAACCTCGGCGAGACGA | 87 |
| 5-2bp-for | TCGTCTCGCCGAGGTTTTGGACTACCTCTGTTT GGGAAAATTGGGGCTCGTGAGACGG | 88 |
| 5-2bp-rev | CCGTCTCACGAGCCCCAATTTTCCCAAACAGAG GTAGTCCAAAACCTCGGCGAGACGA | 89 |
| 5-3bp-for | TCGTCTCGCCGAGGTTTTGGACTTACCTCTGTT TGGGAAAATTGGGGCTCGTGAGACGG | 90 |
| 5-3bp-rev | CCGTCTCACGAGCCCCAATTTTCCCAAACAGAG GTAAGTCCAAAACCTCGGCGAGACGA | 91 |
| 5-4bp-for | TCGTCTCGCCGAGGTTTTGGACTTAACCTCTGT TTGGGAAAATTGGGGCTCGTGAGACGG | 92 |
| 5-4bp-rev | CCGTCTCACGAGCCCCAATTTTCCCAAACAGAG GTTAAGTCCAAAACCTCGGCGAGACGA | 93 |
| 5-5bp-for | TCGTCTCGCCGAGGTTTTGGACTTAGACCTCTG TTTGGGAAAATTGGGGCTCGTGAGACGG | 94 |
| 5-5bp-rev | CCGTCTCACGAGCCCCAATTTTCCCAAACAGAG GTCTAAGTCCAAAACCTCGGCGAGACGA | 95 |
| 5-6bp-for | TCGTCTCGCCGAGGTTTTGGACTTAGCACCTCT GTTTGGGAAAATTGGGGCTCGTGAGACGG | 96 |
| 5-6bp-rev | CCGTCTCACGAGCCCCAATTTTCCCAAACAGAG GTGCTAAGTCCAAAACCTCGGCGAGACGA | 97 |
| 5-7bp-for | TCGTCTCGCCGAGGTTTTGGACTTAGCTACCTC TGTTTGGGAAAATTGGGGCTCGTGAGACGG | 98 |
| 5-7bp-rev | CCGTCTCACGAGCCCCAATTTTCCCAAACAGAG GTAGCTAAGTCCAAAACCTCGGCGAGACGA | 99 |
| 1-Chr10--54913298-54913376-for | TCGTCTCGGCGTCCCCTCCCATCACAGGCCCTG AGGTTTAAGAGAAAACCTGAGACGG | 100 |
| 1-Chr10-54913298-54913376-rev | CCGTCTCAGGTTTTCTCTTAAACCTCAGGGCCT GTGATGGGAGGGGACGCCGAGACGA | 101 |
| 2-Chr10--54913298-54913376-for | TCGTCTCGAACCATGGTTTTGTGGGCCAGGCCC ATGACCCTTCTCCTCTGGGAGTCTGAGACGG | 102 |
| 2-Chr10--54913298-54913376-rev | CCGTCTCAGACTCCCAGAGGAGAAGGGTCATG GGCCTGGCCCACAAAACCATGGTTCGAGACGA | 103 |

TABLE 2-continued

Oligonucleotides and gBlocks for reporter construction

| Construct Name | Sequence | SEQ ID NO: |
|---|---|---|
| 4-Chr10-54913298-54913376-for | TCGTCTCTGCACCCCCTCCCATCACAGGCCCTG AGGTTTAAGAGAAAACCATTGAGACGG | 104 |
| 4-Chr10-54913298-54913376-rev | CCGTCTCAATGGTTTTCTCTTAAACCTCAGGGC CTGTGATGGGAGGGGGTGCAGAGACGA | 105 |
| 5-Chr10-54913298-54913376-for | TCGTCTCGCCATGGTTTTGTGGGCCAGGCCCAT GACCCTTCTCCTCTGGGCTCGTGAGACGG | 106 |
| 5-Chr10-54913298-54913376-rev | CCGTCTCACGAGCCCAGAGGAGAAGGGTCATG GGCCTGGCCCACAAAACCATGGCGAGACGA | 107 |
| 3-for | ATCCGTCTCCAGTCGAGTCGGATTTGATCTGAT CAAGAGACAG | 108 |
| 3-rev | AACCGTCTCGGTGCGTTCGGATTTGATCCAGAC ATGATAAGATAC | 109 |
| Esp3I-insert-for | /Phos/CGCGTTGAGACGCTGCCATCCGTCTCGC | 110 |
| Esp3I-insert-rev | /Phos/TCGAGCGAGACGGATGGCAGCGTCTCAA | 111 |
| Centromere_Chr_1_5_19-1_2* | GTTGTTCGTCTCGGCGTCCTTGTGTTGTGTGTCT TCAACTCACAGAGTTAAACGATGCTTTACACA GAGTAGACTTGAAACACTCTTTTTCTGGAGTCT GAGACGGTTCTGTTTTGGTGTGATTAGTTAT | 112 |
| Centromere_Chr_1_5_19-4_5* | GTTGGTCGTCTCTGCACCCTTGTGTTGTGTGTCT TCAACTCACAGAGTTAAACGATGCTTTACACA GAGTAGACTTGAAACACTCTTTTTCTGGCTCGT GAGACGGTTCTGTTTTGGTGTGATTAGTTAT | 113 |
| Ch5_155183064-155183141-1_2* | GTTGTTCGTCTCGGCGTCCCACCGGCTCATGAG AGGTAGAGCTAAGGTCCAAACCTAGGTTTATC TGAGACCGGAACTCATGTGATTAACTGTGGAG TCTGAGACGGTTCTGTTTTGGTGTGATTAGTTAT | 114 |
| Ch5_155183064-155183141-4_5* | GTTGGTCGTCTCTGCACCCCACCGGCTCATGAG AGGTAGAGCTAAGGTCCAAACCTAGGTTTATC TGAGACCGGAACTCATGTGATTAACTGTGGCTC GTGAGACGGTTCTGTTTTGGTGTGATTAGTTAT | 115 |
| Ch5_169395198-169395274-1_2* | GTTGTTCGTCTCGGCGTCCTTAAGAACATAAAT CCCCAGGAATTCACAGAAACCTTGGTTTGAGCT TTGGATTTCCCGCAGGATGTGGGATAGGAGTCT GAGACGGTTCTGTTTTGGTGTGATTAGTTAT | 116 |
| Ch5_169395198-169395274-4_5* | GTTGGTCGTCTCTGCACCCTTAAGAACATAAAT CCCCAGGAATTCACAGAAACCTTGGTTTGAGCT TTGGATTTCCCGCAGGATGTGGGATAGGCTCGT GAGACGGTTCTGTTTTGGTGTGATTAGTTAT | 117 |
| Ch12_62418577-62418652-1_2* | GTTGTTCGTCTCGGCGTCCACTCCCTCTCCCCC AAAAAGTAAAGGTAGAAAACCAAGGTTTACAG GCAACAAATAGCACAATGAATGGAATGGAGTC TGAGACGGTTCTGTTTTGGTGTGATTAGTTAT | 118 |
| Ch12_62418577-62418652-4_5* | GTTGGTCGTCTCTGCACCCACTCCCTCTCCCCC AAAAAGTAAAGGTAGAAAACCAAGGTTTACAG GCAACAAATAGCACAATGAATGGAATGGCTCG TGAGACGGTTCTGTTTTGGTGTGATTAGTTAT | 119 |
| chr13_102010574-102010650-1_2* | GTTGTTCGTCTCGGCGTCCTAGGGAAGTGATCA TAGCTGAGTTTCTGGAAAAACCTAGGTTTTAAA GTTGAGGAGACTTAAGTCCAAAACCTGGAGTC TGAGACGGTTCTGTTTTGGTGTGATTAGTTAT | 120 |

TABLE 2-continued

Oligonucleotides and gBlocks for reporter construction

| Construct Name | Sequence | SEQ ID NO: |
| --- | --- | --- |
| chr13_102010574-102010650-4_5* | GTTGGTCGTCTCTGCACCCTAGGGAAGTGATCA TAGCTGAGTTTCTGGAAAAACCTAGGTTTTAAA GTTGAGGAGACTTAAGTCCAAAACCTGGCTCG TGAGACGGTTCTGTTTTGGTGTGATTAGTTAT | 121 |

Oligonucleotide sequences were annealed to create the fragments shown in FIG. 1. The names correspond to the fragment number (1, 2, 4, or 5) and then to the number of base pair spacer nucleotides separating the Cas9 binding site from the gix core site.

*Double stranded gBlocks as described in the methods within the supporting material document.

TABLE 3

Oligonucleotides for recCas9 construction

| Oligonucleotide Name | Sequence | SEQ ID NO: |
| --- | --- | --- |
| 1GGS-link-for_BamHI | TTCATCGGATCCGATAAAAAGTATTCTATTG GTTTAGCTATCGGCAC | 122 |
| 5GGS-link-for_BamHI | TTCATCGGATCCGGTGGTTCAGGTGGCAGC GGAG | 123 |
| 8GGS-link-for_BamHI | TTCATCGGATCCGGAGGGTCCGGAGGTAGT GGCGGCAGCGGTGGTTCAGGTGGCAGCGGAG | 124 |
| Cas9-rev-FLAG-NLS-AgeI | AATAACCGGTTCAGACCTTCCTTTTCTTCTT TGGGGAACCTCCCTTGTCGTCATCATCCTTA TAATCGGAGCCACCGTCACCCCCAAGCTGT GACAAATC | 125 |
| 1GGS-rev-BamHI | TGATAAGGATCCACCCTTTGGTGGTCTTCCA AACCGCC | 126 |
| 2GGS-rev-BamH | TGATAAGGATCCACCGCTACCACCCTTTGG TGGTCTTC | 127 |
| Gin-for_NotI | AGATCCGCGGCCGCTAATAC | 128 |
| Esp3I-for-plasmid | TTGAGTcgtctcTATACTCTTCCTTTTTCAATAT TATTGAAGCATTTATCAGGG | 129 |
| Esp3I-rev-plasmid | CTGGAAcgtctcACTGTCAGACCAAGTTTACTC ATATATACTTTAGATTG | 130 |
| spec-Esp3I-for | GGTGTGcgtctcTACAGTTATTTGCCGACTACC TTGGTGATCTCGC | 131 |
| spec-Esp3I-rev | ACACCAcgtctcTGTATGAGGGAAGCGGTGAT CGCC | 132 |
| cpec assembly-for-plasmid | CATACTCTTCCTTTTTCAATATTATTGAAGC ATTTATCAGGG | 133 |
| cpec assembly-rev-plasmid | CTGTCAGACCAAGTTTACTCATATATACTTT AGATTG | 134 |
| cpec assembly-for-spec | CAATCTAAAGTATATATGAGTAAACTTGGT CTGACAGTTTGCCGACTACCTTGGTGATCTCG | 135 |
| cpec assembly-for-spec2 | CAATCTAAAGTATATATGAGTAAACTTGGT CTGACAGTTATTTGCCGACTACCTTGGTGAT CTCG | 136 |
| cpec assembly-rev-spec | CCCTGATAAATGCTTCAATAATATTGAAAA AGGAAGAGTATG | 137 |

TABLE 4

Custom sequencing oligonucleotides

| Oligonucleotide Name | Sequence | SEQ ID NO: |
|---|---|---|
| Fwd CMV | CGCAAATGGGCGGTAGGCGTG | 138 |
| Cas9coRevE1 | CCGTGATGGATTGGTGAATC | 139 |
| Cas9coRevE2 | CCCATACGATTTCACCTGTC | 140 |
| Cas9coRevE3 | GGGTATTTTCCACAGGATGC | 141 |
| Cas9coRevE4 | CTTAGAAAGGCGGGTTTACG | 142 |
| Cas9coRevE5 | CTTACTAAGCTGCAATTTGG | 143 |
| Cas9coRevE6 | TGTATTCATCGGTTATGACAG | 144 |
| bGH_PArev seq1 | CAGGGTCAAGGAAGGCACG | 145 |
| pHU6-gRNA_for | GTTCCGCGCACATTTCC | 146 |
| pHU6-gRNA_rev | GCGGAGCCTATGGAAAAAC | 147 |
| pCALNL-for1 | GCCTTCTTCTTTTTCCTACAGC | 148 |
| pCALNL-for2 | CGCATCGAGCGAGCAC | 149 |

TABLE 5

Genomic PCR primers

| Oligonucleotide Name | Sequence | SEQ ID NO: |
|---|---|---|
| FAM19A2-F1 | TCAAGTAGCAAAAGAAGTAGGAGTCAG | 150 |
| FAM19A2-F2 | TTAGATGCATTCGTGCTTGAAG | 151 |
| FAM19A2-C1 | TTAATTTCTGCTGCTAGAACTAAATCTGG | 152 |
| FAM19A2-R1 | GGGAAGAAAACTGGATGGAGAATG | 153 |
| FAM19A2-R2 | CATAAATGACCTAGTGGAGCTG | 154 |
| FAM19A2-C2 | TGGTTATTTTGCCCATTAGTTGATGC | 155 |

Reporter Construction

A five-piece Golden Gate assembly was used to construct reporters described below. Fragments 1-5 were flanked by Esp3I sites; Esp3I digestion created complementary 5' overhangs specifying the order of fragment assembly (FIG. 6). Fragments 1, 2, 4, and 5 were created by annealing forward and reverse complementary oligonucleotides listed in Table 5. Fragments were annealed by mixing 10 μl of each oligonucleotide (100 μM) in 20 μl of molecular grade water, incubating at 95° C. for 3 minutes and reducing the temperature to 16° C. at a rate of −0.1° C./sec. Fragment 3 was created by PCR amplifying the region containing kanR and a PolyA stop codon with primers 3-for and 3-rev. These primers also appended Esp3I on the 5' and 3' ends of this sequence.

Annealed fragments 1, 2, 4 and 5 were diluted 12,000 fold and 0.625 μl of each fragment were added to a mixture containing the following:

1) 40-50 ng fragment 3
2) 100 ng pCALNL EGFP-Esp3I
3) 1 μL Tango Buffer (10×)
4) 1 μL DTT (10 mM)
5) 1 μL ATP (10 mM)

6) 0.25 uL T7 ligase (3,000 U/μL)
7) 0.75 uL Esp3I (10 U/μL)
8) $H_2O$ up to 10 μL Reactions were incubated in thermal cycler programmed for 20 cycles (37° C. for 5 min, 20° C.).

After completion of the Golden Gate reactions, 7 μL of each reaction was mixed with 1 μL of ATP (10 mM), 1 μL of 10× Plasmid Safe ATP-dependent DNAse buffer (10×), and 1 μL of Plasmid Safe ATP-dependent DNAse (10 U/μL) (Epicentre, Madison, Wis.) to remove linear DNA and reduce background. DNAse digestions were incubated at 37° C. for 30 min and heat killed at 70° C. for 30 min. Half (5 μL) of each reaction was transformed into Mach1-T1 cells. Colonies were analyzed by colony PCR and sequenced.

The protocol was modified for reporters used in FIG. 4. Two gBlocks, encoding target sites to the 5' or 3' of the PolyA terminator were used instead of fragments 1, 2, 4 and 5. These gBlocks (10 ng) were added to the MMX, which was cycled 10 times (37° C. for 5 min, 20° C.) and carried forward as described above.

Plasmids

Unless otherwise stated, DNA fragments were isolated from agarose gels using QIAquick Gel Extraction Kit (Qiagen, Valencia, Calif.) and further purified using DNA Clean & Concentrator-5 (Zymo Research, Irvine, Calif.) or Qiaquick PCR purification kit (Qiagen, Valencia, Calif.). PCR fragments not requiring gel purification were isolated using one of the kits listed above.

The pCALNL-GFP subcloning vector, pCALNL-EGFP-Esp3I, was used to clone all recCas9 reporter plasmids and was based on the previously described pCALNL-GFP vector (Matsuda and Cepko, Controlled expression of transgenes introduced by in vivo electroporation. Proceedings of the National Academy of Sciences of the United States of America 104, 1027-1032 (2007), which is incorporated herein by reference). To create pCALNL-EGFP-Esp3I, pCALNL-GFP vectors were digested with XhoI and MluI and gel purified to remove the loxP sites, the kanamycin resistance marker, and the poly-A terminator. Annealed oligonucleotides formed an EspI-Insert, that contained inverted Esp3I sites as well as XhoI and MluI compatible overhangs; this insert was ligated into the XhoI and MluI digested plasmid and transformed.

pCALNL-GFP recCas9 reporter plasmids were created by Golden Gate assembly with annealed oligos and PCR products containing compatible Esp3I overhangs. Golden Gate reactions were set up and performed as described previously with Esp3I (ThermoFisher Scientific, Waltham, Mass.) (Sanjana et al., A transcription activator-like effector toolbox for genome engineering. Nature protocols 7, 171-192 (2012), the entire contents of which is hereby incorporated by reference). FIG. 6 outlines the general assembly scheme and relevant primers for reporter assembly as well as sequences for all recCas9 target sites are listed in Tables 2 and 6, respectively. A representative DNA sequence containing KanR (bold and underlined) and PolyA terminator (in italics and underlined) flanked by two recCas9 target sites is shown below. The target sites shown are both PAM_NT1-0 bp-gix_core-0bp-NT1_PAM (see Table 6). Protoadjacent spacer motifs (PAMs) are in bold. Base pair spacers are lower case. Gix site or gix-related sites are in italics and dCas9 binding sites are underlined. For the genomic reporter plasmids used in the assays of FIG. 4, a G to T transversion was observed in the kanamycin resistance marker, denoted by a G/T in the sequence below. This was present in all the reporters used in this figure, and it is not expected to affect the results, as it is far removed from the PolyA terminator and recCas9 target sites.

(SEQ ID NO: 156)

ACGCGTCCCCAATTTTCCCAAACAGAGGTCTGTAAACCGAGGTTTTGGAACCTCTGTTTGGGAAAATTGGGGAGTCGAGTCGGATTTGATCTGATCAAGAGACAGGATGAGGATCGTTTCGCATGATTGAACAAGATGGATTGCACGCAGGTTCTCCGGCCGCTTGGGTGGAGAGGCTATTCGGCTATGACTGGGCACAACAGACAATCGGCTGCTCTGATGCCGCCGTGTTCCGGCTGTCAGTCGCAGGGGCGCCCGGTTCTTTTTGTCAAGACCGACCTGTCCGGTGCCCTGAATGAACTGCAGGACGAGGCAGCGCGGCTATCGTGGCTGGCCACGACGGGCGTTCCTTGCGCAGCTGTGCTCGACGTTGTCACTGAAGCGGGAAGGGACTGGCTGCTATTGGGCGAAGTGCCGGGGCAGGATCTCCTGTCATCTCACCTTGCTCCTGCCGAGAAAGTATCCATCATGGCTGATGCAATGCGGCGGCTGCATACGCTTGATCCGGCTACCTGCCCATTCGACCACCAAGCGAAACATCGCATCGAGCGAGCACGTACTCGGATGGAAGCCGGTCTTGTCGATCAGGATGATCTGGACGAAGAGCATCAGGGGCTCGCGCCAGCCGAACTGTTCGCCAGGCTCAAGGC

-continued

GCGCATGCCCGACGGCGAGGATCTCGTCGTGACCCATGGCGATGCCTGCTTGCCGAATATCATGGTGGAAAATGGCCGCTTTTCTGGATTCATCGACTGTGGCCGGCTGGGTGTGGCGGACCGCTATCAGGACATAGCGTTGGCTACCCGTGATATTGCTGAAGAGCTTGGCGGCGAATGGGCTGACCGCTTCCTCGTGCTTTACGGTATCGCCGCTCCCGATTCGCAGCGCATCGCCTTCTATCGCCTTCTTGACGAGTTCTTCTGAGCGGGACTCTGGGGTTCGAAATGACCGACCAAGCGACGCCCAACCTGCCATCACGAGATTTCGATTCCACCGCCGCCTTCTATGAAAGGTTGGGCTTCGGAATCGTTTTCCGGGACGCCGGCTGGATGATCCTCCAGCGCGGGGATCTCATGCTGGAGTTCTTCGCCCACCCCATCGATAACTTGTTTATTGCAGCTTATAATGGTTACAAATAAAGCAATAGCATCACAAATTTCACAAATAAAGCATTTTTTTCACTGCATTCTAGTTGTGGTTTGTCCAAACTCATCAATGTATCTTATCATGTCTGGATCAAATCCGAACGCACCCCCAATTTTCCCAAACAGAGGTCTGTAAACCGAGGTTTTGGAACCTCTGTTTGGGAAAATTGGGGCTCGAG

TABLE 6

List of target site sequences used in reporter assays

| Target site name | Sequence | SEQ ID NO: |
|---|---|---|
| PAM_NT1-0bp-gix_core-0bp-NT1_PAM | CCCCAATTTTCCCAAACAGAGGTtCTGTAAACCGAGGTTTTGGAACCTCTGTTTGGGAAAATTGGGG | 157 |
| PAM_NT1-1bp-gix_core-1bp-NT1_PAM | CCCCAATTTTCCCAAACAGAGGTtCTGTAAACCGAGGTTTTGGcAACCTCTGTTTGGGAAAATTGGGG | 158 |
| PAM_NT1-2bp-gix_core-2bp-NT1_PAM | CCCCAATTTTCCCAAACAGAGGTatCTGTAAACCGAGGTTTTGGctAACCTCTGTTTGGGAAAATTGGGG | 159 |
| PAM_NT1-3bp-gix_core-3bp-NT1_PAM | CCCCAATTTTCCCAAACAGAGGTaatCTGTAAACCGAGGTTTTGGcttAACCTCTGTTTGGGAAAATTGGGG | 160 |
| PAM_NT1-4bp-gix_core-4bp-NT1_PAM | CCCCAATTTTCCCAAACAGAGGTaaatCTGTAAACCGAGGTTTTGGcttaAACCTCTGTTTGGGAAAATTGGGG | 161 |
| PAM_NT1-5bp-gix_core-5bp-NT1_PAM | CCCCAATTTTCCCAAACAGAGGTgaaatCTGTAAACCGAGGTTTTGGcttagAACCTCTGTTTGGGAAAATTGGGG | 162 |
| PAM_NT1-6bp-gix_core-6bp-NT1_PAM | CCCCAATTTTCCCAAACAGAGGTcgaaatCTGTAAACCGAGGTTTTGGcttagcAACCTCTGTTTGGGAAAATTGGGG | 163 |
| PAM_NT1-7bp-gix_core-7bp-NT1_PAM | CCCCAATTTTCCCAAACAGAGGTtcgaaatCTGTAAACCGAGGTTTTGGcttagctAACCTCTGTTTGGGAAAATTGGGG | 164 |
| PAM_NT1-6bp-gix_core-0bp-NT1_PAM | CCCCAATTTTCCCAAACAGAGGTtcgaaatCTGTAAACCGAGGTTTTGGAACCTCTGTTTGGGAAAATTGGGG | 165 |
| PAM_NT1-6bp-gix_core-1bp-NT1_PAM | CCCCAATTTTCCCAAACAGAGGTtcgaaatCTGTAAACCGAGGTTTTGGcAACCTCTGTTTGGGAAAATTGGGG | 166 |

TABLE 6-continued

| List of target site sequences used in reporter assays | | |
|---|---|---|
| Target site name | Sequence | SEQ ID NO: |
| PAM_NT1-6bp-gix_core-2bp-NT1_PAM | CCCCAATTTTCCCAAACAGAGGTcgaaatCTGTAAACCGAGGTTTTGGctAACCTCTGTTTGGGAAAATTGGGG | 167 |
| PAM_NT1-6bp-gix_core-4bp-NT1_PAM | CCCCAATTTTCCCAAACAGAGGTcgaaatCTGTAAACCGAGGTTTTGGcttaAACCTCTGTTTGGGAAAATTGGGG | 168 |
| PAM_NT1-6bp-gix_core-5bp-NT1_PAM | CCCCAATTTTCCCAAACAGAGGTcgaaatCTGTAAACCGAGGTTTTGGcttagAACCTCTGTTTGGGAAAATTGGGG | 169 |
| PAM_NT1-0bp-gix_core-6bp-NT1_PAM | CCCCAATTTTCCCAAACAGAGGTCTGTAAACCGAGGTTTTGGcttagcAACCTCTGTTTGGGAAAATTGGGG | 170 |
| PAM_NT1-1bp-gix_core-6bp-NT1_PAM | CCCCAATTTTCCCAAACAGAGGTtCTGTAAACCGAGGTTTTGGcttagcAACCTCTGTTTGGGAAAATTGGGG | 171 |
| PAM_NT1-2bp-gix_core-6bp-NT1_PAM | CCCCAATTTTCCCAAACAGAGGTatCTGTAAACCGAGGTTTTGGcttagcAACCTCTGTTTGGGAAAATTGGGG | 172 |
| PAM_NT1-3bp-gix_core-6bp-NT1_PAM | CCCCAATTTTCCCAAACAGAGGTaatCTGTAAACCGAGGTTTTGGcttagcAACCTCTGTTTGGGAAAATTGGGG | 173 |
| PAM_NT1-4bp-gix_core-6bp-NT1_PAM | CCCCAATTTTCCCAAACAGAGGTaaatCTGTAAACCGAGGTTTTGGcttagcAACCTCTGTTTGGGAAAATTGGGG | 174 |
| PAM_NT1-5bp-gix_core-6bp-NT1_PAM | CCCCAATTTTCCCAAACAGAGGTgaaatCTGTAAACCGAGGTTTTGGcttagcAACCTCTGTTTGGGAAAATTGGGG | 175 |
| Chromosome_10-54913298-54913376* | CCCCTCCCATCACAGGCCCTGAGgtttaaGAGAAAACCATGGTTTTGTGggccagGCCCATGACCCTTCTCCTCTGGG | 176 |
| Centromere_Chromosomes_1_5_19 | CCTTGTGTTGTGTGTCTTCAACTcacagAGTTAAACGATGCTTTACACagagtaGACTTGAAACACTCTTTTTCTGG | 177 |
| Chromosome_5_155183064-155183141 (site 1) | CCACCGGCTCATGAGAGGTAGAGctaagGTCCAAACCTAGGTTTATCTgagaccGGAACTCATGTGATTAACTGTGG | 178 |
| Chromosome_5_169395198-169395274 (site 2) | CCTTAAGAACATAAATCCCCAGGaattcACAGAAACCTTGGTTTGAGCtttggaTTTCCCGCAGGATGTGGGATAGG | 179 |
| Chromosome_12_62418577-62418652 | CCACTCCCTCTCCCCCAAAAAGTaaaggTAGAAAACCAAGGTTTACAGgcaacAAATAGCACAATGAATGGAATGG | 180 |
| Chromosome_13_102010574-102010650 (FGF14) | CCTAGGGAAGTGATCATAGCTGAgtttctGGAAAAACCTAGGTTTTAAAgttgaGGAGACTTAAGTCCAAAACCTGG | 181 |

Protoadjacent spacer motifs (PAMs) are in bold. Base pair spacers are lower case. Gix site or gix-related sites are in italics and dCas9 binding sites are underlined.
*Chromosome_10 reporter contains two overlapping PAM sites and dCas9 binding sites on the 5' and 3' ends of the gix sites.

Plasmids containing the recCas9 gene were constructed by PCR amplification of a gBlock encoding an evolved, hyperactivated Gin variant (Ginβ) (Gaj et al., A comprehensive approach to zinc-finger recombinase customization enables genomic targeting in human cells. Nucleic acids research 41, 3937-3946 (2013), the entire contents of which is hereby incorporated by reference) with the oligonucleotides 1GGS-rev-BamHI or 2GGS-rev-BamHI (using linker SEQ ID NO: 182) and Gin-for-NotI. PCR fragments were digested with BamHI and NotI, purified and ligated into a previously described expression vector (Addgene plasmid 43861) (see, e.g., Fu et al., High-frequency off-target mutagenesis induced by CRISPR-Cas nucleases in human cells. Nature biotechnology 31, 822-826 (2013), the entire contents of which is hereby incorporated by reference) to produce subcloning vectors pGin-1GGS and pGIN-2GGS (using linker SEQ ID NO: 182). Oligonucleotides 1GGS-link-for-BamHI, 5GGS-link-for-BamHI (using linker SEQ ID NO: 701), or 8GGS-link-for-BamHI (using linker SEQ ID NO: 183) were used with Cas9-rev-FLAG-NLS-AgeI to construct PCR fragments encoding Cas9-FLAG-NLS with a 1, 5, or 8 GGS linker (see Table 3). For DNA sequences encoding the GGS amino acid linkers, see Table 7. PCR fragments and subcloning plasmids were digested with BamHI and AgeI and ligated to create plasmids pGinβ-2×GGS-dCas9-FLAG-NLS (using linker SEQ ID NO: 182), pGinβ-5×GGS-dCas9-FLAG-NLS (using linker SEQ ID NO: 701), and pGinβ-8×GGS-dCas9-FLAG-NLS (using linker SEQ ID NO: 183). For the DNA and amino acid sequence of the pGinβ-8×GGS-dCas9-FLAG-NLS (i.e., rec-Cas9), see below. The sequence encoding Ginβ is shown in bold; those encoding GGS linkers are shown in italics; those encoding dCas9 linkers are black; those encoding the FLAG tag and NLS are underlined and in lowercase, respectively.

(SEQ ID NO: 184)

ATGCTCATTGGCTACGTGCGCGTCTCAACTAACGACCAGAATACCGATCTTC

AGAGGAACGCACTGGTTTGTGCAGGCTGCGAACAGATTTTCGAGGACAAAC

TCAGCGGGACACGGACGGACAGACCTGGCCTCAAGCGAGCACTCAAGAGGC

TGCAGAAAGGAGACACTCTGGTGGTCTGGAAATTGGACCGCCTGGGTCGAA

GCATGAAGCATCTCATTTCTCTGGTTGGCGAACTGCGAGAAAGGGGGATCA

ACTTTCGAAGTCTGACGGATTCCATAGATACAAGCAGCCCCATGGGCCGGT

TCTTCTTCTACGTGATGGGTGCACTGGCTGAAATGGAAAGAGAACTCATTAT

AGAGCGAACCATGGCAGGGCTTGCGGCTGCCAGGAATAAAGGCAGGCGGTT

TGGAAGACCACCAAAG*GGTGGATCCGGAGGGTCCGGAGGTAGTGGCGGCAGCGG*

*TGGTTCAGGTGGCAGCGGAGGGTCAGGAGGCTCT*GATAAAAAGTATTCTATTGGTT

TAGCTATCGGCACTAATTCCGTTGGATGGGCTGTCATAACCGATGAATACAAAGT

ACCTTCAAAGAAATTTAAGGTGTTGGGGAACACAGACCGTCATTCGATTAAAAA

GAATCTTATCGGTGCCCTCCTATTCGATAGTGGCGAAACGGCAGAGGCGACTCGC

CTGAAACGAACCGCTCGGAGAAGGTATACACGTCGCAAGAACCGAATATGTTAC

TTACAAGAAATTTTTAGCAATGAGATGGCCAAAGTTGACGATTCTTTCTTTCACC

GTTTGGAAGAGTCCTTCCTTGTCGAAGAGGACAAGAAACATGAACGGCACCCCA

TCTTTGGAAACATAGTAGATGAGGTGGCATATCATGAAAAGTACCCAACGATTTA

TCACCTCAGAAAAAAGCTAGTTGACTCAACTGATAAAGCGGACCTGAGGTTAAT

CTACTTGGCTCTTGCCCATATGATAAAGTTCCGTGGGCACTTTCTCATTGAGGGTG

ATCTAAATCCGGACAACTCGGATGTCGACAAACTGTTCATCCAGTTAGTACAAAC

CTATAATCAGTTGTTTGAAGAGAACCCTATAAATGCAAGTGGCGTGGATGCGAA

GGCTATTCTTAGCGCCCGCCTCTCTAAATCCCGACGGCTAGAAAACCTGATCGCA

CAATTACCCGGAGAGAAGAAAAATGGGTTGTTCGGTAACCTTATAGCGCTCTCAC

TAGGCCTGACACCAAATTTTAAGTCGAACTTCGACTTAGCTGAAGATGCCAAATT

GCAGCTTAGTAAGGACACGTACGATGACGATCTCGACAATCTACTGGCACAAAT

TGGAGATCAGTATGCGGACTTATTTTTGGCTGCCAAAAACCTTAGCGATGCAATC

CTCCTATCTGACATACTGAGAGTTAATACTGAGATTACCAAGGCGCCGTTATCCG

CTTCAATGATCAAAAGGTACGATGAACATCACCAAGACTTGACACTTCTCAAGGC

CCTAGTCCGTCAGCAACTGCCTGAGAAATATAAGGAAATATTCTTTGATCAGTCG

AAAAACGGGTACGCAGGTTATATTGACGGCGGAGCGAGTCAAGAGGAATTCTAC

AAGTTTATCAAACCCATATTAGAGAAGATGGATGGGACGGAAGAGTTGCTTGTA

AAACTCAATCGCGAAGATCTACTGCGAAAGCAGCGGACTTTCGACAACGGTAGC

ATTCCACATCAAATCCACTTAGGCGAATTGCATGCTATACTTAGAAGGCAGGAGG

ATTTTTATCCGTTCCTCAAAGACAATCGTGAAAAGATTGAGAAAATCCTAACCTT

TCGCATACCTTACTATGTGGGACCCCTGGCCCGAGGGAACTCTCGGTTCGCATGG

-continued

ATGACAAGAAAGTCCGAAGAAACGATTACTCCATGGAATTTTGAGGAAGTTGTC

GATAAAGGTGCGTCAGCTCAATCGTTCATCGAGAGGATGACCAACTTTGACAAG

AATTTACCGAACGAAAAAGTATTGCCTAAGCACAGTTTACTTTACGAGTATTTCA

CAGTGTACAATGAACTCACGAAAGTTAAGTATGTCACTGAGGGCATGCGTAAAC

CCGCCTTTCTAAGCGGAGAACAGAAGAAAGCAATAGTAGATCTGTTATTCAAGA

CCAACCGCAAAGTGACAGTTAAGCAATTGAAAGAGGACTACTTTAAGAAAATTG

AATGCTTCGATTCTGTCGAGATCTCCGGGGTAGAAGATCGATTTAATGCGTCACT

TGGTACGTATCATGACCTCCTAAAGATAATTAAAGATAAGGACTTCCTGGATAAC

GAAGAGAATGAAGATATCTTAGAAGATATAGTGTTGACTCTTACCCTCTTTGAAG

ATCGGGAAATGATTGAGGAAAGACTAAAAACATACGCTCACCTGTTCGACGATA

AGGTTATGAAACAGTTAAAGAGGCGTCGCTATACGGGCTGGGGACGATTGTCGC

GGAAACTTATCAACGGGATAAGAGACAAGCAAAGTGGTAAAACTATTCTCGATT

TTCTAAAGAGCGACGGCTTCGCCAATAGGAACTTTATGCAGCTGATCCATGATGA

CTCTTTAACCTTCAAAGAGGATATACAAAAGGCACAGGTTTCCGGACAAGGGGA

CTCATTGCACGAACATATTGCGAATCTTGCTGGTTCGCCAGCCATCAAAAAGGGC

ATACTCCAGACAGTCAAAGTAGTGGATGAGCTAGTTAAGGTCATGGGACGTCAC

AAACCGGAAAACATTGTAATCGAGATGGCACGCGAAAATCAAACGACTCAGAAG

GGGCAAAAAAACAGTCGAGAGCGGATGAAGAGAATAGAAGAGGGTATTAAAGA

ACTGGGCAGCCAGATCTTAAAGGAGCATCCTGTGGAAAATACCCAATTGCAGAA

CGAGAAACTTTACCTCTATTACCTACAAAATGGAAGGGACATGTATGTTGATCAG

GAACTGGACATAAACCGTTTATCTGATTACGACGTCGATGCCATTGTACCCCAAT

CCTTTTTGAAGGACGATTCAATCGACAATAAAGTGCTTACACGCTCGGATAAGAA

CCGAGGGAAAAGTGACAATGTTCCAAGCGAGGAAGTCGTAAAGAAAATGAAGA

ACTATTGGCGGCAGCTCCTAAATGCGAAACTGATAACGCAAAGAAAGTTCGATA

ACTTAACTAAAGCTGAGAGGGGTGGCTTGTCTGAACTTGACAAGGCCGGATTTAT

TAAACGTCAGCTCGTGGAAACCCGCCAAATCACAAAGCATGTTGCACAGATACT

AGATTCCCGAATGAATACGAAATACGACGAGAACGATAAGCTGATTCGGGAAGT

CAAAGTAATCACTTTAAAGTCAAAATTGGTGTCGGACTTCAGAAAGGATTTTCAA

TTCTATAAAGTTAGGGAGATAAATAACTACCACCATGCGCACGACGCTTATCTTA

ATGCCGTCGTAGGGACCGCACTCATTAAGAAATACCCGAAGCTAGAAAGTGAGT

TTGTGTATGGTGATTACAAAGTTTATGACGTCCGTAAGATGATCGCGAAAAGCGA

ACAGGAGATAGGCAAGGCTACAGCCAAATACTTCTTTTATTCTAACATTATGAAT

TTCTTTAAGACGGAAATCACTCTGGCAAACGGAGAGATACGCAAACGACCTTTA

ATTGAAACCAATGGGGAGACAGGTGAAATCGTATGGGATAAGGGCCGGGACTTC

GCGACGGTGAGAAAAGTTTTGTCCATGCCCCAAGTCAACATAGTAAAGAAAACT

GAGGTGCAGACCGGAGGGTTTTCAAAGGAATCGATTCTTCCAAAAAGGAATAGT

GATAAGCTCATCGCTCGTAAAAAGGACTGGGACCCGAAAAAGTACGGTGGCTTC

GATAGCCCTACAGTTGCCTATTCTGTCCTAGTAGTGGCAAAAGTTGAGAAGGGAA

AATCCAAGAAACTGAAGTCAGTCAAAGAATTATTGGGGATAACGATTATGGAGC

GCTCGTCTTTTGAAAAGAACCCCATCGACTTCCTTGAGGCGAAAGGTTACAAGGA

AGTAAAAAAGGATCTCATAATTAAACTACCAAAGTATAGTCTGTTTGAGTTAGAA

-continued

AATGGCCGAAAACGGATGTTGGCTAGCGCCGGAGAGCTTCAAAAGGGGAACGA

ACTCGCACTACCGTCTAAATACGTGAATTTCCTGTATTTAGCGTCCCATTACGAG

AAGTTGAAAGGTTCACCTGAAGATAACGAACAGAAGCAACTTTTTGTTGAGCAG

CACAAACATTATCTCGACGAAATCATAGAGCAAATTTCGGAATTCAGTAAGAGA

GTCATCCTAGCTGATGCCAATCTGGACAAAGTATTAAGCGCATACAACAAGCAC

AGGGATAAACCCATACGTGAGCAGGCGGAAAATATTATCCATTTGTTTACTCTTA

CCAACCTCGGCGCTCCAGCCGCATTCAAGTATTTTGACACAACGATAGATCGCAA

ACGATACACTTCTACCAAGGAGGTGCTAGACGCGACACTGATTCACCAATCCATC

ACGGGATTATATGAAACTCGGATAGATTTGTCACAGCTTGGGGGTGAC*GGTGGCT*

*CC*GATTATAAGGATGATGACGACAAG*GGAGGTTCC*ccaaagaagaaaaggaaggtcTGA (SEQ ID NO: 185)

MLIGYVRVSTNDQNTDLQRNALVCAGCEQIFEDKLSGTRTDRPGLKRALKRLQ

KGDTLVVWKLDRLGRSMKHLISLVGELRERGINFRSLTDSIDTSSPMGRFFFYV

MGALAEMERELIIERTMAGLAAARNKGRRFGRPPK*GGSGGSGGSGGSGGSGGSG*

*GSGGS*DKKYSIGLAIGTNSVGWAVITDEYKVPSKKFKVLGNTDRHSIKKNLIGALLFD

SGETAEATRLKRTARRRYTRRKNRICYLQEIFSNEMAKVDDSFFHRLEESFLVEEDK

KHERHPIFGNIVDEVAYHEKYPTIYHLRKKLVDSTDKADLRLIYLALAHMIKFRGHFL

IEGDLNPDNSDVDKLFIQLVQTYNQLFEENPINASGVDAKAILSARLSKSRRLENLIAQ

LPGEKKNGLFGNLIALSLGLTPNFKSNFDLAEDAKLQLSKDTYDDDLDNLLAQIGDQ

YADLFLAAKNLSDAILLSDILRVNTEITKAPLSASMIKRYDEHHQDLTLLKALVRQQL

PEKYKEIFFDQSKNGYAGYIDGGASQEEFYKFIKPILEKMDGTEELLVKLNREDLLRK

QRTFDNGSIPHQIHLGELHAILRRQEDFYPFLKDNREKIEKILTFRIPYYVGPLARGNS

RFAWMTRKSEETITPWNFEEVVDKGASAQSFIERMTNFDKNLPNEKVLPKHSLLYEY

FTVYNELTKVKYVTEGMRKPAFLSGEQKKAIVDLLFKTNRKVTVKQLKEDYFKKIE

CFDSVEISGVEDRFNASLGTYHDLLKIIKDKDFLDNEENEDILEDIVLTLTLFEDREMIE

ERLKTYAHLFDDKVMKQLKRRRYTGWGRLSRKLINGIRDKQSGKTILDFLKSDGFA

NRNFMQLIHDDSLTFKEDIQKAQVSGQGDSLHEHIANLAGSPAIKKGILQTVKVVDE

LVKVMGRHKPENIVIEMARENQTTQKGQKNSRERMKRIEEGIKELGSQILKEHPVEN

TQLQNEKLYLYYLQNGRDMYVDQELDINRLSDYDVDAIVPQSFLKDDSIDNKVLTR

SDKNRGKSDNVPSEEVVKKMKNYWRQLLNAKLITQRKFDNLTKAERGGLSELDKA

GFIKRQLVETRQITKHVAQILDSRMNTKYDENDKLIREVKVITLKSKLVSDFRKDFQF

YKVREINNYHHAHDAYLNAVVGTALIKKYPKLESEFVYGDYKVYDVRKMIAKSEQ

EIGKATAKYFFYSNIMNFFKTEITLANGEIRKRPLIETNGETGEIVWDKGRDFATVRK

VLSMPQVNIVKKTEVQTGGFSKESILPKRNSDKLIARKKDWDPKKYGGFDSPTVAYS

VLVVAKVEKGKSKKLKSVKELLGITIMERSSFEKNPIDFLEAKGYKEVKKDLIIKLPK

YSLFELENGRKRMLASAGELQKGNELALPSKYVNFLYLASHYEKLKGSPEDNEQKQ

LFVEQHKHYLDEIIEQISEFSKRVILADANLDKVLSAYNKHRDKPIREQAENIIHLFTLT

NLGAPAAFKYFDTTIDRKRYTSTKEVLDATLIHQSITGLYETRIDLSQLGGD*GGS*DYK

DDDDK*GGS*pkkkrkv Stop

The Gin recombinase catalytic domain, which is amino acids 1-142 of SEQ ID NO: 185, is identical to the sequence of SEQ ID NO: 713. The dCas9 domain, in which is amino acids 167-1533 of SEQ ID NO: 185 is identical to the sequence of SEQ ID NO: 712.

(SEQ ID NO: 713)
MLIGYVRVSTNDQNTDLQRNALVCAGCEQIFEDKLSGTRTDRPGLKRALK
RLQKGDTLVVWKLDRLGRSMKHLISLVGELRERGINFRSLTDSIDTSSPM
GRFFFYVMGALAEMERELIIERTMAGLAAARNKGRRFGRPPK (SEQ ID NO: 712)
DKKYSIGLAIGTNSVGWAVITDEYKVPSKKFKVLGNTDRHSIKKNLIGAL
LFDSGETAEATRLKRTARRRYTRRKNRICYLQEIFSNEMAKVDDSFFHRL
EESFLVEEDKKHERHPIFGNIVDEVAYHEKYPTIYHLRKKLVDSTDKADL
RLIYLALAHMIKFRGHFLIEGDLNPDNSDVDKLFIQLVQTYNQLFEENPI
NASGVDAKAILSARLSKSRRLENLIAQLPGEKKNGLFGNLIALSLGLTPN
FKSNFDLAEDAKLQLSKDTYDDDLDNLLAQIGDQYADLFLAAKNLSDAIL
LSDILRVNTEITKAPLSASMIKRYDEHHQDLTLLKALVRQQLPEKYKEIF
FDQSKNGYAGYIDGGASQEEFYKFIKPILEKMDGTEELLVKLNREDLLRK
QRTFDNGSIPHQIHLGELHAILRRQEDFYPFLKDNREKIEKILTFRIPYY
VGPLARGNSRFAWMTRKSEETITPWNFEEVVDKGASAQSFIERMTNFDKN

-continued

LPNEKVLPKHSLLYEYFTVYNELTKVKYVTEGMRKPAFLSGEQKKAIVDL
LFKTNRKVTVKQLKEDYFKKIECFDSVEISGVEDRFNASLGTYHDLLKII
KDKDFLDNEENEDILEDIVLTLTLFEDREMIEERLKTYAHLFDDKVMKQL
KRRRYTGWGRLSRKLINGIRDKQSGKTILDFLKSDGFANRNFMQLIHDDS
LTFKEDIQKAQVSGQGDSLHEHIANLAGSPAIKKGILQTVKVVDELVKVM
GRHKPENIVIEMARENQTTQKGQKNSRERMKRIEEGIKELGSQILKEHPV
ENTQLQNEKLYLYYLQNGRDMYVDQELDINRLSDYDVDAIVPQSFLKDDS
IDNKVLTRSDKNRGKSDNVPSEEVVKKMKNYWRQLLNAKLITQRKFDNLT
KAERGGLSELDKAGFIKRQLVETRQITKHVAQILDSRMNTKYDENDKLIR
EVKVITLKSKLVSDFRKDFQFYKVREINNYHHAHDAYLNAVVGTALIKKY
PKLESEFVYGDYKVYDVRKMIAKSEQEIGKATAKYFFYSNIMNFFKTEIT
LANGEIRKRPLIETNGETGEIVWDKGRDFATVRKVLSMPQVNIVKKTEVQ
TGGFSKESILPKRNSDKLIARKKDWDPKKYGGFDSPTVAYSVLVVAKVEK
GKSKKLKSVKELLGITIMERSSFEKNPIDFLEAKGYKEVKKDLIIKLPKY
SLFELENGRKRMLASAGELQKGNELALPSKYVNFLYLASHYEKLKGSPED
NEQKQLFVEQHKHYLDEIIEQISEFSKRVILADANLDKVLSAYNKHRDKP
IREQAENIIHLFTLTNLGAPAAFKYFDTTIDRKRYTSTKEVLDATLIHQS
ITGLYETRIDLSQLGGD

TABLE 7

DNA sequences encoding GGS linkers

| GGS linkers | SEQ ID NO: | DNA sequences for GGS linkers | SEQ ID NO: |
|---|---|---|---|
| 2XGGS | 182 | GGTGGTAGCGGTGGATCC | 186 |
| 5XGGS | 701 | GGTGGATCCGGTGGTTCAGGTGGCAGCGGAGGGTCAG GAGGCTCT | 187 |
| 8XGGS | 183 | GGTGGATCCGGAGGGTCCGGAGGTAGTGGCGGCAGC GGTGGTTCAGGTGGCAGCGGAGGGTCAGGAGGCTCT | 188 |

For plasmid sequencing experiments, the AmpR gene in pGinβ-8×GGS-dCas9-FLAG-NLS (using linker SEQ ID NO: 183) was replaced with SpecR by golden gate cloning with PCR fragments. Esp3I sites were introduced into the pGinβ-8×GGS-dCas9-FLAG-NLS (using linker SEQ ID NO: 183) plasmid at sites flanking the AmpR gene by PCR with Esp3I-for-plasmid and Esp3I-rev-plasmid. The primers spec-Esp3I-for and spec-Esp3I-rev were used to amplify the SpecR marker as well as introduce Esp3I sites and Esp3I generated overhangs compatible with those generated by the Esp3I-cleaved plasmid PCR product. Golden gate assembly was performed on the two fragments following the protocol used to generate the reporter plasmids as described herein.

The pHU6-NT1 guide RNA expression vector was based on the previously described pFYF1328 (Fu et al., High-frequency off-target mutagenesis induced by CRISPR-Cas nucleases in human cells. Nature biotechnology 31, 822-826 (2013), the entire contents of which is hereby incorporated by reference) altered to target a region within the bacterial luciferase gene LuxAB. Guide RNA expression vectors were created by PCR amplification of the entire vector with a universal primer R.pHU6.TSS(-1).univ and primers encoding unique guide RNA sequences (Table 1). A list of the guide RNA sequences is given in Table 8. These primers were phosphorylated with T4 polynucleotide kinase. The PCR reaction products and linear guide RNA expression vectors were blunt-end ligated and transformed. Guide RNA expression vectors used in initial optimizations, off target control guide RNA sequences and those targeting Chromosome 10 locus contained AmpR. All other plasmids described in this study contained specR to facilitate sequencing experiments. Spectinomycin resistance was initially introduced into guide RNA expression vectors via CPEC essentially as described (Quan et al., Circular polymerase extension cloning of complex gene libraries and pathways. PloS one 4, e6441 (2009); and Hillson (2010), vol. 2015, pp. CPEC protocol; each of which is incorporated herein by reference) and guide RNA plasmids were then constructed by PCR amplification of the vector, as described above. Reactions were incubated overnight at 37° C. with 40 U of DpnI, purified and transformed. Fragments for CPEC were generated by PCR amplification of a guide RNA expression vector with oligonucleotides cpec-assembly-for-spec2 and cpec assembly-rev. The specR fragment was generated by PCR amplification of the SpecR gene via the oligonucleotides cpec-assembly-for-spec and cpec-assembly-rev-spec. pUC19 (ThermoFisher Scientific, Waltham, Mass.) was similarly modified.

TABLE 8

List of gRNA sequences

| gRNA name | gRNA-sequence | SEQ ID NO: |
|---|---|---|
| on-target_gRNA | ACCTCTGTTTGGGAAAATTG | 189 |
| non-target_gRNA | gCACACTAGTTAGGGATAACA | 190 |
| Chromosome_10-54913298-54913376_gRNA-rev-5 | gCCTCAGGGCCTGTGATGGGA | 191 |
| Chromosome_10-54913298-54913376_gRNA-rev-6 | gCTCAGGGCCTGTGATGGGAG | 192 |
| Chromosome_10-54913298-54913376_gRNA-for-5 | GGCCCATGACCCTTCTCCTC | 193 |
| Chromosome_10-54913298-54913376_gRNA-for-6 | GCCCATGACCCTTCTCCTCT | 194 |
| Centromere_Chromosomes_1_5_19-gRNA-for | GACTTGAAACACTCTTTTTC | 195 |
| Centromere_Chromosomes_1_5_19-gRNA-rev | gAGTTGAAGACACACAACACA | 196 |
| Chromosome_5_155183064-155183141_(site 1)_gRNA-for | GGAACTCATGTGATTAACTG | 197 |
| Chromosome_5_155183064-155183141_(site 1)_gRNA-rev | gTCTACCTCTCATGAGCCGGT | 198 |
| Chromosome_5_169395198-169395274_(site 2)_gRNA-for | gTTTCCCGCAGGATGTGGGAT | 199 |
| Chromosome_5_169395198-169395274_(site 2)_gRNA-rev | gCCTGGGGATTTATGTTCTTA | 200 |
| Chromosome_12_62418577-62418652_gRNA-for | gAAATAGCACAATGAATGGAA | 201 |
| Chromosome_12_62418577-62418652_gRNA-rev | gACTTTTTGGGGGAGAGGGAG | 202 |
| Chromosome_13_102010574-102010650_(FGF14)_gRNA-for | GGAGACTTAAGTCCAAAACC | 203 |
| Chromosome_13_102010574-102010650_(FGF14)_gRNA-rev | gTCAGCTATGATCACTTCCCT | 204 |
| Off target-for (CLTA) | GCAGATGTAGTGTTTCCACA | 205 |
| Off target-rev(VEGF) | GGGTGGGGGGAGTTTGCTCC | 206 |
| Chromosome_12_62098359-62098434_(FAM19A2)_gRNA-rev | gATATCCGTTTATCAGTGTCA | 207 |

TABLE 8-continued

List of gRNA sequences

| gRNA name | gRNA-sequence | SEQ ID NO: |
|---|---|---|
| Chromosome_12_62098359-62098434_(FAM19A2)_gRNA-for | gTTCCTAAGCTTGGGCTGCAG | 208 |
| Chromosome_12_62112591-62112668_(FAM19A2)_gRNA-rev | gCCTAAAAGTGACTGGGAGAA | 209 |
| Chromosome_12_62112591-62112668_(FAM19A2)_gRNA-for | gCACAGTCCCATATTTCTTGG | 210 |

Cell Culture and Transfection

HEK293T cells were purchased from the American Type Culture Collection (ATCC, Manassas, Va.). Cells were cultured in Dulbecco's modified Eagle's medium (DMEM)+GlutaMAX-I (4.5 g/L D glucose+110 mg/mL sodium pyruvate) supplemented with 10% fetal bovine serum (FBS, Life Technologies, Carlsbad, Calif.). Cells were cultured at 37° C. at 5% $CO_2$ in a humidified incubator.

Plasmid used for transfections were isolated from PureYield Plasmid Miniprep System (Promega, Madison, Wis.). The night before transfections, HEK293T cells were seeded at a density of $3\times10^5$ cells per well in 48 well collagen-treated plates (Corning, Corning, N.Y.). Transfections reactions were prepared in 25 µL of Opti-MEM (ThermoFisher Scientific, Waltham, Mass.). For each transfection, 45 ng of each guide RNA expression vector, 9 ng of reporter plasmid, 9 ng of piRFP670-N1 (Addgene Plasmid 45457), and 160 ng of recCas9 expression vector were mixed, combined with 0.8 µL lipofectamine 2000 in Opti-MEM (ThermoFisher Scientific, Waltham, Mass.) and added to individual wells.

Flow Cytometry

After 60-72 hours post-transfection, cells were washed with phosphate buffered saline and harvested with 50 µL of 0.05% trypsin-EDTA (Life Technologies, Carlsbad, Calif.) at 37° C. for 5-10 minutes. Cells were diluted in 250 µL culture media and run on a BD Fortessa analyzer. iRFP fluorescence was excited using a 635 nm laser and emission was collected using a 670/30 band pass filter. EGFP was excited using a 488 nM laser and emission fluorescence acquired with a 505 long pass and 530/30 band pass filters. Data was analyzed on FlowJo Software, gated for live and transfected events (expressing iRFP). Positive GFP-expressing cells were measured as a percentage of transfected cells gated from at least 6,000 live events. For optimization experiments, assay background was determined by measuring the percentage of transfected cells producing eGFP upon cotransfection with reporter plasmid and pUC, without recCas9 or guide RNA expression vectors. This background was then subtracted from percentage of eGFP-positive cells observed when the reporter plasmid was cotransfected with recCas9 and the on-target or non-target guide RNA expression vectors.

Identification of Genomic Target Sites

Searching for appropriate target sites was done using Bioconductor, an open-source bioinformatics package using the R statistical programming (Fu et al., High-frequency off-target mutagenesis induced by CRISPR-Cas nucleases in human cells. Nature biotechnology 31, 822-826 (2013), the entire contents of which is hereby incorporated by reference). The latest release (GRCh38) of the human reference genome published by the Genome Reference Consortium was used to search for sites that matched both the PAM requirement of Cas9 and the evolved gix sequence as described in the text. With the genome loaded into R, each search pattern was represented as a Biostring, a container in R that allowed for string matching and manipulation Scanning both strands of DNA for the entire genome, using the stated parameters, reveals approximately 450 potential targets in the human genome when searching using the GRCh38 reference assembly (Table 9).

TABLE 9 recCas9 genomic targets identified in silico

| Chr. | Start | End | Sequence | Pattern ID | SEQ ID NO: |
|---|---|---|---|---|---|
| chr1 | 34169027 | 34169103 | CCTTTAGTGAAAAGTAGACAGCTCTGAATATGAAAGGTAGGTTTTCATTTCTGGGAAAGAGACGCCAAGTGATGTGG | 2 | 211 |
| chr1 | 51006703 | 51006780 | CCTCCAATAAATATGGGACTATGTGGAAAGACCAAACCTACGTTTGATTGGTGTACCTGAAAGTGACGGGAAGAATGG | 1 | 212 |
| chr1 | 89229373 | 89229450 | CCATTCTGCCCGTCACTTTCAGGTACACCAATCAAACGTAGGTTTAGTCTTTTCACATAGTCCCATATTTCTTGGAGG | 1 | 213 |
| chr1 | 115638077 | 115638154 | CCATTCTCCCCGTCACTTTCAGGTACAACAATCAAACGTAGGTTTGGTCTTTTCACATAGTCCCATATTTCTTGGAGG | 1 | 214 |

TABLE 9-continued recCas9 genomic targets identified in silico

| Chr. | Start | End | Sequence | Pattern ID | SEQ ID NO: |
|---|---|---|---|---|---|
| chr1 | 122552402 | 122552478 | CCTTGTAGTGTGTGTATTCAACTCACAGAGT TAAACGATCCTTTACACAGAGCAGACTTGAA ACACTCTTGTTGTGG | 2 | 215 |
| chr1 | 122609874 | 122609950 | CCTTGTAGTGTGTGTATTCAACTCACAGAGT TAAACGATCCTTTACACAGAGCATACTTGAA ACACTCTTTTTGTGG | 2 | 216 |
| chr1 | 122668677 | 122668753 | CCTTGTGTTGTGTGTATTCAACTCACAGAGT TAAACGATCCTTTACACAGAGCAGACTTGAA ACACTCTTTTTGTGG | 2 | 217 |
| chr1 | 123422419 | 123422495 | CCTTGTGTTGTGTTTATTCAACTCACAGAGTT AAACGATCCTTTACACAGAGCAGACTTGAA ATACTCTTTTTGTGG | 2 | 218 |
| chr1 | 123648614 | 123648690 | CCTTGTAGTGTGTGTATTCAACTCACAGAGT TAAACGATCCTTTACACAGAGCATACTTGAA ACACTCTTTTTGTGG | 2 | 219 |
| chr1 | 123806335 | 123806411 | CCTTGTATTGTGAGTATTCAACTCACAGAGT TAAACGATCCTTTACACAGAGCAGACTTGAA ACACTCTTTTTGTGG | 2 | 220 |
| chr1 | 124078228 | 124078304 | CCTTGTGTTGTGTGTCTTCAACTCACAGAGTT AAACGATGCTTTACACAGAGTAGACTTGAA ACACTCTTTTTCTGG | 2 | 221 |
| chr1 | 124231074 | 124231150 | CCTTGTGTTGTGTGTATTCAACTCACAGAGT TAAACGATCCTTTACACAGAGCAGACTTGTA ACACTCTTTTTGTGG | 2 | 222 |
| chr1 | 124232435 | 124232511 | CCTTGTGTTGTGTGTATTCAACTCACAGAGT TAAACGATCCTTTACACAGAGCAGACGTGA AACACTCTTTTTGTGG | 2 | 223 |
| chr1 | 124344781 | 124344857 | CCTTGTGTTGTGTGTATTCAACTCACAGAGT TAAACGATCCTTTACACAGAGCAGACTTGAA ACACTCTTTTTGTGG | 2 | 224 |
| chr1 | 124435716 | 124435792 | CCTTGTGTTGTGTGTATTCAACTCACAGAGT TAAACGATCCTTTACACAGAGGAGACTTGTA ACACTCTTTTTGTGG | 2 | 225 |
| chr1 | 158677186 | 158677262 | CCTGAGGTTTTCCAGGTTTTAAAAGGAAACC TAAAGGTAGGTTTAGCATTAAGTGTCTTGAA GTTTATTTTAAAAGG | 2 | 226 |
| chr1 | 167629479 | 167629554 | CCAAAATTCCCACAAAACCGAATGCATCAGT CAAAGCAAGGTTTGAAGAAAAGATTTACCA CTTCAGGGAGCTTGG | 4 | 227 |
| chr1 | 167783428 | 167783504 | CCTTTTCTGGATATCGTTGATGCTCTGTATGC AAAAGGTAGGTTTTTGGGTTATGTTGTTAAA CAGTGATTGAATGG | 3 | 228 |
| chr1 | 169409367 | 169409444 | CCTCCAAGAAATATGGAACTATGTGAAAAG ACCAAACCTACGTTTGATTGGTGTACCTGAA AGTGACAGAGAGAATGG | 1 | 229 |
| chr1 | 174145346 | 174145423 | CCTCCAAGAAATATGGGACTATGTGAGAAG ACCAAACCTACGTTTGATTGGTGTACCTGAA AGTGATGGGGAGAATGG | 1 | 230 |
| chr1 | 183750168 | 183750245 | CCATTCTCCCCATCGCTTTCAGGTACACCAA TCAAACGTAGGTTTGGTCTTTTCACATAGTT CCATATTCTTTGGAGG | 1 | 231 |
| chr1 | 200801540 | 200801617 | CCATTCTCCCCATCACTTTCAGGTGTACCGA TCAAACGTAGGTTTGGTCTTTTCACATAGTC CCATATTTCTTGGAGG | 1 | 232 |
| chr1 | 207589936 | 207590013 | CCTCCAAGAAATATGGGACTATGTGAAAAG ACCAAACCTACGTTTGATTGGTGTACCTGAA AGTGACGGGGAGAATGG | 1 | 233 |

TABLE 9-continued recCas9 genomic targets identified in silico

| Chr. | Start | End | Sequence | Pattern ID | SEQ ID NO: |
|---|---|---|---|---|---|
| chr1 | 209768370 | 209768445 | CCTTCAGGGCAGAAACAGCTCTACTAGCAG AGAAAGCAAGCTTTCAATATTGTGCAATACA AAAACGAGAGCAGGG | 4 | 234 |
| chr1 | 218652378 | 218652455 | CCATTCTCCTCATCTCCTTCTGGTACTCCAAT CAAACGTAGGTTTGGTCTTTTCTCATAGTCTC ATATTTCTTGGAGG | 1 | 235 |
| chr1 | 222147250 | 222147327 | CCTCCAAGACATATAGGACTATGTGAAAATA CCAAACCTACGTTTGATTGGTGTACCTGAAA GTGACAGGGAGTATGG | 1 | 236 |
| chr1 | 245870710 | 245870785 | CCTGCCAGATACCAGTAGTCACTGTGAATTA CAAAGCTACGTTTCTTCCATAGGGAAAGTTT GGAGTCCAGCCAGG | 4 | 237 |
| chr2 | 2376037 | 2376114 | CCATTCTCCCTGTCACTTTCAGGTACACCAA TCAAACGTAGGTTTGGTCTTTTCACATAGTC CCATATTTCTTGGAGG | 1 | 238 |
| chr2 | 4119629 | 4119706 | CCATTCTCCCCACCACTTTCAGGTACACCAA TCAAACGTAGGTTTGGTCTTTTCACATAGTC CCATATTTCTTGTAGG | 1 | 239 |
| chr2 | 4909047 | 4909124 | CCTAACCAGAAACTAACTAATAGATATGGG CAGAAAGCATCCTTTCACTTTTGTTCTGGGA GAGGGAAGAAGCAAAGG | 1 | 240 |
| chr2 | 28984877 | 28984953 | CCATTTTGGGGAGGCCTTGATGGGAAGCTGG AAAAGGAAGCTTTCCTCCCAGTCCTGCTGAA GGCCTTGCCAGCTGG | 2 | 241 |
| chr2 | 31755833 | 31755910 | CCTCCAAGAAACACAGGACTATGTGAAAAG ATCAAACCTACGTTTGATTGGTGTTCCTGAA AGTGATGGGGAGAATGG | 1 | 242 |
| chr2 | 39829583 | 39829660 | CCATTCTCTTCATGACTTTCAGGTACACCATT GAAACGTAGGTTTGGTCTTTTCACATTGTCC CATATTTCTTGGAGG | 1 | 243 |
| chr2 | 60205947 | 60206024 | CCATTCTCCCCATCACTTTCAGGTACACCAA TCAAACGTAGGTTTGGTCTTTTCACATAGTC CCGTATTTCTTGGTGG | 1 | 244 |
| chr2 | 79082362 | 79082439 | CCATTCTCCCTGTCACTTTCAGGTACACCAA TCAAACGTAGGTTTGGTCTTTTCACATAGTC CCATATTTCTTGGGGG | 1 | 245 |
| chr2 | 79082362 | 79082438 | CCATTCTCCCTGTCACTTTCAGGTACACCAA TCAAACGTAGGTTTGGTCTTTTCACATAGTC CCATATTTCTTGGGG | 3 | 246 |
| chr2 | 108430915 | 108430992 | CCTCCAAGAAATATGAGATTATATGAAAAG ACCAAACCTACGTTTGATTGGTGTACTTTAA AGTGACGGGGAGAATGG | 1 | 247 |
| chr2 | 115893685 | 115893762 | CCATTCTCCCCGTCATTTTCAGGTACACCAA TCAAACGTAGGTTTGGTCTTTTCACATAGTC CCAAATTTCTTGGAGG | 1 | 248 |
| chr2 | 119620068 | 119620145 | CCCCCAAGAAATGTGGGACTATATGAAAAG ACCAAACCTACGTTTGACTGGTGTACCTAAA AGTGATGGGGAGAATGG | 1 | 249 |
| chr2 | 119620069 | 119620145 | CCCCAAGAAATGTGGGACTATATGAAAAGA CCAAACCTACGTTTGACTGGTGTACCTAAAA GTGATGGGGAGAATGG | 2 | 250 |
| chr2 | 128495068 | 128495144 | CCCATTGGTGCTGACCAGATGGTGAAGGAG GCAAAGGTTGCTTTGAATGACTGTGCTCTGG GGTGAGCCAGGCCTGG | 2 | 251 |
| chr2 | 133133559 | 133133634 | CCCTTTACAGAGGTGAGCTTTGTTATTAGTA AAAAGGTAGGTTTCCCTGTTTTTCTGAAGAA AAGCTGTGAGTGGG | 4 | 252 |

TABLE 9-continued recCas9 genomic targets identified in silico

| Chr. | Start | End | Sequence | Pattern ID | SEQ ID NO: |
|---|---|---|---|---|---|
| chr2 | 134174983 | 134175060 | CCACTGCCCATTGACAGAGTGGCGAGGTGG GTGAAACCTTGCTTTCCTCCTGGCCCATGGG CAGGGTGGGGCTGTGGG | 1 | 253 |
| chr2 | 134174983 | 134175059 | CCACTGCCCATTGACAGAGTGGCGAGGTGG GTGAAACCTTGCTTTCCTCCTGGCCCATGGG CAGGGTGGGGCTGTGG | 3 | 254 |
| chr2 | 138069945 | 138070022 | CCATTCTCCCTGTCACTTTTAGATACACCAAT CAAACGTAGGTTTGGTCTTTTCACATAGTCC CATGTTTCTTGGAGG | 1 | 255 |
| chr2 | 138797420 | 138797496 | CCTCCAAGAAATATCAACTGTGTGAAAAGA CGAAACCTACGTTTGATTAATGTACCTGAAA GTGACAGGGAGAATGG | 2 | 256 |
| chr2 | 145212434 | 145212511 | CCATTCTCCCATTAACTTTCAAGTACACCAA TCAAAGGTAGGTTTGGTGTTTTCCCATAGTC CCGTATTTCTTGGAGG | 1 | 257 |
| chr2 | 147837842 | 147837919 | CCTTTTCATCATGCCCCTTTCACTTTAAGGTG AAAACCTTGCTTTACATGTCAGAGAAAAGA AGAGCCCTCAGCTGGG | 1 | 258 |
| chr2 | 147837842 | 147837918 | CCTTTTCATCATGCCCCTTTCACTTTAAGGTG AAAACCTTGCTTTACATGTCAGAGAAAAGA AGAGCCCTCAGCTGG | 3 | 259 |
| chr2 | 154152540 | 154152617 | CCATTCACCCCGTCACTTTCAGGTACACCAA TCAAACGTAGGTTTGGTCTTTTCACATAGTC CCATATTTCTTGGAGG | 1 | 260 |
| chr2 | 157705943 | 157706019 | CCTCCAAGAAATATGGGACTATGTGAAAAG ACCAAACCTACGTTTGATGGTGTACCCGAAA GTGACAGGGAGAATGG | 3 | 261 |
| chr2 | 158361152 | 158361229 | CCACCAAGAAATATGGGACTATGTGAAAAG ACCAAACCTACGTTTGATAGGTATACCTGAA AGTGACAGGGAGAATGG | 1 | 262 |
| chr2 | 161461006 | 161461083 | CCATTCTCCCCATCACTTTCAGGTGCACCAA TCAAACGTAGGTTTGGTCTTTTCACATAGTC CCATATTTCTTGGAGG | 1 | 263 |
| chr2 | 179077376 | 179077453 | CCCTCAAGAAATATGAGACTATGTGAAAAG ACCAAACCTACGTTTGACTGGTATACCTGAA AGTGACAGGGAGAATGG | 1 | 264 |
| chr2 | 179077377 | 179077453 | CCTCAAGAAATATGAGACTATGTGAAAAGA CCAAACCTACGTTTGACTGGTATACCTGAAA GTGACAGGGAGAATGG | 2 | 265 |
| chr2 | 181090699 | 181090776 | CCTCCAACAAATATGGGACTATGTGAAAAG ACCAAACCTACGTTTGATTGGTGTACCTGAA AGTGACGGGGATAATGG | 1 | 266 |
| chr2 | 182331957 | 182332034 | CCATTCTCTCCCTCACTTTCAAGTACACCAAT CAAACGTAGGTTTGGTCTTTTCACATAGTCT TATATTTCTTGGCGG | 1 | 267 |
| chr2 | 183620562 | 183620638 | CCATTCTCCCTGTCACTGTCAGTACACCAAT CAAACGTAGGTTTGGTCTCTTCACATAGTCC CATATTTCTTGGAGG | 2 | 268 |
| chr2 | 207345927 | 207346003 | CCTCCAAGAAATATGGGACTATGTGAACAG ACCAAACCTACGTTTGATTGGTGTACCTGAA AGTGATGGCAGAATGG | 3 | 269 |
| chr2 | 216652047 | 216652123 | CCACCATGCCTGGCCACCACACATTTTTTTCT AAAGCTTGGTTTTGGCCACAGTGAGAGTTTC TTGGGCTGTCAGGG | 2 | 270 |
| chr2 | 216652047 | 216652122 | CCACCATGCCTGGCCACCACACATTTTTTTCT AAAGCTTGGTTTTGGCCACAGTGAGAGTTTC TTGGGCTGTCAGG | 4 | 271 |

TABLE 9-continued recCas9 genomic targets identified in silico

| Chr. | Start | End | Sequence | Pattern ID | SEQ ID NO: |
|---|---|---|---|---|---|
| chr2 | 223780040 | 223780116 | CCCACTAGGTGGCGATATCTGAGGGTCCAATGAAACCATGCTTTTTACTCAGATCTTCCACTAACCACCTCCCCCGG | 2 | 272 |
| chr2 | 224486595 | 224486672 | CCTCTAAGAAATATGGGACTATGTGAAAAGACCAAACCTACGTTTGACTGGTGTACCTGAAAGTGACGGGGAGAATGG | 1 | 273 |
| chr2 | 230526902 | 230526979 | CCTCCAAGAAATATGGGACTATGTGAAAAGACCAAACCTACGTTTGATTAGTGTACCTGAAAGTGACGGGGAGAATGG | 1 | 274 |
| chr2 | 232036127 | 232036204 | CCATTCTCCCTGTCACTTTCAGGTACATCAATCAAACGTAGGTTTGGTCTTTTCACATAGTCCCATATTTCTTGGAGG | 1 | 275 |
| chr3 | 4072812 | 4072889 | CCTCCAAGAAATATGGGACTATGTGAAAAGACCAAACCTACGTTTGACTGGTGTACCTGAAAGGGATGGGGAGAATGG | 1 | 276 |
| chr3 | 9261677 | 9261754 | CCCCCAAGAAATATGAGACTATGTGAAAAGACCAAACCTACGTTTGATTGGTGTACCTGAAAGTGACAGGGAGAATGG | 1 | 277 |
| chr3 | 9261678 | 9261754 | CCCCAAGAAATATGAGACTATGTGAAAAGACCAAACCTACGTTTGATTGGTGTACCTGAAAGTGACAGGGAGAATGG | 2 | 278 |
| chr3 | 16732146 | 16732223 | CCTCTAAGAAATATGGGACTATGTGAAAAGACCAAACCTACGTTTGATTGGTGTAACTGAAAGTGACAGGGAGAATGG | 1 | 279 |
| chr3 | 17450712 | 17450789 | CCTCCAAGAAATATGCGCCTATGTGAAAAGACCAAACCTACGTTTGATTGGTATACCTGAAAGTGATGGAGAGAATGG | 1 | 280 |
| chr3 | 21559769 | 21559846 | CCATTCTCCCTGTCACTTTGAGGTACACCAATCAAACGTAGGTTTGGTCTTTTCACATATTCGCATATTTCTTGGAGG | 1 | 281 |
| chr3 | 23416658 | 23416735 | CCATTCTCCCCGTCACTTTCAGGTACACCAACCAAACGTTGGTTTGGTCTTTTCACATAGTCCCATATTTCTTGGAGG | 1 | 282 |
| chr3 | 29984019 | 29984096 | CCATTCTCCCTGTCACTTTCCAGTACACCAGTCAAACGTAGGTTTGGTCTTTTCACATACTCCCATATTTCTTGGAGG | 1 | 283 |
| chr3 | 38269551 | 38269627 | CCTGGCCTAATTTTTAATTCTTAGTTTGACTTAAACCTTGCTTTTAGTGTGATGGCGACAAAAGCTGAGCTGAAAGG | 2 | 284 |
| chr3 | 40515213 | 40515288 | CCAGTGCTTTTTGGTTTTAAAGGCAAGCCTCCAAACCTTCCTTTCTCCTGGATGCTGTGGTGGTTGCCATGCATGG | 4 | 285 |
| chr3 | 49233612 | 49233687 | CCCAACTCCTGCGAGAAGTAGCTCACCATGACAAAGCTACCTTTGCTTTTATCGTTTTGCAAAACAAAAAAGGGGG | 4 | 286 |
| chr3 | 66292894 | 66292971 | CCATTCTCCCCGTCACTTTGAGGTGTGCCAATCAAACGTAGGTTTGGTCTTTTCACATAGTCCTATATTTCTTGGAGG | 1 | 287 |
| chr3 | 67541493 | 67541570 | CCTCCAAAAAATATGGGACTACGTAAAAAGACCAAACCTACGTTTGATTGGTGTACCTGAAACTGACAGGGAGAATGG | 1 | 288 |
| chr3 | 82273011 | 82273088 | CCATTCTCCCCGTCACTTTCAGGTACACCAATCAAACGTAGGTTTGGTCTTTTCACATAGTTCCATATTTCTTGGAGG | 1 | 289 |
| chr3 | 98683349 | 98683426 | CCTACAAGATATATGGGACTATGTGAAAAGACCAAACCTACGTTTTACTGGTGTGCCTGAAACTGACGGGGAGAATGG | 1 | 290 |

TABLE 9-continued recCas9 genomic targets identified in silico

| Chr. | Start | End | Sequence | Pattern ID | SEQ ID NO: |
|---|---|---|---|---|---|
| chr3 | 101923653 | 101923730 | CCATTCTCTCTGTCACTTTCAGGTACACCAATCAAACGTAGGTTTGGTCTTTTCACATAGTCCCATATTTCTTGGAGG | 1 | 291 |
| chr3 | 114533467 | 114533544 | CCTCCAAGAAATATGGGACTATGTGAAAAGACCAAACCTACGTTTCATTGGTGTACCTGAAAGTGATAGGGAGAATGG | 1 | 292 |
| chr3 | 132607602 | 132607679 | CCTCCAAAAAATATGGGATGATGTGAAAAGACCAAACCTAGGTTTGACTGGTGTACCTGAAAATGATGGGGAGAATGG | 1 | 293 |
| chr3 | 137545176 | 137545253 | CCTCCAAGAAATATGAGACTATGTGAAAAGACCAAACCTACGTTTGATTGGTGTACCTGAAAGTGACAGGGAGAATGG | 1 | 294 |
| chr3 | 137655679 | 137655756 | CCTCCAAGAAATATGGGACTACGTGAAAAGATCAAACCTACGTTTGATTGTTGTACCTGAAAGTGATGGGGAGAATGG | 1 | 295 |
| chr3 | 137662040 | 137662117 | CCTCCAAGAAATATGGGACTATGTGAAAAGACCAAACCTACGTTTGATTGTTGTACCTGAAAGTGATGGGGAGAATGG | 1 | 296 |
| chr3 | 142133796 | 142133873 | CCTCAAAAGTGTTCTGGTTTTGTTTTGTTTTTTAAACCATGGTTTTACCTCTGGCTTAGTGGGACTAAAAATAGGAGG | 1 | 297 |
| chr3 | 146726949 | 146727026 | CCTCCAAGAAATATGGGACTATGTGAAAAGACCAAACCTACGTTTGACTGGTGTACCTGAAAGTGATGGGGAAAATGG | 1 | 298 |
| chr3 | 152421096 | 152421173 | CCTCCAAGAAATATGGGACTGTGTGTAAAGACCAAACCTACGTTTGATTGGTGTACCTCAAAGTGATGGGGAGAATGG | 1 | 299 |
| chr3 | 170620247 | 170620324 | CCATTCTCCCCATCACATTCAGGTACACCAATCAAACGTAGGTTTGGTCTTTTCACATAGTCCCATATTTCTTGGAGG | 1 | 300 |
| chr3 | 181166873 | 181166949 | CCCCTGGAAAAGTTGGAGCATCACAGGAAAAGCAAACCAACCTTTTTTCTCCCCTAGGTAAACTGGGGAGCCAGGGG | 3 | 301 |
| chr3 | 181166874 | 181166949 | CCCTGGAAAAGTTGGAGCATCACAGGAAAAGCAAACCAACCTTTTTTCTCCCCTAGGTAAACTGGGGAGCCAGGGG | 4 | 302 |
| chr4 | 6604233 | 6604309 | CCTTCCCCAGTTGCAGCAGACAAGAGTCTCGAAAAGCTTGCTTTGGTTGCTGCAGTGGATGGGTTGGTAGGCACAGG | 2 | 303 |
| chr4 | 6626269 | 6626344 | CCCCCACCTCCCAAGCTGCTGGCTTCTCGAATAAAGCTACCTTTCCTTTTACCAAAACTTGTCTCTCGAATGTCGG | 4 | 304 |
| chr4 | 8155396 | 8155472 | CCTTGGCCCTGGACAGCTGCTTTTCCTTCCCTAAACCTTGGTTTCCCCCTTTGTGCAGGTGGGTGGGTTTGGGCTGG | 2 | 305 |
| chr4 | 10386803 | 10386880 | CCTCTTCTAGTGAACCCATGGGGTTACCAAGGGAAAGCAACCTTTTGATAAATATTCCCATCTTTTTATGTTGTCTGG | 1 | 306 |
| chr4 | 20701579 | 20701656 | CCACTTGAAAGGGTTACCAAGGATAAGATTTTTAAAGCTTGCTTTCACAAACAACTCATGCTCCAGGCTTGTCAGTGG | 1 | 307 |
| chr4 | 29594286 | 29594363 | CCTTTCTCCCCATCACTTTCAGGTACACCAATCAAACGTAGGTTTGATCTTTTCACATAGTCCCATATTTCTTGGAGG | 1 | 308 |
| chr4 | 53668422 | 53668499 | CCATTCTCCCCATCAATTTCAGTTACACCAATGAAACGTAGGTTTGGCCTTTTCACATAGTCCCATATTTCTTAGAGG | 1 | 309 |

TABLE 9-continued recCas9 genomic targets identified in silico

| Chr. | Start | End | Sequence | Pattern ID | SEQ ID NO: |
|---|---|---|---|---|---|
| chr4 | 74914802 | 74914879 | CCATTCTCCCTGTCACTCTCAGGTACACCAA TCAAACGTAGGTTTGGTCTTTTCATATAGTC CCATATTTCTTGGAGG | 1 | 310 |
| chr4 | 75332783 | 75332859 | CCTCCAAGAAAATTGGGACTATGTGAAAAA ACCAAACCTACGTTTGATTGATGTACCTGAA AGTGACAGGAGAATGG | 3 | 311 |
| chr4 | 88123643 | 88123720 | CCTTCAAGAAATATGGGACTATGTGAAAGG ACAAAACCTACGTTTTATTGGTGTACCTGAA AGTGACAGGGAGAATGG | 1 | 312 |
| chr4 | 89567192 | 89567269 | CCATTCTCCCCATCACTTTCAGGTACGCTAA TCAAACGTAGGTTTGATCTTTTCACATAGTC TTATATTTCTTGGAGG | 1 | 313 |
| chr4 | 93556577 | 93556654 | CCTCCAAGAAATATGGGACTATGTGAAAAG ACCAAACCTACGTTTGACTGGTGTACCTCAA TGTGACAGGGAGAATGG | 1 | 314 |
| chr4 | 100266379 | 100266456 | CCATTCTCCCTGTCACTTTTAGGTACACCAAT CAAACGTACGTTTGGTCTTTTCACATAGACC CATATTTCTTGGAGG | 1 | 315 |
| chr4 | 103486234 | 103486311 | CCTTCAAGAAATATGGGACTGTGTGAAAAG ACCAAAGCTAGGTTTGATTGGTGTACCTGAA AGTGATGGGGAGAATGG | 1 | 316 |
| chr4 | 105923129 | 105923204 | CCTACTATTCACAGAGTAATGCAGTTTGCTG AAAAGGTTGGTTTTTGCTGACCTCTGAGAGC TCACATTACAGTGG | 4 | 317 |
| chr4 | 106874711 | 106874788 | CCATTCTCTCTGTCACTTTCTGGTACACCAAT CAAACGTAGGTTTGCTCTTTTCACATAATCC CATATTTATTGAAGG | 1 | 318 |
| chr4 | 115805791 | 115805867 | CCATAACATGTATTTGCTGGTGCTAGACTCT CCAAAGCTAGGTTTCTTTCTACAACAATGGC TGGAAGTCTTCTTGG | 3 | 319 |
| chr4 | 122033277 | 122033354 | CCATTCTCCCCATCACTTTCAGGTACACCAA TCAAACGTAGGTTTGGTCTTCTCACACAGTC CCATATTTCTTGGAGG | 1 | 320 |
| chr4 | 129125132 | 129125209 | CCATTCTTCCCATTACTTTCAGGTACACCAAT CAAACGTAGGTTTGGTCTTTTCACATAGTCC CACATTTCTTGGAGG | 1 | 321 |
| chr4 | 135472562 | 135472639 | CCATTCTCCCCCTCACTTTCAGGTACACCAA TCAAACGTAGGTTTGGTCTTTTCACATTGTCC CATATTTCTTGGAGG | 1 | 322 |
| chr4 | 138507099 | 138507176 | CCATTCTCCCCAGCACTTACAGGTACACCAA TCAAACGTAGGTTTGGTCATTTCACATAGTC CCATATTTCTTGGAGG | 1 | 323 |
| chr4 | 144249093 | 144249170 | CCATTCTCCCTGTCACTTTCAGGTACAGCAA TCAAACGTAGGTTTGGTCTTTTCACATGGTC CCATATTTCTTGGAGG | 1 | 324 |
| chr4 | 144436406 | 144436483 | CCTCCAAGAAATATGAGACTATGTGAAAAG ACCAAACCTACGTTTGATTGGTGTACCTGAA AGTGACGGGGAAGATGG | 1 | 325 |
| chr4 | 154110259 | 154110336 | CCTCCAAGAAATATGAGACTATGTGAAAAG ACCAAACCTACGTTTGATTGGTGTACCTGAA AGTGACAGGGAGAATGG | 1 | 326 |
| chr4 | 154893438 | 154893515 | CCTCCAAGAGATATGAGACTATGTAAATAG ACCAAACCTACCTTTGATTGGTGTACGTGAA AGTGACAGGAAGAATGG | 1 | 327 |
| chr4 | 161116854 | 161116931 | CCATTCTCCCCATCACTTTCAGGTACACCAA CCAAACGTAGGTTTGGTCTTTTCACATAGTC TCATATTTCTTGGAGG | 1 | 328 |

TABLE 9-continued recCas9 genomic targets identified in silico

| Chr. | Start | End | Sequence | Pattern ID | SEQ ID NO: |
|---|---|---|---|---|---|
| chr4 | 165140748 | 165140823 | CCTCCATTGACTACTCCTTATCATTGGCTAG AAAACCTACCTTTCAACCAGTTTCTAAGGCC AAGAAACTTGGAGG | 4 | 329 |
| chr4 | 181928508 | 181928585 | CCACCAAGAAATATGGGACTACGTGAAAAG ACCAAACCTACGTTTGATGGGTGTGCCTGAA AGTGACGGGAAGAATGG | 1 | 330 |
| chr4 | 187521958 | 187522035 | CCTCCAAGAAATAAGGGACTATGTGAAAAG ACCAAACCTACGTTTGATTGGTGTACCTGAA GGTGACAGGGAGAATGG | 1 | 331 |
| chr5 | 12675639 | 12675715 | CCAAAGGGCCTTTGTGATTCTACTTTGTAAT ATAAAGGATGGTTTCTTACTACGGTTGGTGT CCTTGCAGGAGTGGG | 3 | 332 |
| chr5 | 29271804 | 29271881 | CCTCCAAGAAATATGGGACTATGTGAAAAG ACCAAACCTACGTTTGATTGGTGTACCTGAA AGTGATGGGGAGAATGG | 1 | 333 |
| chr5 | 35352660 | 35352737 | CCATTCTCCCCGTTACTTTCAGGTACACCAA TAAAACCTAGGTTTGGTCTTTTCACATAGTC CCATATTTCTTGGAGG | 1 | 334 |
| chr5 | 38723235 | 38723310 | CCCATATCTCTGGCAAGGGCAGCTCTCTGGC TAAACCAAGCTTTCCTGTAGAGCTTGAGTTC CAAGGCAGCGTTGG | 4 | 335 |
| chr5 | 47358339 | 47358415 | CCTTGTAGTGTGTGTATTCAACTCACAGAGT TAAACGATCCTTTACACAGAGCAGACTTGAA ACACTCTTGTTGTGG | 2 | 336 |
| chr5 | 47415811 | 47415887 | CCTTGTAGTGTGTGTATTCAACTCACAGAGT TAAACGATCCTTTACACAGAGCATACTTGAA ACACTCTTTTTGTGG | 2 | 337 |
| chr5 | 47474614 | 47474690 | CCTTGTGTTGTGTGTATTCAACTCACAGAGT TAAACGATCCTTTACACAGAGCAGACTTGAA ACACTCTTTTTGTGG | 2 | 338 |
| chr5 | 48228356 | 48228432 | CCTTGTGTTGTGTTTATTCAACTCACAGAGTT AAACGATCCTTTACACAGAGCAGACTTGAA ATACTCTTTTTGTGG | 2 | 339 |
| chr5 | 48454551 | 48454627 | CCTTGTAGTGTGTGTATTCAACTCACAGAGT TAAACGATCCTTTACACAGAGCATACTTGAA ACACTCTTTTTGTGG | 2 | 340 |
| chr5 | 48612272 | 48612348 | CCTTGTATTGTGAGTATTCAACTCACAGAGT TAAACGATCCTTTACACAGAGCAGACTTGAA ACACTCTTTTTGTGG | 2 | 341 |
| chr5 | 48884165 | 48884241 | CCTTGTGTTGTGTGTCTTCAACTCACAGAGTT AAACGATGCTTTACACAGAGTAGACTTGAA ACACTCTTTTTCTGG | 2 | 342 |
| chr5 | 49037011 | 49037087 | CCTTGTGTTGTGTGTATTCAACTCACAGAGT TAAACGATCCTTTACACAGAGCAGACTTGTA ACACTCTTTTTGTGG | 2 | 343 |
| chr5 | 49038372 | 49038448 | CCTTGTGTTGTGTGTATTCAACTCACAGAGT TAAACGATCCTTTACACAGAGCAGACGTGA AACACTCTTTTTGTGG | 2 | 344 |
| chr5 | 49150718 | 49150794 | CCTTGTGTTGTGTGTATTCAACTCACAGAGT TAAACGATCCTTTACACAGAGCAGACTTGAA ACACTCTTTTTGTGG | 2 | 345 |
| chr5 | 49241653 | 49241729 | CCTTGTGTTGTGTGTATTCAACTCACAGAGT TAAACGATCCTTTACACAGAGGAGACTTGTA ACACTCTTTTTGTGG | 2 | 346 |
| chr5 | 88582714 | 88582790 | CCTTTTCATAAGAAGAAAATCGACTCATCAT TGAAACCAAGCTTTGGTACAATTTCATTGAT GTTTCCAGAAGCAGG | 3 | 347 |

TABLE 9-continued recCas9 genomic targets identified in silico

| Chr. | Start | End | Sequence | Pattern ID | SEQ ID NO: |
|---|---|---|---|---|---|
| chr5 | 93497156 | 93497231 | CCCATAGACTATGATAGAAACAAAATAACC CAAAAGCTAGCTTTCTGATTGAGTTTCCATA AATGCAATGTGAAGG | 4 | 348 |
| chr5 | 94295029 | 94295105 | CCATTCACTTGTCACTTTCTGGTACACCAATC AAACGTAGGTTTGGTCTTTTCACATAGTCTC ATATTTCTTGGAGG | 2 | 349 |
| chr5 | 94956746 | 94956823 | CCTCCAAGAAATATGGGACTCTGTAAAGAG ACCAAACCTACGTTTGATTGGTGTACCTGAA AGTGAAGGGGAGAATGG | 1 | 350 |
| chr5 | 106003488 | 106003565 | CCATTCTCCCCGTCATTTTCAGGTACACCAA TCAAACCTAGGTTTGGTCTTTTTACATAGTCC CATATTTCTTGGAGG | 1 | 351 |
| chr5 | 118727905 | 118727982 | CCTCCACGAAACATGGGACTATGTGAAAAG ACCAAACCTACGTTTGATTGGTGTACCTGAA AGTGACAGGGAGAATGG | 1 | 352 |
| chr5 | 132156032 | 132156109 | CCAATTTCCCCCTCACTTTCAGATACACCAA TCAAACGTAGGTTTGGTCTTTTCACATAGTT CCATATTTCCTGGAGG | 1 | 353 |
| chr5 | 152037951 | 152038028 | CCATTCTCCCCATCACTTTCAGGTACACCAA TCAAACGTAGGTTTGGTCTTTTCACATATTCC CATATGTCTTGGAGG | 1 | 354 |
| chr5 | 155183064 | 155183141 | CCCACCGGCTCATGAGAGGTAGAGCTAAGG TCCAAACCTAGGTTTATCTGAGACCGGAACT CATGTGATTAACTGTGG | 1 | 355 |
| chr5 | 155183065 | 155183141 | CCACCGGCTCATGAGAGGTAGAGCTAAGGT CCAAACCTAGGTTTATCTGAGACCGGAACTC ATGTGATTAACTGTGG | 2 | 356 |
| chr5 | 163148211 | 163148288 | CCTTCAAGAAATATGGGACTATGTGAAGAG ACCAAACCTACGTTTGATTGGTGTAGCCAAA AGTGATGGGGAAAATGG | 1 | 357 |
| chr5 | 165889537 | 165889614 | CCTCAGATTAGATTTACTTGCAAAGAGACAT TTAAAGGATCGTTTTGATACTATTTTGAAAG TACTATACAAAGATGG | 1 | 358 |
| chr5 | 169395198 | 169395274 | CCTTAAGAACATAAATCCCCAGGAATTCACA GAAACCTTGGTTTGAGCTTTGGATTTCCCGC AGGATGTGGGATAGG | 2 | 359 |
| chr5 | 171021380 | 171021457 | CCATTCTCTCTGTCACTTTCAGGTACACCAAT CAAACGTAGGTTTGGTCTTTTCTCATAGTCC CATATTTCTTGGAGG | 1 | 360 |
| chr5 | 173059898 | 173059973 | CCATTTACCATCATTCTCTGTCATGGCAGGT GAAAGCAAGCTTTTATATAGACAATGTTCTA CTTAGTTTACAGGG | 4 | 361 |
| chr5 | 174102359 | 174102435 | CCCAAAGTTAATTTTACTCTTTTTCTGAATCA AAAGGAACCTTTCCTCCATGAGAAGAATCCT GCCATATTTCTAGG | 2 | 362 |
| chr5 | 180927811 | 180927888 | CCTCCAAGAAATATGGGACTATGTGAAAAG ACCAAACCTACGTTTGATTGCTATACATGAA AGTGACGGGGAGAATGG | 1 | 363 |
| chr6 | 1752363 | 1752440 | CCTTCAAGAAATATGGGACTATGTGAAAAG ACCAAACCTACCTTTGATTGGTGTACCTGAA AGTGATGGGAAGAATGG | 1 | 364 |
| chr6 | 20595279 | 20595356 | CCATTCTCCCCATCACTTTCAGGTACACCAA TCAAACGTAGGTTTGGTCTTTTCACATAGTC CCATAGTTCTTGGAGG | 1 | 365 |
| chr6 | 23431370 | 23431447 | CCATTCTCCCCGTCACTTTCAGGGACAACAA TCAAACGTAGGTTTGGCCTTTGCACATAGTC TTATATTTCTTGGAGG | 1 | 366 |

TABLE 9-continued

| recCas9 genomic targets identified in silico | | | | | |
|---|---|---|---|---|---|
| Chr. | Start | End | Sequence | Pattern ID | SEQ ID NO: |
| chr6 | 29190624 | 29190701 | CCATTCTCCCCATCACTTTCAGGTACACCAA TCAAACGTAGGTTTGGTCTTTTCACATAGTC CCATATTTCTTGGAGG | 1 | 367 |
| chr6 | 61533266 | 61533343 | CCTCCAAAAAATATGGGACTATGTGAGAAG ACCAAACCTACGTTTTATTAGTGTACCTCAA AGTGACAGGGAGGATGG | 1 | 368 |
| chr6 | 101052764 | 101052841 | CCATTCTCCCCATCACTTTCAGGTACACCAA TGAAACGTAGGTTTGGCCTTTTCACATAGTT TCATATTTCTTGGAGG | 1 | 369 |
| chr6 | 117176355 | 117176432 | CCTCCAAGAAATATGGGACTATGTGAAAAG ACCAAACCTACGTTTGATTGGTGTACCTGAA AGTGATGGGGAGAATGG | 1 | 370 |
| chr6 | 117747073 | 117747149 | CCTACAAGAAATATGGAACTTGTAAAAAGA CCAAACCTACGTTTGATTGGTGTACCTGAAA GTGACGGGGAGAATGG | 2 | 371 |
| chr6 | 118422508 | 118422585 | CCTCCAAGAAATATGGGACAATGTGAAAAG GCCAAAGCTACGTTTGATTGGTGTACCTGAA AGTGACAGGGAGAATGG | 1 | 372 |
| chr6 | 122035019 | 122035096 | CCTTTCAAACTTAGAGGTAAACAAAAGTCCT GAAAACCTAGGTTTGACCATAAGTTGGGACC ATACGAGCATAGAAGG | 1 | 373 |
| chr6 | 134445210 | 134445287 | CCAAAAATAAAAAAAAATTGACTTATAAGT AAGAAAGGTTCGTTTTCTCACATTCAGAAAG AGAACCCACATGTTGGG | 1 | 374 |
| chr6 | 134445210 | 134445286 | CCAAAAATAAAAAAAAATTGACTTATAAGT AAGAAAGGTTCGTTTTCTCACATTCAGAAAG AGAACCCACATGTTGG | 3 | 375 |
| chr6 | 135154944 | 135155021 | CCATTCTCCCCATCACTTTCAGGTACACCAA TCAAACGTAGGTTTGGTCTTTTCACATAGTC CCATATTTCTTGGAGG | 1 | 376 |
| chr6 | 137889995 | 137890072 | CCATTCTCCCCGTCACTTTCAGGTACACCAA TCAAACGTTGGTTTAGTCTATTCACATAGTC CCATATTTCTTGGAGG | 1 | 377 |
| chr6 | 143993904 | 143993981 | CCGAAAAGAATAAGACTATCAGCTGAAGTC TTAAAACGATCCTTTGGCCCCCAGTACTCTA TATGCAGGATAGAAAGG | 1 | 378 |
| chr6 | 152610473 | 152610549 | CCTACAAAAATAGGGGACTATGTGATAAGA CCAAACCTACGTTTGATTGGTGTACCTGAAA GTGATGGGGAGAATGG | 2 | 379 |
| chr6 | 160372604 | 160372681 | CCATTCTACCCATCACTTTCAGGTACACCAA TCAAACGTAGGTTTGGCCTTTTCATATAGTC TCATATTTCTTGGAGG | 1 | 380 |
| chr6 | 169352478 | 169352555 | CCATTCTCCCCATCACTTTCTGGTATACCAAT CAAACGTAGGTTTGGTCTTTTCACATAGTCC CATATTTCTTAGAGG | 1 | 381 |
| chr6_GL000251v2_alt | 677196 | 677273 | CCATTCTCCCCATCACTTTCAGGTACACCAA TCAAACGTAGGTTTGGTCTTTTCACATAGTC CCATATTTCTTGGAGG | 1 | 382 |
| chr6_GL000252v2_alt | 456242 | 456319 | CCATTCTCCCCATCACTTTCAGGTACACCAA TCAAACGTAGGTTTGGTCTTTTCACATAGTC CCATATTTCTTGGAGG | 1 | 383 |
| chr6_GL000253v2_alt | 456279 | 456202 | CCATTCTCCCCATCACTTTCAGGTACACCAA TCAAACGTAGGTTTGGTCTTTTCACATAGTC CCATATTTCTTGGAGG | 1 | 384 |
| chr6_GL000254v2_alt | 456371 | 456448 | CCATTCTCCCCATCACTTTCAGGTACACCAA TCAAACGTAGGTTTGGTCTTTTCACATAGTC CCATATTTCTTGGAGG | 1 | 385 |

TABLE 9-continued recCas9 genomic targets identified in silico

| Chr. | Start | End | Sequence | Pattern ID | SEQ ID NO: |
|---|---|---|---|---|---|
| chr6_GL000255v2_alt | 456225 | 456302 | CCATTCTCCCCATCACTTTCAGGTACACCAA TCAAACGTAGGTTTGGTCTTTTCACATAGTC CCATATTTCTTGGAGG | 1 | 386 |
| chr6_GL000256v2_alt | 500011 | 500088 | CCATTCTCCCCATCACTTTCAGGTACACCAA TCAAACGTAGGTTTGGTCTTTTCACATAGTC CCATATTTCTTGGAGG | 1 | 387 |
| chr7 | 5256551 | 5256627 | CCACCACACCCAGCCTTATGGGATGGTTTTC AAAAGCATCCTTTTTTAGAAGTGGATTCTGA TATATAATCGGATGG | 2 | 388 |
| chr7 | 7392583 | 7392660 | CCATTCTCAATGTCACTTTCAGGTACACCAA TCAAACGTAGGTTTGGTCTTTTCACATAGTC CCATATTTCTTGGAGG | 1 | 389 |
| chr7 | 8737741 | 8737818 | CCATTCTCTCTGTCACTTTCAGGTACACCAGT CAAAGGTAGGTTTGTTTTATTCACACGTTCA CATATTTCTTGGAGG | 1 | 390 |
| chr7 | 11352226 | 11352303 | CCATTCGCCCCATCACTTTCAGGTACACTAG TAAAACGTAGGTTTGGTCTTTTCACATAGTT CCATATTTCTTGGAGG | 1 | 391 |
| chr7 | 15519145 | 15519222 | CCTCCAAGAAATATGGGACTATGTGAAGAG ATCAAACCTAGGTTTGATTGTTGTACCTGAA AGTGATAAGAAGAATGG | 1 | 392 |
| chr7 | 19228341 | 19228418 | CCTCCAATAAATATGGGGCTATGTGAAAAG ACCAAACCTACGTTTGATTGGTGTACCTGAA AGTGACAGGGAGAATGG | 1 | 393 |
| chr7 | 23778445 | 23778522 | CCCTTTTCCCTGTCACTTTCAGGTACACCAGT CAAACGTAGGTTTGGTCTTTTCACATAGTCG AATATTTCTTCAAGG | 1 | 394 |
| chr7 | 23778446 | 23778522 | CCTTTTCCCTGTCACTTTCAGGTACACCAGTC AAACGTAGGTTTGGTCTTTTCACATAGTCGA ATATTTCTTCAAGG | 2 | 395 |
| chr7 | 26769065 | 26769142 | CCATTCTCCCTGTCACTTTCAGGTACACTAAT CAAACGTAGGTTTGGTGTATTCACACAGTCC CATATTTCTTGGAGG | 1 | 396 |
| chr7 | 42864035 | 42864112 | CCATTCTTCCTGTCACTTTCAGGTATACCAAT CAAACGTAGGTTTGGTCTTTTCACATAGTCC CATGTTTCTTGGAGG | 1 | 397 |
| chr7 | 46498923 | 46499000 | CCTCCAAGAAATATGAGACTATATGAAAAT ACCAAACCTACGTTTGATTGGTGTACCTGAA AGAGACAGGGAGAATGG | 1 | 398 |
| chr7 | 51535360 | 51535437 | CCATTCTCCCTATCACTTTCAGGTACACCAA TCAAACGTAGGTTTGGTCTTTTCATGTAGTC CCATATTTCTTGGAGG | 1 | 399 |
| chr7 | 51927106 | 51927183 | CCATTCTGCCCGTCACTTTCAGGTACACCAA TCAAACGTAGGTTTGGTCTTTTCACATAGTC CCATATTTCTTGGAGG | 1 | 400 |
| chr7 | 56976942 | 56977018 | CCGTCCGATTATATATCAGAATCTACTTCTA AAAAAGGATGCTTTTGAAAACCATCCCATAA GGCTGGGTGTGGTGG | 3 | 401 |
| chr7 | 80021598 | 80021675 | CCTACAAGGAATATAGGACTATGTGAAAAT ACCAAACCTACGTTTCACTGCTGTACCTGAA GGTGACAGGGAGAATGG | 1 | 402 |
| chr7 | 89673853 | 89673930 | CCATTCTCCCCATCATTTCCAGGTAAACCAA TCAAAGGTAGGTTTGGTCATTTCACATAGTC CCATATTTCTTGGAGG | 1 | 403 |
| chr7 | 103404790 | 103404867 | CCATTCTCCCCGTCACTTTCAGGTACACCAG TCAAACGTAGGTTTGGTCTTTTCACACAGTC CCATATTTCCTGGAGG | 1 | 404 |

TABLE 9-continued recCas9 genomic targets identified in silico

| Chr. | Start | End | Sequence | Pattern ID | SEQ ID NO: |
|---|---|---|---|---|---|
| chr7 | 113053651 | 113053728 | CCATTCTCCCCATCACTTTCAGGTACAGCAA TCAAACGTAGGTTTGGTCTTTTCACATAGTC CCATATTTCTTGGAGG | 1 | 405 |
| chr7 | 125765204 | 125765279 | CCACTACAGATTCTTGGGTCAAGATGTGTGC AAAAGGATGCTTTAGGGTGATGGATATGAG TGGGATGAAATGAGG | 4 | 406 |
| chr7 | 128042158 | 128042234 | CCTGAAAAAAAACCCTGCCAGCCAGCAACT CTGAAAGGATGCTTTGTGTGAGTGAGCAGTG TCTGAGATGGACAGGG | 3 | 407 |
| chr7 | 130637332 | 130637409 | CCATTCTCCCCATCACTTTCAGGTACGCCAA TCAAACGTAGGTTTGGTCTTTTGACATAGTC CCATATTTCTTGGAGG | 1 | 408 |
| chr7 | 136983050 | 136983127 | CCGTTCTCCCCATCACTTTTAGGTACACCAA TCAAACGTAGGTTTGGTCTTTTCACATAGTC TCATATTTCTTGGAGG | 1 | 409 |
| chr7 | 143579507 | 143579584 | CCATTCTCCTGGTCACTTTCAGGTATACCAA TCAAACGTAGGTTTGGTCTTTTCATGTAGTC CCATATTTCTTGGAGG | 1 | 410 |
| chr7 | 143749881 | 143749958 | CCTCCAAGAAATATGGGACTACATGAAAAG ACCAAACCTACGTTTGATTGGTATACCTGAA AGTGACCAGGAGAATGG | 1 | 411 |
| chr8 | 2338364 | 2338441 | CCTCCAAGAACTATGGGACTATGTGAAAAG ACCAAACCTACGTTTGATTGGTGTACCTGAA AGTGACGGGGAGAATGG | 1 | 412 |
| chr8 | 2383289 | 2383366 | CCATTCTCCCCGTCACTTTCAGGTACACCAA TCAAACGTAGGTTTGGTCTTTTCACATAGTC CCATAGTTCTTGGAGG | 1 | 413 |
| chr8 | 8414568 | 8414645 | CCATTCTCCCCGTCACTTTCAGGTACACCAA TCAAACGTAGGTTTGGTCTTTTCACAGAGTC CCATATTTCTTGGAGG | 1 | 414 |
| chr8 | 24163142 | 24163219 | CCATTCTCCCCGTCACTTTCATGTACACCAA GCAAACGTAGGTTTGATCTTTCCACATAGTC CCGTGTTTCTTGGAGG | 1 | 415 |
| chr8 | 34299051 | 34299128 | CCTCCAAGAAATATGGGACTATGTGAAAAG ACCAAACCTACGTTTGATTGGTGTACTTGAA AGTGACAGGGAGAATGG | 1 | 416 |
| chr8 | 40965485 | 40965562 | CCTCCAAGAAATATGGGACTATGTGAAAAG ACAAAACCTACGTTTCACTGGTGTACCTGAA AGTGACAGGGAGGATGG | 1 | 417 |
| chr8 | 48371659 | 48371735 | CCCCCACCTTTTAAAAACATGCATACATACG GAAACGTTGCTTTCTGCACGATTTCATTTTA ATGGAACAGAACAGG | 2 | 418 |
| chr8 | 82534960 | 82535037 | CCATTTCCCCTGTCACTTTCAGGTACACCAA TCAAACGTAGGTTTGGTCTTTTCACATAGTA TCATATTTCTTGGAGG | 1 | 419 |
| chr8 | 109217624 | 109217700 | CCATTCTCCCCGTCACTTTCAGGTACACCAA TCAAACGTAGGTTTGGTCTTTTCACATAGTC CCATATTTCTGGAGG | 3 | 420 |
| chr8 | 134790285 | 134790361 | CCTTTTGTTAAAGTAATAGAATTCTGCTTCTT AAAGGAACCTTTCAGGCAAGATGGTGGTTA GAGCACCTAAATGGG | 2 | 421 |
| chr8 | 134790285 | 134790360 | CCTTTTGTTAAAGTAATAGAATTCTGCTTCTT AAAGGAACCTTTCAGGCAAGATGGTGGTTA GAGCACCTAAATGG | 4 | 422 |
| chr8_KI270821v1_alt | 519635 | 519712 | CCTCCAAGAACTATGGGACTATGTGAAAAG ACCAAACCTACGTTTGATTGGTGTACCTGAA AGTGACGGGGAGAATGG | 1 | 423 |

TABLE 9-continued recCas9 genomic targets identified in silico

| Chr. | Start | End | Sequence | Pattern ID | SEQ ID NO: |
|---|---|---|---|---|---|
| chr8_KI270821v1_alt | 564557 | 564634 | CCATTCTCCCCGTCACTTTCAGGTACACCAATCAAACGTAGGTTTGGCCTTTTCACATAGTCCCATAGTTCTTGGAGG | 1 | 424 |
| chr9 | 14951207 | 14951283 | CCTCCAAGAAATATGGGACTGGTGAAAAGACCAAACCTACGTTTGACTGGTGTACCTGAAAGTGACGGGGAGACTGG | 2 | 425 |
| chr9 | 23249218 | 23249295 | CCTCCAAGAAACATGGGAATGTGTGAAAAGACCAAACCTACGTTTGATTGGCGTACCTGAAAGTGACGGGGAGTATGG | 1 | 426 |
| chr9 | 26278896 | 26278973 | CCTCCAAGAAATATGGGACTGTGTGAAAAGACCAAACCTACGTTTGATTGGTATACCTGAAAGTGACAGAGAGAATGG | 1 | 427 |
| chr9 | 27323237 | 27323314 | CCATTCTCCCCTTCACTATCAGGTACACCAATCAAACGTAGGTTTAGTCTTTTCACATAGTCCCATATTTCTTGGAGG | 1 | 428 |
| chr9 | 31517993 | 31518070 | CCATTCTCCCCGTCACTTTCAGATACACCAGTCAAACGTAGGTTTGGTCTTTTCACATAGTCCCATATTTCTTGGAGG | 1 | 429 |
| chr9 | 39694860 | 39694937 | CCATCTTACTTTGTACTACACTGTTCTTTAGAGAAAGCTTCCTTTTGGAGACCAACCAGGACTCCTTAGAAGCAGAGG | 1 | 430 |
| chr9 | 42451132 | 42451209 | CCATCTTACTTTGTACTACACTGTTCTTTAGAGAAAGCTTCCTTTTGGAGACCAACCAGGACTCCTTAGAAGCAGAGG | 1 | 431 |
| chr9 | 60776573 | 60776650 | CCTCTGCTTCTAAGGAGTCCTGGTTGGTCTCCAAAAGGAAGCTTTCTCTAAAGAACAGTGTAGTACAAAGTAAGATGG | 1 | 432 |
| chr9 | 62647482 | 62647559 | CCTCTGCTTCTAAGGAGTCCTGGTTGGTCTCCAAAAGGAAGCTTTCTCTAAAGAACAGTGTAGTACAAAGTAAGATGG | 1 | 433 |
| chr9 | 66682030 | 66682107 | CCTCTGCTTCTAAGGAGTCCTGGTTGGTCTCCAAAAGGAAGCTTTCTCTAAAGAACAGTGTAGTACAAAGTAAGATGG | 1 | 434 |
| chr9 | 82264427 | 82264503 | CCACCACTGTGCCTGGCCATTTTCACTATTCTTAAAGGAAGCTTTGGTTTACAAAGGTTTGCTACTGTACTTCCAGG | 3 | 435 |
| chr9 | 84042684 | 84042761 | CCATTCTCCCTGTCACTTTCAGGTACACCATTCAAACGTAGGTTTGGTCTTTTCTCATAGTCCCATATTTCTTGGAGG | 1 | 436 |
| chr9 | 95256012 | 95256089 | CCTCCAAGAAATTCGGGACTATGTGAAAAGACAAAACCTACGTTTAATTGGTGTGTGGTGTACCTGAAAGTGACAAGG | 1 | 437 |
| chr9 | 101816988 | 101817065 | CCTCCAAGAAATATGGGACTATGTGAAAAGACCAAACCTACGTTTGATTGGTGTACCTGAAAGTGACCAGAAGAATGG | 1 | 438 |
| chr9 | 135842327 | 135842403 | CCTCCAAGAAATATGGGACTATGTGAAAAGCCCAAACCTACGTTTGACTGATGTACCTAAAGTGACGGGGAGAATGG | 3 | 439 |
| chr9 | 136910865 | 136910940 | CCCGCACTGTGAGCTTGGCCGAGTGCTGTCTGAAAGCATCCTTTCCCTTCACCTGGAGACTGGAGCGCCATAGAGG | 4 | 440 |
| chr10 | 13710312 | 13710389 | CCTGTCTCCCCCATTCCATGCAAAATAAAACACAAACCAAGCTTTGCTTTAAGTGCTCCCTGATGCAGTTCAGCGTGG | 1 | 441 |
| chr10 | 18938129 | 18938206 | CCATTCTTCCCGTCACATTCAGGTACACCAATCAAACGTAGGTTTGGTCTTTTCCCATAGTCCCATATTTCTTAGAGG | 1 | 442 |

TABLE 9-continued

| recCas9 genomic targets identified in silico | | | | | |
|---|---|---|---|---|---|
| Chr. | Start | End | Sequence | Pattern ID | SEQ ID NO: |
| chr10 | 22712838 | 22712914 | CCCCCTGCTCAGCTTGGGGAAGAAAAATAC AAAAACGATGCTTTTAGGCATTTTAAACAAC TTCACTACATTGAGGG | 2 | 443 |
| chr10 | 22712838 | 22712913 | CCCCCTGCTCAGCTTGGGGAAGAAAAATAC AAAAACGATGCTTTTAGGCATTTTAAACAAC TTCACTACATTGAGG | 4 | 444 |
| chr10 | 40160932 | 40161009 | CCTTTGTGTTGTGTGTATTCAACTCACAGAG TGAAACCTTCCTTTATTCAGAGCAGTTTTGA AACACTCTTTTTGTGG | 1 | 445 |
| chr10 | 40390136 | 40390213 | CCTTTGTGTTGTGTGTATTCAACTCACAGAG TGAAACCTTCCTTTATTCAGAGCAGTTTTGA AAAACACTTTTTGTGG | 1 | 446 |
| chr10 | 40409152 | 40409229 | CCTTTGTGTTGTGTGTATTCAACTCACAGAG TGAAACCTTCCTTTATTCAGAGCAGTTTTGA AAAACTCTTTTTGTGG | 1 | 447 |
| chr10 | 40433940 | 40434017 | CCTTTGTGTTGTGTGTATTCAACTCACAGAG TGAAACCTTCCTTTATTCAGAGCAGTTTTGA AACACTCTTTTTGTGG | 1 | 448 |
| chr10 | 40588155 | 40588232 | CCTTTGTGTTGTGTGTATTCAACTCACAGAG TGAAACCTTCCTTTATTCAGAGCAGTTTTGA AATACTCTTTTTGTGG | 1 | 449 |
| chr10 | 41146207 | 41146284 | CCTTTGTGTTGTGTGTATTCAACTCACAGAG TGAAACCTTCCTTTATTCAGAGCAGTTTTGA AACACTCTTTTTGTGG | 1 | 450 |
| chr10 | 43835183 | 43835260 | CCATTCTCCCTGTCACTTTCAAGTACACCAA TCAAACCTAGGTTTGGTCTTTTCACATAGTTC CATATTTCTTGGAGG | 1 | 451 |
| chr10 | 54913222 | 54913299 | CCCCTCCCATCACAGGCCCTGAGGTTTAAGA GAAAACCATGGTTTTGTGGGCCAGGCCCATG ACCCTTCTCCTCTGGG | 1 | 452 |
| chr10 | 54913222 | 54913298 | CCCCTCCCATCACAGGCCCTGAGGTTTAAGA GAAAACCATGGTTTTGTGGGCCAGGCCCATG ACCCTTCTCCTCTGG | 3 | 453 |
| chr10 | 54913223 | 54913299 | CCCTCCCATCACAGGCCCTGAGGTTTAAGAG AAAACCATGGTTTTGTGGGCCAGGCCCATGA CCCTTCTCCTCTGGG | 2 | 454 |
| chr10 | 54913223 | 54913298 | CCCTCCCATCACAGGCCCTGAGGTTTAAGAG AAAACCATGGTTTTGTGGGCCAGGCCCATGA CCCTTCTCCTCTGG | 4 | 455 |
| chr10 | 58035951 | 58036028 | CCATTCTCCCCATCACTTTCAGGTACACCAA TCAAACGTAGGTTTCATCTTTTCACATAGTC CCACGGTTTTTGGAGG | 1 | 456 |
| chr10 | 58677525 | 58677602 | CCTCCAAGATATATGGGACTATGTGAAAAG ACCAAACCTACGTTTGATTGGTGTACCTGAA ATTGATGGGGAGAATGG | 1 | 457 |
| chr10 | 84021390 | 84021467 | CCTCCAAGAAATATGGGACTGTGTGAAAAG AACAAACCTACGTTTGATTGGTGTACGTGAA AGTGATGGGGAGAATGG | 1 | 458 |
| chr10 | 91442692 | 91442769 | CCATTCCTCCCGTCACTTTCAGATACACCAA AAAAACGTAGGTTTGGTCTCTTCACATAGTC CCACATTTCTTGGAGG | 1 | 459 |
| chr10 | 91446848 | 91446925 | CCTCCAAGAAATGTGGGACTATGTGAAGAG ACCAAACCTACGTTTTTTTGGTGTATCTGAA AGTGACGGGAGGAATGG | 1 | 460 |
| chr10 | 116928784 | 116928860 | CCTCCAAGGGGAATCTGAGTTCTCTGAAGAC AAAAAGCATGGTTTCTTTTCTTCTGTATTTCT TATTGTTTCCTAGG | 3 | 461 |

TABLE 9-continued recCas9 genomic targets identified in silico

| Chr. | Start | End | Sequence | Pattern ID | SEQ ID NO: |
|---|---|---|---|---|---|
| chr10 | 116937771 | 116937848 | CCATTCTCCCTATCACTTTCCAGTACACCAATCAAACGTAGGTTTGGTCTTTTCACATAGTCCCATATTTCTTGGAGG | 1 | 462 |
| chr11 | 31182070 | 31182147 | CCTCCAAGAAATATGGGACTATGTGAAAAGACCAAACCTACGTTTGATTGGTATACTTGAAATTGACAAGGAGAATGG | 1 | 463 |
| chr11 | 34739273 | 34739350 | CCTCCAAGAAATATGGGACTATGTGGAAAGACCAAACCTACGTTTGACTGGTGTACCTGAAAGTGATGGGGAGAATGG | 1 | 464 |
| chr11 | 86646529 | 86646606 | CCTCTAAGAAATATGGGACTATGTGAAGAGATGAAACCTACGTTTGATTGGTGTACCTGAAAGTGACGAGGAGAATGG | 1 | 465 |
| chr11 | 90469791 | 90469867 | CCCTCGTATACTACATGCTATAGTCAAAGCAGTAAACCTTCCTTTCCTTAAGCAGACCACACTCTTTCATGCCTGGG | 3 | 466 |
| chr11 | 90469792 | 90469867 | CCTCGTATACTACATGCTATAGTCAAAGCAGTAAACCTTCCTTTCCTTAAGCAGACCACACTCTTTCATGCCTGGG | 4 | 467 |
| chr11 | 92429985 | 92430062 | CCATTCTCCCCATCACTTTCAGGTATACTAATCAAAGGTAGGTTTGGTCTTTTCACATAGTCCCATATTTCATGGAGG | 1 | 468 |
| chr11 | 102818498 | 102818574 | CCATTCCCCCGTCACTTTCAGGTACACCAATCAAACGTAGGTTTGGTCTTTTCACATAGTCCCATATTTCTTGGAGG | 2 | 469 |
| chr11 | 120765065 | 120765142 | CCATTCTCCCCGTCACTTTCAGGTACACCAATCAAACGTAGGTTTTGTCTTTTCTTATAGTCCCATATTTCTTGGAGG | 1 | 470 |
| chr11 | 123131901 | 123131978 | CCACTGCACCTGACCAAGATCCTTAATTTTTCTAAACCTACGTTTATCATCTATAAAATGAGCCATCTTTTCACATGG | 1 | 471 |
| chr11 | 129468520 | 129468597 | CCTCCGAGAAATATGGGACTATGTGAAAAGACCAAACCTACGTTTGATTGTTGTACCTGAAAGTGACAGGGAGAATGG | 1 | 472 |
| chr11 | 131272361 | 131272438 | CCATTCTCCCCATCACTTTTAGGTACACCAATCAAACGTAGGTTTGGTCCTTTTGCATAGACCCATATTTCTTGGAGG | 1 | 473 |
| chr11 | 132761415 | 132761492 | CCATTTTCCCCGTCAGTTTCATATACACCTATCAAACGTAGGTTTACTGTTTTCACATAGTCCCTTATTTCTTGGAGG | 1 | 474 |
| chr12 | 22367416 | 22367493 | CCTCCAAGAAATATGGGACTATGTGAAAAGACCAAACCTACCTTTGATTGGTGTACCTGAAAGTGACGGGCAGGATGG | 1 | 475 |
| chr12 | 33146384 | 33146461 | CCATTCTTCTCGTCATTTTCAAGTACACCAATCAAACGTAGGTTTGGTCTTTTCGCATAGTCCCATATTTCTTGGAGG | 1 | 476 |
| chr12 | 33198476 | 33198553 | CCATTCTTCTCGTCACTTTCAAGTACACCAATCAAACGTAGGTTTGGTCTTTTCACATAGTCCCATATTTCTTGGAGG | 1 | 477 |
| chr12 | 46038332 | 46038409 | CCTCCAAGAAATATAGGACTATGTGAAAAGACCAAACCTACGTTTGATTGGTGTACTTGAAAGTGACAGGGAGAATGG | 1 | 478 |
| chr12 | 60236126 | 60236203 | CCTCCAAGAAATGTGGAACTATGTGAAAAGACCAAACCTACGTTTGATTGGTGTACCTGAAAGTGACAGGGAGAATGG | 1 | 479 |
| chr12 | 62098359 | 62098434 | CCCTGACACTGATAAACGGATATGAAGAGAAAAAAGCTAGGTTTTCGCTGGAATTCCTAAGCTTGGGCTGCAGTGG | 4 | 480 |

TABLE 9-continued recCas9 genomic targets identified in silico

| Chr. | Start | End | Sequence | Pattern ID | SEQ ID NO: |
|---|---|---|---|---|---|
| chr12 | 62112591 | 62112668 | CCCTTCTCCCAGTCACTTTTAGGTACACCAATGAAACGTAGGTTTGGTCTTTTCACACAGTCCCATATTTCTTGGAGG | 1 | 481 |
| chr12 | 62112592 | 62112668 | CCTTCTCCCAGTCACTTTTAGGTACACCAATGAAACGTAGGTTTGGTCTTTTCACACAGTCCCATATTTCTTGGAGG | 2 | 482 |
| chr12 | 62418577 | 62418652 | CCACTCCCTCTCCCCCAAAAAGTAAAGGTAGAAAACCAAGGTTTACAGGCAACAAATAGCACAATGAATGGAATGG | 4 | 483 |
| chr12 | 71732311 | 71732388 | CCAAACCCGCATCGCACACCCTGTGAGGGGGACAAAGGAACCTTTCCGTTCCAACATCAAGGTTGTTTTGACCCAAGG | 1 | 484 |
| chr12 | 78047816 | 78047893 | CCATTCTTTCTGTCACTTTCAGGTATACCAGTCAAACCTAGGTTTGGTCTTTTCACATAGTCCCATATTTCTTGGAGG | 1 | 485 |
| chr12 | 81480016 | 81480093 | CCATTCTCCCCATCACTTTCAGGTACACCAATCAAACGTAGGTTTGGTCTTTTCACATAGTCCCATATTTCTTGGAGG | 1 | 486 |
| chr12 | 96840231 | 96840307 | CCACACGGTAGAGGATAAACTAGGTGGATTCTCAAAGCAACCTTTGAAATAATCTATGCAGTTTTTCTGGGTACTGG | 3 | 487 |
| chr12 | 99187165 | 99187242 | CCACCAAGAAACATGGGACTATGTGAAAAGACCAAACCTACGTTTGGTTGGTGTACCTGGAAGTGACGGGGAGAGTGG | 1 | 488 |
| chr12 | 107860841 | 107860918 | CCTCCAAGAAATATGGGACCATGTGAAAAGACCAAACCTACGTTTGATTGGTGTACCTGAAAGTGACAGGGAGAATGG | 1 | 489 |
| chr12 | 110882809 | 110882885 | CCTGTAAAAAGGTCACATGGTCAGGTGTGCCTAAACGATCCTTTTATTTATTTATTTATTTATTTTTAAGAAACAGG | 2 | 490 |
| chr12 | 119063321 | 119063397 | CCAGCCCCAAAATGTCAGGGGCTTAGAACAACAAAGGTTCCTTTTCATGTTTATACTACATGTTTGTCATGGGCTGG | 2 | 491 |
| chr13 | 35320704 | 35320781 | CCGTTTTCCCCATCACTTTCAGGTACACCAGTCAAACGTAGGTTTGGTCTTTTCACATGGTCCCACATTTCTTGGAGG | 1 | 492 |
| chr13 | 53133477 | 53133554 | CCTGGAATAGCTTTCCTGACTGTCTGACTTCAAAAACCTTGGTTTGACCACTTCGTCTATATCATGAGGAAGGACTGG | 1 | 493 |
| chr13 | 53184880 | 53184956 | CCCTACTCTGAACCTACCTTGATAAAGCCTAGAAAACCAAGCTTTGACAAGATTTGACAAGAGATGGAATTTGGAGG | 3 | 494 |
| chr13 | 53184881 | 53184956 | CCTACTCTGAACCTACCTTGATAAAGCCTAGAAAACCAAGCTTTGACAAGATTTGACAAGAGATGGAATTTGGAGG | 4 | 495 |
| chr13 | 57896962 | 57897038 | CCCTTATAAAACTGAAAACTTTAACCTTTTTTAAAGCATGCTTTTGAATAAATTCTTTTATTACAAAAAAGACCAGG | 2 | 496 |
| chr13 | 62610100 | 62610177 | CCATTCTCCCTGTCACTTTCAGGTACACCAATCAAACGTAGGTTTGGTCTTTTCACGTAGTCCCATATTTCTTGGAGG | 1 | 497 |
| chr13 | 77004382 | 77004458 | CCCTTTATTATCCAAGTGGTTTCCTGCTCTTCAAACCTTCCTTTCAAAATTTTGTCTCCTACTTAAAACAAGTTAGG | 2 | 498 |
| chr13 | 81646075 | 81646151 | CCTTCTGTTGAGACCTACTGCTAAGAAAACAAAAAAGGTTCCTTTCAAATATTATTGTGAATCAATAATGTACCTGG | 3 | 499 |

TABLE 9-continued recCas9 genomic targets identified in silico

| Chr. | Start | End | Sequence | Pattern ID | SEQ ID NO: |
|---|---|---|---|---|---|
| chr13 | 83755854 | 83755931 | CCTCCAAGAAATATGGGACTATGTGAAAAG ACCAAACCTACGTTTCATTGATGGACCTGAA AGTGATGGGGAGAATGG | 1 | 500 |
| chr13 | 89719199 | 89719275 | CCATTCTCCCTTCACTTTCAGTTACACCAATC AAACGTAGGTTTGGTCTTTTCACATAGTCCC ATATTTCTTGGAGG | 2 | 501 |
| chr13 | 102010574 | 102010650 | CCTAGGGAAGTGATCATAGCTGAGTTTCTGG AAAAACCTAGGTTTTAAAGTTGAGGAGACTT AAGTCCAAAACCTGG | 3 | 502 |
| chr13_KI270841v1_alt | 124240 | 124316 | CCATTCTCCCTTCACTTTCAGTTACACCAATC AAACGTAGGTTTGGTCTTTTCACATAGTCCC ATATTTCTTGGAGG | 2 | 503 |
| chr14 | 25980646 | 25980723 | CCTCCAAGAAATATGGGACTATGTGAAAAG ACTAAACCTACGTTTGATTGGTGTACCTGAA AGTGACAGGGAGAATGG | 1 | 504 |
| chr14 | 35842786 | 35842863 | CCATTCTCCCTGTCACTTTCAGGTATGCCAGT CAAACGTAGGTTTGGTCTTTTCACATAGTCC CATATTCCTTGGAGG | 1 | 505 |
| chr14 | 42646400 | 42646477 | CCTCCAAGAAATATGGGACTATGTAAAAAG ACGAAACCTACGTTTGATTGGTGTACTTAAA AGTGACGAGGAGAATGG | 1 | 506 |
| chr14 | 49063242 | 49063319 | CCTCCAAGAAATATGGGACTATGTGAAAAG ACCAAACCTACGTTTGATTTGTGTACCTGAA AGTGATGGGGAGAATGG | 1 | 507 |
| chr14 | 49130379 | 49130456 | CCATTCTCCCCGTCACTTTCAGGCACACCAA TCAAACGTAGGTTTAGTCTTTTCACATAGTC CCATATTTCTTAGAGG | 1 | 508 |
| chr14 | 51352342 | 51352418 | CCTTAATGCATTCATATTTCATATTTTAAATA AAACCATGGTTTCCCACAGAGTGACTTCTAC TCTAAGAAATGGGG | 2 | 509 |
| chr14 | 51352342 | 51352417 | CCTTAATGCATTCATATTTCATATTTTAAATA AAACCATGGTTTCCCACAGAGTGACTTCTAC TCTAAGAAATGGG | 4 | 510 |
| chr14 | 60835842 | 60835919 | CCGTTCTTTCCGTCACTTTCAGGTACACCAGT CAAACGTAGGTTTGGTCTTTTCACATAGTCC CATATTTCTTGGAGG | 1 | 511 |
| chr14 | 66529072 | 66529148 | CCATTCTCCCCATCACTTTCATGTACACCAAT CAAACGTAGGTTTGGTCTTTGTTAACATAGT CCCATATTTCTTGG | 3 | 512 |
| chr14 | 79210873 | 79210949 | CCCTATAAAGCTTAGAGAAACACAGGGCTCT TTAAACGATCCTTTTTCTCTTTTCTGTTTTAA ATTTCATCACTTGG | 3 | 513 |
| chr14 | 79210874 | 79210949 | CCTATAAAGCTTAGAGAAACACAGGGCTCTT TAAACGATCCTTTTTCTCTTTTCTGTTTTAAA TTTCATCACTTGG | 4 | 514 |
| chr14 | 85371541 | 85371618 | CCATTCTCCCCATCACTTTCAGGTACACTAA TCAAAGGTAGGTTTGGTCTTTTCACATGGTC CTATATTTCTTGGAGG | 1 | 515 |
| chr14 | 92918713 | 92918790 | CCCCATAGCACGATCACATGGGACATTCAGG GGAAAGCAACCTTTTCCAGGAAGGAAAACC CAATGCTGGGACCCAGG | 1 | 516 |
| chr14 | 92918714 | 92918790 | CCCATAGCACGATCACATGGGACATTCAGG GGAAAGCAACCTTTTCCAGGAAGGAAAACC CAATGCTGGGACCCAGG | 2 | 517 |
| chr14 | 103386821 | 103386897 | CCCTTTCAGCGCTCACAGGCTATGGTTTTAT AAAAGGAACCTTTGATTTTGTTCATGTGAAA CTACAAAATGCCAGG | 2 | 518 |

TABLE 9-continued recCas9 genomic targets identified in silico

| Chr. | Start | End | Sequence | Pattern ID | SEQ ID NO: |
|---|---|---|---|---|---|
| chr14_KI270847v1_alt | 33275 | 33352 | CCCCATAGCACGATCACATGGGACATTCAGG GGAAAGCAACCTTTTCCAGGAAGGAAAACC CAATGCTGGGACCCAGG | 1 | 519 |
| chr14_KI270847v1_alt | 33276 | 33352 | CCCATAGCACGATCACATGGGACATTCAGG GGAAAGCAACCTTTTCCAGGAAGGAAAACC CAATGCTGGGACCCAGG | 2 | 520 |
| chr15 | 20630566 | 20630643 | CCTCCAAGAAATATTGGAGTATGTGATAAGA CCAAACCTTCGTTTGACTGGTGTACCTGAAA GTGATGGGGAGAATGG | 1 | 521 |
| chr15 | 21675103 | 21675180 | CCATTCTCCCCGTCACTTTCAGGTACACCAA TCAAACGTAGGTTTGGTCTTTTCACATAGTC CCATATTTCTTGGAGG | 1 | 522 |
| chr15 | 22117571 | 22117648 | CCATTCTCCCCGTCACTTTCAGGTACACCAA TCAAACGTAGGTTTGGTCTTTTCACATAGTC CCATATTTCTTGGAGG | 1 | 523 |
| chr15 | 22369744 | 22369821 | CCATTCTCCCCATCACTTTCAGGTACACCAG TCAAACGAAGGTTTGGTCTTATCACATACTC CAATATTTCTTGGAGG | 1 | 524 |
| chr15 | 42302832 | 42302909 | CCTCCAAGATATATGGGACTATGTGAAAAG GCCAAACCTACCTTTGATTGATACACCTGAA AATGACAGGGAGAATGG | 1 | 525 |
| chr15 | 49967601 | 49967678 | CCTCCAAGAAATATGCGACTATGTGAAAAG ACCAAACCTACGTTTCATTGGTGTACCTGAA AGTGATGGGGAGAATGG | 1 | 526 |
| chr15 | 83964501 | 83964577 | CCTCCAAGAAATATGGGACTATGTGGAAAG ACCAAACCTACGTTTGTTTGGTGTACCTGAA AGTGAGGGGAGAATGG | 3 | 527 |
| chr15 | 87261388 | 87261465 | CCATTCTCCTCATCACTTTCAAGTACACCAA TCAAACGTAGGTTTGGTCTTTTCACATAGTC TTATATTTCTTGGAGG | 1 | 528 |
| chr15_KI270727v1_random | 409348 | 409425 | CCATTCTCCCCGTCACTTTCAGGTACACCAA TCAAACGTAGGTTTGGTCTTTTCACATAGTC CCATATTTCTTGGAGG | 1 | 529 |
| chr15_KI270851v1_alt | 14235 | 14312 | CCATTCTCCCCATCACTTTCAGGTACACCAG TCAAACGAAGGTTTGGTCTTATCACATACTC CAATATTTCTTGGAGG | 1 | 530 |
| chr15_KI270852v1_alt | 440099 | 440176 | CCATTCTCCCCGTCACTTTCAGGTACACCAA TCAAACGTAGGTTTGGTCTTTTCACATAGTC CCATATTTCTTGGAGG | 1 | 531 |
| chr16 | 22123671 | 22123748 | CCAGCAGAAGAATCTGGGGCACAGTCTGTG AAAAAAGGTACCTTTCTTAAGCAGGGTTCTT ATCCTTCATGGGTCTGG | 1 | 532 |
| chr16 | 25557623 | 25557700 | CCTCCAAGAAATATGGGACTATGTGAAAAG ACCAAACCTACGTTTGATTGTTGTACCTGAA AGTGAGGGGGAGAATGG | 1 | 533 |
| chr16 | 36427179 | 36427255 | CCTTGTGTTGTGTGTATTCAACTCACAGAGT TAAACGATCCTTTACACAGAGCAGATTTGAA ACACTGTTTTTCTGG | 2 | 534 |
| chr16 | 36476450 | 36476526 | CCTTGTGTTGTGTGTATTCAACTCACAGAGT TAAACGATCCTTTACACAGAGCAGATTTGAA ACACTGTTTTTCTGG | 2 | 535 |
| chr16 | 36512469 | 36512545 | CCTTGTGTTGTGTGTATTCAACTCACAGAGT TAAACGATCCTTTACACAGAGCAGATTTGAA ACACTGTTTTTCTGG | 2 | 536 |
| chr16 | 36520964 | 36521040 | CCTTGTGTTGTGTGTATTCAACTCACAGAGT TAAACGATCCTTTACACACAGCAGATTTGAA ACACTGTTTTTCTGG | 2 | 537 |

TABLE 9-continued

| recCas9 genomic targets identified in silico | | | | | |
|---|---|---|---|---|---|
| Chr. | Start | End | Sequence | Pattern ID | SEQ ID NO: |
| chr16 | 36524704 | 36524780 | CCTTGTGTTGTGTGTATTCAACTCACAGAGT TAAACGATCCTTTACACAGAGCAGATTTGAA ACACTGTTTTTCTGG | 2 | 538 |
| chr16 | 36566812 | 36566888 | CCTTGTGTTGTGTGTATTCAACTCACAGAGT TAAACGATCCTTTACACAGAGCAGATTTGAA ACACTGTTTTTCTGG | 2 | 539 |
| chr16 | 36573603 | 36573679 | CCTTGTGTTGTGTGTATTCAACTCACAGAGT TAAACGATCCTTTACACAGAGCAGATTTGAA ACACTGTTTTTCTGG | 2 | 540 |
| chr16 | 36667694 | 36667770 | CCTTGTGTTGTGTGTATTCAACTCACAGAGT TAAACGATCCTTTACACAGAGCAGATTTGAA ACACTGTTTTTCTGG | 2 | 541 |
| chr16 | 36677320 | 36677396 | CCTTGTGTTGTGTGTATTCAACTCACAGAGT TAAACGATCCTTTACACAGAGCAGATTTGAA ACACTGTTTTTCTGG | 2 | 542 |
| chr16 | 36683096 | 36683172 | CCTTGTGTTGTGTGTATTCAACTCACAGAGT TAAACGATCCTTTACACAGAGCAGATTTGAA ACACTGTTTTTCTGG | 2 | 543 |
| chr16 | 36691251 | 36691327 | CCTTGTGTTGTGTGTATTCAACTCACAGAGT TAAACGATCCTTTACACAGAGCAGATTTGAA ACACTGTTTTTCTGG | 2 | 544 |
| chr16 | 36710951 | 36711027 | CCTTGTGTTGTGTGTATTCAACTCACAGAGT TAAACGATCCTTTACACAGAGCAGATTTGAA ACACTGTTTTTCTGG | 2 | 545 |
| chr16 | 36750364 | 36750440 | CCTTGTGTTGTGTGTATTCAACTCACAGAGT TAAACGATCCTTTACACAGAGCAGATTTGAA ACACTGTTTTTCTGG | 2 | 546 |
| chr16 | 36791455 | 36791531 | CCTTGTGTTGTGTGTATTCAACTCACAGAGT TAAACGATCCTTTACACACAGCAGATTTGAA ACACTGTTTTTCTGG | 2 | 547 |
| chr16 | 36856683 | 36856759 | CCTTGTGTTGTGTGTATTCAACTCACAGAGT TAAACGATCCTTTACACAGAGCAGATTTGAA ACACTGTTTTTCTGG | 2 | 548 |
| chr16 | 36926655 | 36926731 | CCTTGTGTTGTGTGTATTCAACTCACAGAGT TAAACGATCCTTTACACAGAGCAGATTTGAA ACACTGTTTTTCTGG | 2 | 549 |
| chr16 | 36931752 | 36931828 | CCTTGTGTTGTGTGTATTCAACTCACAGAGT TAAACGATCCTTTACACAGAGCAGATTTGAA ACACTGTTTTTCTGG | 2 | 550 |
| chr16 | 36948058 | 36948134 | CCTTGTGTTGTGTGTATTCAACTCACCGAGTT AAACGATCCTTTACACAGAGCAGATTTGAAA CACTGTTTTTCTGG | 2 | 551 |
| chr16 | 36974541 | 36974617 | CCTTGTGTTGTGTGTATTCAACTCACAGAGT TAAACGATCCTTTACACAGAGCAGATTTGAA ACACTGTTTTTCTGG | 2 | 552 |
| chr16 | 36981331 | 36981407 | CCTTGTGTTGTGTGTATTCAACTCACAGAGT TAAACGATCCTTTACACAGAGCAGATTTGAA ACACTGTTTTTCTGG | 2 | 553 |
| chr16 | 36990839 | 36990915 | CCTTGTGTTGTGTGTATTCAACTCACAGAGT TAAACGATCCTTTACACAGAGCAGATTTGAA ACACTGTTTTTCTGG | 2 | 554 |
| chr16 | 37021075 | 37021151 | CCTTGTGTTGTGTGTATTCAACTCACAGAGT TAAACGATCCTTTACACAGAGCAGATTTGAA ACACTGTTTTTCTGG | 2 | 555 |
| chr16 | 37042812 | 37042888 | CCTTGTGTTGTGTGTATTCAACTCACAGAGT TAAACGATCCTTTACACAGAGCAGATTTGAA ACACTGTTTTTCTGG | 2 | 556 |

TABLE 9-continued recCas9 genomic targets identified in silico

| Chr. | Start | End | Sequence | Pattern ID | SEQ ID NO: |
|---|---|---|---|---|---|
| chr16 | 37085971 | 37086047 | CCTTGTGTTGTGTGTATTCAACTCACAGAGT TAAACGATCCTTTACACAGAGCAGATTTGAA ACACTGTTTTTCTGG | 2 | 557 |
| chr16 | 37129462 | 37129538 | CCTTGTGTTGTGTGTATTCAACTCACAGAGT TAAACGATCCTTTACACAGAGCAGATTTGAA ACACTGTTTTTCTGG | 2 | 558 |
| chr16 | 37146110 | 37146186 | CCTTGTGTTGTGTGTATTCAACTCACAGAGT TAAACGATCCTTTACACACAGCAGATTTGAA ACACTGTTTTTCTGG | 2 | 559 |
| chr16 | 37157309 | 37157385 | CCTTGTGTTGTGTGTATTCAACTCACAGAGT TAAACGATCCTTTACACAGAGCAGATTTGAA ACACTGTTTTTCTGG | 2 | 560 |
| chr16 | 37183118 | 37183194 | CCTTGTGTTGTGTGTATTCAACTCACAGAGT TAAACGATCCTTTACACAGAGCAGATTTGAA ACACTGTTTTTCTGG | 2 | 561 |
| chr16 | 37190924 | 37191000 | CCTTGTGTTGTGTGTATTCAACTCACAGAGT TAAACGATCCTTTACACAGAGCAGATTTGAA ACACTGTTTTTCTGG | 2 | 562 |
| chr16 | 37221808 | 37221884 | CCTTGTGTTGTGTGTATTCAACTCACAGAGT TAAACGATCCTTTACACAGAGCAGATTTGAA ACACTGTTTTTCTGG | 2 | 563 |
| chr16 | 37259501 | 37259577 | CCTTGTGTTGTGTGTATTCAACTCACAGAGT TAAACGATCCTTTACACAGAGCAGATTTGAA ACACTGTTTTTCTGG | 2 | 564 |
| chr16 | 37272409 | 37272485 | CCTTGTGTTGTGTGTATTCAACTCACAGAGT TAAACGATCCTTTACACAGAGCAGATTTGAA ACACTGTTTTTCTGG | 2 | 565 |
| chr16 | 37281923 | 37281999 | CCTTGTGTTGTGTGTATTCAACTCACAGAGT TAAACGATCCTTTACACAGAGCAGATTTGTA ACACTGTTTTTCTGG | 2 | 566 |
| chr16 | 37346472 | 37346548 | CCTTGTGTTGTGTGTATTCAACTCACAGAGT TAAACGATCCTTTACACAGAGCAGATTTGAA ACACTGTTTTTCTGG | 2 | 567 |
| chr16 | 37357000 | 37357076 | CCTTGTGTTGTGTGTATTCAACTCACAGAGT TAAACGATCCTTTACACAGAGCAGATTTGAA ACACTGTTTTTCTGG | 2 | 568 |
| chr16 | 37373301 | 37373377 | CCTTGTGTTGTGTGTATTCAACTCACAGAGT TAAACGATCCTTTACACAGAGCAGATTTGAA ACACTGTTTTTCTGG | 2 | 569 |
| chr16 | 37419498 | 37419574 | CCTTGTGTTGTGTGTATTCAACTCACAGAGT TAAACGATCCTTTACACAGAGCAGATTTGAA ACACTGTTTTTCTGG | 2 | 570 |
| chr16 | 37430714 | 37430790 | CCTTGTGTTGTGTGTATTCAACTCACAGAGT TAAACGATCCTTTACACAGAGCAGATTTGAA ACACTGTTTTTCTGG | 2 | 571 |
| chr16 | 37455845 | 37455921 | CCTTGTGTTGTGTGTATTCAACTCACAGAGT TAAACGATCCTTTACACAGAGCAGATTTGAA ACACTGTTTTTCTGG | 2 | 572 |
| chr16 | 37458558 | 37458634 | CCTTGTGTTGTGTGTATTCAACTCACAGAGT TAAACGATCCTTTACACAGAGCAGATTTGAA ACACTGTTTTTCTGG | 2 | 573 |
| chr16 | 37486127 | 37486203 | CCTTGTGTTGTGTGTATTCAACTCACAGAGT TAAACGATCCTTTACACAGAGCAGATTTGAA ACACTGTTTTTCTGG | 2 | 574 |
| chr16 | 37525183 | 37525259 | CCTTGTGTTGTGTGTATTCAACTCACAGAGT TAAACGATCCTTTACACAGAGCAGATTTGAA ACACTGTTTTTGTGG | 2 | 575 |

TABLE 9-continued recCas9 genomic targets identified in silico

| Chr. | Start | End | Sequence | Pattern ID | SEQ ID NO: |
|---|---|---|---|---|---|
| chr16 | 37536735 | 37536811 | CCTTGTGTTGTGTGTATTCAACTCACAGAGTTAAACGATCCTTTACACAGAGCAGATTTGAAACACTGTTTTTCTGG | 2 | 576 |
| chr16 | 37554730 | 37554806 | CCTTGTGTTGTGTGTATTCAACTCACAGAGTTAAACGATCCTTTACACAGAGCAGATTTGAAACACTGTTTTTCTGG | 2 | 577 |
| chr16 | 37575784 | 37575860 | CCTTGTGTTGTGTGTATTCAACTCACAGAGTTAAACGATCCTTTACACAGAGCAGATTTGAAACACTGTTTTTCTGG | 2 | 578 |
| chr16 | 37577483 | 37577559 | CCTTGTGTTGTGTGTATTCAACTCACAGAGTTAAACGATCCTTTACACAGAGCAGATTTGAAACACTGTTTTTCTGG | 2 | 579 |
| chr16 | 37583598 | 37583674 | CCTTGTGTTGTGTGTATTCAACTCACAGAGTTAAACGATCCTTTACACAGAGCAGATTTGAAACACTGTTTTTCTGG | 2 | 580 |
| chr16 | 37696368 | 37696444 | CCTTGTGTTGTGTGTATTCAACTCACAGAGTTAAACGATCCTTTCCACAGAGCAGATTTGAAACACTGTTTTTCTGG | 2 | 581 |
| chr16 | 37704524 | 37704600 | CCTTGTGTTGTGTGTATTCAACTCACAGAGTTAAACGATCCTTTACACAGAGCAGATTTGAAACACTGTTTTTCTGG | 2 | 582 |
| chr16 | 37706223 | 37706299 | CCTTGTGTTGTGTGTATTCAACTCACAGAGTTAAACGATCCTTTACACAGAGCAGATTTGAAACACTGTTTTTCTGG | 2 | 583 |
| chr16 | 37708941 | 37709017 | CCTTGTGTTGTGTGTATTCAACTCACAGAGTTAAACGATCCTTTACACAGAGCAGATTTGAAACACTGTTTTTCTGG | 2 | 584 |
| chr16 | 37763622 | 37763698 | CCTTGTGTTGTGTGTATTCAACTCACAGAGTTAAACGATCCTTTACACAGAGCAGATTTGAAACACTGTTTTTCTGG | 2 | 585 |
| chr16 | 37772115 | 37772191 | CCTTGTGTTGTGTGTATTCAACTCACAGAGTTAAACGATCCTTTACACAGAGCAGATTTGAAACACTGTTTTTCTGG | 2 | 586 |
| chr16 | 37791815 | 37791891 | CCTTGTGTTGTGTGTATTCAACTCACAGAGTTAAACGATCCTTTACACAGAGCAGATTTGAAACACTGTTTTTCTGG | 2 | 587 |
| chr16 | 37796229 | 37796305 | CCTTGTGTTGTGTGTATTCAACTCACAGAGTTAAACGATCCTTTACACAGAGCAGATTTGAAACACTGTTTTTCTGG | 2 | 588 |
| chr16 | 37797928 | 37798004 | CCTTGTGTTGTGTGTATTCAACTCACAGAGTTAAACGATCCTTTACACAGAGCAGATTTGAAACACTGTTTTTCTGG | 2 | 589 |
| chr16 | 37843453 | 37843529 | CCTTGTGTTGTGTGTATTCAACTCACAGAGTTAAACGATCCTTTACACAGAGCAGATTTGAAACACTGTTTTTCTGG | 2 | 590 |
| chr16 | 37848548 | 37848624 | CCTTGTGTTGTGTGTATTCAACTCACAGAGTTAAACGATCCTTTACACAGAGCAGATTTGAAACACTGTTTTTCTGG | 2 | 591 |
| chr16 | 37864846 | 37864922 | CCTTGTGTTGTGTGTATTCAACTCACCGAGTTAAACGATCCTTTACACAGAGCAGATTTGAAACACTGTTTTTCTGG | 2 | 592 |
| chr16 | 37902550 | 37902626 | CCTTGTGTTGTGTGTATTCAACTCACAGAGTTAAACGATCCTTTACACAGAGCAGATTTGAAACACTGTTTTTCTGG | 2 | 593 |
| chr16 | 37907307 | 37907383 | CCTTGTGTTGTGTGTATTCAACTCACAGAGTTAAACGATCCTTTACACAGAGCAGATTTGAAACACTGTTTTTCTGG | 2 | 594 |

TABLE 9-continued recCas9 genomic targets identified in silico

| Chr. | Start | End | Sequence | Pattern ID | SEQ ID NO: |
|---|---|---|---|---|---|
| chr16 | 37928033 | 37928109 | CCTTGTGTTGTGTGTATTCAACTCACAGAGT TAAACGATCCTTTACACAGAGCAGATTTGAA ACACTGTTTTTCTGG | 2 | 595 |
| chr16 | 37959262 | 37959338 | CCTTGTGTTGTGTGTATTCAACTCACAGAGT TAAACGATCCTTTACACAGAGCAGATTTGAA ACACTGTTTTTCTGG | 2 | 596 |
| chr16 | 37964355 | 37964431 | CCTTGTGTTGTGTGTATTCAACTCACAGAGT TAAACGATCCTTTACACAGAGCAGATTTGAA ACACTGTTTTTCTGG | 2 | 597 |
| chr16 | 37974881 | 37974957 | CCTTGTGTTGTGTGTATTCAACTCACAGAGT TAAACGATCCTTTACACAGAGCAGATTTGAA AAACTGTTTTTCTGG | 2 | 598 |
| chr16 | 37987789 | 37987865 | CCTTGTGTTGTGTGTATTCAACTCACAGAGT AAAACGATCCTTTACACAGAGCAGATTTGAA ACACTGTTTTTCTGG | 2 | 599 |
| chr16 | 37994586 | 37994662 | CCTTGTGTTGTGTGTATTCAACTCACAGAGT TAAACGATCCTTTACACAGAGCAGATTTGAA ACACTGTTTTTGTGG | 2 | 600 |
| chr16 | 38006479 | 38006555 | CCTTGTGTTGTGTGTATTCAACTCACAGAGT TAAACGATCCTTTACACAGAGCAGATTTGAA ACACTGTTTTTCTGG | 2 | 601 |
| chr16 | 38011567 | 38011643 | CCTTGTGTTGTGTGTATTTAACTCACAGAGTT AAACGATCCTTTACACAGAGCAGATTTGAAA CACTGTTTTTCTGG | 2 | 602 |
| chr16 | 38040096 | 38040172 | CCTTGTGTTGTGTGTATTCAACTCACAGAGT TAAACGATCCTTTACACAGAGCAGATTTGAA ACACTGTTTTTCTGG | 2 | 603 |
| chr16 | 38041456 | 38041532 | CCTTGTGTTGTGTGTATTCAACTCACAGAGT TAAACGATCCTTTACACAGAGCAGATTTGAA ACACTGTTTTTCTGG | 2 | 604 |
| chr16 | 38062179 | 38062255 | CCTTGTGTTGTGTGTATTCAACTCACAGAGT TAAACGATCCTTTACACAGAGCAGATTTGAA ACACTGTTTTTCTGG | 2 | 605 |
| chr16 | 38102937 | 38103013 | CCTTGTGTTGTGTGTATTCAACTCACAGAGT TAAACGATCCTTTACACAGAGCAGATTTGAA ACACTGTTTTTCTGG | 2 | 606 |
| chr16 | 38128412 | 38128488 | CCTTGTGTTGTGTGTATTCAACTCACAGAGT TAAACGATCCTTTACACAGAGCAGATTTGAA ACACTGTTTTTCTGG | 2 | 607 |
| chr16 | 38131809 | 38131885 | CCTTGTGTTGTGTGTATTCAACTCACAGAGT TAAACGATCCTTTACACAGAGCAGATTTGAA ACACTGTTTTTCTGG | 2 | 608 |
| chr16 | 38144723 | 38144799 | CCTTGTGTTGTGTGTATTCAACTCACAGAGT TAAACGATCCTTTACACAGAGCAGATTTGAA ACACTGTTTTTCTGG | 2 | 609 |
| chr16 | 38168845 | 38168921 | CCTTGTGTTGTGTGTATTCAACTCACAGAGT TAAACGATCCTTTACACAGAGCAGATTTGAA ACACTGTTTTTCTGG | 2 | 610 |
| chr16 | 38209287 | 38209363 | CCTTGTGTTGTGTGTATTCAACTCACAGAGT TAAACGATCCTTTACACAGAGCAGATTTGAA ACACTGTTTTTCTGG | 2 | 611 |
| chr16 | 38210986 | 38211062 | CCTTGTGTTGTGTGTATTCAACTCACAGAGT TAAACGATCCTTTACACAGAGCAGATTTGAA ACACTGTTTTTCTGG | 2 | 612 |
| chr16 | 38229667 | 38229743 | CCTTGTGTTGTGTGTATTCAACTCACAGAGT TAAACGATCCTTTACACAGAGCAGATTTGAA ACACTGTTTTTCTGG | 2 | 613 |

TABLE 9-continued recCas9 genomic targets identified in silico

| Chr. | Start | End | Sequence | Pattern ID | SEQ ID NO: |
|---|---|---|---|---|---|
| chr16 | 47424037 | 47424114 | CCATTCTCCCTATCACTTTCAGGTACACCAATCAAACGTAGGTTTGGTCTTTTCACATAGTCCCATATTTCTTGGAGG | 1 | 614 |
| chr16 | 60730549 | 60730625 | CCTCGTCACTGCCAGATTTTGTGGCTACCAGCAAAGGATCGTTTTAAGCTGCAACTCAGGAAATTGAGAAAATATGG | 2 | 615 |
| chr16 | 72545014 | 72545091 | CCTCCAAGAAATATGGGACTATGTGAAAAAACCAAACCTACGTTTGATTGGTGTACCTGAAAGTGACAGGGAGAATGG | 1 | 616 |
| chr16 | 81945503 | 81945579 | CCCTGTGTTCTTTTATACTAAAACAAGCCAGCAAACCAACCTTTGAGATGTGTTGCCTTAAACATTACTGAATGGGG | 2 | 617 |
| chr16 | 81945503 | 81945578 | CCCTGTGTTCTTTTATACTAAAACAAGCCAGCAAACCAACCTTTGAGATGTGTTGCCTTAAACATTACTGAATGGG | 4 | 618 |
| chr17 | 16474024 | 16474100 | CCGAGAAACGGCTTTAGCAACAAATAAATATCAAAAGGATGCTTTCTCTTCAGAATAATCTAAAGTAAGTTGGGAGG | 3 | 619 |
| chr17 | 34438512 | 34438589 | CCATGTTACTCCGGATAAGGACAGCAAAGGAGGAAAGGAACCTTTTCTGGGCCACCAGAAGGATGAGCTTGGGCTTGG | 1 | 620 |
| chr17 | 43690782 | 43690859 | CCCAGGGATATGCTGGCCACGGGGAGGAGCCGGAAACCAACCTTTGTGTCACTGTGTAGTGACAAGTGCCTTTGGAGG | 1 | 621 |
| chr17 | 43690783 | 43690859 | CCAGGGATATGCTGGCCACGGGGAGGAGCCGGAAACCAACCTTTGTGTCACTGTGTAGTGACAAGTGCCTTTGGAGG | 2 | 622 |
| chr17 | 69156298 | 69156375 | CCTTAGGGACCCATAATGGCCACAACCAGGAGAAAAGCAAGCTTTGATGCTTAAACACTACTTACAGACATGTACAGG | 1 | 623 |
| chr17 | 74595228 | 74595305 | CCTGCCTCTGTTCCTCCTTCCTGATGGTGGCGGAAAGGATGCTTTTGCCAGATCAACAGTCACACACAACACACCAGG | 1 | 624 |
| chr17 | 83191644 | 83191721 | CCTGACTCCAGCCCTCCTTGACAAGGTCTCCGTAAAGCATGCTTTCTCTTAGGGACCCTCAGAGGGAGGCTTGGTGGG | 1 | 625 |
| chr17 | 83191644 | 83191720 | CCTGACTCCAGCCCTCCTTGACAAGGTCTCCGTAAAGCATGCTTTCTCTTAGGGACCCTCAGAGGGAGGCTTGGTGG | 3 | 626 |
| chr18 | 35135224 | 35135300 | CCTTATTTGGAATGTGACAAGACCCATTTGTTTAAACCTTGGTTTTTATGCAGAAAGAAAAGGAAGGCTGCAGTGGG | 3 | 627 |
| chr18 | 38918861 | 38918938 | CCATTCTCCCTGTCACTTTCAGGTACACTAATCAAACGTAGGTTTGCTGTTTTTACATAGGCTCATATTTCTTGGAGG | 1 | 628 |
| chr18 | 45476589 | 45476666 | CCATTCTCCCCATCACTTTCAGGTACACCAGTCAAACGTAGGTTTGGTCTTTTCACATAGTCCCATATTTCTTGGAGG | 1 | 629 |
| chr18 | 48640821 | 48640896 | CCTGTTTGTTATTTTAGCTAATGTCAAAAAGAAAACCTTGCTTTTTCTGAACCCTTTCAGAGGCAGAAAGTGGGGG | 4 | 630 |
| chr18 | 71096732 | 71096808 | CCATTTTCCCCACCACTTTCACGTACAGCAATCAAACGTAGGTTTGGTCTTTTCACTAGTCCCATATTTCTTGGAGG | 3 | 631 |
| chr19 | 24957844 | 24957920 | CCTTGTAGTGTGTGTATTCAACTCACAGAGTTAAACGATCCTTTACACAGAGCAGACTTGAAACACTCTTGTTGTGG | 2 | 632 |

TABLE 9-continued recCas9 genomic targets identified in silico

| Chr. | Start | End | Sequence | Pattern ID | SEQ ID NO: |
|---|---|---|---|---|---|
| chr19 | 25015316 | 25015392 | CCTTGTAGTGTGTGTATTCAACTCACAGAGT TAAACGATCCTTTACACAGAGCATACTTGAA ACACTCTTTTTGTGG | 2 | 633 |
| chr19 | 25074119 | 25074195 | CCTTGTGTTGTGTGTATTCAACTCACAGAGT TAAACGATCCTTTACACAGAGCAGACTTGAA ACACTCTTTTTGTGG | 2 | 634 |
| chr19 | 25827861 | 25827937 | CCTTGTGTTGTGTTTATTCAACTCACAGAGTT AAACGATCCTTTACACAGAGCAGACTTGAA ATACTCTTTTTGTGG | 2 | 635 |
| chr19 | 26054056 | 26054132 | CCTTGTAGTGTGTGTATTCAACTCACAGAGT TAAACGATCCTTTACACAGAGCATACTTGAA ACACTCTTTTTGTGG | 2 | 636 |
| chr19 | 26211777 | 26211853 | CCTTGTATTGTGAGTATTCAACTCACAGAGT TAAACGATCCTTTACACAGAGCAGACTTGAA ACACTCTTTTTGTGG | 2 | 637 |
| chr19 | 26483670 | 26483746 | CCTTGTGTTGTGTGTCTTCAACTCACAGAGTT AAACGATGCTTTACACAGAGTAGACTTGAA ACACTCTTTTTCTGG | 2 | 638 |
| chr19 | 26636516 | 26636592 | CCTTGTGTTGTGTGTATTCAACTCACAGAGT TAAACGATCCTTTACACAGAGCAGACTTGTA ACACTCTTTTTGTGG | 2 | 639 |
| chr19 | 26637877 | 26637953 | CCTTGTGTTGTGTGTATTCAACTCACAGAGT TAAACGATCCTTTACACAGAGCAGACGTGA AACACTCTTTTTGTGG | 2 | 640 |
| chr19 | 26750223 | 26750299 | CCTTGTGTTGTGTGTATTCAACTCACAGAGT TAAACGATCCTTTACACAGAGCAGACTTGAA ACACTCTTTTTGTGG | 2 | 641 |
| chr19 | 26841158 | 26841234 | CCTTGTGTTGTGTGTATTCAACTCACAGAGT TAAACGATCCTTTACACAGAGGAGACTTGTA ACACTCTTTTTGTGG | 2 | 642 |
| chr19 | 28517220 | 28517297 | CCAGGAAAAAATTTAAACTTTCTTAACTTGA TAAAAGGTAGCTTTCAAAACCTACAATAAAT AACATACTTAGAGTGG | 1 | 643 |
| chr19 | 34566821 | 34566898 | CCATTCTCCTCGTCACTTTCAGGTACACCAA ACAAACGTAGGTTTGGTCTTTTTACGTAGTC CCATATTTCTTGGAGG | 1 | 644 |
| chr19 | 52261770 | 52261847 | CCCTCTTGAAGTTAGGGAAGTAGCATTTAAG GGAAACGTAGCTTTACTATTAAGAATTTCAA ACAGCACTTGTCAGGG | 1 | 645 |
| chr19 | 52261770 | 52261846 | CCCTCTTGAAGTTAGGGAAGTAGCATTTAAG GGAAACGTAGCTTTACTATTAAGAATTTCAA ACAGCACTTGTCAGG | 3 | 646 |
| chr19 | 52261771 | 52261847 | CCTCTTGAAGTTAGGGAAGTAGCATTTAAGG GAAACGTAGCTTTACTATTAAGAATTTCAAA CAGCACTTGTCAGGG | 2 | 647 |
| chr19 | 52261771 | 52261846 | CCTCTTGAAGTTAGGGAAGTAGCATTTAAGG GAAACGTAGCTTTACTATTAAGAATTTCAAA CAGCACTTGTCAGG | 4 | 648 |
| chr20 | 11151392 | 11151469 | CCATTCTCCCCGTCACTTTCAGGTACACCAA TCAAACGTAGGTTTGGTCTTTTCACATATTCC CATATTTCTTGGAGG | 1 | 649 |
| chr20 | 14027067 | 14027143 | CCATTCTCCCTTCACTTTCAGGTACACCAATC AAACGTAGGTTTGGTCTTTTCACATAGTCCC ATATTTTTTGGAGG | 2 | 650 |
| chr20 | 50615399 | 50615476 | CCTATAGTCTCAGTTACTTGGGAGGCTGAGG TAAAAGGATCGTTTGAGCCCAGGAGGTGGA GGTTGCAGTGAGCCGGG | 1 | 651 |

TABLE 9-continued recCas9 genomic targets identified in silico

| Chr. | Start | End | Sequence | Pattern ID | SEQ ID NO: |
|---|---|---|---|---|---|
| chr20 | 50615399 | 50615475 | CCTATAGTCTCAGTTACTTGGGAGGCTGAGGTAAAAGGATCGTTTGAGCCCAGGAGGTGGAGGTTGCAGTGAGCCGG | 3 | 652 |
| chr20 | 60909414 | 60909490 | CCTTTCCCAACTCTGCTATTGCCCCCACATCCTAAAGGAACCTTTCTTTTTTTATATATTTTATTTTAAGTTCCAGG | 3 | 653 |
| chr21 | 16226086 | 16226163 | CCTCCAAGAAATATGGAACTATGTGAAAAGACCAAACCTACGTTTGATTGACGTACCTGAAAGTGACAGGGAGAATGG | 1 | 654 |
| chr21 | 17835234 | 17835309 | CCTCTTCTGAAAGCATTGATAATCAACATTTTAAACGTAGCTTTTCCCCATATTGCTAGGAAGGCTCATTCCCGGG | 4 | 655 |
| chr21 | 19425636 | 19425713 | CCTCCAAGAAATATGGGACTATGTGAAAAGGCCAAACCTACGTTTGATTGCTGTACCCGAGAGTGACGGGGAGAATGG | 1 | 656 |
| chr21 | 32220958 | 32221035 | CCTCCAAGAAATATGGGACTATGTGAAAAGACCAAACCTACGTTTGATTGGTGTACCTGAAAGTGATGGGGAGAATGG | 1 | 657 |
| chr21 | 34335877 | 34335953 | CCCGGGGCCTGGGTGCCCAGTGCCAGTGGTCAGAAAGGTTGCTTTGGTGTTTTTCATTGTTAGTGAGACAGAGATGG | 3 | 658 |
| chr21 | 34335878 | 34335953 | CCGGGGCCTGGGTGCCCAGTGCCAGTGGTCAGAAAGGTTGCTTTGGTGTTTTTCATTGTTAGTGAGACAGAGATGG | 4 | 659 |
| chr21 | 36315276 | 36315353 | CCATTCTCCCCATCATTTTCAGGTACACCAATCAAACGTAGGTTTGATCTTTTCACATAGCCCCATATTTCTTGGAGG | 1 | 660 |
| chr21 | 41547952 | 41548028 | CCACCAGCACTTCTGTTAGAAGTTGCAGCAGAGAAAGGATCCTTTAGGCACATCTCCCAGATCCTTGCGAAGAGGGG | 3 | 661 |
| chr22 | 18973194 | 18973271 | CCTGTGCCAGGGTCCTTCCACTGGGACTGGCAGAAACGTAGGTTTGCATGGAGTGAGAAGCAGGGGAGAGGTTGAGGG | 1 | 662 |
| chr22 | 18973194 | 18973270 | CCTGTGCCAGGGTCCTTCCACTGGGACTGGCAGAAACGTAGGTTTGCATGGAGTGAGAAGCAGGGGAGAGGTTGAGG | 3 | 663 |
| chr22 | 20265462 | 20265539 | CCCTCAGCCTCTCCCCTGCTTCTCACTCCATGCAAACCTACGTTTCTGCCAGTCCCAGCAGAAGGACCCTGGCACGGG | 1 | 664 |
| chr22 | 20265462 | 20265538 | CCCTCAGCCTCTCCCCTGCTTCTCACTCCATGCAAACCTACGTTTCTGCCAGTCCCAGCAGAAGGACCCTGGCACGG | 3 | 665 |
| chr22 | 20265463 | 20265539 | CCTCAGCCTCTCCCCTGCTTCTCACTCCATGCAAACCTACGTTTCTGCCAGTCCCAGCAGAAGGACCCTGGCACGGG | 2 | 666 |
| chr22 | 20265463 | 20265538 | CCTCAGCCTCTCCCCTGCTTCTCACTCCATGCAAACCTACGTTTCTGCCAGTCCCAGCAGAAGGACCCTGGCACGG | 4 | 667 |
| chrX | 27300998 | 27301075 | CCTCCAAGAAATATGGGGCTATGTGAAAAGACCAAACCTACCTTTGATTGGTGTATCTGAAAGTGACGGGGAGAATGG | 1 | 668 |
| chrX | 28456666 | 28456743 | CCTCCAAGAAATATGGGACTATGTGAAAAGACCAAACCTACGTTTGATTTGTGTACCTGAAAGTGATGGGGAGAATGG | 1 | 669 |
| chrX | 35634985 | 35635062 | CCATTCTCCCCGTCACTTTCAGGTACACCAATCAAACGTAGGTTTGGTCTTTTCTCATTGTCCCATATTTCTTGGAGG | 1 | 670 |

TABLE 9-continued recCas9 genomic targets identified in silico

| Chr. | Start | End | Sequence | Pattern ID | SEQ ID NO: |
|---|---|---|---|---|---|
| chrX | 39460148 | 39460223 | CCCATCAAGAGCGGTTGTGCATGGCAACAGT AAAAGGATGGTTTGTTACACTAGTACAAAA AGAGGTGGCCAGAGG | 4 | 671 |
| chrX | 43926403 | 43926480 | CCATTCTCTCTGTCACTTTCAGGTACACCAAT CAAACGTAGGTTTGGTCTTTTCACATAGTCC CATATTTCTTGGAGG | 1 | 672 |
| chrX | 44254600 | 44254677 | CCTCCAAGAAATACGGGACTATGTGAAAAG ACCAAACGTACGTTTGATTGGTGTACCTGAA AGTGATAGGGAGAATGG | 1 | 673 |
| chrX | 46088602 | 46088679 | CCTCCAAGAAATATGGGACTATGTGAAAAG ACCAAACCTACGTTTGATTGGTGTACCTGAA AGTGACTGGGAGAATGG | 1 | 674 |
| chrX | 50222874 | 50222951 | CCATTCTCCCTGTCACTTTCAGGTACACGAA TCAAACGTAGGTTTCATCTTTTCACATAGTC CCATATTTCTTAGAGG | 1 | 675 |
| chrX | 57416835 | 57416911 | CCATTCTCTCTGTCACTTTCTGGTACACCAAT CAAACGTAGGTTTGGTCTTTTCACATAGTTT CACATATTTCTTGG | 3 | 676 |
| chrX | 57856466 | 57856543 | CCTCCAAGAAATATGGGACTATGTGAAAAG ACCAAACCTACGTTTGATTGGTGTACCTGAA AGTGACAAGGAAAATGG | 1 | 677 |
| chrX | 62702479 | 62702556 | CCTGAAAAACATTGTTTCCAACCTGGTAAAT CAAAAGGAAGGTTTAACTTTGTTAGATAAGT CCACATATCACCAAGG | 1 | 678 |
| chrX | 63067129 | 63067206 | CCTCCAAGAAATGTGGGACTATGGGAAAAG ACCAAACCTACCTTTGTTTGGTGTACCTGAA AGTGACGGGGAGAAAGG | 1 | 679 |
| chrX | 64936250 | 64936327 | CCTCCAAGAAATATGGGACTATGTGAAAAG ACCAAACCTACGTTTCATTGGTGTACCTGAA AGTGATGGGTAGAATGG | 1 | 680 |
| chrX | 66720099 | 66720176 | CCTACAAGAAATATGGGACTATGGGAAAAG ACCAAACCTACGTTTGATTGGTACACTGGAA AGTGACAGGGATAATGG | 1 | 681 |
| chrX | 68529086 | 68529163 | CCATTCTCCCTGTCACTTTCTGGTACACCAAT CAAAGGTAGGTTTGGTCTTTTCACATAGTCC CATATTTCTTGGAGG | 1 | 682 |
| chrX | 73893994 | 73894071 | CCTCCAAGAAATATGGGACTATGTGAAAAG ACCAAACCTACGTTTGATTGGTGTACCTGAA AGTGATGGGGAGAATGG | 1 | 683 |
| chrX | 75723201 | 75723278 | CCATTCTCTTTGTCACTTTCAGGTATACCAAT CAAACGTTGGTTTGGTCTTTTTGCATAGTCCC ATATTTTGTGGAGG | 1 | 684 |
| chrX | 75815659 | 75815736 | CCTCCAAGAAATATGAGACTATGTGAAAAG ACCAAACCTACGTTTGATTAGTGTACCTGAA AATGATGGGGAGAATGG | 1 | 685 |
| chrX | 80967103 | 80967180 | CCATTCTTTCTGTCACTTTCAGGTACACCAAT CAAACGTAGGTTTGGTCTTTTCACATAGTCC CATATTTCTTGGAGG | 1 | 686 |
| chrX | 89936425 | 89936502 | CCATTCTCCCTGTCACTTTCAGGTACACCAA TCAAACGTAGGTTTGTTCTTTTCACATAGTCC CATATTTCTTGGAGG | 1 | 687 |
| chrX | 91038768 | 91038845 | CCATTATCCCCATCACTTTCAGGTACACCAA TCAAACGTAGGTTTGGTTTTTTCACATAGTTC AATATTTCTTTGAGG | 1 | 688 |
| chrX | 91471271 | 91471348 | CCTCCAAGAAATATGGGACTATCTGAAAAG ATCAAACCTACGTTTGATTGGTGTACCTGAA AGTGACAGGGAGAATGG | 1 | 689 |

TABLE 9-continued recCas9 genomic targets identified in silico

| Chr. | Start | End | Sequence | Pattern ID | SEQ ID NO: |
|---|---|---|---|---|---|
| chrX | 96428180 | 96428257 | CCTTTCTCCCCATCACTTTCAGGTACACCAAT CAAACGTAGGTTTGGTCTTTTCATATAGTCC CATATTTCTTGGAGG | 1 | 690 |
| chrX | 100268291 | 100268368 | CCTCCAAGAAATATGGGACTATGTGCAAAG ATCAAACCTACGTTTGATTGCTGTACCTGAA AGTGATGGGGAGAATGG | 1 | 691 |
| chrX | 105811046 | 105811123 | CCATTCTCCCCATCACTTTCAGGTACACCAG TCAAACGTAGGTTTGGTCTTTTCACATAATC CCATATTTCTTGGAGG | 1 | 692 |
| chrX | 115673065 | 115673141 | CCTCCAAGAAGTATGGGACCATGGAAAAGA TCAAACCTACGTTTGACTGGTGTACCTGAAA GTGACTGGGAGAATGG | 2 | 693 |
| chrX | 117269846 | 117269923 | CCTCCAAGAAATATGGGACTATGTGAAAAG ACCAAACCTACGTTTGATTGGAGTACTTGAA AATGACAGGGATAATGG | 1 | 694 |
| chrX | 139191369 | 139191445 | CCTTTAAAGACATGCTCTTTGTGCCAGAAAT TCAAAGGTTGCTTTTATGTCCAGTGGGGTGG AGGGAGGAAGCTCGG | 3 | 695 |
| chrX | 147988614 | 147988691 | CCATTCTCCCCGTCACTTTCAGGGACCTCAA TCAAACGTAGGTTTTGTCTTTTCACATAGTCC CATATTTCTTGGAGG | 1 | 696 |
| chrX | 155321041 | 155321118 | CCTCCAAGAAATATAGGACTATGTGAAAAG ACCAAACCTACGTTTGACTGGTGTACCTGAA AGTGACAGGGAGAATGG | 1 | 697 |
| chrY | 15109391 | 15109468 | CCATTCTCCCCATCACTTTCAGGTACACCAA TCAAAGGTAGGTTTGGTCTTTTCACATAGTC CGATATTTCCTGCAGG | 1 | 698 |

Chromosomal sites were identified by searching for $CCX_{(30-31)}$-AAASSWWSSTTT-$X_{(30-31)}$-GG (SEQ ID NO: 699) where W is T or A and S is G or C. Pattern 1 is $CCX_{(31)}$-AAASSWWSSTTT-$X_{(31)}$-GG (SEQ ID NO: 699), 2 is $CCX_{(30)}$-AAASSWWSSTTT-$X_{(31)}$-GG (SEQ ID NO: 699), 3 is $CCX_{(31)}$-AAASSWWSSTTT-$X_{(30)}$-GG (SEQ ID NO: 699), and 4 is $CCX_{(30)}$-AAASSWWSSTTT-$X_{(30)}$-GG (SEQ ID NO: 699). Only the + strand is shown and the start and end corresponds to the first and last base pair in the chromosome (GRCh38) or alternate assembly when applicable.

DNA Sequencing

Transfections of 293T cells were performed as above in sextuplet and incubated for 72 hours. Cells were harvested and replicates were combined. Episomal DNA was extracted using a modified HIRT extraction involving alkaline lysis and spin column purification essentially as described (Quan et al., Circular polymerase extension cloning of complex gene libraries and pathways. PloS one 4, e6441 (2009); and Hillson (2010), vol. 2015, pp. CPEC protocol; the entire contents of each of which are hereby incorporated by reference). Briefly, after harvesting, HEK293T cells were washed in 500 μL of ice cold PBS, resuspended in 250 μL GTE Buffer (50 mM glucose, 25 mM Tris-HCl, 10 mM EDTA and pH 8.0), incubated at room temperature for 5 minutes, and lysed on ice for 5 minutes with 200 μL lysis buffer (200 mM NaOH, 1% sodium dodecyl sulfate). Lysis was neutralized with 150 μL of a potassium acetate solution (5 M acetate, 3 M potassium, pH 6.7). Cell debris were pelleted by centrifugation at 21,130 g for 15 minutes and lysate was applied to Econospin Spin columns (Epoch Life Science, Missouri City, Tex.). Columns were washed twice with 750 μL wash buffer (Omega Bio-tek, Norcross, Ga.) and eluted in 45 μL TE buffer, pH 8.0.

Isolated episomal DNA was digested for 2 hours at 37° C. with RecBCD (10 U) following the manufacturer's instructions and purified into 10 μL EB with a MinElute Reaction Cleanup Kit (Qiagen, Valencia, Calif.). Mach1-T1 chemically competent cells were transformed with 5 μL of episomal extractions and plated on agarose plates selecting for carbenicillin resistance (containing 50 μg/mL carbenicillin). Individual colonies were sequenced with primer pCALNL-for-1 to determine the rate of recombination. Sequencing reads revealed either the 'left' intact non-recombined recCas9 site, the expected recombined product, rare instances of 'left' non-recombined site with small indels, or one instance of a large deletion product.

Analysis of recCas9 Catalyzed Genomic Deletions

HEK293T cells were seeded at a density of $6\times10^5$ cells per well in 24 well collagen-treated plates and grown overnight (Corning, Corning, N.Y.). Transfections reactions were brought to a final volume of 100 μL in Opti-MEM (ThermoFisher Scientific, Waltham, Mass.). For each transfection, 90 ng of each guide RNA expression vector, 20 ng of pmaxGFP (Lonza, Allendale, N.J.) and 320 ng of recCas9 expression vector were combined with 2 μL Lipofectamine 2000 in Opti-MEM (ThermoFisher Scientific, Waltham, Mass.) and added to individual wells. After 48 hours, cells were harvested and sorted for the GFP transfection control on a BD FACS AriaIIIu cell sorter. Cells were sorted on purity mode using a 100 μm nozzle and background fluorescence was determined by comparison with untransfected cells. Sorted cells were collected on ice in PBS, pelleted and washed twice with cold PBS. Genomic DNA was harvested using the E. Z. N. A. Tissue DNA Kit (Omega Bio-Tek, Norcross, Ga.) and eluted in 100 μL EB. Genomic DNA was quantified using the Quant-iT PicoGreen dsDNA kit (ThermoFisher Scientific, Waltham, Mass.) measured on a Tecan Infinite M1000 Pro fluorescence plate reader.

Nested PCR was carried out using Q5 Hot-Start Polymerase 2× Master Mix supplemented with 3% DMSO and diluted with HyClone water, molecular biology grade (GE Life Sciences, Logan, Utah). Primary PCRs were carried out at 25 uL scale with 20 ng of genomic DNA as template using the primer pair FAM19A2-F1 and FAM19A2-R1 (Table 5). The primary PCR conditions were as follows: 98° C. for 1 minute, 35 cycles of (98° C. for 10 seconds, 59° C. for 30 seconds, 72° C. for 30 seconds), 72° C. for 1 minute. A 1:50 dilution of the primary PCR served as template for the secondary PCR, using primers FAM19A2-F2 and FAM19A2-R2. The secondary PCR conditions were as follows: 98° C. for 1 minute, 30 cycles of (98° C. for 10 seconds, 59° C. for 20 seconds, 72° C. for 20 seconds), 72° C. for 1 minute. DNA was analyzed by electrophoresis on a 1% agarose gel in TAE alongside a 1 Kb Plus DNA ladder (ThermoFisher Scientific, Waltham, Mass.). Material to be Sanger sequenced was purified on a Qiagen Minelute column (Valencia, Calif.) using the manufacturer's protocol. Template DNA from 3 biological replicates was used for three independent genomic nested PCRs.

The limit of detection was calculated given that one complete set of human chromosomes weighs approximately $$3.6\ pg\ \left(3.3\cdot 10^{9}\ \text{bp}\times 1\cdot 10^{-21}\frac{\text{g}}{\text{bp}}\right).$$

Therefore, a PCR reaction seeded with 20 ng of genomic DNA template contains approximately 5500 sets of chromosomes.

For quantification of genomic deletion, nested PCR was carried out using the above conditions in triplicate for each of the 3 biological replicates. A two-fold dilution series of genomic DNA was used as template, beginning with the undiluted stock (for sample 1, 47.17 ng/uL; for sample 2, 75.96 ng/uL; and for sample 3, 22.83 ng/uL) to reduce potential sources of pipetting error. The lowest DNA concentration for which a deletion PCR product could be observed was assumed to contain a single deletion product per total genomic DNA.

The number of genomes present in a given amount of template DNA can be inferred, and thus an estimate a minimum deletion efficiency for recCas9 at the FAM19A2 locus can be determined. For example, take the case of a two-fold dilution series, beginning with 20 ng genomic DNA template. After nested PCR, only the well seeded with 20 ng yielded the correct PCR product. At 3.6 pg per genome, that PCR contained approximately 5500 genomes, and since at least one recombined genome must have been present, the minimum deletion efficiency is 1 in 5500 or 0.018%.

Figure 5A:
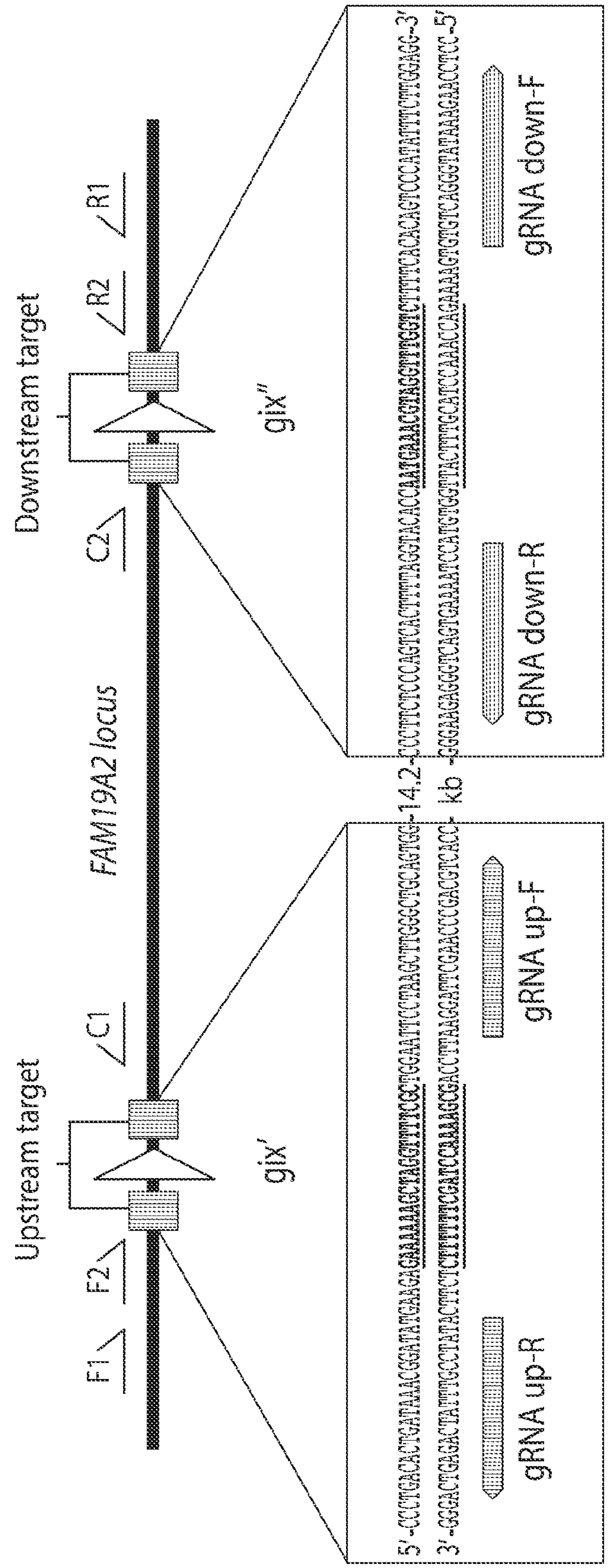
Figure 5B:
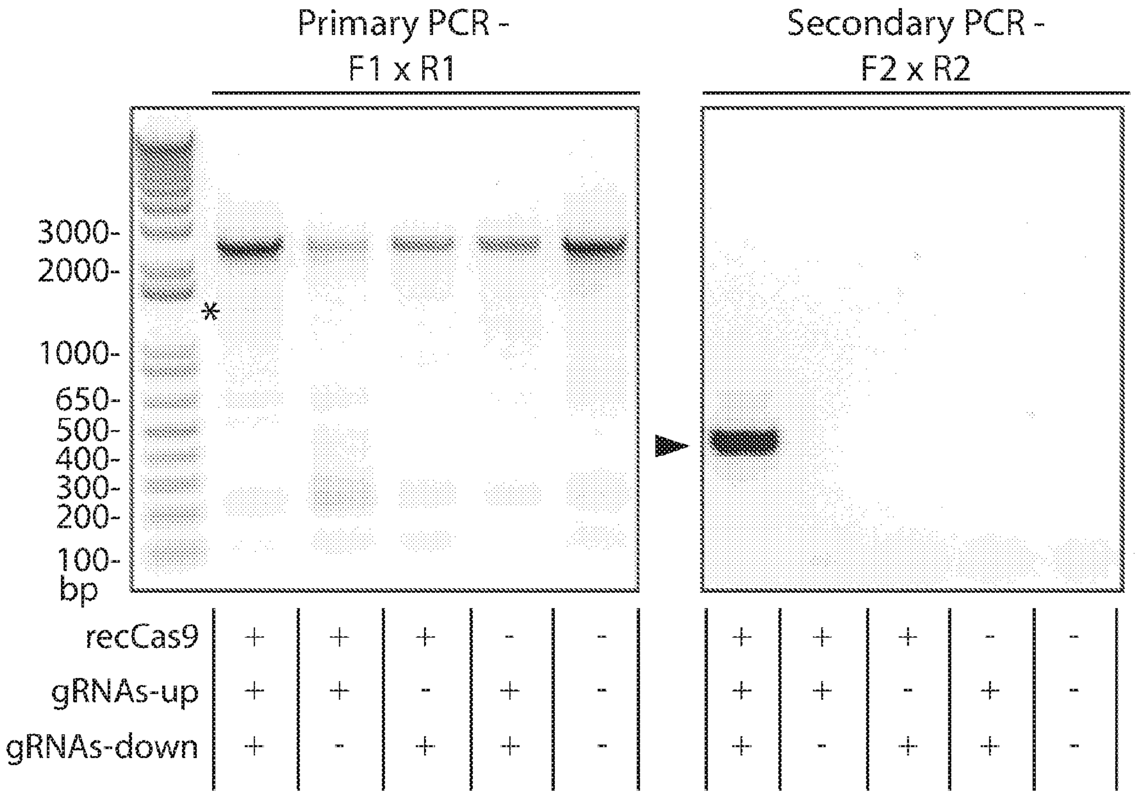

The levels of genomic DNA were quantified using a limiting dilution of genomic template because using quantitative PCR (qPCR) to determine the absolute level of genome editing would require a set of PCR conditions that unambiguously and specifically amplify only from post-recombined genomic DNA. As shown in FIG. 5B, primary PCR using genomic DNA as a template results in a roughly 2.5 kb off-target band as the dominant species; a second round of PCR using nested primers is required to reveal guide RNA- and recCas9-dependent genome editing.

Results

Fusing Gin Recombinase to dCas9

It has been recently demonstrated that the N-terminus of dCas9 may be fused to the FokI nuclease catalytic domain, resulting in a dimeric dCas9-FokI fusion that cleaved DNA sites flanked by two guide RNA-specified sequences (see, e.g., Guilinger et al., Fusion of catalytically inactive Cas9 to FokI nuclease improves the specificity of genome modification. Nature biotechnology, (2014); Tsai et al., Dimeric CRISPR RNA-guided FokI nucleases for highly specific genome editing. Nature biotechnology, (2014); the entire contents of each of which are hereby incorporated by reference). The same fusion orientation was used to connect dCas9 to Ginβ, a highly active catalytic domain of dimeric Gin invertase previously evolved by Barbas and co-workers (Gaj et al., A comprehensive approach to zinc-finger recombinase customization enables genomic targeting in human cells. Nucleic acids research 41, 3937-3946 (2013), the entire contents of which is hereby incorporated by reference). Ginβ promiscuously recombines several 20-bp core "gix" sequences related to the native core sequence CTGTAAACCGAGGTTTTGGA (SEQ ID NO: 700) (Gaj et al., A comprehensive approach to zinc-finger recombinase customization enables genomic targeting in human cells. Nucleic acids research 41, 3937-3946 (2013); Klippel et al., The DNA Invertase Gin of Phage Mu—Formation of a Covalent Complex with DNA Via a Phosphoserine at Amino-Acid Position-9. Embo Journal 7, 1229-1237 (1988); Mertens et al., Site-specific recombination in bacteriophage Mu: characterization of binding sites for the DNA invertase Gin. The EMBO journal 7, 1219-1227 (1988); Plasterk et al., DNA inversions in the chromosome of *Escherichia coli* and in bacteriophage Mu: relationship to other site-specific recombination systems. Proceedings of the National Academy of Sciences of the United States of America 80, 5355-5358 (1983); the entire contents of each of which are hereby incorporated by reference). The guide RNAs localize a recCas9 dimer to a gix site flanked by two guide-RNA specified sequences, enabling the Ginβ domain to catalyze DNA recombination in a guide RNA-programmed manner (FIG. 1D).

Figure 1A:
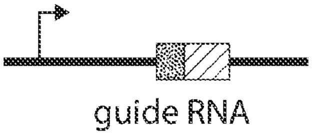
FIGS. 1A-1D. Overview of the experimental setup. Cells are transfected with (FIG. 1A) guide RNA expression vector(s) under the control of an hU6 promoter, (FIG. 1B) a recCas9 expression vector under the control of a CMV promoter, and (FIG. 1C) a recCas9 reporter plasmid. Co-transfection of these components results in reassembly of guide RNA-programmed recCas9 at the target sites (FIG. 1D). This will mediate deletion of the polyA terminator, allowing transcription of GFP. Guide RNA expression vectors and guide RNA sequences are abbreviated as gRNA.
Figure 1B:
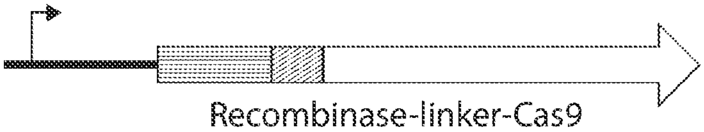
Figure 1C:
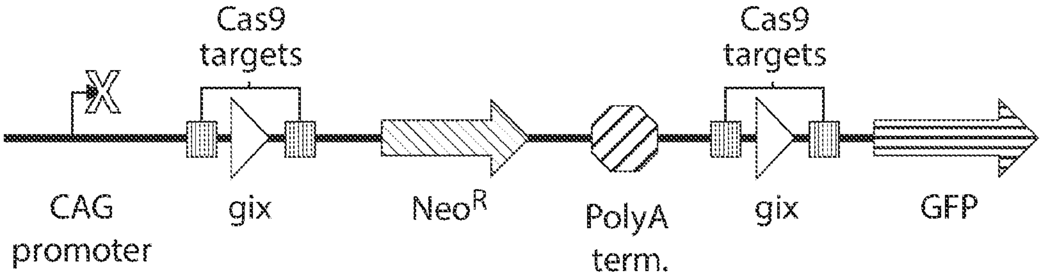
Figure 1D:
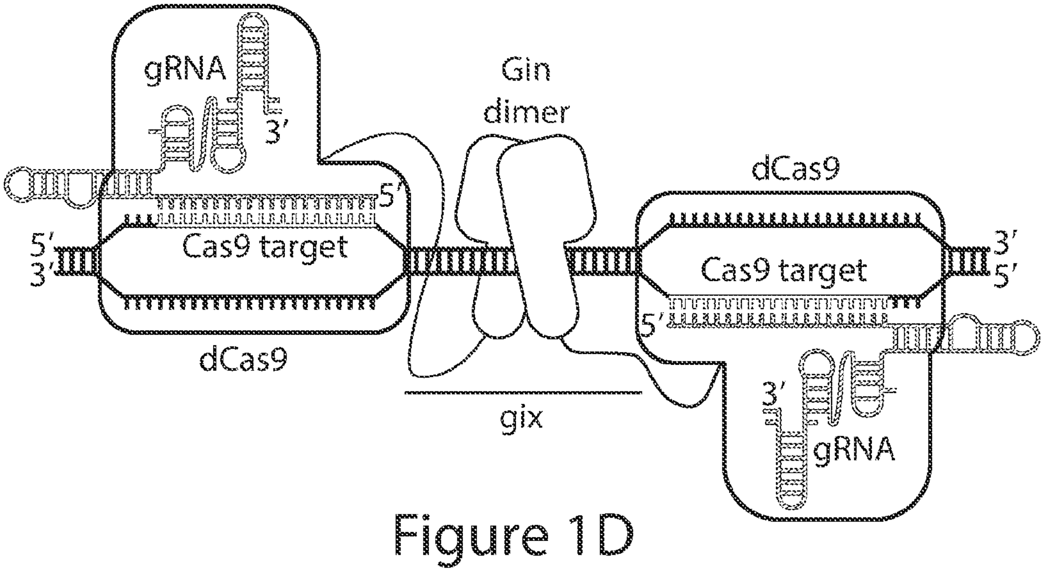

To assay the resulting dCas9-Ginβ (recCas9) fusions, a reporter plasmid containing two recCas9 target sites flanking a poly-A terminator that blocks EGFP transcription was constructed (FIGS. 1A-1C). Each recCas9 target site consisted of a gix core pseudo-site flanked by sites matching a guide RNA protospacer sequence. Recombinase-mediated deletion removed the terminator, restoring transcription of EGFP. HEK293T cells were cotransfected with this reporter plasmid, a plasmid transcribing a guide RNA(s), and a plasmid producing candidate dCas9-Ginβ fusion proteins, and the fraction of cells exhibiting EGFP fluorescence was used to assess the relative activity of each fusion construct.

Figure 2A:
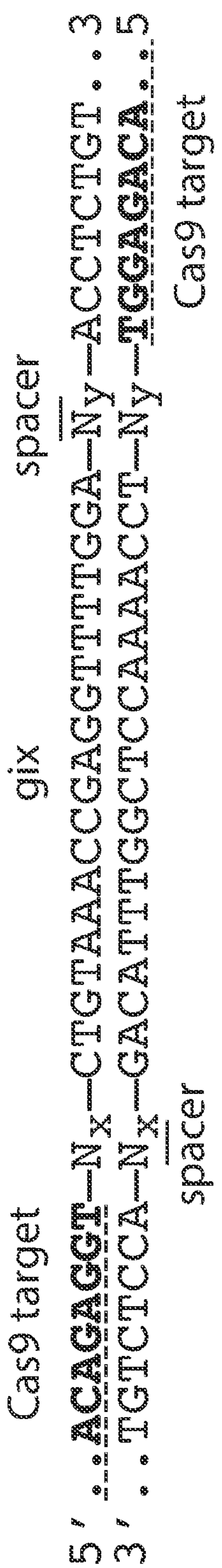
FIGS. 2A-2F. Optimization of fusion linker lengths and target site spacer variants. A single target guide RNA expression vector, pHU6-NT1, or non-target vector pHU6-BC74 was used in these experiments. The sequences can be found in Tables 6-9.
Figure 2B:
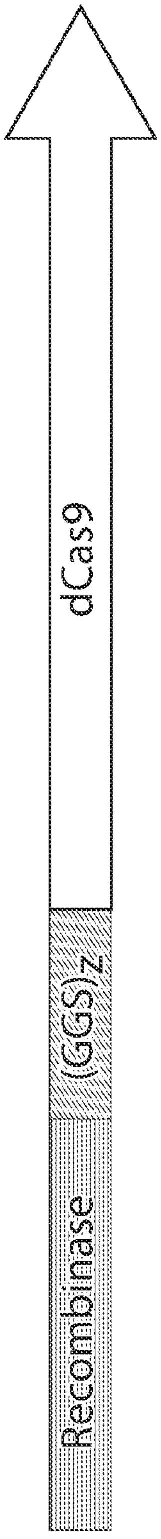
Figure 2C:
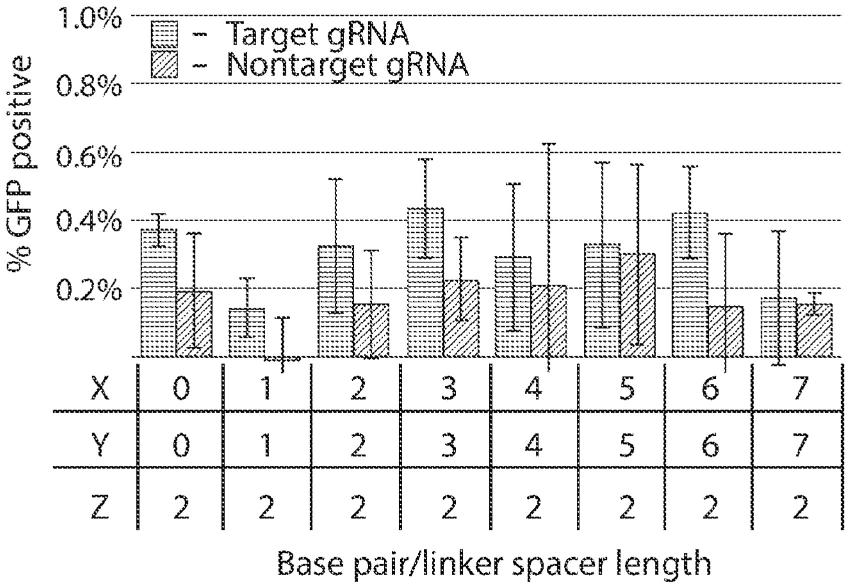
Figure 2D:
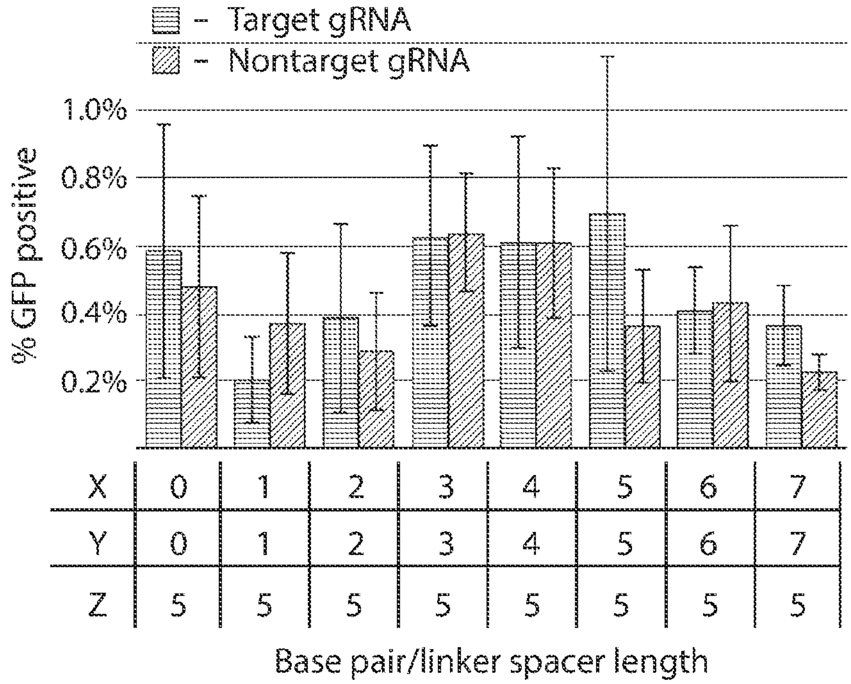
Figure 2E:
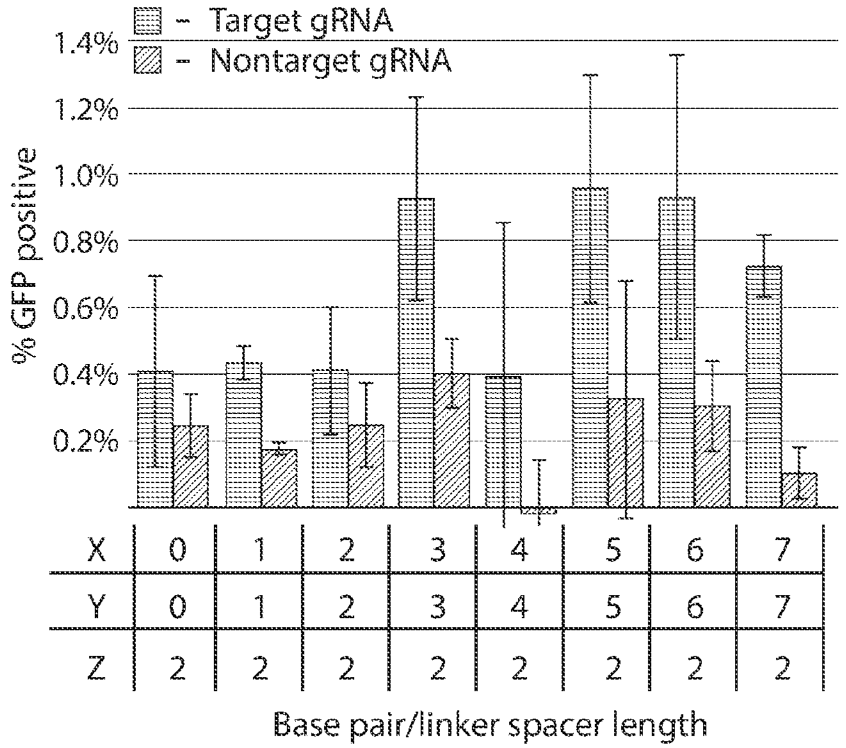
Figure 2F:
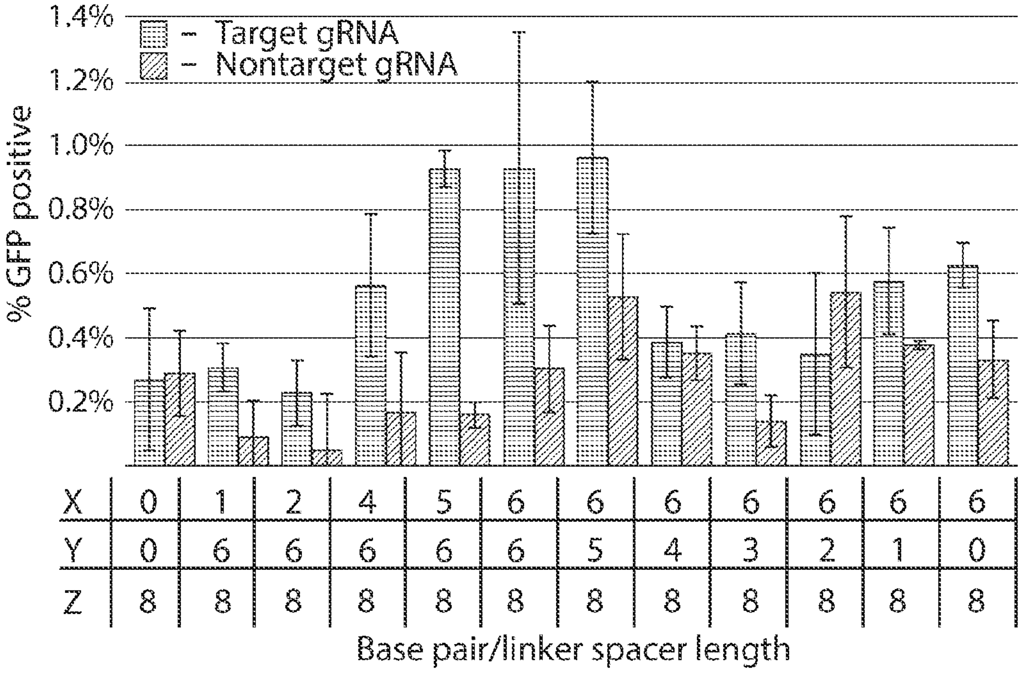

Parameters influencing the architecture of the recCas9 components, including the spacing between the core gix site and the guide RNA-binding site (from 0 to 7 bp), as well as linker length between the dCas9 and Ginβ moieties ($(GGS)_2$ (SEQ ID NO: 182), $(GGS)_5$ (SEQ ID NO: 701), or $(GGS)_8$ (SEQ ID NO: 183)) were varied (FIGS. 2A-2F). Most fusion architectures resulted in no observable guide RNA-dependent EGFP expression (FIGS. 1C-1D). However, one fusion construct containing a linker of eight GGS repeats and 3- to 6-base pair spacers resulted in approximately 1% recombination when a matched, but not mismatched, guide RNA was present (FIGS. 2E-2F). Recombination activity was consistently higher when 5-6 base pairs separated the dCas9 binding sites from the core (FIG. 2F). These results collectively reveal that specific fusion architectures between dCas9 and Ginβ can result in guide RNA-dependent recombination activity at spacer-flanked gix-related core sites in human cells. The 8×GGS linker fusion construct is referred to as "recCas9".

Targeting DNA Sequences Found in the Human Genome with recCas9

Low levels of observed activity may be caused by a suboptimal guide RNA sequence or core gix sequence, consistent with previous reports showing that the efficiency of guide RNA:Cas9 binding is sequence-dependent (see, e.g., Xu et al., Sequence determinants of improved CRISPR sgRNA design. Genome research 25, 1147-1157 (2015), the entire contents of which is hereby incorporated by reference). Moreover, although the present optimization was conducted with the native gix core sequence (see, e.g., Klippel et al., The DNA Invertase Gin of Phage Mu—Formation of a Covalent Complex with DNA Via a Phosphoserine at Amino-Acid Position-9. Embo Journal 7, 1229-1237 (1988); Mertens et al., Site-specific recombination in bacteriophage Mu: characterization of binding sites for the DNA invertase Gin. The EMBO journal 7, 1219-1227 (1988); Plasterk et al., DNA inversions in the chromosome of *Escherichia coli* and in bacteriophage Mu: relationship to other site-specific recombination systems. Proceedings of the National Academy of Sciences of the United States of America 80, 5355-5358 (1983); the entire contents of each of which are hereby incorporated by reference), several studies have shown that zinc finger-Gin or TALE-Gin fusions are active, and in some cases more active, on slightly altered core sites. See, e.g., Gordley et al., 3rd, Synthesis of programmable integrases. Proceedings of the National Academy of Sciences of the United States of America 106, 5053-5058 (2009); Gersbach et al., Targeted plasmid integration into the human genome by an engineered zinc-finger recombinase. Nucleic acids research 39, 7868-7878 (2011); Mercer et al., Chimeric TALE recombinases with programmable DNA sequence specificity. Nucleic acids research 40, 11163-11172 (2012); Gaj et al., A comprehensive approach to zinc-finger recombinase customization enables genomic targeting in human cells. Nucleic acids research 41, 3937-3946 (2013); Gordley et al., 3rd, Evolution of programmable zinc finger-recombinases with activity in human cells. J Mol Biol 367, 802-813 (2007); Gersbach et al., 3rd, Directed evolution of recombinase specificity by split gene reassembly. Nucleic acids research 38, 4198-4206 (2010); and Gaj et al., Structure-guided reprogramming of serine recombinase DNA sequence specificity. Proceedings of the National Academy of Sciences of the United States of America 108, 498-503 (2011); the entire contents of each of which are hereby incorporated by reference). Thus, sequences found within the human genome were targeted in order to test if unmodified human genomic sequences were capable of being targeted by recCas9 and to test if varying the guide RNA and core sequences would increase recCas9 activity.

To identify potential target sites, previous findings that characterized evolved Gin variants (see, e.g., Gaj et al., A comprehensive approach to zinc-finger recombinase customization enables genomic targeting in human cells. Nucleic acids research 41, 3937-3946 (2013), the entire contents of which is hereby incorporated by reference) as well as the observations above were used. Using this information, the human genome was searched for sites that contained CCN$_{(30-31)}$-AAASSWWSSTTT-N$_{(30-31)}$-GG (SEQ ID NO: 699), where W is A or T, S is G or C, and N is any nucleotide. The N$_{(30-31)}$ includes the N of the NGG protospacer adjacent motif (PAM), the 20-base pair Cas9 binding site, a 5- to 6-base pair spacing between the Cas9 and gix sites, and the four outermost base pairs of the gix core site. The internal 12 base pairs of the gix core site (AAASSWWSSTTT, SEQ ID NO: 699) were previously determined to be important for Ginβ activity (see, e.g., Gaj et al., Nucleic acids research 41, 3937-3946 (2013).

Figure 3A:
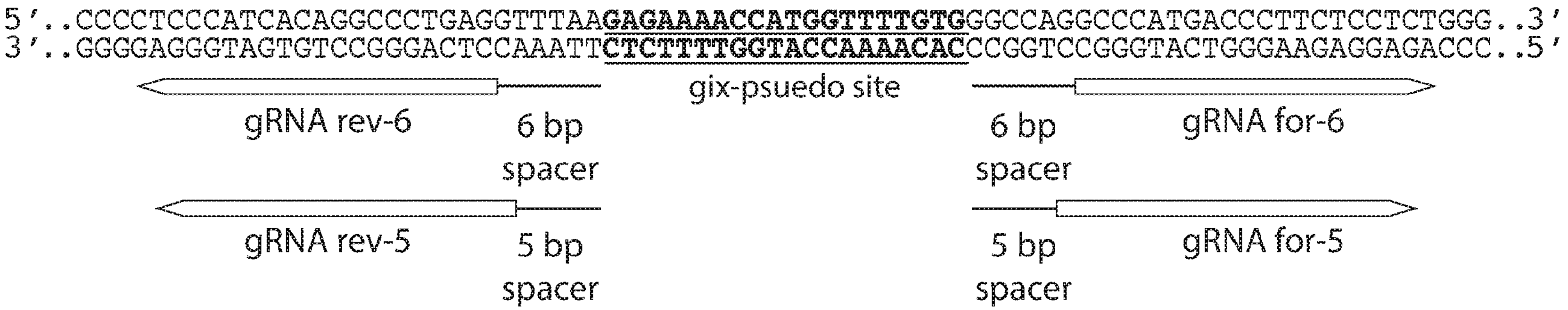
FIGS. 3A-3B. The dependence of forward and reverse guide RNAs on recCas9 activity.

The search revealed approximately 450 such loci in the human genome (Table 9). A reporter construct was created, containing the sequence identical to one of these genomic loci, found in PCDH15, and then guide RNA expression vectors were constructed to direct recCas9 to this sequence (FIG. 3A). These vectors encoded two pairs of guide RNAs, each of which contain spacer sequences that match the 5' and 3' regions flanking the PCDH15 psuedo gix sites. Co-transfection of the reporter plasmid, combinations of these flanking guide RNA expression vectors, and the recCas9 expression vector resulted in EGFP expression in 11%-13% of transfected cells (FIG. 3B), representing a >10-fold improvement in activity over the results shown in FIG. 2. These findings demonstrate that a more judicious choice of recCas9 target sequences can result in substantially improved recombination efficiency at DNA sequences matching those found in the human genome.

Figure 3B:
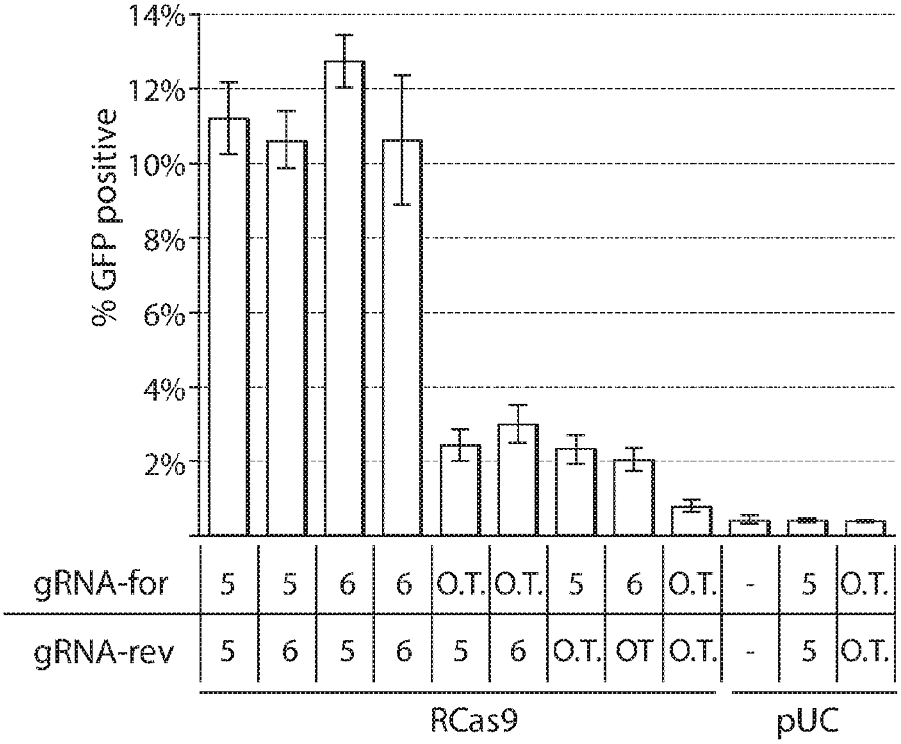

Next, whether both guide RNA sequences were required to cause recCas9-mediated deletion was determined. HEK293T cells were co-transfected with just one of the guide RNA vectors targeting the 5' or 3' flanking sequences of the PCDH15 psuedo-gix core site, the PCDH15 reporter plasmid, and a recCas9 expression vector. These co-transfections resulted in 2.5-3% EGFP expression (FIG. 3B). The low levels of activity observed upon expression of just one of the targeting guide RNAs and recCas9 may be caused by the propensity of hyperactivated gix monomers to form dimers (see, e.g., Gaj et al., Enhancing the Specificity of Recombinase-Mediated Genome Engineering through Dimer Interface Redesign. J Am Chem Soc 136, 5047-5056 (2014), the entire contents of which is hereby incorporated by reference); transient dimerization may occasionally allow a single protospacer sequence to localize the dimer to a target site. No activity was detected above background when using off-target guide RNA vectors or when the recCas9 vector was replaced by pUC (FIG. 3B).

These findings demonstrate that recCas9 activity can be increased substantially over the modest activity observed in the initial experiments by choosing different target sites and matching guide RNA sequences. A greater than 10-fold increase in activity on the PCDH15 site compared to the original target sequences was observed (compare FIG. 3B with FIG. 2F). Further, maximal recombination activity is dependent on the presence of both guide RNAs and recCas9.

Orthogonality of recCas9

Next, whether recCas9 could target multiple, separate loci matching sequences found in the human genome in an orthogonal manner was tested. A subset of the recCas9 target sites in the human genome based on their potential use as a safe-harbor loci for genomic integration, or in one case, based on their location within a gene implicated in genetic disease, were selected.

To identify these sites, ENSEMBL (release 81) was searched to identify which predicted recCas9 target sites fall within annotated genes (see, e.g., Cunningham et al., Ensembl 2015. Nucleic acids research 43, D662-669 (2015), the entire contents of which is hereby incorporated by reference). One such site fell within an intronic region of FGF14. Mutations within FGF14 are believed to cause spinocerebellar ataxia 27 (SCA 27) (see, e.g., van Swieten et al., A mutation in the fibroblast growth factor 14 gene is associated with autosomal dominant cerebellar ataxia [corrected]. Am J Hum Genet 72, 191-199 (2003); Brusse et al., Spinocerebellar ataxia associated with a mutation in the fibroblast growth factor 14 gene (SCA27): A new phenotype. Mov Disord 21, 396-401 (2006); Choquet et al., A novel frameshift mutation in FGF14 causes an autosomal dominant episodic ataxia. Neurogenetics 16, 233-236 (2015); Coebergh et al., A new variable phenotype in spinocerebellar ataxia 27 (SCA 27) caused by a deletion in the FGF14 gene. Eur J Paediatr Neurol 18, 413-415 (2014); Shimojima et al., Spinocerebellar ataxias type 27 derived from a disruption of the fibroblast growth factor 14 gene with mimicking phenotype of paroxysmal non-kinesigenic dyskinesia. Brain Dev 34, 230-233 (2012); the entire contents of each of which are incorporated herein by reference). Finally, a fraction of the predicted recCas9 target sites that did not fall within genes were manually interrogated to determine if some sequences fell within safe harbor loci. Using annotations in ENSEMBL genomic targets that matched most of the five criteria for safe harbor loci described by Bushman and coworkers were identified (Cunningham et al., Ensembl 2015. Nucleic acids research 43, D662-669 (2015); and Sadelain et al., Safe harbours for the integration of new DNA in the human genome. Nat Rev Cancer 12, 51-58 (2012); the entire contents of each of which are incorporated herein by reference). Five reporters and corresponding guide RNA vector pairs containing sequences identical to those in the genome were constructed. To evaluate the orthogonality of recCas9 when programmed with different guide RNAs, all combinations of five guide RNA pairs with five reporters were tested.

Figure 4A:
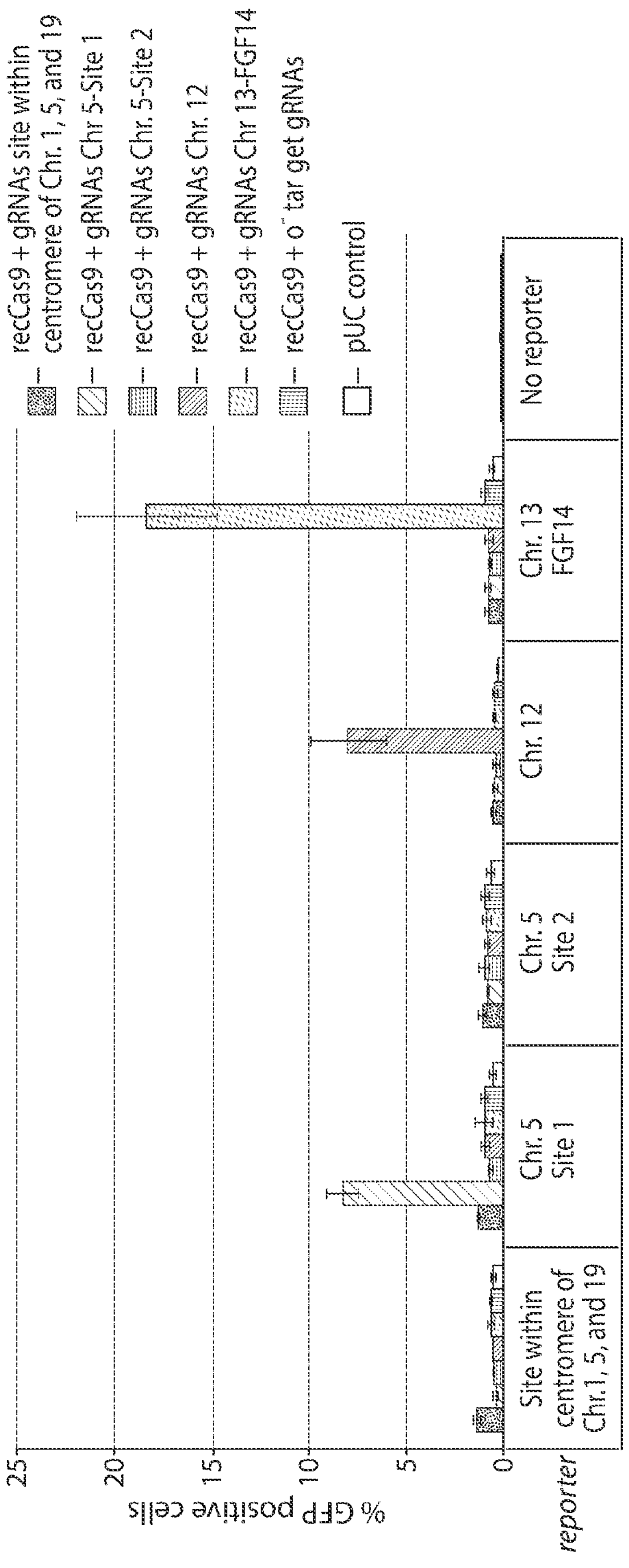

Cotransfection of reporter, guide RNA plasmids, and recCas9 expression vectors revealed that three of the five reporters tested resulted in substantial levels of EGFP-positive cells consistent with recCas9-mediated recombination. This EGFP expression was strictly dependent upon cotransfection with a recCas9 expression vector and guide RNA plasmids matching the target site sequences on the reporter construct (FIG. 4A). The same guide RNA pairs that caused recombination when cotransfected with cognate reporter plasmids and a recCas9 vector were unable to mediate recombination when cotransfected with non-cognate reporter plasmids (FIG. 4A). These results demonstrate that recCas9 activity is orthogonal and will only catalyze recombination at a gix related core sites when programmed with a pair of guide RNAs matching the flanking sequences. No recombinase activity above the background level of the assay was observed when reporter plasmids were transfected without vectors expressing recCas9 and guide RNAs.

Characterization of recCas9 Products

The products of recCas9-mediated recombination of the reporter plasmids were characterized to confirm that EGFP expression was a result of recCas9-mediated removal of the poly-A terminator sequence. Reporter plasmids were sequenced for chromosome 5-site 1, chromosome 12, and chromosome 13 (FGF14 locus) after cotransfection with recCas9 expression vectors and with plasmids producing cognate or non-cognate guide RNA pairs. After incubation for 72 hours, episomal DNA was extracted (as described above) and transformed into *E. coli* to isolate reporter plasmids. Single colonies containing reporter plasmids were sequenced (FIG. 4B).

Individual colonies were expected to contain either an unmodified or a recombined reporter plasmid (FIG. 4C). For each biological replicate, an average of 97 colonies transformed with reporter plasmid isolated from each transfection condition were sequenced. Recombined plasmids were only observed if reporter plasmids were previously cotransfected with cognate guide RNA plasmids and recCas9 expression vectors (FIG. 4D). In two separate experiments, the percent of recombined plasmid ranged from 12% for site 1 in chromosome 5 to an average of 32% for the FGF14 locus in chromosome 13. The sequencing data therefore were consistent with the earlier flow cytometry analysis in FIG. 4A. The absolute levels of recombined plasmid were somewhat higher than the percent of EGFP-positive cells (FIG. 4). This difference likely arises because the flow cytometry assay does not report on multiple recombination events that can occur when multiple copies of the reporter plasmid are present in a single cell; even a single recombination event may result in EGFP fluorescence. As a result, the percentage of EGFP-positive cells may correspond to a lower limit on the actual percentage of recombined reporter plasmids. Alternatively, the difference may reflect the negative correlation between plasmid size and transformation efficiency (see, e.g., Hanahan, Studies on transformation of *Escherichia coli* with plasmids. J Mol Biol 166, 557-580 (1983), the entire contents of which is hereby incorporated by reference); the recombined plasmid is approximately 5,700 base pairs and may transform slightly better than the intact plasmid, which is approximately 6,900 base pairs.

Since zinc finger-recombinases have been reported to cause mutations at recombinase core-site junctions (see, e.g., Gaj et al., A comprehensive approach to zinc-finger recombinase customization enables genomic targeting in human cells. Nucleic acids research 41, 3937-3946 (2013), the entire contents of which is hereby incorporated by reference), whether such mutagenesis occurs from recCas9 treatment was tested. In the reporter construct, recCas9 should delete kanR and the poly-A terminator by first cleaving the central dinucleotide of both gix core sites and then religating the two cores to each other (FIG. 4C). Thus, the recombination product should be a single recombination site consisting of the first half of the 'left' target site and the second half of the 'right' target site. Erroneous or incomplete reactions could result in other products. Strikingly, all of the 134 recombined sequences examined contained the expected recombination products. Further, a total of 2,317 sequencing reads from two separate sets of transfection experiments revealed only three sequencing reads containing potential deletion products at otherwise non-recombined plasmids.

One of these deletion-containing reads was observed in a chromosome 12 reporter plasmid that was transfected with the pUC control and lacked both recCas9 target sites as well as the polyA terminator. This product was attributed to DNA damage that occurred during the transfection, isolation, or subsequent manipulation. Because recCas9 may only localize to sequences when cotransfected with reporter and cognate guide RNA expression vectors, a more relevant metric may be to measure the total number of deletion products observed when reporter plasmids are cotransfected with cognate guide RNA vectors and recCas9 expression vectors. A single indel was observed out of a total of 185 plasmids sequenced from cotransfections with the chromosome 5-site 1 reporter and cognate guide RNA. Similarly, one indel was observed out of 204 plasmids from the chromosome 12 reporter following transfection with cognate guide RNA and recCas9 expression vectors. Notably, out of 202 sequencing reads, no indels were observed from the chromosome 13 reporter following cognate guide RNA and recCas9 cotransfection, despite resulting in the highest observed levels of recombination. These observations collectively suggest that recCas9 mediates predominantly error-free recombination.

Taken together, these results establish that recCas9 can target multiple sites found within the human genome with minimal cross-reactivity or byproduct formation. Substrates undergo efficient recombination only in the presence of cognate guide RNA sequences and recCas9, give clean recombination products in human cells, and generally do not result in mutations at the core-site junctions or products such as indels that arise from cellular DNA repair.

RecCas9-Mediated Genomic Deletion

Finally, whether recCas9 is capable of operating directly on the genomic DNA of cultured human cells was investigated. Using the list of potential recCas9 recognition sites in the human genome (Table 9), pairs of sites that, if targeted by recCas9, would yield chromosomal deletion events detectable by PCR, were sought. Guide RNA expression vectors were designed to direct recCas9 to those recCas9 sites closest to the chromosome 5-site 1 or chromosome 13 (FGF14 locus), sites which were both shown to be recombined in transient transfection assays (FIG. 4). The new target sites ranged from approximately 3 to 23 Mbp upstream and 7 to 10 Mbp downstream of chromosome 5-site 1, and 12 to 44 Mbp upstream of the chromosome 13-FGF14 site. The recCas9 expression vector was cotransfected with each of these new guide RNA pairs and the validated guide RNA pairs used for chromosome 5-site 1 or chromosome 13-FGF14, but evidence of chromosomal deletions by genomic PCR was not observed.

Figures 5C, 5D:
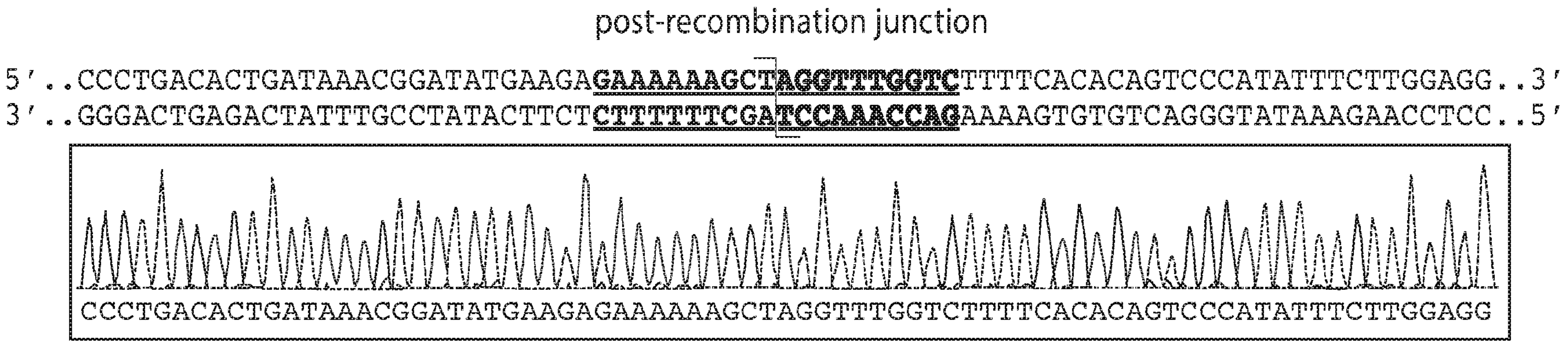

It was thought that genomic deletion might be more efficient if the recCas9 target sites were closer to each other on the genome. Two recCas9 sites separated by 14.2 kb within an intronic region of FAM19A2 were identified; these sites also contained identical dinucleotide cores which should facilitate deletion. FAM19A2 is one of five closely related TAFA-family genes encoding small, secreted proteins that are thought to have a regulatory role in immune and nerve cells (see, e.g., Parker et al., Admixture mapping identifies a quantitative trait locus associated with FEV1/FVC in the COPDGene Study. Genet Epidemiol 38, 652-659 (2014), the entire contents of which is hereby incorporated by reference). Small nucleotide polymorphisms located in intronic sequences of FAM19A2 have been associated with elevated risk for systemic lupus erythematosus (SLE) and chronic obstructive pulmonary disease (COPD) in genome-wide association studies (see, e.g., Parker et al., Admixture mapping identifies a quantitative trait locus associated with FEV1/FVC in the COPDGene Study. Genet Epidemiol 38, 652-659 (2014), the entire contents of which is hereby incorporated by reference); deletion of the intronic regions of this gene might therefore provide insights into the causes of these diseases. Four guide RNA sequences were cloned in expression vectors designed to mediate recCas9 deletion between these two FAM19A2 sites. Vectors expressing these guide RNAs were cotransfected with the recCas9 expression vector (FIG. 5A). RecCas9-mediated recombination between the two sites should result in deletion of the 14.2 kb intervening region. Indeed, this deletion event was detected by nested PCR using gene-specific primers that flank the two FAM19A2 recCas9 targets. The expected PCR product that is consistent with recCas9-mediated deletion was observed only in genomic DNA isolated from cells cotransfected with the recCas9 and all four guide RNA expression vectors (FIG. 5B). The deletion PCR product was not detected in the genomic DNA of cells transfected without either the upstream or downstream pair of guide RNA expression vectors alone, without the recCas9 expression plasmid, or for the genomic DNA of untransfected control cells (FIG. 5B). The estimated limit of detection for these nested PCR products was approximately 1 deletion event per 5,500 chromosomal copies. The 415-bp PCR product corresponding to the predicted genomic deletion was isolated and sequenced. Sequencing confirmed that the PCR product matched the predicted junction expected from the recombinase-mediated genomic deletion and did not contain any insertions or deletions suggestive of NHEJ (FIG. 5C).

A lower limit on the minimum genomic deletion efficiency was estimated using nested PCR on the serial dilutions of genomic template (see above or, e.g., Sykes et al., Quantitation of targets for PCR by use of limiting dilution. Biotechniques 13, 444-449 (1992), the entire contents of which is hereby incorporated by reference, for greater detail). A given amount of genomic DNA that yields the recCas9-specific nested PCR product must contain at least one edited chromosome. To establish a lower limit on this recCas9-mediated genomic deletion event, nested PCR was performed on serial dilutions of genomic DNA (isolated from cells transfected with recCas9 and the four FAM19A2 guide RNA expression vectors) to determine the lowest concentration of genomic template DNA that results in a detectable deletion product. These experiments revealed a lower limit of deletion efficiency of 0.023±0.017% (average of three biological replicates) (FIG. 5D), suggesting that recCas9-mediated genomic deletion proceeds with at least this efficiency. Nested PCR of the genomic DNA of untransfected cells resulted in no product, with an estimated limit of detection of <0.0072% recombination.

Use of Other Alternative Recombinases

A Cre recombinase evolved to target a site in the Rosa locus of the human genome called "36C6" was fused to to dCas9. This fusion was then used to recombine a plasmid-based reporter containing the Rosa target site in a guide-RNA dependent fashion. FIG. 7A demonstrates the results of linker optimization using wild-type Cre and 36C6. The 1×2×, 5×, and 8× linkers shown are the number of GGS repeats in the linker. Reversion analysis demonstrated that making mutations to 36C6 fused to dCas9 could impact the relative guide dependence of the chimeric fusion (FIG. 7B). Reversions are labeled with their non-mutated amino acids. For example, position 306, which had been mutated to an M, was reverted to an I before the assay was performed. A GinB construct, targeting its cognate reporter, was used as a control for the experimental data shown in FIGS. 7A and 7B. The on-target guides were the chr13-102010574 guides (plasmids BC165 and 166). Abbreviations shown are GGS-36C6: dCas9-GGS-36C6; 2GGS-36C6 (using linker SEQ ID NO: 182): sdCas9-GGSGGS-36C6 (using linker SEQ ID NO: 182).

The target sequence used for 36C6 and all variant transfections is shown below: (guides—italics; Rosa site—bold):

(SEQ ID NO: 760)

CCT*AGGGAAGTGATCATAGCTGAG*TTTCTATCTCATGGTTTATGCTAAA

CTATATGTTGACATGTTGA*GGAGACTTAAGTCCAAAACC*TGG

In FIGS. 7A, 7B, 8, 9A, and 9B, the on-target guides for GinB were the chr13-102010574 guides (plasmids BC165 and 166). All off-target guides in FIGS. 7A, 7B, 8, 9A, and 9B were composed of the chr12-62418577 guides (BC163 and BC164).

PAMs were identified flanking the Rosa26 site in the human genome that could support dCas9 binding (FIG. 8, top). Guide RNAs and a plasmid reporter were then designed to test whether the endogenous protospacers could support dCas9-36C6 activity. A GinB construct, targeting its cognate reporter, was used as a control. See FIG. 8. Mix: equal parts mixture of all 5 linker variants between Cas9 and 36C6. For hRosa, the target sequence, including guide RNA tagets, are below: (guides—italics; Rosa site—bold)

(SEQ ID NO: 767)
CCT*GAAATAATGCAAGTGTAGAA*TAACTTTTTAAAATCTCATGGTTTAT
GCTAAACTATATGTTGACATAAG*AGTGGTGATAAGGCAACAGT*AGG

The on target guide plasmids for hRosa are identical to the other gRNA expression plasmids, except the protospacers are replaced with those shown above (FIG. 8).

Several tested Cre truncations of dCas9-Cre recombinase fusions are shown in FIG. 9A. Truncated variants of Cre recombinase fused to dCas9 showed both appreciable recombinase activity as well as a strict reliance on the presence of guide RNA in a Lox plasmid reporter system (FIG. 9B). Truncated variants are labeled with the residue at which the truncated Cre begins. The linker for all fusion proteins shown in FIGS. 9A and 9B is 8×GGS. Wild type Cre fused to dCas9 was used as a positive control. The target sequence used for 36C6 and all variant transfections is shown below: (guides—italics; Rosa site—bold):

(SEQ ID NO: 768)
CCT*AGGGAAGTGATCATAGCTGA*GTTTCTATCTCATGGTTTATGCTAAA
CTATATGTTGACATGTTGA*GGAGACTTAAGTCCAAAACC*TGG

The on-target guides used were the chr13-102010574 guides (plasmids BC165 and 166) and the off-target guides were the chr12-62418577 guide (BC163 and BC164).

REFERENCES

1. J. A. Doudna, E. Charpentier, Genome editing. The new frontier of genome engineering with CRISPR-Cas9. *Science* 346, 1258096 (2014).
2. M. R. Capecchi, Altering the genome by homologous recombination. *Science* 244, 1288-1292 (1989).
3. K. R. Thomas, K. R. Folger, M. R. Capecchi, High frequency targeting of genes to specific sites in the mammalian genome. Cell 44, 419-428 (1986).
4. A. Choulika, A. Perrin, B. Dujon, J. F. Nicolas, Induction of homologous recombination in mammalian chromosomes by using the I-SceI system of *Saccharomyces cerevisiae*. *Mol Cell Biol* 15, 1968-1973 (1995).
5. D. Carroll, Progress and prospects: zinc-finger nucleases as gene therapy agents. *Gene Ther* 15, 1463-1468 (2008).
6. J. C. Miller et al., A TALE nuclease architecture for efficient genome editing. *Nature biotechnology* 29, 143-U149 (2011).
7. J. K. Joung, J. D. Sander, TALENs: a widely applicable technology for targeted genome editing. *Nat Rev Mol Cell Biol* 14, 49-55 (2013).
8. P. Mali et al., RNA-guided human genome engineering via Cas9. *Science* 339, 823-826 (2013).
9. L. Cong et al., Multiplex genome engineering using CRISPR/Cas systems. *Science* 339, 819-823 (2013).
10. J. P. Guilinger, D. B. Thompson, D. R. Liu, Fusion of catalytically inactive Cas9 to FokI nuclease improves the specificity of genome modification. *Nature biotechnology*, (2014).
11. S. Q. Tsai et al., Dimeric CRISPR RNA-guided FokI nucleases for highly specific genome editing. *Nature biotechnology*, (2014).
12. H. Fung, D. M. Weinstock, Repair at single targeted DNA double-strand breaks in pluripotent and differentiated human cells. *PloS one* 6, e20514 (2011).
13. W. D. Heyer, K. T. Ehmsen, J. Liu, Regulation of homologous recombination in eukaryotes. *Annu Rev Genet* 44, 113-139 (2010).
14. D. Branzei, M. Foiani, Regulation of DNA repair throughout the cell cycle. *Nat Rev Mol Cell* Bio 9, 297-308 (2008).
15. V. T. Chu et al., Increasing the efficiency of homology-directed repair for CRISPR-Cas9-induced precise gene editing in mammalian cells. *Nature biotechnology*, (2015).
16. T. Maruyama et al., Increasing the efficiency of precise genome editing with CRISPR-Cas9 by inhibition of non-homologous end joining. *Nature biotechnology*, (2015).
17. S. Lin, B. T. Staahl, R. K. Alla, J. A. Doudna, Enhanced homology-directed human genome engineering by controlled timing of CRISPR/Cas9 delivery. *eLife* 3, e04766 (2014).
18. S. Turan, C. Zehe, J. Kuehle, J. H. Qiao, J. Bode, Recombinase-mediated cassette exchange (RMCE)—A rapidly-expanding toolbox for targeted genomic modifications. *Gene* 515, 1-27 (2013).
19. T. Gaj, S. J. Sirk, C. F. Barbas, Expanding the Scope of Site-Specific Recombinases for Genetic and Metabolic Engineering. *Biotechnology and bioengineering* 111, 1-15 (2014).
20. N. D. F. Grindley, K. L. Whiteson, P. A. Rice, Mechanisms of site-specific recombination. *Annu Rev Biochem* 75, 567-605 (2006).
21. C. R. Sclimenti, B. Thyagarajan, M. P. Calos, Directed evolution of a recombinase for improved genomic integration at a native human sequence. *Nucleic acids research* 29, 5044-5051 (2001).
22. R. Shah, F. Li, E. Voziyanova, Y. Voziyanov, Target-specific variants of Flp recombinase mediate genome engineering reactions in mammalian cells. *The FEBS journal* 282, 3323-3333 (2015).
23. J. Karpinski et al., Directed evolution of a recombinase that excises the provirus of most HIV-1 primary isolates with high specificity. *Nature biotechnology*, (2016).
24. F. Buchholz, A. F. Stewart, Alteration of Cre recombinase site specificity by substrate-linked protein evolution. *Nature biotechnology* 19, 1047-1052 (2001).
25. B. Thyagarajan, E. C. Olivares, R. P. Hollis, D. S. Ginsburg, M. P. Calos, Site-specific genomic integration in mammalian cells mediated by phage phiC31 integrase. *Mol Cell Biol* 21, 3926-3934 (2001).
26. B. Thyagarajan, M. J. Guimaraes, A. C. Groth, M. P. Calos, Mammalian genomes contain active recombinase recognition sites. *Gene* 244, 47-54 (2000).
27. A. Akopian, J. He, M. R. Boocock, W. M. Stark, Chimeric recombinases with designed DNA sequence recognition. *Proceedings of the National Academy of Sciences of the United States of America* 100, 8688-8691 (2003).
28. R. M. Gordley, C. A. Gersbach, C. F. Barbas, 3rd, Synthesis of programmable integrases. *Proceedings of the National Academy of Sciences of the United States of America* 106, 5053-5058 (2009).
29. M. M. Prorocic et al., Zinc-finger recombinase activities in vitro. *Nucleic acids research* 39, 9316-9328 (2011).

30. C. A. Gersbach, T. Gaj, R. M. Gordley, A. C. Mercer, C. F. Barbas, Targeted plasmid integration into the human genome by an engineered zinc-finger recombinase. *Nucleic acids research* 39, 7868-7878 (2011).
31. A. C. Mercer, T. Gaj, R. P. Fuller, C. F. Barbas, Chimeric TALE recombinases with programmable DNA sequence specificity. *Nucleic acids research* 40, 11163-11172 (2012).
32. T. Matsuda, C. L. Cepko, Controlled expression of transgenes introduced by in vivo electroporation. *Proceedings of the National Academy of Sciences of the United States of America* 104, 1027-1032 (2007).
33. N. E. Sanjana et al., A transcription activator-like effector toolbox for genome engineering. *Nature protocols* 7, 171-192 (2012).
34. T. Gaj, A. C. Mercer, S. J. Sirk, H. L. Smith, C. F. Barbas, A comprehensive approach to zinc-finger recombinase customization enables genomic targeting in human cells. *Nucleic acids research* 41, 3937-3946 (2013).
35. Y. Fu et al., High-frequency off-target mutagenesis induced by CRISPR-Cas nucleases in human cells. *Nature biotechnology* 31, 822-826 (2013).
36. J. Quan, J. Tian, Circular polymerase extension cloning of complex gene libraries and pathways. *PloS one* 4, e6441 (2009).
37. N. Hillson. (2010), vol. 2015, pp. CPEC protocol.
38. R. C. Gentleman et al., Bioconductor: open software development for computational biology and bioinformatics. *Genome Biol* 5, R80 (2004).
39. K. Motmans, S. Thirion, J. Raus, C. Vandevyver, Isolation and quantification of episomal expression vectors in human T cells. *Biotechniques* 23, 1044-1046 (1997).
40. B. Hirt, Selective extraction of polyoma DNA from infected mouse cell cultures. *J Mol Biol* 26, 365-369 (1967).
41. A. Klippel, G. Mertens, T. Patschinsky, R. Kahmann, The DNA Invertase Gin of Phage Mu—Formation of a Covalent Complex with DNA Via a Phosphoserine at Amino-Acid Position-9. *Embo Journal* 7, 1229-1237 (1988).
42. G. Mertens et al., Site-specific recombination in bacteriophage Mu: characterization of binding sites for the DNA invertase Gin. *The EMBO journal* 7, 1219-1227 (1988).
43. R. H. Plasterk, A. Brinkman, P. van de Putte, DNA inversions in the chromosome of *Escherichia coli* and in bacteriophage Mu: relationship to other site-specific recombination systems. *Proceedings of the National Academy of Sciences of the United States of America* 80, 5355-5358 (1983).
44. H. Xu et al., Sequence determinants of improved CRISPR sgRNA design. *Genome research* 25, 1147-1157 (2015).
45. R. M. Gordley, J. D. Smith, T. Graslund, C. F. Barbas, 3rd, Evolution of programmable zinc finger-recombinases with activity in human cells. *J Mol Biol* 367, 802-813 (2007).
46. C. A. Gersbach, T. Gaj, R. M. Gordley, C. F. Barbas, 3rd, Directed evolution of recombinase specificity by split gene reassembly. *Nucleic acids research* 38, 4198-4206 (2010).
47. T. Gaj, A. C. Mercer, C. A. Gersbach, R. M. Gordley, C. F. Barbas, Structure-guided reprogramming of serine recombinase DNA sequence specificity. *Proceedings of the National Academy of Sciences of the United States of America* 108, 498-503 (2011).
48. T. Gaj et al., *Enhancing the Specificity of Recombinase-Mediated Genome* Engineering through Dimer Interface Redesign. *J Am Chem Soc* 136, 5047-5056 (2014).
49. F. Cunningham et al., Ensembl 2015. *Nucleic acids research* 43, D662-669 (2015).
50. J. C. van Swieten et al., A mutation in the fibroblast growth factor 14 gene is associated with autosomal dominant cerebellar ataxia [corrected]. *Am J Hum Genet* 72, 191-199 (2003).
51. E. Brusse et al., Spinocerebellar ataxia associated with a mutation in the fibroblast growth factor 14 gene (SCA27): A new phenotype. *Mov Disord* 21, 396-401 (2006).
52. K. Choquet, R. La Piana, B. Brais, A novel frameshift mutation in FGF14 causes an autosomal dominant episodic ataxia. *Neurogenetics* 16, 233-236 (2015).
53. J. A. Coebergh et al., A new variable phenotype in spinocerebellar ataxia 27 (SCA 27) caused by a deletion in the FGF14 gene. *Eur J Paediatr Neurol* 18, 413-415 (2014).
54. K. Shimojima et al., Spinocerebellar ataxias type 27 derived from a disruption of the fibroblast growth factor 14 gene with mimicking phenotype of paroxysmal non-kinesigenic dyskinesia. *Brain Dev* 34, 230-233 (2012).
55. M. Sadelain, E. P. Papapetrou, F. D. Bushman, Safe harbours for the integration of new DNA in the human genome. *Nat Rev Cancer* 12, 51-58 (2012).
56. D. Hanahan, Studies on transformation of *Escherichia coli* with plasmids. *J Mol Biol* 166, 557-580 (1983).
57. M. M. Parker et al., Admixture mapping identifies a quantitative trait locus associated with FEV1/FVC in the COPDGene Study. *Genet Epidemiol* 38, 652-659 (2014).
58. P. J. Sykes et al., Quantitation of targets for PCR by use of limiting dilution. *Biotechniques* 13, 444-449 (1992).
59. A. Rath, R. Hromas, A. De Benedetti, Fidelity of end joining in mammalian episomes and the impact of Metnase on joint processing. *BMC Mol Biol* 15, 6 (2014).
60. P. Rebuzzini et al., New mammalian cellular systems to study mutations introduced at the break site by non-homologous end-joining. *DNA Repair* (*Amst*) 4, 546-555 (2005).
61. J. Smith, C. Baldeyron, I. De Oliveira, M. Sala-Trepat, D. Papadopoulo, The influence of DNA double-strand break structure on end-joining in human cells. *Nucleic acids research* 29, 4783-4792 (2001).
62. S. Turan et al., Recombinase-mediated cassette exchange (RMCE): traditional concepts and current challenges. *J Mol Biol* 407, 193-221 (2011).
63. S. J. Sirk, T. Gaj, A. Jonsson, A. C. Mercer, C. F. Barbas, Expanding the zinc-finger recombinase repertoire: directed evolution and mutational analysis of serine recombinase specificity determinants. *Nucleic acids research* 42, 4755-4766 (2014).
64. B. P. Kleinstiver et al., Broadening the targeting range of *Staphylococcus aureus* CRISPR-Cas9 by modifying PAM recognition. *Nature biotechnology* 33, 1293-1298 (2015).
65. B. P. Kleinstiver et al., Engineered CRISPR-Cas9 nucleases with altered PAM specificities. *Nature* 523, 481-U249 (2015).
66. K. M. Esvelt et al., Orthogonal Cas9 proteins for RNA-guided gene regulation and editing. *Nature methods* 10, 1116-1121 (2013).
67. B. Zetsche et al., Cpf1 Is a Single RNA-Guided Endonuclease of a Class 2 CRISPR-Cas System. *Cell* 163, 759-771 (2015).
68. K. Dormiani et al., Long-term and efficient expression of human beta-globin gene in a hematopoietic cell line using a new site-specific integrating non-viral system. *Gene Ther* 22, 663-674 (2015).

69. E. Wijnker, H. de Jong, Managing meiotic recombination in plant breeding. *Trends in plant science* 13, 640-646 (2008).
70. J. F. Petolino, V. Srivastava, H. Daniell, Editing Plant Genomes: a new era of crop improvement. *Plant Biotechnol J* 14, 435-436 (2016).

EQUIVALENTS AND SCOPE

Those skilled in the art will recognize, or be able to ascertain using no more than routine experimentation, many equivalents to the specific embodiments of the invention described herein. The scope of the present invention is not intended to be limited to the above description, but rather is as set forth in the appended claims.

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process.

Furthermore, it is to be understood that the invention encompasses all variations, combinations, and permutations in which one or more limitations, elements, clauses, descriptive terms, etc., from one or more of the claims or from relevant portions of the description is introduced into another claim. For example, any claim that is dependent on another claim can be modified to include one or more limitations found in any other claim that is dependent on the same base claim. Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise.

Where elements are presented as lists, e.g., in Markush group format, it is to be understood that each subgroup of the elements is also disclosed, and any element(s) can be removed from the group. It is also noted that the term "comprising" is intended to be open and permits the inclusion of additional elements or steps. It should be understood that, in general, where the invention, or aspects of the invention, is/are referred to as comprising particular elements, features, steps, etc., certain embodiments of the invention or aspects of the invention consist, or consist essentially of, such elements, features, steps, etc. For purposes of simplicity those embodiments have not been specifically set forth in haec verba herein. Thus for each embodiment of the invention that comprises one or more elements, features, steps, etc., the invention also provides embodiments that consist or consist essentially of those elements, features, steps, etc.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in different embodiments of the invention, to the tenth of the unit of the lower limit of the range, unless the context clearly dictates otherwise. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

In addition, it is to be understood that any particular embodiment of the present invention may be explicitly excluded from any one or more of the claims. Where ranges are given, any value within the range may explicitly be excluded from any one or more of the claims. Any embodiment, element, feature, application, or aspect of the compositions and/or methods of the invention, can be excluded from any one or more claims. For purposes of brevity, all of the embodiments in which one or more elements, features, purposes, or aspects is excluded are not set forth explicitly herein.

All publications, patents and sequence database entries mentioned herein, including those items listed above, are hereby incorporated by reference in their entirety as if each individual publication or patent was specifically and individually indicated to be incorporated by reference. In case of conflict, the present application, including any definitions herein, will control.

What is claimed is:

1. A fusion protein comprising:

(i) a Cas9 protein that binds a guide RNA (gRNA), wherein the gRNA is capable of binding a target DNA sequence on a target DNA molecule;

(ii) a linker comprising $(GGS)_8$ of SEQ ID NO: 183; and (iii) a Gin recombinase that binds to a gix core or gix-related core sequence on the target DNA molecule, wherein the Gin recombinase is an amino acid sequence that has at least 95% sequence identity with SEQ ID NO: 713, and wherein the amino acid sequence of Gin recombinase catalytic domain comprises one or more mutations from the group consisting of H106Y, I127L, I136R and G137F in SEQ ID NO:713, wherein the linker covalently connects the Cas9 protein and the Gin recombinase, wherein the gix core or gix-related core sequence is separated from the target DNA sequence by 3 to 7 base pairs, wherein the target DNA molecule comprises the gix core or gix-related core sequence flanked on either side by the gRNA target DNA sequence, and wherein the fusion protein catalyzes recombination on the target DNA molecule.

2. The fusion protein of claim 1, wherein the Cas9 protein is a nuclease inactive Cas9 (dCas9) protein.

3. The fusion protein of claim 2, wherein the amino acid sequence of the dCas9 protein has 95% or greater sequence identity with SEQ ID NO: 712.

4. The fusion protein of claim 1, wherein the Cas9 protein is a nuclease inactive Cas9 (dCas9) protein.

5. The fusion protein of claim 4, wherein the dCas9 protein comprises the amino acid sequence of SEQ ID NO: 712.

6. The fusion protein of claim 1, wherein the Gin recombinase comprises the amino acid sequence of SEQ ID NO: 713.

7. The fusion protein of claim 1, wherein the fusion protein comprises the amino acid sequence of SEQ ID NO: 185.

8. The fusion protein of claim 1, wherein the gix core comprises the nucleotide sequence NNNNAAASSWWSSTTTNNNN (SEQ ID NO: 19), wherein N is defined as any nucleotide sequence, W is an A or a T, and S is a G or a C.

9. The fusion protein of claim 1, wherein the gix core comprises the nucleotide sequence CTGTAAACCGAGGTTTTGGA (SEQ ID NO: 700).

10. The fusion protein of claim 1, wherein the distance between the gix core or gix-related core sequence and the target DNA sequence is from 5 to 6 base pairs.

11. The fusion protein of claim 1, wherein at least two of residues Y106, L127, R136, and F137 of the Gin recombinase are not mutated relative to SEQ ID NO: 713.

12. The fusion protein of claim 1 further comprising one or more affinity tags.

13. The fusion protein of claim 12, wherein the one or more affinity tags are selected from the group consisting of FLAG tags, polyhistidine (poly-His) tags, polyarginine (poly-Arg) tags, Myc tags, and HA tags.

* * * * *

SEQUENCE LISTING

```
<160> NUMBER OF SEQ ID NOS: 777

<210> SEQ ID NO 1
<211> LENGTH: 1368
<212> TYPE: PRT
<213> ORGANISM: Artificial Sequence
<220> FEATURE:
<223> OTHER INFORMATION: Synthetic Polypeptide

<400> SEQUENCE: 1

Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45
```

-continued

```
Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460
```

-continued

```
Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp Ala Ile Val Pro Gln Ser Phe Leu Lys
        835                 840                 845

Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Lys Met Lys
865                 870                 875                 880
```

-continued

```
Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys  Tyr Pro Lys Leu Glu  Ser Glu Phe
        995                 1000                1005

Val Tyr  Gly Asp Tyr Lys Val  Tyr Asp Val Arg Lys  Met Ile Ala
    1010                1015                1020

Lys Ser  Glu Gln Glu Ile Gly  Lys Ala Thr Ala Lys  Tyr Phe Phe
    1025                1030                1035

Tyr Ser  Asn Ile Met Asn Phe  Phe Lys Thr Glu Ile  Thr Leu Ala
    1040                1045                1050

Asn Gly  Glu Ile Arg Lys Arg  Pro Leu Ile Glu Thr  Asn Gly Glu
    1055                1060                1065

Thr Gly  Glu Ile Val Trp Asp  Lys Gly Arg Asp Phe  Ala Thr Val
    1070                1075                1080

Arg Lys  Val Leu Ser Met Pro  Gln Val Asn Ile Val  Lys Lys Thr
    1085                1090                1095

Glu Val  Gln Thr Gly Gly Phe  Ser Lys Glu Ser Ile  Leu Pro Lys
    1100                1105                1110

Arg Asn  Ser Asp Lys Leu Ile  Ala Arg Lys Lys Asp  Trp Asp Pro
    1115                1120                1125

Lys Lys  Tyr Gly Gly Phe Asp  Ser Pro Thr Val Ala  Tyr Ser Val
    1130                1135                1140

Leu Val  Val Ala Lys Val Glu  Lys Gly Lys Ser Lys  Lys Leu Lys
    1145                1150                1155

Ser Val  Lys Glu Leu Leu Gly  Ile Thr Ile Met Glu  Arg Ser Ser
    1160                1165                1170

Phe Glu  Lys Asn Pro Ile Asp  Phe Leu Glu Ala Lys  Gly Tyr Lys
    1175                1180                1185

Glu Val  Lys Lys Asp Leu Ile  Ile Lys Leu Pro Lys  Tyr Ser Leu
    1190                1195                1200

Phe Glu  Leu Glu Asn Gly Arg  Lys Arg Met Leu Ala  Ser Ala Gly
    1205                1210                1215

Glu Leu  Gln Lys Gly Asn Glu  Leu Ala Leu Pro Ser  Lys Tyr Val
    1220                1225                1230

Asn Phe  Leu Tyr Leu Ala Ser  His Tyr Glu Lys Leu  Lys Gly Ser
    1235                1240                1245

Pro Glu  Asp Asn Glu Gln Lys  Gln Leu Phe Val Glu  Gln His Lys
    1250                1255                1260

His Tyr  Leu Asp Glu Ile Ile  Glu Gln Ile Ser Glu  Phe Ser Lys
    1265                1270                1275
```

-continued

```
Arg Val  Ile Leu Ala Asp Ala  Asn Leu Asp Lys Val  Leu Ser Ala
    1280                 1285                 1290

Tyr Asn  Lys His Arg Asp Lys  Pro Ile Arg Glu Gln  Ala Glu Asn
    1295                 1300                 1305

Ile Ile  His Leu Phe Thr Leu  Thr Asn Leu Gly Ala  Pro Ala Ala
    1310                 1315                 1320

Phe Lys  Tyr Phe Asp Thr Thr  Ile Asp Arg Lys Arg  Tyr Thr Ser
    1325                 1330                 1335

Thr Lys  Glu Val Leu Asp Ala  Thr Leu Ile His Gln  Ser Ile Thr
    1340                 1345                 1350

Gly Leu  Tyr Glu Thr Arg Ile  Asp Leu Ser Gln Leu  Gly Gly Asp
    1355                 1360                 1365
```

<210> SEQ ID NO 2
<211> LENGTH: 4104
<212> TYPE: DNA
<213> ORGANISM: Streptococcus pyogenes

<400> SEQUENCE: 2

```
atggataaga aatactcaat aggcttagat atcggcacaa atagcgtcgg atgggcggtg     60

atcactgatg attataaggt tccgtctaaa aagttcaagg ttctgggaaa tacagaccgc    120

cacagtatca aaaaaaatct tataggggct cttttatttg gcagtggaga gacagcggaa    180

gcgactcgtc tcaaacggac agctcgtaga aggtatacac gtcggaagaa tcgtatttgt    240

tatctacagg agattttttc aaatgagatg gcgaaagtag atgatagttt ctttcatcga    300

cttgaagagt cttttttggt ggaagaagac aagaagcatg aacgtcatcc tatttttgga    360

aatatagtag atgaagttgc ttatcatgag aaatatccaa ctatctatca tctgcgaaaa    420

aaattggcag attctactga taaagcggat ttgcgcttaa tctatttggc cttagcgcat    480

atgattaagt ttcgtggtca tttttttgatt gagggagatt taaatcctga taatagtgat    540

gtggacaaac tatttatcca gttggtacaa atctacaatc aattatttga agaaaaccct    600

attaacgcaa gtagagtaga tgctaaagcg attctttctg cacgattgag taaatcaaga    660

cgattagaaa atctcattgc tcagctcccc ggtgagaaga gaaatggctt gtttgggaat    720

ctcattgctt tgtcattggg attgacccct aattttaaat caaattttga tttggcagaa    780

gatgctaaat tacagctttc aaaagatact tacgatgatg atttagataa tttattggcg    840

caaattggag atcaatatgc tgatttgttt ttggcagcta agaatttatc agatgctatt    900

ttactttcag atatcctaag agtaaatagt gaaataacta aggctcccct atcagcttca    960

atgattaagc gctacgatga acatcatcaa gacttgactc ttttaaaagc tttagttcga   1020

caacaacttc cagaaaagta taaagaaatc ttttttgatc aatcaaaaaa cggatatgca   1080

ggttatattg atgggggagc tagccaagaa gaattttata aatttatcaa accaatttta   1140

gaaaaaatgg atggtactga ggaattattg gtgaaactaa atcgtgaaga tttgctgcgc   1200

aagcaacgga cctttgacaa cggctctatt ccccatcaaa ttcacttggg tgagctgcat   1260

gctattttga gaagacaaga agacttttat ccatttttaa aagacaatcg tgagaagatt   1320

gaaaaaatct tgacttttcg aattccttat tatgttggtc cattggcgcg tggcaatagt   1380

cgttttgcat ggatgactcg gaagtctgaa gaaacaatta ccccatggaa ttttgaagaa   1440

gttgtcgata aaggtgcttc agctcaatca tttattgaac gcatgacaaa ctttgataaa   1500

aatcttccaa atgaaaaagt actaccaaaa catagtttgc tttatgagta ttttacggtt   1560

tataacgaat tgacaaaggt caaatatgtt actgagggaa tgcgaaaacc agcatttctt   1620
```

-continued

```
tcaggtgaac agaagaaagc cattgttgat ttactcttca aaacaaatcg aaaagtaacc   1680
gttaagcaat taaaagaaga ttatttcaaa aaaatagaat gttttgatag tgttgaaatt   1740
tcaggagttg aagatagatt taatgcttca ttaggcgcct accatgattt gctaaaaatt   1800
attaaagata aagatttttt ggataatgaa gaaaatgaag atatcttaga ggatattgtt   1860
ttaacattga ccttatttga agataggggg atgattgagg aaagacttaa aacatatgct   1920
cacctctttg atgataaggt gatgaaacag cttaaacgtc gccgttatac tggttgggga   1980
cgtttgtctc gaaaattgat taatggtatt agggataagc aatctggcaa aacaatatta   2040
gatttttga aatcagatgg ttttgccaat cgcaatttta tgcagctgat ccatgatgat   2100
agtttgacat ttaaagaaga tattcaaaaa gcacaggtgt ctggacaagg ccatagttta   2160
catgaacaga ttgctaactt agctggcagt cctgctatta aaaaaggtat tttacagact   2220
gtaaaaattg ttgatgaact ggtcaaagta atggggcata agccagaaaa tatcgttatt   2280
gaaatggcac gtgaaaatca gacaactcaa aagggccaga aaaattcgcg agagcgtatg   2340
aaacgaatcg aagaaggtat caaagaatta ggaagtcaga ttcttaaaga gcatcctgtt   2400
gaaaatactc aattgcaaaa tgaaaagctc tatctctatt atctacaaaa tggaagagac   2460
atgtatgtgg accaagaatt agatattaat cgtttaagtg attatgatgt cgatcacatt   2520
gttccacaaa gtttcattaa agacgattca atagacaata aggtactaac gcgttctgat   2580
aaaaatcgtg gtaaatcgga taacgttcca agtgaagaag tagtcaaaaa gatgaaaaac   2640
tattggagac aacttctaaa cgccaagtta atcactcaac gtaagtttga taatttaacg   2700
aaagctgaac gtggaggttt gagtgaactt gataaagctg gttttatcaa acgccaattg   2760
gttgaaactc gccaaatcac taagcatgtg gcacaaattt tggatagtcg catgaatact   2820
aaatacgatg aaaatgataa acttattcga gaggttaaag tgattacctt aaaatctaaa   2880
ttagtttctg acttccgaaa agatttccaa ttctataaag tacgtgagat taacaattac   2940
catcatgccc atgatgcgta tctaaatgcc gtcgttggaa ctgctttgat taagaaatat   3000
ccaaaacttg aatcggagtt tgtctatggt gattataaag tttatgatgt tcgtaaaatg   3060
attgctaagt ctgagcaaga aataggcaaa gcaaccgcaa aatatttctt ttactctaat   3120
atcatgaact tcttcaaaac agaaattaca cttgcaaatg gagagattcg caaacgccct   3180
ctaatcgaaa ctaatgggga aactggagaa attgtctggg ataaagggcg agattttgcc   3240
acagtgcgca aagtattgtc catgccccaa gtcaatattg tcaagaaaac agaagtacag   3300
acaggcggat tctccaagga gtcaatttta ccaaaaagaa attcggacaa gcttattgct   3360
cgtaaaaaag actgggatcc aaaaaaatat ggtggttttg atagtccaac ggtagcttat   3420
tcagtcctag tggttgctaa ggtggaaaaa gggaaatcga agaagttaaa atccgttaaa   3480
gagttactag ggatcacaat tatggaaaga agttcctttg aaaaaaatcc gattgacttt   3540
ttagaagcta aaggatataa ggaagttaaa aaagacttaa tcattaaact acctaaatat   3600
agtctttttg agttagaaaa cggtcgtaaa cggatgctgg ctagtgccgg agaattacaa   3660
aaaggaaatg agctggctct gccaagcaaa tatgtgaatt ttttatattt agctagtcat   3720
tatgaaaagt tgaagggtag tccagaagat aacgaacaaa aacaattgtt tgtggagcag   3780
cataagcatt atttagatga gattattgag caaatcagtg aattttctaa gcgtgttatt   3840
ttagcagatg ccaatttaga taaagttctt agtgcatata acaaacatag agacaaacca   3900
atacgtgaac aagcagaaaa tattattcat ttatttacgt tgacgaatct tggagctccc   3960
gctgctttta aatattttga tacaacaatt gatcgtaaac gatatacgtc tacaaaagaa   4020
```

-continued gttttagatg ccactcttat ccatcaatcc atcactggtc tttatgaaac acgcattgat 4080
ttgagtcagc taggaggtga ctga 4104

<210> SEQ ID NO 3
<211> LENGTH: 1367
<212> TYPE: PRT
<213> ORGANISM: Streptococcus pyogenes

<400> SEQUENCE: 3

```
Met Asp Lys Lys Tyr Ser Ile Gly Leu Asp Ile Gly Thr Asn Ser Val
1               5                   10                  15

Gly Trp Ala Val Ile Thr Asp Asp Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Gly Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Ala Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Ile Tyr
            180                 185                 190

Asn Gln Leu Phe Glu Glu Asn Pro Ile Asn Ala Ser Arg Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Arg Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Ser Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350
```

-continued

```
Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Ala Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Gly Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly His Ser Leu
705                 710                 715                 720

His Glu Gln Ile Ala Asn Leu Ala Gly Ser Pro Ala Ile Lys Lys Gly
                725                 730                 735

Ile Leu Gln Thr Val Lys Ile Val Asp Glu Leu Val Lys Val Met Gly
            740                 745                 750

His Lys Pro Glu Asn Ile Val Ile Glu Met Ala Arg Glu Asn Gln Thr
        755                 760                 765

Thr Gln Lys Gly Gln Lys Asn Ser Arg Glu Arg Met Lys Arg Ile Glu
```

```
    770                 775                 780

Glu Gly Ile Lys Glu Leu Gly Ser Gln Ile Leu Lys Glu His Pro Val
785                 790                 795                 800

Glu Asn Thr Gln Leu Gln Asn Glu Lys Leu Tyr Leu Tyr Tyr Leu Gln
                805                 810                 815

Asn Gly Arg Asp Met Tyr Val Asp Gln Glu Leu Asp Ile Asn Arg Leu
            820                 825                 830

Ser Asp Tyr Asp Val Asp His Ile Val Pro Gln Ser Phe Ile Lys Asp
        835                 840                 845

Asp Ser Ile Asp Asn Lys Val Leu Thr Arg Ser Asp Lys Asn Arg Gly
    850                 855                 860

Lys Ser Asp Asn Val Pro Ser Glu Glu Val Val Lys Lys Met Lys Asn
865                 870                 875                 880

Tyr Trp Arg Gln Leu Leu Asn Ala Lys Leu Ile Thr Gln Arg Lys Phe
                885                 890                 895

Asp Asn Leu Thr Lys Ala Glu Arg Gly Gly Leu Ser Glu Leu Asp Lys
            900                 905                 910

Ala Gly Phe Ile Lys Arg Gln Leu Val Glu Thr Arg Gln Ile Thr Lys
        915                 920                 925

His Val Ala Gln Ile Leu Asp Ser Arg Met Asn Thr Lys Tyr Asp Glu
    930                 935                 940

Asn Asp Lys Leu Ile Arg Glu Val Lys Val Ile Thr Leu Lys Ser Lys
945                 950                 955                 960

Leu Val Ser Asp Phe Arg Lys Asp Phe Gln Phe Tyr Lys Val Arg Glu
                965                 970                 975

Ile Asn Asn Tyr His His Ala His Asp Ala Tyr Leu Asn Ala Val Val
            980                 985                 990

Gly Thr Ala Leu Ile Lys Lys Tyr  Pro Lys Leu Glu Ser  Glu Phe Val
        995                 1000                1005

Tyr Gly  Asp Tyr Lys Val Tyr  Asp Val Arg Lys Met  Ile Ala Lys
    1010                 1015                 1020

Ser Glu  Gln Glu Ile Gly Lys  Ala Thr Ala Lys Tyr  Phe Phe Tyr
    1025                 1030                 1035

Ser Asn  Ile Met Asn Phe Phe  Lys Thr Glu Ile Thr  Leu Ala Asn
    1040                 1045                 1050

Gly Glu  Ile Arg Lys Arg Pro  Leu Ile Glu Thr Asn  Gly Glu Thr
    1055                 1060                 1065

Gly Glu  Ile Val Trp Asp Lys  Gly Arg Asp Phe Ala  Thr Val Arg
    1070                 1075                 1080

Lys Val  Leu Ser Met Pro Gln  Val Asn Ile Val Lys  Lys Thr Glu
    1085                 1090                 1095

Val Gln  Thr Gly Gly Phe Ser  Lys Glu Ser Ile Leu  Pro Lys Arg
    1100                 1105                 1110

Asn Ser  Asp Lys Leu Ile Ala  Arg Lys Lys Asp Trp  Asp Pro Lys
    1115                 1120                 1125

Lys Tyr  Gly Gly Phe Asp Ser  Pro Thr Val Ala Tyr  Ser Val Leu
    1130                 1135                 1140

Val Val  Ala Lys Val Glu Lys  Gly Lys Ser Lys Lys  Leu Lys Ser
    1145                 1150                 1155

Val Lys  Glu Leu Leu Gly Ile  Thr Ile Met Glu Arg  Ser Ser Phe
    1160                 1165                 1170

Glu Lys  Asn Pro Ile Asp Phe  Leu Glu Ala Lys Gly  Tyr Lys Glu
    1175                 1180                 1185
```

-continued

```
Val Lys  Lys Asp Leu Ile Ile  Lys Leu Pro Lys Tyr  Ser Leu Phe
    1190                 1195                 1200

Glu Leu  Glu Asn Gly Arg Lys  Arg Met Leu Ala Ser  Ala Gly Glu
    1205                 1210                 1215

Leu Gln  Lys Gly Asn Glu Leu  Ala Leu Pro Ser Lys  Tyr Val Asn
    1220                 1225                 1230

Phe Leu  Tyr Leu Ala Ser His  Tyr Glu Lys Leu Lys  Gly Ser Pro
    1235                 1240                 1245

Glu Asp  Asn Glu Gln Lys Gln  Leu Phe Val Glu Gln  His Lys His
    1250                 1255                 1260

Tyr Leu  Asp Glu Ile Ile Glu  Gln Ile Ser Glu Phe  Ser Lys Arg
    1265                 1270                 1275

Val Ile  Leu Ala Asp Ala Asn  Leu Asp Lys Val Leu  Ser Ala Tyr
    1280                 1285                 1290

Asn Lys  His Arg Asp Lys Pro  Ile Arg Glu Gln Ala  Glu Asn Ile
    1295                 1300                 1305

Ile His  Leu Phe Thr Leu Thr  Asn Leu Gly Ala Pro  Ala Ala Phe
    1310                 1315                 1320

Lys Tyr  Phe Asp Thr Thr Ile  Asp Arg Lys Arg Tyr  Thr Ser Thr
    1325                 1330                 1335

Lys Glu  Val Leu Asp Ala Thr  Leu Ile His Gln Ser  Ile Thr Gly
    1340                 1345                 1350

Leu Tyr  Glu Thr Arg Ile Asp  Leu Ser Gln Leu Gly  Gly Asp
    1355                 1360                 1365


<210> SEQ ID NO 4
<211> LENGTH: 4212
<212> TYPE: DNA
<213> ORGANISM: Artificial Sequence
<220> FEATURE:
<223> OTHER INFORMATION: Synthetic Polynucleotide

<400> SEQUENCE: 4

atggataaaa agtattctat tggtttagac atcggcacta attccgttgg atgggctgtc      60

ataaccgatg aatacaaagt accttcaaag aaatttaagg tgttggggaa cacagaccgt     120

cattcgatta aaaagaatct tatcggtgcc ctcctattcg atagtggcga aacggcagag     180

gcgactcgcc tgaaacgaac cgctcggaga aggtatacac gtcgcaagaa ccgaatatgt     240

tacttacaag aaatttttag caatgagatg gccaaagttg acgattcttt ctttcaccgt     300

ttggaagagt ccttccttgt cgaagaggac aagaaacatg aacggcaccc catctttgga     360

aacatagtag atgaggtggc atatcatgaa aagtacccaa cgatttatca cctcagaaaa     420

aagctagttg actcaactga taaagcggac ctgaggttaa tctacttggc tcttgcccat     480

atgataaagt tccgtgggca ctttctcatt gagggtgatc taaatccgga caactcggat     540

gtcgacaaac tgttcatcca gttagtacaa acctataatc agttgtttga agagaaccct     600

ataaatgcaa gtggcgtgga tgcgaaggct attcttagcg cccgcctctc taaatcccga     660

cggctagaaa acctgatcgc acaattaccc ggagagaaga aaaatgggtt gttcggtaac     720

cttatagcgc tctcactagg cctgacacca aattttaagt cgaacttcga cttagctgaa     780

gatgccaaat tgcagcttag taaggacacg tacgatgacg atctcgacaa tctactggca     840

caaattggag atcagtatgc ggacttattt ttggctgcca aaaaccttag cgatgcaatc     900

ctcctatctg acatactgag agttaatact gagattacca aggcgccgtt atccgcttca     960
```

```
atgatcaaaa ggtacgatga acatcaccaa gacttgacac ttctcaaggc cctagtccgt   1020
cagcaactgc ctgagaaata taaggaaata ttctttgatc agtcgaaaaa cgggtacgca   1080
ggttatattg acggcggagc gagtcaagag gaattctaca agtttatcaa acccatatta   1140
gagaagatgg atgggacgga agagttgctt gtaaaactca atcgcgaaga tctactgcga   1200
aagcagcgga ctttcgacaa cggtagcatt ccacatcaaa tccacttagg cgaattgcat   1260
gctatactta gaaggcagga ggatttttat ccgttcctca aagacaatcg tgaaaagatt   1320
gagaaaatcc taacctttcg cataccttac tatgtgggac ccctggcccg agggaactct   1380
cggttcgcat ggatgacaag aaagtccgaa gaaacgatta ctccatggaa ttttgaggaa   1440
gttgtcgata aaggtgcgtc agctcaatcg ttcatcgaga ggatgaccaa ctttgacaag   1500
aatttaccga acgaaaaagt attgcctaag cacagtttac tttacgagta tttcacagtg   1560
tacaatgaac tcacgaaagt taagtatgtc actgagggca tgcgtaaacc cgcctttcta   1620
agcggagaac agaagaaagc aatagtagat ctgttattca agaccaaccg caaagtgaca   1680
gttaagcaat tgaaagagga ctactttaag aaaattgaat gcttcgattc tgtcgagatc   1740
tccggggtag aagatcgatt taatgcgtca cttggtacgt atcatgacct cctaaagata   1800
attaaagata aggacttcct ggataacgaa gagaatgaag atatcttaga agatatagtg   1860
ttgactctta ccctctttga agatcgggaa atgattgagg aaagactaaa aacatacgct   1920
cacctgttcg acgataaggt tatgaaacag ttaaagaggc gtcgctatac gggctgggga   1980
cgattgtcgc ggaaacttat caacgggata agagacaagc aaagtggtaa aactattctc   2040
gattttctaa agagcgacgg cttcgccaat aggaacttta tgcagctgat ccatgatgac   2100
tctttaacct tcaaagagga tatacaaaag gcacaggttt ccggacaagg ggactcattg   2160
cacgaacata ttgcgaatct tgctggttcg ccagccatca aaaagggcat actccagaca   2220
gtcaaagtag tggatgagct agttaaggtc atgggacgtc acaaaccgga aaacattgta   2280
atcgagatgg cacgcgaaaa tcaaacgact cagaaggggc aaaaaaacag tcgagagcgg   2340
atgaagagaa tagaagaggg tattaaagaa ctgggcagcc agatcttaaa ggagcatcct   2400
gtggaaaata cccaattgca gaacgagaaa ctttacctct attacctaca aaatggaagg   2460
gacatgtatg ttgatcagga actggacata aaccgtttat ctgattacga cgtcgatcac   2520
attgtacccc aatccttttt gaaggacgat tcaatcgaca ataaagtgct tacacgctcg   2580
gataagaacc gagggaaaag tgacaatgtt ccaagcgagg aagtcgtaaa gaaaatgaag   2640
aactattggc ggcagctcct aaatgcgaaa ctgataacgc aaagaaagtt cgataactta   2700
actaaagctg agaggggtgg cttgtctgaa cttgacaagg ccggatttat taaacgtcag   2760
ctcgtggaaa cccgccaaat cacaaagcat gttgcacaga tactagattc ccgaatgaat   2820
acgaaatacg acgagaacga taagctgatt cgggaagtca aagtaatcac tttaaagtca   2880
aaattggtgt cggacttcag aaaggatttt caattctata aagttaggga gataaataac   2940
taccaccatg cgcacgacgc ttatcttaat gccgtcgtag ggaccgcact cattaagaaa   3000
tacccgaagc tagaaagtga gtttgtgtat ggtgattaca aagtttatga cgtccgtaag   3060
atgatcgcga aaagcgaaca ggagataggc aaggctacag ccaaatactt cttttattct   3120
aacattatga atttctttaa gacggaaatc actctggcaa acggagagat acgcaaacga   3180
cctttaattg aaaccaatgg ggagacaggt gaaatcgtat gggataaggg ccgggacttc   3240
gcgacggtga gaaaagtttt gtccatgccc caagtcaaca tagtaaagaa aactgaggtg   3300
cagaccggag ggttttcaaa ggaatcgatt cttccaaaaa ggaatagtga taagctcatc   3360
```

gctcgtaaaa aggactggga cccgaaaaag tacggtggct tcgatagccc tacagttgcc 3420
tattctgtcc tagtagtggc aaaagttgag aagggaaaat ccaagaaact gaagtcagtc 3480
aaagaattat tggggataac gattatggag cgctcgtctt ttgaaaagaa ccccatcgac 3540
ttccttgagg cgaaaggtta caaggaagta aaaaaggatc tcataattaa actaccaaag 3600
tatagtctgt ttgagttaga aaatggccga aaacggatgt tggctagcgc cggagagctt 3660
caaaagggga acgaactcgc actaccgtct aaatacgtga atttcctgta tttagcgtcc 3720
cattacgaga agttgaaagg ttcacctgaa gataacgaac agaagcaact ttttgttgag 3780
cagcacaaac attatctcga cgaaatcata gagcaaattt cggaattcag taagagagtc 3840
atcctagctg atgccaatct ggacaaagta ttaagcgcat acaacaagca cagggataaa 3900
cccatacgtg agcaggcgga aaatattatc catttgttta ctcttaccaa cctcggcgct 3960
ccagccgcat tcaagtattt tgacacaacg atagatcgca aacgatacac ttctaccaag 4020
gaggtgctag acgcgacact gattcaccaa tccatcacgg gattatatga aactcggata 4080
gatttgtcac agcttggggg tgacggatcc cccaagaaga agaggaaagt ctcgagcgac 4140
tacaaagacc atgacggtga ttataaagat catgacatcg attacaagga tgacgatgac 4200
aaggctgcag ga 4212

<210> SEQ ID NO 5
<211> LENGTH: 1368
<212> TYPE: PRT
<213> ORGANISM: Artificial Sequence
<220> FEATURE:
<223> OTHER INFORMATION: Synthetic Polypeptide

<400> SEQUENCE: 5

Met Asp Lys Lys Tyr Ser Ile Gly Leu Ala Ile Gly Thr Asn Ser Val
1 5 10 15

Gly Trp Ala Val Ile Thr Asp Glu Tyr Lys Val Pro Ser Lys Lys Phe
20 25 30

Lys Val Leu Gly Asn Thr Asp Arg His Ser Ile Lys Lys Asn Leu Ile
35 40 45

Gly Ala Leu Leu Phe Asp Ser Gly Glu Thr Ala Glu Ala Thr Arg Leu
50 55 60

Lys Arg Thr Ala Arg Arg Arg Tyr Thr Arg Arg Lys Asn Arg Ile Cys
65 70 75 80

Tyr Leu Gln Glu Ile Phe Ser Asn Glu Met Ala Lys Val Asp Asp Ser
85 90 95

Phe Phe His Arg Leu Glu Glu Ser Phe Leu Val Glu Glu Asp Lys Lys
100 105 110

His Glu Arg His Pro Ile Phe Gly Asn Ile Val Asp Glu Val Ala Tyr
115 120 125

His Glu Lys Tyr Pro Thr Ile Tyr His Leu Arg Lys Lys Leu Val Asp
130 135 140

Ser Thr Asp Lys Ala Asp Leu Arg Leu Ile Tyr Leu Ala Leu Ala His
145 150 155 160

Met Ile Lys Phe Arg Gly His Phe Leu Ile Glu Gly Asp Leu Asn Pro
165 170 175

Asp Asn Ser Asp Val Asp Lys Leu Phe Ile Gln Leu Val Gln Thr Tyr
180 185 190

Asn Gln Leu Phe Glu Glu Asn Pro Ile Asn Ala Ser Gly Val Asp Ala
195 200 205

-continued

```
Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620
```

```
Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
        835                 840                 845

Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys  Tyr Pro Lys Leu Glu  Ser Glu Phe
        995                 1000                1005

Val Tyr  Gly Asp Tyr Lys Val  Tyr Asp Val Arg Lys  Met Ile Ala
    1010                1015                1020

Lys Ser  Glu Gln Glu Ile Gly  Lys Ala Thr Ala Lys  Tyr Phe Phe
    1025                1030                1035

Tyr Ser  Asn Ile Met Asn Phe  Phe Lys Thr Glu Ile  Thr Leu Ala
```

-continued

```
    1040                1045                1050

Asn Gly  Glu Ile Arg Lys Arg  Pro Leu Ile Glu Thr  Asn Gly Glu
    1055                1060                1065

Thr Gly  Glu Ile Val Trp Asp  Lys Gly Arg Asp Phe  Ala Thr Val
    1070                1075                1080

Arg Lys  Val Leu Ser Met Pro  Gln Val Asn Ile Val  Lys Lys Thr
    1085                1090                1095

Glu Val  Gln Thr Gly Gly Phe  Ser Lys Glu Ser Ile  Leu Pro Lys
    1100                1105                1110

Arg Asn  Ser Asp Lys Leu Ile  Ala Arg Lys Lys Asp  Trp Asp Pro
    1115                1120                1125

Lys Lys  Tyr Gly Gly Phe Asp  Ser Pro Thr Val Ala  Tyr Ser Val
    1130                1135                1140

Leu Val  Val Ala Lys Val Glu  Lys Gly Lys Ser Lys  Lys Leu Lys
    1145                1150                1155

Ser Val  Lys Glu Leu Leu Gly  Ile Thr Ile Met Glu  Arg Ser Ser
    1160                1165                1170

Phe Glu  Lys Asn Pro Ile Asp  Phe Leu Glu Ala Lys  Gly Tyr Lys
    1175                1180                1185

Glu Val  Lys Lys Asp Leu Ile  Ile Lys Leu Pro Lys  Tyr Ser Leu
    1190                1195                1200

Phe Glu  Leu Glu Asn Gly Arg  Lys Arg Met Leu Ala  Ser Ala Gly
    1205                1210                1215

Glu Leu  Gln Lys Gly Asn Glu  Leu Ala Leu Pro Ser  Lys Tyr Val
    1220                1225                1230

Asn Phe  Leu Tyr Leu Ala Ser  His Tyr Glu Lys Leu  Lys Gly Ser
    1235                1240                1245

Pro Glu  Asp Asn Glu Gln Lys  Gln Leu Phe Val Glu  Gln His Lys
    1250                1255                1260

His Tyr  Leu Asp Glu Ile Ile  Glu Gln Ile Ser Glu  Phe Ser Lys
    1265                1270                1275

Arg Val  Ile Leu Ala Asp Ala  Asn Leu Asp Lys Val  Leu Ser Ala
    1280                1285                1290

Tyr Asn  Lys His Arg Asp Lys  Pro Ile Arg Glu Gln  Ala Glu Asn
    1295                1300                1305

Ile Ile  His Leu Phe Thr Leu  Thr Asn Leu Gly Ala  Pro Ala Ala
    1310                1315                1320

Phe Lys  Tyr Phe Asp Thr Thr  Ile Asp Arg Lys Arg  Tyr Thr Ser
    1325                1330                1335

Thr Lys  Glu Val Leu Asp Ala  Thr Leu Ile His Gln  Ser Ile Thr
    1340                1345                1350

Gly Leu  Tyr Glu Thr Arg Ile  Asp Leu Ser Gln Leu  Gly Gly Asp
    1355                1360                1365


<210> SEQ ID NO 6
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 6

Gly Gly Ser Gly Gly Ser Gly Gly Ser Gly Gly Ser Gly Gly Ser Gly
1               5                   10                  15

Gly Ser
```

<210> SEQ ID NO 7
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 7

Ser Gly Ser Glu Thr Pro Gly Thr Ser Glu Ser Ala Thr Pro Glu Ser
1 5 10 15

<210> SEQ ID NO 8
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 8

Ser Gly Ser Glu Thr Pro Gly Thr Ser Glu Ser Ala
1 5 10

<210> SEQ ID NO 9
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 9

Ser Gly Ser Glu Thr Pro Gly Thr Ser Glu Ser Ala Thr Pro Glu Gly
1 5 10 15

Gly Ser Gly Gly Ser
20

<210> SEQ ID NO 10
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 10

Val Pro Phe Leu Leu Glu Pro Asp Asn Ile Asn Gly Lys Thr Cys
1 5 10 15

<210> SEQ ID NO 11
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 11

Gly Ser Ala Gly Ser Ala Ala Gly Ser Gly Glu Phe
1 5 10

<210> SEQ ID NO 12
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 12

-continued

Ser Ile Val Ala Gln Leu Ser Arg Pro Asp Pro Ala
1 5 10

<210> SEQ ID NO 13
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 13

Met Lys Ile Ile Glu Gln Leu Pro Ser Ala
1 5 10

<210> SEQ ID NO 14
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 14

Val Arg His Lys Leu Lys Arg Val Gly Ser
1 5 10

<210> SEQ ID NO 15
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 15

Gly His Gly Thr Gly Ser Thr Gly Ser Gly Ser Ser
1 5 10

<210> SEQ ID NO 16
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 16

Met Ser Arg Pro Asp Pro Ala
1 5

<210> SEQ ID NO 17
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 17

Gly Gly Ser Met
1

<210> SEQ ID NO 18

<400> SEQUENCE: 18

000

<210> SEQ ID NO 19
<211> LENGTH: 17
<212> TYPE: RNA

<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(4)
<223> OTHER INFORMATION: n is a, c, g, or u
<220> FEATURE:
<221> NAME/KEY: misc_feature
<222> LOCATION: (8)..(9)
<223> OTHER INFORMATION: s is g or c
<220> FEATURE:
<221> NAME/KEY: misc_feature
<222> LOCATION: (10)..(11)
<223> OTHER INFORMATION: w is a, t or u
<220> FEATURE:
<221> NAME/KEY: misc_feature
<222> LOCATION: (12)..(13)
<223> OTHER INFORMATION: s is g or c
<220> FEATURE:
<221> NAME/KEY: misc_feature
<222> LOCATION: (14)..(17)
<223> OTHER INFORMATION: n is a, c, g, or u

<400> SEQUENCE: 19
nnnnaaassw wssnnnn 17

<210> SEQ ID NO 20
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 20
ggtgtttcgt cctttccaca ag 22

<210> SEQ ID NO 21
<211> LENGTH: 41
<212> TYPE: DNA
<213> ORGANISM: Artificial Sequence
<220> FEATURE:
<223> OTHER INFORMATION: Synthetic Polynucleotide

<400> SEQUENCE: 21
gcacactagt tagggataac agttttagag ctagaaatag c 41

<210> SEQ ID NO 22
<211> LENGTH: 40
<212> TYPE: DNA
<213> ORGANISM: Artificial Sequence
<220> FEATURE:
<223> OTHER INFORMATION: Synthetic Polynucleotide

<400> SEQUENCE: 22
gcccatgacc cttctcctct gttttagagc tagaaatagc 40

<210> SEQ ID NO 23
<211> LENGTH: 41
<212> TYPE: DNA
<213> ORGANISM: Artificial Sequence
<220> FEATURE:
<223> OTHER INFORMATION: Synthetic Polynucleotide

<400> SEQUENCE: 23
gctcagggcc tgtgatggga ggttttagag ctagaaatag c 41

<210> SEQ ID NO 24
<211> LENGTH: 40

<212> TYPE: DNA
<213> ORGANISM: Artificial Sequence
<220> FEATURE:
<223> OTHER INFORMATION: Synthetic Polynucleotide

<400> SEQUENCE: 24
ggcccatgac ccttctcctc gttttagagc tagaaatagc 40

<210> SEQ ID NO 25
<211> LENGTH: 41
<212> TYPE: DNA
<213> ORGANISM: Artificial Sequence
<220> FEATURE:
<223> OTHER INFORMATION: Synthetic Polynucleotide

<400> SEQUENCE: 25
gcctcagggc ctgtgatggg agttttagag ctagaaatag c 41

<210> SEQ ID NO 26
<211> LENGTH: 40
<212> TYPE: DNA
<213> ORGANISM: Artificial Sequence
<220> FEATURE:
<223> OTHER INFORMATION: Synthetic Polynucleotide

<400> SEQUENCE: 26
gacttgaaac actctttttc gttttagagc tagaaatagc 40

<210> SEQ ID NO 27
<211> LENGTH: 41
<212> TYPE: DNA
<213> ORGANISM: Artificial Sequence
<220> FEATURE:
<223> OTHER INFORMATION: Synthetic Polynucleotide

<400> SEQUENCE: 27
gagttgaaga cacacaacac agttttagag ctagaaatag c 41

<210> SEQ ID NO 28
<211> LENGTH: 40
<212> TYPE: DNA
<213> ORGANISM: Artificial Sequence
<220> FEATURE:
<223> OTHER INFORMATION: Synthetic Polynucleotide

<400> SEQUENCE: 28
ggaactcatg tgattaactg gttttagagc tagaaatagc 40

<210> SEQ ID NO 29
<211> LENGTH: 41
<212> TYPE: DNA
<213> ORGANISM: Artificial Sequence
<220> FEATURE:
<223> OTHER INFORMATION: Synthetic Polynucleotide

<400> SEQUENCE: 29
gtctacctct catgagccgg tgttttagag ctagaaatag c 41

<210> SEQ ID NO 30
<211> LENGTH: 41
<212> TYPE: DNA
<213> ORGANISM: Artificial Sequence
<220> FEATURE:
<223> OTHER INFORMATION: Synthetic Polynucleotide

<400> SEQUENCE: 30
gtttcccgca ggatgtggga tgttttagag ctagaaatag c 41

<210> SEQ ID NO 31
<211> LENGTH: 41
<212> TYPE: DNA
<213> ORGANISM: Artificial Sequence
<220> FEATURE:
<223> OTHER INFORMATION: Synthetic Polynucleotide

<400> SEQUENCE: 31
gcctggggat ttatgttctt agttttagag ctagaaatag c 41

<210> SEQ ID NO 32
<211> LENGTH: 41
<212> TYPE: DNA
<213> ORGANISM: Artificial Sequence
<220> FEATURE:
<223> OTHER INFORMATION: Synthetic Polynucleotide

<400> SEQUENCE: 32
gaaatagcac aatgaatgga agttttagag ctagaaatag c 41

<210> SEQ ID NO 33
<211> LENGTH: 41
<212> TYPE: DNA
<213> ORGANISM: Artificial Sequence
<220> FEATURE:
<223> OTHER INFORMATION: Synthetic Polynucleotide

<400> SEQUENCE: 33
gactttttgg gggagaggga ggttttagag ctagaaatag c 41

<210> SEQ ID NO 34
<211> LENGTH: 40
<212> TYPE: DNA
<213> ORGANISM: Artificial Sequence
<220> FEATURE:
<223> OTHER INFORMATION: Synthetic Polynucleotide

<400> SEQUENCE: 34
ggagacttaa gtccaaaacc gttttagagc tagaaatagc 40

<210> SEQ ID NO 35
<211> LENGTH: 41
<212> TYPE: DNA
<213> ORGANISM: Artificial Sequence
<220> FEATURE:
<223> OTHER INFORMATION: Synthetic Polynucleotide

<400> SEQUENCE: 35
gtcagctatg atcacttccc tgttttagag ctagaaatag c 41

<210> SEQ ID NO 36
<211> LENGTH: 56
<212> TYPE: DNA
<213> ORGANISM: Artificial Sequence
<220> FEATURE:
<223> OTHER INFORMATION: Synthetic Polynucleotide

<400> SEQUENCE: 36
tcgtctcggc gtccccaatt ttcccaaaca gaggtctgta aaccgaggtg agacgg 56

<210> SEQ ID NO 37
<211> LENGTH: 56
<212> TYPE: DNA
<213> ORGANISM: Artificial Sequence
<220> FEATURE:
<223> OTHER INFORMATION: Synthetic Polynucleotide

<400> SEQUENCE: 37
ccgtctcacc tcggtttaca gacctctgtt tgggaaaatt ggggacgccg agacga 56

<210> SEQ ID NO 38
<211> LENGTH: 57
<212> TYPE: DNA
<213> ORGANISM: Artificial Sequence
<220> FEATURE:
<223> OTHER INFORMATION: Synthetic Polynucleotide

<400> SEQUENCE: 38
tcgtctcggc gtccccaatt ttcccaaaca gaggttctgt aaaccgaggt gagacgg 57

<210> SEQ ID NO 39
<211> LENGTH: 57
<212> TYPE: DNA
<213> ORGANISM: Artificial Sequence
<220> FEATURE:
<223> OTHER INFORMATION: Synthetic Polynucleotide

<400> SEQUENCE: 39
ccgtctcacc tcggtttaca gaacctctgt ttgggaaaat tggggacgcc gagacga 57

<210> SEQ ID NO 40
<211> LENGTH: 58
<212> TYPE: DNA
<213> ORGANISM: Artificial Sequence
<220> FEATURE:
<223> OTHER INFORMATION: Synthetic Polynucleotide

<400> SEQUENCE: 40
tcgtctcggc gtccccaatt ttcccaaaca gaggtatctg taaaccgagg tgagacgg 58

<210> SEQ ID NO 41
<211> LENGTH: 58
<212> TYPE: DNA
<213> ORGANISM: Artificial Sequence
<220> FEATURE:
<223> OTHER INFORMATION: Synthetic Polynucleotide

<400> SEQUENCE: 41
ccgtctcacc tcggtttaca gatacctctg tttgggaaaa ttggggacgc cgagacga 58

<210> SEQ ID NO 42
<211> LENGTH: 59
<212> TYPE: DNA
<213> ORGANISM: Artificial Sequence
<220> FEATURE:
<223> OTHER INFORMATION: Synthetic Polynucleotide

<400> SEQUENCE: 42
tcgtctcggc gtccccaatt ttcccaaaca gaggtaatct gtaaaccgag gtgagacgg 59

<210> SEQ ID NO 43
<211> LENGTH: 59
<212> TYPE: DNA
<213> ORGANISM: Artificial Sequence
<220> FEATURE:
<223> OTHER INFORMATION: Synthetic Polynucleotide

<400> SEQUENCE: 43
ccgtctcacc tcggtttaca gattacctct gtttgggaaa attggggacg ccgagacga 59

<210> SEQ ID NO 44
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 44
tcgtctcggc gtccccaatt ttcccaaaca gaggtaaatc tgtaaaccga ggtgagacgg 60

<210> SEQ ID NO 45
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 45
ccgtctcacc tcggtttaca gatttacctc tgtttgggaa aattggggac gccgagacga 60

<210> SEQ ID NO 46
<211> LENGTH: 61
<212> TYPE: DNA
<213> ORGANISM: Artificial Sequence
<220> FEATURE:
<223> OTHER INFORMATION: Synthetic Polynucleotide

<400> SEQUENCE: 46
tcgtctcggc gtccccaatt ttcccaaaca gaggtgaaat ctgtaaaccg aggtgagacg 60
g 61

<210> SEQ ID NO 47
<211> LENGTH: 61
<212> TYPE: DNA
<213> ORGANISM: Artificial Sequence
<220> FEATURE:
<223> OTHER INFORMATION: Synthetic Polynucleotide

<400> SEQUENCE: 47
ccgtctcacc tcggtttaca gatttcacct ctgtttggga aaattgggga cgccgagacg 60
a 61

<210> SEQ ID NO 48
<211> LENGTH: 62
<212> TYPE: DNA
<213> ORGANISM: Artificial Sequence
<220> FEATURE:
<223> OTHER INFORMATION: Synthetic Polynucleotide

<400> SEQUENCE: 48
tcgtctcggc gtccccaatt ttcccaaaca gaggtcgaaa tctgtaaacc gaggtgagac 60
gg 62

<210> SEQ ID NO 49
<211> LENGTH: 62
<212> TYPE: DNA
<213> ORGANISM: Artificial Sequence
<220> FEATURE:
<223> OTHER INFORMATION: Synthetic Polynucleotide

<400> SEQUENCE: 49
ccgtctcacc tcggtttaca gatttcgacc tctgtttggg aaaattgggg acgccgagac 60
ga 62

<210> SEQ ID NO 50
<211> LENGTH: 63
<212> TYPE: DNA
<213> ORGANISM: Artificial Sequence
<220> FEATURE:
<223> OTHER INFORMATION: Synthetic Polynucleotide

<400> SEQUENCE: 50
tcgtctcggc gtccccaatt ttcccaaaca gaggttcgaa atctgtaaac cgaggtgaga 60
cgg 63

<210> SEQ ID NO 51
<211> LENGTH: 63
<212> TYPE: DNA
<213> ORGANISM: Artificial Sequence
<220> FEATURE:
<223> OTHER INFORMATION: Synthetic Polynucleotide

<400> SEQUENCE: 51
ccgtctcacc tcggtttaca gatttcgaac ctctgtttgg gaaaattggg gacgccgaga 60
cga 63

<210> SEQ ID NO 52
<211> LENGTH: 54
<212> TYPE: DNA
<213> ORGANISM: Artificial Sequence
<220> FEATURE:
<223> OTHER INFORMATION: Synthetic Polynucleotide

<400> SEQUENCE: 52
tcgtctcgga ggttttggaa cctctgtttg ggaaaattgg ggagtctgag acgg 54

<210> SEQ ID NO 53
<211> LENGTH: 54
<212> TYPE: DNA
<213> ORGANISM: Artificial Sequence
<220> FEATURE:
<223> OTHER INFORMATION: Synthetic Polynucleotide

<400> SEQUENCE: 53
ccgtctcaga ctccccaatt ttcccaaaca gaggttccaa aacctccgag acga 54

<210> SEQ ID NO 54
<211> LENGTH: 55
<212> TYPE: DNA
<213> ORGANISM: Artificial Sequence
<220> FEATURE:
<223> OTHER INFORMATION: Synthetic Polynucleotide

<400> SEQUENCE: 54
tcgtctcgga ggttttggac acctctgttt gggaaaattg gggagtctga gacgg 55

<210> SEQ ID NO 55
<211> LENGTH: 55
<212> TYPE: DNA
<213> ORGANISM: Artificial Sequence
<220> FEATURE:
<223> OTHER INFORMATION: Synthetic Polynucleotide

<400> SEQUENCE: 55
ccgtctcaga ctccccaatt ttcccaaaca gaggtgtcca aaacctccga gacga 55

<210> SEQ ID NO 56

<211> LENGTH: 56
<212> TYPE: DNA
<213> ORGANISM: Artificial Sequence
<220> FEATURE:
<223> OTHER INFORMATION: Synthetic Polynucleotide

<400> SEQUENCE: 56
tcgtctcgga ggttttggac tacctctgtt tgggaaaatt ggggagtctg agacgg 56

<210> SEQ ID NO 57
<211> LENGTH: 56
<212> TYPE: DNA
<213> ORGANISM: Artificial Sequence
<220> FEATURE:
<223> OTHER INFORMATION: Synthetic Polynucleotide

<400> SEQUENCE: 57
ccgtctcaga ctccccaatt ttcccaaaca gaggtagtcc aaaacctccg agacga 56

<210> SEQ ID NO 58
<211> LENGTH: 57
<212> TYPE: DNA
<213> ORGANISM: Artificial Sequence
<220> FEATURE:
<223> OTHER INFORMATION: Synthetic Polynucleotide

<400> SEQUENCE: 58
tcgtctcgga ggttttggac ttacctctgt ttgggaaaat tggggagtct gagacgg 57

<210> SEQ ID NO 59
<211> LENGTH: 57
<212> TYPE: DNA
<213> ORGANISM: Artificial Sequence
<220> FEATURE:
<223> OTHER INFORMATION: Synthetic Polynucleotide

<400> SEQUENCE: 59
ccgtctcaga ctccccaatt ttcccaaaca gaggtaagtc caaaacctcc gagacga 57

<210> SEQ ID NO 60
<211> LENGTH: 58
<212> TYPE: DNA
<213> ORGANISM: Artificial Sequence
<220> FEATURE:
<223> OTHER INFORMATION: Synthetic Polynucleotide

<400> SEQUENCE: 60
tcgtctcgga ggttttggac ttaacctctg tttgggaaaa ttggggagtc tgagacgg 58

<210> SEQ ID NO 61
<211> LENGTH: 58
<212> TYPE: DNA
<213> ORGANISM: Artificial Sequence
<220> FEATURE:
<223> OTHER INFORMATION: Synthetic Polynucleotide

<400> SEQUENCE: 61
ccgtctcaga ctccccaatt ttcccaaaca gaggttaagt ccaaaacctc cgagacga 58

<210> SEQ ID NO 62
<211> LENGTH: 59
<212> TYPE: DNA
<213> ORGANISM: Artificial Sequence
<220> FEATURE:
<223> OTHER INFORMATION: Synthetic Polynucleotide

<400> SEQUENCE: 62
tcgtctcgga ggttttggac ttagacctct gtttgggaaa attggggagt ctgagacgg 59

<210> SEQ ID NO 63
<211> LENGTH: 59
<212> TYPE: DNA
<213> ORGANISM: Artificial Sequence
<220> FEATURE:
<223> OTHER INFORMATION: Synthetic Polynucleotide

<400> SEQUENCE: 63
ccgtctcaga ctccccaatt ttcccaaaca gaggtctaag tccaaaacct ccgagacga 59

<210> SEQ ID NO 64
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 64
tcgtctcgga ggttttggac ttagcacctc tgtttgggaa aattggggag tctgagacgg 60

<210> SEQ ID NO 65
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 65
ccgtctcaga ctccccaatt ttcccaaaca gaggtgctaa gtccaaaacc tccgagacga 60

<210> SEQ ID NO 66
<211> LENGTH: 61
<212> TYPE: DNA
<213> ORGANISM: Artificial Sequence
<220> FEATURE:
<223> OTHER INFORMATION: Synthetic Polynucleotide

<400> SEQUENCE: 66
tcgtctcgga ggttttggac ttagctacct ctgtttggga aaattgggga gtctgagacg 60
g 61

<210> SEQ ID NO 67
<211> LENGTH: 61
<212> TYPE: DNA
<213> ORGANISM: Artificial Sequence
<220> FEATURE:
<223> OTHER INFORMATION: Synthetic Polynucleotide

<400> SEQUENCE: 67
ccgtctcaga ctccccaatt ttcccaaaca gaggtagcta agtccaaaac ctccgagacg 60
a 61

<210> SEQ ID NO 68
<211> LENGTH: 54
<212> TYPE: DNA
<213> ORGANISM: Artificial Sequence
<220> FEATURE:
<223> OTHER INFORMATION: Synthetic Polynucleotide

<400> SEQUENCE: 68
tcgtctctgc acccccaatt ttcccaaaca gaggtctgta aaccgatgag acgg 54

<210> SEQ ID NO 69
<211> LENGTH: 54
<212> TYPE: DNA
<213> ORGANISM: Artificial Sequence
<220> FEATURE:
<223> OTHER INFORMATION: Synthetic Polynucleotide

<400> SEQUENCE: 69
ccgtctcatc ggtttacaga cctctgtttg ggaaaattgg gggtgcagag acga 54

<210> SEQ ID NO 70
<211> LENGTH: 55
<212> TYPE: DNA
<213> ORGANISM: Artificial Sequence
<220> FEATURE:
<223> OTHER INFORMATION: Synthetic Polynucleotide

<400> SEQUENCE: 70
tcgtctctgc acccccaatt ttcccaaaca gaggttctgt aaaccgatga gacgg 55

<210> SEQ ID NO 71
<211> LENGTH: 55
<212> TYPE: DNA
<213> ORGANISM: Artificial Sequence
<220> FEATURE:
<223> OTHER INFORMATION: Synthetic Polynucleotide

<400> SEQUENCE: 71
ccgtctcatc ggtttacaga acctctgttt gggaaaattg ggggtgcaga gacga 55

<210> SEQ ID NO 72
<211> LENGTH: 56
<212> TYPE: DNA
<213> ORGANISM: Artificial Sequence
<220> FEATURE:
<223> OTHER INFORMATION: Synthetic Polynucleotide

<400> SEQUENCE: 72
tcgtctctgc acccccaatt ttcccaaaca gaggtatctg taaaccgatg agacgg 56

<210> SEQ ID NO 73
<211> LENGTH: 56
<212> TYPE: DNA
<213> ORGANISM: Artificial Sequence
<220> FEATURE:
<223> OTHER INFORMATION: Synthetic Polynucleotide

<400> SEQUENCE: 73
ccgtctcatc ggtttacaga tacctctgtt tgggaaaatt gggggtgcag agacga 56

<210> SEQ ID NO 74
<211> LENGTH: 57
<212> TYPE: DNA
<213> ORGANISM: Artificial Sequence
<220> FEATURE:
<223> OTHER INFORMATION: Synthetic Polynucleotide

<400> SEQUENCE: 74
tcgtctctgc acccccaatt ttcccaaaca gaggtaatct gtaaaccgat gagacgg 57

<210> SEQ ID NO 75
<211> LENGTH: 57
<212> TYPE: DNA
<213> ORGANISM: Artificial Sequence
<220> FEATURE:
<223> OTHER INFORMATION: Synthetic Polynucleotide

<400> SEQUENCE: 75
ccgtctcatc ggtttacaga ttacctctgt ttgggaaaat tgggggtgca gagacga 57

<210> SEQ ID NO 76
<211> LENGTH: 58
<212> TYPE: DNA
<213> ORGANISM: Artificial Sequence
<220> FEATURE:
<223> OTHER INFORMATION: Synthetic Polynucleotide

<400> SEQUENCE: 76
tcgtctctgc acccccaatt ttcccaaaca gaggtaaatc tgtaaaccga tgagacgg 58

<210> SEQ ID NO 77
<211> LENGTH: 58
<212> TYPE: DNA
<213> ORGANISM: Artificial Sequence
<220> FEATURE:
<223> OTHER INFORMATION: Synthetic Polynucleotide

<400> SEQUENCE: 77
ccgtctcatc ggtttacaga tttacctctg tttgggaaaa ttgggggtgc agagacga 58

<210> SEQ ID NO 78
<211> LENGTH: 59
<212> TYPE: DNA
<213> ORGANISM: Artificial Sequence
<220> FEATURE:
<223> OTHER INFORMATION: Synthetic Polynucleotide

<400> SEQUENCE: 78
tcgtctctgc acccccaatt ttcccaaaca gaggtgaaat ctgtaaaccg atgagacgg 59

<210> SEQ ID NO 79
<211> LENGTH: 59
<212> TYPE: DNA
<213> ORGANISM: Artificial Sequence
<220> FEATURE:
<223> OTHER INFORMATION: Synthetic Polynucleotide

<400> SEQUENCE: 79
ccgtctcatc ggtttacaga tttcacctct gtttgggaaa attgggggtg cagagacga 59

<210> SEQ ID NO 80
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 80
tcgtctctgc acccccaatt ttcccaaaca gaggtcgaaa tctgtaaacc gatgagacgg 60

<210> SEQ ID NO 81
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 81
ccgtctcatc ggtttacaga tttcgacctc tgtttgggaa aattgggggt gcagagacga 60

<210> SEQ ID NO 82

<211> LENGTH: 61
<212> TYPE: DNA
<213> ORGANISM: Artificial Sequence
<220> FEATURE:
<223> OTHER INFORMATION: Synthetic Polynucleotide

<400> SEQUENCE: 82
tcgtctctgc acccccaatt ttcccaaaca gaggttcgaa atctgtaaac cgatgagacg 60
g 61

<210> SEQ ID NO 83
<211> LENGTH: 61
<212> TYPE: DNA
<213> ORGANISM: Artificial Sequence
<220> FEATURE:
<223> OTHER INFORMATION: Synthetic Polynucleotide

<400> SEQUENCE: 83
ccgtctcatc ggtttacaga tttcgaacct ctgtttggga aaattggggg tgcagagacg 60
a 61

<210> SEQ ID NO 84
<211> LENGTH: 56
<212> TYPE: DNA
<213> ORGANISM: Artificial Sequence
<220> FEATURE:
<223> OTHER INFORMATION: Synthetic Polynucleotide

<400> SEQUENCE: 84
tcgtctcgcc gaggttttgg aacctctgtt tgggaaaatt ggggctcgtg agacgg 56

<210> SEQ ID NO 85
<211> LENGTH: 56
<212> TYPE: DNA
<213> ORGANISM: Artificial Sequence
<220> FEATURE:
<223> OTHER INFORMATION: Synthetic Polynucleotide

<400> SEQUENCE: 85
ccgtctcacg agccccaatt ttcccaaaca gaggttccaa aacctcggcg agacga 56

<210> SEQ ID NO 86
<211> LENGTH: 57
<212> TYPE: DNA
<213> ORGANISM: Artificial Sequence
<220> FEATURE:
<223> OTHER INFORMATION: Synthetic Polynucleotide

<400> SEQUENCE: 86
tcgtctcgcc gaggttttgg acacctctgt ttgggaaaat tggggctcgt gagacgg 57

<210> SEQ ID NO 87
<211> LENGTH: 57
<212> TYPE: DNA
<213> ORGANISM: Artificial Sequence
<220> FEATURE:
<223> OTHER INFORMATION: Synthetic Polynucleotide

<400> SEQUENCE: 87
ccgtctcacg agccccaatt ttcccaaaca gaggtgtcca aaacctcggc gagacga 57

<210> SEQ ID NO 88
<211> LENGTH: 58
<212> TYPE: DNA
<213> ORGANISM: Artificial Sequence
<220> FEATURE:
<223> OTHER INFORMATION: Synthetic Polynucleotide

<400> SEQUENCE: 88
tcgtctcgcc gaggttttgg actacctctg tttgggaaaa ttggggctcg tgagacgg 58

<210> SEQ ID NO 89
<211> LENGTH: 58
<212> TYPE: DNA
<213> ORGANISM: Artificial Sequence
<220> FEATURE:
<223> OTHER INFORMATION: Synthetic Polynucleotide

<400> SEQUENCE: 89
ccgtctcacg agccccaatt ttcccaaaca gaggtagtcc aaaacctcgg cgagacga 58

<210> SEQ ID NO 90
<211> LENGTH: 59
<212> TYPE: DNA
<213> ORGANISM: Artificial Sequence
<220> FEATURE:
<223> OTHER INFORMATION: Synthetic Polynucleotide

<400> SEQUENCE: 90
tcgtctcgcc gaggttttgg acttacctct gtttgggaaa attggggctc gtgagacgg 59

<210> SEQ ID NO 91
<211> LENGTH: 59
<212> TYPE: DNA
<213> ORGANISM: Artificial Sequence
<220> FEATURE:
<223> OTHER INFORMATION: Synthetic Polynucleotide

<400> SEQUENCE: 91
ccgtctcacg agccccaatt ttcccaaaca gaggtaagtc caaaacctcg gcgagacga 59

<210> SEQ ID NO 92
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 92
tcgtctcgcc gaggttttgg acttaacctc tgtttgggaa aattggggct cgtgagacgg 60

<210> SEQ ID NO 93
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 93
ccgtctcacg agccccaatt ttcccaaaca gaggttaagt ccaaaacctc ggcgagacga 60

<210> SEQ ID NO 94
<211> LENGTH: 61
<212> TYPE: DNA
<213> ORGANISM: Artificial Sequence
<220> FEATURE:
<223> OTHER INFORMATION: Synthetic Polynucleotide

<400> SEQUENCE: 94
tcgtctcgcc gaggttttgg acttagacct ctgtttggga aaattggggc tcgtgagacg 60
g 61

<210> SEQ ID NO 95
<211> LENGTH: 61
<212> TYPE: DNA
<213> ORGANISM: Artificial Sequence
<220> FEATURE:
<223> OTHER INFORMATION: Synthetic Polynucleotide

<400> SEQUENCE: 95
ccgtctcacg agccccaatt ttcccaaaca gaggtctaag tccaaaacct cggcgagacg 60
a 61

<210> SEQ ID NO 96
<211> LENGTH: 62
<212> TYPE: DNA
<213> ORGANISM: Artificial Sequence
<220> FEATURE:
<223> OTHER INFORMATION: Synthetic Polynucleotide

<400> SEQUENCE: 96
tcgtctcgcc gaggttttgg acttagcacc tctgtttggg aaaattgggg ctcgtgagac 60
gg 62

<210> SEQ ID NO 97
<211> LENGTH: 62
<212> TYPE: DNA
<213> ORGANISM: Artificial Sequence
<220> FEATURE:
<223> OTHER INFORMATION: Synthetic Polynucleotide

<400> SEQUENCE: 97
ccgtctcacg agccccaatt ttcccaaaca gaggtgctaa gtccaaaacc tcggcgagac 60
ga 62

<210> SEQ ID NO 98
<211> LENGTH: 63
<212> TYPE: DNA
<213> ORGANISM: Artificial Sequence
<220> FEATURE:
<223> OTHER INFORMATION: Synthetic Polynucleotide

<400> SEQUENCE: 98
tcgtctcgcc gaggttttgg acttagctac ctctgtttgg gaaaattggg gctcgtgaga 60
cgg 63

<210> SEQ ID NO 99
<211> LENGTH: 63
<212> TYPE: DNA
<213> ORGANISM: Artificial Sequence
<220> FEATURE:
<223> OTHER INFORMATION: Synthetic Polynucleotide

<400> SEQUENCE: 99
ccgtctcacg agccccaatt ttcccaaaca gaggtagcta agtccaaaac ctcggcgaga 60
cga 63

<210> SEQ ID NO 100
<211> LENGTH: 58
<212> TYPE: DNA
<213> ORGANISM: Artificial Sequence
<220> FEATURE:
<223> OTHER INFORMATION: Synthetic Polynucleotide

<400> SEQUENCE: 100
tcgtctcggc gtcccctccc atcacaggcc ctgaggttta agagaaaacc tgagacgg 58

<210> SEQ ID NO 101
<211> LENGTH: 58
<212> TYPE: DNA
<213> ORGANISM: Artificial Sequence
<220> FEATURE:
<223> OTHER INFORMATION: Synthetic Polynucleotide

<400> SEQUENCE: 101
ccgtctcagg ttttctctta aacctcaggg cctgtgatgg gaggggacgc cgagacga 58

<210> SEQ ID NO 102
<211> LENGTH: 64
<212> TYPE: DNA
<213> ORGANISM: Artificial Sequence
<220> FEATURE:
<223> OTHER INFORMATION: Synthetic Polynucleotide

<400> SEQUENCE: 102
tcgtctcgaa ccatggtttt gtgggccagg cccatgaccc ttctcctctg ggagtctgag 60
acgg 64

<210> SEQ ID NO 103
<211> LENGTH: 64
<212> TYPE: DNA
<213> ORGANISM: Artificial Sequence
<220> FEATURE:
<223> OTHER INFORMATION: Synthetic Polynucleotide

<400> SEQUENCE: 103
ccgtctcaga ctcccagagg agaagggtca tgggcctggc ccacaaaacc atggttcgag 60
acga 64

<210> SEQ ID NO 104
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 104
tcgtctctgc accccctccc atcacaggcc ctgaggttta agagaaaacc attgagacgg 60

<210> SEQ ID NO 105
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 105
ccgtctcaat ggttttctct taaacctcag ggcctgtgat gggagggggt gcagagacga 60

<210> SEQ ID NO 106
<211> LENGTH: 62
<212> TYPE: DNA
<213> ORGANISM: Artificial Sequence
<220> FEATURE:
<223> OTHER INFORMATION: Synthetic Polynucleotide

<400> SEQUENCE: 106
tcgtctcgcc atggttttgt gggccaggcc catgaccctt ctcctctggg ctcgtgagac 60
gg 62

<210> SEQ ID NO 107
<211> LENGTH: 62
<212> TYPE: DNA
<213> ORGANISM: Artificial Sequence
<220> FEATURE:
<223> OTHER INFORMATION: Synthetic Polynucleotide

<400> SEQUENCE: 107
ccgtctcacg agcccagagg agaagggtca tgggcctggc ccacaaaacc atggcgagac 60
ga 62

<210> SEQ ID NO 108
<211> LENGTH: 43
<212> TYPE: DNA
<213> ORGANISM: Artificial Sequence
<220> FEATURE:
<223> OTHER INFORMATION: Synthetic Polynucleotide

<400> SEQUENCE: 108
atccgtctcc agtcgagtcg gatttgatct gatcaagaga cag 43

<210> SEQ ID NO 109
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 109
aaccgtctcg gtgcgttcgg atttgatcca gacatgataa gatac 45

<210> SEQ ID NO 110
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 110
hscgcgttga gacgctgcca tccgtctcgc 30

<210> SEQ ID NO 111
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 111
hstcgagcga gacggatggc agcgtctcaa 30

<210> SEQ ID NO 112
<211> LENGTH: 130
<212> TYPE: DNA
<213> ORGANISM: Artificial Sequence
<220> FEATURE:
<223> OTHER INFORMATION: Synthetic Polynucleotide

<400> SEQUENCE: 112
gttgttcgtc tcggcgtcct tgtgttgtgt gtcttcaact cacagagtta aacgatgctt 60
tacacagagt agacttgaaa cactcttttt ctggagtctg agacggttct gttttggtgt 120
gattagttat 130

<210> SEQ ID NO 113
<211> LENGTH: 130
<212> TYPE: DNA
<213> ORGANISM: Artificial Sequence
<220> FEATURE:
<223> OTHER INFORMATION: Synthetic Polynucleotide

<400> SEQUENCE: 113
gttggtcgtc tctgcaccct tgtgttgtgt gtcttcaact cacagagtta aacgatgctt 60
tacacagagt agacttgaaa cactcttttt ctggctcgtg agacggttct gttttggtgt 120
gattagttat 130

<210> SEQ ID NO 114
<211> LENGTH: 131
<212> TYPE: DNA
<213> ORGANISM: Artificial Sequence
<220> FEATURE:
<223> OTHER INFORMATION: Synthetic Polynucleotide

<400> SEQUENCE: 114
gttgttcgtc tcggcgtccc accggctcat gagaggtaga gctaaggtcc aaacctaggt 60
ttatctgaga ccggaactca tgtgattaac tgtggagtct gagacggttc tgttttggtg 120
tgattagtta t 131

<210> SEQ ID NO 115
<211> LENGTH: 131
<212> TYPE: DNA
<213> ORGANISM: Artificial Sequence
<220> FEATURE:
<223> OTHER INFORMATION: Synthetic Polynucleotide

<400> SEQUENCE: 115
gttggtcgtc tctgcacccc accggctcat gagaggtaga gctaaggtcc aaacctaggt 60
ttatctgaga ccggaactca tgtgattaac tgtggctcgt gagacggttc tgttttggtg 120
tgattagtta t 131

<210> SEQ ID NO 116
<211> LENGTH: 130
<212> TYPE: DNA
<213> ORGANISM: Artificial Sequence
<220> FEATURE:
<223> OTHER INFORMATION: Synthetic Polynucleotide

<400> SEQUENCE: 116
gttgttcgtc tcggcgtcct taagaacata aatccccagg aattcacaga aaccttggtt 60
tgagctttgg atttcccgca ggatgtggga taggagtctg agacggttct gttttggtgt 120
gattagttat 130

<210> SEQ ID NO 117
<211> LENGTH: 130
<212> TYPE: DNA
<213> ORGANISM: Artificial Sequence
<220> FEATURE:
<223> OTHER INFORMATION: Synthetic Polynucleotide

<400> SEQUENCE: 117
gttggtcgtc tctgcaccct taagaacata aatccccagg aattcacaga aaccttggtt 60
tgagctttgg atttcccgca ggatgtggga taggctcgtg agacggttct gttttggtgt 120
gattagttat 130

<210> SEQ ID NO 118
<211> LENGTH: 129
<212> TYPE: DNA
<213> ORGANISM: Artificial Sequence
<220> FEATURE:
<223> OTHER INFORMATION: Synthetic Polynucleotide

<400> SEQUENCE: 118
gttgttcgtc tcggcgtcca ctccctctcc cccaaaaagt aaaggtagaa aaccaaggtt 60
tacaggcaac aaatagcaca atgaatggaa tggagtctga gacggttctg ttttggtgtg 120
attagttat 129

<210> SEQ ID NO 119
<211> LENGTH: 129
<212> TYPE: DNA
<213> ORGANISM: Artificial Sequence
<220> FEATURE:
<223> OTHER INFORMATION: Synthetic Polynucleotide

<400> SEQUENCE: 119
gttggtcgtc tctgcaccca ctccctctcc cccaaaaagt aaaggtagaa aaccaaggtt 60
tacaggcaac aaatagcaca atgaatggaa tggctcgtga gacggttctg ttttggtgtg 120
attagttat 129

<210> SEQ ID NO 120
<211> LENGTH: 130
<212> TYPE: DNA
<213> ORGANISM: Artificial Sequence
<220> FEATURE:
<223> OTHER INFORMATION: Synthetic Polynucleotide

<400> SEQUENCE: 120
gttgttcgtc tcggcgtcct agggaagtga tcatagctga gtttctggaa aaacctaggt 60
tttaaagttg aggagactta agtccaaaac ctggagtctg agacggttct gttttggtgt 120
gattagttat 130

<210> SEQ ID NO 121
<211> LENGTH: 130
<212> TYPE: DNA
<213> ORGANISM: Artificial Sequence
<220> FEATURE:
<223> OTHER INFORMATION: Synthetic Polynucleotide

<400> SEQUENCE: 121
gttggtcgtc tctgcaccct agggaagtga tcatagctga gtttctggaa aaacctaggt 60
tttaaagttg aggagactta agtccaaaac ctggctcgtg agacggttct gttttggtgt 120
gattagttat 130

<210> SEQ ID NO 122
<211> LENGTH: 47
<212> TYPE: DNA
<213> ORGANISM: Artificial Sequence
<220> FEATURE:
<223> OTHER INFORMATION: Synthetic Polynucleotide

<400> SEQUENCE: 122
ttcatcggat ccgataaaaa gtattctatt ggtttagcta tcggcac 47

<210> SEQ ID NO 123
<211> LENGTH: 34
<212> TYPE: DNA
<213> ORGANISM: Artificial Sequence
<220> FEATURE:
<223> OTHER INFORMATION: Synthetic Polynucleotide

<400> SEQUENCE: 123
ttcatcggat ccggtggttc aggtggcagc ggag 34

<210> SEQ ID NO 124
<211> LENGTH: 61
<212> TYPE: DNA
<213> ORGANISM: Artificial Sequence
<220> FEATURE:
<223> OTHER INFORMATION: Synthetic Polynucleotide

<400> SEQUENCE: 124
ttcatcggat ccggagggtc cggaggtagt ggcggcagcg gtggttcagg tggcagcgga 60
g 61

<210> SEQ ID NO 125
<211> LENGTH: 100
<212> TYPE: DNA
<213> ORGANISM: Artificial Sequence
<220> FEATURE:
<223> OTHER INFORMATION: Synthetic Polynucleotide

<400> SEQUENCE: 125
aataaccggt tcagaccttc cttttcttct ttggggaacc tcccttgtcg tcatcatcct 60
tataatcgga gccaccgtca cccccaagct gtgacaaatc 100

<210> SEQ ID NO 126
<211> LENGTH: 38
<212> TYPE: DNA
<213> ORGANISM: Artificial Sequence
<220> FEATURE:
<223> OTHER INFORMATION: Synthetic Polynucleotide

<400> SEQUENCE: 126
tgataaggat ccaccctttg gtggtcttcc aaaccgcc 38

<210> SEQ ID NO 127
<211> LENGTH: 38
<212> TYPE: DNA
<213> ORGANISM: Artificial Sequence
<220> FEATURE:
<223> OTHER INFORMATION: Synthetic Polynucleotide

<400> SEQUENCE: 127
tgataaggat ccaccgctac caccctttgg tggtcttc 38

<210> SEQ ID NO 128
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 128
agatccgcgg ccgctaatac 20

<210> SEQ ID NO 129

<211> LENGTH: 54
<212> TYPE: DNA
<213> ORGANISM: Artificial Sequence
<220> FEATURE:
<223> OTHER INFORMATION: Synthetic Polynucleotide

<400> SEQUENCE: 129
ttgagtcgtc tctatactct tcctttttca atattattga agcatttatc aggg 54

<210> SEQ ID NO 130
<211> LENGTH: 50
<212> TYPE: DNA
<213> ORGANISM: Artificial Sequence
<220> FEATURE:
<223> OTHER INFORMATION: Synthetic Polynucleotide

<400> SEQUENCE: 130
ctggaacgtc tcactgtcag accaagttta ctcatatata ctttagattg 50

<210> SEQ ID NO 131
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 131
ggtgtgcgtc tctacagtta tttgccgact accttggtga tctcgc 46

<210> SEQ ID NO 132
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 132
acaccacgtc tctgtatgag ggaagcggtg atcgcc 36

<210> SEQ ID NO 133
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 133
catactcttc ctttttcaat attattgaag catttatcag gg 42

<210> SEQ ID NO 134
<211> LENGTH: 37
<212> TYPE: DNA
<213> ORGANISM: Artificial Sequence
<220> FEATURE:
<223> OTHER INFORMATION: Synthetic Polynucleotide

<400> SEQUENCE: 134
ctgtcagacc aagtttactc atatatactt tagattg 37

<210> SEQ ID NO 135
<211> LENGTH: 62
<212> TYPE: DNA
<213> ORGANISM: Artificial Sequence
<220> FEATURE:
<223> OTHER INFORMATION: Synthetic Polynucleotide

<400> SEQUENCE: 135
caatctaaag tatatatgag taaacttggt ctgacagttt gccgactacc ttggtgatct 60
cg 62

<210> SEQ ID NO 136
<211> LENGTH: 65
<212> TYPE: DNA
<213> ORGANISM: Artificial Sequence
<220> FEATURE:
<223> OTHER INFORMATION: Synthetic Polynucleotide

<400> SEQUENCE: 136
caatctaaag tatatatgag taaacttggt ctgacagtta tttgccgact accttggtga 60
tctcg 65

<210> SEQ ID NO 137
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 137
ccctgataaa tgcttcaata atattgaaaa aggaagagta tg 42

<210> SEQ ID NO 138
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 138
cgcaaatggg cggtaggcgt g 21

<210> SEQ ID NO 139
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 139
ccgtgatgga ttggtgaatc 20

<210> SEQ ID NO 140
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 140
cccatacgat ttcacctgtc 20

<210> SEQ ID NO 141
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 141
gggtattttc cacaggatgc 20

<210> SEQ ID NO 142
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 142
cttagaaagg cgggtttacg 20

<210> SEQ ID NO 143
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 143
cttactaagc tgcaatttgg 20

<210> SEQ ID NO 144
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 144
tgtattcatc ggttatgaca g 21

<210> SEQ ID NO 145
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 145
cagggtcaag gaaggcacg 19

<210> SEQ ID NO 146
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 146
gttccgcgca catttcc 17

<210> SEQ ID NO 147
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 147
gcggagccta tggaaaaac 19

<210> SEQ ID NO 148
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 148
gccttcttct ttttcctaca gc 22

<210> SEQ ID NO 149
<211> LENGTH: 16
<212> TYPE: DNA
<213> ORGANISM: Artificial Sequence
<220> FEATURE:
<223> OTHER INFORMATION: Synthetic Polynucleotide

<400> SEQUENCE: 149
cgcatcgagc gagcac 16

<210> SEQ ID NO 150
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 150
tcaagtagca aaagaagtag gagtcag 27

<210> SEQ ID NO 151
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 151
ttagatgcat tcgtgcttga ag 22

<210> SEQ ID NO 152
<211> LENGTH: 29
<212> TYPE: DNA
<213> ORGANISM: Artificial Sequence
<220> FEATURE:
<223> OTHER INFORMATION: Synthetic Polynucleotide

<400> SEQUENCE: 152
ttaatttctg ctgctagaac taaatctgg 29

<210> SEQ ID NO 153
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 153
gggaagaaaa ctggatggag aatg 24

<210> SEQ ID NO 154
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 154
cataaatgac ctagtggagc tg 22

<210> SEQ ID NO 155

<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 155
tggttatttt gcccattagt tgatgc 26

<210> SEQ ID NO 156
<211> LENGTH: 1318
<212> TYPE: DNA
<213> ORGANISM: Artificial Sequence
<220> FEATURE:
<223> OTHER INFORMATION: Synthetic Polynucleotide

<400> SEQUENCE: 156
acgcgtcccc aattttccca aacagaggtc tgtaaaccga ggttttggaa cctctgtttg 60
ggaaaattgg ggagtcgagt cggatttgat ctgatcaaga gacaggatga ggatcgtttc 120
gcatgattga acaagatgga ttgcacgcag gttctccggc cgcttgggtg gagaggctat 180
tcggctatga ctgggcacaa cagacaatcg gctgctctga tgccgccgtg ttccggctgt 240
cagtcgcagg ggcgcccggt tctttttgtc aagaccgacc tgtccggtgc cctgaatgaa 300
ctgcaggacg aggcagcgcg gctatcgtgg ctggccacga cgggcgttcc ttgcgcagct 360
gtgctcgacg ttgtcactga agcgggaagg gactggctgc tattgggcga agtgccgggg 420
caggatctcc tgtcatctca ccttgctcct gccgagaaag tatccatcat ggctgatgca 480
atgcggcggc tgcatacgct tgatccggct acctgcccat tcgaccacca agcgaaacat 540
cgcatcgagc gagcacgtac tcggatggaa gccggtcttg tcgatcagga tgatctggac 600
gaagagcatc aggggctcgc gccagccgaa ctgttcgcca ggctcaaggc gcgcatgccc 660
gacggcgagg atctcgtcgt gacccatggc gatgcctgct tgccgaatat catggtggaa 720
aatggccgct tttctggatt catcgactgt ggccggctgg gtgtggcgga ccgctatcag 780
gacatagcgt tggctacccg tgatattgct gaagagcttg gcggcgaatg ggctgaccgc 840
ttcctcgtgc tttacggtat cgccgctccc gattcgcagc gcatcgcctt ctatcgcctt 900
cttgacgagt tcttctgagc gggactctgg ggttcgaaat gaccgaccaa gcgacgccca 960
acctgccatc acgagatttc gattccaccg ccgccttcta tgaaaggttg ggcttcggaa 1020
tcgttttccg ggacgccggc tggatgatcc tccagcgcgg ggatctcatg ctggagttct 1080
tcgcccaccc catcgataac ttgtttattg cagcttataa tggttacaaa taaagcaata 1140
gcatcacaaa tttcacaaat aaagcatttt tttcactgca ttctagttgt ggtttgtcca 1200
aactcatcaa tgtatcttat catgtctgga tcaaatccga acgcaccccc aattttccca 1260
aacagaggtc tgtaaaccga ggttttggaa cctctgtttg ggaaaattgg ggctcgag 1318

<210> SEQ ID NO 157
<211> LENGTH: 67
<212> TYPE: DNA
<213> ORGANISM: Artificial Sequence
<220> FEATURE:
<223> OTHER INFORMATION: Synthetic Polynucleotide

<400> SEQUENCE: 157
ccccaatttt cccaaacaga ggttctgtaa accgaggttt tggaacctct gtttgggaaa 60
attgggg 67

<210> SEQ ID NO 158
<211> LENGTH: 68
<212> TYPE: DNA
<213> ORGANISM: Artificial Sequence
<220> FEATURE:
<223> OTHER INFORMATION: Synthetic Polynucleotide

<400> SEQUENCE: 158
ccccaatttt cccaaacaga ggttctgtaa accgaggttt tggcaacctc tgtttgggaa 60
aattgggg 68

<210> SEQ ID NO 159
<211> LENGTH: 70
<212> TYPE: DNA
<213> ORGANISM: Artificial Sequence
<220> FEATURE:
<223> OTHER INFORMATION: Synthetic Polynucleotide

<400> SEQUENCE: 159
ccccaatttt cccaaacaga ggtatctgta aaccgaggtt ttggctaacc tctgtttggg 60
aaaattgggg 70

<210> SEQ ID NO 160
<211> LENGTH: 72
<212> TYPE: DNA
<213> ORGANISM: Artificial Sequence
<220> FEATURE:
<223> OTHER INFORMATION: Synthetic Polynucleotide

<400> SEQUENCE: 160
ccccaatttt cccaaacaga ggtaatctgt aaaccgaggt tttggcttaa cctctgtttg 60
ggaaaattgg gg 72

<210> SEQ ID NO 161
<211> LENGTH: 74
<212> TYPE: DNA
<213> ORGANISM: Artificial Sequence
<220> FEATURE:
<223> OTHER INFORMATION: Synthetic Polynucleotide

<400> SEQUENCE: 161
ccccaatttt cccaaacaga ggtaaatctg taaaccgagg ttttggctta aacctctgtt 60
tgggaaaatt gggg 74

<210> SEQ ID NO 162
<211> LENGTH: 76
<212> TYPE: DNA
<213> ORGANISM: Artificial Sequence
<220> FEATURE:
<223> OTHER INFORMATION: Synthetic Polynucleotide

<400> SEQUENCE: 162
ccccaatttt cccaaacaga ggtgaaatct gtaaaccgag gttttggctt agaacctctg 60
tttgggaaaa ttgggg 76

<210> SEQ ID NO 163
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 163
ccccaatttt cccaaacaga ggtcgaaatc tgtaaaccga ggttttggct tagcaacctc 60
tgtttgggaa aattgggg 78

<210> SEQ ID NO 164
<211> LENGTH: 80
<212> TYPE: DNA
<213> ORGANISM: Artificial Sequence
<220> FEATURE:
<223> OTHER INFORMATION: Synthetic Polynucleotide

<400> SEQUENCE: 164
ccccaatttt cccaaacaga ggttcgaaat ctgtaaaccg aggttttggc ttagctaacc 60
tctgtttggg aaaattgggg 80

<210> SEQ ID NO 165
<211> LENGTH: 73
<212> TYPE: DNA
<213> ORGANISM: Artificial Sequence
<220> FEATURE:
<223> OTHER INFORMATION: Synthetic Polynucleotide

<400> SEQUENCE: 165
ccccaatttt cccaaacaga ggttcgaaat ctgtaaaccg aggttttgga acctctgttt 60
gggaaaattg ggg 73

<210> SEQ ID NO 166
<211> LENGTH: 74
<212> TYPE: DNA
<213> ORGANISM: Artificial Sequence
<220> FEATURE:
<223> OTHER INFORMATION: Synthetic Polynucleotide

<400> SEQUENCE: 166
ccccaatttt cccaaacaga ggttcgaaat ctgtaaaccg aggttttggc aacctctgtt 60
tgggaaaatt gggg 74

<210> SEQ ID NO 167
<211> LENGTH: 74
<212> TYPE: DNA
<213> ORGANISM: Artificial Sequence
<220> FEATURE:
<223> OTHER INFORMATION: Synthetic Polynucleotide

<400> SEQUENCE: 167
ccccaatttt cccaaacaga ggtcgaaatc tgtaaaccga ggttttggct aacctctgtt 60
tgggaaaatt gggg 74

<210> SEQ ID NO 168
<211> LENGTH: 76
<212> TYPE: DNA
<213> ORGANISM: Artificial Sequence
<220> FEATURE:
<223> OTHER INFORMATION: Synthetic Polynucleotide

<400> SEQUENCE: 168
ccccaatttt cccaaacaga ggtcgaaatc tgtaaaccga ggttttggct taaacctctg 60
tttgggaaaa ttgggg 76

<210> SEQ ID NO 169
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 169
ccccaatttt cccaaacaga ggtcgaaatc tgtaaaccga ggttttggct tagaacctct 60
gtttgggaaa attgggg 77

<210> SEQ ID NO 170
<211> LENGTH: 72
<212> TYPE: DNA
<213> ORGANISM: Artificial Sequence
<220> FEATURE:
<223> OTHER INFORMATION: Synthetic Polynucleotide

<400> SEQUENCE: 170
ccccaatttt cccaaacaga ggtctgtaaa ccgaggtttt ggcttagcaa cctctgtttg 60
ggaaaattgg gg 72

<210> SEQ ID NO 171
<211> LENGTH: 73
<212> TYPE: DNA
<213> ORGANISM: Artificial Sequence
<220> FEATURE:
<223> OTHER INFORMATION: Synthetic Polynucleotide

<400> SEQUENCE: 171
ccccaatttt cccaaacaga ggttctgtaa accgaggttt tggcttagca acctctgttt 60
gggaaaattg ggg 73

<210> SEQ ID NO 172
<211> LENGTH: 74
<212> TYPE: DNA
<213> ORGANISM: Artificial Sequence
<220> FEATURE:
<223> OTHER INFORMATION: Synthetic Polynucleotide

<400> SEQUENCE: 172
ccccaatttt cccaaacaga ggtatctgta aaccgaggtt ttggcttagc aacctctgtt 60
tgggaaaatt gggg 74

<210> SEQ ID NO 173
<211> LENGTH: 75
<212> TYPE: DNA
<213> ORGANISM: Artificial Sequence
<220> FEATURE:
<223> OTHER INFORMATION: Synthetic Polynucleotide

<400> SEQUENCE: 173
ccccaatttt cccaaacaga ggtaatctgt aaaccgaggt tttggcttag caacctctgt 60
ttgggaaaat tgggg 75

<210> SEQ ID NO 174
<211> LENGTH: 76
<212> TYPE: DNA
<213> ORGANISM: Artificial Sequence
<220> FEATURE:
<223> OTHER INFORMATION: Synthetic Polynucleotide

<400> SEQUENCE: 174
ccccaatttt cccaaacaga ggtaaatctg taaaccgagg ttttggctta gcaacctctg 60
tttgggaaaa ttgggg 76

<210> SEQ ID NO 175
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 175
ccccaatttt cccaaacaga ggtgaaatct gtaaaccgag gttttggctt agcaacctct 60
gtttgggaaa attgggg 77

<210> SEQ ID NO 176
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 176
cccctcccat cacaggccct gaggtttaag agaaaaccat ggttttgtgg gccaggccca 60
tgacccttct cctctggg 78

<210> SEQ ID NO 177
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 177
ccttgtgttg tgtgtcttca actcacagag ttaaacgatg ctttacacag agtagacttg 60
aaacactctt tttctgg 77

<210> SEQ ID NO 178
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 178
ccaccggctc atgagaggta gagctaaggt ccaaacctag gtttatctga gaccggaact 60
catgtgatta actgtgg 77

<210> SEQ ID NO 179
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 179
ccttaagaac ataaatcccc aggaattcac agaaaccttg gtttgagctt tggatttccc 60
gcaggatgtg ggatagg 77

<210> SEQ ID NO 180
<211> LENGTH: 76
<212> TYPE: DNA
<213> ORGANISM: Artificial Sequence
<220> FEATURE:
<223> OTHER INFORMATION: Synthetic Polynucleotide

<400> SEQUENCE: 180
ccactccctc tcccccaaaa agtaaaggta gaaaaccaag gtttacaggc aacaaatagc 60
acaatgaatg gaatgg 76

<210> SEQ ID NO 181
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 181
cctagggaag tgatcatagc tgagtttctg gaaaaaccta ggttttaaag ttgaggagac 60
ttaagtccaa aacctgg 77

<210> SEQ ID NO 182
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 182

Gly Gly Ser Gly Gly Ser
1 5

<210> SEQ ID NO 183
<211> LENGTH: 24
<212> TYPE: PRT
<213> ORGANISM: Artificial Sequence
<220> FEATURE:
<223> OTHER INFORMATION: Synthetic Polypeptide

<400> SEQUENCE: 183

Gly Gly Ser Gly Gly Ser Gly Gly Ser Gly Gly Ser Gly Gly Ser Gly
1 5 10 15

Gly Ser Gly Gly Ser Gly Gly Ser
20

<210> SEQ ID NO 184
<211> LENGTH: 4665
<212> TYPE: DNA
<213> ORGANISM: Artificial Sequence
<220> FEATURE:
<223> OTHER INFORMATION: Synthetic Polynucleotide

<400> SEQUENCE: 184
atgctcattg gctacgtgcg cgtctcaact aacgaccaga ataccgatct tcagaggaac 60
gcactggttt gtgcaggctg cgaacagatt ttcgaggaca aactcagcgg gacacggacg 120
gacagacctg gcctcaagcg agcactcaag aggctgcaga aaggagacac tctggtggtc 180
tggaaattgg accgcctggg tcgaagcatg aagcatctca tttctctggt tggcgaactg 240
cgagaaaggg ggatcaactt tcgaagtctg acggattcca tagatacaag cagccccatg 300
ggccggttct tcttctacgt gatgggtgca ctggctgaaa tggaaagaga actcattata 360
gagcgaacca tggcagggct tgcggctgcc aggaataaag gcaggcggtt tggaagacca 420
ccaaagggtg gatccggagg gtccggaggt agtggcggca gcggtggttc aggtggcagc 480
ggagggtcag gaggctctga taaaaagtat tctattggtt tagctatcgg cactaattcc 540
gttggatggg ctgtcataac cgatgaatac aaagtacctt caaagaaatt taaggtgttg 600
gggaacacag accgtcattc gattaaaaag aatcttatcg gtgccctcct attcgatagt 660

```
ggcgaaacgg cagaggcgac tcgcctgaaa cgaaccgctc ggagaaggta tacacgtcgc    720
aagaaccgaa tatgttactt acaagaaatt tttagcaatg agatggccaa agttgacgat    780
tctttctttc accgtttgga agagtccttc cttgtcgaag aggacaagaa acatgaacgg    840
caccccatct ttggaaacat agtagatgag gtggcatatc atgaaaagta cccaacgatt    900
tatcacctca gaaaaaagct agttgactca actgataaag cggacctgag gttaatctac    960
ttggctcttg cccatatgat aaagttccgt gggcactttc tcattgaggg tgatctaaat   1020
ccggacaact cggatgtcga caaactgttc atccagttag tacaaaccta taatcagttg   1080
tttgaagaga accctataaa tgcaagtggc gtggatgcga aggctattct tagcgcccgc   1140
ctctctaaat cccgacggct agaaaacctg atcgcacaat tacccggaga gaagaaaaat   1200
gggttgttcg gtaaccttat agcgctctca ctaggcctga caccaaattt taagtcgaac   1260
ttcgacttag ctgaagatgc caaattgcag cttagtaagg acacgtacga tgacgatctc   1320
gacaatctac tggcacaaat tggagatcag tatgcggact tatttttggc tgccaaaaac   1380
cttagcgatg caatcctcct atctgacata ctgagagtta atactgagat taccaaggcg   1440
ccgttatccg cttcaatgat caaaaggtac gatgaacatc accaagactt gacacttctc   1500
aaggccctag tccgtcagca actgcctgag aaatataagg aaatattctt tgatcagtcg   1560
aaaaacgggt acgcaggtta tattgacggc ggagcgagtc aagaggaatt ctacaagttt   1620
atcaaaccca tattagagaa gatggatggg acggaagagt tgcttgtaaa actcaatcgc   1680
gaagatctac tgcgaaagca gcggactttc gacaacggta gcattccaca tcaaatccac   1740
ttaggcgaat tgcatgctat acttagaagg caggaggatt tttatccgtt cctcaaagac   1800
aatcgtgaaa agattgagaa aatcctaacc tttcgcatac cttactatgt gggacccctg   1860
gcccgaggga actctcggtt cgcatggatg acaagaaagt ccgaagaaac gattactcca   1920
tggaattttg aggaagttgt cgataaaggt gcgtcagctc aatcgttcat cgagaggatg   1980
accaactttg acaagaattt accgaacgaa aaagtattgc ctaagcacag tttactttac   2040
gagtatttca cagtgtacaa tgaactcacg aaagttaagt atgtcactga gggcatgcgt   2100
aaacccgcct ttctaagcgg agaacagaag aaagcaatag tagatctgtt attcaagacc   2160
aaccgcaaag tgacagttaa gcaattgaaa gaggactact ttaagaaaat tgaatgcttc   2220
gattctgtcg agatctccgg ggtagaagat cgatttaatg cgtcacttgg tacgtatcat   2280
gacctcctaa agataattaa agataaggac ttcctggata acgaagagaa tgaagatatc   2340
ttagaagata tagtgttgac tcttaccctc tttgaagatc gggaaatgat tgaggaaaga   2400
ctaaaaacat acgctcacct gttcgacgat aaggttatga aacagttaaa gaggcgtcgc   2460
tatacgggct ggggacgatt gtcgcggaaa cttatcaacg ggataagaga caagcaaagt   2520
ggtaaaacta ttctcgattt tctaaagagc gacggcttcg ccaataggaa ctttatgcag   2580
ctgatccatg atgactcttt aaccttcaaa gaggatatac aaaaggcaca ggtttccgga   2640
caaggggact cattgcacga acatattgcg aatcttgctg gttcgccagc catcaaaaag   2700
ggcatactcc agacagtcaa agtagtggat gagctagtta aggtcatggg acgtcacaaa   2760
ccggaaaaca ttgtaatcga gatggcacgc gaaaatcaaa cgactcagaa ggggcaaaaa   2820
aacagtcgag agcggatgaa gagaatagaa gagggtatta aagaactggg cagccagatc   2880
ttaaaggagc atcctgtgga aaatacccaa ttgcagaacg agaaacttta cctctattac   2940
ctacaaaatg gaagggacat gtatgttgat caggaactgg acataaaccg tttatctgat   3000
```

-continued

```
tacgacgtcg atgccattgt accccaatcc tttttgaagg acgattcaat cgacaataaa   3060

gtgcttacac gctcggataa gaaccgaggg aaaagtgaca atgttccaag cgaggaagtc   3120

gtaaagaaaa tgaagaacta ttggcggcag ctcctaaatg cgaaactgat aacgcaaaga   3180

aagttcgata acttaactaa agctgagagg ggtggcttgt ctgaacttga caaggccgga   3240

tttattaaac gtcagctcgt ggaaacccgc caaatcacaa agcatgttgc acagatacta   3300

gattcccgaa tgaatacgaa atacgacgag aacgataagc tgattcggga agtcaaagta   3360

atcactttaa agtcaaaatt ggtgtcggac ttcagaaagg attttcaatt ctataaagtt   3420

agggagataa ataactacca ccatgcgcac gacgcttatc ttaatgccgt cgtagggacc   3480

gcactcatta agaaataccc gaagctagaa agtgagtttg tgtatggtga ttacaaagtt   3540

tatgacgtcc gtaagatgat cgcgaaaagc gaacaggaga taggcaaggc tacagccaaa   3600

tacttctttt attctaacat tatgaatttc tttaagacgg aaatcactct ggcaaacgga   3660

gagatacgca aacgaccttt aattgaaacc aatggggaga caggtgaaat cgtatgggat   3720

aagggccggg acttcgcgac ggtgagaaaa gttttgtcca tgccccaagt caacatagta   3780

aagaaaactg aggtgcagac cggagggttt tcaaaggaat cgattcttcc aaaaaggaat   3840

agtgataagc tcatcgctcg taaaaaggac tgggacccga aaaagtacgg tggcttcgat   3900

agccctacag ttgcctattc tgtcctagta gtggcaaaag ttgagaaggg aaaatccaag   3960

aaactgaagt cagtcaaaga attattgggg ataacgatta tggagcgctc gtcttttgaa   4020

aagaacccca tcgacttcct tgaggcgaaa ggttacaagg aagtaaaaaa ggatctcata   4080

attaaactac caaagtatag tctgtttgag ttagaaaatg gccgaaaacg gatgttggct   4140

agcgccggag agcttcaaaa ggggaacgaa ctcgcactac cgtctaaata cgtgaatttc   4200

ctgtatttag cgtcccatta cgagaagttg aaaggttcac ctgaagataa cgaacagaag   4260

caactttttg ttgagcagca caaacattat ctcgacgaaa tcatagagca aatttcggaa   4320

ttcagtaaga gagtcatcct agctgatgcc aatctggaca aagtattaag cgcatacaac   4380

aagcacaggg ataaacccat acgtgagcag gcggaaaata ttatccattt gtttactctt   4440

accaacctcg gcgctccagc cgcattcaag tattttgaca caacgataga tcgcaaacga   4500

tacacttcta ccaaggaggt gctagacgcg acactgattc accaatccat cacgggatta   4560

tatgaaactc ggatagattt gtcacagctt gggggtgacg gtggctccga ttataaggat   4620

gatgacgaca agggaggttc cccaaagaag aaaaggaagg tctga                   4665
```

<210> SEQ ID NO 185
<211> LENGTH: 1554
<212> TYPE: PRT
<213> ORGANISM: Artificial Sequence
<220> FEATURE:
<223> OTHER INFORMATION: Synthetic Polypeptide

<400> SEQUENCE: 185

```
Met Leu Ile Gly Tyr Val Arg Val Ser Thr Asn Asp Gln Asn Thr Asp
1               5                   10                  15

Leu Gln Arg Asn Ala Leu Val Cys Ala Gly Cys Glu Gln Ile Phe Glu
            20                  25                  30

Asp Lys Leu Ser Gly Thr Arg Thr Asp Arg Pro Gly Leu Lys Arg Ala
        35                  40                  45

Leu Lys Arg Leu Gln Lys Gly Asp Thr Leu Val Val Trp Lys Leu Asp
    50                  55                  60

Arg Leu Gly Arg Ser Met Lys His Leu Ile Ser Leu Val Gly Glu Leu
```

```
65                  70                  75                  80

Arg Glu Arg Gly Ile Asn Phe Arg Ser Leu Thr Asp Ser Ile Asp Thr
                85                  90                  95

Ser Ser Pro Met Gly Arg Phe Phe Phe Tyr Val Met Gly Ala Leu Ala
            100                 105                 110

Glu Met Glu Arg Glu Leu Ile Ile Glu Arg Thr Met Ala Gly Leu Ala
        115                 120                 125

Ala Ala Arg Asn Lys Gly Arg Arg Phe Gly Arg Pro Pro Lys Gly Gly
    130                 135                 140

Ser Gly Gly Ser Gly Gly Ser Gly Gly Ser Gly Gly Ser Gly Gly Ser
145                 150                 155                 160

Gly Gly Ser Gly Gly Ser Asp Lys Lys Tyr Ser Ile Gly Leu Ala Ile
                165                 170                 175

Gly Thr Asn Ser Val Gly Trp Ala Val Ile Thr Asp Glu Tyr Lys Val
            180                 185                 190

Pro Ser Lys Lys Phe Lys Val Leu Gly Asn Thr Asp Arg His Ser Ile
        195                 200                 205

Lys Lys Asn Leu Ile Gly Ala Leu Leu Phe Asp Ser Gly Glu Thr Ala
    210                 215                 220

Glu Ala Thr Arg Leu Lys Arg Thr Ala Arg Arg Arg Tyr Thr Arg Arg
225                 230                 235                 240

Lys Asn Arg Ile Cys Tyr Leu Gln Glu Ile Phe Ser Asn Glu Met Ala
                245                 250                 255

Lys Val Asp Asp Ser Phe Phe His Arg Leu Glu Glu Ser Phe Leu Val
            260                 265                 270

Glu Glu Asp Lys Lys His Glu Arg His Pro Ile Phe Gly Asn Ile Val
        275                 280                 285

Asp Glu Val Ala Tyr His Glu Lys Tyr Pro Thr Ile Tyr His Leu Arg
    290                 295                 300

Lys Lys Leu Val Asp Ser Thr Asp Lys Ala Asp Leu Arg Leu Ile Tyr
305                 310                 315                 320

Leu Ala Leu Ala His Met Ile Lys Phe Arg Gly His Phe Leu Ile Glu
                325                 330                 335

Gly Asp Leu Asn Pro Asp Asn Ser Asp Val Asp Lys Leu Phe Ile Gln
            340                 345                 350

Leu Val Gln Thr Tyr Asn Gln Leu Phe Glu Glu Asn Pro Ile Asn Ala
        355                 360                 365

Ser Gly Val Asp Ala Lys Ala Ile Leu Ser Ala Arg Leu Ser Lys Ser
    370                 375                 380

Arg Arg Leu Glu Asn Leu Ile Ala Gln Leu Pro Gly Glu Lys Lys Asn
385                 390                 395                 400

Gly Leu Phe Gly Asn Leu Ile Ala Leu Ser Leu Gly Leu Thr Pro Asn
                405                 410                 415

Phe Lys Ser Asn Phe Asp Leu Ala Glu Asp Ala Lys Leu Gln Leu Ser
            420                 425                 430

Lys Asp Thr Tyr Asp Asp Asp Leu Asp Asn Leu Leu Ala Gln Ile Gly
        435                 440                 445

Asp Gln Tyr Ala Asp Leu Phe Leu Ala Ala Lys Asn Leu Ser Asp Ala
    450                 455                 460

Ile Leu Leu Ser Asp Ile Leu Arg Val Asn Thr Glu Ile Thr Lys Ala
465                 470                 475                 480

Pro Leu Ser Ala Ser Met Ile Lys Arg Tyr Asp Glu His His Gln Asp
                485                 490                 495
```

Leu Thr Leu Leu Lys Ala Leu Val Arg Gln Gln Leu Pro Glu Lys Tyr
500 505 510

Lys Glu Ile Phe Phe Asp Gln Ser Lys Asn Gly Tyr Ala Gly Tyr Ile
515 520 525

Asp Gly Gly Ala Ser Gln Glu Glu Phe Tyr Lys Phe Ile Lys Pro Ile
530 535 540

Leu Glu Lys Met Asp Gly Thr Glu Glu Leu Leu Val Lys Leu Asn Arg
545 550 555 560

Glu Asp Leu Leu Arg Lys Gln Arg Thr Phe Asp Asn Gly Ser Ile Pro
565 570 575

His Gln Ile His Leu Gly Glu Leu His Ala Ile Leu Arg Arg Gln Glu
580 585 590

Asp Phe Tyr Pro Phe Leu Lys Asp Asn Arg Glu Lys Ile Glu Lys Ile
595 600 605

Leu Thr Phe Arg Ile Pro Tyr Tyr Val Gly Pro Leu Ala Arg Gly Asn
610 615 620

Ser Arg Phe Ala Trp Met Thr Arg Lys Ser Glu Glu Thr Ile Thr Pro
625 630 635 640

Trp Asn Phe Glu Glu Val Val Asp Lys Gly Ala Ser Ala Gln Ser Phe
645 650 655

Ile Glu Arg Met Thr Asn Phe Asp Lys Asn Leu Pro Asn Glu Lys Val
660 665 670

Leu Pro Lys His Ser Leu Leu Tyr Glu Tyr Phe Thr Val Tyr Asn Glu
675 680 685

Leu Thr Lys Val Lys Tyr Val Thr Glu Gly Met Arg Lys Pro Ala Phe
690 695 700

Leu Ser Gly Glu Gln Lys Lys Ala Ile Val Asp Leu Leu Phe Lys Thr
705 710 715 720

Asn Arg Lys Val Thr Val Lys Gln Leu Lys Glu Asp Tyr Phe Lys Lys
725 730 735

Ile Glu Cys Phe Asp Ser Val Glu Ile Ser Gly Val Glu Asp Arg Phe
740 745 750

Asn Ala Ser Leu Gly Thr Tyr His Asp Leu Leu Lys Ile Ile Lys Asp
755 760 765

Lys Asp Phe Leu Asp Asn Glu Glu Asn Glu Asp Ile Leu Glu Asp Ile
770 775 780

Val Leu Thr Leu Thr Leu Phe Glu Asp Arg Glu Met Ile Glu Glu Arg
785 790 795 800

Leu Lys Thr Tyr Ala His Leu Phe Asp Asp Lys Val Met Lys Gln Leu
805 810 815

Lys Arg Arg Arg Tyr Thr Gly Trp Gly Arg Leu Ser Arg Lys Leu Ile
820 825 830

Asn Gly Ile Arg Asp Lys Gln Ser Gly Lys Thr Ile Leu Asp Phe Leu
835 840 845

Lys Ser Asp Gly Phe Ala Asn Arg Asn Phe Met Gln Leu Ile His Asp
850 855 860

Asp Ser Leu Thr Phe Lys Glu Asp Ile Gln Lys Ala Gln Val Ser Gly
865 870 875 880

Gln Gly Asp Ser Leu His Glu His Ile Ala Asn Leu Ala Gly Ser Pro
885 890 895

Ala Ile Lys Lys Gly Ile Leu Gln Thr Val Lys Val Val Asp Glu Leu
900 905 910

```
Val Lys Val Met Gly Arg His Lys Pro Glu Asn Ile Val Ile Glu Met
        915                 920                 925

Ala Arg Glu Asn Gln Thr Thr Gln Lys Gly Gln Lys Asn Ser Arg Glu
    930                 935                 940

Arg Met Lys Arg Ile Glu Glu Gly Ile Lys Glu Leu Gly Ser Gln Ile
945                 950                 955                 960

Leu Lys Glu His Pro Val Glu Asn Thr Gln Leu Gln Asn Glu Lys Leu
                965                 970                 975

Tyr Leu Tyr Tyr Leu Gln Asn Gly Arg Asp Met Tyr Val Asp Gln Glu
            980                 985                 990

Leu Asp Ile Asn Arg Leu Ser Asp  Tyr Asp Val Asp Ala  Ile Val Pro
        995                 1000                 1005

Gln Ser  Phe Leu Lys Asp Asp  Ser Ile Asp Asn Lys  Val Leu Thr
    1010                 1015                 1020

Arg Ser  Asp Lys Asn Arg Gly  Lys Ser Asp Asn Val  Pro Ser Glu
    1025                 1030                 1035

Glu Val  Val Lys Lys Met Lys  Asn Tyr Trp Arg Gln  Leu Leu Asn
    1040                 1045                 1050

Ala Lys  Leu Ile Thr Gln Arg  Lys Phe Asp Asn Leu  Thr Lys Ala
    1055                 1060                 1065

Glu Arg  Gly Gly Leu Ser Glu  Leu Asp Lys Ala Gly  Phe Ile Lys
    1070                 1075                 1080

Arg Gln  Leu Val Glu Thr Arg  Gln Ile Thr Lys His  Val Ala Gln
    1085                 1090                 1095

Ile Leu  Asp Ser Arg Met Asn  Thr Lys Tyr Asp Glu  Asn Asp Lys
    1100                 1105                 1110

Leu Ile  Arg Glu Val Lys Val  Ile Thr Leu Lys Ser  Lys Leu Val
    1115                 1120                 1125

Ser Asp  Phe Arg Lys Asp Phe  Gln Phe Tyr Lys Val  Arg Glu Ile
    1130                 1135                 1140

Asn Asn  Tyr His His Ala His  Asp Ala Tyr Leu Asn  Ala Val Val
    1145                 1150                 1155

Gly Thr  Ala Leu Ile Lys Lys  Tyr Pro Lys Leu Glu  Ser Glu Phe
    1160                 1165                 1170

Val Tyr  Gly Asp Tyr Lys Val  Tyr Asp Val Arg Lys  Met Ile Ala
    1175                 1180                 1185

Lys Ser  Glu Gln Glu Ile Gly  Lys Ala Thr Ala Lys  Tyr Phe Phe
    1190                 1195                 1200

Tyr Ser  Asn Ile Met Asn Phe  Phe Lys Thr Glu Ile  Thr Leu Ala
    1205                 1210                 1215

Asn Gly  Glu Ile Arg Lys Arg  Pro Leu Ile Glu Thr  Asn Gly Glu
    1220                 1225                 1230

Thr Gly  Glu Ile Val Trp Asp  Lys Gly Arg Asp Phe  Ala Thr Val
    1235                 1240                 1245

Arg Lys  Val Leu Ser Met Pro  Gln Val Asn Ile Val  Lys Lys Thr
    1250                 1255                 1260

Glu Val  Gln Thr Gly Gly Phe  Ser Lys Glu Ser Ile  Leu Pro Lys
    1265                 1270                 1275

Arg Asn  Ser Asp Lys Leu Ile  Ala Arg Lys Lys Asp  Trp Asp Pro
    1280                 1285                 1290

Lys Lys  Tyr Gly Gly Phe Asp  Ser Pro Thr Val Ala  Tyr Ser Val
    1295                 1300                 1305

Leu Val  Val Ala Lys Val Glu  Lys Gly Lys Ser Lys  Lys Leu Lys
```

```
    1310                1315                1320

Ser Val  Lys Glu Leu Leu Gly  Ile Thr Ile Met Glu  Arg Ser Ser
    1325                1330                1335

Phe Glu  Lys Asn Pro Ile Asp  Phe Leu Glu Ala Lys  Gly Tyr Lys
    1340                1345                1350

Glu Val  Lys Lys Asp Leu Ile  Ile Lys Leu Pro Lys  Tyr Ser Leu
    1355                1360                1365

Phe Glu  Leu Glu Asn Gly Arg  Lys Arg Met Leu Ala  Ser Ala Gly
    1370                1375                1380

Glu Leu  Gln Lys Gly Asn Glu  Leu Ala Leu Pro Ser  Lys Tyr Val
    1385                1390                1395

Asn Phe  Leu Tyr Leu Ala Ser  His Tyr Glu Lys Leu  Lys Gly Ser
    1400                1405                1410

Pro Glu  Asp Asn Glu Gln Lys  Gln Leu Phe Val Glu  Gln His Lys
    1415                1420                1425

His Tyr  Leu Asp Glu Ile Ile  Glu Gln Ile Ser Glu  Phe Ser Lys
    1430                1435                1440

Arg Val  Ile Leu Ala Asp Ala  Asn Leu Asp Lys Val  Leu Ser Ala
    1445                1450                1455

Tyr Asn  Lys His Arg Asp Lys  Pro Ile Arg Glu Gln  Ala Glu Asn
    1460                1465                1470

Ile Ile  His Leu Phe Thr Leu  Thr Asn Leu Gly Ala  Pro Ala Ala
    1475                1480                1485

Phe Lys  Tyr Phe Asp Thr Thr  Ile Asp Arg Lys Arg  Tyr Thr Ser
    1490                1495                1500

Thr Lys  Glu Val Leu Asp Ala  Thr Leu Ile His Gln  Ser Ile Thr
    1505                1510                1515

Gly Leu  Tyr Glu Thr Arg Ile  Asp Leu Ser Gln Leu  Gly Gly Asp
    1520                1525                1530

Gly Gly  Ser Asp Tyr Lys Asp  Asp Asp Asp Lys Gly  Gly Ser Pro
    1535                1540                1545

Lys Lys  Lys Arg Lys Val
    1550
```

<210> SEQ ID NO 186
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 186
ggtggtagcg gtggatcc 18

<210> SEQ ID NO 187
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 187
ggtggatccg gtggttcagg tggcagcgga gggtcaggag gctct 45

<210> SEQ ID NO 188
<211> LENGTH: 72
<212> TYPE: DNA
<213> ORGANISM: Artificial Sequence
<220> FEATURE:
<223> OTHER INFORMATION: Synthetic Polynucleotide

<400> SEQUENCE: 188
ggtggatccg gagggtccgg aggtagtggc ggcagcggtg gttcaggtgg cagcggaggg 60
tcaggaggct ct 72

<210> SEQ ID NO 189
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 189
acctctgttt gggaaaattg 20

<210> SEQ ID NO 190
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 190
gcacactagt tagggataac a 21

<210> SEQ ID NO 191
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 191
gcctcagggc ctgtgatggg a 21

<210> SEQ ID NO 192
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 192
gctcagggcc tgtgatggga g 21

<210> SEQ ID NO 193
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 193
ggcccatgac ccttctcctc 20

<210> SEQ ID NO 194
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 194
gcccatgacc cttctcctct 20

<210> SEQ ID NO 195
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 195
gacttgaaac actctttttc 20

<210> SEQ ID NO 196
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 196
gagttgaaga cacacaacac a 21

<210> SEQ ID NO 197
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 197
ggaactcatg tgattaactg 20

<210> SEQ ID NO 198
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 198
gtctacctct catgagccgg t 21

<210> SEQ ID NO 199
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 199
gtttcccgca ggatgtggga t 21

<210> SEQ ID NO 200
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 200
gcctggggat ttatgttctt a 21

<210> SEQ ID NO 201
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 201
gaaatagcac aatgaatgga a 21

<210> SEQ ID NO 202
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 202
gactttttgg gggagaggga g 21

<210> SEQ ID NO 203
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 203
ggagacttaa gtccaaaacc 20

<210> SEQ ID NO 204
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 204
gtcagctatg atcacttccc t 21

<210> SEQ ID NO 205
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 205
gcagatgtag tgtttccaca 20

<210> SEQ ID NO 206
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 206
gggtgggggg agtttgctcc 20

<210> SEQ ID NO 207
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 207
gatatccgtt tatcagtgtc a 21

<210> SEQ ID NO 208
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 208
gttcctaagc ttgggctgca g 21

<210> SEQ ID NO 209
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 209
gcctaaaagt gactgggaga a 21

<210> SEQ ID NO 210
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 210
gcacagtccc atatttcttg g 21

<210> SEQ ID NO 211
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 211
cctttagtga aaagtagaca gctctgaata tgaaaggtag gttttcattt ctgggaaaga 60
gacgccaagt gatgtgg 77

<210> SEQ ID NO 212
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 212
cctccaataa atatgggact atgtggaaag accaaaccta cgtttgattg gtgtacctga 60
aagtgacggg aagaatgg 78

<210> SEQ ID NO 213
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 213
ccattctgcc cgtcactttc aggtacacca atcaaacgta ggtttagtct tttcacatag 60
tcccatattt cttggagg 78

<210> SEQ ID NO 214
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 214
ccattctccc cgtcactttc aggtacaaca atcaaacgta ggtttggtct tttcacatag 60
tcccatattt cttggagg 78

<210> SEQ ID NO 215
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 215
ccttgtagtg tgtgtattca actcacagag ttaaacgatc ctttacacag agcagacttg 60
aaacactctt gttgtgg 77

<210> SEQ ID NO 216
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 216
ccttgtagtg tgtgtattca actcacagag ttaaacgatc ctttacacag agcatacttg 60
aaacactctt tttgtgg 77

<210> SEQ ID NO 217
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 217
ccttgtgttg tgtgtattca actcacagag ttaaacgatc ctttacacag agcagacttg 60
aaacactctt tttgtgg 77

<210> SEQ ID NO 218
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 218
ccttgtgttg tgtttattca actcacagag ttaaacgatc ctttacacag agcagacttg 60
aaatactctt tttgtgg 77

<210> SEQ ID NO 219
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 219
ccttgtagtg tgtgtattca actcacagag ttaaacgatc ctttacacag agcatacttg 60
aaacactctt tttgtgg 77

<210> SEQ ID NO 220
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 220
ccttgtattg tgagtattca actcacagag ttaaacgatc ctttacacag agcagacttg 60
aaacactctt tttgtgg 77

<210> SEQ ID NO 221
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 221
ccttgtgttg tgtgtcttca actcacagag ttaaacgatg ctttacacag agtagacttg 60
aaacactctt tttctgg 77

<210> SEQ ID NO 222
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 222
ccttgtgttg tgtgtattca actcacagag ttaaacgatc ctttacacag agcagacttg 60
taacactctt tttgtgg 77

<210> SEQ ID NO 223
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 223
ccttgtgttg tgtgtattca actcacagag ttaaacgatc ctttacacag agcagacgtg 60
aaacactctt tttgtgg 77

<210> SEQ ID NO 224
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 224
ccttgtgttg tgtgtattca actcacagag ttaaacgatc ctttacacag agcagacttg 60
aaacactctt tttgtgg 77

<210> SEQ ID NO 225
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 225
ccttgtgttg tgtgtattca actcacagag ttaaacgatc ctttacacag aggagacttg 60
taacactctt tttgtgg 77

<210> SEQ ID NO 226
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 226
cctgaggttt tccaggtttt aaaaggaaac ctaaaggtag gtttagcatt aagtgtcttg 60
aagtttattt taaaagg 77

<210> SEQ ID NO 227
<211> LENGTH: 76
<212> TYPE: DNA
<213> ORGANISM: Artificial Sequence
<220> FEATURE:
<223> OTHER INFORMATION: Synthetic Polynucleotide

<400> SEQUENCE: 227
ccaaaattcc cacaaaaccg aatgcatcag tcaaagcaag gtttgaagaa aagatttacc 60
acttcaggga gcttgg 76

<210> SEQ ID NO 228
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 228
ccttttctgg atatcgttga tgctctgtat gcaaaaggta ggtttttggg ttatgttgtt 60
aaacagtgat tgaatgg 77

<210> SEQ ID NO 229
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 229
cctccaagaa atatggaact atgtgaaaag accaaaccta cgtttgattg gtgtacctga 60
aagtgacaga gagaatgg 78

<210> SEQ ID NO 230
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 230
cctccaagaa atatgggact atgtgagaag accaaaccta cgtttgattg gtgtacctga 60
aagtgatggg gagaatgg 78

<210> SEQ ID NO 231
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 231
ccattctccc catcgctttc aggtacacca atcaaacgta ggtttggtct tttcacatag 60
ttccatattc tttggagg 78

<210> SEQ ID NO 232
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 232
ccattctccc catcactttc aggtgtaccg atcaaacgta ggtttggtct tttcacatag 60
tcccatattt cttggagg 78

<210> SEQ ID NO 233
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 233
cctccaagaa atatgggact atgtgaaaag accaaaccta cgtttgattg gtgtacctga 60
aagtgacggg gagaatgg 78

<210> SEQ ID NO 234
<211> LENGTH: 76
<212> TYPE: DNA
<213> ORGANISM: Artificial Sequence
<220> FEATURE:
<223> OTHER INFORMATION: Synthetic Polynucleotide

<400> SEQUENCE: 234
ccttcagggc agaaacagct ctactagcag agaaagcaag ctttcaatat tgtgcaatac 60
aaaaacgaga gcaggg 76

<210> SEQ ID NO 235
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 235
ccattctcct catctccttc tggtactcca atcaaacgta ggtttggtct tttctcatag 60
tctcatattt cttggagg 78

<210> SEQ ID NO 236
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 236
cctccaagac atataggact atgtgaaaat accaaaccta cgtttgattg gtgtacctga 60
aagtgacagg gagtatgg 78

<210> SEQ ID NO 237
<211> LENGTH: 76
<212> TYPE: DNA
<213> ORGANISM: Artificial Sequence
<220> FEATURE:
<223> OTHER INFORMATION: Synthetic Polynucleotide

<400> SEQUENCE: 237
cctgccagat accagtagtc actgtgaatt acaaagctac gtttcttcca tagggaaagt 60
ttggagtcca gccagg 76

<210> SEQ ID NO 238
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 238
ccattctccc tgtcactttc aggtacacca atcaaacgta ggtttggtct tttcacatag 60
tcccatattt cttggagg 78

<210> SEQ ID NO 239
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 239
ccattctccc caccactttc aggtacacca atcaaacgta ggtttggtct tttcacatag 60
tcccatattt cttgtagg 78

<210> SEQ ID NO 240
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 240
cctaaccaga aactaactaa tagatatggg cagaaagcat cctttcactt ttgttctggg 60
agagggaaga agcaaagg 78

<210> SEQ ID NO 241
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 241
ccattttggg gaggccttga tgggaagctg gaaaaggaag ctttcctccc agtcctgctg 60
aaggccttgc cagctgg 77

<210> SEQ ID NO 242
<211> LENGTH: 78
<212> TYPE: DNA

<213> ORGANISM: Artificial Sequence
<220> FEATURE:
<223> OTHER INFORMATION: Synthetic Polynucleotide

<400> SEQUENCE: 242
cctccaagaa acacaggact atgtgaaaag atcaaaccta cgtttgattg gtgttcctga 60
aagtgatggg gagaatgg 78

<210> SEQ ID NO 243
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 243
ccattctctt catgactttc aggtacacca ttgaaacgta ggtttggtct tttcacattg 60
tcccatattt cttggagg 78

<210> SEQ ID NO 244
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 244
ccattctccc catcactttc aggtacacca atcaaacgta ggtttggtct tttcacatag 60
tcccgtattt cttggtgg 78

<210> SEQ ID NO 245
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 245
ccattctccc tgtcactttc aggtacacca atcaaacgta ggtttggtct tttcacatag 60
tcccatattt cttggggg 78

<210> SEQ ID NO 246
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 246
ccattctccc tgtcactttc aggtacacca atcaaacgta ggtttggtct tttcacatag 60
tcccatattt cttgggg 77

<210> SEQ ID NO 247
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 247
cctccaagaa atatgagatt atatgaaaag accaaaccta cgtttgattg gtgtacttta 60
aagtgacggg gagaatgg 78

<210> SEQ ID NO 248
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 248
ccattctccc cgtcattttc aggtacacca atcaaacgta ggtttggtct tttcacatag 60
tcccaaattt cttggagg 78

<210> SEQ ID NO 249
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 249
cccccaagaa atgtgggact atatgaaaag accaaaccta cgtttgactg gtgtacctaa 60
aagtgatggg gagaatgg 78

<210> SEQ ID NO 250
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 250
ccccaagaaa tgtgggacta tatgaaaaga ccaaacctac gtttgactgg tgtacctaaa 60
agtgatgggg agaatgg 77

<210> SEQ ID NO 251
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 251
cccattggtg ctgaccagat ggtgaaggag gcaaaggttg ctttgaatga ctgtgctctg 60
gggtgagcca ggcctgg 77

<210> SEQ ID NO 252
<211> LENGTH: 76
<212> TYPE: DNA
<213> ORGANISM: Artificial Sequence
<220> FEATURE:
<223> OTHER INFORMATION: Synthetic Polynucleotide

<400> SEQUENCE: 252
ccctttacag aggtgagctt tgttattagt aaaaaggtag gtttccctgt ttttctgaag 60
aaaagctgtg agtggg 76

<210> SEQ ID NO 253
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 253
ccactgccca ttgacagagt ggcgaggtgg gtgaaacctt gctttcctcc tggcccatgg 60
gcagggtggg gctgtggg 78

<210> SEQ ID NO 254
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 254
ccactgccca ttgacagagt ggcgaggtgg gtgaaacctt gctttcctcc tggcccatgg 60
gcagggtggg gctgtgg 77

<210> SEQ ID NO 255
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 255
ccattctccc tgtcactttt agatacacca atcaaacgta ggtttggtct tttcacatag 60
tcccatgttt cttggagg 78

<210> SEQ ID NO 256
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 256
cctccaagaa atatcaactg tgtgaaaaga cgaaacctac gtttgattaa tgtacctgaa 60
agtgacaggg agaatgg 77

<210> SEQ ID NO 257
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 257
ccattctccc attaactttc aagtacacca atcaaaggta ggtttggtgt tttcccatag 60
tcccgtattt cttggagg 78

<210> SEQ ID NO 258
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 258
ccttttcatc atgccccttt cactttaagg tgaaaacctt gctttacatg tcagagaaaa 60
gaagagccct cagctggg 78

<210> SEQ ID NO 259
<211> LENGTH: 77

<212> TYPE: DNA
<213> ORGANISM: Artificial Sequence
<220> FEATURE:
<223> OTHER INFORMATION: Synthetic Polynucleotide

<400> SEQUENCE: 259
ccttttcatc atgccccttt cactttaagg tgaaaacctt gctttacatg tcagagaaaa 60
gaagagccct cagctgg 77

<210> SEQ ID NO 260
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 260
ccattcaccc cgtcactttc aggtacacca atcaaacgta ggtttggtct tttcacatag 60
tcccatattt cttggagg 78

<210> SEQ ID NO 261
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 261
cctccaagaa atatgggact atgtgaaaag accaaaccta cgtttgatgg tgtacccgaa 60
agtgacaggg agaatgg 77

<210> SEQ ID NO 262
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 262
ccaccaagaa atatgggact atgtgaaaag accaaaccta cgtttgatag gtatacctga 60
aagtgacagg gagaatgg 78

<210> SEQ ID NO 263
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 263
ccattctccc catcactttc aggtgcacca atcaaacgta ggtttggtct tttcacatag 60
tcccatattt cttggagg 78

<210> SEQ ID NO 264
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 264
ccctcaagaa atatgagact atgtgaaaag accaaaccta cgtttgactg gtatacctga 60

-continued aagtgacagg gagaatgg 78

<210> SEQ ID NO 265
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 265
cctcaagaaa tatgagacta tgtgaaaaga ccaaacctac gtttgactgg tatacctgaa 60
agtgacaggg agaatgg 77

<210> SEQ ID NO 266
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 266
cctccaacaa atatgggact atgtgaaaag accaaaccta cgtttgattg gtgtacctga 60
aagtgacggg gataatgg 78

<210> SEQ ID NO 267
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 267
ccattctctc cctcactttc aagtacacca atcaaacgta ggtttggtct tttcacatag 60
tcttatattt cttggcgg 78

<210> SEQ ID NO 268
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 268
ccattctccc tgtcactgtc agtacaccaa tcaaacgtag gtttggtctc ttcacatagt 60
cccatatttc ttggagg 77

<210> SEQ ID NO 269
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 269
cctccaagaa atatgggact atgtgaacag accaaaccta cgtttgattg gtgtacctga 60
aagtgatggc agaatgg 77

<210> SEQ ID NO 270
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 270
ccaccatgcc tggccaccac acattttttt ctaaagcttg gttttggcca cagtgagagt 60
ttcttgggct gtcaggg 77

<210> SEQ ID NO 271
<211> LENGTH: 76
<212> TYPE: DNA
<213> ORGANISM: Artificial Sequence
<220> FEATURE:
<223> OTHER INFORMATION: Synthetic Polynucleotide

<400> SEQUENCE: 271
ccaccatgcc tggccaccac acattttttt ctaaagcttg gttttggcca cagtgagagt 60
ttcttgggct gtcagg 76

<210> SEQ ID NO 272
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 272
cccactaggt ggcgatatct gagggtccaa tgaaaccatg ctttttactc agatcttcca 60
ctaaccacct cccccgg 77

<210> SEQ ID NO 273
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 273
cctctaagaa atatgggact atgtgaaaag accaaaccta cgtttgactg gtgtacctga 60
aagtgacggg gagaatgg 78

<210> SEQ ID NO 274
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 274
cctccaagaa atatgggact atgtgaaaag accaaaccta cgtttgatta gtgtacctga 60
aagtgacggg gagaatgg 78

<210> SEQ ID NO 275
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 275
ccattctccc tgtcactttc aggtacatca atcaaacgta ggtttggtct tttcacatag 60
tcccatattt cttggagg 78

<210> SEQ ID NO 276

<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 276
cctccaagaa atatgggact atgtgaaaag accaaaccta cgtttgactg gtgtacctga 60
aagggatggg gagaatgg 78

<210> SEQ ID NO 277
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 277
cccccaagaa atatgagact atgtgaaaag accaaaccta cgtttgattg gtgtacctga 60
aagtgacagg gagaatgg 78

<210> SEQ ID NO 278
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 278
ccccaagaaa tatgagacta tgtgaaaaga ccaaacctac gtttgattgg tgtacctgaa 60
agtgacaggg agaatgg 77

<210> SEQ ID NO 279
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 279
cctctaagaa atatgggact atgtgaaaag accaaaccta cgtttgattg gtgtaactga 60
aagtgacagg gagaatgg 78

<210> SEQ ID NO 280
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 280
cctccaagaa atatgcgcct atgtgaaaag accaaaccta cgtttgattg gtatacctga 60
aagtgatgga gagaatgg 78

<210> SEQ ID NO 281
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 281
ccattctccc tgtcactttg aggtacacca atcaaacgta ggtttggtct tttcacatat 60
tcgcatattt cttggagg 78

<210> SEQ ID NO 282
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 282
ccattctccc cgtcactttc aggtacacca accaaacgtt ggtttggtct tttcacatag 60
tcccatattt cttggagg 78

<210> SEQ ID NO 283
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 283
ccattctccc tgtcactttc cagtacacca gtcaaacgta ggtttggtct tttcacatac 60
tcccatattt cttggagg 78

<210> SEQ ID NO 284
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 284
cctggcctaa tttttaattc ttagtttgac ttaaaccttg cttttagtgt gatggcgaca 60
aaagctgagc tgaaagg 77

<210> SEQ ID NO 285
<211> LENGTH: 76
<212> TYPE: DNA
<213> ORGANISM: Artificial Sequence
<220> FEATURE:
<223> OTHER INFORMATION: Synthetic Polynucleotide

<400> SEQUENCE: 285
ccagtgcttt ttggttttaa aggcaagcct ccaaaccttc ctttctcctg gatgctgtgg 60
tggttgccat gcatgg 76

<210> SEQ ID NO 286
<211> LENGTH: 76
<212> TYPE: DNA
<213> ORGANISM: Artificial Sequence
<220> FEATURE:
<223> OTHER INFORMATION: Synthetic Polynucleotide

<400> SEQUENCE: 286
cccaactcct gcgagaagta gctcaccatg acaaagctac ctttgctttt atcgttttgc 60
aaaacaaaaa aggggg 76

<210> SEQ ID NO 287
<211> LENGTH: 78
<212> TYPE: DNA
<213> ORGANISM: Artificial Sequence
<220> FEATURE:

<223> OTHER INFORMATION: Synthetic Polynucleotide

<400> SEQUENCE: 287
ccattctccc cgtcactttg aggtgtgcca atcaaacgta ggtttggtct tttcacatag 60
tcctatattt cttggagg 78

<210> SEQ ID NO 288
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 288
cctccaaaaa atatgggact acgtaaaaag accaaaccta cgtttgattg gtgtacctga 60
aactgacagg gagaatgg 78

<210> SEQ ID NO 289
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 289
ccattctccc cgtcactttc aggtacacca atcaaacgta ggtttggtct tttcacatag 60
ttccatattt cttggagg 78

<210> SEQ ID NO 290
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 290
cctacaagat atatgggact atgtgaaaag accaaaccta cgttttactg gtgtgcctga 60
aactgacggg gagaatgg 78

<210> SEQ ID NO 291
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 291
ccattctctc tgtcactttc aggtacacca atcaaacgta ggtttggtct tttcacatag 60
tcccatattt cttggagg 78

<210> SEQ ID NO 292
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 292
cctccaagaa atatgggact atgtgaaaag accaaaccta cgtttcattg gtgtacctga 60
aagtgatagg gagaatgg 78

<210> SEQ ID NO 293
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 293
cctccaaaaa atatgggatg atgtgaaaag accaaaccta ggtttgactg gtgtacctga 60
aaatgatggg gagaatgg 78

<210> SEQ ID NO 294
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 294
cctccaagaa atatgagact atgtgaaaag accaaaccta cgtttgattg gtgtacctga 60
aagtgacagg gagaatgg 78

<210> SEQ ID NO 295
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 295
cctccaagaa atatgggact acgtgaaaag atcaaaccta cgtttgattg ttgtacctga 60
aagtgatggg gagaatgg 78

<210> SEQ ID NO 296
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 296
cctccaagaa atatgggact atgtgaaaag accaaaccta cgtttgattg ttgtacctga 60
aagtgatggg gagaatgg 78

<210> SEQ ID NO 297
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 297
cctcaaaagt gttctggttt tgttttgttt tttaaaccat ggttttacct ctggcttagt 60
gggactaaaa ataggagg 78

<210> SEQ ID NO 298
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 298

```
cctccaagaa atatgggact atgtgaaaag accaaaccta cgtttgactg gtgtacctga    60

aagtgatggg gaaaatgg                                                  78

<210> SEQ ID NO 299
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 299

cctccaagaa atatgggact gtgtgtaaag accaaaccta cgtttgattg gtgtacctca    60

aagtgatggg gagaatgg                                                  78

<210> SEQ ID NO 300
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 300

ccattctccc catcacattc aggtacacca atcaaacgta ggtttggtct tttcacatag    60

tcccatattt cttggagg                                                  78

<210> SEQ ID NO 301
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 301

cccctggaaa agttggagca tcacaggaaa agcaaaccaa ccttttttct ccccctaggta    60

aactggggag ccagggg                                                   77

<210> SEQ ID NO 302
<211> LENGTH: 76
<212> TYPE: DNA
<213> ORGANISM: Artificial Sequence
<220> FEATURE:
<223> OTHER INFORMATION: Synthetic Polynucleotide

<400> SEQUENCE: 302

ccctggaaaa gttggagcat cacaggaaaa gcaaaccaac cttttttctc ccctaggtaa    60

actggggagc caggggg                                                   76

<210> SEQ ID NO 303
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 303

ccttccccag ttgcagcaga caagagtctc gaaaagcttg ctttggttgc tgcagtggat    60

gggttggtag gcacagg                                                   77

<210> SEQ ID NO 304
<211> LENGTH: 76
<212> TYPE: DNA
<213> ORGANISM: Artificial Sequence
```

<220> FEATURE:
<223> OTHER INFORMATION: Synthetic Polynucleotide

<400> SEQUENCE: 304
cccccacctc ccaagctgct ggcttctcga ataaagctac ctttcctttt accaaaactt 60
gtctctcgaa tgtcgg 76

<210> SEQ ID NO 305
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 305
ccttggccct ggacagctgc ttttccttcc ctaaaccttg gtttccccct ttgtgcaggt 60
gggtgggttt gggctgg 77

<210> SEQ ID NO 306
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 306
cctcttctag tgaacccatg gggttaccaa gggaaagcaa ccttttgata aatattccca 60
tctttttatg ttgtctgg 78

<210> SEQ ID NO 307
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 307
ccacttgaaa gggttaccaa ggataagatt tttaaagctt gctttcacaa acaactcatg 60
ctccaggctt gtcagtgg 78

<210> SEQ ID NO 308
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 308
cctttctccc catcactttc aggtacacca atcaaacgta ggtttgatct tttcacatag 60
tcccatattt cttggagg 78

<210> SEQ ID NO 309
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 309
ccattctccc catcaatttc agttacacca atgaaacgta ggtttggcct tttcacatag 60
tcccatattt cttagagg 78

<210> SEQ ID NO 310
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 310
ccattctccc tgtcactctc aggtacacca atcaaacgta ggtttggtct tttcatatag 60
tcccatattt cttggagg 78

<210> SEQ ID NO 311
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 311
cctccaagaa aattgggact atgtgaaaaa accaaaccta cgtttgattg atgtacctga 60
aagtgacagg agaatgg 77

<210> SEQ ID NO 312
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 312
ccttcaagaa atatgggact atgtgaaagg acaaaaccta cgttttattg gtgtacctga 60
aagtgacagg gagaatgg 78

<210> SEQ ID NO 313
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 313
ccattctccc catcactttc aggtacgcta atcaaacgta ggtttgatct tttcacatag 60
tcttatattt cttggagg 78

<210> SEQ ID NO 314
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 314
cctccaagaa atatgggact atgtgaaaag accaaaccta cgtttgactg gtgtacctca 60
atgtgacagg gagaatgg 78

<210> SEQ ID NO 315
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 315
ccattctccc tgtcactttt aggtacacca atcaaacgta cgtttggtct tttcacatag 60
acccatattt cttggagg 78

<210> SEQ ID NO 316
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 316
ccttcaagaa atatgggact gtgtgaaaag accaaagcta ggtttgattg gtgtacctga 60
aagtgatggg gagaatgg 78

<210> SEQ ID NO 317
<211> LENGTH: 76
<212> TYPE: DNA
<213> ORGANISM: Artificial Sequence
<220> FEATURE:
<223> OTHER INFORMATION: Synthetic Polynucleotide

<400> SEQUENCE: 317
cctactattc acagagtaat gcagtttgct gaaaaggttg gtttttgctg acctctgaga 60
gctcacatta cagtgg 76

<210> SEQ ID NO 318
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 318
ccattctctc tgtcactttc tggtacacca atcaaacgta ggtttgctct tttcacataa 60
tcccatattt attgaagg 78

<210> SEQ ID NO 319
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 319
ccataacatg tatttgctgg tgctagactc tccaaagcta ggtttctttc tacaacaatg 60
gctggaagtc ttcttgg 77

<210> SEQ ID NO 320
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 320
ccattctccc catcactttc aggtacacca atcaaacgta ggtttggtct tctcacacag 60
tcccatattt cttggagg 78

<210> SEQ ID NO 321
<211> LENGTH: 78
<212> TYPE: DNA

<213> ORGANISM: Artificial Sequence
<220> FEATURE:
<223> OTHER INFORMATION: Synthetic Polynucleotide

<400> SEQUENCE: 321
ccattcttcc cattactttc aggtacacca atcaaacgta ggtttggtct tttcacatag 60
tcccacattt cttggagg 78

<210> SEQ ID NO 322
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 322
ccattctccc cctcactttc aggtacacca atcaaacgta ggtttggtct tttcacattg 60
tcccatattt cttggagg 78

<210> SEQ ID NO 323
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 323
ccattctccc cagcacttac aggtacacca atcaaacgta ggtttggtca tttcacatag 60
tcccatattt cttggagg 78

<210> SEQ ID NO 324
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 324
ccattctccc tgtcactttc aggtacagca atcaaacgta ggtttggtct tttcacatgg 60
tcccatattt cttggagg 78

<210> SEQ ID NO 325
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 325
cctccaagaa atatgagact atgtgaaaag accaaaccta cgtttgattg gtgtacctga 60
aagtgacggg gaagatgg 78

<210> SEQ ID NO 326
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 326
cctccaagaa atatgagact atgtgaaaag accaaaccta cgtttgattg gtgtacctga 60
aagtgacagg gagaatgg 78

<210> SEQ ID NO 327
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 327
cctccaagag atatgagact atgtaaatag accaaaccta cctttgattg gtgtacgtga 60
aagtgacagg aagaatgg 78

<210> SEQ ID NO 328
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 328
ccattctccc catcactttc aggtacacca accaaacgta ggtttggtct tttcacatag 60
tctcatattt cttggagg 78

<210> SEQ ID NO 329
<211> LENGTH: 76
<212> TYPE: DNA
<213> ORGANISM: Artificial Sequence
<220> FEATURE:
<223> OTHER INFORMATION: Synthetic Polynucleotide

<400> SEQUENCE: 329
cctccattga ctactcctta tcattggcta gaaaacctac ctttcaacca gtttctaagg 60
ccaagaaact tggagg 76

<210> SEQ ID NO 330
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 330
ccaccaagaa atatgggact acgtgaaaag accaaaccta cgtttgatgg gtgtgcctga 60
aagtgacggg aagaatgg 78

<210> SEQ ID NO 331
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 331
cctccaagaa ataagggact atgtgaaaag accaaaccta cgtttgattg gtgtacctga 60
aggtgacagg gagaatgg 78

<210> SEQ ID NO 332
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 332
ccaaagggcc tttgtgattc tactttgtaa tataaaggat ggtttcttac tacggttggt 60
gtccttgcag gagtggg 77

<210> SEQ ID NO 333
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 333
cctccaagaa atatgggact atgtgaaaag accaaaccta cgtttgattg gtgtacctga 60
aagtgatggg gagaatgg 78

<210> SEQ ID NO 334
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 334
ccattctccc cgttactttc aggtacacca ataaaaccta ggtttggtct tttcacatag 60
tcccatattt cttggagg 78

<210> SEQ ID NO 335
<211> LENGTH: 76
<212> TYPE: DNA
<213> ORGANISM: Artificial Sequence
<220> FEATURE:
<223> OTHER INFORMATION: Synthetic Polynucleotide

<400> SEQUENCE: 335
cccatatctc tggcaagggc agctctctgg ctaaaccaag ctttcctgta gagcttgagt 60
tccaaggcag cgttgg 76

<210> SEQ ID NO 336
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 336
ccttgtagtg tgtgtattca actcacagag ttaaacgatc ctttacacag agcagacttg 60
aaacactctt gttgtgg 77

<210> SEQ ID NO 337
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 337
ccttgtagtg tgtgtattca actcacagag ttaaacgatc ctttacacag agcatacttg 60
aaacactctt tttgtgg 77

<210> SEQ ID NO 338
<211> LENGTH: 77

<212> TYPE: DNA
<213> ORGANISM: Artificial Sequence
<220> FEATURE:
<223> OTHER INFORMATION: Synthetic Polynucleotide

<400> SEQUENCE: 338
ccttgtgttg tgtgtattca actcacagag ttaaacgatc ctttacacag agcagacttg 60
aaacactctt tttgtgg 77

<210> SEQ ID NO 339
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 339
ccttgtgttg tgtttattca actcacagag ttaaacgatc ctttacacag agcagacttg 60
aaatactctt tttgtgg 77

<210> SEQ ID NO 340
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 340
ccttgtagtg tgtgtattca actcacagag ttaaacgatc ctttacacag agcatacttg 60
aaacactctt tttgtgg 77

<210> SEQ ID NO 341
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 341
ccttgtattg tgagtattca actcacagag ttaaacgatc ctttacacag agcagacttg 60
aaacactctt tttgtgg 77

<210> SEQ ID NO 342
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 342
ccttgtgttg tgtgtcttca actcacagag ttaaacgatg ctttacacag agtagacttg 60
aaacactctt tttctgg 77

<210> SEQ ID NO 343
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 343
ccttgtgttg tgtgtattca actcacagag ttaaacgatc ctttacacag agcagacttg 60
taacactctt tttgtgg 77

<210> SEQ ID NO 344
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 344
ccttgtgttg tgtgtattca actcacagag ttaaacgatc ctttacacag agcagacgtg 60
aaacactctt tttgtgg 77

<210> SEQ ID NO 345
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 345
ccttgtgttg tgtgtattca actcacagag ttaaacgatc ctttacacag agcagacttg 60
aaacactctt tttgtgg 77

<210> SEQ ID NO 346
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 346
ccttgtgttg tgtgtattca actcacagag ttaaacgatc ctttacacag aggagacttg 60
taacactctt tttgtgg 77

<210> SEQ ID NO 347
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 347
ccttttcata agaagaaaat cgactcatca ttgaaaccaa gctttggtac aatttcattg 60
atgtttccag aagcagg 77

<210> SEQ ID NO 348
<211> LENGTH: 76
<212> TYPE: DNA
<213> ORGANISM: Artificial Sequence
<220> FEATURE:
<223> OTHER INFORMATION: Synthetic Polynucleotide

<400> SEQUENCE: 348
cccatagact atgatagaaa caaaataacc caaaagctag ctttctgatt gagtttccat 60
aaatgcaatg tgaagg 76

<210> SEQ ID NO 349
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 349
ccattcactt gtcactttct ggtacaccaa tcaaacgtag gtttggtctt ttcacatagt    60
ctcatatttc ttggagg                                                  77

<210> SEQ ID NO 350
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 350
cctccaagaa atatgggact ctgtaaagag accaaaccta cgtttgattg gtgtacctga    60
aagtgaaggg gagaatgg                                                 78

<210> SEQ ID NO 351
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 351
ccattctccc cgtcattttc aggtacacca atcaaaccta ggtttggtct ttttacatag    60
tcccatattt cttggagg                                                 78

<210> SEQ ID NO 352
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 352
cctccacgaa acatgggact atgtgaaaag accaaaccta cgtttgattg gtgtacctga    60
aagtgacagg gagaatgg                                                 78

<210> SEQ ID NO 353
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 353
ccaatttccc cctcactttc agatacacca atcaaacgta ggtttggtct tttcacatag    60
ttccatattt cctggagg                                                 78

<210> SEQ ID NO 354
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 354
ccattctccc catcactttc aggtacacca atcaaacgta ggtttggtct tttcacatat    60
tcccatatgt cttggagg                                                 78

<210> SEQ ID NO 355

<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 355
cccaccggct catgagaggt agagctaagg tccaaaccta ggtttatctg agaccggaac 60
tcatgtgatt aactgtgg 78

<210> SEQ ID NO 356
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 356
ccaccggctc atgagaggta gagctaaggt ccaaacctag gtttatctga gaccggaact 60
catgtgatta actgtgg 77

<210> SEQ ID NO 357
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 357
ccttcaagaa atatgggact atgtgaagag accaaaccta cgtttgattg gtgtagccaa 60
aagtgatggg gaaaatgg 78

<210> SEQ ID NO 358
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 358
cctcagatta gatttacttg caaagagaca tttaaaggat cgttttgata ctattttgaa 60
agtactatac aaagatgg 78

<210> SEQ ID NO 359
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 359
ccttaagaac ataaatcccc aggaattcac agaaaccttg gtttgagctt tggatttccc 60
gcaggatgtg ggatagg 77

<210> SEQ ID NO 360
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 360
ccattctctc tgtcactttc aggtacacca atcaaacgta ggtttggtct tttctcatag 60
tcccatattt cttggagg 78

<210> SEQ ID NO 361
<211> LENGTH: 76
<212> TYPE: DNA
<213> ORGANISM: Artificial Sequence
<220> FEATURE:
<223> OTHER INFORMATION: Synthetic Polynucleotide

<400> SEQUENCE: 361
ccatttacca tcattctctg tcatggcagg tgaaagcaag cttttatata gacaatgttc 60
tacttagttt acaggg 76

<210> SEQ ID NO 362
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 362
cccaaagtta attttactct ttttctgaat caaaaggaac ctttcctcca tgagaagaat 60
cctgccatat ttctagg 77

<210> SEQ ID NO 363
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 363
cctccaagaa atatgggact atgtgaaaag accaaaccta cgtttgattg ctatacatga 60
aagtgacggg gagaatgg 78

<210> SEQ ID NO 364
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 364
ccttcaagaa atatgggact atgtgaaaag accaaaccta cctttgattg gtgtacctga 60
aagtgatggg aagaatgg 78

<210> SEQ ID NO 365
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 365
ccattctccc catcactttc aggtacacca atcaaacgta ggtttggtct tttcacatag 60
tcccatagtt cttggagg 78

<210> SEQ ID NO 366
<211> LENGTH: 78
<212> TYPE: DNA
<213> ORGANISM: Artificial Sequence
<220> FEATURE:

<223> OTHER INFORMATION: Synthetic Polynucleotide

<400> SEQUENCE: 366
ccattctccc cgtcactttc agggacaaca atcaaacgta ggtttggcct ttgcacatag 60
tcttatattt cttggagg 78

<210> SEQ ID NO 367
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 367
ccattctccc catcactttc aggtacacca atcaaacgta ggtttggtct tttcacatag 60
tcccatattt cttggagg 78

<210> SEQ ID NO 368
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 368
cctccaaaaa atatgggact atgtgagaag accaaaccta cgttttatta gtgtacctca 60
aagtgacagg gaggatgg 78

<210> SEQ ID NO 369
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 369
ccattctccc catcactttc aggtacacca atgaaacgta ggtttggcct tttcacatag 60
tttcatattt cttggagg 78

<210> SEQ ID NO 370
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 370
cctccaagaa atatgggact atgtgaaaag accaaaccta cgtttgattg gtgtacctga 60
aagtgatggg gagaatgg 78

<210> SEQ ID NO 371
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 371
cctacaagaa atatggaact tgtaaaaaga ccaaacctac gtttgattgg tgtacctgaa 60
agtgacgggg agaatgg 77

<210> SEQ ID NO 372
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 372
cctccaagaa atatgggaca atgtgaaaag gccaaagcta cgtttgattg gtgtacctga 60
aagtgacagg gagaatgg 78

<210> SEQ ID NO 373
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 373
cctttcaaac ttagaggtaa acaaaagtcc tgaaaaccta ggtttgacca taagttggga 60
ccatacgagc atagaagg 78

<210> SEQ ID NO 374
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 374
ccaaaaataa aaaaaaattg acttataagt aagaaaggtt cgttttctca cattcagaaa 60
gagaacccac atgttggg 78

<210> SEQ ID NO 375
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 375
ccaaaaataa aaaaaaattg acttataagt aagaaaggtt cgttttctca cattcagaaa 60
gagaacccac atgttgg 77

<210> SEQ ID NO 376
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 376
ccattctccc catcactttc aggtacacca atcaaacgta ggtttggtct tttcacatag 60
tcccatattt cttggagg 78

<210> SEQ ID NO 377
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 377
ccattctccc cgtcactttc aggtacacca atcaaacgtt ggtttagtct attcacatag 60
tcccatattt cttggagg 78

<210> SEQ ID NO 378
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 378
ccgaaaagaa taagactatc agctgaagtc ttaaaacgat cctttggccc ccagtactct 60
atatgcagga tagaaagg 78

<210> SEQ ID NO 379
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 379
cctacaaaaa taggggacta tgtgataaga ccaaacctac gtttgattgg tgtacctgaa 60
agtgatgggg agaatgg 77

<210> SEQ ID NO 380
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 380
ccattctacc catcactttc aggtacacca atcaaacgta ggtttggcct tttcatatag 60
tctcatattt cttggagg 78

<210> SEQ ID NO 381
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 381
ccattctccc catcactttc tggtatacca atcaaacgta ggtttggtct tttcacatag 60
tcccatattt cttagagg 78

<210> SEQ ID NO 382
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 382
ccattctccc catcactttc aggtacacca atcaaacgta ggtttggtct tttcacatag 60
tcccatattt cttggagg 78

<210> SEQ ID NO 383
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 383
ccattctccc catcactttc aggtacacca atcaaacgta ggtttggtct tttcacatag    60
tcccatattt cttggagg                                                  78

<210> SEQ ID NO 384
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 384
ccattctccc catcactttc aggtacacca atcaaacgta ggtttggtct tttcacatag    60
tcccatattt cttggagg                                                  78

<210> SEQ ID NO 385
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 385
ccattctccc catcactttc aggtacacca atcaaacgta ggtttggtct tttcacatag    60
tcccatattt cttggagg                                                  78

<210> SEQ ID NO 386
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 386
ccattctccc catcactttc aggtacacca atcaaacgta ggtttggtct tttcacatag    60
tcccatattt cttggagg                                                  78

<210> SEQ ID NO 387
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 387
ccattctccc catcactttc aggtacacca atcaaacgta ggtttggtct tttcacatag    60
tcccatattt cttggagg                                                  78

<210> SEQ ID NO 388
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 388
ccaccacacc cagccttatg ggatggtttt caaaagcatc cttttttaga agtggattct    60
gatatataat cggatgg                                                   77

<210> SEQ ID NO 389
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 389
ccattctcaa tgtcactttc aggtacacca atcaaacgta ggtttggtct tttcacatag 60
tcccatattt cttggagg 78

<210> SEQ ID NO 390
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 390
ccattctctc tgtcactttc aggtacacca gtcaaaggta ggtttgtttt attcacacgt 60
tcacatattt cttggagg 78

<210> SEQ ID NO 391
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 391
ccattcgccc catcactttc aggtacacta gtaaaacgta ggtttggtct tttcacatag 60
ttccatattt cttggagg 78

<210> SEQ ID NO 392
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 392
cctccaagaa atatgggact atgtgaagag atcaaaccta ggtttgattg ttgtacctga 60
aagtgataag aagaatgg 78

<210> SEQ ID NO 393
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 393
cctccaataa atatggggct atgtgaaaag accaaaccta cgtttgattg gtgtacctga 60
aagtgacagg gagaatgg 78

<210> SEQ ID NO 394
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 394

```
cccttttccc tgtcactttc aggtacacca gtcaaacgta ggtttggtct tttcacatag    60

tcgaatattt cttcaagg                                                 78

<210> SEQ ID NO 395
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 395

ccttttccct gtcactttca ggtacaccag tcaaacgtag gtttggtctt ttcacatagt    60

cgaatatttc ttcaagg                                                  77

<210> SEQ ID NO 396
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 396

ccattctccc tgtcactttc aggtacacta atcaaacgta ggtttggtgt attcacacag    60

tcccatattt cttggagg                                                 78

<210> SEQ ID NO 397
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 397

ccattcttcc tgtcactttc aggtatacca atcaaacgta ggtttggtct tttcacatag    60

tcccatgttt cttggagg                                                 78

<210> SEQ ID NO 398
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 398

cctccaagaa atatgagact atatgaaaat accaaaccta cgtttgattg gtgtacctga    60

aagagacagg gagaatgg                                                 78

<210> SEQ ID NO 399
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 399

ccattctccc tatcactttc aggtacacca atcaaacgta ggtttggtct tttcatgtag    60

tcccatattt cttggagg                                                 78

<210> SEQ ID NO 400
<211> LENGTH: 78
<212> TYPE: DNA
```

<213> ORGANISM: Artificial Sequence
<220> FEATURE:
<223> OTHER INFORMATION: Synthetic Polynucleotide

<400> SEQUENCE: 400
ccattctgcc cgtcactttc aggtacacca atcaaacgta ggtttggtct tttcacatag 60
tcccatattt cttggagg 78

<210> SEQ ID NO 401
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 401
ccgtccgatt atatatcaga atctacttct aaaaaaggat gcttttgaaa accatcccat 60
aaggctgggt gtggtgg 77

<210> SEQ ID NO 402
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 402
cctacaagga atataggact atgtgaaaat accaaaccta cgtttcactg ctgtacctga 60
aggtgacagg gagaatgg 78

<210> SEQ ID NO 403
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 403
ccattctccc catcatttcc aggtaaacca atcaaaggta ggtttggtca tttcacatag 60
tcccatattt cttggagg 78

<210> SEQ ID NO 404
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 404
ccattctccc cgtcactttc aggtacacca gtcaaacgta ggtttggtct tttcacacag 60
tcccatattt cctggagg 78

<210> SEQ ID NO 405
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 405
ccattctccc catcactttc aggtacagca atcaaacgta ggtttggtct tttcacatag 60
tcccatattt cttggagg 78

<210> SEQ ID NO 406
<211> LENGTH: 76
<212> TYPE: DNA
<213> ORGANISM: Artificial Sequence
<220> FEATURE:
<223> OTHER INFORMATION: Synthetic Polynucleotide

<400> SEQUENCE: 406
ccactacaga ttcttgggtc aagatgtgtg caaaaggatg ctttagggtg atggatatga 60
gtgggatgaa atgagg 76

<210> SEQ ID NO 407
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 407
cctgaaaaaa aaccctgcca gccagcaact ctgaaaggat gctttgtgtg agtgagcagt 60
gtctgagatg gacaggg 77

<210> SEQ ID NO 408
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 408
ccattctccc catcactttc aggtacgcca atcaaacgta ggtttggtct tttgacatag 60
tcccatattt cttggagg 78

<210> SEQ ID NO 409
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 409
ccgttctccc catcactttt aggtacacca atcaaacgta ggtttggtct tttcacatag 60
tctcatattt cttggagg 78

<210> SEQ ID NO 410
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 410
ccattctcct ggtcactttc aggtatacca atcaaacgta ggtttggtct tttcatgtag 60
tcccatattt cttggagg 78

<210> SEQ ID NO 411
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 411
cctccaagaa atatgggact acatgaaaag accaaaccta cgtttgattg gtatacctga 60
aagtgaccag gagaatgg 78

<210> SEQ ID NO 412
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 412
cctccaagaa ctatgggact atgtgaaaag accaaaccta cgtttgattg gtgtacctga 60
aagtgacggg gagaatgg 78

<210> SEQ ID NO 413
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 413
ccattctccc cgtcactttc aggtacacca atcaaacgta ggtttggtct tttcacatag 60
tcccatagtt cttggagg 78

<210> SEQ ID NO 414
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 414
ccattctccc cgtcactttc aggtacacca atcaaacgta ggtttggtct tttcacagag 60
tcccatattt cttggagg 78

<210> SEQ ID NO 415
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 415
ccattctccc cgtcactttc atgtacacca agcaaacgta ggtttgatct ttccacatag 60
tcccgtgttt cttggagg 78

<210> SEQ ID NO 416
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 416
cctccaagaa atatgggact atgtgaaaag accaaaccta cgtttgattg gtgtacttga 60
aagtgacagg gagaatgg 78

<210> SEQ ID NO 417
<211> LENGTH: 78

<212> TYPE: DNA
<213> ORGANISM: Artificial Sequence
<220> FEATURE:
<223> OTHER INFORMATION: Synthetic Polynucleotide

<400> SEQUENCE: 417
cctccaagaa atatgggact atgtgaaaag acaaaaccta cgtttcactg gtgtacctga 60
aagtgacagg gaggatgg 78

<210> SEQ ID NO 418
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 418
cccccacctt ttaaaaacat gcatacatac ggaaacgttg ctttctgcac gatttcattt 60
taatggaaca gaacagg 77

<210> SEQ ID NO 419
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 419
ccatttcccc tgtcactttc aggtacacca atcaaacgta ggtttggtct tttcacatag 60
tatcatattt cttggagg 78

<210> SEQ ID NO 420
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 420
ccattctccc cgtcactttc aggtacacca atcaaacgta ggtttggtct tttcacatag 60
tcccatattt ctggagg 77

<210> SEQ ID NO 421
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 421
ccttttgtta aagtaataga attctgcttc ttaaaggaac ctttcaggca agatggtggt 60
tagagcacct aaatggg 77

<210> SEQ ID NO 422
<211> LENGTH: 76
<212> TYPE: DNA
<213> ORGANISM: Artificial Sequence
<220> FEATURE:
<223> OTHER INFORMATION: Synthetic Polynucleotide

<400> SEQUENCE: 422
ccttttgtta aagtaataga attctgcttc ttaaaggaac ctttcaggca agatggtggt 60
tagagcacct aaatgg 76

<210> SEQ ID NO 423
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 423
cctccaagaa ctatgggact atgtgaaaag accaaaccta cgtttgattg gtgtacctga 60
aagtgacggg gagaatgg 78

<210> SEQ ID NO 424
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 424
ccattctccc cgtcactttc aggtacacca atcaaacgta ggtttggcct tttcacatag 60
tcccatagtt cttggagg 78

<210> SEQ ID NO 425
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 425
cctccaagaa atatgggact ggtgaaaaga ccaaacctac gtttgactgg tgtacctgaa 60
agtgacgggg agactgg 77

<210> SEQ ID NO 426
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 426
cctccaagaa acatgggaat gtgtgaaaag accaaaccta cgtttgattg gcgtacctga 60
aagtgacggg gagtatgg 78

<210> SEQ ID NO 427
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 427
cctccaagaa atatgggact gtgtgaaaag accaaaccta cgtttgattg gtatacctga 60
aagtgacaga gagaatgg 78

<210> SEQ ID NO 428
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 428
ccattctccc cttcactatc aggtacacca atcaaacgta ggtttagtct tttcacatag 60
tcccatattt cttggagg 78

<210> SEQ ID NO 429
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 429
ccattctccc cgtcactttc agatacacca gtcaaacgta ggtttggtct tttcacatag 60
tcccatattt cttggagg 78

<210> SEQ ID NO 430
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 430
ccatcttact ttgtactaca ctgttcttta gagaaagctt ccttttggag accaaccagg 60
actccttaga agcagagg 78

<210> SEQ ID NO 431
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 431
ccatcttact ttgtactaca ctgttcttta gagaaagctt ccttttggag accaaccagg 60
actccttaga agcagagg 78

<210> SEQ ID NO 432
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 432
cctctgcttc taaggagtcc tggttggtct ccaaaaggaa gctttctcta aagaacagtg 60
tagtacaaag taagatgg 78

<210> SEQ ID NO 433
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 433
cctctgcttc taaggagtcc tggttggtct ccaaaaggaa gctttctcta aagaacagtg 60
tagtacaaag taagatgg 78

<210> SEQ ID NO 434

<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 434
cctctgcttc taaggagtcc tggttggtct ccaaaaggaa gctttctcta aagaacagtg 60
tagtacaaag taagatgg 78

<210> SEQ ID NO 435
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 435
ccaccactgt gcctggccat tttcactatt cttaaaggaa gctttggttt acaaaggttt 60
gctactgtac ttccagg 77

<210> SEQ ID NO 436
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 436
ccattctccc tgtcactttc aggtacacca ttcaaacgta ggtttggtct tttctcatag 60
tcccatattt cttggagg 78

<210> SEQ ID NO 437
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 437
cctccaagaa attcgggact atgtgaaaag acaaaaccta cgtttaattg gtgtgtggtg 60
tacctgaaag tgacaagg 78

<210> SEQ ID NO 438
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 438
cctccaagaa atatgggact atgtgaaaag accaaaccta cgtttgattg gtgtacctga 60
aagtgaccag aagaatgg 78

<210> SEQ ID NO 439
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 439
cctccaagaa atatgggact atgtgaaaag cccaaaccta cgtttgactg atgtacctaa 60
agtgacgggg agaatgg 77

<210> SEQ ID NO 440
<211> LENGTH: 76
<212> TYPE: DNA
<213> ORGANISM: Artificial Sequence
<220> FEATURE:
<223> OTHER INFORMATION: Synthetic Polynucleotide

<400> SEQUENCE: 440
cccgcactgt gagcttggcc gagtgctgtc tgaaagcatc ctttcccttc acctggagac 60
tggagcgcca tagagg 76

<210> SEQ ID NO 441
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 441
cctgtctccc ccattccatg caaaataaaa cacaaaccaa gctttgcttt aagtgctccc 60
tgatgcagtt cagcgtgg 78

<210> SEQ ID NO 442
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 442
ccattcttcc cgtcacattc aggtacacca atcaaacgta ggtttggtct tttcccatag 60
tcccatattt cttagagg 78

<210> SEQ ID NO 443
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 443
ccccctgctc agcttgggga agaaaaatac aaaaacgatg cttttaggca ttttaaacaa 60
cttcactaca ttgaggg 77

<210> SEQ ID NO 444
<211> LENGTH: 76
<212> TYPE: DNA
<213> ORGANISM: Artificial Sequence
<220> FEATURE:
<223> OTHER INFORMATION: Synthetic Polynucleotide

<400> SEQUENCE: 444
ccccctgctc agcttgggga agaaaaatac aaaaacgatg cttttaggca ttttaaacaa 60
cttcactaca ttgagg 76

<210> SEQ ID NO 445
<211> LENGTH: 78
<212> TYPE: DNA
<213> ORGANISM: Artificial Sequence
<220> FEATURE:

<223> OTHER INFORMATION: Synthetic Polynucleotide

<400> SEQUENCE: 445
cctttgtgtt gtgtgtattc aactcacaga gtgaaacctt cctttattca gagcagtttt 60
gaaacactct ttttgtgg 78

<210> SEQ ID NO 446
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 446
cctttgtgtt gtgtgtattc aactcacaga gtgaaacctt cctttattca gagcagtttt 60
gaaaaacact ttttgtgg 78

<210> SEQ ID NO 447
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 447
cctttgtgtt gtgtgtattc aactcacaga gtgaaacctt cctttattca gagcagtttt 60
gaaaaactct ttttgtgg 78

<210> SEQ ID NO 448
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 448
cctttgtgtt gtgtgtattc aactcacaga gtgaaacctt cctttattca gagcagtttt 60
gaaacactct ttttgtgg 78

<210> SEQ ID NO 449
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 449
cctttgtgtt gtgtgtattc aactcacaga gtgaaacctt cctttattca gagcagtttt 60
gaaatactct ttttgtgg 78

<210> SEQ ID NO 450
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 450
cctttgtgtt gtgtgtattc aactcacaga gtgaaacctt cctttattca gagcagtttt 60
gaaacactct ttttgtgg 78

<210> SEQ ID NO 451
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 451
ccattctccc tgtcactttc aagtacacca atcaaaccta ggtttggtct tttcacatag 60
ttccatattt cttggagg 78

<210> SEQ ID NO 452
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 452
cccctcccat cacaggccct gaggtttaag agaaaaccat ggttttgtgg gccaggccca 60
tgacccttct cctctggg 78

<210> SEQ ID NO 453
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 453
cccctcccat cacaggccct gaggtttaag agaaaaccat ggttttgtgg gccaggccca 60
tgacccttct cctctgg 77

<210> SEQ ID NO 454
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 454
ccctcccatc acaggccctg aggtttaaga gaaaaccatg gttttgtggg ccaggcccat 60
gacccttctc ctctggg 77

<210> SEQ ID NO 455
<211> LENGTH: 76
<212> TYPE: DNA
<213> ORGANISM: Artificial Sequence
<220> FEATURE:
<223> OTHER INFORMATION: Synthetic Polynucleotide

<400> SEQUENCE: 455
ccctcccatc acaggccctg aggtttaaga gaaaaccatg gttttgtggg ccaggcccat 60
gacccttctc ctctgg 76

<210> SEQ ID NO 456
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 456
ccattctccc catcactttc aggtacacca atcaaacgta ggtttcatct tttcacatag 60
tcccacggtt tttggagg 78

<210> SEQ ID NO 457
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 457
cctccaagat atatgggact atgtgaaaag accaaaccta cgtttgattg gtgtacctga 60
aattgatggg gagaatgg 78

<210> SEQ ID NO 458
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 458
cctccaagaa atatgggact gtgtgaaaag aacaaaccta cgtttgattg gtgtacgtga 60
aagtgatggg gagaatgg 78

<210> SEQ ID NO 459
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 459
ccattcctcc cgtcactttc agatacacca aaaaaacgta ggtttggtct cttcacatag 60
tcccacattt cttggagg 78

<210> SEQ ID NO 460
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 460
cctccaagaa atgtgggact atgtgaagag accaaaccta cgttttttttg gtgtatctga 60 aagtgacggg aggaatgg 78

<210> SEQ ID NO 461
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 461
cctccaaggg gaatctgagt tctctgaaga caaaaagcat ggtttctttt cttctgtatt 60
tcttattgtt tcctagg 77

<210> SEQ ID NO 462
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 462
ccattctccc tatcactttc cagtacacca atcaaacgta ggtttggtct tttcacatag 60
tcccatattt cttggagg 78

<210> SEQ ID NO 463
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 463
cctccaagaa atatgggact atgtgaaaag accaaaccta cgtttgattg gtatacttga 60
aattgacaag gagaatgg 78

<210> SEQ ID NO 464
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 464
cctccaagaa atatgggact atgtggaaag accaaaccta cgtttgactg gtgtacctga 60
aagtgatggg gagaatgg 78

<210> SEQ ID NO 465
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 465
cctctaagaa atatgggact atgtgaagag atgaaaccta cgtttgattg gtgtacctga 60
aagtgacgag gagaatgg 78

<210> SEQ ID NO 466
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 466
ccctcgtata ctacatgcta tagtcaaagc agtaaacctt cctttcctta agcagaccac 60
actctttcat gcctggg 77

<210> SEQ ID NO 467
<211> LENGTH: 76
<212> TYPE: DNA
<213> ORGANISM: Artificial Sequence
<220> FEATURE:
<223> OTHER INFORMATION: Synthetic Polynucleotide

<400> SEQUENCE: 467
cctcgtatac tacatgctat agtcaaagca gtaaaccttc ctttccttaa gcagaccaca 60
ctctttcatg cctggg 76

<210> SEQ ID NO 468
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 468
ccattctccc catcactttc aggtatacta atcaaaggta ggtttggtct tttcacatag 60
tcccatattt catggagg 78

<210> SEQ ID NO 469
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 469
ccattccccc gtcactttca ggtacaccaa tcaaacgtag gtttggtctt ttcacatagt 60
cccatatttc ttggagg 77

<210> SEQ ID NO 470
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 470
ccattctccc cgtcactttc aggtacacca atcaaacgta ggttttgtct tttcttatag 60
tcccatattt cttggagg 78

<210> SEQ ID NO 471
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 471
ccactgcacc tgaccaagat ccttaatttt tctaaaccta cgtttatcat ctataaaatg 60
agccatcttt tcacatgg 78

<210> SEQ ID NO 472
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 472
cctccgagaa atatgggact atgtgaaaag accaaaccta cgtttgattg ttgtacctga 60
aagtgacagg gagaatgg 78

<210> SEQ ID NO 473
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 473
ccattctccc catcactttt aggtacacca atcaaacgta ggtttggtcc ttttgcatag 60
acccatattt cttggagg 78

<210> SEQ ID NO 474
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 474
ccattttccc cgtcagtttc atatacacct atcaaacgta ggtttactgt tttcacatag 60
tcccttattt cttggagg 78

<210> SEQ ID NO 475
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 475
cctccaagaa atatgggact atgtgaaaag accaaaccta cctttgattg gtgtacctga 60
aagtgacggg caggatgg 78

<210> SEQ ID NO 476
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 476
ccattcttct cgtcattttc aagtacacca atcaaacgta ggtttggtct tttcgcatag 60
tcccatattt cttggagg 78

<210> SEQ ID NO 477
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 477
ccattcttct cgtcactttc aagtacacca atcaaacgta ggtttggtct tttcacatag 60
tcccatattt cttggagg 78

<210> SEQ ID NO 478
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 478
cctccaagaa atataggact atgtgaaaag accaaaccta cgtttgattg gtgtacttga 60
aagtgacagg gagaatgg 78

<210> SEQ ID NO 479
<211> LENGTH: 78
<212> TYPE: DNA

<213> ORGANISM: Artificial Sequence
<220> FEATURE:
<223> OTHER INFORMATION: Synthetic Polynucleotide

<400> SEQUENCE: 479
cctccaagaa atgtggaact atgtgaaaag accaaaccta cgtttgattg gtgtacctga 60
aagtgacagg gagaatgg 78

<210> SEQ ID NO 480
<211> LENGTH: 76
<212> TYPE: DNA
<213> ORGANISM: Artificial Sequence
<220> FEATURE:
<223> OTHER INFORMATION: Synthetic Polynucleotide

<400> SEQUENCE: 480
ccctgacact gataaacgga tatgaagaga aaaaagctag gttttcgctg gaattcctaa 60
gcttgggctg cagtgg 76

<210> SEQ ID NO 481
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 481
cccttctccc agtcactttt aggtacacca atgaaacgta ggtttggtct tttcacacag 60
tcccatattt cttggagg 78

<210> SEQ ID NO 482
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 482
ccttctccca gtcactttta ggtacaccaa tgaaacgtag gtttggtctt ttcacacagt 60
cccatatttc ttggagg 77

<210> SEQ ID NO 483
<211> LENGTH: 76
<212> TYPE: DNA
<213> ORGANISM: Artificial Sequence
<220> FEATURE:
<223> OTHER INFORMATION: Synthetic Polynucleotide

<400> SEQUENCE: 483
ccactccctc tcccccaaaa agtaaaggta gaaaaccaag gtttacaggc aacaaatagc 60
acaatgaatg gaatgg 76

<210> SEQ ID NO 484
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 484
ccaaacccgc atcgcacacc ctgtgagggg gacaaaggaa cctttccgtt ccaacatcaa 60
ggttgttttg acccaagg 78

<210> SEQ ID NO 485
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 485
ccattctttc tgtcactttc aggtatacca gtcaaaccta ggtttggtct tttcacatag 60
tcccatattt cttggagg 78

<210> SEQ ID NO 486
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 486
ccattctccc catcactttc aggtacacca atcaaacgta ggtttggtct tttcacatag 60
tcccatattt cttggagg 78

<210> SEQ ID NO 487
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 487
ccacacggta gaggataaac taggtggatt ctcaaagcaa cctttgaaat aatctatgca 60
gtttttctgg gtactgg 77

<210> SEQ ID NO 488
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 488
ccaccaagaa acatgggact atgtgaaaag accaaaccta cgtttggttg gtgtacctgg 60
aagtgacggg gagagtgg 78

<210> SEQ ID NO 489
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 489
cctccaagaa atatgggacc atgtgaaaag accaaaccta cgtttgattg gtgtacctga 60
aagtgacagg gagaatgg 78

<210> SEQ ID NO 490
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 490
cctgtaaaaa ggtcacatgg tcaggtgtgc ctaaacgatc cttttattta tttatttatt 60
tatttttaag aaacagg 77

<210> SEQ ID NO 491
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 491
ccagccccaa aatgtcaggg gcttagaaca acaaaggttc cttttcatgt ttatactaca 60
tgtttgtcat gggctgg 77

<210> SEQ ID NO 492
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 492
ccgttttccc catcactttc aggtacacca gtcaaacgta ggtttggtct tttcacatgg 60
tcccacattt cttggagg 78

<210> SEQ ID NO 493
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 493
cctggaatag ctttcctgac tgtctgactt caaaaacctt ggtttgacca cttcgtctat 60
atcatgagga aggactgg 78

<210> SEQ ID NO 494
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 494
ccctactctg aacctacctt gataaagcct agaaaaccaa gctttgacaa gatttgacaa 60
gagatggaat ttggagg 77

<210> SEQ ID NO 495
<211> LENGTH: 76
<212> TYPE: DNA
<213> ORGANISM: Artificial Sequence
<220> FEATURE:
<223> OTHER INFORMATION: Synthetic Polynucleotide

<400> SEQUENCE: 495
cctactctga acctaccttg ataaagccta gaaaaccaag ctttgacaag atttgacaag 60
agatggaatt tggagg 76

<210> SEQ ID NO 496
<211> LENGTH: 77

<212> TYPE: DNA
<213> ORGANISM: Artificial Sequence
<220> FEATURE:
<223> OTHER INFORMATION: Synthetic Polynucleotide

<400> SEQUENCE: 496
cccttataaa actgaaaact ttaacctttt ttaaagcatg cttttgaata aattctttta 60
ttacaaaaaa gaccagg 77

<210> SEQ ID NO 497
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 497
ccattctccc tgtcactttc aggtacacca atcaaacgta ggtttggtct tttcacgtag 60
tcccatattt cttggagg 78

<210> SEQ ID NO 498
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 498
ccctttatta tccaagtggt ttcctgctct tcaaaccttc ctttcaaaat tttgtctcct 60
acttaaaaca agttagg 77

<210> SEQ ID NO 499
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 499
ccttctgttg agacctactg ctaagaaaac aaaaaaggtt cctttcaaat attattgtga 60
atcaataatg tacctgg 77

<210> SEQ ID NO 500
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 500
cctccaagaa atatgggact atgtgaaaag accaaaccta cgtttcattg atggacctga 60
aagtgatggg gagaatgg 78

<210> SEQ ID NO 501
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 501
ccattctccc ttcactttca gttacaccaa tcaaacgtag gtttggtctt ttcacatagt 60
cccatatttc ttggagg 77

<210> SEQ ID NO 502
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 502
cctagggaag tgatcatagc tgagtttctg gaaaaaccta ggttttaaag ttgaggagac 60
ttaagtccaa aacctgg 77

<210> SEQ ID NO 503
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 503
ccattctccc ttcactttca gttacaccaa tcaaacgtag gtttggtctt ttcacatagt 60
cccatatttc ttggagg 77

<210> SEQ ID NO 504
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 504
cctccaagaa atatgggact atgtgaaaag actaaaccta cgtttgattg gtgtacctga 60
aagtgacagg gagaatgg 78

<210> SEQ ID NO 505
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 505
ccattctccc tgtcactttc aggtatgcca gtcaaacgta ggtttggtct tttcacatag 60
tcccatattc cttggagg 78

<210> SEQ ID NO 506
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 506
cctccaagaa atatgggact atgtaaaaag acgaaaccta cgtttgattg gtgtacttaa 60
aagtgacgag gagaatgg 78

<210> SEQ ID NO 507
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 507
cctccaagaa atatgggact atgtgaaaag accaaaccta cgtttgattt gtgtacctga 60
aagtgatggg gagaatgg 78

<210> SEQ ID NO 508
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 508
ccattctccc cgtcactttc aggcacacca atcaaacgta ggtttagtct tttcacatag 60
tcccatattt cttagagg 78

<210> SEQ ID NO 509
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 509
ccttaatgca ttcatatttc atattttaaa taaaaccatg gtttcccaca gagtgacttc 60
tactctaaga aatgggg 77

<210> SEQ ID NO 510
<211> LENGTH: 76
<212> TYPE: DNA
<213> ORGANISM: Artificial Sequence
<220> FEATURE:
<223> OTHER INFORMATION: Synthetic Polynucleotide

<400> SEQUENCE: 510
ccttaatgca ttcatatttc atattttaaa taaaaccatg gtttcccaca gagtgacttc 60
tactctaaga aatggg 76

<210> SEQ ID NO 511
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 511
ccgttctttc cgtcactttc aggtacacca gtcaaacgta ggtttggtct tttcacatag 60
tcccatattt cttggagg 78

<210> SEQ ID NO 512
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 512
ccattctccc catcactttc atgtacacca atcaaacgta ggtttggtct ttgttaacat 60
agtcccatat ttcttgg 77

<210> SEQ ID NO 513

<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 513
ccctataaag cttagagaaa cacagggctc tttaaacgat ccttttctc ttttctgttt 60 taaatttcat cacttgg 77

<210> SEQ ID NO 514
<211> LENGTH: 76
<212> TYPE: DNA
<213> ORGANISM: Artificial Sequence
<220> FEATURE:
<223> OTHER INFORMATION: Synthetic Polynucleotide

<400> SEQUENCE: 514
cctataaagc ttagagaaac acagggctct ttaaacgatc cttttctct tttctgtttt 60 aaatttcatc acttgg 76

<210> SEQ ID NO 515
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 515
ccattctccc catcactttc aggtacacta atcaaaggta ggtttggtct tttcacatgg 60
tcctatattt cttggagg 78

<210> SEQ ID NO 516
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 516
ccccatagca cgatcacatg ggacattcag gggaaagcaa ccttttccag gaaggaaaac 60
ccaatgctgg gacccagg 78

<210> SEQ ID NO 517
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 517
cccatagcac gatcacatgg gacattcagg ggaaagcaac cttttccagg aaggaaaacc 60
caatgctggg acccagg 77

<210> SEQ ID NO 518
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 518
ccctttcagc gctcacaggc tatggtttta taaaaggaac ctttgatttt gttcatgtga 60
aactacaaaa tgccagg 77

<210> SEQ ID NO 519
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 519
ccccatagca cgatcacatg ggacattcag gggaaagcaa ccttttccag gaaggaaaac 60
ccaatgctgg gacccagg 78

<210> SEQ ID NO 520
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 520
cccatagcac gatcacatgg gacattcagg ggaaagcaac cttttccagg aaggaaaacc 60
caatgctggg acccagg 77

<210> SEQ ID NO 521
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 521
cctccaagaa atattggagt atgtgataag accaaacctt cgtttgactg gtgtacctga 60
aagtgatggg gagaatgg 78

<210> SEQ ID NO 522
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 522
ccattctccc cgtcactttc aggtacacca atcaaacgta ggtttggtct tttcacatag 60
tcccatattt cttggagg 78

<210> SEQ ID NO 523
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 523
ccattctccc cgtcactttc aggtacacca atcaaacgta ggtttggtct tttcacatag 60
tcccatattt cttggagg 78

<210> SEQ ID NO 524
<211> LENGTH: 78
<212> TYPE: DNA
<213> ORGANISM: Artificial Sequence
<220> FEATURE:

<223> OTHER INFORMATION: Synthetic Polynucleotide

<400> SEQUENCE: 524
ccattctccc catcactttc aggtacacca gtcaaacgaa ggtttggtct tatcacatac 60
tccaatattt cttggagg 78

<210> SEQ ID NO 525
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 525
cctccaagat atatgggact atgtgaaaag gccaaaccta cctttgattg atacacctga 60
aaatgacagg gagaatgg 78

<210> SEQ ID NO 526
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 526
cctccaagaa atatgcgact atgtgaaaag accaaaccta cgtttcattg gtgtacctga 60
aagtgatggg gagaatgg 78

<210> SEQ ID NO 527
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 527
cctccaagaa atatgggact atgtggaaag accaaaccta cgtttgtttg gtgtacctga 60
aagtgagggg agaatgg 77

<210> SEQ ID NO 528
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 528
ccattctcct catcactttc aagtacacca atcaaacgta ggtttggtct tttcacatag 60
tcttatattt cttggagg 78

<210> SEQ ID NO 529
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 529
ccattctccc cgtcactttc aggtacacca atcaaacgta ggtttggtct tttcacatag 60
tcccatattt cttggagg 78

<210> SEQ ID NO 530
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 530
ccattctccc catcactttc aggtacacca gtcaaacgaa ggtttggtct tatcacatac 60
tccaatattt cttggagg 78

<210> SEQ ID NO 531
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 531
ccattctccc cgtcactttc aggtacacca atcaaacgta ggtttggtct tttcacatag 60
tcccatattt cttggagg 78

<210> SEQ ID NO 532
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 532
ccagcagaag aatctggggc acagtctgtg aaaaaaggta cctttcttaa gcagggttct 60
tatccttcat gggtctgg 78

<210> SEQ ID NO 533
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 533
cctccaagaa atatgggact atgtgaaaag accaaaccta cgtttgattg ttgtacctga 60
aagtgagggg gagaatgg 78

<210> SEQ ID NO 534
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 534
ccttgtgttg tgtgtattca actcacagag ttaaacgatc ctttacacag agcagatttg 60
aaacactgtt tttctgg 77

<210> SEQ ID NO 535
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 535
ccttgtgttg tgtgtattca actcacagag ttaaacgatc ctttacacag agcagatttg 60
aaacactgtt tttctgg 77

<210> SEQ ID NO 536
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 536
ccttgtgttg tgtgtattca actcacagag ttaaacgatc ctttacacag agcagatttg 60
aaacactgtt tttctgg 77

<210> SEQ ID NO 537
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 537
ccttgtgttg tgtgtattca actcacagag ttaaacgatc ctttacacac agcagatttg 60
aaacactgtt tttctgg 77

<210> SEQ ID NO 538
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 538
ccttgtgttg tgtgtattca actcacagag ttaaacgatc ctttacacag agcagatttg 60
aaacactgtt tttctgg 77

<210> SEQ ID NO 539
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 539
ccttgtgttg tgtgtattca actcacagag ttaaacgatc ctttacacag agcagatttg 60
aaacactgtt tttctgg 77

<210> SEQ ID NO 540
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 540
ccttgtgttg tgtgtattca actcacagag ttaaacgatc ctttacacag agcagatttg 60
aaacactgtt tttctgg 77

<210> SEQ ID NO 541
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 541
ccttgtgttg tgtgtattca actcacagag ttaaacgatc ctttacacag agcagatttg 60
aaacactgtt tttctgg 77

<210> SEQ ID NO 542
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 542
ccttgtgttg tgtgtattca actcacagag ttaaacgatc ctttacacag agcagatttg 60
aaacactgtt tttctgg 77

<210> SEQ ID NO 543
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 543
ccttgtgttg tgtgtattca actcacagag ttaaacgatc ctttacacag agcagatttg 60
aaacactgtt tttctgg 77

<210> SEQ ID NO 544
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 544
ccttgtgttg tgtgtattca actcacagag ttaaacgatc ctttacacag agcagatttg 60
aaacactgtt tttctgg 77

<210> SEQ ID NO 545
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 545
ccttgtgttg tgtgtattca actcacagag ttaaacgatc ctttacacag agcagatttg 60
aaacactgtt tttctgg 77

<210> SEQ ID NO 546
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 546
ccttgtgttg tgtgtattca actcacagag ttaaacgatc ctttacacag agcagatttg 60
aaacactgtt tttctgg 77

<210> SEQ ID NO 547
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 547
ccttgtgttg tgtgtattca actcacagag ttaaacgatc ctttacacac agcagatttg 60
aaacactgtt tttctgg 77

<210> SEQ ID NO 548
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 548
ccttgtgttg tgtgtattca actcacagag ttaaacgatc ctttacacag agcagatttg 60
aaacactgtt tttctgg 77

<210> SEQ ID NO 549
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 549
ccttgtgttg tgtgtattca actcacagag ttaaacgatc ctttacacag agcagatttg 60
aaacactgtt tttctgg 77

<210> SEQ ID NO 550
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 550
ccttgtgttg tgtgtattca actcacagag ttaaacgatc ctttacacag agcagatttg 60
aaacactgtt tttctgg 77

<210> SEQ ID NO 551
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 551
ccttgtgttg tgtgtattca actcaccgag ttaaacgatc ctttacacag agcagatttg 60
aaacactgtt tttctgg 77

<210> SEQ ID NO 552
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 552
ccttgtgttg tgtgtattca actcacagag ttaaacgatc ctttacacag agcagatttg 60
aaacactgtt tttctgg 77

<210> SEQ ID NO 553
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 553
ccttgtgttg tgtgtattca actcacagag ttaaacgatc ctttacacag agcagatttg 60
aaacactgtt tttctgg 77

<210> SEQ ID NO 554
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 554
ccttgtgttg tgtgtattca actcacagag ttaaacgatc ctttacacag agcagatttg 60
aaacactgtt tttctgg 77

<210> SEQ ID NO 555
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 555
ccttgtgttg tgtgtattca actcacagag ttaaacgatc ctttacacag agcagatttg 60
aaacactgtt tttctgg 77

<210> SEQ ID NO 556
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 556
ccttgtgttg tgtgtattca actcacagag ttaaacgatc ctttacacag agcagatttg 60
aaacactgtt tttctgg 77

<210> SEQ ID NO 557
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 557
ccttgtgttg tgtgtattca actcacagag ttaaacgatc ctttacacag agcagatttg 60
aaacactgtt tttctgg 77

<210> SEQ ID NO 558
<211> LENGTH: 77
<212> TYPE: DNA

<213> ORGANISM: Artificial Sequence
<220> FEATURE:
<223> OTHER INFORMATION: Synthetic Polynucleotide

<400> SEQUENCE: 558
ccttgtgttg tgtgtattca actcacagag ttaaacgatc ctttacacag agcagatttg 60
aaacactgtt tttctgg 77

<210> SEQ ID NO 559
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 559
ccttgtgttg tgtgtattca actcacagag ttaaacgatc ctttacacac agcagatttg 60
aaacactgtt tttctgg 77

<210> SEQ ID NO 560
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 560
ccttgtgttg tgtgtattca actcacagag ttaaacgatc ctttacacag agcagatttg 60
aaacactgtt tttctgg 77

<210> SEQ ID NO 561
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 561
ccttgtgttg tgtgtattca actcacagag ttaaacgatc ctttacacag agcagatttg 60
aaacactgtt tttctgg 77

<210> SEQ ID NO 562
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 562
ccttgtgttg tgtgtattca actcacagag ttaaacgatc ctttacacag agcagatttg 60
aaacactgtt tttctgg 77

<210> SEQ ID NO 563
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 563
ccttgtgttg tgtgtattca actcacagag ttaaacgatc ctttacacag agcagatttg 60
aaacactgtt tttctgg 77

<210> SEQ ID NO 564
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 564
ccttgtgttg tgtgtattca actcacagag ttaaacgatc ctttacacag agcagatttg 60
aaacactgtt tttctgg 77

<210> SEQ ID NO 565
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 565
ccttgtgttg tgtgtattca actcacagag ttaaacgatc ctttacacag agcagatttg 60
aaacactgtt tttctgg 77

<210> SEQ ID NO 566
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 566
ccttgtgttg tgtgtattca actcacagag ttaaacgatc ctttacacag agcagatttg 60
taacactgtt tttctgg 77

<210> SEQ ID NO 567
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 567
ccttgtgttg tgtgtattca actcacagag ttaaacgatc ctttacacag agcagatttg 60
aaacactgtt tttctgg 77

<210> SEQ ID NO 568
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 568
ccttgtgttg tgtgtattca actcacagag ttaaacgatc ctttacacag agcagatttg 60
aaacactgtt tttctgg 77

<210> SEQ ID NO 569
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 569
ccttgtgttg tgtgtattca actcacagag ttaaacgatc ctttacacag agcagatttg 60
aaacactgtt tttctgg 77

<210> SEQ ID NO 570
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 570
ccttgtgttg tgtgtattca actcacagag ttaaacgatc ctttacacag agcagatttg 60
aaacactgtt tttctgg 77

<210> SEQ ID NO 571
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 571
ccttgtgttg tgtgtattca actcacagag ttaaacgatc ctttacacag agcagatttg 60
aaacactgtt tttctgg 77

<210> SEQ ID NO 572
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 572
ccttgtgttg tgtgtattca actcacagag ttaaacgatc ctttacacag agcagatttg 60
aaacactgtt tttctgg 77

<210> SEQ ID NO 573
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 573
ccttgtgttg tgtgtattca actcacagag ttaaacgatc ctttacacag agcagatttg 60
aaacactgtt tttctgg 77

<210> SEQ ID NO 574
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 574
ccttgtgttg tgtgtattca actcacagag ttaaacgatc ctttacacag agcagatttg 60
aaacactgtt tttctgg 77

<210> SEQ ID NO 575
<211> LENGTH: 77

<212> TYPE: DNA
<213> ORGANISM: Artificial Sequence
<220> FEATURE:
<223> OTHER INFORMATION: Synthetic Polynucleotide

<400> SEQUENCE: 575
ccttgtgttg tgtgtattca actcacagag ttaaacgatc ctttacacag agcagatttg 60
aaacactgtt tttgtgg 77

<210> SEQ ID NO 576
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 576
ccttgtgttg tgtgtattca actcacagag ttaaacgatc ctttacacag agcagatttg 60
aaacactgtt tttctgg 77

<210> SEQ ID NO 577
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 577
ccttgtgttg tgtgtattca actcacagag ttaaacgatc ctttacacag agcagatttg 60
aaacactgtt tttctgg 77

<210> SEQ ID NO 578
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 578
ccttgtgttg tgtgtattca actcacagag ttaaacgatc ctttacacag agcagatttg 60
aaacactgtt tttctgg 77

<210> SEQ ID NO 579
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 579
ccttgtgttg tgtgtattca actcacagag ttaaacgatc ctttacacag agcagatttg 60
aaacactgtt tttctgg 77

<210> SEQ ID NO 580
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 580
ccttgtgttg tgtgtattca actcacagag ttaaacgatc ctttacacag agcagatttg 60
aaacactgtt tttctgg 77

<210> SEQ ID NO 581
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 581
ccttgtgttg tgtgtattca actcacagag ttaaacgatc ctttccacag agcagatttg 60
aaacactgtt tttctgg 77

<210> SEQ ID NO 582
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 582
ccttgtgttg tgtgtattca actcacagag ttaaacgatc ctttacacag agcagatttg 60
aaacactgtt tttctgg 77

<210> SEQ ID NO 583
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 583
ccttgtgttg tgtgtattca actcacagag ttaaacgatc ctttacacag agcagatttg 60
aaacactgtt tttctgg 77

<210> SEQ ID NO 584
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 584
ccttgtgttg tgtgtattca actcacagag ttaaacgatc ctttacacag agcagatttg 60
aaacactgtt tttctgg 77

<210> SEQ ID NO 585
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 585
ccttgtgttg tgtgtattca actcacagag ttaaacgatc ctttacacag agcagatttg 60
aaacactgtt tttctgg 77

<210> SEQ ID NO 586
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 586
ccttgtgttg tgtgtattca actcacagag ttaaacgatc ctttacacag agcagatttg 60
aaacactgtt tttctgg 77

<210> SEQ ID NO 587
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 587
ccttgtgttg tgtgtattca actcacagag ttaaacgatc ctttacacag agcagatttg 60
aaacactgtt tttctgg 77

<210> SEQ ID NO 588
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 588
ccttgtgttg tgtgtattca actcacagag ttaaacgatc ctttacacag agcagatttg 60
aaacactgtt tttctgg 77

<210> SEQ ID NO 589
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 589
ccttgtgttg tgtgtattca actcacagag ttaaacgatc ctttacacag agcagatttg 60
aaacactgtt tttctgg 77

<210> SEQ ID NO 590
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 590
ccttgtgttg tgtgtattca actcacagag ttaaacgatc ctttacacag agcagatttg 60
aaacactgtt tttctgg 77

<210> SEQ ID NO 591
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 591
ccttgtgttg tgtgtattca actcacagag ttaaacgatc ctttacacag agcagatttg 60
aaacactgtt tttctgg 77

<210> SEQ ID NO 592

<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 592
ccttgtgttg tgtgtattca actcaccgag ttaaacgatc ctttacacag agcagatttg 60
aaacactgtt tttctgg 77

<210> SEQ ID NO 593
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 593
ccttgtgttg tgtgtattca actcacagag ttaaacgatc ctttacacag agcagatttg 60
aaacactgtt tttctgg 77

<210> SEQ ID NO 594
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 594
ccttgtgttg tgtgtattca actcacagag ttaaacgatc ctttacacag agcagatttg 60
aaacactgtt tttctgg 77

<210> SEQ ID NO 595
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 595
ccttgtgttg tgtgtattca actcacagag ttaaacgatc ctttacacag agcagatttg 60
aaacactgtt tttctgg 77

<210> SEQ ID NO 596
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 596
ccttgtgttg tgtgtattca actcacagag ttaaacgatc ctttacacag agcagatttg 60
aaacactgtt tttctgg 77

<210> SEQ ID NO 597
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 597
ccttgtgttg tgtgtattca actcacagag ttaaacgatc ctttacacag agcagatttg 60
aaacactgtt tttctgg 77

<210> SEQ ID NO 598
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 598
ccttgtgttg tgtgtattca actcacagag ttaaacgatc ctttacacag agcagatttg 60
aaaaactgtt tttctgg 77

<210> SEQ ID NO 599
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 599
ccttgtgttg tgtgtattca actcacagag taaaacgatc ctttacacag agcagatttg 60
aaacactgtt tttctgg 77

<210> SEQ ID NO 600
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 600
ccttgtgttg tgtgtattca actcacagag ttaaacgatc ctttacacag agcagatttg 60
aaacactgtt tttgtgg 77

<210> SEQ ID NO 601
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 601
ccttgtgttg tgtgtattca actcacagag ttaaacgatc ctttacacag agcagatttg 60
aaacactgtt tttctgg 77

<210> SEQ ID NO 602
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 602
ccttgtgttg tgtgtattta actcacagag ttaaacgatc ctttacacag agcagatttg 60
aaacactgtt tttctgg 77

<210> SEQ ID NO 603
<211> LENGTH: 77
<212> TYPE: DNA
<213> ORGANISM: Artificial Sequence
<220> FEATURE:

<223> OTHER INFORMATION: Synthetic Polynucleotide

<400> SEQUENCE: 603
ccttgtgttg tgtgtattca actcacagag ttaaacgatc ctttacacag agcagatttg 60
aaacactgtt tttctgg 77

<210> SEQ ID NO 604
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 604
ccttgtgttg tgtgtattca actcacagag ttaaacgatc ctttacacag agcagatttg 60
aaacactgtt tttctgg 77

<210> SEQ ID NO 605
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 605
ccttgtgttg tgtgtattca actcacagag ttaaacgatc ctttacacag agcagatttg 60
aaacactgtt tttctgg 77

<210> SEQ ID NO 606
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 606
ccttgtgttg tgtgtattca actcacagag ttaaacgatc ctttacacag agcagatttg 60
aaacactgtt tttctgg 77

<210> SEQ ID NO 607
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 607
ccttgtgttg tgtgtattca actcacagag ttaaacgatc ctttacacag agcagatttg 60
aaacactgtt tttctgg 77

<210> SEQ ID NO 608
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 608
ccttgtgttg tgtgtattca actcacagag ttaaacgatc ctttacacag agcagatttg 60
aaacactgtt tttctgg 77

<210> SEQ ID NO 609
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 609
ccttgtgttg tgtgtattca actcacagag ttaaacgatc ctttacacag agcagatttg 60
aaacactgtt tttctgg 77

<210> SEQ ID NO 610
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 610
ccttgtgttg tgtgtattca actcacagag ttaaacgatc ctttacacag agcagatttg 60
aaacactgtt tttctgg 77

<210> SEQ ID NO 611
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 611
ccttgtgttg tgtgtattca actcacagag ttaaacgatc ctttacacag agcagatttg 60
aaacactgtt tttctgg 77

<210> SEQ ID NO 612
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 612
ccttgtgttg tgtgtattca actcacagag ttaaacgatc ctttacacag agcagatttg 60
aaacactgtt tttctgg 77

<210> SEQ ID NO 613
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 613
ccttgtgttg tgtgtattca actcacagag ttaaacgatc ctttacacag agcagatttg 60
aaacactgtt tttctgg 77

<210> SEQ ID NO 614
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 614
ccattctccc tatcactttc aggtacacca atcaaacgta ggtttggtct tttcacatag 60
tcccatattt cttggagg 78

<210> SEQ ID NO 615
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 615
cctcgtcact gccagatttt gtggctacca gcaaaggatc gttttaagct gcaactcagg 60
aaattgagaa aatatgg 77

<210> SEQ ID NO 616
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 616
cctccaagaa atatgggact atgtgaaaaa accaaaccta cgtttgattg gtgtacctga 60
aagtgacagg gagaatgg 78

<210> SEQ ID NO 617
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 617
ccctgtgttc ttttatacta aaacaagcca gcaaaccaac ctttgagatg tgttgcctta 60
aacattactg aatgggg 77

<210> SEQ ID NO 618
<211> LENGTH: 76
<212> TYPE: DNA
<213> ORGANISM: Artificial Sequence
<220> FEATURE:
<223> OTHER INFORMATION: Synthetic Polynucleotide

<400> SEQUENCE: 618
ccctgtgttc ttttatacta aaacaagcca gcaaaccaac ctttgagatg tgttgcctta 60
aacattactg aatggg 76

<210> SEQ ID NO 619
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 619
ccgagaaacg gctttagcaa caaataaata tcaaaaggat gctttctctt cagaataatc 60
taaagtaagt tgggagg 77

<210> SEQ ID NO 620
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 620
ccatgttact ccggataagg acagcaaagg aggaaaggaa ccttttctgg gccaccagaa 60
ggatgagctt gggcttgg 78

<210> SEQ ID NO 621
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 621
cccagggata tgctggccac ggggaggagc cggaaaccaa cctttgtgtc actgtgtagt 60
gacaagtgcc tttggagg 78

<210> SEQ ID NO 622
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 622
ccagggatat gctggccacg gggaggagcc ggaaaccaac ctttgtgtca ctgtgtagtg 60
acaagtgcct ttggagg 77

<210> SEQ ID NO 623
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 623
ccttagggac ccataatggc cacaaccagg agaaaagcaa gctttgatgc ttaaacacta 60
cttacagaca tgtacagg 78

<210> SEQ ID NO 624
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 624
cctgcctctg ttcctccttc ctgatggtgg cggaaaggat gcttttgcca gatcaacagt 60
cacacacaac acaccagg 78

<210> SEQ ID NO 625
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 625
cctgactcca gccctccttg acaaggtctc cgtaaagcat gctttctctt agggaccctc 60
agagggaggc ttggtggg 78

<210> SEQ ID NO 626
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 626
cctgactcca gccctccttg acaaggtctc cgtaaagcat gctttctctt agggaccctc 60
agagggaggc ttggtgg 77

<210> SEQ ID NO 627
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 627
ccttatttgg aatgtgacaa gacccatttg tttaaacctt ggtttttatg cagaaagaaa 60
aggaaggctg cagtggg 77

<210> SEQ ID NO 628
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 628
ccattctccc tgtcactttc aggtacacta atcaaacgta ggtttgctgt ttttacatag 60
gctcatattt cttggagg 78

<210> SEQ ID NO 629
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 629
ccattctccc catcactttc aggtacacca gtcaaacgta ggtttggtct tttcacatag 60
tcccatattt cttggagg 78

<210> SEQ ID NO 630
<211> LENGTH: 76
<212> TYPE: DNA
<213> ORGANISM: Artificial Sequence
<220> FEATURE:
<223> OTHER INFORMATION: Synthetic Polynucleotide

<400> SEQUENCE: 630
cctgtttgtt attttagcta atgtcaaaaa gaaaaccttg ctttttctga accctttcag 60
aggcagaaag tggggg 76

<210> SEQ ID NO 631
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 631
ccattttccc caccactttc acgtacagca atcaaacgta ggtttggtct tttcactagt 60
cccatatttc ttggagg 77

<210> SEQ ID NO 632
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 632
ccttgtagtg tgtgtattca actcacagag ttaaacgatc ctttacacag agcagacttg 60
aaacactctt gttgtgg 77

<210> SEQ ID NO 633
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 633
ccttgtagtg tgtgtattca actcacagag ttaaacgatc ctttacacag agcatacttg 60
aaacactctt tttgtgg 77

<210> SEQ ID NO 634
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 634
ccttgtgttg tgtgtattca actcacagag ttaaacgatc ctttacacag agcagacttg 60
aaacactctt tttgtgg 77

<210> SEQ ID NO 635
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 635
ccttgtgttg tgtttattca actcacagag ttaaacgatc ctttacacag agcagacttg 60
aaatactctt tttgtgg 77

<210> SEQ ID NO 636
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 636
ccttgtagtg tgtgtattca actcacagag ttaaacgatc ctttacacag agcatacttg 60
aaacactctt tttgtgg 77

<210> SEQ ID NO 637
<211> LENGTH: 77
<212> TYPE: DNA

<213> ORGANISM: Artificial Sequence
<220> FEATURE:
<223> OTHER INFORMATION: Synthetic Polynucleotide

<400> SEQUENCE: 637
ccttgtattg tgagtattca actcacagag ttaaacgatc ctttacacag agcagacttg 60
aaacactctt tttgtgg 77

<210> SEQ ID NO 638
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 638
ccttgtgttg tgtgtcttca actcacagag ttaaacgatg ctttacacag agtagacttg 60
aaacactctt tttctgg 77

<210> SEQ ID NO 639
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 639
ccttgtgttg tgtgtattca actcacagag ttaaacgatc ctttacacag agcagacttg 60
taacactctt tttgtgg 77

<210> SEQ ID NO 640
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 640
ccttgtgttg tgtgtattca actcacagag ttaaacgatc ctttacacag agcagacgtg 60
aaacactctt tttgtgg 77

<210> SEQ ID NO 641
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 641
ccttgtgttg tgtgtattca actcacagag ttaaacgatc ctttacacag agcagacttg 60
aaacactctt tttgtgg 77

<210> SEQ ID NO 642
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 642
ccttgtgttg tgtgtattca actcacagag ttaaacgatc ctttacacag aggagacttg 60
taacactctt tttgtgg 77

<210> SEQ ID NO 643
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 643
ccaggaaaaa atttaaactt tcttaacttg ataaaaggta gctttcaaaa cctacaataa 60
ataacatact tagagtgg 78

<210> SEQ ID NO 644
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 644
ccattctcct cgtcactttc aggtacacca aacaaacgta ggtttggtct ttttacgtag 60
tcccatattt cttggagg 78

<210> SEQ ID NO 645
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 645
ccctcttgaa gttagggaag tagcatttaa gggaaacgta gctttactat taagaatttc 60
aaacagcact tgtcaggg 78

<210> SEQ ID NO 646
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 646
ccctcttgaa gttagggaag tagcatttaa gggaaacgta gctttactat taagaatttc 60
aaacagcact tgtcagg 77

<210> SEQ ID NO 647
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 647
cctcttgaag ttagggaagt agcatttaag ggaaacgtag ctttactatt aagaatttca 60
aacagcactt gtcaggg 77

<210> SEQ ID NO 648
<211> LENGTH: 76
<212> TYPE: DNA
<213> ORGANISM: Artificial Sequence
<220> FEATURE:
<223> OTHER INFORMATION: Synthetic Polynucleotide

<400> SEQUENCE: 648
cctcttgaag ttagggaagt agcatttaag ggaaacgtag ctttactatt aagaatttca 60
aacagcactt gtcagg 76

<210> SEQ ID NO 649
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 649
ccattctccc cgtcactttc aggtacacca atcaaacgta ggtttggtct tttcacatat 60
tcccatattt cttggagg 78

<210> SEQ ID NO 650
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 650
ccattctccc ttcactttca ggtacaccaa tcaaacgtag gtttggtctt ttcacatagt 60
cccatatttt ttggagg 77

<210> SEQ ID NO 651
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 651
cctatagtct cagttacttg ggaggctgag gtaaaaggat cgtttgagcc caggaggtgg 60
aggttgcagt gagccggg 78

<210> SEQ ID NO 652
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 652
cctatagtct cagttacttg ggaggctgag gtaaaaggat cgtttgagcc caggaggtgg 60
aggttgcagt gagccgg 77

<210> SEQ ID NO 653
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 653
cctttcccaa ctctgctatt gcccccacat cctaaaggaa cctttctttt tttatatatt 60
ttattttaag ttccagg 77

<210> SEQ ID NO 654
<211> LENGTH: 78

<212> TYPE: DNA
<213> ORGANISM: Artificial Sequence
<220> FEATURE:
<223> OTHER INFORMATION: Synthetic Polynucleotide

<400> SEQUENCE: 654
cctccaagaa atatggaact atgtgaaaag accaaaccta cgtttgattg acgtacctga 60
aagtgacagg gagaatgg 78

<210> SEQ ID NO 655
<211> LENGTH: 76
<212> TYPE: DNA
<213> ORGANISM: Artificial Sequence
<220> FEATURE:
<223> OTHER INFORMATION: Synthetic Polynucleotide

<400> SEQUENCE: 655
cctcttctga aagcattgat aatcaacatt ttaaacgtag cttttcccca tattgctagg 60
aaggctcatt cccggg 76

<210> SEQ ID NO 656
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 656
cctccaagaa atatgggact atgtgaaaag gccaaaccta cgtttgattg ctgtacccga 60
gagtgacggg gagaatgg 78

<210> SEQ ID NO 657
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 657
cctccaagaa atatgggact atgtgaaaag accaaaccta cgtttgattg gtgtacctga 60
aagtgatggg gagaatgg 78

<210> SEQ ID NO 658
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 658
cccggggcct gggtgcccag tgccagtggt cagaaaggtt gctttggtgt ttttcattgt 60
tagtgagaca gagatgg 77

<210> SEQ ID NO 659
<211> LENGTH: 76
<212> TYPE: DNA
<213> ORGANISM: Artificial Sequence
<220> FEATURE:
<223> OTHER INFORMATION: Synthetic Polynucleotide

<400> SEQUENCE: 659
ccggggcctg ggtgcccagt gccagtggtc agaaaggttg ctttggtgtt tttcattgtt 60
agtgagacag agatgg 76

<210> SEQ ID NO 660
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 660
ccattctccc catcattttc aggtacacca atcaaacgta ggtttgatct tttcacatag 60
ccccatattt cttggagg 78

<210> SEQ ID NO 661
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 661
ccaccagcac ttctgttaga agttgcagca gagaaaggat cctttaggca catctcccag 60
atccttgcga agagggg 77

<210> SEQ ID NO 662
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 662
cctgtgccag ggtccttcca ctgggactgg cagaaacgta ggtttgcatg gagtgagaag 60
caggggagag gttgaggg 78

<210> SEQ ID NO 663
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 663
cctgtgccag ggtccttcca ctgggactgg cagaaacgta ggtttgcatg gagtgagaag 60
caggggagag gttgagg 77

<210> SEQ ID NO 664
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 664
ccctcagcct ctcccctgct tctcactcca tgcaaaccta cgtttctgcc agtcccagca 60
gaaggaccct ggcacggg 78

<210> SEQ ID NO 665
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 665
ccctcagcct ctcccctgct tctcactcca tgcaaaccta cgtttctgcc agtcccagca 60
gaaggaccct ggcacgg 77

<210> SEQ ID NO 666
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 666
cctcagcctc tcccctgctt ctcactccat gcaaacctac gtttctgcca gtcccagcag 60
aaggaccctg gcacggg 77

<210> SEQ ID NO 667
<211> LENGTH: 76
<212> TYPE: DNA
<213> ORGANISM: Artificial Sequence
<220> FEATURE:
<223> OTHER INFORMATION: Synthetic Polynucleotide

<400> SEQUENCE: 667
cctcagcctc tcccctgctt ctcactccat gcaaacctac gtttctgcca gtcccagcag 60
aaggaccctg gcacgg 76

<210> SEQ ID NO 668
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 668
cctccaagaa atatggggct atgtgaaaag accaaaccta cctttgattg gtgtatctga 60
aagtgacggg gagaatgg 78

<210> SEQ ID NO 669
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 669
cctccaagaa atatgggact atgtgaaaag accaaaccta cgtttgattt gtgtacctga 60
aagtgatggg gagaatgg 78

<210> SEQ ID NO 670
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 670
ccattctccc cgtcactttc aggtacacca atcaaacgta ggtttggtct tttctcattg 60
tcccatattt cttggagg 78

<210> SEQ ID NO 671

<211> LENGTH: 76
<212> TYPE: DNA
<213> ORGANISM: Artificial Sequence
<220> FEATURE:
<223> OTHER INFORMATION: Synthetic Polynucleotide

<400> SEQUENCE: 671
cccatcaaga gcggttgtgc atggcaacag taaaaggatg gtttgttaca ctagtacaaa 60
aagaggtggc cagagg 76

<210> SEQ ID NO 672
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 672
ccattctctc tgtcactttc aggtacacca atcaaacgta ggtttggtct tttcacatag 60
tcccatattt cttggagg 78

<210> SEQ ID NO 673
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 673
cctccaagaa atacgggact atgtgaaaag accaaacgta cgtttgattg gtgtacctga 60
aagtgatagg gagaatgg 78

<210> SEQ ID NO 674
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 674
cctccaagaa atatgggact atgtgaaaag accaaaccta cgtttgattg gtgtacctga 60
aagtgactgg gagaatgg 78

<210> SEQ ID NO 675
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 675
ccattctccc tgtcactttc aggtacacga atcaaacgta ggtttcatct tttcacatag 60
tcccatattt cttagagg 78

<210> SEQ ID NO 676
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 676
ccattctctc tgtcactttc tggtacacca atcaaacgta ggtttggtct tttcacatag 60
tttcacatat ttcttgg 77

<210> SEQ ID NO 677
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 677
cctccaagaa atatgggact atgtgaaaag accaaaccta cgtttgattg gtgtacctga 60
aagtgacaag gaaaatgg 78

<210> SEQ ID NO 678
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 678
cctgaaaaac attgtttcca acctggtaaa tcaaaaggaa ggtttaactt tgttagataa 60
gtccacatat caccaagg 78

<210> SEQ ID NO 679
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 679
cctccaagaa atgtgggact atgggaaaag accaaaccta cctttgtttg gtgtacctga 60
aagtgacggg gagaaagg 78

<210> SEQ ID NO 680
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 680
cctccaagaa atatgggact atgtgaaaag accaaaccta cgtttcattg gtgtacctga 60
aagtgatggg tagaatgg 78

<210> SEQ ID NO 681
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 681
cctacaagaa atatgggact atgggaaaag accaaaccta cgtttgattg gtacactgga 60
aagtgacagg gataatgg 78

<210> SEQ ID NO 682
<211> LENGTH: 78
<212> TYPE: DNA
<213> ORGANISM: Artificial Sequence
<220> FEATURE:

<223> OTHER INFORMATION: Synthetic Polynucleotide

<400> SEQUENCE: 682
ccattctccc tgtcactttc tggtacacca atcaaaggta ggtttggtct tttcacatag 60
tcccatattt cttggagg 78

<210> SEQ ID NO 683
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 683
cctccaagaa atatgggact atgtgaaaag accaaaccta cgtttgattg gtgtacctga 60
aagtgatggg gagaatgg 78

<210> SEQ ID NO 684
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 684
ccattctctt tgtcactttc aggtatacca atcaaacgtt ggtttggtct ttttgcatag 60
tcccatattt tgtggagg 78

<210> SEQ ID NO 685
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 685
cctccaagaa atatgagact atgtgaaaag accaaaccta cgtttgatta gtgtacctga 60
aaatgatggg gagaatgg 78

<210> SEQ ID NO 686
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 686
ccattctttc tgtcactttc aggtacacca atcaaacgta ggtttggtct tttcacatag 60
tcccatattt cttggagg 78

<210> SEQ ID NO 687
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 687
ccattctccc tgtcactttc aggtacacca atcaaacgta ggtttgttct tttcacatag 60
tcccatattt cttggagg 78

<210> SEQ ID NO 688
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 688
ccattatccc catcactttc aggtacacca atcaaacgta ggtttggttt tttcacatag 60
ttcaatattt ctttgagg 78

<210> SEQ ID NO 689
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 689
cctccaagaa atatgggact atctgaaaag atcaaaccta cgtttgattg gtgtacctga 60
aagtgacagg gagaatgg 78

<210> SEQ ID NO 690
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 690
cctttctccc catcactttc aggtacacca atcaaacgta ggtttggtct tttcatatag 60
tcccatattt cttggagg 78

<210> SEQ ID NO 691
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 691
cctccaagaa atatgggact atgtgcaaag atcaaaccta cgtttgattg ctgtacctga 60
aagtgatggg gagaatgg 78

<210> SEQ ID NO 692
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 692
ccattctccc catcactttc aggtacacca gtcaaacgta ggtttggtct tttcacataa 60
tcccatattt cttggagg 78

<210> SEQ ID NO 693
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 693
cctccaagaa gtatgggacc atggaaaaga tcaaacctac gtttgactgg tgtacctgaa 60
agtgactggg agaatgg 77

<210> SEQ ID NO 694
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 694
cctccaagaa atatgggact atgtgaaaag accaaaccta cgtttgattg gagtacttga 60
aaatgacagg gataatgg 78

<210> SEQ ID NO 695
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 695
cctttaaaga catgctcttt gtgccagaaa ttcaaaggtt gcttttatgt ccagtggggt 60
ggagggagga agctcgg 77

<210> SEQ ID NO 696
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 696
ccattctccc cgtcactttc agggacctca atcaaacgta ggttttgtct tttcacatag 60
tcccatattt cttggagg 78

<210> SEQ ID NO 697
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 697
cctccaagaa atataggact atgtgaaaag accaaaccta cgtttgactg gtgtacctga 60
aagtgacagg gagaatgg 78

<210> SEQ ID NO 698
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 698
ccattctccc catcactttc aggtacacca atcaaaggta ggtttggtct tttcacatag 60
tccgatattt cctgcagg 78

<210> SEQ ID NO 699
<211> LENGTH: 12
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (4)..(5)
<223> OTHER INFORMATION: s is g or c
<220> FEATURE:
<221> NAME/KEY: misc_feature
<222> LOCATION: (6)..(7)
<223> OTHER INFORMATION: w is a, t or u
<220> FEATURE:
<221> NAME/KEY: misc_feature
<222> LOCATION: (8)..(9)
<223> OTHER INFORMATION: s is g or c

<400> SEQUENCE: 699
aaasswwsst tt 12

<210> SEQ ID NO 700
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 700
ctgtaaaccg aggttttgga 20

<210> SEQ ID NO 701
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 701

Gly Gly Ser Gly Gly Ser Gly Gly Ser Gly Gly Ser Gly Gly Ser
1 5 10 15

<210> SEQ ID NO 702
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 702

Pro Lys Lys Lys Arg Lys Val
1 5

<210> SEQ ID NO 703
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 703
tccaaaacct cggtttacag 20

<210> SEQ ID NO 704
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 704
cccctcccat cacaggccct gaggtttaag agaaaaccat ggttttgtgg gccaggccca 60
tgacccttct cctctggg 78

<210> SEQ ID NO 705
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 705
cccagaggag aagggtcatg ggcctggccc acaaaaccat ggttttctct taaacctcag 60
ggcctgtgat gggagggg 78

<210> SEQ ID NO 706
<211> LENGTH: 76
<212> TYPE: DNA
<213> ORGANISM: Artificial Sequence
<220> FEATURE:
<223> OTHER INFORMATION: Synthetic Polynucleotide

<400> SEQUENCE: 706
ccctgacact gataaacgga tatgaagaga aaaaagctag gttttcgctg gaattcctaa 60
gcttgggctg cagtgg 76

<210> SEQ ID NO 707
<211> LENGTH: 76
<212> TYPE: DNA
<213> ORGANISM: Artificial Sequence
<220> FEATURE:
<223> OTHER INFORMATION: Synthetic Polynucleotide

<400> SEQUENCE: 707
ccactgcagc ccaagcttag gaattccagc gaaaacctag cttttttctc ttcatatccg 60
tttatcagag tcaggg 76

<210> SEQ ID NO 708
<211> LENGTH: 78
<212> TYPE: DNA
<213> ORGANISM: Artificial Sequence
<220> FEATURE:
<223> OTHER INFORMATION: Synthetic Polunucleotide

<400> SEQUENCE: 708
cccttctccc agtcactttt aggtacacca atgaaacgta ggtttggtct tttcacacag 60
tcccatattt cttggagg 78

<210> SEQ ID NO 709
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 709
cctccaagaa atatgggact gtgtgaaaag accaaaccta cgtttcattg gtgtacctaa 60
aagtgactgg gagaaggg 78

<210> SEQ ID NO 710
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 710
ccctgacact gataaacgga tatgaagaga aaaaagctag gtttggtctt ttcacacagt 60
cccatatttc ttggagg 77

<210> SEQ ID NO 711
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 711
cctccaagaa atatgggact gtgtgaaaag accaaaccta gcttttttct cttcatatcc 60
gtttatcaga gtcaggg 77

<210> SEQ ID NO 712
<211> LENGTH: 1367
<212> TYPE: PRT
<213> ORGANISM: Artificial Sequence
<220> FEATURE:
<223> OTHER INFORMATION: Synthetic Polypeptide

<400> SEQUENCE: 712

Asp Lys Lys Tyr Ser Ile Gly Leu Ala Ile Gly Thr Asn Ser Val Gly
1 5 10 15

Trp Ala Val Ile Thr Asp Glu Tyr Lys Val Pro Ser Lys Lys Phe Lys
20 25 30

Val Leu Gly Asn Thr Asp Arg His Ser Ile Lys Lys Asn Leu Ile Gly
35 40 45

Ala Leu Leu Phe Asp Ser Gly Glu Thr Ala Glu Ala Thr Arg Leu Lys
50 55 60

Arg Thr Ala Arg Arg Arg Tyr Thr Arg Arg Lys Asn Arg Ile Cys Tyr
65 70 75 80

Leu Gln Glu Ile Phe Ser Asn Glu Met Ala Lys Val Asp Asp Ser Phe
85 90 95

Phe His Arg Leu Glu Glu Ser Phe Leu Val Glu Glu Asp Lys Lys His
100 105 110

Glu Arg His Pro Ile Phe Gly Asn Ile Val Asp Glu Val Ala Tyr His
115 120 125

Glu Lys Tyr Pro Thr Ile Tyr His Leu Arg Lys Lys Leu Val Asp Ser
130 135 140

Thr Asp Lys Ala Asp Leu Arg Leu Ile Tyr Leu Ala Leu Ala His Met
145 150 155 160

Ile Lys Phe Arg Gly His Phe Leu Ile Glu Gly Asp Leu Asn Pro Asp
165 170 175

Asn Ser Asp Val Asp Lys Leu Phe Ile Gln Leu Val Gln Thr Tyr Asn
180 185 190

Gln Leu Phe Glu Glu Asn Pro Ile Asn Ala Ser Gly Val Asp Ala Lys
195 200 205

Ala Ile Leu Ser Ala Arg Leu Ser Lys Ser Arg Arg Leu Glu Asn Leu
210 215 220

Ile Ala Gln Leu Pro Gly Glu Lys Lys Asn Gly Leu Phe Gly Asn Leu
225 230 235 240

Ile Ala Leu Ser Leu Gly Leu Thr Pro Asn Phe Lys Ser Asn Phe Asp

-continued

```
                245                 250                 255

Leu Ala Glu Asp Ala Lys Leu Gln Leu Ser Lys Asp Thr Tyr Asp Asp
            260                 265                 270

Asp Leu Asp Asn Leu Leu Ala Gln Ile Gly Asp Gln Tyr Ala Asp Leu
        275                 280                 285

Phe Leu Ala Ala Lys Asn Leu Ser Asp Ala Ile Leu Leu Ser Asp Ile
    290                 295                 300

Leu Arg Val Asn Thr Glu Ile Thr Lys Ala Pro Leu Ser Ala Ser Met
305                 310                 315                 320

Ile Lys Arg Tyr Asp Glu His His Gln Asp Leu Thr Leu Leu Lys Ala
                325                 330                 335

Leu Val Arg Gln Gln Leu Pro Glu Lys Tyr Lys Glu Ile Phe Phe Asp
            340                 345                 350

Gln Ser Lys Asn Gly Tyr Ala Gly Tyr Ile Asp Gly Gly Ala Ser Gln
        355                 360                 365

Glu Glu Phe Tyr Lys Phe Ile Lys Pro Ile Leu Glu Lys Met Asp Gly
    370                 375                 380

Thr Glu Glu Leu Leu Val Lys Leu Asn Arg Glu Asp Leu Leu Arg Lys
385                 390                 395                 400

Gln Arg Thr Phe Asp Asn Gly Ser Ile Pro His Gln Ile His Leu Gly
                405                 410                 415

Glu Leu His Ala Ile Leu Arg Arg Gln Glu Asp Phe Tyr Pro Phe Leu
            420                 425                 430

Lys Asp Asn Arg Glu Lys Ile Glu Lys Ile Leu Thr Phe Arg Ile Pro
        435                 440                 445

Tyr Tyr Val Gly Pro Leu Ala Arg Gly Asn Ser Arg Phe Ala Trp Met
    450                 455                 460

Thr Arg Lys Ser Glu Glu Thr Ile Thr Pro Trp Asn Phe Glu Glu Val
465                 470                 475                 480

Val Asp Lys Gly Ala Ser Ala Gln Ser Phe Ile Glu Arg Met Thr Asn
                485                 490                 495

Phe Asp Lys Asn Leu Pro Asn Glu Lys Val Leu Pro Lys His Ser Leu
            500                 505                 510

Leu Tyr Glu Tyr Phe Thr Val Tyr Asn Glu Leu Thr Lys Val Lys Tyr
        515                 520                 525

Val Thr Glu Gly Met Arg Lys Pro Ala Phe Leu Ser Gly Glu Gln Lys
    530                 535                 540

Lys Ala Ile Val Asp Leu Leu Phe Lys Thr Asn Arg Lys Val Thr Val
545                 550                 555                 560

Lys Gln Leu Lys Glu Asp Tyr Phe Lys Lys Ile Glu Cys Phe Asp Ser
                565                 570                 575

Val Glu Ile Ser Gly Val Glu Asp Arg Phe Asn Ala Ser Leu Gly Thr
            580                 585                 590

Tyr His Asp Leu Leu Lys Ile Ile Lys Asp Lys Asp Phe Leu Asp Asn
        595                 600                 605

Glu Glu Asn Glu Asp Ile Leu Glu Asp Ile Val Leu Thr Leu Thr Leu
    610                 615                 620

Phe Glu Asp Arg Glu Met Ile Glu Glu Arg Leu Lys Thr Tyr Ala His
625                 630                 635                 640

Leu Phe Asp Asp Lys Val Met Lys Gln Leu Lys Arg Arg Arg Tyr Thr
                645                 650                 655

Gly Trp Gly Arg Leu Ser Arg Lys Leu Ile Asn Gly Ile Arg Asp Lys
            660                 665                 670
```

```
Gln Ser Gly Lys Thr Ile Leu Asp Phe Leu Lys Ser Asp Gly Phe Ala
        675                 680                 685

Asn Arg Asn Phe Met Gln Leu Ile His Asp Asp Ser Leu Thr Phe Lys
    690                 695                 700

Glu Asp Ile Gln Lys Ala Gln Val Ser Gly Gln Gly Asp Ser Leu His
705                 710                 715                 720

Glu His Ile Ala Asn Leu Ala Gly Ser Pro Ala Ile Lys Lys Gly Ile
                725                 730                 735

Leu Gln Thr Val Lys Val Val Asp Glu Leu Val Lys Val Met Gly Arg
            740                 745                 750

His Lys Pro Glu Asn Ile Val Ile Glu Met Ala Arg Glu Asn Gln Thr
        755                 760                 765

Thr Gln Lys Gly Gln Lys Asn Ser Arg Glu Arg Met Lys Arg Ile Glu
    770                 775                 780

Glu Gly Ile Lys Glu Leu Gly Ser Gln Ile Leu Lys Glu His Pro Val
785                 790                 795                 800

Glu Asn Thr Gln Leu Gln Asn Glu Lys Leu Tyr Leu Tyr Tyr Leu Gln
                805                 810                 815

Asn Gly Arg Asp Met Tyr Val Asp Gln Glu Leu Asp Ile Asn Arg Leu
            820                 825                 830

Ser Asp Tyr Asp Val Asp Ala Ile Val Pro Gln Ser Phe Leu Lys Asp
        835                 840                 845

Asp Ser Ile Asp Asn Lys Val Leu Thr Arg Ser Asp Lys Asn Arg Gly
    850                 855                 860

Lys Ser Asp Asn Val Pro Ser Glu Glu Val Val Lys Lys Met Lys Asn
865                 870                 875                 880

Tyr Trp Arg Gln Leu Leu Asn Ala Lys Leu Ile Thr Gln Arg Lys Phe
                885                 890                 895

Asp Asn Leu Thr Lys Ala Glu Arg Gly Gly Leu Ser Glu Leu Asp Lys
            900                 905                 910

Ala Gly Phe Ile Lys Arg Gln Leu Val Glu Thr Arg Gln Ile Thr Lys
        915                 920                 925

His Val Ala Gln Ile Leu Asp Ser Arg Met Asn Thr Lys Tyr Asp Glu
    930                 935                 940

Asn Asp Lys Leu Ile Arg Glu Val Lys Val Ile Thr Leu Lys Ser Lys
945                 950                 955                 960

Leu Val Ser Asp Phe Arg Lys Asp Phe Gln Phe Tyr Lys Val Arg Glu
                965                 970                 975

Ile Asn Asn Tyr His His Ala His Asp Ala Tyr Leu Asn Ala Val Val
            980                 985                 990

Gly Thr Ala Leu Ile Lys Lys Tyr  Pro Lys Leu Glu Ser  Glu Phe Val
        995                 1000                1005

Tyr Gly  Asp Tyr Lys Val Tyr  Asp Val Arg Lys Met  Ile Ala Lys
    1010                1015                1020

Ser Glu  Gln Glu Ile Gly Lys  Ala Thr Ala Lys Tyr  Phe Phe Tyr
    1025                1030                1035

Ser Asn  Ile Met Asn Phe Phe  Lys Thr Glu Ile Thr  Leu Ala Asn
    1040                1045                1050

Gly Glu  Ile Arg Lys Arg Pro  Leu Ile Glu Thr Asn  Gly Glu Thr
    1055                1060                1065

Gly Glu  Ile Val Trp Asp Lys  Gly Arg Asp Phe Ala  Thr Val Arg
    1070                1075                1080
```

Lys Val Leu Ser Met Pro Gln Val Asn Ile Val Lys Lys Thr Glu
1085 1090 1095

Val Gln Thr Gly Gly Phe Ser Lys Glu Ser Ile Leu Pro Lys Arg
1100 1105 1110

Asn Ser Asp Lys Leu Ile Ala Arg Lys Lys Asp Trp Asp Pro Lys
1115 1120 1125

Lys Tyr Gly Gly Phe Asp Ser Pro Thr Val Ala Tyr Ser Val Leu
1130 1135 1140

Val Val Ala Lys Val Glu Lys Gly Lys Ser Lys Lys Leu Lys Ser
1145 1150 1155

Val Lys Glu Leu Leu Gly Ile Thr Ile Met Glu Arg Ser Ser Phe
1160 1165 1170

Glu Lys Asn Pro Ile Asp Phe Leu Glu Ala Lys Gly Tyr Lys Glu
1175 1180 1185

Val Lys Lys Asp Leu Ile Ile Lys Leu Pro Lys Tyr Ser Leu Phe
1190 1195 1200

Glu Leu Glu Asn Gly Arg Lys Arg Met Leu Ala Ser Ala Gly Glu
1205 1210 1215

Leu Gln Lys Gly Asn Glu Leu Ala Leu Pro Ser Lys Tyr Val Asn
1220 1225 1230

Phe Leu Tyr Leu Ala Ser His Tyr Glu Lys Leu Lys Gly Ser Pro
1235 1240 1245

Glu Asp Asn Glu Gln Lys Gln Leu Phe Val Glu Gln His Lys His
1250 1255 1260

Tyr Leu Asp Glu Ile Ile Glu Gln Ile Ser Glu Phe Ser Lys Arg
1265 1270 1275

Val Ile Leu Ala Asp Ala Asn Leu Asp Lys Val Leu Ser Ala Tyr
1280 1285 1290

Asn Lys His Arg Asp Lys Pro Ile Arg Glu Gln Ala Glu Asn Ile
1295 1300 1305

Ile His Leu Phe Thr Leu Thr Asn Leu Gly Ala Pro Ala Ala Phe
1310 1315 1320

Lys Tyr Phe Asp Thr Thr Ile Asp Arg Lys Arg Tyr Thr Ser Thr
1325 1330 1335

Lys Glu Val Leu Asp Ala Thr Leu Ile His Gln Ser Ile Thr Gly
1340 1345 1350

Leu Tyr Glu Thr Arg Ile Asp Leu Ser Gln Leu Gly Gly Asp
1355 1360 1365

<210> SEQ ID NO 713
<211> LENGTH: 142
<212> TYPE: PRT
<213> ORGANISM: Artificial Sequence
<220> FEATURE:
<223> OTHER INFORMATION: Synthetic Polypeptide

<400> SEQUENCE: 713

Met Leu Ile Gly Tyr Val Arg Val Ser Thr Asn Asp Gln Asn Thr Asp
1 5 10 15

Leu Gln Arg Asn Ala Leu Val Cys Ala Gly Cys Glu Gln Ile Phe Glu
20 25 30

Asp Lys Leu Ser Gly Thr Arg Thr Asp Arg Pro Gly Leu Lys Arg Ala
35 40 45

Leu Lys Arg Leu Gln Lys Gly Asp Thr Leu Val Val Trp Lys Leu Asp
50 55 60

```
Arg Leu Gly Arg Ser Met Lys His Leu Ile Ser Leu Val Gly Glu Leu
65                  70                  75                  80

Arg Glu Arg Gly Ile Asn Phe Arg Ser Leu Thr Asp Ser Ile Asp Thr
                85                  90                  95

Ser Ser Pro Met Gly Arg Phe Phe Phe Tyr Val Met Gly Ala Leu Ala
            100                 105                 110

Glu Met Glu Arg Glu Leu Ile Ile Glu Arg Thr Met Ala Gly Leu Ala
        115                 120                 125

Ala Ala Arg Asn Lys Gly Arg Arg Phe Gly Arg Pro Pro Lys
    130                 135                 140


<210> SEQ ID NO 714
<211> LENGTH: 1300
<212> TYPE: PRT
<213> ORGANISM: Francisella novicida

<400> SEQUENCE: 714

Met Ser Ile Tyr Gln Glu Phe Val Asn Lys Tyr Ser Leu Ser Lys Thr
1               5                   10                  15

Leu Arg Phe Glu Leu Ile Pro Gln Gly Lys Thr Leu Glu Asn Ile Lys
            20                  25                  30

Ala Arg Gly Leu Ile Leu Asp Asp Glu Lys Arg Ala Lys Asp Tyr Lys
        35                  40                  45

Lys Ala Lys Gln Ile Ile Asp Lys Tyr His Gln Phe Phe Ile Glu Glu
    50                  55                  60

Ile Leu Ser Ser Val Cys Ile Ser Glu Asp Leu Leu Gln Asn Tyr Ser
65                  70                  75                  80

Asp Val Tyr Phe Lys Leu Lys Lys Ser Asp Asp Asp Asn Leu Gln Lys
                85                  90                  95

Asp Phe Lys Ser Ala Lys Asp Thr Ile Lys Lys Gln Ile Ser Glu Tyr
            100                 105                 110

Ile Lys Asp Ser Glu Lys Phe Lys Asn Leu Phe Asn Gln Asn Leu Ile
        115                 120                 125

Asp Ala Lys Lys Gly Gln Glu Ser Asp Leu Ile Leu Trp Leu Lys Gln
    130                 135                 140

Ser Lys Asp Asn Gly Ile Glu Leu Phe Lys Ala Asn Ser Asp Ile Thr
145                 150                 155                 160

Asp Ile Asp Glu Ala Leu Glu Ile Ile Lys Ser Phe Lys Gly Trp Thr
                165                 170                 175

Thr Tyr Phe Lys Gly Phe His Glu Asn Arg Lys Asn Val Tyr Ser Ser
            180                 185                 190

Asn Asp Ile Pro Thr Ser Ile Ile Tyr Arg Ile Val Asp Asp Asn Leu
        195                 200                 205

Pro Lys Phe Leu Glu Asn Lys Ala Lys Tyr Glu Ser Leu Lys Asp Lys
    210                 215                 220

Ala Pro Glu Ala Ile Asn Tyr Glu Gln Ile Lys Lys Asp Leu Ala Glu
225                 230                 235                 240

Glu Leu Thr Phe Asp Ile Asp Tyr Lys Thr Ser Glu Val Asn Gln Arg
                245                 250                 255

Val Phe Ser Leu Asp Glu Val Phe Glu Ile Ala Asn Phe Asn Asn Tyr
            260                 265                 270

Leu Asn Gln Ser Gly Ile Thr Lys Phe Asn Thr Ile Ile Gly Gly Lys
        275                 280                 285

Phe Val Asn Gly Glu Asn Thr Lys Arg Lys Gly Ile Asn Glu Tyr Ile
    290                 295                 300
```

```
Asn Leu Tyr Ser Gln Gln Ile Asn Asp Lys Thr Leu Lys Lys Tyr Lys
305                 310                 315                 320

Met Ser Val Leu Phe Lys Gln Ile Leu Ser Asp Thr Glu Ser Lys Ser
                325                 330                 335

Phe Val Ile Asp Lys Leu Glu Asp Asp Ser Asp Val Val Thr Thr Met
            340                 345                 350

Gln Ser Phe Tyr Glu Gln Ile Ala Ala Phe Lys Thr Val Glu Glu Lys
        355                 360                 365

Ser Ile Lys Glu Thr Leu Ser Leu Leu Phe Asp Asp Leu Lys Ala Gln
    370                 375                 380

Lys Leu Asp Leu Ser Lys Ile Tyr Phe Lys Asn Asp Lys Ser Leu Thr
385                 390                 395                 400

Asp Leu Ser Gln Gln Val Phe Asp Asp Tyr Ser Val Ile Gly Thr Ala
                405                 410                 415

Val Leu Glu Tyr Ile Thr Gln Gln Ile Ala Pro Lys Asn Leu Asp Asn
            420                 425                 430

Pro Ser Lys Lys Glu Gln Glu Leu Ile Ala Lys Lys Thr Glu Lys Ala
        435                 440                 445

Lys Tyr Leu Ser Leu Glu Thr Ile Lys Leu Ala Leu Glu Glu Phe Asn
    450                 455                 460

Lys His Arg Asp Ile Asp Lys Gln Cys Arg Phe Glu Glu Ile Leu Ala
465                 470                 475                 480

Asn Phe Ala Ala Ile Pro Met Ile Phe Asp Glu Ile Ala Gln Asn Lys
                485                 490                 495

Asp Asn Leu Ala Gln Ile Ser Ile Lys Tyr Gln Asn Gln Gly Lys Lys
            500                 505                 510

Asp Leu Leu Gln Ala Ser Ala Glu Asp Asp Val Lys Ala Ile Lys Asp
        515                 520                 525

Leu Leu Asp Gln Thr Asn Asn Leu Leu His Lys Leu Lys Ile Phe His
    530                 535                 540

Ile Ser Gln Ser Glu Asp Lys Ala Asn Ile Leu Asp Lys Asp Glu His
545                 550                 555                 560

Phe Tyr Leu Val Phe Glu Glu Cys Tyr Phe Glu Leu Ala Asn Ile Val
                565                 570                 575

Pro Leu Tyr Asn Lys Ile Arg Asn Tyr Ile Thr Gln Lys Pro Tyr Ser
            580                 585                 590

Asp Glu Lys Phe Lys Leu Asn Phe Glu Asn Ser Thr Leu Ala Asn Gly
        595                 600                 605

Trp Asp Lys Asn Lys Glu Pro Asp Asn Thr Ala Ile Leu Phe Ile Lys
    610                 615                 620

Asp Asp Lys Tyr Tyr Leu Gly Val Met Asn Lys Lys Asn Asn Lys Ile
625                 630                 635                 640

Phe Asp Asp Lys Ala Ile Lys Glu Asn Lys Gly Glu Gly Tyr Lys Lys
                645                 650                 655

Ile Val Tyr Lys Leu Leu Pro Gly Ala Asn Lys Met Leu Pro Lys Val
            660                 665                 670

Phe Phe Ser Ala Lys Ser Ile Lys Phe Tyr Asn Pro Ser Glu Asp Ile
        675                 680                 685

Leu Arg Ile Arg Asn His Ser Thr His Thr Lys Asn Gly Ser Pro Gln
    690                 695                 700

Lys Gly Tyr Glu Lys Phe Glu Phe Asn Ile Glu Asp Cys Arg Lys Phe
705                 710                 715                 720
```

-continued

```
Ile Asp Phe Tyr Lys Gln Ser Ile Ser Lys His Pro Glu Trp Lys Asp
                725                 730                 735

Phe Gly Phe Arg Phe Ser Asp Thr Gln Arg Tyr Asn Ser Ile Asp Glu
            740                 745                 750

Phe Tyr Arg Glu Val Glu Asn Gln Gly Tyr Lys Leu Thr Phe Glu Asn
        755                 760                 765

Ile Ser Glu Ser Tyr Ile Asp Ser Val Val Asn Gln Gly Lys Leu Tyr
    770                 775                 780

Leu Phe Gln Ile Tyr Asn Lys Asp Phe Ser Ala Tyr Ser Lys Gly Arg
785                 790                 795                 800

Pro Asn Leu His Thr Leu Tyr Trp Lys Ala Leu Phe Asp Glu Arg Asn
                805                 810                 815

Leu Gln Asp Val Val Tyr Lys Leu Asn Gly Glu Ala Glu Leu Phe Tyr
            820                 825                 830

Arg Lys Gln Ser Ile Pro Lys Lys Ile Thr His Pro Ala Lys Glu Ala
        835                 840                 845

Ile Ala Asn Lys Asn Lys Asp Asn Pro Lys Lys Glu Ser Val Phe Glu
    850                 855                 860

Tyr Asp Leu Ile Lys Asp Lys Arg Phe Thr Glu Asp Lys Phe Phe Phe
865                 870                 875                 880

His Cys Pro Ile Thr Ile Asn Phe Lys Ser Ser Gly Ala Asn Lys Phe
                885                 890                 895

Asn Asp Glu Ile Asn Leu Leu Leu Lys Glu Lys Ala Asn Asp Val His
            900                 905                 910

Ile Leu Ser Ile Asp Arg Gly Glu Arg His Leu Ala Tyr Tyr Thr Leu
        915                 920                 925

Val Asp Gly Lys Gly Asn Ile Ile Lys Gln Asp Thr Phe Asn Ile Ile
    930                 935                 940

Gly Asn Asp Arg Met Lys Thr Asn Tyr His Asp Lys Leu Ala Ala Ile
945                 950                 955                 960

Glu Lys Asp Arg Asp Ser Ala Arg Lys Asp Trp Lys Lys Ile Asn Asn
                965                 970                 975

Ile Lys Glu Met Lys Glu Gly Tyr Leu Ser Gln Val Val His Glu Ile
            980                 985                 990

Ala Lys Leu Val Ile Glu Tyr Asn  Ala Ile Val Val Phe  Glu Asp Leu
        995                 1000                 1005

Asn Phe  Gly Phe Lys Arg Gly  Arg Phe Lys Val Glu  Lys Gln Val
    1010                 1015                 1020

Tyr Gln  Lys Leu Glu Lys Met  Leu Ile Glu Lys Leu  Asn Tyr Leu
    1025                 1030                 1035

Val Phe  Lys Asp Asn Glu Phe  Asp Lys Thr Gly Gly  Val Leu Arg
    1040                 1045                 1050

Ala Tyr  Gln Leu Thr Ala Pro  Phe Glu Thr Phe Lys  Lys Met Gly
    1055                 1060                 1065

Lys Gln  Thr Gly Ile Ile Tyr  Tyr Val Pro Ala Gly  Phe Thr Ser
    1070                 1075                 1080

Lys Ile  Cys Pro Val Thr Gly  Phe Val Asn Gln Leu  Tyr Pro Lys
    1085                 1090                 1095

Tyr Glu  Ser Val Ser Lys Ser  Gln Glu Phe Phe Ser  Lys Phe Asp
    1100                 1105                 1110

Lys Ile  Cys Tyr Asn Leu Asp  Lys Gly Tyr Phe Glu  Phe Ser Phe
    1115                 1120                 1125

Asp Tyr  Lys Asn Phe Gly Asp  Lys Ala Ala Lys Gly  Lys Trp Thr
```

```
    1130                1135                1140

Ile Ala  Ser Phe Gly Ser Arg  Leu Ile Asn Phe Arg  Asn Ser Asp
    1145                1150                1155

Lys Asn  His Asn Trp Asp Thr  Arg Glu Val Tyr Pro  Thr Lys Glu
    1160                1165                1170

Leu Glu  Lys Leu Leu Lys Asp  Tyr Ser Ile Glu Tyr  Gly His Gly
    1175                1180                1185

Glu Cys  Ile Lys Ala Ala Ile  Cys Gly Glu Ser Asp  Lys Lys Phe
    1190                1195                1200

Phe Ala  Lys Leu Thr Ser Val  Leu Asn Thr Ile Leu  Gln Met Arg
    1205                1210                1215

Asn Ser  Lys Thr Gly Thr Glu  Leu Asp Tyr Leu Ile  Ser Pro Val
    1220                1225                1230

Ala Asp  Val Asn Gly Asn Phe  Phe Asp Ser Arg Gln  Ala Pro Lys
    1235                1240                1245

Asn Met  Pro Gln Asp Ala Asp  Ala Asn Gly Ala Tyr  His Ile Gly
    1250                1255                1260

Leu Lys  Gly Leu Met Leu Leu  Gly Arg Ile Lys Asn  Asn Gln Glu
    1265                1270                1275

Gly Lys  Lys Leu Asn Leu Val  Ile Lys Asn Glu Glu  Tyr Phe Glu
    1280                1285                1290

Phe Val  Gln Asn Arg Asn Asn
    1295                1300


<210> SEQ ID NO 715
<211> LENGTH: 1300
<212> TYPE: PRT
<213> ORGANISM: Francisella novicida

<400> SEQUENCE: 715

Met Ser Ile Tyr Gln Glu Phe Val Asn Lys Tyr Ser Leu Ser Lys Thr
1               5                   10                  15

Leu Arg Phe Glu Leu Ile Pro Gln Gly Lys Thr Leu Glu Asn Ile Lys
            20                  25                  30

Ala Arg Gly Leu Ile Leu Asp Asp Glu Lys Arg Ala Lys Asp Tyr Lys
        35                  40                  45

Lys Ala Lys Gln Ile Ile Asp Lys Tyr His Gln Phe Phe Ile Glu Glu
    50                  55                  60

Ile Leu Ser Ser Val Cys Ile Ser Glu Asp Leu Leu Gln Asn Tyr Ser
65                  70                  75                  80

Asp Val Tyr Phe Lys Leu Lys Lys Ser Asp Asp Asp Asn Leu Gln Lys
                85                  90                  95

Asp Phe Lys Ser Ala Lys Asp Thr Ile Lys Lys Gln Ile Ser Glu Tyr
            100                 105                 110

Ile Lys Asp Ser Glu Lys Phe Lys Asn Leu Phe Asn Gln Asn Leu Ile
        115                 120                 125

Asp Ala Lys Lys Gly Gln Glu Ser Asp Leu Ile Leu Trp Leu Lys Gln
    130                 135                 140

Ser Lys Asp Asn Gly Ile Glu Leu Phe Lys Ala Asn Ser Asp Ile Thr
145                 150                 155                 160

Asp Ile Asp Glu Ala Leu Glu Ile Ile Lys Ser Phe Lys Gly Trp Thr
                165                 170                 175

Thr Tyr Phe Lys Gly Phe His Glu Asn Arg Lys Asn Val Tyr Ser Ser
            180                 185                 190
```

-continued

```
Asn Asp Ile Pro Thr Ser Ile Ile Tyr Arg Ile Val Asp Asp Asn Leu
        195                 200                 205

Pro Lys Phe Leu Glu Asn Lys Ala Lys Tyr Glu Ser Leu Lys Asp Lys
    210                 215                 220

Ala Pro Glu Ala Ile Asn Tyr Glu Gln Ile Lys Lys Asp Leu Ala Glu
225                 230                 235                 240

Glu Leu Thr Phe Asp Ile Asp Tyr Lys Thr Ser Glu Val Asn Gln Arg
                245                 250                 255

Val Phe Ser Leu Asp Glu Val Phe Glu Ile Ala Asn Phe Asn Asn Tyr
            260                 265                 270

Leu Asn Gln Ser Gly Ile Thr Lys Phe Asn Thr Ile Ile Gly Gly Lys
        275                 280                 285

Phe Val Asn Gly Glu Asn Thr Lys Arg Lys Gly Ile Asn Glu Tyr Ile
    290                 295                 300

Asn Leu Tyr Ser Gln Gln Ile Asn Asp Lys Thr Leu Lys Lys Tyr Lys
305                 310                 315                 320

Met Ser Val Leu Phe Lys Gln Ile Leu Ser Asp Thr Glu Ser Lys Ser
                325                 330                 335

Phe Val Ile Asp Lys Leu Glu Asp Asp Ser Asp Val Val Thr Thr Met
            340                 345                 350

Gln Ser Phe Tyr Glu Gln Ile Ala Ala Phe Lys Thr Val Glu Glu Lys
        355                 360                 365

Ser Ile Lys Glu Thr Leu Ser Leu Leu Phe Asp Asp Leu Lys Ala Gln
    370                 375                 380

Lys Leu Asp Leu Ser Lys Ile Tyr Phe Lys Asn Asp Lys Ser Leu Thr
385                 390                 395                 400

Asp Leu Ser Gln Gln Val Phe Asp Asp Tyr Ser Val Ile Gly Thr Ala
                405                 410                 415

Val Leu Glu Tyr Ile Thr Gln Gln Ile Ala Pro Lys Asn Leu Asp Asn
            420                 425                 430

Pro Ser Lys Lys Glu Gln Glu Leu Ile Ala Lys Lys Thr Glu Lys Ala
        435                 440                 445

Lys Tyr Leu Ser Leu Glu Thr Ile Lys Leu Ala Leu Glu Glu Phe Asn
    450                 455                 460

Lys His Arg Asp Ile Asp Lys Gln Cys Arg Phe Glu Glu Ile Leu Ala
465                 470                 475                 480

Asn Phe Ala Ala Ile Pro Met Ile Phe Asp Glu Ile Ala Gln Asn Lys
                485                 490                 495

Asp Asn Leu Ala Gln Ile Ser Ile Lys Tyr Gln Asn Gln Gly Lys Lys
            500                 505                 510

Asp Leu Leu Gln Ala Ser Ala Glu Asp Asp Val Lys Ala Ile Lys Asp
        515                 520                 525

Leu Leu Asp Gln Thr Asn Asn Leu Leu His Lys Leu Lys Ile Phe His
    530                 535                 540

Ile Ser Gln Ser Glu Asp Lys Ala Asn Ile Leu Asp Lys Asp Glu His
545                 550                 555                 560

Phe Tyr Leu Val Phe Glu Glu Cys Tyr Phe Glu Leu Ala Asn Ile Val
                565                 570                 575

Pro Leu Tyr Asn Lys Ile Arg Asn Tyr Ile Thr Gln Lys Pro Tyr Ser
            580                 585                 590

Asp Glu Lys Phe Lys Leu Asn Phe Glu Asn Ser Thr Leu Ala Asn Gly
        595                 600                 605

Trp Asp Lys Asn Lys Glu Pro Asp Asn Thr Ala Ile Leu Phe Ile Lys
```

```
    610                 615                 620

Asp Asp Lys Tyr Tyr Leu Gly Val Met Asn Lys Lys Asn Asn Lys Ile
625                 630                 635                 640

Phe Asp Asp Lys Ala Ile Lys Glu Asn Lys Gly Glu Gly Tyr Lys Lys
                645                 650                 655

Ile Val Tyr Lys Leu Leu Pro Gly Ala Asn Lys Met Leu Pro Lys Val
            660                 665                 670

Phe Phe Ser Ala Lys Ser Ile Lys Phe Tyr Asn Pro Ser Glu Asp Ile
        675                 680                 685

Leu Arg Ile Arg Asn His Ser Thr His Thr Lys Asn Gly Ser Pro Gln
    690                 695                 700

Lys Gly Tyr Glu Lys Phe Glu Phe Asn Ile Glu Asp Cys Arg Lys Phe
705                 710                 715                 720

Ile Asp Phe Tyr Lys Gln Ser Ile Ser Lys His Pro Glu Trp Lys Asp
                725                 730                 735

Phe Gly Phe Arg Phe Ser Asp Thr Gln Arg Tyr Asn Ser Ile Asp Glu
            740                 745                 750

Phe Tyr Arg Glu Val Glu Asn Gln Gly Tyr Lys Leu Thr Phe Glu Asn
        755                 760                 765

Ile Ser Glu Ser Tyr Ile Asp Ser Val Val Asn Gln Gly Lys Leu Tyr
    770                 775                 780

Leu Phe Gln Ile Tyr Asn Lys Asp Phe Ser Ala Tyr Ser Lys Gly Arg
785                 790                 795                 800

Pro Asn Leu His Thr Leu Tyr Trp Lys Ala Leu Phe Asp Glu Arg Asn
                805                 810                 815

Leu Gln Asp Val Val Tyr Lys Leu Asn Gly Glu Ala Glu Leu Phe Tyr
            820                 825                 830

Arg Lys Gln Ser Ile Pro Lys Lys Ile Thr His Pro Ala Lys Glu Ala
        835                 840                 845

Ile Ala Asn Lys Asn Lys Asp Asn Pro Lys Lys Glu Ser Val Phe Glu
    850                 855                 860

Tyr Asp Leu Ile Lys Asp Lys Arg Phe Thr Glu Asp Lys Phe Phe Phe
865                 870                 875                 880

His Cys Pro Ile Thr Ile Asn Phe Lys Ser Ser Gly Ala Asn Lys Phe
                885                 890                 895

Asn Asp Glu Ile Asn Leu Leu Leu Lys Glu Lys Ala Asn Asp Val His
            900                 905                 910

Ile Leu Ser Ile Ala Arg Gly Glu Arg His Leu Ala Tyr Tyr Thr Leu
        915                 920                 925

Val Asp Gly Lys Gly Asn Ile Ile Lys Gln Asp Thr Phe Asn Ile Ile
    930                 935                 940

Gly Asn Asp Arg Met Lys Thr Asn Tyr His Asp Lys Leu Ala Ala Ile
945                 950                 955                 960

Glu Lys Asp Arg Asp Ser Ala Arg Lys Asp Trp Lys Lys Ile Asn Asn
                965                 970                 975

Ile Lys Glu Met Lys Glu Gly Tyr Leu Ser Gln Val Val His Glu Ile
            980                 985                 990

Ala Lys Leu Val Ile Glu Tyr Asn  Ala Ile Val Val Phe  Glu Asp Leu
        995                 1000                1005

Asn Phe  Gly Phe Lys Arg Gly  Arg Phe Lys Val Glu  Lys Gln Val
    1010                1015                1020

Tyr Gln  Lys Leu Glu Lys Met  Leu Ile Glu Lys Leu  Asn Tyr Leu
    1025                1030                1035
```

Val Phe Lys Asp Asn Glu Phe Asp Lys Thr Gly Gly Val Leu Arg
1040 1045 1050

Ala Tyr Gln Leu Thr Ala Pro Phe Glu Thr Phe Lys Lys Met Gly
1055 1060 1065

Lys Gln Thr Gly Ile Ile Tyr Tyr Val Pro Ala Gly Phe Thr Ser
1070 1075 1080

Lys Ile Cys Pro Val Thr Gly Phe Val Asn Gln Leu Tyr Pro Lys
1085 1090 1095

Tyr Glu Ser Val Ser Lys Ser Gln Glu Phe Phe Ser Lys Phe Asp
1100 1105 1110

Lys Ile Cys Tyr Asn Leu Asp Lys Gly Tyr Phe Glu Phe Ser Phe
1115 1120 1125

Asp Tyr Lys Asn Phe Gly Asp Lys Ala Ala Lys Gly Lys Trp Thr
1130 1135 1140

Ile Ala Ser Phe Gly Ser Arg Leu Ile Asn Phe Arg Asn Ser Asp
1145 1150 1155

Lys Asn His Asn Trp Asp Thr Arg Glu Val Tyr Pro Thr Lys Glu
1160 1165 1170

Leu Glu Lys Leu Leu Lys Asp Tyr Ser Ile Glu Tyr Gly His Gly
1175 1180 1185

Glu Cys Ile Lys Ala Ala Ile Cys Gly Glu Ser Asp Lys Lys Phe
1190 1195 1200

Phe Ala Lys Leu Thr Ser Val Leu Asn Thr Ile Leu Gln Met Arg
1205 1210 1215

Asn Ser Lys Thr Gly Thr Glu Leu Asp Tyr Leu Ile Ser Pro Val
1220 1225 1230

Ala Asp Val Asn Gly Asn Phe Phe Asp Ser Arg Gln Ala Pro Lys
1235 1240 1245

Asn Met Pro Gln Asp Ala Asp Ala Asn Gly Ala Tyr His Ile Gly
1250 1255 1260

Leu Lys Gly Leu Met Leu Leu Gly Arg Ile Lys Asn Asn Gln Glu
1265 1270 1275

Gly Lys Lys Leu Asn Leu Val Ile Lys Asn Glu Glu Tyr Phe Glu
1280 1285 1290

Phe Val Gln Asn Arg Asn Asn
1295 1300

<210> SEQ ID NO 716
<211> LENGTH: 1300
<212> TYPE: PRT
<213> ORGANISM: Francisella novicida

<400> SEQUENCE: 716

Met Ser Ile Tyr Gln Glu Phe Val Asn Lys Tyr Ser Leu Ser Lys Thr
1 5 10 15

Leu Arg Phe Glu Leu Ile Pro Gln Gly Lys Thr Leu Glu Asn Ile Lys
20 25 30

Ala Arg Gly Leu Ile Leu Asp Asp Glu Lys Arg Ala Lys Asp Tyr Lys
35 40 45

Lys Ala Lys Gln Ile Ile Asp Lys Tyr His Gln Phe Phe Ile Glu Glu
50 55 60

Ile Leu Ser Ser Val Cys Ile Ser Glu Asp Leu Leu Gln Asn Tyr Ser
65 70 75 80

Asp Val Tyr Phe Lys Leu Lys Lys Ser Asp Asp Asp Asn Leu Gln Lys

```
                85                  90                  95

Asp Phe Lys Ser Ala Lys Asp Thr Ile Lys Lys Gln Ile Ser Glu Tyr
            100                 105                 110

Ile Lys Asp Ser Glu Lys Phe Lys Asn Leu Phe Asn Gln Asn Leu Ile
        115                 120                 125

Asp Ala Lys Lys Gly Gln Glu Ser Asp Leu Ile Leu Trp Leu Lys Gln
    130                 135                 140

Ser Lys Asp Asn Gly Ile Glu Leu Phe Lys Ala Asn Ser Asp Ile Thr
145                 150                 155                 160

Asp Ile Asp Glu Ala Leu Glu Ile Ile Lys Ser Phe Lys Gly Trp Thr
                165                 170                 175

Thr Tyr Phe Lys Gly Phe His Glu Asn Arg Lys Asn Val Tyr Ser Ser
            180                 185                 190

Asn Asp Ile Pro Thr Ser Ile Ile Tyr Arg Ile Val Asp Asp Asn Leu
        195                 200                 205

Pro Lys Phe Leu Glu Asn Lys Ala Lys Tyr Glu Ser Leu Lys Asp Lys
    210                 215                 220

Ala Pro Glu Ala Ile Asn Tyr Glu Gln Ile Lys Lys Asp Leu Ala Glu
225                 230                 235                 240

Glu Leu Thr Phe Asp Ile Asp Tyr Lys Thr Ser Glu Val Asn Gln Arg
                245                 250                 255

Val Phe Ser Leu Asp Glu Val Phe Glu Ile Ala Asn Phe Asn Asn Tyr
            260                 265                 270

Leu Asn Gln Ser Gly Ile Thr Lys Phe Asn Thr Ile Ile Gly Gly Lys
        275                 280                 285

Phe Val Asn Gly Glu Asn Thr Lys Arg Lys Gly Ile Asn Glu Tyr Ile
    290                 295                 300

Asn Leu Tyr Ser Gln Gln Ile Asn Asp Lys Thr Leu Lys Lys Tyr Lys
305                 310                 315                 320

Met Ser Val Leu Phe Lys Gln Ile Leu Ser Asp Thr Glu Ser Lys Ser
                325                 330                 335

Phe Val Ile Asp Lys Leu Glu Asp Asp Ser Asp Val Val Thr Thr Met
            340                 345                 350

Gln Ser Phe Tyr Glu Gln Ile Ala Ala Phe Lys Thr Val Glu Glu Lys
        355                 360                 365

Ser Ile Lys Glu Thr Leu Ser Leu Leu Phe Asp Asp Leu Lys Ala Gln
    370                 375                 380

Lys Leu Asp Leu Ser Lys Ile Tyr Phe Lys Asn Asp Lys Ser Leu Thr
385                 390                 395                 400

Asp Leu Ser Gln Gln Val Phe Asp Asp Tyr Ser Val Ile Gly Thr Ala
                405                 410                 415

Val Leu Glu Tyr Ile Thr Gln Gln Ile Ala Pro Lys Asn Leu Asp Asn
            420                 425                 430

Pro Ser Lys Lys Glu Gln Glu Leu Ile Ala Lys Lys Thr Glu Lys Ala
        435                 440                 445

Lys Tyr Leu Ser Leu Glu Thr Ile Lys Leu Ala Leu Glu Glu Phe Asn
    450                 455                 460

Lys His Arg Asp Ile Asp Lys Gln Cys Arg Phe Glu Glu Ile Leu Ala
465                 470                 475                 480

Asn Phe Ala Ala Ile Pro Met Ile Phe Asp Glu Ile Ala Gln Asn Lys
                485                 490                 495

Asp Asn Leu Ala Gln Ile Ser Ile Lys Tyr Gln Asn Gln Gly Lys Lys
            500                 505                 510
```

```
Asp Leu Leu Gln Ala Ser Ala Glu Asp Asp Val Lys Ala Ile Lys Asp
        515                 520                 525

Leu Leu Asp Gln Thr Asn Asn Leu Leu His Lys Leu Lys Ile Phe His
    530                 535                 540

Ile Ser Gln Ser Glu Asp Lys Ala Asn Ile Leu Asp Lys Asp Glu His
545                 550                 555                 560

Phe Tyr Leu Val Phe Glu Glu Cys Tyr Phe Glu Leu Ala Asn Ile Val
                565                 570                 575

Pro Leu Tyr Asn Lys Ile Arg Asn Tyr Ile Thr Gln Lys Pro Tyr Ser
            580                 585                 590

Asp Glu Lys Phe Lys Leu Asn Phe Glu Asn Ser Thr Leu Ala Asn Gly
        595                 600                 605

Trp Asp Lys Asn Lys Glu Pro Asp Asn Thr Ala Ile Leu Phe Ile Lys
    610                 615                 620

Asp Asp Lys Tyr Tyr Leu Gly Val Met Asn Lys Lys Asn Asn Lys Ile
625                 630                 635                 640

Phe Asp Asp Lys Ala Ile Lys Glu Asn Lys Gly Glu Gly Tyr Lys Lys
                645                 650                 655

Ile Val Tyr Lys Leu Leu Pro Gly Ala Asn Lys Met Leu Pro Lys Val
            660                 665                 670

Phe Phe Ser Ala Lys Ser Ile Lys Phe Tyr Asn Pro Ser Glu Asp Ile
        675                 680                 685

Leu Arg Ile Arg Asn His Ser Thr His Thr Lys Asn Gly Ser Pro Gln
    690                 695                 700

Lys Gly Tyr Glu Lys Phe Glu Phe Asn Ile Glu Asp Cys Arg Lys Phe
705                 710                 715                 720

Ile Asp Phe Tyr Lys Gln Ser Ile Ser Lys His Pro Glu Trp Lys Asp
                725                 730                 735

Phe Gly Phe Arg Phe Ser Asp Thr Gln Arg Tyr Asn Ser Ile Asp Glu
            740                 745                 750

Phe Tyr Arg Glu Val Glu Asn Gln Gly Tyr Lys Leu Thr Phe Glu Asn
        755                 760                 765

Ile Ser Glu Ser Tyr Ile Asp Ser Val Val Asn Gln Gly Lys Leu Tyr
    770                 775                 780

Leu Phe Gln Ile Tyr Asn Lys Asp Phe Ser Ala Tyr Ser Lys Gly Arg
785                 790                 795                 800

Pro Asn Leu His Thr Leu Tyr Trp Lys Ala Leu Phe Asp Glu Arg Asn
                805                 810                 815

Leu Gln Asp Val Val Tyr Lys Leu Asn Gly Glu Ala Glu Leu Phe Tyr
            820                 825                 830

Arg Lys Gln Ser Ile Pro Lys Lys Ile Thr His Pro Ala Lys Glu Ala
        835                 840                 845

Ile Ala Asn Lys Asn Lys Asp Asn Pro Lys Lys Glu Ser Val Phe Glu
    850                 855                 860

Tyr Asp Leu Ile Lys Asp Lys Arg Phe Thr Glu Asp Lys Phe Phe Phe
865                 870                 875                 880

His Cys Pro Ile Thr Ile Asn Phe Lys Ser Ser Gly Ala Asn Lys Phe
                885                 890                 895

Asn Asp Glu Ile Asn Leu Leu Leu Lys Glu Lys Ala Asn Asp Val His
            900                 905                 910

Ile Leu Ser Ile Asp Arg Gly Glu Arg His Leu Ala Tyr Tyr Thr Leu
        915                 920                 925
```

Val Asp Gly Lys Gly Asn Ile Ile Lys Gln Asp Thr Phe Asn Ile Ile
930 935 940

Gly Asn Asp Arg Met Lys Thr Asn Tyr His Asp Lys Leu Ala Ala Ile
945 950 955 960

Glu Lys Asp Arg Asp Ser Ala Arg Lys Asp Trp Lys Lys Ile Asn Asn
965 970 975

Ile Lys Glu Met Lys Glu Gly Tyr Leu Ser Gln Val Val His Glu Ile
980 985 990

Ala Lys Leu Val Ile Glu Tyr Asn Ala Ile Val Val Phe Ala Asp Leu
995 1000 1005

Asn Phe Gly Phe Lys Arg Gly Arg Phe Lys Val Glu Lys Gln Val
1010 1015 1020

Tyr Gln Lys Leu Glu Lys Met Leu Ile Glu Lys Leu Asn Tyr Leu
1025 1030 1035

Val Phe Lys Asp Asn Glu Phe Asp Lys Thr Gly Gly Val Leu Arg
1040 1045 1050

Ala Tyr Gln Leu Thr Ala Pro Phe Glu Thr Phe Lys Lys Met Gly
1055 1060 1065

Lys Gln Thr Gly Ile Ile Tyr Tyr Val Pro Ala Gly Phe Thr Ser
1070 1075 1080

Lys Ile Cys Pro Val Thr Gly Phe Val Asn Gln Leu Tyr Pro Lys
1085 1090 1095

Tyr Glu Ser Val Ser Lys Ser Gln Glu Phe Phe Ser Lys Phe Asp
1100 1105 1110

Lys Ile Cys Tyr Asn Leu Asp Lys Gly Tyr Phe Glu Phe Ser Phe
1115 1120 1125

Asp Tyr Lys Asn Phe Gly Asp Lys Ala Ala Lys Gly Lys Trp Thr
1130 1135 1140

Ile Ala Ser Phe Gly Ser Arg Leu Ile Asn Phe Arg Asn Ser Asp
1145 1150 1155

Lys Asn His Asn Trp Asp Thr Arg Glu Val Tyr Pro Thr Lys Glu
1160 1165 1170

Leu Glu Lys Leu Leu Lys Asp Tyr Ser Ile Glu Tyr Gly His Gly
1175 1180 1185

Glu Cys Ile Lys Ala Ala Ile Cys Gly Glu Ser Asp Lys Lys Phe
1190 1195 1200

Phe Ala Lys Leu Thr Ser Val Leu Asn Thr Ile Leu Gln Met Arg
1205 1210 1215

Asn Ser Lys Thr Gly Thr Glu Leu Asp Tyr Leu Ile Ser Pro Val
1220 1225 1230

Ala Asp Val Asn Gly Asn Phe Phe Asp Ser Arg Gln Ala Pro Lys
1235 1240 1245

Asn Met Pro Gln Asp Ala Asp Ala Asn Gly Ala Tyr His Ile Gly
1250 1255 1260

Leu Lys Gly Leu Met Leu Leu Gly Arg Ile Lys Asn Asn Gln Glu
1265 1270 1275

Gly Lys Lys Leu Asn Leu Val Ile Lys Asn Glu Glu Tyr Phe Glu
1280 1285 1290

Phe Val Gln Asn Arg Asn Asn
1295 1300

<210> SEQ ID NO 717
<211> LENGTH: 1300
<212> TYPE: PRT

<213> ORGANISM: Francisella novicida

<400> SEQUENCE: 717

Met Ser Ile Tyr Gln Glu Phe Val Asn Lys Tyr Ser Leu Ser Lys Thr
1 5 10 15

Leu Arg Phe Glu Leu Ile Pro Gln Gly Lys Thr Leu Glu Asn Ile Lys
20 25 30

Ala Arg Gly Leu Ile Leu Asp Asp Glu Lys Arg Ala Lys Asp Tyr Lys
35 40 45

Lys Ala Lys Gln Ile Ile Asp Lys Tyr His Gln Phe Phe Ile Glu Glu
50 55 60

Ile Leu Ser Ser Val Cys Ile Ser Glu Asp Leu Leu Gln Asn Tyr Ser
65 70 75 80

Asp Val Tyr Phe Lys Leu Lys Lys Ser Asp Asp Asp Asn Leu Gln Lys
85 90 95

Asp Phe Lys Ser Ala Lys Asp Thr Ile Lys Lys Gln Ile Ser Glu Tyr
100 105 110

Ile Lys Asp Ser Glu Lys Phe Lys Asn Leu Phe Asn Gln Asn Leu Ile
115 120 125

Asp Ala Lys Lys Gly Gln Glu Ser Asp Leu Ile Leu Trp Leu Lys Gln
130 135 140

Ser Lys Asp Asn Gly Ile Glu Leu Phe Lys Ala Asn Ser Asp Ile Thr
145 150 155 160

Asp Ile Asp Glu Ala Leu Glu Ile Ile Lys Ser Phe Lys Gly Trp Thr
165 170 175

Thr Tyr Phe Lys Gly Phe His Glu Asn Arg Lys Asn Val Tyr Ser Ser
180 185 190

Asn Asp Ile Pro Thr Ser Ile Ile Tyr Arg Ile Val Asp Asp Asn Leu
195 200 205

Pro Lys Phe Leu Glu Asn Lys Ala Lys Tyr Glu Ser Leu Lys Asp Lys
210 215 220

Ala Pro Glu Ala Ile Asn Tyr Glu Gln Ile Lys Lys Asp Leu Ala Glu
225 230 235 240

Glu Leu Thr Phe Asp Ile Asp Tyr Lys Thr Ser Glu Val Asn Gln Arg
245 250 255

Val Phe Ser Leu Asp Glu Val Phe Glu Ile Ala Asn Phe Asn Asn Tyr
260 265 270

Leu Asn Gln Ser Gly Ile Thr Lys Phe Asn Thr Ile Ile Gly Gly Lys
275 280 285

Phe Val Asn Gly Glu Asn Thr Lys Arg Lys Gly Ile Asn Glu Tyr Ile
290 295 300

Asn Leu Tyr Ser Gln Gln Ile Asn Asp Lys Thr Leu Lys Lys Tyr Lys
305 310 315 320

Met Ser Val Leu Phe Lys Gln Ile Leu Ser Asp Thr Glu Ser Lys Ser
325 330 335

Phe Val Ile Asp Lys Leu Glu Asp Asp Ser Asp Val Val Thr Thr Met
340 345 350

Gln Ser Phe Tyr Glu Gln Ile Ala Ala Phe Lys Thr Val Glu Glu Lys
355 360 365

Ser Ile Lys Glu Thr Leu Ser Leu Leu Phe Asp Asp Leu Lys Ala Gln
370 375 380

Lys Leu Asp Leu Ser Lys Ile Tyr Phe Lys Asn Asp Lys Ser Leu Thr
385 390 395 400

```
Asp Leu Ser Gln Gln Val Phe Asp Asp Tyr Ser Val Ile Gly Thr Ala
                405                 410                 415

Val Leu Glu Tyr Ile Thr Gln Gln Ile Ala Pro Lys Asn Leu Asp Asn
            420                 425                 430

Pro Ser Lys Lys Glu Gln Glu Leu Ile Ala Lys Lys Thr Glu Lys Ala
        435                 440                 445

Lys Tyr Leu Ser Leu Glu Thr Ile Lys Leu Ala Leu Glu Glu Phe Asn
    450                 455                 460

Lys His Arg Asp Ile Asp Lys Gln Cys Arg Phe Glu Glu Ile Leu Ala
465                 470                 475                 480

Asn Phe Ala Ala Ile Pro Met Ile Phe Asp Glu Ile Ala Gln Asn Lys
                485                 490                 495

Asp Asn Leu Ala Gln Ile Ser Ile Lys Tyr Gln Asn Gln Gly Lys Lys
            500                 505                 510

Asp Leu Leu Gln Ala Ser Ala Glu Asp Asp Val Lys Ala Ile Lys Asp
        515                 520                 525

Leu Leu Asp Gln Thr Asn Asn Leu Leu His Lys Leu Lys Ile Phe His
    530                 535                 540

Ile Ser Gln Ser Glu Asp Lys Ala Asn Ile Leu Asp Lys Asp Glu His
545                 550                 555                 560

Phe Tyr Leu Val Phe Glu Glu Cys Tyr Phe Glu Leu Ala Asn Ile Val
                565                 570                 575

Pro Leu Tyr Asn Lys Ile Arg Asn Tyr Ile Thr Gln Lys Pro Tyr Ser
            580                 585                 590

Asp Glu Lys Phe Lys Leu Asn Phe Glu Asn Ser Thr Leu Ala Asn Gly
        595                 600                 605

Trp Asp Lys Asn Lys Glu Pro Asp Asn Thr Ala Ile Leu Phe Ile Lys
    610                 615                 620

Asp Asp Lys Tyr Tyr Leu Gly Val Met Asn Lys Lys Asn Asn Lys Ile
625                 630                 635                 640

Phe Asp Asp Lys Ala Ile Lys Glu Asn Lys Gly Glu Gly Tyr Lys Lys
                645                 650                 655

Ile Val Tyr Lys Leu Leu Pro Gly Ala Asn Lys Met Leu Pro Lys Val
            660                 665                 670

Phe Phe Ser Ala Lys Ser Ile Lys Phe Tyr Asn Pro Ser Glu Asp Ile
        675                 680                 685

Leu Arg Ile Arg Asn His Ser Thr His Thr Lys Asn Gly Ser Pro Gln
    690                 695                 700

Lys Gly Tyr Glu Lys Phe Glu Phe Asn Ile Glu Asp Cys Arg Lys Phe
705                 710                 715                 720

Ile Asp Phe Tyr Lys Gln Ser Ile Ser Lys His Pro Glu Trp Lys Asp
                725                 730                 735

Phe Gly Phe Arg Phe Ser Asp Thr Gln Arg Tyr Asn Ser Ile Asp Glu
            740                 745                 750

Phe Tyr Arg Glu Val Glu Asn Gln Gly Tyr Lys Leu Thr Phe Glu Asn
        755                 760                 765

Ile Ser Glu Ser Tyr Ile Asp Ser Val Val Asn Gln Gly Lys Leu Tyr
    770                 775                 780

Leu Phe Gln Ile Tyr Asn Lys Asp Phe Ser Ala Tyr Ser Lys Gly Arg
785                 790                 795                 800

Pro Asn Leu His Thr Leu Tyr Trp Lys Ala Leu Phe Asp Glu Arg Asn
                805                 810                 815

Leu Gln Asp Val Val Tyr Lys Leu Asn Gly Glu Ala Glu Leu Phe Tyr
```

```
            820                 825                 830

Arg Lys Gln Ser Ile Pro Lys Lys Ile Thr His Pro Ala Lys Glu Ala
        835                 840                 845

Ile Ala Asn Lys Asn Lys Asp Asn Pro Lys Lys Glu Ser Val Phe Glu
    850                 855                 860

Tyr Asp Leu Ile Lys Asp Lys Arg Phe Thr Glu Asp Lys Phe Phe Phe
865                 870                 875                 880

His Cys Pro Ile Thr Ile Asn Phe Lys Ser Ser Gly Ala Asn Lys Phe
                885                 890                 895

Asn Asp Glu Ile Asn Leu Leu Leu Lys Glu Lys Ala Asn Asp Val His
            900                 905                 910

Ile Leu Ser Ile Asp Arg Gly Glu Arg His Leu Ala Tyr Tyr Thr Leu
        915                 920                 925

Val Asp Gly Lys Gly Asn Ile Ile Lys Gln Asp Thr Phe Asn Ile Ile
    930                 935                 940

Gly Asn Asp Arg Met Lys Thr Asn Tyr His Asp Lys Leu Ala Ala Ile
945                 950                 955                 960

Glu Lys Asp Arg Asp Ser Ala Arg Lys Asp Trp Lys Lys Ile Asn Asn
                965                 970                 975

Ile Lys Glu Met Lys Glu Gly Tyr Leu Ser Gln Val Val His Glu Ile
            980                 985                 990

Ala Lys Leu Val Ile Glu Tyr Asn  Ala Ile Val Val Phe  Glu Asp Leu
        995                 1000                1005

Asn Phe  Gly Phe Lys Arg Gly  Arg Phe Lys Val Glu  Lys Gln Val
    1010                1015                1020

Tyr Gln  Lys Leu Glu Lys Met  Leu Ile Glu Lys Leu  Asn Tyr Leu
    1025                1030                1035

Val Phe  Lys Asp Asn Glu Phe  Asp Lys Thr Gly Gly  Val Leu Arg
    1040                1045                1050

Ala Tyr  Gln Leu Thr Ala Pro  Phe Glu Thr Phe Lys  Lys Met Gly
    1055                1060                1065

Lys Gln  Thr Gly Ile Ile Tyr  Tyr Val Pro Ala Gly  Phe Thr Ser
    1070                1075                1080

Lys Ile  Cys Pro Val Thr Gly  Phe Val Asn Gln Leu  Tyr Pro Lys
    1085                1090                1095

Tyr Glu  Ser Val Ser Lys Ser  Gln Glu Phe Phe Ser  Lys Phe Asp
    1100                1105                1110

Lys Ile  Cys Tyr Asn Leu Asp  Lys Gly Tyr Phe Glu  Phe Ser Phe
    1115                1120                1125

Asp Tyr  Lys Asn Phe Gly Asp  Lys Ala Ala Lys Gly  Lys Trp Thr
    1130                1135                1140

Ile Ala  Ser Phe Gly Ser Arg  Leu Ile Asn Phe Arg  Asn Ser Asp
    1145                1150                1155

Lys Asn  His Asn Trp Asp Thr  Arg Glu Val Tyr Pro  Thr Lys Glu
    1160                1165                1170

Leu Glu  Lys Leu Leu Lys Asp  Tyr Ser Ile Glu Tyr  Gly His Gly
    1175                1180                1185

Glu Cys  Ile Lys Ala Ala Ile  Cys Gly Glu Ser Asp  Lys Lys Phe
    1190                1195                1200

Phe Ala  Lys Leu Thr Ser Val  Leu Asn Thr Ile Leu  Gln Met Arg
    1205                1210                1215

Asn Ser  Lys Thr Gly Thr Glu  Leu Asp Tyr Leu Ile  Ser Pro Val
    1220                1225                1230
```

```
Ala Asp  Val Asn Gly Asn Phe  Phe Asp Ser Arg Gln  Ala Pro Lys
    1235                 1240                 1245

Asn Met  Pro Gln Asp Ala Ala  Ala Asn Gly Ala Tyr  His Ile Gly
    1250                 1255                 1260

Leu Lys  Gly Leu Met Leu Leu  Gly Arg Ile Lys Asn  Asn Gln Glu
    1265                 1270                 1275

Gly Lys  Lys Leu Asn Leu Val  Ile Lys Asn Glu Glu  Tyr Phe Glu
    1280                 1285                 1290

Phe Val  Gln Asn Arg Asn Asn
    1295                 1300


<210> SEQ ID NO 718
<211> LENGTH: 887
<212> TYPE: PRT
<213> ORGANISM: Natronobacterium gregoryi

<400> SEQUENCE: 718

Met Thr Val Ile Asp Leu Asp Ser Thr Thr Thr Ala Asp Glu Leu Thr
1               5                   10                  15

Ser Gly His Thr Tyr Asp Ile Ser Val Thr Leu Thr Gly Val Tyr Asp
            20                  25                  30

Asn Thr Asp Glu Gln His Pro Arg Met Ser Leu Ala Phe Glu Gln Asp
        35                  40                  45

Asn Gly Glu Arg Arg Tyr Ile Thr Leu Trp Lys Asn Thr Thr Pro Lys
    50                  55                  60

Asp Val Phe Thr Tyr Asp Tyr Ala Thr Gly Ser Thr Tyr Ile Phe Thr
65                  70                  75                  80

Asn Ile Asp Tyr Glu Val Lys Asp Gly Tyr Glu Asn Leu Thr Ala Thr
                85                  90                  95

Tyr Gln Thr Thr Val Glu Asn Ala Thr Ala Gln Glu Val Gly Thr Thr
            100                 105                 110

Asp Glu Asp Glu Thr Phe Ala Gly Gly Glu Pro Leu Asp His His Leu
        115                 120                 125

Asp Asp Ala Leu Asn Glu Thr Pro Asp Asp Ala Glu Thr Glu Ser Asp
    130                 135                 140

Ser Gly His Val Met Thr Ser Phe Ala Ser Arg Asp Gln Leu Pro Glu
145                 150                 155                 160

Trp Thr Leu His Thr Tyr Thr Leu Thr Ala Thr Asp Gly Ala Lys Thr
                165                 170                 175

Asp Thr Glu Tyr Ala Arg Arg Thr Leu Ala Tyr Thr Val Arg Gln Glu
            180                 185                 190

Leu Tyr Thr Asp His Asp Ala Ala Pro Val Ala Thr Asp Gly Leu Met
        195                 200                 205

Leu Leu Thr Pro Glu Pro Leu Gly Glu Thr Pro Leu Asp Leu Asp Cys
    210                 215                 220

Gly Val Arg Val Glu Ala Asp Glu Thr Arg Thr Leu Asp Tyr Thr Thr
225                 230                 235                 240

Ala Lys Asp Arg Leu Leu Ala Arg Glu Leu Val Glu Glu Gly Leu Lys
                245                 250                 255

Arg Ser Leu Trp Asp Asp Tyr Leu Val Arg Gly Ile Asp Glu Val Leu
            260                 265                 270

Ser Lys Glu Pro Val Leu Thr Cys Asp Glu Phe Asp Leu His Glu Arg
        275                 280                 285

Tyr Asp Leu Ser Val Glu Val Gly His Ser Gly Arg Ala Tyr Leu His
```

```
    290                 295                 300

Ile Asn Phe Arg His Arg Phe Val Pro Lys Leu Thr Leu Ala Asp Ile
305                 310                 315                 320

Asp Asp Asp Asn Ile Tyr Pro Gly Leu Arg Val Lys Thr Thr Tyr Arg
                325                 330                 335

Pro Arg Arg Gly His Ile Val Trp Gly Leu Arg Asp Glu Cys Ala Thr
            340                 345                 350

Asp Ser Leu Asn Thr Leu Gly Asn Gln Ser Val Val Ala Tyr His Arg
        355                 360                 365

Asn Asn Gln Thr Pro Ile Asn Thr Asp Leu Leu Asp Ala Ile Glu Ala
    370                 375                 380

Ala Asp Arg Arg Val Val Glu Thr Arg Arg Gln Gly His Gly Asp Asp
385                 390                 395                 400

Ala Val Ser Phe Pro Gln Glu Leu Leu Ala Val Glu Pro Asn Thr His
                405                 410                 415

Gln Ile Lys Gln Phe Ala Ser Asp Gly Phe His Gln Gln Ala Arg Ser
            420                 425                 430

Lys Thr Arg Leu Ser Ala Ser Arg Cys Ser Glu Lys Ala Gln Ala Phe
        435                 440                 445

Ala Glu Arg Leu Asp Pro Val Arg Leu Asn Gly Ser Thr Val Glu Phe
    450                 455                 460

Ser Ser Glu Phe Phe Thr Gly Asn Asn Glu Gln Gln Leu Arg Leu Leu
465                 470                 475                 480

Tyr Glu Asn Gly Glu Ser Val Leu Thr Phe Arg Asp Gly Ala Arg Gly
                485                 490                 495

Ala His Pro Asp Glu Thr Phe Ser Lys Gly Ile Val Asn Pro Pro Glu
            500                 505                 510

Ser Phe Glu Val Ala Val Val Leu Pro Glu Gln Gln Ala Asp Thr Cys
        515                 520                 525

Lys Ala Gln Trp Asp Thr Met Ala Asp Leu Leu Asn Gln Ala Gly Ala
    530                 535                 540

Pro Pro Thr Arg Ser Glu Thr Val Gln Tyr Asp Ala Phe Ser Ser Pro
545                 550                 555                 560

Glu Ser Ile Ser Leu Asn Val Ala Gly Ala Ile Asp Pro Ser Glu Val
                565                 570                 575

Asp Ala Ala Phe Val Val Leu Pro Pro Asp Gln Glu Gly Phe Ala Asp
            580                 585                 590

Leu Ala Ser Pro Thr Glu Thr Tyr Asp Glu Leu Lys Lys Ala Leu Ala
        595                 600                 605

Asn Met Gly Ile Tyr Ser Gln Met Ala Tyr Phe Asp Arg Phe Arg Asp
    610                 615                 620

Ala Lys Ile Phe Tyr Thr Arg Asn Val Ala Leu Gly Leu Leu Ala Ala
625                 630                 635                 640

Ala Gly Gly Val Ala Phe Thr Thr Glu His Ala Met Pro Gly Asp Ala
                645                 650                 655

Asp Met Phe Ile Gly Ile Asp Val Ser Arg Ser Tyr Pro Glu Asp Gly
            660                 665                 670

Ala Ser Gly Gln Ile Asn Ile Ala Ala Thr Ala Thr Ala Val Tyr Lys
        675                 680                 685

Asp Gly Thr Ile Leu Gly His Ser Ser Thr Arg Pro Gln Leu Gly Glu
    690                 695                 700

Lys Leu Gln Ser Thr Asp Val Arg Asp Ile Met Lys Asn Ala Ile Leu
705                 710                 715                 720
```

Gly Tyr Gln Gln Val Thr Gly Glu Ser Pro Thr His Ile Val Ile His
725 730 735

Arg Asp Gly Phe Met Asn Glu Asp Leu Asp Pro Ala Thr Glu Phe Leu
740 745 750

Asn Glu Gln Gly Val Glu Tyr Asp Ile Val Glu Ile Arg Lys Gln Pro
755 760 765

Gln Thr Arg Leu Leu Ala Val Ser Asp Val Gln Tyr Asp Thr Pro Val
770 775 780

Lys Ser Ile Ala Ala Ile Asn Gln Asn Glu Pro Arg Ala Thr Val Ala
785 790 795 800

Thr Phe Gly Ala Pro Glu Tyr Leu Ala Thr Arg Asp Gly Gly Gly Leu
805 810 815

Pro Arg Pro Ile Gln Ile Glu Arg Val Ala Gly Glu Thr Asp Ile Glu
820 825 830

Thr Leu Thr Arg Gln Val Tyr Leu Leu Ser Gln Ser His Ile Gln Val
835 840 845

His Asn Ser Thr Ala Arg Leu Pro Ile Thr Thr Ala Tyr Ala Asp Gln
850 855 860

Ala Ser Thr His Ala Thr Lys Gly Tyr Leu Val Gln Thr Gly Ala Phe
865 870 875 880

Glu Ser Asn Val Gly Phe Leu
885

<210> SEQ ID NO 719
<211> LENGTH: 1544
<212> TYPE: PRT
<213> ORGANISM: Artificial Sequence
<220> FEATURE:
<223> OTHER INFORMATION: Synthetic Polypeptide

<400> SEQUENCE: 719

Met Leu Ile Gly Tyr Val Arg Val Ser Thr Asn Asp Gln Asn Thr Asp
1 5 10 15

Leu Gln Arg Asn Ala Leu Val Cys Ala Gly Cys Glu Gln Ile Phe Glu
20 25 30

Asp Lys Leu Ser Gly Thr Arg Thr Asp Arg Pro Gly Leu Lys Arg Ala
35 40 45

Leu Lys Arg Leu Gln Lys Gly Asp Thr Leu Val Val Trp Lys Leu Asp
50 55 60

Arg Leu Gly Arg Ser Met Lys His Leu Ile Ser Leu Val Gly Glu Leu
65 70 75 80

Arg Glu Arg Gly Ile Asn Phe Arg Ser Leu Thr Asp Ser Ile Asp Thr
85 90 95

Ser Ser Pro Met Gly Arg Phe Phe Phe Tyr Val Met Gly Ala Leu Ala
100 105 110

Glu Met Glu Arg Glu Leu Ile Ile Glu Arg Thr Met Ala Gly Leu Ala
115 120 125

Ala Ala Arg Asn Lys Gly Arg Arg Phe Gly Arg Pro Pro Lys Gly Gly
130 135 140

Ser Gly Gly Ser Gly Gly Ser Gly Gly Ser Gly Gly Ser Gly Gly Ser
145 150 155 160

Gly Gly Ser Gly Gly Ser Asp Lys Lys Tyr Ser Ile Gly Leu Ala Ile
165 170 175

Gly Thr Asn Ser Val Gly Trp Ala Val Ile Thr Asp Glu Tyr Lys Val
180 185 190

-continued

```
Pro Ser Lys Lys Phe Lys Val Leu Gly Asn Thr Asp Arg His Ser Ile
        195                 200                 205

Lys Lys Asn Leu Ile Gly Ala Leu Leu Phe Asp Ser Gly Glu Thr Ala
    210                 215                 220

Glu Ala Thr Arg Leu Lys Arg Thr Ala Arg Arg Arg Tyr Thr Arg Arg
225                 230                 235                 240

Lys Asn Arg Ile Cys Tyr Leu Gln Glu Ile Phe Ser Asn Glu Met Ala
                245                 250                 255

Lys Val Asp Asp Ser Phe Phe His Arg Leu Glu Glu Ser Phe Leu Val
            260                 265                 270

Glu Glu Asp Lys Lys His Glu Arg His Pro Ile Phe Gly Asn Ile Val
        275                 280                 285

Asp Glu Val Ala Tyr His Glu Lys Tyr Pro Thr Ile Tyr His Leu Arg
    290                 295                 300

Lys Lys Leu Val Asp Ser Thr Asp Lys Ala Asp Leu Arg Leu Ile Tyr
305                 310                 315                 320

Leu Ala Leu Ala His Met Ile Lys Phe Arg Gly His Phe Leu Ile Glu
                325                 330                 335

Gly Asp Leu Asn Pro Asp Asn Ser Asp Val Asp Lys Leu Phe Ile Gln
            340                 345                 350

Leu Val Gln Thr Tyr Asn Gln Leu Phe Glu Glu Asn Pro Ile Asn Ala
        355                 360                 365

Ser Gly Val Asp Ala Lys Ala Ile Leu Ser Ala Arg Leu Ser Lys Ser
    370                 375                 380

Arg Arg Leu Glu Asn Leu Ile Ala Gln Leu Pro Gly Glu Lys Lys Asn
385                 390                 395                 400

Gly Leu Phe Gly Asn Leu Ile Ala Leu Ser Leu Gly Leu Thr Pro Asn
                405                 410                 415

Phe Lys Ser Asn Phe Asp Leu Ala Glu Asp Ala Lys Leu Gln Leu Ser
            420                 425                 430

Lys Asp Thr Tyr Asp Asp Asp Leu Asp Asn Leu Leu Ala Gln Ile Gly
        435                 440                 445

Asp Gln Tyr Ala Asp Leu Phe Leu Ala Ala Lys Asn Leu Ser Asp Ala
    450                 455                 460

Ile Leu Leu Ser Asp Ile Leu Arg Val Asn Thr Glu Ile Thr Lys Ala
465                 470                 475                 480

Pro Leu Ser Ala Ser Met Ile Lys Arg Tyr Asp Glu His His Gln Asp
                485                 490                 495

Leu Thr Leu Leu Lys Ala Leu Val Arg Gln Gln Leu Pro Glu Lys Tyr
            500                 505                 510

Lys Glu Ile Phe Phe Asp Gln Ser Lys Asn Gly Tyr Ala Gly Tyr Ile
        515                 520                 525

Asp Gly Gly Ala Ser Gln Glu Glu Phe Tyr Lys Phe Ile Lys Pro Ile
    530                 535                 540

Leu Glu Lys Met Asp Gly Thr Glu Glu Leu Leu Val Lys Leu Asn Arg
545                 550                 555                 560

Glu Asp Leu Leu Arg Lys Gln Arg Thr Phe Asp Asn Gly Ser Ile Pro
                565                 570                 575

His Gln Ile His Leu Gly Glu Leu His Ala Ile Leu Arg Arg Gln Glu
            580                 585                 590

Asp Phe Tyr Pro Phe Leu Lys Asp Asn Arg Glu Lys Ile Glu Lys Ile
        595                 600                 605
```

```
Leu Thr Phe Arg Ile Pro Tyr Tyr Val Gly Pro Leu Ala Arg Gly Asn
    610                 615                 620

Ser Arg Phe Ala Trp Met Thr Arg Lys Ser Glu Glu Thr Ile Thr Pro
625                 630                 635                 640

Trp Asn Phe Glu Glu Val Val Asp Lys Gly Ala Ser Ala Gln Ser Phe
                645                 650                 655

Ile Glu Arg Met Thr Asn Phe Asp Lys Asn Leu Pro Asn Glu Lys Val
            660                 665                 670

Leu Pro Lys His Ser Leu Leu Tyr Glu Tyr Phe Thr Val Tyr Asn Glu
        675                 680                 685

Leu Thr Lys Val Lys Tyr Val Thr Glu Gly Met Arg Lys Pro Ala Phe
    690                 695                 700

Leu Ser Gly Glu Gln Lys Lys Ala Ile Val Asp Leu Leu Phe Lys Thr
705                 710                 715                 720

Asn Arg Lys Val Thr Val Lys Gln Leu Lys Glu Asp Tyr Phe Lys Lys
                725                 730                 735

Ile Glu Cys Phe Asp Ser Val Glu Ile Ser Gly Val Glu Asp Arg Phe
            740                 745                 750

Asn Ala Ser Leu Gly Thr Tyr His Asp Leu Leu Lys Ile Ile Lys Asp
        755                 760                 765

Lys Asp Phe Leu Asp Asn Glu Glu Asn Glu Asp Ile Leu Glu Asp Ile
    770                 775                 780

Val Leu Thr Leu Thr Leu Phe Glu Asp Arg Glu Met Ile Glu Glu Arg
785                 790                 795                 800

Leu Lys Thr Tyr Ala His Leu Phe Asp Asp Lys Val Met Lys Gln Leu
                805                 810                 815

Lys Arg Arg Arg Tyr Thr Gly Trp Gly Arg Leu Ser Arg Lys Leu Ile
            820                 825                 830

Asn Gly Ile Arg Asp Lys Gln Ser Gly Lys Thr Ile Leu Asp Phe Leu
        835                 840                 845

Lys Ser Asp Gly Phe Ala Asn Arg Asn Phe Met Gln Leu Ile His Asp
    850                 855                 860

Asp Ser Leu Thr Phe Lys Glu Asp Ile Gln Lys Ala Gln Val Ser Gly
865                 870                 875                 880

Gln Gly Asp Ser Leu His Glu His Ile Ala Asn Leu Ala Gly Ser Pro
                885                 890                 895

Ala Ile Lys Lys Gly Ile Leu Gln Thr Val Lys Val Val Asp Glu Leu
            900                 905                 910

Val Lys Val Met Gly Arg His Lys Pro Glu Asn Ile Val Ile Glu Met
        915                 920                 925

Ala Arg Glu Asn Gln Thr Thr Gln Lys Gly Gln Lys Asn Ser Arg Glu
    930                 935                 940

Arg Met Lys Arg Ile Glu Glu Gly Ile Lys Glu Leu Gly Ser Gln Ile
945                 950                 955                 960

Leu Lys Glu His Pro Val Glu Asn Thr Gln Leu Gln Asn Glu Lys Leu
                965                 970                 975

Tyr Leu Tyr Tyr Leu Gln Asn Gly Arg Asp Met Tyr Val Asp Gln Glu
            980                 985                 990

Leu Asp Ile Asn Arg Leu Ser Asp  Tyr Asp Val Asp Ala  Ile Val Pro
        995                 1000                 1005

Gln Ser  Phe Leu Lys Asp Asp  Ser Ile Asp Asn Lys  Val Leu Thr
    1010                 1015                 1020

Arg Ser  Asp Lys Asn Arg Gly  Lys Ser Asp Asn Val  Pro Ser Glu
```

```
    1025                1030                1035

Glu Val  Val Lys Lys Met Lys  Asn Tyr Trp Arg Gln  Leu Leu Asn
    1040                1045                1050

Ala Lys  Leu Ile Thr Gln Arg  Lys Phe Asp Asn Leu  Thr Lys Ala
    1055                1060                1065

Glu Arg  Gly Gly Leu Ser Glu  Leu Asp Lys Ala Gly  Phe Ile Lys
    1070                1075                1080

Arg Gln  Leu Val Glu Thr Arg  Gln Ile Thr Lys His  Val Ala Gln
    1085                1090                1095

Ile Leu  Asp Ser Arg Met Asn  Thr Lys Tyr Asp Glu  Asn Asp Lys
    1100                1105                1110

Leu Ile  Arg Glu Val Lys Val  Ile Thr Leu Lys Ser  Lys Leu Val
    1115                1120                1125

Ser Asp  Phe Arg Lys Asp Phe  Gln Phe Tyr Lys Val  Arg Glu Ile
    1130                1135                1140

Asn Asn  Tyr His His Ala His  Asp Ala Tyr Leu Asn  Ala Val Val
    1145                1150                1155

Gly Thr  Ala Leu Ile Lys Lys  Tyr Pro Lys Leu Glu  Ser Glu Phe
    1160                1165                1170

Val Tyr  Gly Asp Tyr Lys Val  Tyr Asp Val Arg Lys  Met Ile Ala
    1175                1180                1185

Lys Ser  Glu Gln Glu Ile Gly  Lys Ala Thr Ala Lys  Tyr Phe Phe
    1190                1195                1200

Tyr Ser  Asn Ile Met Asn Phe  Phe Lys Thr Glu Ile  Thr Leu Ala
    1205                1210                1215

Asn Gly  Glu Ile Arg Lys Arg  Pro Leu Ile Glu Thr  Asn Gly Glu
    1220                1225                1230

Thr Gly  Glu Ile Val Trp Asp  Lys Gly Arg Asp Phe  Ala Thr Val
    1235                1240                1245

Arg Lys  Val Leu Ser Met Pro  Gln Val Asn Ile Val  Lys Lys Thr
    1250                1255                1260

Glu Val  Gln Thr Gly Gly Phe  Ser Lys Glu Ser Ile  Leu Pro Lys
    1265                1270                1275

Arg Asn  Ser Asp Lys Leu Ile  Ala Arg Lys Lys Asp  Trp Asp Pro
    1280                1285                1290

Lys Lys  Tyr Gly Gly Phe Asp  Ser Pro Thr Val Ala  Tyr Ser Val
    1295                1300                1305

Leu Val  Val Ala Lys Val Glu  Lys Gly Lys Ser Lys  Lys Leu Lys
    1310                1315                1320

Ser Val  Lys Glu Leu Leu Gly  Ile Thr Ile Met Glu  Arg Ser Ser
    1325                1330                1335

Phe Glu  Lys Asn Pro Ile Asp  Phe Leu Glu Ala Lys  Gly Tyr Lys
    1340                1345                1350

Glu Val  Lys Lys Asp Leu Ile  Ile Lys Leu Pro Lys  Tyr Ser Leu
    1355                1360                1365

Phe Glu  Leu Glu Asn Gly Arg  Lys Arg Met Leu Ala  Ser Ala Gly
    1370                1375                1380

Glu Leu  Gln Lys Gly Asn Glu  Leu Ala Leu Pro Ser  Lys Tyr Val
    1385                1390                1395

Asn Phe  Leu Tyr Leu Ala Ser  His Tyr Glu Lys Leu  Lys Gly Ser
    1400                1405                1410

Pro Glu  Asp Asn Glu Gln Lys  Gln Leu Phe Val Glu  Gln His Lys
    1415                1420                1425
```

His Tyr Leu Asp Glu Ile Ile Glu Gln Ile Ser Glu Phe Ser Lys
1430 1435 1440

Arg Val Ile Leu Ala Asp Ala Asn Leu Asp Lys Val Leu Ser Ala
1445 1450 1455

Tyr Asn Lys His Arg Asp Lys Pro Ile Arg Glu Gln Ala Glu Asn
1460 1465 1470

Ile Ile His Leu Phe Thr Leu Thr Asn Leu Gly Ala Pro Ala Ala
1475 1480 1485

Phe Lys Tyr Phe Asp Thr Thr Ile Asp Arg Lys Arg Tyr Thr Ser
1490 1495 1500

Thr Lys Glu Val Leu Asp Ala Thr Leu Ile His Gln Ser Ile Thr
1505 1510 1515

Gly Leu Tyr Glu Thr Arg Ile Asp Leu Ser Gln Leu Gly Gly Asp
1520 1525 1530

Gly Gly Ser Asp Tyr Lys Asp Asp Asp Asp Lys
1535 1540

<210> SEQ ID NO 720
<211> LENGTH: 1367
<212> TYPE: PRT
<213> ORGANISM: Artificial Sequence
<220> FEATURE:
<223> OTHER INFORMATION: Synthetic polypeptide

<400> SEQUENCE: 720

Asp Lys Lys Tyr Ser Ile Gly Leu Ala Ile Gly Thr Asn Ser Val Gly
1 5 10 15

Trp Ala Val Ile Thr Asp Glu Tyr Lys Val Pro Ser Lys Lys Phe Lys
20 25 30

Val Leu Gly Asn Thr Asp Arg His Ser Ile Lys Lys Asn Leu Ile Gly
35 40 45

Ala Leu Leu Phe Asp Ser Gly Glu Thr Ala Glu Ala Thr Arg Leu Lys
50 55 60

Arg Thr Ala Arg Arg Arg Tyr Thr Arg Arg Lys Asn Arg Ile Cys Tyr
65 70 75 80

Leu Gln Glu Ile Phe Ser Asn Glu Met Ala Lys Val Asp Asp Ser Phe
85 90 95

Phe His Arg Leu Glu Glu Ser Phe Leu Val Glu Glu Asp Lys Lys His
100 105 110

Glu Arg His Pro Ile Phe Gly Asn Ile Val Asp Glu Val Ala Tyr His
115 120 125

Glu Lys Tyr Pro Thr Ile Tyr His Leu Arg Lys Lys Leu Val Asp Ser
130 135 140

Thr Asp Lys Ala Asp Leu Arg Leu Ile Tyr Leu Ala Leu Ala His Met
145 150 155 160

Ile Lys Phe Arg Gly His Phe Leu Ile Glu Gly Asp Leu Asn Pro Asp
165 170 175

Asn Ser Asp Val Asp Lys Leu Phe Ile Gln Leu Val Gln Thr Tyr Asn
180 185 190

Gln Leu Phe Glu Glu Asn Pro Ile Asn Ala Ser Gly Val Asp Ala Lys
195 200 205

Ala Ile Leu Ser Ala Arg Leu Ser Lys Ser Arg Arg Leu Glu Asn Leu
210 215 220

Ile Ala Gln Leu Pro Gly Glu Lys Lys Asn Gly Leu Phe Gly Asn Leu
225 230 235 240

```
Ile Ala Leu Ser Leu Gly Leu Thr Pro Asn Phe Lys Ser Asn Phe Asp
                245                 250                 255

Leu Ala Glu Asp Ala Lys Leu Gln Leu Ser Lys Asp Thr Tyr Asp Asp
            260                 265                 270

Asp Leu Asp Asn Leu Leu Ala Gln Ile Gly Asp Gln Tyr Ala Asp Leu
        275                 280                 285

Phe Leu Ala Ala Lys Asn Leu Ser Asp Ala Ile Leu Leu Ser Asp Ile
    290                 295                 300

Leu Arg Val Asn Thr Glu Ile Thr Lys Ala Pro Leu Ser Ala Ser Met
305                 310                 315                 320

Ile Lys Arg Tyr Asp Glu His His Gln Asp Leu Thr Leu Leu Lys Ala
                325                 330                 335

Leu Val Arg Gln Gln Leu Pro Glu Lys Tyr Lys Glu Ile Phe Phe Asp
            340                 345                 350

Gln Ser Lys Asn Gly Tyr Ala Gly Tyr Ile Asp Gly Gly Ala Ser Gln
        355                 360                 365

Glu Glu Phe Tyr Lys Phe Ile Lys Pro Ile Leu Glu Lys Met Asp Gly
    370                 375                 380

Thr Glu Glu Leu Leu Val Lys Leu Asn Arg Glu Asp Leu Leu Arg Lys
385                 390                 395                 400

Gln Arg Thr Phe Asp Asn Gly Ser Ile Pro His Gln Ile His Leu Gly
                405                 410                 415

Glu Leu His Ala Ile Leu Arg Arg Gln Glu Asp Phe Tyr Pro Phe Leu
            420                 425                 430

Lys Asp Asn Arg Glu Lys Ile Glu Lys Ile Leu Thr Phe Arg Ile Pro
        435                 440                 445

Tyr Tyr Val Gly Pro Leu Ala Arg Gly Asn Ser Arg Phe Ala Trp Met
    450                 455                 460

Thr Arg Lys Ser Glu Glu Thr Ile Thr Pro Trp Asn Phe Glu Glu Val
465                 470                 475                 480

Val Asp Lys Gly Ala Ser Ala Gln Ser Phe Ile Glu Arg Met Thr Ala
                485                 490                 495

Phe Asp Lys Asn Leu Pro Asn Glu Lys Val Leu Pro Lys His Ser Leu
            500                 505                 510

Leu Tyr Glu Tyr Phe Thr Val Tyr Asn Glu Leu Thr Lys Val Lys Tyr
        515                 520                 525

Val Thr Glu Gly Met Arg Lys Pro Ala Phe Leu Ser Gly Glu Gln Lys
    530                 535                 540

Lys Ala Ile Val Asp Leu Leu Phe Lys Thr Asn Arg Lys Val Thr Val
545                 550                 555                 560

Lys Gln Leu Lys Glu Asp Tyr Phe Lys Lys Ile Glu Cys Phe Asp Ser
                565                 570                 575

Val Glu Ile Ser Gly Val Glu Asp Arg Phe Asn Ala Ser Leu Gly Thr
            580                 585                 590

Tyr His Asp Leu Leu Lys Ile Ile Lys Asp Lys Asp Phe Leu Asp Asn
        595                 600                 605

Glu Glu Asn Glu Asp Ile Leu Glu Asp Ile Val Leu Thr Leu Thr Leu
    610                 615                 620

Phe Glu Asp Arg Glu Met Ile Glu Glu Arg Leu Lys Thr Tyr Ala His
625                 630                 635                 640

Leu Phe Asp Asp Lys Val Met Lys Gln Leu Lys Arg Arg Arg Tyr Thr
                645                 650                 655
```

-continued

```
Gly Trp Gly Ala Leu Ser Arg Lys Leu Ile Asn Gly Ile Arg Asp Lys
            660                 665                 670

Gln Ser Gly Lys Thr Ile Leu Asp Phe Leu Lys Ser Asp Gly Phe Ala
        675                 680                 685

Asn Arg Asn Phe Met Ala Leu Ile His Asp Asp Ser Leu Thr Phe Lys
    690                 695                 700

Glu Asp Ile Gln Lys Ala Gln Val Ser Gly Gln Gly Asp Ser Leu His
705                 710                 715                 720

Glu His Ile Ala Asn Leu Ala Gly Ser Pro Ala Ile Lys Lys Gly Ile
                725                 730                 735

Leu Gln Thr Val Lys Val Val Asp Glu Leu Val Lys Val Met Gly Arg
            740                 745                 750

His Lys Pro Glu Asn Ile Val Ile Glu Met Ala Arg Glu Asn Gln Thr
        755                 760                 765

Thr Gln Lys Gly Gln Lys Asn Ser Arg Glu Arg Met Lys Arg Ile Glu
    770                 775                 780

Glu Gly Ile Lys Glu Leu Gly Ser Gln Ile Leu Lys Glu His Pro Val
785                 790                 795                 800

Glu Asn Thr Gln Leu Gln Asn Glu Lys Leu Tyr Leu Tyr Tyr Leu Gln
                805                 810                 815

Asn Gly Arg Asp Met Tyr Val Asp Gln Glu Leu Asp Ile Asn Arg Leu
            820                 825                 830

Ser Asp Tyr Asp Val Asp His Ile Val Pro Gln Ser Phe Leu Lys Asp
        835                 840                 845

Asp Ser Ile Asp Asn Lys Val Leu Thr Arg Ser Asp Lys Asn Arg Gly
    850                 855                 860

Lys Ser Asp Asn Val Pro Ser Glu Glu Val Val Lys Lys Met Lys Asn
865                 870                 875                 880

Tyr Trp Arg Gln Leu Leu Asn Ala Lys Leu Ile Thr Gln Arg Lys Phe
                885                 890                 895

Asp Asn Leu Thr Lys Ala Glu Arg Gly Gly Leu Ser Glu Leu Asp Lys
            900                 905                 910

Ala Gly Phe Ile Lys Arg Gln Leu Val Glu Thr Arg Ala Ile Thr Lys
        915                 920                 925

His Val Ala Gln Ile Leu Asp Ser Arg Met Asn Thr Lys Tyr Asp Glu
    930                 935                 940

Asn Asp Lys Leu Ile Arg Glu Val Lys Val Ile Thr Leu Lys Ser Lys
945                 950                 955                 960

Leu Val Ser Asp Phe Arg Lys Asp Phe Gln Phe Tyr Lys Val Arg Glu
                965                 970                 975

Ile Asn Asn Tyr His His Ala His Asp Ala Tyr Leu Asn Ala Val Val
            980                 985                 990

Gly Thr Ala Leu Ile Lys Lys Tyr  Pro Lys Leu Glu Ser  Glu Phe Val
        995                 1000                 1005

Tyr Gly  Asp Tyr Lys Val Tyr  Asp Val Arg Lys Met  Ile Ala Lys
    1010                 1015                 1020

Ser Glu  Gln Glu Ile Gly Lys  Ala Thr Ala Lys Tyr  Phe Phe Tyr
    1025                 1030                 1035

Ser Asn  Ile Met Asn Phe Phe  Lys Thr Glu Ile Thr  Leu Ala Asn
    1040                 1045                 1050

Gly Glu  Ile Arg Lys Arg Pro  Leu Ile Glu Thr Asn  Gly Glu Thr
    1055                 1060                 1065

Gly Glu  Ile Val Trp Asp Lys  Gly Arg Asp Phe Ala  Thr Val Arg
```

1070 1075 1080

Lys Val Leu Ser Met Pro Gln Val Asn Ile Val Lys Lys Thr Glu
1085 1090 1095

Val Gln Thr Gly Gly Phe Ser Lys Glu Ser Ile Leu Pro Lys Arg
1100 1105 1110

Asn Ser Asp Lys Leu Ile Ala Arg Lys Lys Asp Trp Asp Pro Lys
1115 1120 1125

Lys Tyr Gly Gly Phe Asp Ser Pro Thr Val Ala Tyr Ser Val Leu
1130 1135 1140

Val Val Ala Lys Val Glu Lys Gly Lys Ser Lys Lys Leu Lys Ser
1145 1150 1155

Val Lys Glu Leu Leu Gly Ile Thr Ile Met Glu Arg Ser Ser Phe
1160 1165 1170

Glu Lys Asn Pro Ile Asp Phe Leu Glu Ala Lys Gly Tyr Lys Glu
1175 1180 1185

Val Lys Lys Asp Leu Ile Ile Lys Leu Pro Lys Tyr Ser Leu Phe
1190 1195 1200

Glu Leu Glu Asn Gly Arg Lys Arg Met Leu Ala Ser Ala Gly Glu
1205 1210 1215

Leu Gln Lys Gly Asn Glu Leu Ala Leu Pro Ser Lys Tyr Val Asn
1220 1225 1230

Phe Leu Tyr Leu Ala Ser His Tyr Glu Lys Leu Lys Gly Ser Pro
1235 1240 1245

Glu Asp Asn Glu Gln Lys Gln Leu Phe Val Glu Gln His Lys His
1250 1255 1260

Tyr Leu Asp Glu Ile Ile Glu Gln Ile Ser Glu Phe Ser Lys Arg
1265 1270 1275

Val Ile Leu Ala Asp Ala Asn Leu Asp Lys Val Leu Ser Ala Tyr
1280 1285 1290

Asn Lys His Arg Asp Lys Pro Ile Arg Glu Gln Ala Glu Asn Ile
1295 1300 1305

Ile His Leu Phe Thr Leu Thr Asn Leu Gly Ala Pro Ala Ala Phe
1310 1315 1320

Lys Tyr Phe Asp Thr Thr Ile Asp Arg Lys Arg Tyr Thr Ser Thr
1325 1330 1335

Lys Glu Val Leu Asp Ala Thr Leu Ile His Gln Ser Ile Thr Gly
1340 1345 1350

Leu Tyr Glu Thr Arg Ile Asp Leu Ser Gln Leu Gly Gly Asp
1355 1360 1365

<210> SEQ ID NO 721
<211> LENGTH: 1612
<212> TYPE: PRT
<213> ORGANISM: Artificial Sequence
<220> FEATURE:
<223> OTHER INFORMATION: Synthetic polypeptide

<400> SEQUENCE: 721

Met Ser Ser Glu Thr Gly Pro Val Ala Val Asp Pro Thr Leu Arg Arg
1 5 10 15

Arg Ile Glu Pro His Glu Phe Glu Val Phe Phe Asp Pro Arg Glu Leu
20 25 30

Arg Lys Glu Thr Cys Leu Leu Tyr Glu Ile Asn Trp Gly Gly Arg His
35 40 45

Ser Ile Trp Arg His Thr Ser Gln Asn Thr Asn Lys His Val Glu Val

-continued

```
    50                  55                  60

Asn Phe Ile Glu Lys Phe Thr Thr Glu Arg Tyr Phe Cys Pro Asn Thr
65                  70                  75                  80

Arg Cys Ser Ile Thr Trp Phe Leu Ser Trp Ser Pro Cys Gly Glu Cys
                85                  90                  95

Ser Arg Ala Ile Thr Glu Phe Leu Ser Arg Tyr Pro His Val Thr Leu
            100                 105                 110

Phe Ile Tyr Ile Ala Arg Leu Tyr His His Ala Asp Pro Arg Asn Arg
        115                 120                 125

Gln Gly Leu Arg Asp Leu Ile Ser Ser Gly Val Thr Ile Gln Ile Met
    130                 135                 140

Thr Glu Gln Glu Ser Gly Tyr Cys Trp Arg Asn Phe Val Asn Tyr Ser
145                 150                 155                 160

Pro Ser Asn Glu Ala His Trp Pro Arg Tyr Pro His Leu Trp Val Arg
                165                 170                 175

Leu Tyr Val Leu Glu Leu Tyr Cys Ile Ile Leu Gly Leu Pro Pro Cys
            180                 185                 190

Leu Asn Ile Leu Arg Arg Lys Gln Pro Gln Leu Thr Phe Phe Thr Ile
        195                 200                 205

Ala Leu Gln Ser Cys His Tyr Gln Arg Leu Pro Pro His Ile Leu Trp
    210                 215                 220

Ala Thr Gly Leu Lys Ser Gly Ser Glu Thr Pro Gly Thr Ser Glu Ser
225                 230                 235                 240

Ala Thr Pro Glu Ser Asp Lys Lys Tyr Ser Ile Gly Leu Ala Ile Gly
                245                 250                 255

Thr Asn Ser Val Gly Trp Ala Val Ile Thr Asp Glu Tyr Lys Val Pro
            260                 265                 270

Ser Lys Lys Phe Lys Val Leu Gly Asn Thr Asp Arg His Ser Ile Lys
        275                 280                 285

Lys Asn Leu Ile Gly Ala Leu Leu Phe Asp Ser Gly Glu Thr Ala Glu
    290                 295                 300

Ala Thr Arg Leu Lys Arg Thr Ala Arg Arg Arg Tyr Thr Arg Arg Lys
305                 310                 315                 320

Asn Arg Ile Cys Tyr Leu Gln Glu Ile Phe Ser Asn Glu Met Ala Lys
                325                 330                 335

Val Asp Asp Ser Phe Phe His Arg Leu Glu Glu Ser Phe Leu Val Glu
            340                 345                 350

Glu Asp Lys Lys His Glu Arg His Pro Ile Phe Gly Asn Ile Val Asp
        355                 360                 365

Glu Val Ala Tyr His Glu Lys Tyr Pro Thr Ile Tyr His Leu Arg Lys
    370                 375                 380

Lys Leu Val Asp Ser Thr Asp Lys Ala Asp Leu Arg Leu Ile Tyr Leu
385                 390                 395                 400

Ala Leu Ala His Met Ile Lys Phe Arg Gly His Phe Leu Ile Glu Gly
                405                 410                 415

Asp Leu Asn Pro Asp Asn Ser Asp Val Asp Lys Leu Phe Ile Gln Leu
            420                 425                 430

Val Gln Thr Tyr Asn Gln Leu Phe Glu Glu Asn Pro Ile Asn Ala Ser
        435                 440                 445

Gly Val Asp Ala Lys Ala Ile Leu Ser Ala Arg Leu Ser Lys Ser Arg
    450                 455                 460

Arg Leu Glu Asn Leu Ile Ala Gln Leu Pro Gly Glu Lys Lys Asn Gly
465                 470                 475                 480
```

-continued

```
Leu Phe Gly Asn Leu Ile Ala Leu Ser Leu Gly Leu Thr Pro Asn Phe
                485                 490                 495

Lys Ser Asn Phe Asp Leu Ala Glu Asp Ala Lys Leu Gln Leu Ser Lys
            500                 505                 510

Asp Thr Tyr Asp Asp Asp Leu Asp Asn Leu Leu Ala Gln Ile Gly Asp
        515                 520                 525

Gln Tyr Ala Asp Leu Phe Leu Ala Ala Lys Asn Leu Ser Asp Ala Ile
    530                 535                 540

Leu Leu Ser Asp Ile Leu Arg Val Asn Thr Glu Ile Thr Lys Ala Pro
545                 550                 555                 560

Leu Ser Ala Ser Met Ile Lys Arg Tyr Asp Glu His His Gln Asp Leu
                565                 570                 575

Thr Leu Leu Lys Ala Leu Val Arg Gln Gln Leu Pro Glu Lys Tyr Lys
            580                 585                 590

Glu Ile Phe Phe Asp Gln Ser Lys Asn Gly Tyr Ala Gly Tyr Ile Asp
        595                 600                 605

Gly Gly Ala Ser Gln Glu Glu Phe Tyr Lys Phe Ile Lys Pro Ile Leu
    610                 615                 620

Glu Lys Met Asp Gly Thr Glu Glu Leu Leu Val Lys Leu Asn Arg Glu
625                 630                 635                 640

Asp Leu Leu Arg Lys Gln Arg Thr Phe Asp Asn Gly Ser Ile Pro His
                645                 650                 655

Gln Ile His Leu Gly Glu Leu His Ala Ile Leu Arg Arg Gln Glu Asp
            660                 665                 670

Phe Tyr Pro Phe Leu Lys Asp Asn Arg Glu Lys Ile Glu Lys Ile Leu
        675                 680                 685

Thr Phe Arg Ile Pro Tyr Tyr Val Gly Pro Leu Ala Arg Gly Asn Ser
    690                 695                 700

Arg Phe Ala Trp Met Thr Arg Lys Ser Glu Glu Thr Ile Thr Pro Trp
705                 710                 715                 720

Asn Phe Glu Glu Val Val Asp Lys Gly Ala Ser Ala Gln Ser Phe Ile
                725                 730                 735

Glu Arg Met Thr Ala Phe Asp Lys Asn Leu Pro Asn Glu Lys Val Leu
            740                 745                 750

Pro Lys His Ser Leu Leu Tyr Glu Tyr Phe Thr Val Tyr Asn Glu Leu
        755                 760                 765

Thr Lys Val Lys Tyr Val Thr Glu Gly Met Arg Lys Pro Ala Phe Leu
    770                 775                 780

Ser Gly Glu Gln Lys Lys Ala Ile Val Asp Leu Leu Phe Lys Thr Asn
785                 790                 795                 800

Arg Lys Val Thr Val Lys Gln Leu Lys Glu Asp Tyr Phe Lys Lys Ile
                805                 810                 815

Glu Cys Phe Asp Ser Val Glu Ile Ser Gly Val Glu Asp Arg Phe Asn
            820                 825                 830

Ala Ser Leu Gly Thr Tyr His Asp Leu Leu Lys Ile Ile Lys Asp Lys
        835                 840                 845

Asp Phe Leu Asp Asn Glu Glu Asn Glu Asp Ile Leu Glu Asp Ile Val
    850                 855                 860

Leu Thr Leu Thr Leu Phe Glu Asp Arg Glu Met Ile Glu Glu Arg Leu
865                 870                 875                 880

Lys Thr Tyr Ala His Leu Phe Asp Asp Lys Val Met Lys Gln Leu Lys
                885                 890                 895
```

```
Arg Arg Arg Tyr Thr Gly Trp Gly Ala Leu Ser Arg Lys Leu Ile Asn
            900                 905                 910

Gly Ile Arg Asp Lys Gln Ser Gly Lys Thr Ile Leu Asp Phe Leu Lys
        915                 920                 925

Ser Asp Gly Phe Ala Asn Arg Asn Phe Met Ala Leu Ile His Asp Asp
    930                 935                 940

Ser Leu Thr Phe Lys Glu Asp Ile Gln Lys Ala Gln Val Ser Gly Gln
945                 950                 955                 960

Gly Asp Ser Leu His Glu His Ile Ala Asn Leu Ala Gly Ser Pro Ala
                965                 970                 975

Ile Lys Lys Gly Ile Leu Gln Thr Val Lys Val Val Asp Glu Leu Val
            980                 985                 990

Lys Val Met Gly Arg His Lys Pro  Glu Asn Ile Val Ile  Glu Met Ala
        995                 1000                1005

Arg Glu  Asn Gln Thr Thr Gln  Lys Gly Gln Lys Asn  Ser Arg Glu
    1010                1015                1020

Arg Met  Lys Arg Ile Glu Glu  Gly Ile Lys Glu Leu  Gly Ser Gln
    1025                1030                1035

Ile Leu  Lys Glu His Pro Val  Glu Asn Thr Gln Leu  Gln Asn Glu
    1040                1045                1050

Lys Leu  Tyr Leu Tyr Tyr Leu  Gln Asn Gly Arg Asp  Met Tyr Val
    1055                1060                1065

Asp Gln  Glu Leu Asp Ile Asn  Arg Leu Ser Asp Tyr  Asp Val Asp
    1070                1075                1080

His Ile  Val Pro Gln Ser Phe  Leu Lys Asp Asp Ser  Ile Asp Asn
    1085                1090                1095

Lys Val  Leu Thr Arg Ser Asp  Lys Asn Arg Gly Lys  Ser Asp Asn
    1100                1105                1110

Val Pro  Ser Glu Glu Val Val  Lys Lys Met Lys Asn  Tyr Trp Arg
    1115                1120                1125

Gln Leu  Leu Asn Ala Lys Leu  Ile Thr Gln Arg Lys  Phe Asp Asn
    1130                1135                1140

Leu Thr  Lys Ala Glu Arg Gly  Gly Leu Ser Glu Leu  Asp Lys Ala
    1145                1150                1155

Gly Phe  Ile Lys Arg Gln Leu  Val Glu Thr Arg Ala  Ile Thr Lys
    1160                1165                1170

His Val  Ala Gln Ile Leu Asp  Ser Arg Met Asn Thr  Lys Tyr Asp
    1175                1180                1185

Glu Asn  Asp Lys Leu Ile Arg  Glu Val Lys Val Ile  Thr Leu Lys
    1190                1195                1200

Ser Lys  Leu Val Ser Asp Phe  Arg Lys Asp Phe Gln  Phe Tyr Lys
    1205                1210                1215

Val Arg  Glu Ile Asn Asn Tyr  His His Ala His Asp  Ala Tyr Leu
    1220                1225                1230

Asn Ala  Val Val Gly Thr Ala  Leu Ile Lys Lys Tyr  Pro Lys Leu
    1235                1240                1245

Glu Ser  Glu Phe Val Tyr Gly  Asp Tyr Lys Val Tyr  Asp Val Arg
    1250                1255                1260

Lys Met  Ile Ala Lys Ser Glu  Gln Glu Ile Gly Lys  Ala Thr Ala
    1265                1270                1275

Lys Tyr  Phe Phe Tyr Ser Asn  Ile Met Asn Phe Phe  Lys Thr Glu
    1280                1285                1290

Ile Thr  Leu Ala Asn Gly Glu  Ile Arg Lys Arg Pro  Leu Ile Glu
```

-continued

```
    1295                1300                1305

Thr Asn  Gly Glu Thr Gly Glu  Ile Val Trp Asp Lys  Gly Arg Asp
    1310                1315                1320

Phe Ala  Thr Val Arg Lys Val  Leu Ser Met Pro Gln  Val Asn Ile
    1325                1330                1335

Val Lys  Lys Thr Glu Val Gln  Thr Gly Gly Phe Ser  Lys Glu Ser
    1340                1345                1350

Ile Leu  Pro Lys Arg Asn Ser  Asp Lys Leu Ile Ala  Arg Lys Lys
    1355                1360                1365

Asp Trp  Asp Pro Lys Lys Tyr  Gly Gly Phe Asp Ser  Pro Thr Val
    1370                1375                1380

Ala Tyr  Ser Val Leu Val Val  Ala Lys Val Glu Lys  Gly Lys Ser
    1385                1390                1395

Lys Lys  Leu Lys Ser Val Lys  Glu Leu Leu Gly Ile  Thr Ile Met
    1400                1405                1410

Glu Arg  Ser Ser Phe Glu Lys  Asn Pro Ile Asp Phe  Leu Glu Ala
    1415                1420                1425

Lys Gly  Tyr Lys Glu Val Lys  Lys Asp Leu Ile Ile  Lys Leu Pro
    1430                1435                1440

Lys Tyr  Ser Leu Phe Glu Leu  Glu Asn Gly Arg Lys  Arg Met Leu
    1445                1450                1455

Ala Ser  Ala Gly Glu Leu Gln  Lys Gly Asn Glu Leu  Ala Leu Pro
    1460                1465                1470

Ser Lys  Tyr Val Asn Phe Leu  Tyr Leu Ala Ser His  Tyr Glu Lys
    1475                1480                1485

Leu Lys  Gly Ser Pro Glu Asp  Asn Glu Gln Lys Gln  Leu Phe Val
    1490                1495                1500

Glu Gln  His Lys His Tyr Leu  Asp Glu Ile Ile Glu  Gln Ile Ser
    1505                1510                1515

Glu Phe  Ser Lys Arg Val Ile  Leu Ala Asp Ala Asn  Leu Asp Lys
    1520                1525                1530

Val Leu  Ser Ala Tyr Asn Lys  His Arg Asp Lys Pro  Ile Arg Glu
    1535                1540                1545

Gln Ala  Glu Asn Ile Ile His  Leu Phe Thr Leu Thr  Asn Leu Gly
    1550                1555                1560

Ala Pro  Ala Ala Phe Lys Tyr  Phe Asp Thr Thr Ile  Asp Arg Lys
    1565                1570                1575

Arg Tyr  Thr Ser Thr Lys Glu  Val Leu Asp Ala Thr  Leu Ile His
    1580                1585                1590

Gln Ser  Ile Thr Gly Leu Tyr  Glu Thr Arg Ile Asp  Leu Ser Gln
    1595                1600                1605

Leu Gly  Gly Asp
    1610


<210> SEQ ID NO 722
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 722

Gly Gly Gly Gly Ser
1               5
```

<210> SEQ ID NO 723
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 723

Glu Ala Ala Ala Lys
1 5

<210> SEQ ID NO 724
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 724

Ser Gly Ser Glu Thr Pro Gly Thr Ser Glu Ser Ala Thr Pro Glu Ser
1 5 10 15

<210> SEQ ID NO 725
<211> LENGTH: 343
<212> TYPE: PRT
<213> ORGANISM: Artificial Sequence
<220> FEATURE:
<223> OTHER INFORMATION: Synthetic polypeptide

<400> SEQUENCE: 725

Met Ser Asn Leu Leu Thr Val His Gln Asn Leu Pro Ala Leu Pro Val
1 5 10 15

Asp Ala Thr Ser Asp Glu Val Arg Lys Asn Leu Met Asp Met Phe Arg
20 25 30

Asp Arg Gln Ala Phe Ser Glu His Thr Trp Lys Met Leu Leu Ser Val
35 40 45

Cys Arg Ser Trp Ala Ala Trp Cys Lys Leu Asn Asn Arg Lys Trp Phe
50 55 60

Pro Ala Glu Pro Glu Asp Val Arg Asp Tyr Leu Leu Tyr Leu Gln Ala
65 70 75 80

Arg Gly Leu Ala Val Lys Thr Ile Gln Gln His Leu Gly Gln Leu Asn
85 90 95

Met Leu His Arg Arg Ser Gly Leu Pro Arg Pro Ser Asp Ser Asn Ala
100 105 110

Val Ser Leu Val Met Arg Arg Ile Arg Lys Glu Asn Val Asp Ala Gly
115 120 125

Glu Arg Ala Lys Gln Ala Leu Ala Phe Glu Arg Thr Asp Phe Asp Gln
130 135 140

Val Arg Ser Leu Met Glu Asn Ser Asp Arg Cys Gln Asp Ile Arg Asn
145 150 155 160

Leu Ala Phe Leu Gly Ile Ala Tyr Asn Thr Leu Leu Arg Ile Ala Glu
165 170 175

Ile Ala Arg Ile Arg Val Lys Asp Ile Ser Arg Thr Asp Gly Gly Arg
180 185 190

Met Leu Ile His Ile Gly Arg Thr Lys Thr Leu Val Ser Thr Ala Gly
195 200 205

Val Glu Lys Ala Leu Ser Leu Gly Val Thr Lys Leu Val Glu Arg Trp
210 215 220

Ile Ser Val Ser Gly Val Ala Asp Asp Pro Asn Asn Tyr Leu Phe Cys
225 230 235 240

Arg Val Arg Lys Asn Gly Val Ala Ala Pro Ser Ala Thr Ser Gln Leu
245 250 255

Ser Thr Arg Ala Leu Glu Gly Ile Phe Glu Ala Thr His Arg Leu Ile
260 265 270

Tyr Gly Ala Lys Asp Asp Ser Gly Gln Arg Tyr Leu Ala Trp Ser Gly
275 280 285

His Ser Ala Arg Val Gly Ala Ala Arg Asp Met Ala Arg Ala Gly Val
290 295 300

Ser Ile Pro Glu Ile Met Gln Ala Gly Gly Trp Thr Asn Val Asn Ile
305 310 315 320

Val Met Asn Tyr Ile Arg Asn Leu Asp Ser Glu Thr Gly Ala Met Val
325 330 335

Arg Leu Leu Glu Asp Gly Asp
340

<210> SEQ ID NO 726
<211> LENGTH: 423
<212> TYPE: PRT
<213> ORGANISM: Artificial Sequence
<220> FEATURE:
<223> OTHER INFORMATION: Synthetic polypeptide

<400> SEQUENCE: 726

Met Pro Gln Phe Gly Ile Leu Cys Lys Thr Pro Pro Lys Val Leu Val
1 5 10 15

Arg Gln Phe Val Glu Arg Phe Glu Arg Pro Ser Gly Glu Lys Ile Ala
20 25 30

Leu Cys Ala Ala Glu Leu Thr Tyr Leu Cys Trp Met Ile Thr His Asn
35 40 45

Gly Thr Ala Ile Lys Arg Ala Thr Phe Met Ser Tyr Asn Thr Ile Ile
50 55 60

Ser Asn Ser Leu Ser Phe Asp Ile Val Asn Lys Ser Leu Gln Phe Lys
65 70 75 80

Tyr Lys Thr Gln Lys Ala Thr Ile Leu Glu Ala Ser Leu Lys Lys Leu
85 90 95

Ile Pro Ala Trp Glu Phe Thr Ile Ile Pro Tyr Tyr Gly Gln Lys His
100 105 110

Gln Ser Asp Ile Thr Asp Ile Val Ser Ser Leu Gln Leu Gln Phe Glu
115 120 125

Ser Ser Glu Glu Ala Asp Lys Gly Asn Ser His Ser Lys Lys Met Leu
130 135 140

Lys Ala Leu Leu Ser Glu Gly Glu Ser Ile Trp Glu Ile Thr Glu Lys
145 150 155 160

Ile Leu Asn Ser Phe Glu Tyr Thr Ser Arg Phe Thr Lys Thr Lys Thr
165 170 175

Leu Tyr Gln Phe Leu Phe Leu Ala Thr Phe Ile Asn Cys Gly Arg Phe
180 185 190

Ser Asp Ile Lys Asn Val Asp Pro Lys Ser Phe Lys Leu Val Gln Asn
195 200 205

Lys Tyr Leu Gly Val Ile Ile Gln Cys Leu Val Thr Glu Thr Lys Thr
210 215 220

Ser Val Ser Arg His Ile Tyr Phe Phe Ser Ala Arg Gly Arg Ile Asp
225 230 235 240

Pro Leu Val Tyr Leu Asp Glu Phe Leu Arg Asn Ser Glu Pro Val Leu
245 250 255

```
Lys Arg Val Asn Arg Thr Gly Asn Ser Ser Ser Asn Lys Gln Glu Tyr
            260                 265                 270

Gln Leu Leu Lys Asp Asn Leu Val Arg Ser Tyr Asn Lys Ala Leu Lys
        275                 280                 285

Lys Asn Ala Pro Tyr Ser Ile Phe Ala Ile Lys Asn Gly Pro Lys Ser
    290                 295                 300

His Ile Gly Arg His Leu Met Thr Ser Phe Leu Ser Met Lys Gly Leu
305                 310                 315                 320

Thr Glu Leu Thr Asn Val Val Gly Asn Trp Ser Asp Lys Arg Ala Ser
                325                 330                 335

Ala Val Ala Arg Thr Thr Tyr Thr His Gln Ile Thr Ala Ile Pro Asp
            340                 345                 350

His Tyr Phe Ala Leu Val Ser Arg Tyr Tyr Ala Tyr Asp Pro Ile Ser
        355                 360                 365

Lys Glu Met Ile Ala Leu Lys Asp Glu Thr Asn Pro Ile Glu Glu Trp
    370                 375                 380

Gln His Ile Glu Gln Leu Lys Gly Ser Ala Glu Gly Ser Ile Arg Tyr
385                 390                 395                 400

Pro Ala Trp Asn Gly Ile Ile Ser Gln Glu Val Leu Asp Tyr Leu Ser
                405                 410                 415

Ser Tyr Ile Asn Arg Arg Ile
            420
```

<210> SEQ ID NO 727
<211> LENGTH: 144
<212> TYPE: PRT
<213> ORGANISM: Artificial Sequence
<220> FEATURE:
<223> OTHER INFORMATION: Synthetic polypeptide

<400> SEQUENCE: 727

```
Met Arg Leu Phe Gly Tyr Ala Arg Val Ser Thr Ser Gln Gln Ser Leu
1               5                   10                  15

Asp Ile Gln Val Arg Ala Leu Lys Asp Ala Gly Val Lys Ala Asn Arg
            20                  25                  30

Ile Phe Thr Asp Lys Ala Ser Gly Ser Ser Ser Asp Arg Lys Gly Leu
        35                  40                  45

Asp Leu Leu Arg Met Lys Val Glu Glu Gly Asp Val Ile Leu Val Lys
    50                  55                  60

Lys Leu Asp Arg Leu Gly Arg Asp Thr Ala Asp Met Ile Gln Leu Ile
65                  70                  75                  80

Lys Glu Phe Asp Ala Gln Gly Val Ser Ile Arg Phe Ile Asp Asp Gly
                85                  90                  95

Ile Ser Thr Asp Gly Glu Met Gly Lys Met Val Val Thr Ile Leu Ser
            100                 105                 110

Ala Val Ala Gln Ala Glu Arg Gln Arg Ile Leu Glu Arg Thr Asn Glu
        115                 120                 125

Gly Arg Gln Glu Ala Met Ala Lys Gly Val Val Phe Gly Arg Lys Arg
    130                 135                 140
```

<210> SEQ ID NO 728
<211> LENGTH: 144
<212> TYPE: PRT
<213> ORGANISM: Artificial Sequence
<220> FEATURE:
<223> OTHER INFORMATION: Synthetic polypeptide

<400> SEQUENCE: 728

Met Arg Leu Phe Gly Tyr Ala Arg Val Ser Thr Ser Gln Gln Ser Leu
1               5                   10                  15

Asp Ile Gln Val Arg Ala Leu Lys Asp Ala Gly Val Lys Ala Asn Arg
            20                  25                  30

Ile Phe Thr Asp Lys Ala Ser Gly Ser Ser Ser Asp Arg Lys Gly Leu
        35                  40                  45

Asp Leu Leu Arg Met Lys Val Glu Glu Gly Asp Val Ile Leu Val Lys
    50                  55                  60

Lys Leu Asp Arg Leu Gly Arg Asp Thr Ala Asp Met Ile Gln Leu Ile
65                  70                  75                  80

Lys Glu Phe Asp Ala Gln Gly Val Ser Ile Arg Phe Ile Asp Asp Gly
                85                  90                  95

Ile Ser Thr Asp Gly Glu Met Gly Lys Met Val Val Thr Ile Leu Ser
            100                 105                 110

Ala Val Ala Gln Ala Glu Arg Gln Arg Ile Leu Glu Arg Thr Asn Glu
        115                 120                 125

Gly Arg Gln Glu Ala Met Ala Lys Gly Val Val Phe Gly Arg Lys Arg
    130                 135                 140

<210> SEQ ID NO 729
<211> LENGTH: 144
<212> TYPE: PRT
<213> ORGANISM: Artificial Sequence
<220> FEATURE:
<223> OTHER INFORMATION: Synthetic polypeptide

<400> SEQUENCE: 729

Met Arg Leu Phe Gly Tyr Ala Arg Val Ser Thr Ser Gln Gln Ser Leu
1               5                   10                  15

Asp Ile Gln Val Arg Ala Leu Lys Asp Ala Gly Val Lys Ala Asn Arg
            20                  25                  30

Ile Phe Thr Asp Lys Ala Ser Gly Ser Ser Ser Asp Arg Lys Gly Leu
        35                  40                  45

Asp Leu Leu Arg Met Lys Val Glu Glu Gly Asp Val Ile Leu Val Lys
    50                  55                  60

Lys Leu Asp Arg Leu Gly Arg Asp Thr Ala Asp Met Ile Gln Leu Ile
65                  70                  75                  80

Lys Glu Phe Asp Ala Gln Gly Val Ser Ile Arg Phe Ile Asp Asp Gly
                85                  90                  95

Ile Ser Thr Asp Gly Tyr Met Gly Lys Met Val Val Thr Ile Leu Ser
            100                 105                 110

Ala Val Ala Gln Ala Glu Arg Gln Arg Ile Leu Gln Arg Thr Asn Glu
        115                 120                 125

Gly Arg Gln Glu Ala Met Ala Lys Gly Val Val Phe Gly Arg Lys Arg
    130                 135                 140

<210> SEQ ID NO 730
<211> LENGTH: 147
<212> TYPE: PRT
<213> ORGANISM: Artificial Sequence
<220> FEATURE:
<223> OTHER INFORMATION: Synthetic polypeptide

<400> SEQUENCE: 730

Met Ala Lys Ile Gly Tyr Ala Arg Val Ser Ser Lys Glu Gln Asn Leu
1               5                   10                  15

Asp Arg Gln Leu Gln Ala Leu Gln Gly Val Ser Lys Val Phe Ser Asp
20 25 30

Lys Leu Ser Gly Gln Ser Val Glu Arg Pro Gln Leu Gln Ala Met Leu
35 40 45

Asn Tyr Ile Arg Glu Gly Asp Ile Val Val Val Thr Glu Leu Asp Arg
50 55 60

Leu Gly Arg Asn Asn Lys Glu Leu Thr Glu Leu Met Asn Ala Ile Gln
65 70 75 80

Gln Lys Gly Ala Thr Leu Glu Val Leu Asp Leu Pro Ser Met Asn Gly
85 90 95

Ile Glu Asp Glu Asn Leu Arg Arg Leu Ile Asn Asn Leu Val Ile Glu
100 105 110

Leu Tyr Lys Tyr Gln Ala Glu Ser Glu Arg Lys Arg Ile Lys Glu Arg
115 120 125

Gln Ala Gln Gly Ile Glu Ile Ala Lys Ser Lys Gly Lys Phe Lys Gly
130 135 140

Arg Gln His
145

<210> SEQ ID NO 731
<211> LENGTH: 147
<212> TYPE: PRT
<213> ORGANISM: Artificial Sequence
<220> FEATURE:
<223> OTHER INFORMATION: Synthetic polypeptide

<400> SEQUENCE: 731

Met Ala Lys Ile Gly Tyr Ala Arg Val Ser Ser Lys Glu Gln Asn Leu
1 5 10 15

Asp Arg Gln Leu Gln Ala Leu Gln Gly Val Ser Lys Val Phe Ser Asp
20 25 30

Lys Leu Ser Gly Gln Ser Val Glu Arg Pro Gln Leu Gln Ala Met Leu
35 40 45

Asn Tyr Ile Arg Glu Gly Asp Ile Val Val Val Thr Glu Leu Asp Arg
50 55 60

Leu Gly Arg Asn Asn Lys Glu Leu Thr Glu Leu Met Asn Ala Ile Gln
65 70 75 80

Gln Lys Gly Ala Thr Leu Glu Val Leu Asp Leu Pro Ser Met Asp Gly
85 90 95

Ile Glu Asp Glu Asn Leu Arg Arg Leu Ile Asn Asn Leu Val Ile Glu
100 105 110

Leu Tyr Lys Tyr Gln Ala Glu Ser Glu Arg Lys Arg Ile Lys Glu Arg
115 120 125

Gln Ala Gln Gly Ile Glu Ile Ala Lys Ser Lys Gly Lys Phe Lys Gly
130 135 140

Arg Gln His
145

<210> SEQ ID NO 732
<211> LENGTH: 150
<212> TYPE: PRT
<213> ORGANISM: Artificial Sequence
<220> FEATURE:
<223> OTHER INFORMATION: Synthetic polypeptide

<400> SEQUENCE: 732

Met Ile Ile Gly Tyr Ala Arg Val Ser Ser Leu Asp Gln Asn Leu Glu
1 5 10 15

```
Arg Gln Leu Glu Asn Leu Lys Thr Phe Gly Ala Glu Lys Ile Phe Thr
            20                  25                  30

Glu Lys Gln Ser Gly Lys Ser Ile Glu Asn Arg Pro Ile Leu Gln Lys
        35                  40                  45

Ala Leu Asn Phe Val Arg Met Gly Asp Arg Phe Ile Val Glu Ser Ile
    50                  55                  60

Asp Arg Leu Gly Arg Asn Tyr Asn Glu Val Ile His Thr Val Asn Tyr
65                  70                  75                  80

Leu Lys Asp Lys Glu Val Gln Leu Met Ile Thr Ser Leu Pro Met Met
                85                  90                  95

Asn Glu Val Ile Gly Asn Pro Leu Leu Asp Lys Phe Met Lys Asp Leu
            100                 105                 110

Ile Ile Gln Ile Leu Ala Met Val Ser Glu Gln Glu Arg Asn Glu Ser
        115                 120                 125

Lys Arg Arg Gln Ala Gln Gly Ile Gln Val Ala Lys Glu Lys Gly Val
    130                 135                 140

Tyr Lys Gly Arg Pro Leu
145                 150


<210> SEQ ID NO 733
<211> LENGTH: 150
<212> TYPE: PRT
<213> ORGANISM: Artificial Sequence
<220> FEATURE:
<223> OTHER INFORMATION: Synthetic polypeptide

<400> SEQUENCE: 733

Met Ile Ile Gly Tyr Ala Arg Val Ser Ser Leu Asp Gln Asn Leu Glu
1               5                   10                  15

Arg Gln Leu Glu Asn Leu Lys Thr Phe Gly Ala Glu Lys Ile Phe Thr
            20                  25                  30

Glu Lys Gln Ser Gly Lys Ser Ile Glu Asn Arg Pro Ile Leu Gln Lys
        35                  40                  45

Ala Leu Asn Phe Val Arg Met Gly Asp Arg Phe Ile Val Glu Ser Ile
    50                  55                  60

Asp Arg Leu Gly Arg Asn Tyr Asn Glu Val Ile His Thr Val Asn Tyr
65                  70                  75                  80

Leu Lys Asp Lys Glu Val Arg Leu Met Ile Thr Ser Leu Pro Met Met
                85                  90                  95

Asn Glu Val Ile Gly Asn Pro Leu Leu Asp Lys Phe Met Lys Asp Leu
            100                 105                 110

Ile Ile Arg Ile Leu Ala Met Val Ser Glu Gln Glu Arg Asn Glu Ser
        115                 120                 125

Lys Arg Arg Gln Ala Gln Gly Ile Gln Val Ala Lys Glu Lys Gly Val
    130                 135                 140

Tyr Lys Gly Arg Pro Leu
145                 150


<210> SEQ ID NO 734
<211> LENGTH: 144
<212> TYPE: PRT
<213> ORGANISM: Artificial Sequence
<220> FEATURE:
<223> OTHER INFORMATION: Synthetic polypeptide

<400> SEQUENCE: 734

Met Arg Leu Phe Gly Tyr Ala Arg Val Ser Thr Ser Gln Gln Ser Leu
```

-continued

```
1               5                   10                  15

Asp Leu Gln Val Arg Ala Leu Lys Asp Ala Gly Val Lys Ala Asn Arg
            20                  25                  30

Ile Phe Thr Asp Lys Ala Ser Gly Ser Ser Thr Asp Arg Glu Gly Leu
        35                  40                  45

Asp Leu Leu Arg Met Lys Val Lys Glu Gly Asp Val Ile Leu Val Lys
    50                  55                  60

Lys Leu Asp Arg Leu Gly Arg Asp Thr Ala Asp Met Leu Gln Leu Ile
65                  70                  75                  80

Lys Glu Phe Asp Ala Gln Gly Val Ala Val Arg Phe Ile Asp Asp Gly
                85                  90                  95

Ile Ser Thr Asp Gly Asp Met Gly Gln Met Val Val Thr Ile Leu Ser
            100                 105                 110

Ala Val Ala Gln Ala Glu Arg Arg Arg Ile Leu Glu Arg Thr Asn Glu
        115                 120                 125

Gly Arg Gln Glu Ala Lys Leu Lys Gly Ile Lys Phe Gly Arg Arg Arg
    130                 135                 140
```

<210> SEQ ID NO 735
<211> LENGTH: 144
<212> TYPE: PRT
<213> ORGANISM: Artificial Sequence
<220> FEATURE:
<223> OTHER INFORMATION: Sythetic polypeptide

<400> SEQUENCE: 735

```
Met Arg Leu Phe Gly Tyr Ala Arg Val Ser Thr Ser Gln Gln Ser Leu
1               5                   10                  15

Asp Leu Gln Val Arg Ala Leu Lys Asp Ala Gly Val Lys Ala Asn Arg
            20                  25                  30

Ile Phe Thr Asp Lys Ala Ser Gly Ser Ser Thr Asp Arg Glu Gly Leu
        35                  40                  45

Asp Leu Leu Arg Met Lys Val Lys Glu Gly Asp Val Ile Leu Val Lys
    50                  55                  60

Lys Leu Asp Arg Leu Ser Arg Asp Thr Ala Asp Met Leu Gln Leu Ile
65                  70                  75                  80

Lys Glu Phe Asp Ala Gln Gly Val Ala Val Arg Phe Ile Asp Asp Gly
                85                  90                  95

Ile Ser Thr Asp Gly Tyr Met Gly Gln Met Val Val Thr Ile Leu Ser
            100                 105                 110

Ala Val Ala Gln Ala Glu Arg Arg Arg Ile Leu Gln Arg Thr Asn Glu
        115                 120                 125

Gly Arg Gln Glu Ala Lys Leu Lys Gly Ile Lys Phe Gly Arg Arg Arg
    130                 135                 140
```

<210> SEQ ID NO 736
<211> LENGTH: 142
<212> TYPE: PRT
<213> ORGANISM: Artificial Sequence
<220> FEATURE:
<223> OTHER INFORMATION: Synthetic polypeptide

<400> SEQUENCE: 736

```
Met Ala Thr Ile Gly Tyr Ile Arg Val Ser Thr Ile Asp Gln Asn Ile
1               5                   10                  15

Asp Leu Gln Arg Asn Ala Leu Thr Ser Ala Asn Cys Asp Arg Ile Phe
            20                  25                  30
```

```
Glu Asp Arg Ile Ser Gly Lys Ile Ala Asn Arg Pro Gly Leu Lys Arg
        35                  40                  45

Ala Leu Lys Tyr Val Asn Lys Gly Asp Thr Leu Val Val Trp Lys Leu
    50                  55                  60

Asp Arg Leu Gly Arg Ser Val Lys Asn Leu Val Ala Leu Ile Ser Glu
65                  70                  75                  80

Leu His Glu Arg Gly Ala His Phe His Ser Leu Thr Asp Ser Ile Asp
                85                  90                  95

Thr Ser Ser Ala Met Gly Arg Phe Phe Phe His Val Met Ser Ala Leu
            100                 105                 110

Ala Glu Met Glu Arg Glu Leu Ile Val Glu Arg Thr Leu Ala Gly Leu
        115                 120                 125

Ala Ala Ala Arg Ala Gln Gly Arg Leu Gly Gly Arg Pro Val
    130                 135                 140
```

<210> SEQ ID NO 737
<211> LENGTH: 142
<212> TYPE: PRT
<213> ORGANISM: Artificial Sequence
<220> FEATURE:
<223> OTHER INFORMATION: Synthetic polypeptide

<400> SEQUENCE: 737

```
Met Ala Thr Ile Gly Tyr Ile Arg Val Ser Thr Ile Asp Gln Asn Ile
1               5                   10                  15

Asp Leu Gln Arg Asn Ala Leu Thr Ser Ala Asn Cys Asp Arg Ile Phe
            20                  25                  30

Glu Asp Arg Ile Ser Gly Lys Ile Ala Asn Arg Pro Gly Leu Lys Arg
        35                  40                  45

Ala Leu Lys Tyr Val Asn Lys Gly Asp Thr Leu Val Val Trp Lys Leu
    50                  55                  60

Asp Arg Leu Gly Arg Ser Val Lys Asn Leu Val Ala Leu Ile Ser Glu
65                  70                  75                  80

Leu His Glu Arg Gly Ala His Phe His Ser Leu Thr Asp Ser Ile Asp
                85                  90                  95

Thr Ser Ser Ala Met Gly Arg Phe Phe Phe Tyr Val Met Ser Ala Leu
            100                 105                 110

Ala Glu Met Glu Arg Glu Leu Ile Val Glu Arg Thr Leu Ala Gly Leu
        115                 120                 125

Ala Ala Ala Arg Ala Gln Gly Arg Leu Gly Gly Arg Pro Val
    130                 135                 140
```

<210> SEQ ID NO 738
<211> LENGTH: 608
<212> TYPE: PRT
<213> ORGANISM: Artificial Sequence
<220> FEATURE:
<223> OTHER INFORMATION: Synthetic polypeptide

<400> SEQUENCE: 738

```
Met Asp Thr Tyr Ala Gly Ala Tyr Asp Arg Gln Ser Arg Glu Arg Glu
1               5                   10                  15

Asn Ser Ser Ala Ala Ser Pro Ala Thr Gln Arg Ser Ala Asn Glu Asp
            20                  25                  30

Lys Ala Ala Asp Leu Gln Arg Glu Val Glu Arg Asp Gly Gly Arg Phe
        35                  40                  45

Arg Phe Val Gly His Phe Ser Glu Ala Pro Gly Thr Ser Ala Phe Gly
    50                  55                  60
```

```
Thr Ala Glu Arg Pro Glu Phe Glu Arg Ile Leu Asn Glu Cys Arg Ala
65                  70                  75                  80

Gly Arg Leu Asn Met Ile Ile Val Tyr Asp Val Ser Arg Phe Ser Arg
                85                  90                  95

Leu Lys Val Met Asp Ala Ile Pro Ile Val Ser Glu Leu Leu Ala Leu
            100                 105                 110

Gly Val Thr Ile Val Ser Thr Gln Glu Gly Val Phe Arg Gln Gly Asn
        115                 120                 125

Val Met Asp Leu Ile His Leu Ile Met Arg Leu Asp Ala Ser His Lys
    130                 135                 140

Glu Ser Ser Leu Lys Ser Ala Lys Ile Leu Asp Thr Lys Asn Leu Gln
145                 150                 155                 160

Arg Glu Leu Gly Gly Tyr Val Gly Gly Lys Ala Pro Tyr Gly Phe Glu
                165                 170                 175

Leu Val Ser Glu Thr Lys Glu Ile Thr Arg Asn Gly Arg Met Val Asn
            180                 185                 190

Val Val Ile Asn Lys Leu Ala His Ser Thr Thr Pro Leu Thr Gly Pro
        195                 200                 205

Phe Glu Phe Glu Pro Asp Val Ile Arg Trp Trp Trp Arg Glu Ile Lys
    210                 215                 220

Thr His Lys His Leu Pro Phe Lys Pro Gly Ser Gln Ala Ala Ile His
225                 230                 235                 240

Pro Gly Ser Ile Thr Gly Leu Cys Lys Arg Met Asp Ala Asp Ala Val
                245                 250                 255

Pro Thr Arg Gly Glu Thr Ile Gly Lys Lys Thr Ala Ser Ser Ala Trp
            260                 265                 270

Asp Pro Ala Thr Val Met Arg Ile Leu Arg Asp Pro Arg Ile Ala Gly
        275                 280                 285

Phe Ala Ala Glu Val Ile Tyr Lys Lys Lys Pro Asp Gly Thr Pro Thr
    290                 295                 300

Thr Lys Ile Glu Gly Tyr Arg Ile Gln Arg Asp Pro Ile Thr Leu Arg
305                 310                 315                 320

Pro Val Glu Leu Asp Cys Gly Pro Ile Ile Glu Pro Ala Glu Trp Tyr
                325                 330                 335

Glu Leu Gln Ala Trp Leu Asp Gly Arg Gly Arg Gly Lys Gly Leu Ser
            340                 345                 350

Arg Gly Gln Ala Ile Leu Ser Ala Met Asp Lys Leu Tyr Cys Glu Cys
        355                 360                 365

Gly Ala Val Met Thr Ser Lys Arg Gly Glu Glu Ser Ile Lys Asp Ser
    370                 375                 380

Tyr Arg Cys Arg Arg Arg Lys Val Val Asp Pro Ser Ala Pro Gly Gln
385                 390                 395                 400

His Glu Gly Thr Cys Asn Val Ser Met Ala Ala Leu Asp Lys Phe Val
                405                 410                 415

Ala Glu Arg Ile Phe Asn Lys Ile Arg His Ala Glu Gly Asp Glu Glu
            420                 425                 430

Thr Leu Ala Leu Leu Trp Glu Ala Ala Arg Arg Phe Gly Lys Leu Thr
        435                 440                 445

Glu Ala Pro Glu Lys Ser Gly Glu Arg Ala Asn Leu Val Ala Glu Arg
    450                 455                 460

Ala Asp Ala Leu Asn Ala Leu Glu Glu Leu Tyr Glu Asp Arg Ala Ala
465                 470                 475                 480
```

```
Gly Ala Tyr Asp Gly Pro Val Gly Arg Lys His Phe Arg Lys Gln Gln
                485                 490                 495

Ala Ala Leu Thr Leu Arg Gln Gln Gly Ala Glu Glu Arg Leu Ala Glu
            500                 505                 510

Leu Glu Ala Ala Glu Ala Pro Lys Leu Pro Leu Asp Gln Trp Phe Pro
        515                 520                 525

Glu Asp Ala Asp Ala Asp Pro Thr Gly Pro Lys Ser Trp Trp Gly Arg
    530                 535                 540

Ala Ser Val Asp Asp Lys Arg Val Phe Val Gly Leu Phe Val Asp Lys
545                 550                 555                 560

Ile Val Val Thr Lys Ser Thr Thr Gly Arg Gly Gln Gly Thr Pro Ile
                565                 570                 575

Glu Lys Arg Ala Ser Ile Thr Trp Ala Lys Pro Pro Thr Asp Asp Asp
            580                 585                 590

Glu Asp Asp Ala Gln Asp Gly Thr Glu Asp Val Ala Ala Thr Gly Ala
        595                 600                 605


<210> SEQ ID NO 739
<211> LENGTH: 34
<212> TYPE: DNA
<213> ORGANISM: Artificial Sequence
<220> FEATURE:
<223> OTHER INFORMATION: Synthetic polynucleotide

<400> SEQUENCE: 739

ataacttcgt atagcataca ttatacgaag ttat                              34


<210> SEQ ID NO 740
<211> LENGTH: 34
<212> TYPE: DNA
<213> ORGANISM: Artificial Sequence
<220> FEATURE:
<223> OTHER INFORMATION: Synthetic polynucleotide

<400> SEQUENCE: 740

gaagttccta ttctctagaa agtataggaa cttc                              34


<210> SEQ ID NO 741
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 741

Asn Gly Ala Asn
1


<210> SEQ ID NO 742
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 742

Asn Gly Asn Gly
1


<210> SEQ ID NO 743
<211> LENGTH: 4
<212> TYPE: PRT
<213> ORGANISM: Artificial Sequence
```

<220> FEATURE:
<223> OTHER INFORMATION: Synthetic polypeptide

<400> SEQUENCE: 743

Asn Gly Ala Gly
1

<210> SEQ ID NO 744
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 744

Asn Gly Cys Gly
1

<210> SEQ ID NO 745
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 745

Asn Asn Gly Arg Arg Thr
1               5

<210> SEQ ID NO 746
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 746

Asn Gly Arg Arg Asn
1               5

<210> SEQ ID NO 747
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 747

Asn Asn Asn Arg Arg Thr
1               5

<210> SEQ ID NO 748
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 748

Asn Asn Asn Gly Ala Thr Thr
1               5

<210> SEQ ID NO 749
<211> LENGTH: 7
<212> TYPE: PRT
<213> ORGANISM: Artificial Sequence
<220> FEATURE:

<223> OTHER INFORMATION: Synthetic polypeptide

<400> SEQUENCE: 749

Asn Asn Ala Gly Ala Ala Trp
1               5

<210> SEQ ID NO 750
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 750

Asn Ala Ala Ala Cys
1               5

<210> SEQ ID NO 751
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 751

Thr Thr Thr Asn
1

<210> SEQ ID NO 752
<211> LENGTH: 1367
<212> TYPE: PRT
<213> ORGANISM: Artificial Sequence
<220> FEATURE:
<223> OTHER INFORMATION: Synthetic Polypeptide

<400> SEQUENCE: 752

Asp Lys Lys Tyr Ser Ile Gly Leu Ala Ile Gly Thr Asn Ser Val Gly
1               5                   10                  15

Trp Ala Val Ile Thr Asp Glu Tyr Lys Val Pro Ser Lys Lys Phe Lys
            20                  25                  30

Val Leu Gly Asn Thr Asp Arg His Ser Ile Lys Lys Asn Leu Ile Gly
        35                  40                  45

Ala Leu Leu Phe Asp Ser Gly Glu Thr Ala Glu Ala Thr Arg Leu Lys
    50                  55                  60

Arg Thr Ala Arg Arg Arg Tyr Thr Arg Arg Lys Asn Arg Ile Cys Tyr
65                  70                  75                  80

Leu Gln Glu Ile Phe Ser Asn Glu Met Ala Lys Val Asp Asp Ser Phe
                85                  90                  95

Phe His Arg Leu Glu Glu Ser Phe Leu Val Glu Glu Asp Lys Lys His
            100                 105                 110

Glu Arg His Pro Ile Phe Gly Asn Ile Val Asp Glu Val Ala Tyr His
        115                 120                 125

Glu Lys Tyr Pro Thr Ile Tyr His Leu Arg Lys Lys Leu Val Asp Ser
    130                 135                 140

Thr Asp Lys Ala Asp Leu Arg Leu Ile Tyr Leu Ala Leu Ala His Met
145                 150                 155                 160

Ile Lys Phe Arg Gly His Phe Leu Ile Glu Gly Asp Leu Asn Pro Asp
                165                 170                 175

Asn Ser Asp Val Asp Lys Leu Phe Ile Gln Leu Val Gln Thr Tyr Asn
            180                 185                 190

Gln Leu Phe Glu Glu Asn Pro Ile Asn Ala Ser Gly Val Asp Ala Lys
195 200 205

Ala Ile Leu Ser Ala Arg Leu Ser Lys Ser Arg Arg Leu Glu Asn Leu
210 215 220

Ile Ala Gln Leu Pro Gly Glu Lys Lys Asn Gly Leu Phe Gly Asn Leu
225 230 235 240

Ile Ala Leu Ser Leu Gly Leu Thr Pro Asn Phe Lys Ser Asn Phe Asp
245 250 255

Leu Ala Glu Asp Ala Lys Leu Gln Leu Ser Lys Asp Thr Tyr Asp Asp
260 265 270

Asp Leu Asp Asn Leu Leu Ala Gln Ile Gly Asp Gln Tyr Ala Asp Leu
275 280 285

Phe Leu Ala Ala Lys Asn Leu Ser Asp Ala Ile Leu Leu Ser Asp Ile
290 295 300

Leu Arg Val Asn Thr Glu Ile Thr Lys Ala Pro Leu Ser Ala Ser Met
305 310 315 320

Ile Lys Arg Tyr Asp Glu His His Gln Asp Leu Thr Leu Leu Lys Ala
325 330 335

Leu Val Arg Gln Gln Leu Pro Glu Lys Tyr Lys Glu Ile Phe Phe Asp
340 345 350

Gln Ser Lys Asn Gly Tyr Ala Gly Tyr Ile Asp Gly Gly Ala Ser Gln
355 360 365

Glu Glu Phe Tyr Lys Phe Ile Lys Pro Ile Leu Glu Lys Met Asp Gly
370 375 380

Thr Glu Glu Leu Leu Val Lys Leu Asn Arg Glu Asp Leu Leu Arg Lys
385 390 395 400

Gln Arg Thr Phe Asp Asn Gly Ser Ile Pro His Gln Ile His Leu Gly
405 410 415

Glu Leu His Ala Ile Leu Arg Arg Gln Glu Asp Phe Tyr Pro Phe Leu
420 425 430

Lys Asp Asn Arg Glu Lys Ile Glu Lys Ile Leu Thr Phe Arg Ile Pro
435 440 445

Tyr Tyr Val Gly Pro Leu Ala Arg Gly Asn Ser Arg Phe Ala Trp Met
450 455 460

Thr Arg Lys Ser Glu Glu Thr Ile Thr Pro Trp Asn Phe Glu Glu Val
465 470 475 480

Val Asp Lys Gly Ala Ser Ala Gln Ser Phe Ile Glu Arg Met Thr Asn
485 490 495

Phe Asp Lys Asn Leu Pro Asn Glu Lys Val Leu Pro Lys His Ser Leu
500 505 510

Leu Tyr Glu Tyr Phe Thr Val Tyr Asn Glu Leu Thr Lys Val Lys Tyr
515 520 525

Val Thr Glu Gly Met Arg Lys Pro Ala Phe Leu Ser Gly Glu Gln Lys
530 535 540

Lys Ala Ile Val Asp Leu Leu Phe Lys Thr Asn Arg Lys Val Thr Val
545 550 555 560

Lys Gln Leu Lys Glu Asp Tyr Phe Lys Lys Ile Glu Cys Phe Asp Ser
565 570 575

Val Glu Ile Ser Gly Val Glu Asp Arg Phe Asn Ala Ser Leu Gly Thr
580 585 590

Tyr His Asp Leu Leu Lys Ile Ile Lys Asp Lys Asp Phe Leu Asp Asn
595 600 605

Glu Glu Asn Glu Asp Ile Leu Glu Asp Ile Val Leu Thr Leu Thr Leu

```
    610                 615                 620

Phe Glu Asp Arg Glu Met Ile Glu Glu Arg Leu Lys Thr Tyr Ala His
625                 630                 635                 640

Leu Phe Asp Asp Lys Val Met Lys Gln Leu Lys Arg Arg Arg Tyr Thr
                645                 650                 655

Gly Trp Gly Arg Leu Ser Arg Lys Leu Ile Asn Gly Ile Arg Asp Lys
            660                 665                 670

Gln Ser Gly Lys Thr Ile Leu Asp Phe Leu Lys Ser Asp Gly Phe Ala
        675                 680                 685

Asn Arg Asn Phe Met Gln Leu Ile His Asp Asp Ser Leu Thr Phe Lys
    690                 695                 700

Glu Asp Ile Gln Lys Ala Gln Val Ser Gly Gln Gly Asp Ser Leu His
705                 710                 715                 720

Glu His Ile Ala Asn Leu Ala Gly Ser Pro Ala Ile Lys Lys Gly Ile
                725                 730                 735

Leu Gln Thr Val Lys Val Val Asp Glu Leu Val Lys Val Met Gly Arg
            740                 745                 750

His Lys Pro Glu Asn Ile Val Ile Glu Met Ala Arg Glu Asn Gln Thr
        755                 760                 765

Thr Gln Lys Gly Gln Lys Asn Ser Arg Glu Arg Met Lys Arg Ile Glu
    770                 775                 780

Glu Gly Ile Lys Glu Leu Gly Ser Gln Ile Leu Lys Glu His Pro Val
785                 790                 795                 800

Glu Asn Thr Gln Leu Gln Asn Glu Lys Leu Tyr Leu Tyr Tyr Leu Gln
                805                 810                 815

Asn Gly Arg Asp Met Tyr Val Asp Gln Glu Leu Asp Ile Asn Arg Leu
            820                 825                 830

Ser Asp Tyr Asp Val Asp Ala Ile Val Pro Gln Ser Phe Leu Lys Asp
        835                 840                 845

Asp Ser Ile Asp Asn Lys Val Leu Thr Arg Ser Asp Lys Asn Arg Gly
    850                 855                 860

Lys Ser Asp Asn Val Pro Ser Glu Glu Val Val Lys Lys Met Lys Asn
865                 870                 875                 880

Tyr Trp Arg Gln Leu Leu Asn Ala Lys Leu Ile Thr Gln Arg Lys Phe
                885                 890                 895

Asp Asn Leu Thr Lys Ala Glu Arg Gly Gly Leu Ser Glu Leu Asp Lys
            900                 905                 910

Ala Gly Phe Ile Lys Arg Gln Leu Val Glu Thr Arg Gln Ile Thr Lys
        915                 920                 925

His Val Ala Gln Ile Leu Asp Ser Arg Met Asn Thr Lys Tyr Asp Glu
    930                 935                 940

Asn Asp Lys Leu Ile Arg Glu Val Lys Val Ile Thr Leu Lys Ser Lys
945                 950                 955                 960

Leu Val Ser Asp Phe Arg Lys Asp Phe Gln Phe Tyr Lys Val Arg Glu
                965                 970                 975

Ile Asn Asn Tyr His His Ala His Asp Ala Tyr Leu Asn Ala Val Val
            980                 985                 990

Gly Thr Ala Leu Ile Lys Lys Tyr  Pro Lys Leu Glu Ser  Glu Phe Val
        995                 1000                1005

Tyr Gly  Asp Tyr Lys Val Tyr  Asp Val Arg Lys Met  Ile Ala Lys
    1010                1015                1020

Ser Glu  Gln Glu Ile Gly Lys  Ala Thr Ala Lys Tyr  Phe Phe Tyr
    1025                1030                1035
```

Ser Asn Ile Met Asn Phe Phe Lys Thr Glu Ile Thr Leu Ala Asn
1040 1045 1050

Gly Glu Ile Arg Lys Arg Pro Leu Ile Glu Thr Asn Gly Glu Thr
1055 1060 1065

Gly Glu Ile Val Trp Asp Lys Gly Arg Asp Phe Ala Thr Val Arg
1070 1075 1080

Lys Val Leu Ser Met Pro Gln Val Asn Ile Val Lys Lys Thr Glu
1085 1090 1095

Val Gln Thr Gly Gly Phe Ser Lys Glu Ser Ile Leu Pro Lys Arg
1100 1105 1110

Asn Ser Asp Lys Leu Ile Ala Arg Lys Lys Asp Trp Asp Pro Lys
1115 1120 1125

Lys Tyr Gly Gly Phe Asp Ser Pro Thr Val Ala Tyr Ser Val Leu
1130 1135 1140

Val Val Ala Lys Val Glu Lys Gly Lys Ser Lys Lys Leu Lys Ser
1145 1150 1155

Val Lys Glu Leu Leu Gly Ile Thr Ile Met Glu Arg Ser Ser Phe
1160 1165 1170

Glu Lys Asn Pro Ile Asp Phe Leu Glu Ala Lys Gly Tyr Lys Glu
1175 1180 1185

Val Lys Lys Asp Leu Ile Ile Lys Leu Pro Lys Tyr Ser Leu Phe
1190 1195 1200

Glu Leu Glu Asn Gly Arg Lys Arg Met Leu Ala Ser Ala Gly Glu
1205 1210 1215

Leu Gln Lys Gly Asn Glu Leu Ala Leu Pro Ser Lys Tyr Val Asn
1220 1225 1230

Phe Leu Tyr Leu Ala Ser His Tyr Glu Lys Leu Lys Gly Ser Pro
1235 1240 1245

Glu Asp Asn Glu Gln Lys Gln Leu Phe Val Glu Gln His Lys His
1250 1255 1260

Tyr Leu Asp Glu Ile Ile Glu Gln Ile Ser Glu Phe Ser Lys Arg
1265 1270 1275

Val Ile Leu Ala Asp Ala Asn Leu Asp Lys Val Leu Ser Ala Tyr
1280 1285 1290

Asn Lys His Arg Asp Lys Pro Ile Arg Glu Gln Ala Glu Asn Ile
1295 1300 1305

Ile His Leu Phe Thr Leu Thr Asn Leu Gly Ala Pro Ala Ala Phe
1310 1315 1320

Lys Tyr Phe Asp Thr Thr Ile Asp Arg Lys Arg Tyr Thr Ser Thr
1325 1330 1335

Lys Glu Val Leu Asp Ala Thr Leu Ile His Gln Ser Ile Thr Gly
1340 1345 1350

Leu Tyr Glu Thr Arg Ile Asp Leu Ser Gln Leu Gly Gly Asp
1355 1360 1365

<210> SEQ ID NO 753
<211> LENGTH: 1367
<212> TYPE: PRT
<213> ORGANISM: Artificial Sequence
<220> FEATURE:
<223> OTHER INFORMATION: Synthetic Polypeptide

<400> SEQUENCE: 753

Asp Lys Lys Tyr Ser Ile Gly Leu Ala Ile Gly Thr Asn Ser Val Gly
1 5 10 15

-continued

```
Trp Ala Val Ile Thr Asp Glu Tyr Lys Val Pro Ser Lys Lys Phe Lys
            20                  25                  30

Val Leu Gly Asn Thr Asp Arg His Ser Ile Lys Lys Asn Leu Ile Gly
        35                  40                  45

Ala Leu Leu Phe Asp Ser Gly Glu Thr Ala Glu Ala Thr Arg Leu Lys
    50                  55                  60

Arg Thr Ala Arg Arg Arg Tyr Thr Arg Arg Lys Asn Arg Ile Cys Tyr
65                  70                  75                  80

Leu Gln Glu Ile Phe Ser Asn Glu Met Ala Lys Val Asp Asp Ser Phe
                85                  90                  95

Phe His Arg Leu Glu Glu Ser Phe Leu Val Glu Glu Asp Lys Lys His
            100                 105                 110

Glu Arg His Pro Ile Phe Gly Asn Ile Val Asp Glu Val Ala Tyr His
        115                 120                 125

Glu Lys Tyr Pro Thr Ile Tyr His Leu Arg Lys Lys Leu Val Asp Ser
    130                 135                 140

Thr Asp Lys Ala Asp Leu Arg Leu Ile Tyr Leu Ala Leu Ala His Met
145                 150                 155                 160

Ile Lys Phe Arg Gly His Phe Leu Ile Glu Gly Asp Leu Asn Pro Asp
                165                 170                 175

Asn Ser Asp Val Asp Lys Leu Phe Ile Gln Leu Val Gln Thr Tyr Asn
            180                 185                 190

Gln Leu Phe Glu Glu Asn Pro Ile Asn Ala Ser Gly Val Asp Ala Lys
        195                 200                 205

Ala Ile Leu Ser Ala Arg Leu Ser Lys Ser Arg Arg Leu Glu Asn Leu
    210                 215                 220

Ile Ala Gln Leu Pro Gly Glu Lys Lys Asn Gly Leu Phe Gly Asn Leu
225                 230                 235                 240

Ile Ala Leu Ser Leu Gly Leu Thr Pro Asn Phe Lys Ser Asn Phe Asp
                245                 250                 255

Leu Ala Glu Asp Ala Lys Leu Gln Leu Ser Lys Asp Thr Tyr Asp Asp
            260                 265                 270

Asp Leu Asp Asn Leu Leu Ala Gln Ile Gly Asp Gln Tyr Ala Asp Leu
        275                 280                 285

Phe Leu Ala Ala Lys Asn Leu Ser Asp Ala Ile Leu Leu Ser Asp Ile
    290                 295                 300

Leu Arg Val Asn Thr Glu Ile Thr Lys Ala Pro Leu Ser Ala Ser Met
305                 310                 315                 320

Ile Lys Arg Tyr Asp Glu His His Gln Asp Leu Thr Leu Leu Lys Ala
                325                 330                 335

Leu Val Arg Gln Gln Leu Pro Glu Lys Tyr Lys Glu Ile Phe Phe Asp
            340                 345                 350

Gln Ser Lys Asn Gly Tyr Ala Gly Tyr Ile Asp Gly Gly Ala Ser Gln
        355                 360                 365

Glu Glu Phe Tyr Lys Phe Ile Lys Pro Ile Leu Glu Lys Met Asp Gly
    370                 375                 380

Thr Glu Glu Leu Leu Val Lys Leu Asn Arg Glu Asp Leu Leu Arg Lys
385                 390                 395                 400

Gln Arg Thr Phe Asp Asn Gly Ser Ile Pro His Gln Ile His Leu Gly
                405                 410                 415

Glu Leu His Ala Ile Leu Arg Arg Gln Glu Asp Phe Tyr Pro Phe Leu
            420                 425                 430
```

-continued

```
Lys Asp Asn Arg Glu Lys Ile Glu Lys Ile Leu Thr Phe Arg Ile Pro
        435                 440                 445

Tyr Tyr Val Gly Pro Leu Ala Arg Gly Asn Ser Arg Phe Ala Trp Met
    450                 455                 460

Thr Arg Lys Ser Glu Glu Thr Ile Thr Pro Trp Asn Phe Glu Glu Val
465                 470                 475                 480

Val Asp Lys Gly Ala Ser Ala Gln Ser Phe Ile Glu Arg Met Thr Asn
                485                 490                 495

Phe Asp Lys Asn Leu Pro Asn Glu Lys Val Leu Pro Lys His Ser Leu
            500                 505                 510

Leu Tyr Glu Tyr Phe Thr Val Tyr Asn Glu Leu Thr Lys Val Lys Tyr
        515                 520                 525

Val Thr Glu Gly Met Arg Lys Pro Ala Phe Leu Ser Gly Glu Gln Lys
    530                 535                 540

Lys Ala Ile Val Asp Leu Leu Phe Lys Thr Asn Arg Lys Val Thr Val
545                 550                 555                 560

Lys Gln Leu Lys Glu Asp Tyr Phe Lys Lys Ile Glu Cys Phe Asp Ser
                565                 570                 575

Val Glu Ile Ser Gly Val Glu Asp Arg Phe Asn Ala Ser Leu Gly Thr
            580                 585                 590

Tyr His Asp Leu Leu Lys Ile Ile Lys Asp Lys Asp Phe Leu Asp Asn
        595                 600                 605

Glu Glu Asn Glu Asp Ile Leu Glu Asp Ile Val Leu Thr Leu Thr Leu
    610                 615                 620

Phe Glu Asp Arg Glu Met Ile Glu Glu Arg Leu Lys Thr Tyr Ala His
625                 630                 635                 640

Leu Phe Asp Asp Lys Val Met Lys Gln Leu Lys Arg Arg Arg Tyr Thr
                645                 650                 655

Gly Trp Gly Arg Leu Ser Arg Lys Leu Ile Asn Gly Ile Arg Asp Lys
            660                 665                 670

Gln Ser Gly Lys Thr Ile Leu Asp Phe Leu Lys Ser Asp Gly Phe Ala
        675                 680                 685

Asn Arg Asn Phe Met Gln Leu Ile His Asp Asp Ser Leu Thr Phe Lys
    690                 695                 700

Glu Asp Ile Gln Lys Ala Gln Val Ser Gly Gln Gly Asp Ser Leu His
705                 710                 715                 720

Glu His Ile Ala Asn Leu Ala Gly Ser Pro Ala Ile Lys Lys Gly Ile
                725                 730                 735

Leu Gln Thr Val Lys Val Val Asp Glu Leu Val Lys Val Met Gly Arg
            740                 745                 750

His Lys Pro Glu Asn Ile Val Ile Glu Met Ala Arg Glu Asn Gln Thr
        755                 760                 765

Thr Gln Lys Gly Gln Lys Asn Ser Arg Glu Arg Met Lys Arg Ile Glu
    770                 775                 780

Glu Gly Ile Lys Glu Leu Gly Ser Gln Ile Leu Lys Glu His Pro Val
785                 790                 795                 800

Glu Asn Thr Gln Leu Gln Asn Glu Lys Leu Tyr Leu Tyr Tyr Leu Gln
                805                 810                 815

Asn Gly Arg Asp Met Tyr Val Asp Gln Glu Leu Asp Ile Asn Arg Leu
            820                 825                 830

Ser Asp Tyr Asp Val Asp His Ile Val Pro Gln Ser Phe Leu Lys Asp
        835                 840                 845

Asp Ser Ile Asp Asn Lys Val Leu Thr Arg Ser Asp Lys Asn Arg Gly
```

```
    850                 855                 860

Lys Ser Asp Asn Val Pro Ser Glu Glu Val Val Lys Lys Met Lys Asn
865                 870                 875                 880

Tyr Trp Arg Gln Leu Leu Asn Ala Lys Leu Ile Thr Gln Arg Lys Phe
                885                 890                 895

Asp Asn Leu Thr Lys Ala Glu Arg Gly Gly Leu Ser Glu Leu Asp Lys
            900                 905                 910

Ala Gly Phe Ile Lys Arg Gln Leu Val Glu Thr Arg Gln Ile Thr Lys
        915                 920                 925

His Val Ala Gln Ile Leu Asp Ser Arg Met Asn Thr Lys Tyr Asp Glu
    930                 935                 940

Asn Asp Lys Leu Ile Arg Glu Val Lys Val Ile Thr Leu Lys Ser Lys
945                 950                 955                 960

Leu Val Ser Asp Phe Arg Lys Asp Phe Gln Phe Tyr Lys Val Arg Glu
                965                 970                 975

Ile Asn Asn Tyr His His Ala His Asp Ala Tyr Leu Asn Ala Val Val
            980                 985                 990

Gly Thr Ala Leu Ile Lys Lys Tyr  Pro Lys Leu Glu Ser  Glu Phe Val
        995                 1000                1005

Tyr Gly  Asp Tyr Lys Val Tyr  Asp Val Arg Lys Met  Ile Ala Lys
    1010                1015                1020

Ser Glu  Gln Glu Ile Gly Lys  Ala Thr Ala Lys Tyr  Phe Phe Tyr
    1025                1030                1035

Ser Asn  Ile Met Asn Phe Phe  Lys Thr Glu Ile Thr  Leu Ala Asn
    1040                1045                1050

Gly Glu  Ile Arg Lys Arg Pro  Leu Ile Glu Thr Asn  Gly Glu Thr
    1055                1060                1065

Gly Glu  Ile Val Trp Asp Lys  Gly Arg Asp Phe Ala  Thr Val Arg
    1070                1075                1080

Lys Val  Leu Ser Met Pro Gln  Val Asn Ile Val Lys  Lys Thr Glu
    1085                1090                1095

Val Gln  Thr Gly Gly Phe Ser  Lys Glu Ser Ile Leu  Pro Lys Arg
    1100                1105                1110

Asn Ser  Asp Lys Leu Ile Ala  Arg Lys Lys Asp Trp  Asp Pro Lys
    1115                1120                1125

Lys Tyr  Gly Gly Phe Asp Ser  Pro Thr Val Ala Tyr  Ser Val Leu
    1130                1135                1140

Val Val  Ala Lys Val Glu Lys  Gly Lys Ser Lys Lys  Leu Lys Ser
    1145                1150                1155

Val Lys  Glu Leu Leu Gly Ile  Thr Ile Met Glu Arg  Ser Ser Phe
    1160                1165                1170

Glu Lys  Asn Pro Ile Asp Phe  Leu Glu Ala Lys Gly  Tyr Lys Glu
    1175                1180                1185

Val Lys  Lys Asp Leu Ile Ile  Lys Leu Pro Lys Tyr  Ser Leu Phe
    1190                1195                1200

Glu Leu  Glu Asn Gly Arg Lys  Arg Met Leu Ala Ser  Ala Gly Glu
    1205                1210                1215

Leu Gln  Lys Gly Asn Glu Leu  Ala Leu Pro Ser Lys  Tyr Val Asn
    1220                1225                1230

Phe Leu  Tyr Leu Ala Ser His  Tyr Glu Lys Leu Lys  Gly Ser Pro
    1235                1240                1245

Glu Asp  Asn Glu Gln Lys Gln  Leu Phe Val Glu Gln  His Lys His
    1250                1255                1260
```

Tyr Leu Asp Glu Ile Ile Glu Gln Ile Ser Glu Phe Ser Lys Arg
1265 1270 1275

Val Ile Leu Ala Asp Ala Asn Leu Asp Lys Val Leu Ser Ala Tyr
1280 1285 1290

Asn Lys His Arg Asp Lys Pro Ile Arg Glu Gln Ala Glu Asn Ile
1295 1300 1305

Ile His Leu Phe Thr Leu Thr Asn Leu Gly Ala Pro Ala Ala Phe
1310 1315 1320

Lys Tyr Phe Asp Thr Thr Ile Asp Arg Lys Arg Tyr Thr Ser Thr
1325 1330 1335

Lys Glu Val Leu Asp Ala Thr Leu Ile His Gln Ser Ile Thr Gly
1340 1345 1350

Leu Tyr Glu Thr Arg Ile Asp Leu Ser Gln Leu Gly Gly Asp
1355 1360 1365

<210> SEQ ID NO 754
<211> LENGTH: 1367
<212> TYPE: PRT
<213> ORGANISM: Artificial Sequence
<220> FEATURE:
<223> OTHER INFORMATION: Synthetic Polypeptide

<400> SEQUENCE: 754

Asp Lys Lys Tyr Ser Ile Gly Leu Asp Ile Gly Thr Asn Ser Val Gly
1 5 10 15

Trp Ala Val Ile Thr Asp Glu Tyr Lys Val Pro Ser Lys Lys Phe Lys
20 25 30

Val Leu Gly Asn Thr Asp Arg His Ser Ile Lys Lys Asn Leu Ile Gly
35 40 45

Ala Leu Leu Phe Asp Ser Gly Glu Thr Ala Glu Ala Thr Arg Leu Lys
50 55 60

Arg Thr Ala Arg Arg Arg Tyr Thr Arg Arg Lys Asn Arg Ile Cys Tyr
65 70 75 80

Leu Gln Glu Ile Phe Ser Asn Glu Met Ala Lys Val Asp Asp Ser Phe
85 90 95

Phe His Arg Leu Glu Glu Ser Phe Leu Val Glu Glu Asp Lys Lys His
100 105 110

Glu Arg His Pro Ile Phe Gly Asn Ile Val Asp Glu Val Ala Tyr His
115 120 125

Glu Lys Tyr Pro Thr Ile Tyr His Leu Arg Lys Lys Leu Val Asp Ser
130 135 140

Thr Asp Lys Ala Asp Leu Arg Leu Ile Tyr Leu Ala Leu Ala His Met
145 150 155 160

Ile Lys Phe Arg Gly His Phe Leu Ile Glu Gly Asp Leu Asn Pro Asp
165 170 175

Asn Ser Asp Val Asp Lys Leu Phe Ile Gln Leu Val Gln Thr Tyr Asn
180 185 190

Gln Leu Phe Glu Glu Asn Pro Ile Asn Ala Ser Gly Val Asp Ala Lys
195 200 205

Ala Ile Leu Ser Ala Arg Leu Ser Lys Ser Arg Arg Leu Glu Asn Leu
210 215 220

Ile Ala Gln Leu Pro Gly Glu Lys Lys Asn Gly Leu Phe Gly Asn Leu
225 230 235 240

Ile Ala Leu Ser Leu Gly Leu Thr Pro Asn Phe Lys Ser Asn Phe Asp
245 250 255

```
Leu Ala Glu Asp Ala Lys Leu Gln Leu Ser Lys Asp Thr Tyr Asp Asp
            260                 265                 270

Asp Leu Asp Asn Leu Leu Ala Gln Ile Gly Asp Gln Tyr Ala Asp Leu
        275                 280                 285

Phe Leu Ala Ala Lys Asn Leu Ser Asp Ala Ile Leu Leu Ser Asp Ile
    290                 295                 300

Leu Arg Val Asn Thr Glu Ile Thr Lys Ala Pro Leu Ser Ala Ser Met
305                 310                 315                 320

Ile Lys Arg Tyr Asp Glu His His Gln Asp Leu Thr Leu Leu Lys Ala
                325                 330                 335

Leu Val Arg Gln Gln Leu Pro Glu Lys Tyr Lys Glu Ile Phe Phe Asp
            340                 345                 350

Gln Ser Lys Asn Gly Tyr Ala Gly Tyr Ile Asp Gly Gly Ala Ser Gln
        355                 360                 365

Glu Glu Phe Tyr Lys Phe Ile Lys Pro Ile Leu Glu Lys Met Asp Gly
    370                 375                 380

Thr Glu Glu Leu Leu Val Lys Leu Asn Arg Glu Asp Leu Leu Arg Lys
385                 390                 395                 400

Gln Arg Thr Phe Asp Asn Gly Ser Ile Pro His Gln Ile His Leu Gly
                405                 410                 415

Glu Leu His Ala Ile Leu Arg Arg Gln Glu Asp Phe Tyr Pro Phe Leu
            420                 425                 430

Lys Asp Asn Arg Glu Lys Ile Glu Lys Ile Leu Thr Phe Arg Ile Pro
        435                 440                 445

Tyr Tyr Val Gly Pro Leu Ala Arg Gly Asn Ser Arg Phe Ala Trp Met
    450                 455                 460

Thr Arg Lys Ser Glu Glu Thr Ile Thr Pro Trp Asn Phe Glu Glu Val
465                 470                 475                 480

Val Asp Lys Gly Ala Ser Ala Gln Ser Phe Ile Glu Arg Met Thr Asn
                485                 490                 495

Phe Asp Lys Asn Leu Pro Asn Glu Lys Val Leu Pro Lys His Ser Leu
            500                 505                 510

Leu Tyr Glu Tyr Phe Thr Val Tyr Asn Glu Leu Thr Lys Val Lys Tyr
        515                 520                 525

Val Thr Glu Gly Met Arg Lys Pro Ala Phe Leu Ser Gly Glu Gln Lys
    530                 535                 540

Lys Ala Ile Val Asp Leu Leu Phe Lys Thr Asn Arg Lys Val Thr Val
545                 550                 555                 560

Lys Gln Leu Lys Glu Asp Tyr Phe Lys Lys Ile Glu Cys Phe Asp Ser
                565                 570                 575

Val Glu Ile Ser Gly Val Glu Asp Arg Phe Asn Ala Ser Leu Gly Thr
            580                 585                 590

Tyr His Asp Leu Leu Lys Ile Ile Lys Asp Lys Asp Phe Leu Asp Asn
        595                 600                 605

Glu Glu Asn Glu Asp Ile Leu Glu Asp Ile Val Leu Thr Leu Thr Leu
    610                 615                 620

Phe Glu Asp Arg Glu Met Ile Glu Glu Arg Leu Lys Thr Tyr Ala His
625                 630                 635                 640

Leu Phe Asp Asp Lys Val Met Lys Gln Leu Lys Arg Arg Arg Tyr Thr
                645                 650                 655

Gly Trp Gly Arg Leu Ser Arg Lys Leu Ile Asn Gly Ile Arg Asp Lys
            660                 665                 670
```

-continued

```
Gln Ser Gly Lys Thr Ile Leu Asp Phe Leu Lys Ser Asp Gly Phe Ala
        675                 680                 685

Asn Arg Asn Phe Met Gln Leu Ile His Asp Asp Ser Leu Thr Phe Lys
    690                 695                 700

Glu Asp Ile Gln Lys Ala Gln Val Ser Gly Gln Gly Asp Ser Leu His
705                 710                 715                 720

Glu His Ile Ala Asn Leu Ala Gly Ser Pro Ala Ile Lys Lys Gly Ile
                725                 730                 735

Leu Gln Thr Val Lys Val Val Asp Glu Leu Val Lys Val Met Gly Arg
            740                 745                 750

His Lys Pro Glu Asn Ile Val Ile Glu Met Ala Arg Glu Asn Gln Thr
        755                 760                 765

Thr Gln Lys Gly Gln Lys Asn Ser Arg Glu Arg Met Lys Arg Ile Glu
    770                 775                 780

Glu Gly Ile Lys Glu Leu Gly Ser Gln Ile Leu Lys Glu His Pro Val
785                 790                 795                 800

Glu Asn Thr Gln Leu Gln Asn Glu Lys Leu Tyr Leu Tyr Tyr Leu Gln
                805                 810                 815

Asn Gly Arg Asp Met Tyr Val Asp Gln Glu Leu Asp Ile Asn Arg Leu
            820                 825                 830

Ser Asp Tyr Asp Val Asp His Ile Val Pro Gln Ser Phe Leu Lys Asp
        835                 840                 845

Asp Ser Ile Asp Asn Lys Val Leu Thr Arg Ser Asp Lys Asn Arg Gly
    850                 855                 860

Lys Ser Asp Asn Val Pro Ser Glu Glu Val Val Lys Lys Met Lys Asn
865                 870                 875                 880

Tyr Trp Arg Gln Leu Leu Asn Ala Lys Leu Ile Thr Gln Arg Lys Phe
                885                 890                 895

Asp Asn Leu Thr Lys Ala Glu Arg Gly Gly Leu Ser Glu Leu Asp Lys
            900                 905                 910

Ala Gly Phe Ile Lys Arg Gln Leu Val Glu Thr Arg Gln Ile Thr Lys
        915                 920                 925

His Val Ala Gln Ile Leu Asp Ser Arg Met Asn Thr Lys Tyr Asp Glu
    930                 935                 940

Asn Asp Lys Leu Ile Arg Glu Val Lys Val Ile Thr Leu Lys Ser Lys
945                 950                 955                 960

Leu Val Ser Asp Phe Arg Lys Asp Phe Gln Phe Tyr Lys Val Arg Glu
                965                 970                 975

Ile Asn Asn Tyr His His Ala His Asp Ala Tyr Leu Asn Ala Val Val
            980                 985                 990

Gly Thr Ala Leu Ile Lys Lys Tyr  Pro Lys Leu Glu Ser  Glu Phe Val
        995                 1000                1005

Tyr Gly  Asp Tyr Lys Val Tyr  Asp Val Arg Lys Met  Ile Ala Lys
    1010                1015                1020

Ser Glu  Gln Glu Ile Gly Lys  Ala Thr Ala Lys Tyr  Phe Phe Tyr
    1025                1030                1035

Ser Asn  Ile Met Asn Phe Phe  Lys Thr Glu Ile Thr  Leu Ala Asn
    1040                1045                1050

Gly Glu  Ile Arg Lys Arg Pro  Leu Ile Glu Thr Asn  Gly Glu Thr
    1055                1060                1065

Gly Glu  Ile Val Trp Asp Lys  Gly Arg Asp Phe Ala  Thr Val Arg
    1070                1075                1080

Lys Val  Leu Ser Met Pro Gln  Val Asn Ile Val Lys  Lys Thr Glu
```

```
    1085                1090                1095

Val Gln  Thr Gly Gly Phe Ser  Lys Glu Ser Ile Leu  Pro Lys Arg
    1100                1105                1110

Asn Ser  Asp Lys Leu Ile Ala  Arg Lys Lys Asp Trp  Asp Pro Lys
    1115                1120                1125

Lys Tyr  Gly Gly Phe Asp Ser  Pro Thr Val Ala Tyr  Ser Val Leu
    1130                1135                1140

Val Val  Ala Lys Val Glu Lys  Gly Lys Ser Lys Lys  Leu Lys Ser
    1145                1150                1155

Val Lys  Glu Leu Leu Gly Ile  Thr Ile Met Glu Arg  Ser Ser Phe
    1160                1165                1170

Glu Lys  Asn Pro Ile Asp Phe  Leu Glu Ala Lys Gly  Tyr Lys Glu
    1175                1180                1185

Val Lys  Lys Asp Leu Ile Ile  Lys Leu Pro Lys Tyr  Ser Leu Phe
    1190                1195                1200

Glu Leu  Glu Asn Gly Arg Lys  Arg Met Leu Ala Ser  Ala Gly Glu
    1205                1210                1215

Leu Gln  Lys Gly Asn Glu Leu  Ala Leu Pro Ser Lys  Tyr Val Asn
    1220                1225                1230

Phe Leu  Tyr Leu Ala Ser His  Tyr Glu Lys Leu Lys  Gly Ser Pro
    1235                1240                1245

Glu Asp  Asn Glu Gln Lys Gln  Leu Phe Val Glu Gln  His Lys His
    1250                1255                1260

Tyr Leu  Asp Glu Ile Ile Glu  Gln Ile Ser Glu Phe  Ser Lys Arg
    1265                1270                1275

Val Ile  Leu Ala Asp Ala Asn  Leu Asp Lys Val Leu  Ser Ala Tyr
    1280                1285                1290

Asn Lys  His Arg Asp Lys Pro  Ile Arg Glu Gln Ala  Glu Asn Ile
    1295                1300                1305

Ile His  Leu Phe Thr Leu Thr  Asn Leu Gly Ala Pro  Ala Ala Phe
    1310                1315                1320

Lys Tyr  Phe Asp Thr Thr Ile  Asp Arg Lys Arg Tyr  Thr Ser Thr
    1325                1330                1335

Lys Glu  Val Leu Asp Ala Thr  Leu Ile His Gln Ser  Ile Thr Gly
    1340                1345                1350

Leu Tyr  Glu Thr Arg Ile Asp  Leu Ser Gln Leu Gly  Gly Asp
    1355                1360                1365


<210> SEQ ID NO 755
<211> LENGTH: 345
<212> TYPE: PRT
<213> ORGANISM: Sulfolobus islandicus

<400> SEQUENCE: 755

Met Glu Val Pro Leu Tyr Asn Ile Phe Gly Asp Asn Tyr Ile Ile Gln
1               5                   10                  15

Val Ala Thr Glu Ala Glu Asn Ser Thr Ile Tyr Asn Asn Lys Val Glu
            20                  25                  30

Ile Asp Asp Glu Glu Leu Arg Asn Val Leu Asn Leu Ala Tyr Lys Ile
        35                  40                  45

Ala Lys Asn Asn Glu Asp Ala Ala Ala Glu Arg Arg Gly Lys Ala Lys
    50                  55                  60

Lys Lys Lys Gly Glu Glu Gly Glu Thr Thr Thr Ser Asn Ile Ile Leu
65                  70                  75                  80
```

Pro Leu Ser Gly Asn Asp Lys Asn Pro Trp Thr Glu Thr Leu Lys Cys
85 90 95

Tyr Asn Phe Pro Thr Thr Val Ala Leu Ser Glu Val Phe Lys Asn Phe
100 105 110

Ser Gln Val Lys Glu Cys Glu Glu Val Ser Ala Pro Ser Phe Val Lys
115 120 125

Pro Glu Phe Tyr Glu Phe Gly Arg Ser Pro Gly Met Val Glu Arg Thr
130 135 140

Arg Arg Val Lys Leu Glu Val Glu Pro His Tyr Leu Ile Ile Ala Ala
145 150 155 160

Ala Gly Trp Val Leu Thr Arg Leu Gly Lys Ala Lys Val Ser Glu Gly
165 170 175

Asp Tyr Val Gly Val Asn Val Phe Thr Pro Thr Arg Gly Ile Leu Tyr
180 185 190

Ser Leu Ile Gln Asn Val Asn Gly Ile Val Pro Gly Ile Lys Pro Glu
195 200 205

Thr Ala Phe Gly Leu Trp Ile Ala Arg Lys Val Val Ser Ser Val Thr
210 215 220

Asn Pro Asn Val Ser Val Val Arg Ile Tyr Thr Ile Ser Asp Ala Val
225 230 235 240

Gly Gln Asn Pro Thr Thr Ile Asn Gly Gly Phe Ser Ile Asp Leu Thr
245 250 255

Lys Leu Leu Glu Lys Arg Tyr Leu Leu Ser Glu Arg Leu Glu Ala Ile
260 265 270

Ala Arg Asn Ala Leu Ser Ile Ser Ser Asn Met Arg Glu Arg Tyr Ile
275 280 285

Val Leu Ala Asn Tyr Ile Tyr Glu Tyr Leu Thr Gly Ser Lys Arg Leu
290 295 300

Glu Asp Leu Leu Tyr Phe Ala Asn Arg Asp Leu Ile Met Asn Leu Asn
305 310 315 320

Ser Asp Asp Gly Lys Val Arg Asp Leu Lys Leu Ile Ser Ala Tyr Val
325 330 335

Asn Gly Glu Leu Ile Arg Gly Glu Gly
340 345

<210> SEQ ID NO 756
<211> LENGTH: 345
<212> TYPE: PRT
<213> ORGANISM: Sulfolobus islandicus

<400> SEQUENCE: 756

Met Glu Val Pro Leu Tyr Asn Ile Phe Gly Asp Asn Tyr Ile Ile Gln
1 5 10 15

Val Ala Thr Glu Ala Glu Asn Ser Thr Ile Tyr Asn Asn Lys Val Glu
20 25 30

Ile Asp Asp Glu Glu Leu Arg Asn Val Leu Asn Leu Ala Tyr Lys Ile
35 40 45

Ala Lys Asn Asn Glu Asp Ala Ala Ala Glu Arg Arg Gly Lys Ala Lys
50 55 60

Lys Lys Lys Gly Glu Glu Gly Glu Thr Thr Thr Ser Asn Ile Ile Leu
65 70 75 80

Pro Leu Ser Gly Asn Asp Lys Asn Pro Trp Thr Glu Thr Leu Lys Cys
85 90 95

Tyr Asn Phe Pro Thr Thr Val Ala Leu Ser Glu Val Phe Lys Asn Phe
100 105 110

Ser Gln Val Lys Glu Cys Glu Glu Val Ser Ala Pro Ser Phe Val Lys
115 120 125

Pro Glu Phe Tyr Lys Phe Gly Arg Ser Pro Gly Met Val Glu Arg Thr
130 135 140

Arg Arg Val Lys Leu Glu Val Glu Pro His Tyr Leu Ile Met Ala Ala
145 150 155 160

Ala Gly Trp Val Leu Thr Arg Leu Gly Lys Ala Lys Val Ser Glu Gly
165 170 175

Asp Tyr Val Gly Val Asn Val Phe Thr Pro Thr Arg Gly Ile Leu Tyr
180 185 190

Ser Leu Ile Gln Asn Val Asn Gly Ile Val Pro Gly Ile Lys Pro Glu
195 200 205

Thr Ala Phe Gly Leu Trp Ile Ala Arg Lys Val Val Ser Ser Val Thr
210 215 220

Asn Pro Asn Val Ser Val Val Ser Ile Tyr Thr Ile Ser Asp Ala Val
225 230 235 240

Gly Gln Asn Pro Thr Thr Ile Asn Gly Gly Phe Ser Ile Asp Leu Thr
245 250 255

Lys Leu Leu Glu Lys Arg Asp Leu Leu Ser Glu Arg Leu Glu Ala Ile
260 265 270

Ala Arg Asn Ala Leu Ser Ile Ser Ser Asn Met Arg Glu Arg Tyr Ile
275 280 285

Val Leu Ala Asn Tyr Ile Tyr Glu Tyr Leu Thr Gly Ser Lys Arg Leu
290 295 300

Glu Asp Leu Leu Tyr Phe Ala Asn Arg Asp Leu Ile Met Asn Leu Asn
305 310 315 320

Ser Asp Asp Gly Lys Val Arg Asp Leu Lys Leu Ile Ser Ala Tyr Val
325 330 335

Asn Gly Glu Leu Ile Arg Gly Glu Gly
340 345

<210> SEQ ID NO 757
<211> LENGTH: 1210
<212> TYPE: PRT
<213> ORGANISM: Unknown
<220> FEATURE:
<223> OTHER INFORMATION: Percubacteria

<400> SEQUENCE: 757

Met Ser Lys Arg His Pro Arg Ile Ser Gly Val Lys Gly Tyr Arg Leu
1 5 10 15

His Ala Gln Arg Leu Glu Tyr Thr Gly Lys Ser Gly Ala Met Arg Thr
20 25 30

Ile Lys Tyr Pro Leu Tyr Ser Ser Pro Ser Gly Gly Arg Thr Val Pro
35 40 45

Arg Glu Ile Val Ser Ala Ile Asn Asp Asp Tyr Val Gly Leu Tyr Gly
50 55 60

Leu Ser Asn Phe Asp Asp Leu Tyr Asn Ala Glu Lys Arg Asn Glu Glu
65 70 75 80

Lys Val Tyr Ser Val Leu Asp Phe Trp Tyr Asp Cys Val Gln Tyr Gly
85 90 95

Ala Val Phe Ser Tyr Thr Ala Pro Gly Leu Leu Lys Asn Val Ala Glu
100 105 110

Val Arg Gly Gly Ser Tyr Glu Leu Thr Lys Thr Leu Lys Gly Ser His
115 120 125

```
Leu Tyr Asp Glu Leu Gln Ile Asp Lys Val Ile Lys Phe Leu Asn Lys
    130                 135                 140

Lys Glu Ile Ser Arg Ala Asn Gly Ser Leu Asp Lys Leu Lys Lys Asp
145                 150                 155                 160

Ile Ile Asp Cys Phe Lys Ala Glu Tyr Arg Glu Arg His Lys Asp Gln
                165                 170                 175

Cys Asn Lys Leu Ala Asp Asp Ile Lys Asn Ala Lys Lys Asp Ala Gly
            180                 185                 190

Ala Ser Leu Gly Glu Arg Gln Lys Lys Leu Phe Arg Asp Phe Phe Gly
        195                 200                 205

Ile Ser Glu Gln Ser Glu Asn Asp Lys Pro Ser Phe Thr Asn Pro Leu
    210                 215                 220

Asn Leu Thr Cys Cys Leu Leu Pro Phe Asp Thr Val Asn Asn Asn Arg
225                 230                 235                 240

Asn Arg Gly Glu Val Leu Phe Asn Lys Leu Lys Glu Tyr Ala Gln Lys
                245                 250                 255

Leu Asp Lys Asn Glu Gly Ser Leu Glu Met Trp Glu Tyr Ile Gly Ile
            260                 265                 270

Gly Asn Ser Gly Thr Ala Phe Ser Asn Phe Leu Gly Glu Gly Phe Leu
        275                 280                 285

Gly Arg Leu Arg Glu Asn Lys Ile Thr Glu Leu Lys Lys Ala Met Met
    290                 295                 300

Asp Ile Thr Asp Ala Trp Arg Gly Gln Glu Gln Glu Glu Glu Leu Glu
305                 310                 315                 320

Lys Arg Leu Arg Ile Leu Ala Ala Leu Thr Ile Lys Leu Arg Glu Pro
                325                 330                 335

Lys Phe Asp Asn His Trp Gly Gly Tyr Arg Ser Asp Ile Asn Gly Lys
            340                 345                 350

Leu Ser Ser Trp Leu Gln Asn Tyr Ile Asn Gln Thr Val Lys Ile Lys
        355                 360                 365

Glu Asp Leu Lys Gly His Lys Lys Asp Leu Lys Lys Ala Lys Glu Met
    370                 375                 380

Ile Asn Arg Phe Gly Glu Ser Asp Thr Lys Glu Glu Ala Val Val Ser
385                 390                 395                 400

Ser Leu Leu Glu Ser Ile Glu Lys Ile Val Pro Asp Asp Ser Ala Asp
                405                 410                 415

Asp Glu Lys Pro Asp Ile Pro Ala Ile Ala Ile Tyr Arg Arg Phe Leu
            420                 425                 430

Ser Asp Gly Arg Leu Thr Leu Asn Arg Phe Val Gln Arg Glu Asp Val
        435                 440                 445

Gln Glu Ala Leu Ile Lys Glu Arg Leu Glu Ala Glu Lys Lys Lys Lys
    450                 455                 460

Pro Lys Lys Arg Lys Lys Lys Ser Asp Ala Glu Asp Glu Lys Glu Thr
465                 470                 475                 480

Ile Asp Phe Lys Glu Leu Phe Pro His Leu Ala Lys Pro Leu Lys Leu
                485                 490                 495

Val Pro Asn Phe Tyr Gly Asp Ser Lys Arg Glu Leu Tyr Lys Lys Tyr
            500                 505                 510

Lys Asn Ala Ala Ile Tyr Thr Asp Ala Leu Trp Lys Ala Val Glu Lys
        515                 520                 525

Ile Tyr Lys Ser Ala Phe Ser Ser Ser Leu Lys Asn Ser Phe Phe Asp
    530                 535                 540
```

-continued

```
Thr Asp Phe Asp Lys Asp Phe Phe Ile Lys Arg Leu Gln Lys Ile Phe
545                 550                 555                 560

Ser Val Tyr Arg Arg Phe Asn Thr Asp Lys Trp Lys Pro Ile Val Lys
                565                 570                 575

Asn Ser Phe Ala Pro Tyr Cys Asp Ile Val Ser Leu Ala Glu Asn Glu
            580                 585                 590

Val Leu Tyr Lys Pro Lys Gln Ser Arg Ser Arg Lys Ser Ala Ala Ile
        595                 600                 605

Asp Lys Asn Arg Val Arg Leu Pro Ser Thr Glu Asn Ile Ala Lys Ala
    610                 615                 620

Gly Ile Ala Leu Ala Arg Glu Leu Ser Val Ala Gly Phe Asp Trp Lys
625                 630                 635                 640

Asp Leu Leu Lys Lys Glu Glu His Glu Glu Tyr Ile Asp Leu Ile Glu
                645                 650                 655

Leu His Lys Thr Ala Leu Ala Leu Leu Leu Ala Val Thr Glu Thr Gln
            660                 665                 670

Leu Asp Ile Ser Ala Leu Asp Phe Val Glu Asn Gly Thr Val Lys Asp
        675                 680                 685

Phe Met Lys Thr Arg Asp Gly Asn Leu Val Leu Glu Gly Arg Phe Leu
    690                 695                 700

Glu Met Phe Ser Gln Ser Ile Val Phe Ser Glu Leu Arg Gly Leu Ala
705                 710                 715                 720

Gly Leu Met Ser Arg Lys Glu Phe Ile Thr Arg Ser Ala Ile Gln Thr
                725                 730                 735

Met Asn Gly Lys Gln Ala Glu Leu Leu Tyr Ile Pro His Glu Phe Gln
            740                 745                 750

Ser Ala Lys Ile Thr Thr Pro Lys Glu Met Ser Arg Ala Phe Leu Asp
        755                 760                 765

Leu Ala Pro Ala Glu Phe Ala Thr Ser Leu Glu Pro Glu Ser Leu Ser
    770                 775                 780

Glu Lys Ser Leu Leu Lys Leu Lys Gln Met Arg Tyr Tyr Pro His Tyr
785                 790                 795                 800

Phe Gly Tyr Glu Leu Thr Arg Thr Gly Gln Gly Ile Asp Gly Gly Val
                805                 810                 815

Ala Glu Asn Ala Leu Arg Leu Glu Lys Ser Pro Val Lys Lys Arg Glu
            820                 825                 830

Ile Lys Cys Lys Gln Tyr Lys Thr Leu Gly Arg Gly Gln Asn Lys Ile
        835                 840                 845

Val Leu Tyr Val Arg Ser Ser Tyr Tyr Gln Thr Gln Phe Leu Glu Trp
    850                 855                 860

Phe Leu His Arg Pro Lys Asn Val Gln Thr Asp Val Ala Val Ser Gly
865                 870                 875                 880

Ser Phe Leu Ile Asp Glu Lys Lys Val Lys Thr Arg Trp Asn Tyr Asp
                885                 890                 895

Ala Leu Thr Val Ala Leu Glu Pro Val Ser Gly Ser Glu Arg Val Phe
            900                 905                 910

Val Ser Gln Pro Phe Thr Ile Phe Pro Glu Lys Ser Ala Glu Glu Glu
        915                 920                 925

Gly Gln Arg Tyr Leu Gly Ile Asp Ile Gly Glu Tyr Gly Ile Ala Tyr
    930                 935                 940

Thr Ala Leu Glu Ile Thr Gly Asp Ser Ala Lys Ile Leu Asp Gln Asn
945                 950                 955                 960

Phe Ile Ser Asp Pro Gln Leu Lys Thr Leu Arg Glu Glu Val Lys Gly
```

-continued

```
            965                 970                 975

Leu Lys Leu Asp Gln Arg Arg Gly Thr Phe Ala Met Pro Ser Thr Lys
            980                 985                 990

Ile Ala Arg Ile Arg Glu Ser Leu  Val His Ser Leu Arg  Asn Arg Ile
        995                 1000                1005

His His  Leu Ala Leu Lys His  Lys Ala Lys Ile Val  Tyr Glu Leu
    1010                 1015                 1020

Glu Val  Ser Arg Phe Glu Glu  Gly Lys Gln Lys Ile  Lys Lys Val
    1025                 1030                 1035

Tyr Ala  Thr Leu Lys Lys Ala  Asp Val Tyr Ser Glu  Ile Asp Ala
    1040                 1045                 1050

Asp Lys  Asn Leu Gln Thr Thr  Val Trp Gly Lys Leu  Ala Val Ala
    1055                 1060                 1065

Ser Glu  Ile Ser Ala Ser Tyr  Thr Ser Gln Phe Cys  Gly Ala Cys
    1070                 1075                 1080

Lys Lys  Leu Trp Arg Ala Glu  Met Gln Val Asp Glu  Thr Ile Thr
    1085                 1090                 1095

Thr Gln  Glu Leu Ile Gly Thr  Val Arg Val Ile Lys  Gly Gly Thr
    1100                 1105                 1110

Leu Ile  Asp Ala Ile Lys Asp  Phe Met Arg Pro Pro  Ile Phe Asp
    1115                 1120                 1125

Glu Asn  Asp Thr Pro Phe Pro  Lys Tyr Arg Asp Phe  Cys Asp Lys
    1130                 1135                 1140

His His  Ile Ser Lys Lys Met  Arg Gly Asn Ser Cys  Leu Phe Ile
    1145                 1150                 1155

Cys Pro  Phe Cys Arg Ala Asn  Ala Asp Ala Asp Ile  Gln Ala Ser
    1160                 1165                 1170

Gln Thr  Ile Ala Leu Leu Arg  Tyr Val Lys Glu Glu  Lys Lys Val
    1175                 1180                 1185

Glu Asp  Tyr Phe Glu Arg Phe  Arg Lys Leu Lys Asn  Ile Lys Val
    1190                 1195                 1200

Leu Gly  Gln Met Lys Lys Ile
    1205                 1210
```

<210> SEQ ID NO 758
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 758

Ser Gly Gly Ser
1

<210> SEQ ID NO 759
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 759

Gly Gly Gly Ser
1

<210> SEQ ID NO 760
<211> LENGTH: 91

<212> TYPE: DNA
<213> ORGANISM: Artificial Sequence
<220> FEATURE:
<223> OTHER INFORMATION: Synthetic Polynucleotide

<400> SEQUENCE: 760
cctagggaag tgatcatagc tgagtttcta tctcatggtt tatgctaaac tatatgttga 60
catgttgagg agacttaagt ccaaaacctg g 91

<210> SEQ ID NO 761
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 761

Met Asp Ser Leu Leu Met Asn Arg Arg Lys Phe Leu Tyr Gln Phe Lys
1 5 10 15

Asn Val Arg Trp Ala Lys Gly Arg Arg Glu Thr Tyr Leu Cys
20 25 30

<210> SEQ ID NO 762
<211> LENGTH: 1129
<212> TYPE: PRT
<213> ORGANISM: Alicyclobacillus acidoterrestris

<400> SEQUENCE: 762

Met Ala Val Lys Ser Ile Lys Val Lys Leu Arg Leu Asp Asp Met Pro
1 5 10 15

Glu Ile Arg Ala Gly Leu Trp Lys Leu His Lys Glu Val Asn Ala Gly
20 25 30

Val Arg Tyr Tyr Thr Glu Trp Leu Ser Leu Leu Arg Gln Glu Asn Leu
35 40 45

Tyr Arg Arg Ser Pro Asn Gly Asp Gly Glu Gln Glu Cys Asp Lys Thr
50 55 60

Ala Glu Glu Cys Lys Ala Glu Leu Leu Glu Arg Leu Arg Ala Arg Gln
65 70 75 80

Val Glu Asn Gly His Arg Gly Pro Ala Gly Ser Asp Asp Glu Leu Leu
85 90 95

Gln Leu Ala Arg Gln Leu Tyr Glu Leu Leu Val Pro Gln Ala Ile Gly
100 105 110

Ala Lys Gly Asp Ala Gln Gln Ile Ala Arg Lys Phe Leu Ser Pro Leu
115 120 125

Ala Asp Lys Asp Ala Val Gly Gly Leu Gly Ile Ala Lys Ala Gly Asn
130 135 140

Lys Pro Arg Trp Val Arg Met Arg Glu Ala Gly Glu Pro Gly Trp Glu
145 150 155 160

Glu Glu Lys Glu Lys Ala Glu Thr Arg Lys Ser Ala Asp Arg Thr Ala
165 170 175

Asp Val Leu Arg Ala Leu Ala Asp Phe Gly Leu Lys Pro Leu Met Arg
180 185 190

Val Tyr Thr Asp Ser Glu Met Ser Ser Val Glu Trp Lys Pro Leu Arg
195 200 205

Lys Gly Gln Ala Val Arg Thr Trp Asp Arg Asp Met Phe Gln Gln Ala
210 215 220

Ile Glu Arg Met Met Ser Trp Glu Ser Trp Asn Gln Arg Val Gly Gln
225 230 235 240

```
Glu Tyr Ala Lys Leu Val Glu Gln Lys Asn Arg Phe Glu Gln Lys Asn
                245                 250                 255

Phe Val Gly Gln Glu His Leu Val His Leu Val Asn Gln Leu Gln Gln
            260                 265                 270

Asp Met Lys Glu Ala Ser Pro Gly Leu Glu Ser Lys Glu Gln Thr Ala
        275                 280                 285

His Tyr Val Thr Gly Arg Ala Leu Arg Gly Ser Asp Lys Val Phe Glu
    290                 295                 300

Lys Trp Gly Lys Leu Ala Pro Asp Ala Pro Phe Asp Leu Tyr Asp Ala
305                 310                 315                 320

Glu Ile Lys Asn Val Gln Arg Arg Asn Thr Arg Arg Phe Gly Ser His
                325                 330                 335

Asp Leu Phe Ala Lys Leu Ala Glu Pro Glu Tyr Gln Ala Leu Trp Arg
            340                 345                 350

Glu Asp Ala Ser Phe Leu Thr Arg Tyr Ala Val Tyr Asn Ser Ile Leu
        355                 360                 365

Arg Lys Leu Asn His Ala Lys Met Phe Ala Thr Phe Thr Leu Pro Asp
    370                 375                 380

Ala Thr Ala His Pro Ile Trp Thr Arg Phe Asp Lys Leu Gly Gly Asn
385                 390                 395                 400

Leu His Gln Tyr Thr Phe Leu Phe Asn Glu Phe Gly Glu Arg Arg His
                405                 410                 415

Ala Ile Arg Phe His Lys Leu Leu Lys Val Glu Asn Gly Val Ala Arg
            420                 425                 430

Glu Val Asp Asp Val Thr Val Pro Ile Ser Met Ser Glu Gln Leu Asp
        435                 440                 445

Asn Leu Leu Pro Arg Asp Pro Asn Glu Pro Ile Ala Leu Tyr Phe Arg
    450                 455                 460

Asp Tyr Gly Ala Glu Gln His Phe Thr Gly Glu Phe Gly Gly Ala Lys
465                 470                 475                 480

Ile Gln Cys Arg Arg Asp Gln Leu Ala His Met His Arg Arg Arg Gly
                485                 490                 495

Ala Arg Asp Val Tyr Leu Asn Val Ser Val Arg Val Gln Ser Gln Ser
            500                 505                 510

Glu Ala Arg Gly Glu Arg Arg Pro Pro Tyr Ala Ala Val Phe Arg Leu
        515                 520                 525

Val Gly Asp Asn His Arg Ala Phe Val His Phe Asp Lys Leu Ser Asp
    530                 535                 540

Tyr Leu Ala Glu His Pro Asp Asp Gly Lys Leu Gly Ser Glu Gly Leu
545                 550                 555                 560

Leu Ser Gly Leu Arg Val Met Ser Val Asp Leu Gly Leu Arg Thr Ser
                565                 570                 575

Ala Ser Ile Ser Val Phe Arg Val Ala Arg Lys Asp Glu Leu Lys Pro
            580                 585                 590

Asn Ser Lys Gly Arg Val Pro Phe Phe Phe Pro Ile Lys Gly Asn Asp
        595                 600                 605

Asn Leu Val Ala Val His Glu Arg Ser Gln Leu Leu Lys Leu Pro Gly
    610                 615                 620

Glu Thr Glu Ser Lys Asp Leu Arg Ala Ile Arg Glu Glu Arg Gln Arg
625                 630                 635                 640

Thr Leu Arg Gln Leu Arg Thr Gln Leu Ala Tyr Leu Arg Leu Leu Val
                645                 650                 655
```

-continued

```
Arg Cys Gly Ser Glu Asp Val Gly Arg Arg Glu Arg Ser Trp Ala Lys
            660                 665                 670

Leu Ile Glu Gln Pro Val Asp Ala Ala Asn His Met Thr Pro Asp Trp
        675                 680                 685

Arg Glu Ala Phe Glu Asn Glu Leu Gln Lys Leu Lys Ser Leu His Gly
    690                 695                 700

Ile Cys Ser Asp Lys Glu Trp Met Asp Ala Val Tyr Glu Ser Val Arg
705                 710                 715                 720

Arg Val Trp Arg His Met Gly Lys Gln Val Arg Asp Trp Arg Lys Asp
                725                 730                 735

Val Arg Ser Gly Glu Arg Pro Lys Ile Arg Gly Tyr Ala Lys Asp Val
            740                 745                 750

Val Gly Gly Asn Ser Ile Glu Gln Ile Glu Tyr Leu Glu Arg Gln Tyr
        755                 760                 765

Lys Phe Leu Lys Ser Trp Ser Phe Phe Gly Lys Val Ser Gly Gln Val
    770                 775                 780

Ile Arg Ala Glu Lys Gly Ser Arg Phe Ala Ile Thr Leu Arg Glu His
785                 790                 795                 800

Ile Asp His Ala Lys Glu Asp Arg Leu Lys Lys Leu Ala Asp Arg Ile
                805                 810                 815

Ile Met Glu Ala Leu Gly Tyr Val Tyr Ala Leu Asp Glu Arg Gly Lys
            820                 825                 830

Gly Lys Trp Val Ala Lys Tyr Pro Pro Cys Gln Leu Ile Leu Leu Glu
        835                 840                 845

Glu Leu Ser Glu Tyr Gln Phe Asn Asn Asp Arg Pro Pro Ser Glu Asn
    850                 855                 860

Asn Gln Leu Met Gln Trp Ser His Arg Gly Val Phe Gln Glu Leu Ile
865                 870                 875                 880

Asn Gln Ala Gln Val His Asp Leu Leu Val Gly Thr Met Tyr Ala Ala
                885                 890                 895

Phe Ser Ser Arg Phe Asp Ala Arg Thr Gly Ala Pro Gly Ile Arg Cys
            900                 905                 910

Arg Arg Val Pro Ala Arg Cys Thr Gln Glu His Asn Pro Glu Pro Phe
        915                 920                 925

Pro Trp Trp Leu Asn Lys Phe Val Val Glu His Thr Leu Asp Ala Cys
    930                 935                 940

Pro Leu Arg Ala Asp Asp Leu Ile Pro Thr Gly Glu Gly Glu Ile Phe
945                 950                 955                 960

Val Ser Pro Phe Ser Ala Glu Glu Gly Asp Phe His Gln Ile His Ala
                965                 970                 975

Asp Leu Asn Ala Ala Gln Asn Leu Gln Gln Arg Leu Trp Ser Asp Phe
            980                 985                 990

Asp Ile Ser Gln Ile Arg Leu Arg  Cys Asp Trp Gly Glu  Val Asp Gly
        995                 1000                1005

Glu Leu  Val Leu Ile Pro Arg  Leu Thr Gly Lys Arg  Thr Ala Asp
    1010                1015                1020

Ser Tyr  Ser Asn Lys Val Phe  Tyr Thr Asn Thr Gly  Val Thr Tyr
    1025                1030                1035

Tyr Glu  Arg Glu Arg Gly Lys  Lys Arg Arg Lys Val  Phe Ala Gln
    1040                1045                1050

Glu Lys  Leu Ser Glu Glu Glu  Ala Glu Leu Leu Val  Glu Ala Asp
    1055                1060                1065

Glu Ala  Arg Glu Lys Ser Val  Val Leu Met Arg Asp  Pro Ser Gly
```

```
    1070                1075                1080

Ile Ile  Asn Arg Gly Asn Trp  Thr Arg Gln Lys Glu  Phe Trp Ser
    1085                1090                1095

Met Val  Asn Gln Arg Ile Glu  Gly Tyr Leu Val Lys  Gln Ile Arg
    1100                1105                1110

Ser Arg  Val Pro Leu Gln Asp  Ser Ala Cys Glu Asn  Thr Gly Asp
    1115                1120                1125

Ile


<210> SEQ ID NO 763
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 763

Asn Gly Gly Asn Gly
1               5


<210> SEQ ID NO 764
<211> LENGTH: 1389
<212> TYPE: PRT
<213> ORGANISM: Leptotrichia shahii

<400> SEQUENCE: 764

Met Gly Asn Leu Phe Gly His Lys Arg Trp Tyr Glu Val Arg Asp Lys
1               5                   10                  15

Lys Asp Phe Lys Ile Lys Arg Lys Val Lys Val Lys Arg Asn Tyr Asp
            20                  25                  30

Gly Asn Lys Tyr Ile Leu Asn Ile Asn Glu Asn Asn Asn Lys Glu Lys
        35                  40                  45

Ile Asp Asn Asn Lys Phe Ile Arg Lys Tyr Ile Asn Tyr Lys Lys Asn
    50                  55                  60

Asp Asn Ile Leu Lys Glu Phe Thr Arg Lys Phe His Ala Gly Asn Ile
65                  70                  75                  80

Leu Phe Lys Leu Lys Gly Lys Glu Gly Ile Ile Arg Ile Glu Asn Asn
                85                  90                  95

Asp Asp Phe Leu Glu Thr Glu Glu Val Val Leu Tyr Ile Glu Ala Tyr
            100                 105                 110

Gly Lys Ser Glu Lys Leu Lys Ala Leu Gly Ile Thr Lys Lys Lys Ile
        115                 120                 125

Ile Asp Glu Ala Ile Arg Gln Gly Ile Thr Lys Asp Asp Lys Lys Ile
    130                 135                 140

Glu Ile Lys Arg Gln Glu Asn Glu Glu Glu Ile Glu Ile Asp Ile Arg
145                 150                 155                 160

Asp Glu Tyr Thr Asn Lys Thr Leu Asn Asp Cys Ser Ile Ile Leu Arg
                165                 170                 175

Ile Ile Glu Asn Asp Glu Leu Glu Thr Lys Lys Ser Ile Tyr Glu Ile
            180                 185                 190

Phe Lys Asn Ile Asn Met Ser Leu Tyr Lys Ile Ile Glu Lys Ile Ile
        195                 200                 205

Glu Asn Glu Thr Glu Lys Val Phe Glu Asn Arg Tyr Tyr Glu Glu His
    210                 215                 220

Leu Arg Glu Lys Leu Leu Lys Asp Asp Lys Ile Asp Val Ile Leu Thr
225                 230                 235                 240
```

```
Asn Phe Met Glu Ile Arg Glu Lys Ile Lys Ser Asn Leu Glu Ile Leu
                245                 250                 255

Gly Phe Val Lys Phe Tyr Leu Asn Val Gly Gly Asp Lys Lys Lys Ser
            260                 265                 270

Lys Asn Lys Lys Met Leu Val Glu Lys Ile Leu Asn Ile Asn Val Asp
        275                 280                 285

Leu Thr Val Glu Asp Ile Ala Asp Phe Val Ile Lys Glu Leu Glu Phe
    290                 295                 300

Trp Asn Ile Thr Lys Arg Ile Glu Lys Val Lys Lys Val Asn Asn Glu
305                 310                 315                 320

Phe Leu Glu Lys Arg Arg Asn Arg Thr Tyr Ile Lys Ser Tyr Val Leu
                325                 330                 335

Leu Asp Lys His Glu Lys Phe Lys Ile Glu Arg Glu Asn Lys Lys Asp
            340                 345                 350

Lys Ile Val Lys Phe Phe Val Glu Asn Ile Lys Asn Asn Ser Ile Lys
        355                 360                 365

Glu Lys Ile Glu Lys Ile Leu Ala Glu Phe Lys Ile Asp Glu Leu Ile
    370                 375                 380

Lys Lys Leu Glu Lys Glu Leu Lys Lys Gly Asn Cys Asp Thr Glu Ile
385                 390                 395                 400

Phe Gly Ile Phe Lys Lys His Tyr Lys Val Asn Phe Asp Ser Lys Lys
                405                 410                 415

Phe Ser Lys Lys Ser Asp Glu Glu Lys Glu Leu Tyr Lys Ile Ile Tyr
            420                 425                 430

Arg Tyr Leu Lys Gly Arg Ile Glu Lys Ile Leu Val Asn Glu Gln Lys
        435                 440                 445

Val Arg Leu Lys Lys Met Glu Lys Ile Glu Ile Glu Lys Ile Leu Asn
    450                 455                 460

Glu Ser Ile Leu Ser Glu Lys Ile Leu Lys Arg Val Lys Gln Tyr Thr
465                 470                 475                 480

Leu Glu His Ile Met Tyr Leu Gly Lys Leu Arg His Asn Asp Ile Asp
                485                 490                 495

Met Thr Thr Val Asn Thr Asp Asp Phe Ser Arg Leu His Ala Lys Glu
            500                 505                 510

Glu Leu Asp Leu Glu Leu Ile Thr Phe Phe Ala Ser Thr Asn Met Glu
        515                 520                 525

Leu Asn Lys Ile Phe Ser Arg Glu Asn Ile Asn Asn Asp Glu Asn Ile
    530                 535                 540

Asp Phe Phe Gly Gly Asp Arg Glu Lys Asn Tyr Val Leu Asp Lys Lys
545                 550                 555                 560

Ile Leu Asn Ser Lys Ile Lys Ile Ile Arg Asp Leu Asp Phe Ile Asp
                565                 570                 575

Asn Lys Asn Asn Ile Thr Asn Asn Phe Ile Arg Lys Phe Thr Lys Ile
            580                 585                 590

Gly Thr Asn Glu Arg Asn Arg Ile Leu His Ala Ile Ser Lys Glu Arg
        595                 600                 605

Asp Leu Gln Gly Thr Gln Asp Asp Tyr Asn Lys Val Ile Asn Ile Ile
    610                 615                 620

Gln Asn Leu Lys Ile Ser Asp Glu Glu Val Ser Lys Ala Leu Asn Leu
625                 630                 635                 640

Asp Val Val Phe Lys Asp Lys Lys Asn Ile Ile Thr Lys Ile Asn Asp
                645                 650                 655

Ile Lys Ile Ser Glu Glu Asn Asn Asn Asp Ile Lys Tyr Leu Pro Ser
```

```
            660                 665                 670

Phe Ser Lys Val Leu Pro Glu Ile Leu Asn Leu Tyr Arg Asn Asn Pro
        675                 680                 685

Lys Asn Glu Pro Phe Asp Thr Ile Glu Thr Glu Lys Ile Val Leu Asn
    690                 695                 700

Ala Leu Ile Tyr Val Asn Lys Glu Leu Tyr Lys Lys Leu Ile Leu Glu
705                 710                 715                 720

Asp Asp Leu Glu Glu Asn Glu Ser Lys Asn Ile Phe Leu Gln Glu Leu
                725                 730                 735

Lys Lys Thr Leu Gly Asn Ile Asp Glu Ile Asp Glu Asn Ile Ile Glu
            740                 745                 750

Asn Tyr Tyr Lys Asn Ala Gln Ile Ser Ala Ser Lys Gly Asn Asn Lys
        755                 760                 765

Ala Ile Lys Lys Tyr Gln Lys Lys Val Ile Glu Cys Tyr Ile Gly Tyr
    770                 775                 780

Leu Arg Lys Asn Tyr Glu Glu Leu Phe Asp Phe Ser Asp Phe Lys Met
785                 790                 795                 800

Asn Ile Gln Glu Ile Lys Lys Gln Ile Lys Asp Ile Asn Asp Asn Lys
                805                 810                 815

Thr Tyr Glu Arg Ile Thr Val Lys Thr Ser Asp Lys Thr Ile Val Ile
            820                 825                 830

Asn Asp Asp Phe Glu Tyr Ile Ile Ser Ile Phe Ala Leu Leu Asn Ser
        835                 840                 845

Asn Ala Val Ile Asn Lys Ile Arg Asn Arg Phe Phe Ala Thr Ser Val
    850                 855                 860

Trp Leu Asn Thr Ser Glu Tyr Gln Asn Ile Ile Asp Ile Leu Asp Glu
865                 870                 875                 880

Ile Met Gln Leu Asn Thr Leu Arg Asn Glu Cys Ile Thr Glu Asn Trp
                885                 890                 895

Asn Leu Asn Leu Glu Glu Phe Ile Gln Lys Met Lys Glu Ile Glu Lys
            900                 905                 910

Asp Phe Asp Asp Phe Lys Ile Gln Thr Lys Lys Glu Ile Phe Asn Asn
        915                 920                 925

Tyr Tyr Glu Asp Ile Lys Asn Asn Ile Leu Thr Glu Phe Lys Asp Asp
    930                 935                 940

Ile Asn Gly Cys Asp Val Leu Glu Lys Lys Leu Glu Lys Ile Val Ile
945                 950                 955                 960

Phe Asp Asp Glu Thr Lys Phe Glu Ile Asp Lys Lys Ser Asn Ile Leu
                965                 970                 975

Gln Asp Glu Gln Arg Lys Leu Ser Asn Ile Asn Lys Lys Asp Leu Lys
            980                 985                 990

Lys Lys Val Asp Gln Tyr Ile Lys  Asp Lys Asp Gln Glu  Ile Lys Ser
        995                 1000                 1005

Lys Ile  Leu Cys Arg Ile Ile  Phe Asn Ser Asp Phe  Leu Lys Lys
    1010                 1015                 1020

Tyr Lys  Lys Glu Ile Asp Asn  Leu Ile Glu Asp Met  Glu Ser Glu
    1025                 1030                 1035

Asn Glu  Asn Lys Phe Gln Glu  Ile Tyr Tyr Pro Lys  Glu Arg Lys
    1040                 1045                 1050

Asn Glu  Leu Tyr Ile Tyr Lys  Lys Asn Leu Phe Leu  Asn Ile Gly
    1055                 1060                 1065

Asn Pro  Asn Phe Asp Lys Ile  Tyr Gly Leu Ile Ser  Asn Asp Ile
    1070                 1075                 1080
```

```
Lys Met  Ala Asp Ala Lys Phe  Leu Phe Asn Ile Asp  Gly Lys Asn
    1085                 1090                 1095

Ile Arg  Lys Asn Lys Ile Ser  Glu Ile Asp Ala Ile  Leu Lys Asn
    1100                 1105                 1110

Leu Asn  Asp Lys Leu Asn Gly  Tyr Ser Lys Glu Tyr  Lys Glu Lys
    1115                 1120                 1125

Tyr Ile  Lys Lys Leu Lys Glu  Asn Asp Asp Phe Phe  Ala Lys Asn
    1130                 1135                 1140

Ile Gln  Asn Lys Asn Tyr Lys  Ser Phe Glu Lys Asp  Tyr Asn Arg
    1145                 1150                 1155

Val Ser  Glu Tyr Lys Lys Ile  Arg Asp Leu Val Glu  Phe Asn Tyr
    1160                 1165                 1170

Leu Asn  Lys Ile Glu Ser Tyr  Leu Ile Asp Ile Asn  Trp Lys Leu
    1175                 1180                 1185

Ala Ile  Gln Met Ala Arg Phe  Glu Arg Asp Met His  Tyr Ile Val
    1190                 1195                 1200

Asn Gly  Leu Arg Glu Leu Gly  Ile Ile Lys Leu Ser  Gly Tyr Asn
    1205                 1210                 1215

Thr Gly  Ile Ser Arg Ala Tyr  Pro Lys Arg Asn Gly  Ser Asp Gly
    1220                 1225                 1230

Phe Tyr  Thr Thr Thr Ala Tyr  Tyr Lys Phe Phe Asp  Glu Glu Ser
    1235                 1240                 1245

Tyr Lys  Lys Phe Glu Lys Ile  Cys Tyr Gly Phe Gly  Ile Asp Leu
    1250                 1255                 1260

Ser Glu  Asn Ser Glu Ile Asn  Lys Pro Glu Asn Glu  Ser Ile Arg
    1265                 1270                 1275

Asn Tyr  Ile Ser His Phe Tyr  Ile Val Arg Asn Pro  Phe Ala Asp
    1280                 1285                 1290

Tyr Ser  Ile Ala Glu Gln Ile  Asp Arg Val Ser Asn  Leu Leu Ser
    1295                 1300                 1305

Tyr Ser  Thr Arg Tyr Asn Asn  Ser Thr Tyr Ala Ser  Val Phe Glu
    1310                 1315                 1320

Val Phe  Lys Lys Asp Val Asn  Leu Asp Tyr Asp Glu  Leu Lys Lys
    1325                 1330                 1335

Lys Phe  Lys Leu Ile Gly Asn  Asn Asp Ile Leu Glu  Arg Leu Met
    1340                 1345                 1350

Lys Pro  Lys Lys Val Ser Val  Leu Glu Leu Glu Ser  Tyr Asn Ser
    1355                 1360                 1365

Asp Tyr  Ile Lys Asn Leu Ile  Ile Glu Leu Leu Thr  Lys Ile Glu
    1370                 1375                 1380

Asn Thr  Asn Asp Thr Leu
    1385
```

<210> SEQ ID NO 765
<211> LENGTH: 5268
<212> TYPE: DNA
<213> ORGANISM: Artificial Sequence
<220> FEATURE:
<223> OTHER INFORMATION: Synthetic Polynucleotide

<400> SEQUENCE: 765

```
atgtccaacc tccttaccgt ccaccagaat ctccctgccc ttccggtgga tgccacctct     60

gatgaagtgc gaaaaaacct gatggatatg tttcgcgata ggcaagcttt ttctgaacac    120

acgtggaaga tgctcctgtc agtgtgtaga agctgggcag cttggtgcaa gttgaacaac    180
```

-continued

```
cgaaaatggt ttcctgccga acccgaagat gtgagagact acctcctcta cctgcaggct    240
cgagggctcg ccgtgaaaac aatccaacaa cacttgggtc agctcaacat gctgcacagg    300
agatctgggc tgccccggcc gagtgactct aatgccgtta gtctcgtaat gcggcgcatt    360
cgcaaagaga atgtggatgc tggagaacgg gcgaaacagg cactggcttt tgaacggacc    420
gacttcgatc aggtgcggag tcttatggag aatagtgaca gatgccagga cattcggaac    480
cttgcattcc tgggtatcgc gtataatacc ctgctgagaa tcgctgagat cgccagaatc    540
agggtaaagg atatttctcg aacggacggg ggacggatgt tgattcatat cggtcgcact    600
aaaacacttg tgagtaccgc cggggtagag aaagccctga gccttggagt tactaaactg    660
gtggagcggt ggattagcgt gtccggcgtg gcggatgacc caaacaatta cttgttttgt    720
agggtgcgga aaaatggtgt agccgctcca tccgctacct cacagttgag tacacgcgcg    780
ttggagggga ttttcgaagc cacacatcgc ttgatctacg gcgccaagga cgattcaggc    840
cagcgatatc ttgcctggag cgggcatagt gcccgggtgg gtgccgcccg agacatggca    900
agggctggcg tgtcaattcc tgaaatcatg caggccggcg ggtggaccaa cgtgaacatt    960
gtgatgaact atatccggaa cctggatagc gagaccggag caatggtcag actgcttgag   1020
gatggcgacg gtggatccgg agggtccgga ggtagtggcg gcagcggtgg ttcaggtggc   1080
agcggagggt caggaggctc tgataaaaag tattctattg gtttagctat cggcactaat   1140
tccgttggat gggctgtcat aaccgatgaa tacaaagtac cttcaaagaa atttaaggtg   1200
ttggggaaca cagaccgtca ttcgattaaa aagaatctta tcggtgccct cctattcgat   1260
agtggcgaaa cggcagaggc gactcgcctg aaacgaaccg ctcggagaag gtatacacgt   1320
cgcaagaacc gaatatgtta cttacaagaa atttttagca atgagatggc caaagttgac   1380
gattctttct ttcaccgttt ggaagagtcc ttccttgtcg aagaggacaa gaaacatgaa   1440
cggcacccca tctttggaaa catagtagat gaggtggcat atcatgaaaa gtacccaacg   1500
atttatcacc tcagaaaaaa gctagttgac tcaactgata aagcggacct gaggttaatc   1560
tacttggctc ttgcccatat gataaagttc cgtgggcact ttctcattga gggtgatcta   1620
aatccggaca actcggatgt cgacaaactg ttcatccagt tagtacaaac ctataatcag   1680
ttgtttgaag agaaccctat aaatgcaagt ggcgtggatg cgaaggctat tcttagcgcc   1740
cgcctctcta aatcccgacg gctagaaaac ctgatcgcac aattacccgg agagaagaaa   1800
aatgggttgt tcggtaacct tatagcgctc tcactaggcc tgacaccaaa ttttaagtcg   1860
aacttcgact tagctgaaga tgccaaattg cagcttagta aggacacgta cgatgacgat   1920
ctcgacaatc tactggcaca aattggagat cagtatgcgg acttattttt ggctgccaaa   1980
aaccttagcg atgcaatcct cctatctgac atactgagag ttaatactga gattaccaag   2040
gcgccgttat ccgcttcaat gatcaaaagg tacgatgaac atcaccaaga cttgacactt   2100
ctcaaggccc tagtccgtca gcaactgcct gagaaatata aggaaatatt ctttgatcag   2160
tcgaaaaacg ggtacgcagg ttatattgac ggcggagcga gtcaagagga attctacaag   2220
tttatcaaac ccatattaga gaagatggat gggacggaag agttgcttgt aaaactcaat   2280
cgcgaagatc tactgcgaaa gcagcggact ttcgacaacg gtagcattcc acatcaaatc   2340
cacttaggcg aattgcatgc tatacttaga aggcaggagg atttttatcc gttcctcaaa   2400
gacaatcgtg aaaagattga gaaaatccta acctttcgca taccttacta tgtgggaccc   2460
ctggcccgag ggaactctcg gttcgcatgg atgacaagaa agtccgaaga aacgattact   2520
```

```
ccatggaatt ttgaggaagt tgtcgataaa ggtgcgtcag ctcaatcgtt catcgagagg   2580
atgaccaact ttgacaagaa tttaccgaac gaaaaagtat tgcctaagca cagtttactt   2640
tacgagtatt tcacagtgta caatgaactc acgaaagtta agtatgtcac tgagggcatg   2700
cgtaaacccg cctttctaag cggagaacag aagaaagcaa tagtagatct gttattcaag   2760
accaaccgca aagtgacagt taagcaattg aaagaggact actttaagaa aattgaatgc   2820
ttcgattctg tcgagatctc cggggtagaa gatcgattta atgcgtcact tggtacgtat   2880
catgacctcc taaagataat taaagataag gacttcctgg ataacgaaga gaatgaagat   2940
atcttagaag atatagtgtt gactcttacc ctctttgaag atcgggaaat gattgaggaa   3000
agactaaaaa catacgctca cctgttcgac gataaggtta tgaaacagtt aaagaggcgt   3060
cgctatacgg gctggggacg attgtcgcgg aaacttatca acgggataag agacaagcaa   3120
agtggtaaaa ctattctcga ttttctaaag agcgacggct tcgccaatag gaactttatg   3180
cagctgatcc atgatgactc tttaaccttc aaagaggata tacaaaaggc acaggtttcc   3240
ggacaagggg actcattgca cgaacatatt gcgaatcttg ctggttcgcc agccatcaaa   3300
aagggcatac tccagacagt caaagtagtg gatgagctag ttaaggtcat gggacgtcac   3360
aaaccggaaa acattgtaat cgagatggca cgcgaaaatc aaacgactca gaaggggcaa   3420
aaaaacagtc gagagcggat gaagagaata gaagagggta ttaaagaact gggcagccag   3480
atcttaaagg agcatcctgt ggaaaatacc caattgcaga acgagaaact ttacctctat   3540
tacctacaaa atggaaggga catgtatgtt gatcaggaac tggacataaa ccgtttatct   3600
gattacgacg tcgatgccat tgtaccccaa tcctttttga aggacgattc aatcgacaat   3660
aaagtgctta cacgctcgga taagaaccga gggaaaagtg acaatgttcc aagcgaggaa   3720
gtcgtaaaga aaatgaagaa ctattggcgg cagctcctaa atgcgaaact gataacgcaa   3780
agaaagttcg ataacttaac taaagctgag aggggtggct tgtctgaact tgacaaggcc   3840
ggatttatta aacgtcagct cgtggaaacc cgccaaatca caaagcatgt tgcacagata   3900
ctagattccc gaatgaatac gaaatacgac gagaacgata agctgattcg ggaagtcaaa   3960
gtaatcactt taaagtcaaa attggtgtcg gacttcagaa aggattttca attctataaa   4020
gttagggaga taaataacta ccaccatgcg cacgacgctt atcttaatgc cgtcgtaggg   4080
accgcactca ttaagaaata cccgaagcta gaaagtgagt ttgtgtatgg tgattacaaa   4140
gtttatgacg tccgtaagat gatcgcgaaa agcgaacagg agataggcaa ggctacagcc   4200
aaatacttct tttattctaa cattatgaat ttctttaaga cggaaatcac tctggcaaac   4260
ggagagatac gcaaacgacc tttaattgaa accaatgggg agacaggtga aatcgtatgg   4320
gataagggcc gggacttcgc gacggtgaga aaagttttgt ccatgcccca agtcaacata   4380
gtaaagaaaa ctgaggtgca gaccggaggg ttttcaaagg aatcgattct tccaaaaagg   4440
aatagtgata agctcatcgc tcgtaaaaag gactgggacc cgaaaaagta cggtggcttc   4500
gatagcccta cagttgccta ttctgtccta gtagtggcaa aagttgagaa gggaaaatcc   4560
aagaaactga agtcagtcaa agaattattg gggataacga ttatggagcg ctcgtctttt   4620
gaaaagaacc ccatcgactt ccttgaggcg aaaggttaca aggaagtaaa aaaggatctc   4680
ataattaaac taccaaagta tagtctgttt gagttagaaa atggccgaaa acggatgttg   4740
gctagcgccg gagagcttca aaaggggaac gaactcgcac taccgtctaa atacgtgaat   4800
ttcctgtatt tagcgtccca ttacgagaag ttgaaaggtt cacctgaaga taacgaacag   4860
aagcaacttt ttgttgagca gcacaaacat tatctcgacg aaatcataga gcaaatttcg   4920
```

```
gaattcagta agagagtcat cctagctgat gccaatctgg acaaagtatt aagcgcatac   4980

aacaagcaca gggataaacc catacgtgag caggcggaaa atattatcca tttgtttact   5040

cttaccaacc tcggcgctcc agccgcattc aagtattttg acacaacgat agatcgcaaa   5100

cgatacactt ctaccaagga ggtgctagac gcgacactga ttcaccaatc catcacggga   5160

ttatatgaaa ctcggataga tttgtcacag cttgggggtg acggtggctc cgattataag   5220

gatgatgacg acaagggagg ttccccaaag aagaaaagga aggtctga                 5268
```

```
<210> SEQ ID NO 766
<211> LENGTH: 1755
<212> TYPE: PRT
<213> ORGANISM: Artificial Sequence
<220> FEATURE:
<223> OTHER INFORMATION: Synthetic Polypeptide

<400> SEQUENCE: 766

Met Ser Asn Leu Leu Thr Val His Gln Asn Leu Pro Ala Leu Pro Val
1               5                   10                  15

Asp Ala Thr Ser Asp Glu Val Arg Lys Asn Leu Met Asp Met Phe Arg
            20                  25                  30

Asp Arg Gln Ala Phe Ser Glu His Thr Trp Lys Met Leu Leu Ser Val
        35                  40                  45

Cys Arg Ser Trp Ala Ala Trp Cys Lys Leu Asn Asn Arg Lys Trp Phe
    50                  55                  60

Pro Ala Glu Pro Glu Asp Val Arg Asp Tyr Leu Leu Tyr Leu Gln Ala
65                  70                  75                  80

Arg Gly Leu Ala Val Lys Thr Ile Gln Gln His Leu Gly Gln Leu Asn
                85                  90                  95

Met Leu His Arg Arg Ser Gly Leu Pro Arg Pro Ser Asp Ser Asn Ala
            100                 105                 110

Val Ser Leu Val Met Arg Arg Ile Arg Lys Glu Asn Val Asp Ala Gly
        115                 120                 125

Glu Arg Ala Lys Gln Ala Leu Ala Phe Glu Arg Thr Asp Phe Asp Gln
    130                 135                 140

Val Arg Ser Leu Met Glu Asn Ser Asp Arg Cys Gln Asp Ile Arg Asn
145                 150                 155                 160

Leu Ala Phe Leu Gly Ile Ala Tyr Asn Thr Leu Leu Arg Ile Ala Glu
                165                 170                 175

Ile Ala Arg Ile Arg Val Lys Asp Ile Ser Arg Thr Asp Gly Gly Arg
            180                 185                 190

Met Leu Ile His Ile Gly Arg Thr Lys Thr Leu Val Ser Thr Ala Gly
        195                 200                 205

Val Glu Lys Ala Leu Ser Leu Gly Val Thr Lys Leu Val Glu Arg Trp
    210                 215                 220

Ile Ser Val Ser Gly Val Ala Asp Asp Pro Asn Asn Tyr Leu Phe Cys
225                 230                 235                 240

Arg Val Arg Lys Asn Gly Val Ala Ala Pro Ser Ala Thr Ser Gln Leu
                245                 250                 255

Ser Thr Arg Ala Leu Glu Gly Ile Phe Glu Ala Thr His Arg Leu Ile
            260                 265                 270

Tyr Gly Ala Lys Asp Asp Ser Gly Gln Arg Tyr Leu Ala Trp Ser Gly
        275                 280                 285

His Ser Ala Arg Val Gly Ala Ala Arg Asp Met Ala Arg Ala Gly Val
    290                 295                 300
```

```
Ser Ile Pro Glu Ile Met Gln Ala Gly Gly Trp Thr Asn Val Asn Ile
305                 310                 315                 320

Val Met Asn Tyr Ile Arg Asn Leu Asp Ser Glu Thr Gly Ala Met Val
                325                 330                 335

Arg Leu Leu Glu Asp Gly Asp Gly Gly Ser Gly Gly Ser Gly Gly Ser
            340                 345                 350

Gly Gly Ser Gly Gly Ser Gly Gly Ser Gly Gly Ser Gly Gly Ser Asp
        355                 360                 365

Lys Lys Tyr Ser Ile Gly Leu Ala Ile Gly Thr Asn Ser Val Gly Trp
    370                 375                 380

Ala Val Ile Thr Asp Glu Tyr Lys Val Pro Ser Lys Lys Phe Lys Val
385                 390                 395                 400

Leu Gly Asn Thr Asp Arg His Ser Ile Lys Lys Asn Leu Ile Gly Ala
                405                 410                 415

Leu Leu Phe Asp Ser Gly Glu Thr Ala Glu Ala Thr Arg Leu Lys Arg
            420                 425                 430

Thr Ala Arg Arg Arg Tyr Thr Arg Arg Lys Asn Arg Ile Cys Tyr Leu
        435                 440                 445

Gln Glu Ile Phe Ser Asn Glu Met Ala Lys Val Asp Asp Ser Phe Phe
    450                 455                 460

His Arg Leu Glu Glu Ser Phe Leu Val Glu Glu Asp Lys Lys His Glu
465                 470                 475                 480

Arg His Pro Ile Phe Gly Asn Ile Val Asp Glu Val Ala Tyr His Glu
                485                 490                 495

Lys Tyr Pro Thr Ile Tyr His Leu Arg Lys Lys Leu Val Asp Ser Thr
            500                 505                 510

Asp Lys Ala Asp Leu Arg Leu Ile Tyr Leu Ala Leu Ala His Met Ile
        515                 520                 525

Lys Phe Arg Gly His Phe Leu Ile Glu Gly Asp Leu Asn Pro Asp Asn
    530                 535                 540

Ser Asp Val Asp Lys Leu Phe Ile Gln Leu Val Gln Thr Tyr Asn Gln
545                 550                 555                 560

Leu Phe Glu Glu Asn Pro Ile Asn Ala Ser Gly Val Asp Ala Lys Ala
                565                 570                 575

Ile Leu Ser Ala Arg Leu Ser Lys Ser Arg Arg Leu Glu Asn Leu Ile
            580                 585                 590

Ala Gln Leu Pro Gly Glu Lys Lys Asn Gly Leu Phe Gly Asn Leu Ile
        595                 600                 605

Ala Leu Ser Leu Gly Leu Thr Pro Asn Phe Lys Ser Asn Phe Asp Leu
    610                 615                 620

Ala Glu Asp Ala Lys Leu Gln Leu Ser Lys Asp Thr Tyr Asp Asp Asp
625                 630                 635                 640

Leu Asp Asn Leu Leu Ala Gln Ile Gly Asp Gln Tyr Ala Asp Leu Phe
                645                 650                 655

Leu Ala Ala Lys Asn Leu Ser Asp Ala Ile Leu Leu Ser Asp Ile Leu
            660                 665                 670

Arg Val Asn Thr Glu Ile Thr Lys Ala Pro Leu Ser Ala Ser Met Ile
        675                 680                 685

Lys Arg Tyr Asp Glu His His Gln Asp Leu Thr Leu Leu Lys Ala Leu
    690                 695                 700

Val Arg Gln Gln Leu Pro Glu Lys Tyr Lys Glu Ile Phe Phe Asp Gln
705                 710                 715                 720
```

-continued

```
Ser Lys Asn Gly Tyr Ala Gly Tyr Ile Asp Gly Gly Ala Ser Gln Glu
                725                 730                 735

Glu Phe Tyr Lys Phe Ile Lys Pro Ile Leu Glu Lys Met Asp Gly Thr
            740                 745                 750

Glu Glu Leu Leu Val Lys Leu Asn Arg Glu Asp Leu Leu Arg Lys Gln
        755                 760                 765

Arg Thr Phe Asp Asn Gly Ser Ile Pro His Gln Ile His Leu Gly Glu
    770                 775                 780

Leu His Ala Ile Leu Arg Arg Gln Glu Asp Phe Tyr Pro Phe Leu Lys
785                 790                 795                 800

Asp Asn Arg Glu Lys Ile Glu Lys Ile Leu Thr Phe Arg Ile Pro Tyr
                805                 810                 815

Tyr Val Gly Pro Leu Ala Arg Gly Asn Ser Arg Phe Ala Trp Met Thr
            820                 825                 830

Arg Lys Ser Glu Glu Thr Ile Thr Pro Trp Asn Phe Glu Glu Val Val
        835                 840                 845

Asp Lys Gly Ala Ser Ala Gln Ser Phe Ile Glu Arg Met Thr Asn Phe
    850                 855                 860

Asp Lys Asn Leu Pro Asn Glu Lys Val Leu Pro Lys His Ser Leu Leu
865                 870                 875                 880

Tyr Glu Tyr Phe Thr Val Tyr Asn Glu Leu Thr Lys Val Lys Tyr Val
                885                 890                 895

Thr Glu Gly Met Arg Lys Pro Ala Phe Leu Ser Gly Glu Gln Lys Lys
            900                 905                 910

Ala Ile Val Asp Leu Leu Phe Lys Thr Asn Arg Lys Val Thr Val Lys
        915                 920                 925

Gln Leu Lys Glu Asp Tyr Phe Lys Lys Ile Glu Cys Phe Asp Ser Val
    930                 935                 940

Glu Ile Ser Gly Val Glu Asp Arg Phe Asn Ala Ser Leu Gly Thr Tyr
945                 950                 955                 960

His Asp Leu Leu Lys Ile Ile Lys Asp Lys Asp Phe Leu Asp Asn Glu
                965                 970                 975

Glu Asn Glu Asp Ile Leu Glu Asp Ile Val Leu Thr Leu Thr Leu Phe
            980                 985                 990

Glu Asp Arg Glu Met Ile Glu Glu  Arg Leu Lys Thr Tyr  Ala His Leu
        995                 1000                1005

Phe Asp  Asp Lys Val Met Lys  Gln Leu Lys Arg Arg  Arg Tyr Thr
    1010                1015                1020

Gly Trp  Gly Arg Leu Ser Arg  Lys Leu Ile Asn Gly  Ile Arg Asp
    1025                1030                1035

Lys Gln  Ser Gly Lys Thr Ile  Leu Asp Phe Leu Lys  Ser Asp Gly
    1040                1045                1050

Phe Ala  Asn Arg Asn Phe Met  Gln Leu Ile His Asp  Asp Ser Leu
    1055                1060                1065

Thr Phe  Lys Glu Asp Ile Gln  Lys Ala Gln Val Ser  Gly Gln Gly
    1070                1075                1080

Asp Ser  Leu His Glu His Ile  Ala Asn Leu Ala Gly  Ser Pro Ala
    1085                1090                1095

Ile Lys  Lys Gly Ile Leu Gln  Thr Val Lys Val Val  Asp Glu Leu
    1100                1105                1110

Val Lys  Val Met Gly Arg His  Lys Pro Glu Asn Ile  Val Ile Glu
    1115                1120                1125

Met Ala  Arg Glu Asn Gln Thr  Thr Gln Lys Gly Gln  Lys Asn Ser
```

```
    1130                1135                1140

Arg Glu  Arg Met Lys Arg Ile  Glu Glu Gly Ile Lys  Glu Leu Gly
    1145                1150                1155

Ser Gln  Ile Leu Lys Glu His  Pro Val Glu Asn Thr  Gln Leu Gln
    1160                1165                1170

Asn Glu  Lys Leu Tyr Leu Tyr  Tyr Leu Gln Asn Gly  Arg Asp Met
    1175                1180                1185

Tyr Val  Asp Gln Glu Leu Asp  Ile Asn Arg Leu Ser  Asp Tyr Asp
    1190                1195                1200

Val Asp  Ala Ile Val Pro Gln  Ser Phe Leu Lys Asp  Asp Ser Ile
    1205                1210                1215

Asp Asn  Lys Val Leu Thr Arg  Ser Asp Lys Asn Arg  Gly Lys Ser
    1220                1225                1230

Asp Asn  Val Pro Ser Glu Glu  Val Val Lys Lys Met  Lys Asn Tyr
    1235                1240                1245

Trp Arg  Gln Leu Leu Asn Ala  Lys Leu Ile Thr Gln  Arg Lys Phe
    1250                1255                1260

Asp Asn  Leu Thr Lys Ala Glu  Arg Gly Gly Leu Ser  Glu Leu Asp
    1265                1270                1275

Lys Ala  Gly Phe Ile Lys Arg  Gln Leu Val Glu Thr  Arg Gln Ile
    1280                1285                1290

Thr Lys  His Val Ala Gln Ile  Leu Asp Ser Arg Met  Asn Thr Lys
    1295                1300                1305

Tyr Asp  Glu Asn Asp Lys Leu  Ile Arg Glu Val Lys  Val Ile Thr
    1310                1315                1320

Leu Lys  Ser Lys Leu Val Ser  Asp Phe Arg Lys Asp  Phe Gln Phe
    1325                1330                1335

Tyr Lys  Val Arg Glu Ile Asn  Asn Tyr His His Ala  His Asp Ala
    1340                1345                1350

Tyr Leu  Asn Ala Val Val Gly  Thr Ala Leu Ile Lys  Lys Tyr Pro
    1355                1360                1365

Lys Leu  Glu Ser Glu Phe Val  Tyr Gly Asp Tyr Lys  Val Tyr Asp
    1370                1375                1380

Val Arg  Lys Met Ile Ala Lys  Ser Glu Gln Glu Ile  Gly Lys Ala
    1385                1390                1395

Thr Ala  Lys Tyr Phe Phe Tyr  Ser Asn Ile Met Asn  Phe Phe Lys
    1400                1405                1410

Thr Glu  Ile Thr Leu Ala Asn  Gly Glu Ile Arg Lys  Arg Pro Leu
    1415                1420                1425

Ile Glu  Thr Asn Gly Glu Thr  Gly Glu Ile Val Trp  Asp Lys Gly
    1430                1435                1440

Arg Asp  Phe Ala Thr Val Arg  Lys Val Leu Ser Met  Pro Gln Val
    1445                1450                1455

Asn Ile  Val Lys Lys Thr Glu  Val Gln Thr Gly Gly  Phe Ser Lys
    1460                1465                1470

Glu Ser  Ile Leu Pro Lys Arg  Asn Ser Asp Lys Leu  Ile Ala Arg
    1475                1480                1485

Lys Lys  Asp Trp Asp Pro Lys  Lys Tyr Gly Gly Phe  Asp Ser Pro
    1490                1495                1500

Thr Val  Ala Tyr Ser Val Leu  Val Val Ala Lys Val  Glu Lys Gly
    1505                1510                1515

Lys Ser  Lys Lys Leu Lys Ser  Val Lys Glu Leu Leu  Gly Ile Thr
    1520                1525                1530
```

```
Ile Met  Glu Arg Ser Ser Phe  Glu Lys Asn Pro Ile  Asp Phe Leu
    1535                 1540                 1545

Glu Ala  Lys Gly Tyr Lys Glu  Val Lys Lys Asp Leu  Ile Ile Lys
    1550                 1555                 1560

Leu Pro  Lys Tyr Ser Leu Phe  Glu Leu Glu Asn Gly  Arg Lys Arg
    1565                 1570                 1575

Met Leu  Ala Ser Ala Gly Glu  Leu Gln Lys Gly Asn  Glu Leu Ala
    1580                 1585                 1590

Leu Pro  Ser Lys Tyr Val Asn  Phe Leu Tyr Leu Ala  Ser His Tyr
    1595                 1600                 1605

Glu Lys  Leu Lys Gly Ser Pro  Glu Asp Asn Glu Gln  Lys Gln Leu
    1610                 1615                 1620

Phe Val  Glu Gln His Lys His  Tyr Leu Asp Glu Ile  Ile Glu Gln
    1625                 1630                 1635

Ile Ser  Glu Phe Ser Lys Arg  Val Ile Leu Ala Asp  Ala Asn Leu
    1640                 1645                 1650

Asp Lys  Val Leu Ser Ala Tyr  Asn Lys His Arg Asp  Lys Pro Ile
    1655                 1660                 1665

Arg Glu  Gln Ala Glu Asn Ile  Ile His Leu Phe Thr  Leu Thr Asn
    1670                 1675                 1680

Leu Gly  Ala Pro Ala Ala Phe  Lys Tyr Phe Asp Thr  Thr Ile Asp
    1685                 1690                 1695

Arg Lys  Arg Tyr Thr Ser Thr  Lys Glu Val Leu Asp  Ala Thr Leu
    1700                 1705                 1710

Ile His  Gln Ser Ile Thr Gly  Leu Tyr Glu Thr Arg  Ile Asp Leu
    1715                 1720                 1725

Ser Gln  Leu Gly Gly Asp Gly  Gly Ser Asp Tyr Lys  Asp Asp Asp
    1730                 1735                 1740

Asp Lys  Gly Gly Ser Pro Lys  Lys Lys Arg Lys Val
    1745                 1750                 1755
```

<210> SEQ ID NO 767
<211> LENGTH: 95
<212> TYPE: DNA
<213> ORGANISM: Artificial Sequence
<220> FEATURE:
<223> OTHER INFORMATION: Synthetic Polynucleotide

<400> SEQUENCE: 767

```
cctgaaataa tgcaagtgta gaataacttt ttaaaatctc atggtttatg ctaaactata     60

tgttgacata agagtggtga taaggcaaca gtagg                                95
```

<210> SEQ ID NO 768
<211> LENGTH: 91
<212> TYPE: DNA
<213> ORGANISM: Artificial Sequence
<220> FEATURE:
<223> OTHER INFORMATION: Synthetic Polynucleotide

<400> SEQUENCE: 768

```
cctagggaag tgatcatagc tgagtttcta tctcatggtt tatgctaaac tatatgttga     60

catgttgagg agacttaagt ccaaaacctg g                                    91
```

<210> SEQ ID NO 769
<211> LENGTH: 105
<212> TYPE: DNA
<213> ORGANISM: Artificial Sequence
<220> FEATURE:
<223> OTHER INFORMATION: Synthetic Polynucleotide

<400> SEQUENCE: 769
atgtcctgaa ataatgcaag tgtagaataa ctttttaaaa tctcatggtt tatgctaaac 60
tatatgttga cataagagtg gtgataaggc aacagtaggt aaaag 105

<210> SEQ ID NO 770
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (3)..(3)
<223> OTHER INFORMATION: Xaa is a stop codon
<220> FEATURE:
<221> NAME/KEY: MISC_FEATURE
<222> LOCATION: (10)..(10)
<223> OTHER INFORMATION: Xaa is a stop codon
<220> FEATURE:
<221> NAME/KEY: MISC_FEATURE
<222> LOCATION: (25)..(25)
<223> OTHER INFORMATION: Xaa is a stop codon
<220> FEATURE:
<221> NAME/KEY: MISC_FEATURE
<222> LOCATION: (28)..(29)
<223> OTHER INFORMATION: Xaa is a stop codon
<220> FEATURE:
<221> NAME/KEY: MISC_FEATURE
<222> LOCATION: (34)..(34)
<223> OTHER INFORMATION: Xaa is a stop codon

<400> SEQUENCE: 770

Asn Asn Ala Ser Val Glu
1 5

<210> SEQ ID NO 771
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 771

Asn Ala Ala Arg
1

<210> SEQ ID NO 772
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 772

Ala Gly Val Phe
1

<210> SEQ ID NO 773
<211> LENGTH: 4
<212> TYPE: PRT
<213> ORGANISM: Artificial Sequence
<220> FEATURE:
<223> OTHER INFORMATION: Synthetic Polypeptide

```
<400> SEQUENCE: 773

Gly Phe Leu Gly
1


<210> SEQ ID NO 774
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 774

Ala Leu Ala Leu
1


<210> SEQ ID NO 775
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 775

Ala Leu Ala Leu Ala
1               5


<210> SEQ ID NO 776
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 776

Leu Phe Lys Ile Ser Trp Phe Met Leu Asn Tyr Met Leu Thr
1               5                   10


<210> SEQ ID NO 777
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 777

Gly Asn Ser Arg
1
```